US012331359B2

(12) United States Patent
Luksza et al.

(10) Patent No.: US 12,331,359 B2
(45) Date of Patent: Jun. 17, 2025

(54) NEOANTIGENS AND USES THEREOF FOR TREATING CANCER

(71) Applicants: Icahn School of Medicine at Mount Sinai, New York, NY (US); The Simons Center for Systems Biology at the Institute for Advanced Study, Princeton, NJ (US); Memorial Sloan Kettering Cancer Center, New York, NY (US); Michael Laessig, New York, NY (US)

(72) Inventors: Marta Luksza, New York, NY (US); Vinod P. Balachandran, New York, NY (US); Arnold J. Levine, Princeton, NJ (US); Jedd D. Wolchok, New York, NY (US); Taha Merghoub, Jersey City, NJ (US); Steven D. Leach, New York, NY (US); Timothy A. Chan, New York, NY (US); Benjamin D. Greenbaum, New York, NY (US); Michael Laessig, Cologne (DE)

(73) Assignees: Michael Laessig, New York, NY (US); Icahn School of Medicine at Mount Sinai, New York, NY (US); The Simons Center for Systems Biology at the Institute for Advanced Study, Princeton, NJ (US); Memorial Sloan Kettering Cancer Center, New York, NY (US)

( * ) Notice: Subject to any disclaimer, the term of this patent is extended or adjusted under 35 U.S.C. 154(b) by 1362 days.

(21) Appl. No.: 16/478,818

(22) PCT Filed: Jan. 18, 2018

(86) PCT No.: PCT/US2018/014282
§ 371 (c)(1),
(2) Date: Jul. 17, 2019

(87) PCT Pub. No.: WO2018/136664
PCT Pub. Date: Jul. 26, 2018

(65) Prior Publication Data
US 2020/0232040 A1  Jul. 23, 2020

Related U.S. Application Data

(60) Provisional application No. 62/618,540, filed on Jan. 17, 2018, provisional application No. 62/582,851, (Continued)

(51) Int. Cl.
*G16B 30/10* (2019.01)
*A61K 35/15* (2015.01)
(Continued)

(52) U.S. Cl.
CPC .......... *C12Q 1/6886* (2013.01); *A61K 35/15* (2013.01); *A61K 35/17* (2013.01); *A61K 39/00* (2013.01);
(Continued)

(58) Field of Classification Search
CPC .. G01N 33/574; G01N 2800/52; G16B 20/10; G16B 20/20; G16B 20/30;
(Continued)

(56) References Cited

U.S. PATENT DOCUMENTS 10,738,355 B2 * 8/2020 Sahin ................ A61K 39/0011
2014/0134197 A1 * 5/2014 Calenoff ................ C07K 7/06
530/300

(Continued)

FOREIGN PATENT DOCUMENTS

WO  WO 2015/103037 A2  7/2015
WO  WO 2016/081947 A2  5/2016
(Continued)

OTHER PUBLICATIONS

Mandal, R. and Chan, T.A. Cancer Discovery 6(7):703-713. Jul. 2016. (Year: 2016).*
(Continued)

*Primary Examiner* — Karlheinz R. Skowronek
*Assistant Examiner* — Emilie A Neulen
(74) *Attorney, Agent, or Firm* — Foley & Lardner LLP

(57) ABSTRACT

Systems and methods for determining the likely responsiveness of a human cancer subject to a checkpoint blockade immunotherapy regimen are provided. Sequencing reads are obtained from samples from the subject representative of the cancer. A human leukocyte antigen type and a plurality of clones is determined from the sequencing reads. For each clone, an initial frequency $X_\alpha$ in the one or more samples is
(Continued)

determined and a corresponding clone fitness score of the clone is computed, thereby computing clone fitness scores. Each such fitness score is computed by identifying neoantigens in the respective clone, computing a recognition potential for each neoantigen, and determining the corresponding clone fitness score of the respective clone as an aggregate of these recognition potentials. A total fitness, quantifying the likely responsiveness of the subject to the regimen, is computed by summing the clone fitness scores across the plurality of clones.

21 Claims, 150 Drawing Sheets

Specification includes a Sequence Listing.

Related U.S. Application Data filed on Nov. 7, 2017, provisional application No. 62/554,232, filed on Sep. 5, 2017, provisional application No. 62/448,247, filed on Jan. 19, 2017, provisional application No. 62/448,291, filed on Jan. 19, 2017, provisional application No. 62/447,852, filed on Jan. 18, 2017.

(51) Int. Cl.
| A61K 35/17 | (2015.01) |
| A61K 39/00 | (2006.01) |
| C12Q 1/6886 | (2018.01) |
| G01N 33/569 | (2006.01) |
| G01N 33/574 | (2006.01) |
| G16B 20/10 | (2019.01) |
| G16B 20/20 | (2019.01) |
| G16B 20/30 | (2019.01) |
| G16B 30/20 | (2019.01) |
| G16B 50/00 | (2019.01) |
| G16B 30/00 | (2019.01) |

(52) U.S. Cl.
CPC .... *A61K 39/0011* (2013.01); *A61K 39/00117* (2018.08); *G01N 33/56977* (2013.01); *G01N 33/57438* (2013.01); *G16B 20/10* (2019.02); *G16B 20/20* (2019.02); *G16B 20/30* (2019.02); *G16B 30/10* (2019.02); *G16B 30/20* (2019.02); *G16B 50/00* (2019.02); *C12Q 2600/106* (2013.01); *C12Q 2600/156* (2013.01); *G01N 33/574* (2013.01); *G01N 2800/52* (2013.01); *G16B 30/00* (2019.02)

(58) Field of Classification Search
CPC ........ G16B 30/10; G16B 30/20; G16B 50/00; G16B 30/00
See application file for complete search history.

(56) References Cited

U.S. PATENT DOCUMENTS

| 2018/0251553 A1* | 9/2018 | McGranahan | G16B 30/00 |
| 2019/0127803 A1* | 5/2019 | Hacohen | G01N 33/57407 |

FOREIGN PATENT DOCUMENTS

| WO | WO 2016/187508 A2 | 1/2017 |
| WO | WO 2017/106638 A1 | 6/2017 |

OTHER PUBLICATIONS

Kamil A. Lipinski, Louise J. Barber, Matthew N. Davies, Matthew Ashenden, Andrea Sottoriva, Marco Gerlinger, Cancer Evolution and the Limits of Predictability in Precision Cancer Medicine, Trends in Cancer, vol. 2, Issue 1, 2016, pp. 49-63, https://doi.org/10.1016/j.trecan.2015.11.003. (Year: 2016).*

Balachandran, V., et al., "Identification of unique neoantigen qualities in long-term survivors of pancreatic cancer," NATURE (LONDON), vol. 551, No. 7681, Nov. 23, 2017 (Nov. 23, 2017), pp. 512-516.

Champiat, S., et al: "Exomics and Immunogenics," ONCOIMMUNOLOGY, vol. 3, No. 1 (Jan. 1, 2014), pp. e27817-1, 6 pages.

Fritsch, E.F et al., "HLA-Binding Properties of Tumor Neoepitopes in Humans", Cancer Immunology Research, vol. 2, No. 6, Mar. 3, 2014 (Mar. 3, 2014), pp. 522-529.

Harndahl, M., et al. "Peptide-MHC class I stability is a better predictor than peptide affinity of CTL immunogenicity: Antigen processing", European Journal of Immunology, vol. 42, No. 6, Jun. 1, 2012 (Jun. 1, 2012), pp. 1405-1416.

Luksza, M. et al., "A neoantigen fitness model predicts tumour response to checkpoint blockade immunotherapy," NATURE, Nov. 8, 2017 (Nov. 8, 2017) 20 pages.

Bailey, P. et al., "Genomic analyses identify molecular subtypes of pancreatic cancer," Nature 531, 47-52 (2016).

Biankin, A.V. et al., "Pancreatic cancer genomes reveal aberrations in axon guidance pathway genes," Nature 491, 399-405 (2012).

Bindea, G. et al., "Spatiotemporal Dynamics of Intratumoral Immune Cells Reveal the Immune Landscape in Human Cancer," Immunity 39, 782-795 (2013).

Bjerregaard, A.-M., et al., MuPeXI: prediction of neo-epitopes from tumor sequencingdata, Cancer Immunology, Immunotherapy 66.9 (20.004.2017: 1123-1130).

Chauvin, J.-M. et al., "TIGIT and PD-1 impair tumor antigen-specific CD8+ T cells in melanoma patients," The Journal of Clinical Investigation 125, 2046-2058 (2015).

Chekmasova, A. A. et al., "Successful eradication of established peritoneal ovarian tumors in SCID-Beige mice following adoptive transfer of T cells genetically targeted to the MUC16 antigen," Clin Cancer Res 16, 3594-3606 (2010).

Dal Molin, M. et al., "Very Long-term Survival Following Resection for Pancreatic Cancer Is Not Explained by Commonly Mutated Genes: Results of Whole-Exome Sequencing Analysis," Clin Cancer Res 21, 1944-1950 (2015).

Das, S. et al., "Carboxyl-terminal domain of MUC16 imparts tumorigenic and metastatic functions through nuclear translocation of JAK2 to pancreatic cancer cells," Oncotarget 6, 5772-5787 (2015).

Deshwar, A. G. et al., "PhyloWGS: reconstructing subclonal composition and evolution from whole-genome sequencing of tumors," Genome Biol. 16, 35 (2015), 20 pages.

Gros, A. et al., "PD-1 identifies the patient-specific CD8+ tumor-reactive repertoire infiltrating human tumors," The Journal of Clinical Investigation 124, 2246-2259 (2014).

Gros, A. et al., "Prospective identification of neoantigen-specific lymphocytes in the peripheral blood of melanoma patients," Nat Med 22, 433-438 (2016).

Gross, L., "Intradermal Immunization of C3H Mice against a Sarcoma That Originated in an Animal of the Same Line," Cancer Res 3, 326-333 (1943).

Gubin, M. M. et al., "Checkpoint blockade cancer immunotherapy targets tumour-specific mutant antigens," Nature 515, 577-581 (2014).

Hidalgo, M. Pancreatic cancer, The New England Journal of Medicine 362, 1605-1617 (2010).

Hiraoka, N. et al., "Intratumoral tertiary lymphoid organ is a favourable prognosticator in patients with pancreatic cancer," Br J Cancer 112, 1782-1790 (2015).

Haridas, D et al., "Pathobiological implications of MUC16 expression in pancreatic cancer," PLOS ONE 6, e26839 (2011), 9 pages.

Hundal, J. et al., "pVAC-Seq: A genome-guided in silico approach to identifying tumor neoantigens," Genome Med 8, 11 (2016), 11 pages.

Ino, Y. et al., "Immune cell infiltration as an indicator of the immune microenvironment of pancreatic cancer," Br J Cancer 108, 914-923 (2013).

Kleeff, J. et al. Pancreatic cancer, Nature Publishing Group 2, 16022 (2016), 22 pages.

(56) References Cited

OTHER PUBLICATIONS

Knudsen, E.S., et al., "Stratification of Pancreatic Ductal Adenocarcinoma: Combinatorial Genetic, Stromal, and Immunologic Markers," Clinical Cancer Research 23.15 (Mar. 27, 2017) 4429-4440.
Liu, Q. et al., "C-terminus of MUC16 activates Wnt signaling pathway through its interaction with ß-catenin to promote tumorigenesis and metastasis," Oncotarget 7, 36800-36813 (2016).
Łuksza, M. & Lässig, M, "A predictive fitness model for influenza," Nature 507, 57-61 (2014).
McAllister, F. et al., "Oncogenic Kras activates a hematopoietic-to-epithelial IL-17 signaling axis in preinvasive pancreatic neoplasia," Cancer Cell 25, 621-637 (2014).
McLaren, W. et al., "The Ensembl Variant Effect Predictor," Genome Biol. 17, 122 (2016), 14 pages.
Morgado, M. et al., "Tumor necrosis factor-α and interferon-γ stimulate MUC16 (CA125) expression in breast, endometrial and ovarian cancers through NFκB.," Oncotarget 7, 14871-14884 (2016).
Muniyan, S. et al., "MUC16 contributes to the metastasis of pancreatic ductal adenocarcinoma through focal adhesion mediated signaling mechanism," Genes Cancer 7, 110-124 (2016).
Nathanson, T., et al., "Somatic Mutations and Neoepitope Homology in Melanomas Treated with CTLA-4 Blockade," Cancer Immunology Research 5.1 (Dec. 12, 2016): 84-91.
Nielsen, M. et al., "NetMHCpan, a method for quantitative predictions of peptide binding to any HLA-A and -B locus protein of known sequence," PLOS ONE 2, e796 (2007), 10 pages.
Pearson, H. et al., "MHC class I-associated peptides derive from selective regions of the human genome," The Journal of Clinical Investigation (2016). doi:10. 1172/JCI88590,13 pages.
Remark, R., Merghoub, T. & Grabe, N, "In-depth tissue profiling using multiplexed immunohistochemical consecutive staining on single slide," Science (2016), 12 pages.
Rizvi, N.A. et al., "Cancer immunology. Mutational landscape determines sensitivity to PD-1 blockade in non-small cell lung cancer," Science 348, 124-128 (2015).
Royal, R.E. et al., "Phase 2 trial of single agent Ipilimumab (anti-CTLA-4) for locally advanced or metastatic pancreatic adenocarcinoma," Journal of Immunotherapy 33, 828-833 (2010).
Rubinsteyn, A., et al., "Computational Pipeline for the PGV-001 Neoantigen Vaccine Trial," bioRxiv (Oct. 8, 2017); 174516, 7 pages https://www.biorxiv.org/content/biorxiv/early/2017/08/10/174516.full.pdf.
Ryschich, E. et al., "Control of T-cell-mediated immune response by HLA class I in human pancreatic carcinoma," Clin Cancer Res 11, 498-504 (2005).
Sausen, M. et al., "Clinical implications of genomic alterations in the tumour and circulation of pancreatic cancer patients," Nat Commun 6, 7686 (2015), 6 pages.
Schumacher, T.N. & Schreiber, R.D., "Neoantigens in cancer immunotherapy," Science 348, 69-74 (2015).
Shukla, S. K. et al., "MUC16-mediated activation of mTOR and c-Myc reprograms pancreatic cancer metabolism," Oncotarget 6, 19118-19131 (2015).
Siegel, R.L., Miller, K.D. & Jemal, A. Cancer Statistics 65, 5-29 (2015).
Snyder, A. et al. "Genetic basis for clinical response to CTLA-4 blockade in melanoma," N Engl J Med 371, 2189-2199 (2014).
Tumeh, P.C. et al., "PD-1 blockade induces responses by inhibiting adaptive immune resistance," Nature 515, 568-571 (2014).
Valsecchi, M.E., Diaz-Canton, E., de la Vega, M. & Littman, S. J., "Recent treatment advances and novel therapies in pancreas cancer: a review," Journal of Gastrointestinal Cancer 45, 190-201 (2014).
Van Allen, E. M. et al., "Genomic correlates of response to CTLA-4 blockade in metastatic melanoma," Science 350, 207-211 (2015).
Vétizou, M. et al., "Anticancer immunotherapy by CTLA-4 blockade relies on the gut microbiota," Science 350, 1079-1084 (2015).
Wang et al., "Expression of the Carboxy-Terminal Portion of MUC16/CA125 Induces Transformation and Tumor Invasion," PLOS ONE 75, 4669-4674 (2015).
Witkiewicz, A.K. et al., "Whole-exome sequencing of pancreatic cancer defines genetic diversity and therapeutic targets," Nat Commun 6, 6744 (2015), 11 pages.
Yu, H., Pardoll, D. & Jove, R., "STATs in cancer inflammation and immunity: a leading role for STAT3," Nat Rev Cancer 9, 798-809 (2009).
Zhou, Z., et al., "TSNAD: an Integrated Software for Cancer Somatic Mutation and Tumour-Specific Neoantigen Detection," Royal Society open science 4.4 (May 4, 2017) 170050,12 pages.
Zitvogel, L., Ayyoub, M., Routy, B. & Kroemer, G., "Microbiome and Anticancer Immunosurveillance," Cell 165, 276-287 (2016).

* cited by examiner (B)

↓

┌─────────────────────────────────────────────────────────────────────┐ — 338
│ For each respective clone α in the plurality of clones, compute a corresponding │
│ clone fitness score of the respective clone, thereby computing a plurality of clone │
│ fitness scores, each corresponding clone fitness score computed for a respective │
│ clone α by a first procedure comprising:                            │ — 340
│  ┌────────────────────────────────────────────────────────────┐    │
│  │ Identify a plurality of neoantigens in the respective clone α. │ — 342
│  │  ┌──────────────────────────────────────────────────────┐  │
│  │  │ Each neoantigen in the plurality of neoantigens of a clone in the plurality │
│  │  │ of clones is a nonamer peptide (332).                │  │ — 344
│  │  └──────────────────────────────────────────────────────┘  │
│  │  ┌──────────────────────────────────────────────────────┐  │
│  │  │ Each neoantigen in the plurality of neoantigens of a clone in the plurality │
│  │  │ of clones is a peptide that is eight, nine, ten, or eleven residues in length. │
│  │  │ (334).                                                │  │
│  │  └──────────────────────────────────────────────────────┘  │
│  └────────────────────────────────────────────────────────────┘    │ — 346
│                                                                     │
│  ┌────────────────────────────────────────────────────────────┐    │
│  │ Compute a cross reactivity load of each respective neoantigen in the │
│  │ plurality of neoantigens in the respective clone α by a second procedure │
│  │ comprising:                                                  │ — 348
│  │  ┌──────────────────────────────────────────────────────┐  │
│  │  │ Compute an amplitude A of the respective neoantigen as a function of the │
│  │  │ relative major histocompatibility complex (MHC) affinity of the │
│  │  │ respective neoantigen and the wild type counterpart of the respective │
│  │  │ neoantigen given the HLA type of the subject.         │  │
│  │  │                                                        │ — 350
│  │  │  ┌────────────────────────────────────────────────┐  │
│  │  │  │ The function of the relative class I MHC affinity of the respective │
│  │  │  │ neoantigen and the wild type counterpart of the respective neoantigen │
│  │  │  │ given the HLA type of the human cancer subject is a ratio of the │
│  │  │  │ relative class I MHC affinity of the respective neoantigen and the wild │
│  │  │  │ type counterpart of the respective neoantigen given the HLA type of │
│  │  │  │ the subject.                                    │  │
│  │  │  └────────────────────────────────────────────────┘  │ — 352
│  │  │  ┌────────────────────────────────────────────────┐  │
│  │  │  │ The function of the relative class I MHC affinity of the respective │
│  │  │  │ neoantigen and the wild type counterpart of the respective neoantigen │
│  │  │  │ given the HLA type of the subject is a ratio of: (1) a dissociation │
│  │  │  │ constant between the respective neoantigen and the class I MHC │
│  │  │  │ presented by the cancer subject given the HLA type of the cancer │
│  │  │  │ subject, and (2) a dissociation constant between the wild type │
│  │  │  │ counterpart of the respective neoantigen and the class I MHC presented │
│  │  │  │ by the cancer subject given the HLA type of the cancer subject. │
│  │  │  └────────────────────────────────────────────────┘  │
│  │  └──────────────────────────────────────────────────────┘  │
│  └────────────────────────────────────────────────────────────┘    │
└─────────────────────────────────────────────────────────────────────┘

338 (cont.)

346 (cont.)

348 (cont.)

352 (cont.)

354 The dissociation constant between the respective neoantigen and the class I MHC presented by the cancer subject is obtained as output from a first classifier upon inputting into the first classifier the amino acid sequence of the neoantigen. The dissociation constant between the wild type counterpart of the respective neoantigen and the class I MHC presented by the cancer subject of the HLA type of the subject is obtained as output from the first classifier upon inputting into the first classifier the amino acid sequence of the respective wild type counterpart of the neoantigen (e.g., the first classifier is specific to the HLA type of the cancer subject and has been trained with the respective class I MHC binding coefficient and sequence data of each peptide epitope in a plurality of epitopes presented by class I MHC in a training population having the HLA type of the subject).

356 Compute a probability of T-cell receptor recognition $R$ of the respective neoantigen as a probability that the respective neoantigen binds one or more epitopes that are positively recognized by T-cells after class I MHC presentation.

358 The probability that the respective neoantigen binds one or more epitopes that are positively recognized by T-cells after class I MHC presentation is determined by a third procedure that comprises: (a) selecting a respective epitope $e$ from an epitope database IEDB, wherein the respective epitope $e$ is positively recognized by T-cells after class I MHC presentation; (b) computing, for the respective epitope $e$, the probability $$\Pr_{\text{binding}}(\mathbf{s}, \mathbf{e}) = \frac{1}{1 + e^{-k(|\mathbf{s},\mathbf{e}|-a)}}$$

where, $|\mathbf{s}, \mathbf{e}|$ is a sequence alignment score between the sequence of the respective neoantigen and the sequence of the respective epitope, and $k$ and $a$ are constants (e.g., $a$ is set to 23 and $k$ is set to 1); (c) performing the selecting (a) and the computing (b) for each respective epitope $e$ in a plurality of epitopes in the epitope database IEDB, thereby computing a plurality of probabilities $\Pr_{\text{binding}}(\mathbf{s}, \mathbf{e})$; and (d) computing the probability of T-cell receptor recognition $R$ of the respective neoantigen as:

$$R = 1 - \prod_{e \in \text{IEDB}}[1 - \Pr_{\text{binding}}(\mathbf{s}, \mathbf{e})],$$

where IEDB is the plurality of epitopes.

Fig. 3D (E)

Compute a total fitness for the one or more samples as a sum of the clone fitness scores across the plurality of clones, where each clone fitness score is weighted by the initial frequency $X_\alpha$ of the corresponding clone $\alpha$, and the total fitness quantifies the likelihood that the human subject afflicted with the cancer will be responsive to the treatment regimen.

The computing a total fitness for the one or more samples as a sum of the clone fitness scores across the plurality of clones is computed as:

$$n(\tau) = \sum_\alpha X_\alpha \exp(F_\alpha \tau),$$

where $\tau$ is a characteristic evolutionary time scale.

A lower total fitness score is associated with (a) a higher likelihood that the cancer subject will be responsive to the immunotherapy and (b) a longer term survival of the cancer patient.

Fig. 3F

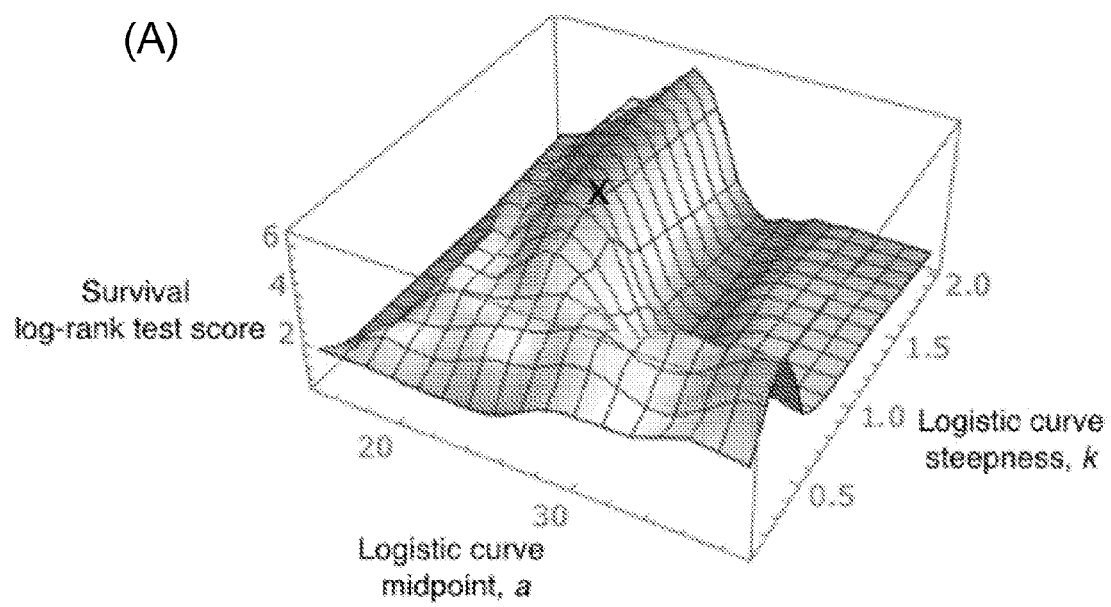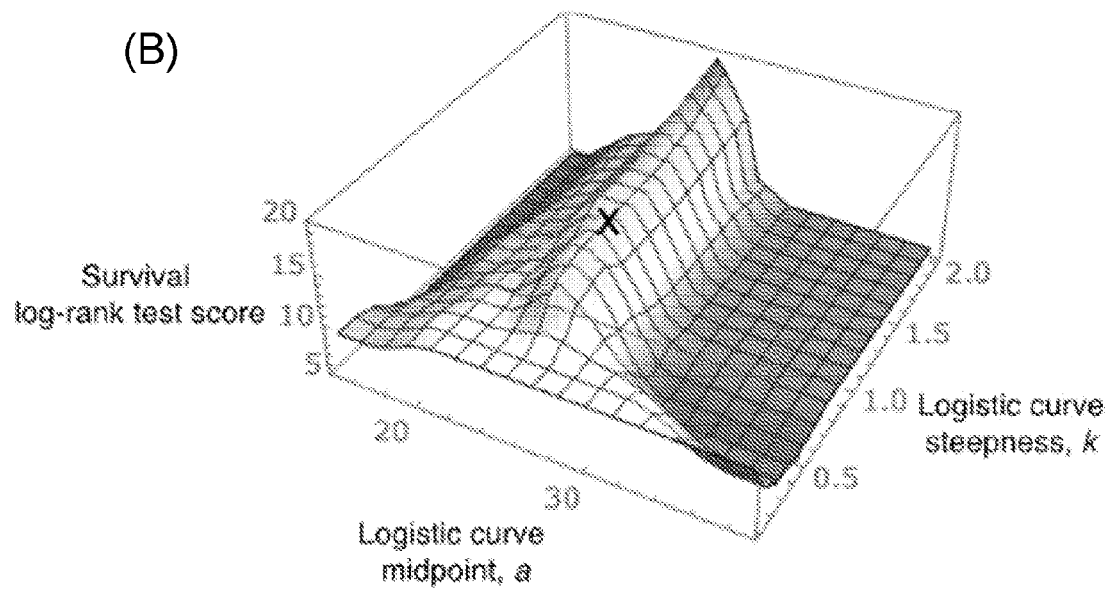
Fig. 17

Van Allen et al., Melanoma anti-CTLA-4

| Models | Parameters trained on Snyder | | | | | | Log-rank test | | | |
|---|---|---|---|---|---|---|---|---|---|---|
| | τ | | a | | k | | Score | | Significance | Equation |
| | Mean | Std | Mean | Std | Mean | Std | Mean | Std | | |
| A × R | 0.09003 | ±0.077 | 26 | ±2.988 | 4.19761 | ±0.01 | 7.92 | ±0.49 | 0.00489 *** | (2) |
| Partial models: | | | | | | | | | | |
| A | 0.00131 | ±0.0001 | | | | | 0.65 | ±0.03 | | (12) |
| R | 12.33338 | ±1.827 | 12.5 | ±1.074 | 1.89795 | ±24.161 | 1.68 | ±0.01 | | (13) |
| 1/kdM × R | 0.03851 | ±1.711 | 21.3 | ±0.353 | 1.50243 | ±0.02 | 2.01 | ±0.45 | | (14) |
| 1/kdM | 0.3386 | ±0.0001 | | | | | 1.46 | ±0.23 | | (14) |
| kdW × R | 0.00048 | ±0.0001 | 31 | ±2.911 | 6.26907 | ±0.001 | 0.09 | ±0.25 | | (15) |
| kdW | 0.00307 | ±0.0001 | | | | | 0.04 | ±0.2 | | (15) |
| Alternative models: | | | | | | | | | | |
| Neoantigen load | 16.39039 | ±0.0001 | | | | | 1.48 | ±0.12 | | (17) |
| A × R, sum over neoantigens | 18.3366 | ±0.471 | 38.3 | ±0.001 | 10.1531 | ±29.105 | 0.21 | ±0.08 | | (16) |
| A × R, alignments at positions 3-8 | 0.0716 | ±1.011 | 22.3 | ±0.273 | 0.46591 | ±0.022 | 0.94 | ±0.13 | | (2) |
| A × R, negative IEDB assays | 0.00091 | ±0.58 | 15.8 | ±0.056 | 0.45236 | ±0.001 | 0.98 | ±0.03 | | (2) |
| A × R, all neoantigens | 0.01602 | ±0.559 | 34.9 | ±0.051 | 0.53933 | ±0.834 | 0.13 | ±0.03 | | (2) |
| A × R, average fitness | | | 26.3 | ±0.252 | 1.06061 | ±0.001 | 4.03 | ±0.84 | 0.04476 · | (2) and (19) |

Fig. 23

| Snyder et al., Melanoma anti-CTLA-4 | Parameters trained on Van Allen | | | | | | Log-rank test | | | |
|---|---|---|---|---|---|---|---|---|---|---|
| | τ | | a | | k | | Score | | | |
| Models | Mean | Std | Mean | Std | Mean | Std | Mean | Std | Significance | Equation |
| A × R | 0.02326 | ±0.479 | 26 | ±3.835 | 3.44101 | ±0.088 | 9.1 | ±0.92 | 0.00256 *** | (2) |
| Partial models: | | | | | | | | | | |
| A | 0.1007 | ±0.0001 | - | - | - | - | 0.09 | ±0.68 | | (12) |
| R | 1.3483 | ±17.017 | 21.2 | ±5.133 | 5.57735 | ±27.093 | 1.17 | ±0.38 | | (13) |
| 1/kdM × R | 0.0786 | ±5.21 | 22 | ±0.445 | 1.4779 | ±0.065 | 0.41 | ±0.65 | | (14) |
| 1/kdM | 0.06196 | ±0.0001 | - | - | - | - | 0.63 | ±0.61 | | (14) |
| kdW × R | 0.00096 | ±15.302 | 27 | ±4.14 | 5.53499 | ±0.001 | 0.53 | ±0.22 | | (15) |
| kdW | 13.33274 | ±0.0001 | - | - | - | - | 1.21 | ±0.75 | | (15) |
| Alternative models: | | | | | | | | | | |
| Neoantigen load | 0.10065 | ±0.0001 | - | - | - | - | 0.64 | ±0.21 | | (17) |
| A × R, sum over neoantigens | 0.08928 | ±27.215 | 27 | ±8.827 | 5.01847 | ±34.399 | 0.09 | ±0.53 | | (16) |
| A × R, alignments at positions 3-8 | 1.82771 | ±11.104 | 24.9 | ±8.066 | 8.08455 | ±1.826 | 5.33 | ±1.05 | 0.021 * | (2) |
| A × R, negative IEDB assays | 0.16414 | ±10.716 | 11.7 | ±0.768 | 0.89312 | ±0.164 | 1.83 | ±0.97 | | (2) |
| A × R, all neoantigens | 0.00772 | ±23.665 | 25.7 | ±7.145 | 7.16555 | ±0.834 | 2.63 | ±0.92 | | (2) |
| A × R, average fitness | - | - | 26 | ±3.158 | 3.34043 | ±0.001 | 8.03 | ±0.92 | 0.00459 *** | (2) and (19) |

Fig. 24

| Rizvi et al., Lung anti-PD-1 | Parameters trained on Van Allen and Snyder | | | | | | Log-rank test | | | |
|---|---|---|---|---|---|---|---|---|---|---|
| Models | τ | | a | | k | | Score | | Significance | Equation |
| | Mean | Std | Mean | Std | Mean | Std | Mean | Std | | |
| A × R | 0.08958 | ±0.458 | 26 | ±1.679 | 4.8714 | ±0.014 | 7.48 | ±1.17 | 0.00624 *** | (2) |
| Partial models: | | | | | | | | | | |
| A | 0.09278 | ±0.0001 | - | - | - | - | 1.86 | ±1.17 | | (12) |
| R | 1.9744 | ±13.288 | 18.4 | ±4.897 | 5.36039 | ±27.055 | 0.07 | ±0.01 | | (13) |
| 1/kdM × R | 1.50385 | ±6.017 | 22.2 | ±0.74 | 1.71159 | ±1.503 | 0.1 | ±0.16 | | (14) |
| 1/kdM | 3.42166 | ±0.0001 | - | - | - | - | 0.52 | ±0.13 | | (14) |
| kdW × R | 0.78791 | ±5.582 | 30.5 | ±4.853 | 4.92212 | ±0.788 | 1.62 | ±0.54 | | (15) |
| kdW | 7.31748 | ±0.0001 | - | - | - | - | 0.62 | ±0.75 | | (15) |
| Alternative models: | | | | | | | | | | |
| Neoantigen load | 3.89326 | - | - | - | - | - | 0.49 | ±1.15 | | (17) |
| A × R, sum over neoantigens | 22.06719 | ±1.493 | 38.4 | ±0.004 | 10.1531 | ±26.389 | 0 | ±0.11 | | (16) |
| A × R, alignments at positions 3-8 | 0.06281 | ±6.254 | 21.4 | ±0.34 | 0.63805 | ±0.041 | 2.55 | ±0.59 | | (2) |
| A × R, negative IEDB assays | 0.01993 | ±5.485 | 16.8 | ±0.485 | 0.66568 | ±0.02 | 3.39 | ±0.51 | | (2) |
| A × R, all neoantigens | 0.44272 | ±9.228 | 33.7 | ±0.484 | 0.71345 | ±0.707 | 0.88 | ±0.84 | | (2) |
| A × R, average fitness | - | - | 26 | ±1.502 | 1.85617 | ±0.001 | 4.49 | ±1.17 | 0.03402 * | (2) and (19) |

Fig. 25

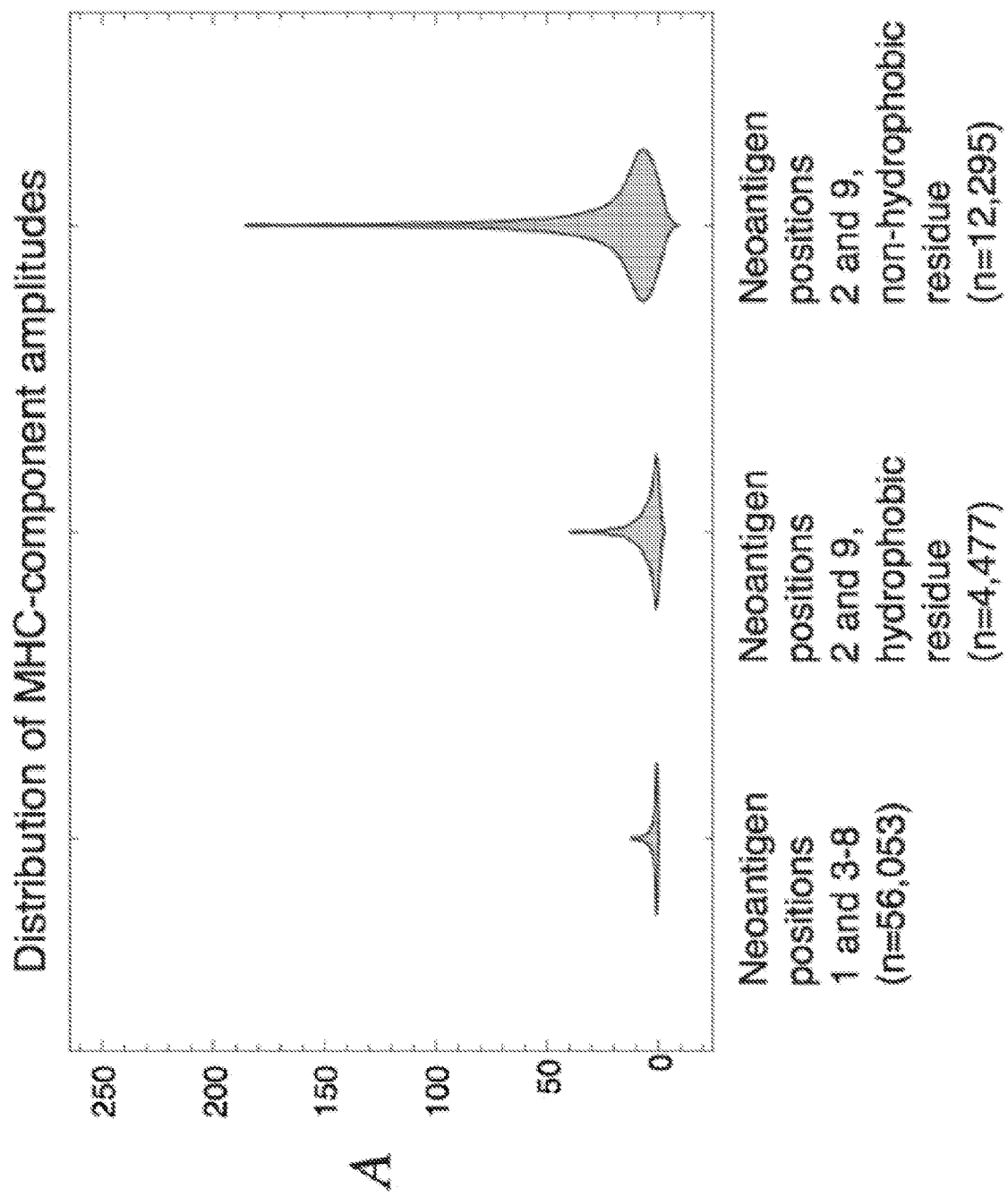

| Van Allen et al., Melanoma anti-CTLA-4 Models | Parameters trained on Snyder et al. dataset | | | | Log-rank test | | | |
|---|---|---|---|---|---|---|---|---|
| | a | | k | | Score | | Significance | Equation |
| | Mean | Std | Mean | Std | Mean | Std | | |
| A x R | 18.5 | ±0.152 | 0.59845 | ±0.001 | 0.61 | ±0.24 | | (2) |
| Partial models: | | | | | | | | |
| A | - | - | - | - | 0.05 | ±0.03 | | (12) |
| R | 18.2 | ±2.995 | 4.54981 | ±0.001 | 0.2 | ±0.03 | | (13) |
| 1/kdM x R | 26.6 | ±1.609 | 1.34421 | ±0.001 | 1.41 | ±0.61 | | (14) |
| 1/kdM | - | - | - | - | 0.69 | ±0.23 | | (14) |
| kdW x R | 23.7 | ±2.593 | 3.83397 | ±0.001 | 1.35 | ±0.34 | | (15) |
| kdW | - | - | - | - | 0.46 | ±0.2 | | (15) |
| Alternative models: | | | | | | | | |
| Neoantigen load | - | - | - | - | 0.24 | ±0.12 | | (17) |
| A x R, sum over neoantigens | 25.1 | ±3.308 | 4.89176 | ±0.001 | 1.57 | ±0.39 | | (16) |
| A x R, alignments at positions 3-8 | 21.9 | ±2.871 | 3.1276 | ±0.001 | 0.35 | ±0.36 | | (2) |
| A x R, negative IEDB assays | 14.4 | ±2.58 | 2.20223 | ±0.001 | 0.04 | ±0.03 | | (2) |
| A x R, all neoantigens | 29.2 | ±2.892 | 3.88642 | ±0.001 | 0.24 | ±0.19 | | (2) |

Fig. 32A

| Snyder et al., Melanoma anti-CTLA-4 | Parameters trained on Van Allen et al. dataset | | | | Log-rank test | | | Equation |
|---|---|---|---|---|---|---|---|---|
| | a | | k | | Score | | | |
| Models | Mean | Std | Mean | Std | Mean | Std | Significance | |
| A x R | 26.4 | ±0.892 | 1.0851 | ±0.001 | 6.55 | ±0.9 | 0.01047 * | (2) |
| Partial models: | | | | | | | | |
| A | 29.7 | ±4.829 | - | - | 4.44 | ±0.68 | 0.03507 * | (12) |
| R | 26 | ±1.929 | 2.51962 | ±0.001 | 1.26 | ±0.34 | | (13) |
| 1/kdM x R | 26.9 | ±2.735 | 0.82074 | ±0.001 | 3.65 | ±0.81 | | (14) |
| 1/kdM | - | - | - | - | 3.44 | ±0.61 | | (14) |
| kdW x R | - | - | 3.73387 | ±0.001 | 1.67 | ±0.22 | | (15) |
| kdW | - | - | - | - | 3.11 | ±0.75 | | (15) |
| Alternative models: | | | | | | | | |
| Neoantigen load | 27 | ±3.005 | 5.08369 | ±0.001 | 0.42 | ±0.21 | | (17) |
| A x R, sum over neoantigens | 30 | ±4.023 | 1.35553 | ±0.001 | 1.63 | ±0.53 | | (16) |
| A x R, alignments at positions 3-8 | 36 | ±9.57 | 10.1531 | ±0.001 | 2.73 | ±0.65 | | (2) |
| A x R, negative iEDB assays | 26 | ±1.95 | 5.22216 | ±0.001 | 0.23 | ±0.65 | | (2) |
| A x R, all neoantigens | | | | | 0.59 | ±0.92 | | (2) |

Fig. 32B

| Rizvi et al., Lung anti-PD-1 | Parameters trained on Van Allen et al. and Snyder et al. datasets | | | | Log-rank test | | | |
|---|---|---|---|---|---|---|---|---|
| | a | | k | | Score | | | |
| Models | Mean | Std | Mean | Std | Mean | Std | Significance | Equation |
| A x R | 27 | ±0.787 | 1.00032 | ±0.001 | 6.48 | ±1.14 | 0.01047 * | (2) |
| Partial models: | | | | | | | | |
| A | 19.6 | ±3.355 | 4.29127 | ±0.001 | 4.65 | ±1.17 | 0.03507 * | (12) |
| R | 21 | ±2.027 | 0.53498 | ±0.001 | 1.53 | ±0.29 | | (13) |
| 1/kdM x R | - | - | - | - | 0.02 | ±0.07 | | (14) |
| 1/kdM | - | - | - | - | 0.17 | ±0.13 | | (14) |
| kdW x R | 23 | ±2.737 | 5.37707 | ±0.001 | 10.48 | ±1.71 | 0.00121 *** | (15) |
| kdW | - | - | - | - | 4.49 | ±0.75 | 0.03416 * | (15) |
| Alternative models: | | | | | | | | |
| Neoantigen load | - | - | - | - | 4.93 | ±1.15 | 0.023639 * | (17) |
| A x R, sum over neoantigens | 25 | ±4.316 | 4.03113 | ±0.001 | 3.09 | ±1.09 | | (16) |
| A x R, alignments at positions 3-8 | 22 | ±3.042 | 5.2228 | ±0.001 | 2.3 | ±0.82 | | (2) |
| A x R, negative IEDB assays | 14.5 | ±2.806 | 1.90577 | ±0.001 | 1 | ±0.45 | | (2) |
| A x R, all neoantigens | 29 | ±4.469 | 1.87092 | ±0.001 | 0.75 | ±0.62 | | (2) |

Fig. 32C

| | | Snyder | | | Van Allen | |
|---|---|---|---|---|---|---|
| Variable | HR | 95% CI | p-value | HR | 95% CI | p-value |
| n(τ) > Median | 3.88 | 1.72 – 8.75 | 0.001 | 1.99 | 1.25 – 3.15 | 0.004 |
| Stage M1b | 1.36 | 0.3 – 6.15 | 0.69 | 0.8 | 0.27 – 2.40 | 0.703 |
| Stage M1c | 2.41 | 0.69 – 8.40 | 0.168 | 1.52 | 0.60 – 3.88 | 0.372 |
| Age | 1 | 0.98 – 1.03 | 0.802 | 1 | 0.99 – 1.02 | 0.43 |
| Gender (Male) | 0.82 | 0.40 – 1.69 | 0.59 | 0.72 | 0.43 – 1.21 | 0.218 |

| | | Rizvi | |
|---|---|---|---|
| Variable | HR | 95% CI | p-value |
| n(τ) > Median | 4.85 | 1.34 – 17.45 | 0.016 |
| Age | 1 | 0.95 – 1.05 | 0.962 |
| Gender (Male) | 1.61 | 0.61 – 4.25 | 0.339 |
| Pack-Years Smoked | 1 | 0.98 – 1.03 | 0.534 |

Fig. 36

```
###############################################################
# Compute neoantigen fitness cost (recognition potential)

# Directory structure:

# InputData:
# 1. neoantigen-data files for 3 cohorts (Van Allen et al., Snyder et al. and Rizvi et al.)
# 2. iedb.fasta: fasta file with IEDB epitope sequences
# 3. neoantigen alignment folders with precomputed blastp alignments for all neoantigens, split into files for each sample.
# eg. run as
# blastp -query <InputData/neoantigen_alignments_Rizvi/neoantigens_AL4602.fasta> -db
#    InputData/iedb.fasta -outfmt 5 -evalue 100000000 -gapopen 11 -gapextend 1 >
#    <InputData/neoantigen_alignments_Rizvi/neoantigens_AL4602.xml>

# src:
# source code folder

# Output:
# source code output folder: neoantigens with computed fitness cost
###############################################################

# fitness model parameters
a=26.
k=4.86936
python src/main.py InputData/neoantigens_VanAllen.txt InputData/neoantigen_alignments_VanAllen $a $k Output/neoantigen_fitness_VanAllen.txt
python src/main.py InputData/neoantigens_Snyder.txt InputData/neoantigen_alignments_Snyder $a $k Output/neoantigen_fitness_Snyder.txt
python src/main.py InputData/neoantigens_Rizvi.txt InputData/neoantigen_alignments_Rizvi $a $k Output/neoantigen_fitness_Rizvi.txt
```

Fig. 37

```
1   '''
2   @author: Marta Łuksza mluksza@bios.edu
3   '''
4   from Bio.Blast import NCBIXML
5   from Bio import pairwise2
6   from Bio.SubsMat import MatrixInfo as matlist
7   from math import log, exp
8
9   class Aligner(object):
10      '''
11      Class to compute alignment score of neoantigens with IEDB epitopes and compute TCR-recognition
12      probabilities.
13      '''
14      INF = float("inf")
15
16      @staticmethod
17      def align(seq1,seq2):
18          '''
19          Smith-Waterman alignment with default parameters.
20          '''
21          matrix = matlist.blosum62
22          gap_open = -11
23          gap_extend = -1
24          aln = pairwise2.align.localds(seq1.upper(), seq2.upper(), matrix,gap_open,gap_extend)
25          return aln
26
27      @staticmethod
28      def logSum(v):
29          '''
30          compute the logarithm of a sum of exponentials
31          '''
32          if len(v)==0:
33              return -Aligner.INF
34          ma = max(v)
35          if ma==-Aligner.INF:
36              return -Aligner.INF
37          return log(sum(map(lambda x: exp(x-ma),v)))+ma
38
39      def __init__(self):
```

Fig. 38A

```python
    #dictionary of computed RL-values mapped to neoantigen identifiers
    self.RL={}
    #dictionary of IEDB epitope alignments mapped to neoantigen identifiers
    self.alignments={}
    #dictionary of the highest scoring alignments mapped to neoantigen identifiers
    self.maximum_alignment={} def readAllBlastAlignments(self,xmlpath):
    '''
    Read precomputed blasto alignments from xml files,
    compute alignment scores,
    find the highest scoring alignment for each neoantigen.
    '''
    f = open(xmlpath)
    blast_records = NCBIXML.parse(f)
    maxscore={}
    try:
        for brecord in blast_records:
            tab=str(brecord.query).split("|")
            ptype=tab[1]
            nid=int(tab[2])
            if ptype=="MUT":
                if not nid in maxscore:
                    maxscore[nid]=0
                for alignment in brecord.alignments:
                    if not nid in self.alignments:
                        self.alignments[nid]={}
                        self.maximum_alignment[nid]=None
                        self.maximum_alignment[nid]=0
                        maxscore[nid]=0
                    species=".".join(str(alignment).split()[1:-3])
                    for hsp in alignment.hsps:
                        if not "-" in hsp.query and not "-" in hsp.sbjct:
                            al=Aligner.align(hsp.query, hsp.sbjct)
                            if len(al)>0:
                                al=al[0]
                                self.alignments[nid][species]=al
                                if al[2]>maxscore[nid]:
                                    self.maximum_alignment[nid]=al[2]
                                    maxscore[nid]=al[2]
```

Fig. 38B

```
 81     except ValueError:
 82         print "error"
 83         pass
 84     f.close()
 85 
 86 def computeR(self,a=26,k=4.86936):
 87     """
 88     Compute TCR-recognition probabilities for each neoantigen.
 89     """
 90     #iterate over all neoantigens
 91     for i in self.alignments:
 92         #energies of all bound states of neoantigen i
 93         bindingEnergies=map(lambda el: -k*(a-el[2]), self.alignments[i].values())
 94         #partition function, over all bound states and an unbound state
 95         lZ=Aligner.logSum(bindingEnergies+[0])
 96         lGb=Aligner.logSum(bindingEnergies)
 97         R=exp(lGb-lZ)
 98         self.Ri[i]=R
 99 
100 def getR(self,i):
101     """
102     Return precomputed R value for a given neoantigen i.
103     """
104     if i in self.Ri:
105         return self.Ri[i]
106     return 0.
107 
```

Fig. 38C

```
'''
@author: Marta Luksza, mluksza@ias.edu
''' import sys
from Aligner import Aligner from Neoantigen import Neoantigen def readNeoantigens(neofilename):
    neoantigens={}
    f=open(neofilename)
    header=f.readline()
    htab=header.strip().split("\t")
    hdict={}
    for i in range(0,len(htab)):
        hdict[htab[i]]=i line=f.readline()
    while line:
        line=line.strip()
        nparams=line.split("\t")
        if nparams[7]=="NA":
            line=f.readline()
            continue
        neoantigen=Neoantigen(nparams)
        neoantigens[neoantigen.id]=neoantigen
        neoantigen.setA()
        line=f.readline()
    f.close()
    samples=set(map(lambda neo: neo.getSampleName(),neoantigens.values()))
    return [neoantigens,samples]

def main(argv):

'''
    command line parameters:
    neofile - text file with neoantigen data (supplementary data)
    alignmentDirectory - folder with precomputed alignments
    a - midpoint parameter of the logistic function, alignment score threshold
    k - slope parameter of the logistic function
    outfile - path to a file where to output neoantigen fitness computation
    '''
```

```
1   '''
2   @author: Marta Luksza, mluksza@ias.edu
3   '''
4
5   class Neoantigen(object):
6       '''
7       classdocs
8       '''
9       L=1. #default concentration of peptides
10      M=1. #default concentration of mutant peptides
11      W=1. #default concentration of wildtype peptides
12
13      WEPS=0.0003
14      WTCAP=float("inf")
15
16
17      HYDROPHOBIC_RESIDUES="AILMFWYV"
18      WEIRD_RESIDUES="CGP"
19
20      AGGR="MAX"
21      KDnormalize=1
22      AGGRnum=float("inf")
23
24      @staticmethod
25      def residueChangeClass(res1,res2):
26          code=""
27          if res1 in Neoantigen.HYDROPHOBIC_RESIDUES:
28              code+="H"
29          elif res2 in Neoantigen.WEIRD_RESIDUES:
30              code+="W"
31          else:
32              code+="N"
33          if res2 in Neoantigen.HYDROPHOBIC_RESIDUES:
34              code+="H"
35          elif res2 in Neoantigen.WEIRD_RESIDUES:
36              code+="W"
37          else:
38              code+="N"
39          return code
40
```

```
        kd=self.wtkD
        prb=Neoantigen.W/(Neoantigen.W+kd)
        prm=kd/(Neoantigen.W+kd)
        eps=Neoantigen.NEPS
        prb+=eps
        prm+=eps
        z=1+2*eps
        prb/=z
        prm/=z
        return prm/prb def getWeight(self):
        '''
        Returns 0 for neoantigens that mutated from a non-hydrophobic residues on position 2 or 9;
        these are excluded from analysis. Returns 1 for all other neoantigens
        '''
        w=1
        if self.residueChange()[0]!="H" and (self.position==2 or self.position==9):
            w=0
        return w def setA(self):
        '''
        Computes MHC amplitude A
        '''
        self.A=Neoantigen.W/self.kD=self.correctWT()

def getA(self):
        '''
        Return MHC amplitude A
        '''
        return self.A
```

Fig. 40C

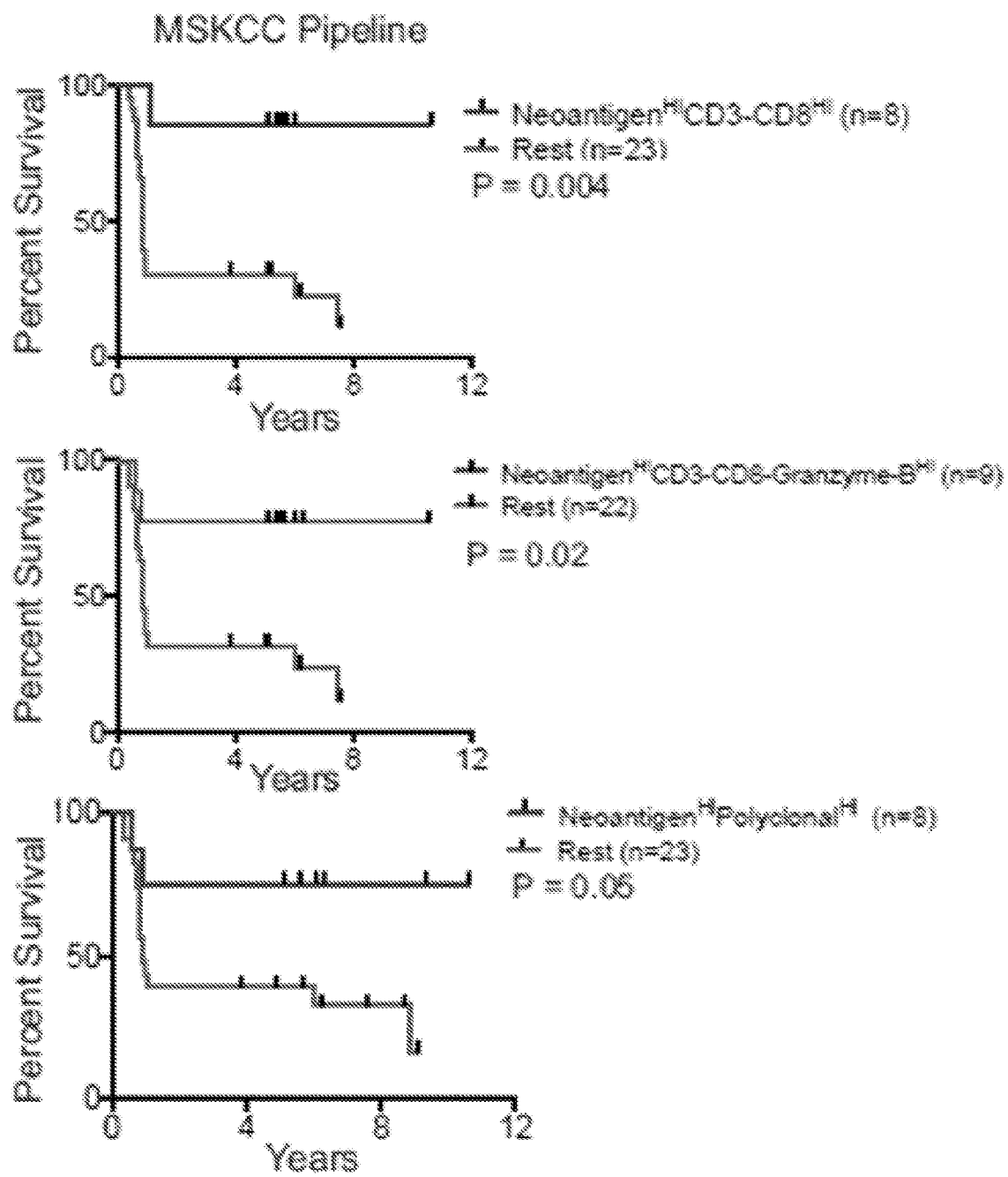
Fig. 48B1

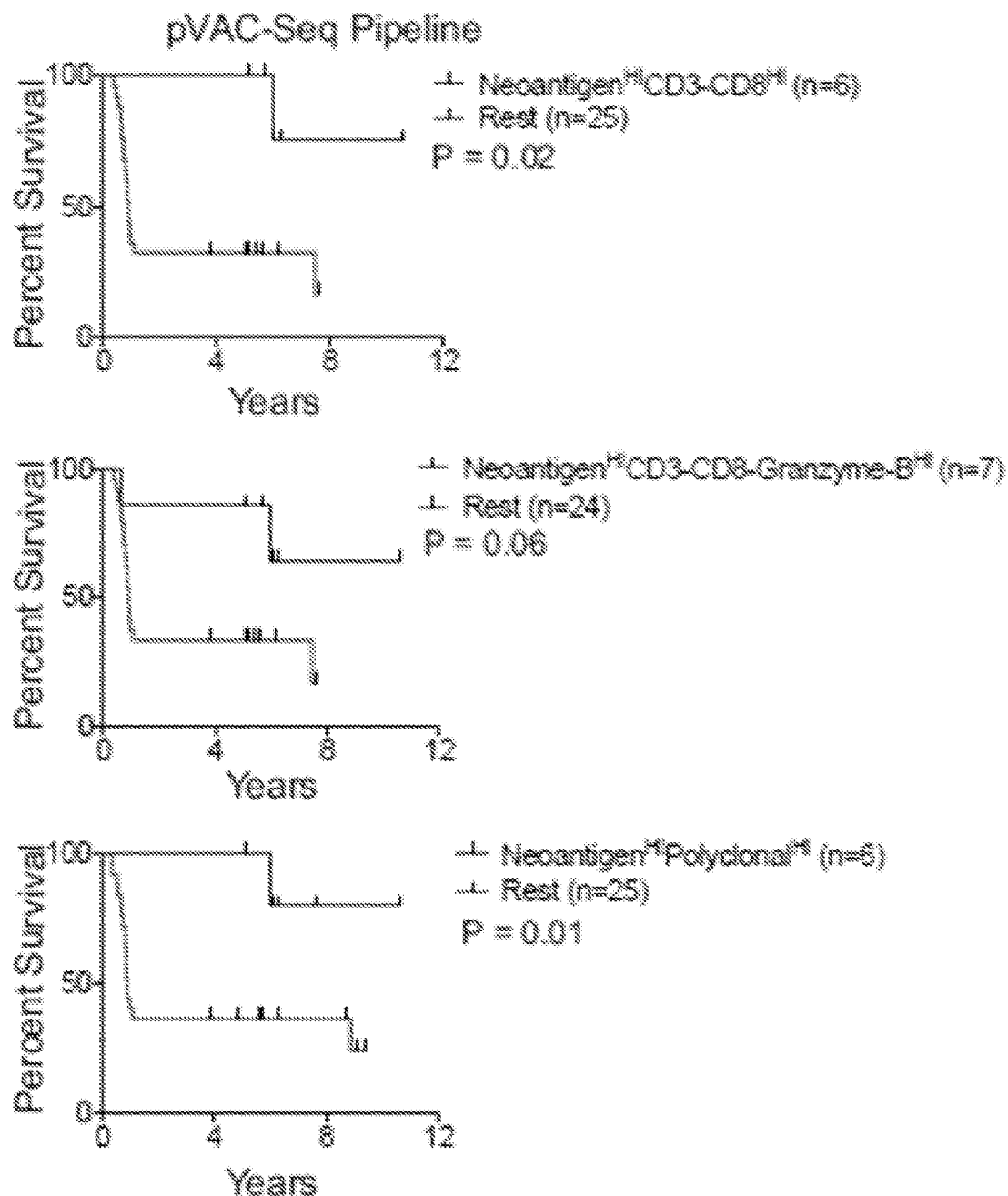
Fig. 48B2

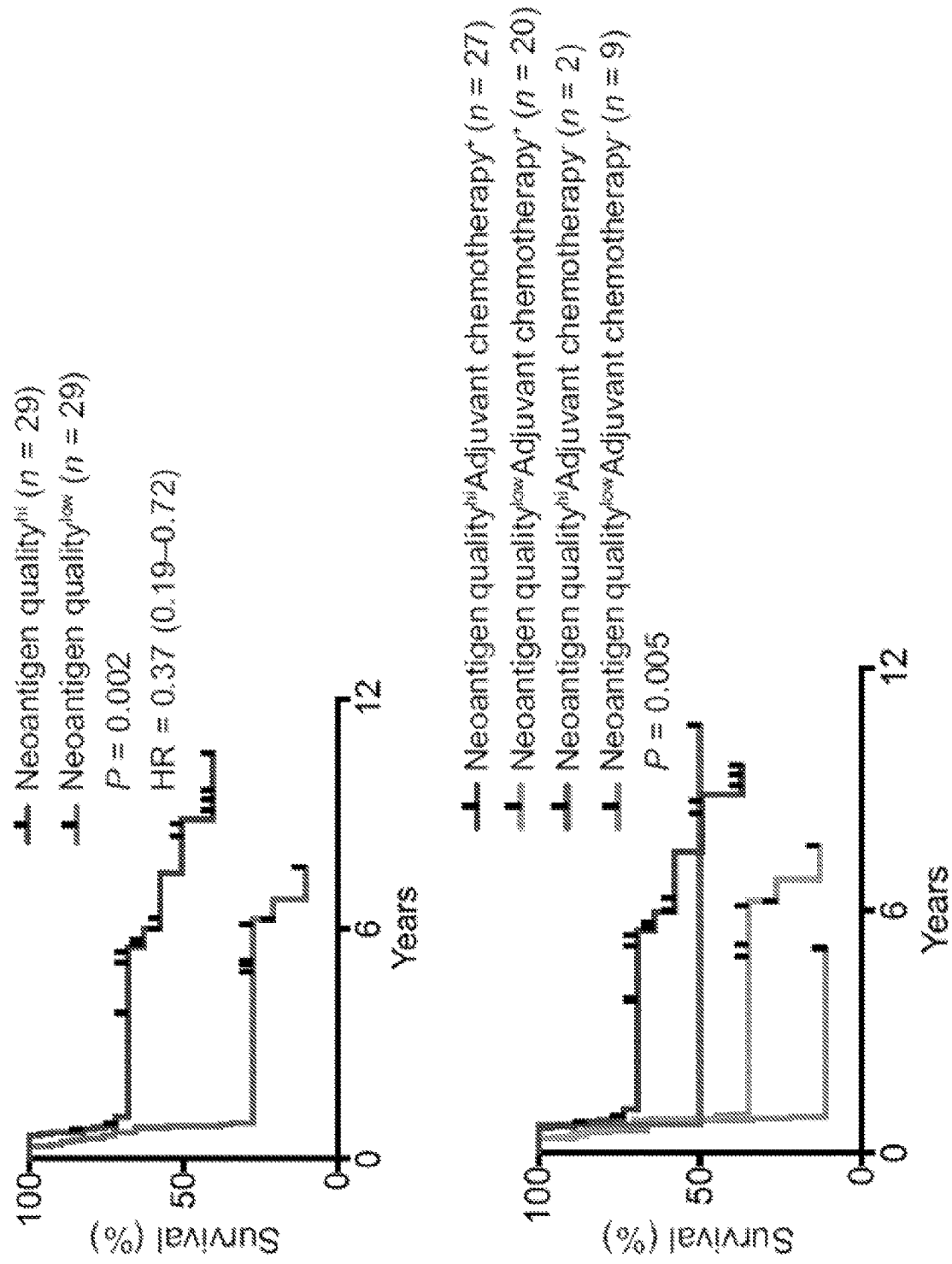
Fig. 54E1

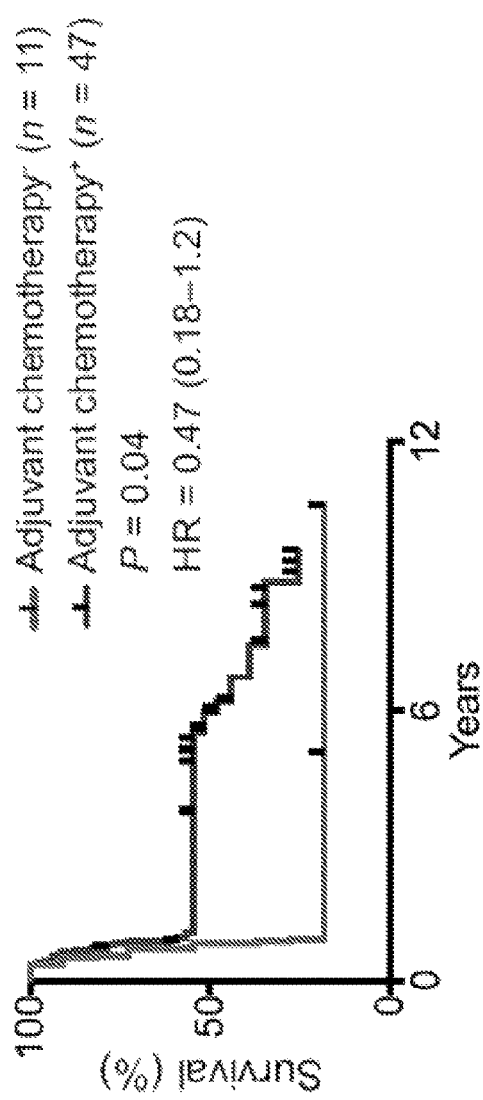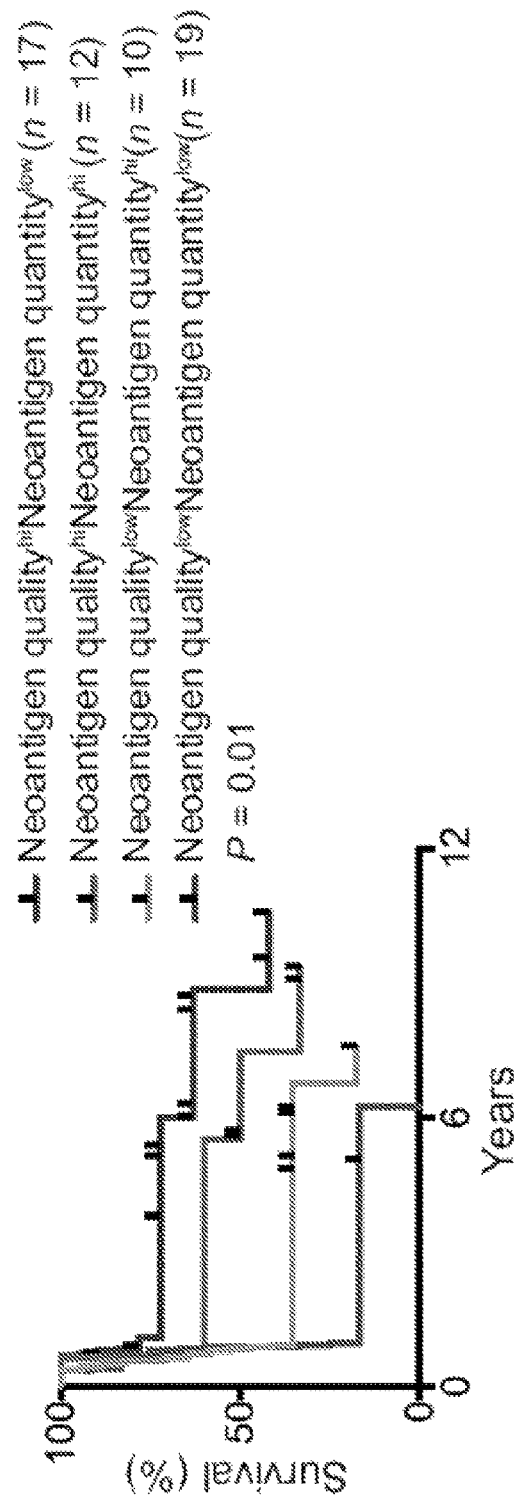
Fig. 54E2

| Variable | Univariate | | | Multivariate | | |
|---|---|---|---|---|---|---|
| | Hazard Ratio | 95% CI | P-Value | Hazard Ratio | 95% CI | P-Value |
| Adjuvant chemotherapy | 0.4 | 0.1–0.9 | 0.02 | 0.5 | 0.2–1.2 | 0.1 |
| Pathologic stage | 1.4 | 0.5–4.1 | 0.4 | - | - | - |
| Margin | 1.5 | 0.7–3.4 | 0.2 | - | - | - |
| Neoantigen quality | 0.3 | 0.1–0.7 | 0.003 | 0.3 | 0.1–0.7 | 0.008 |

Fig. 54E3

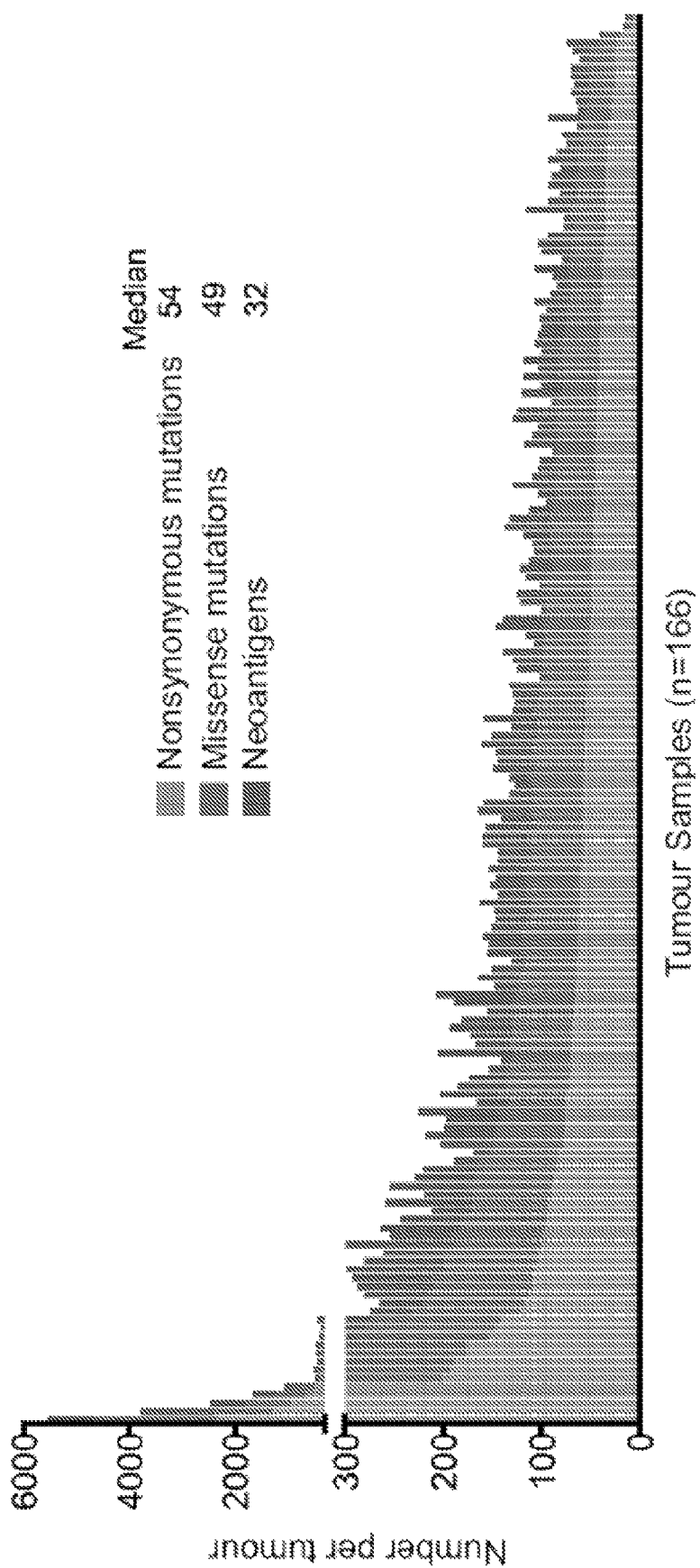
Fig. 54G1

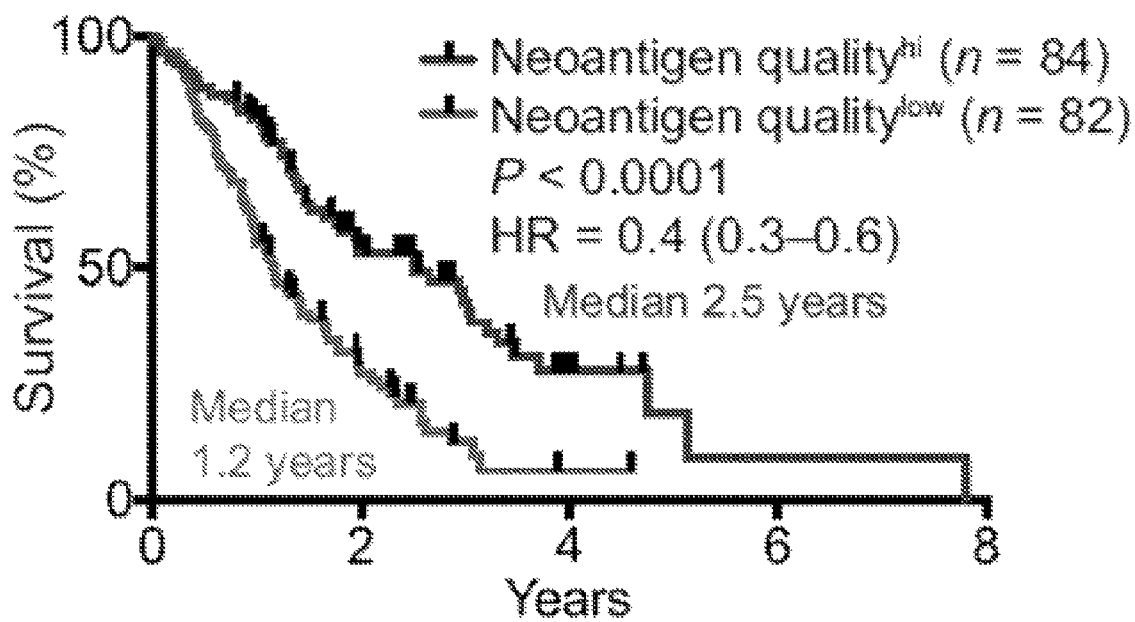
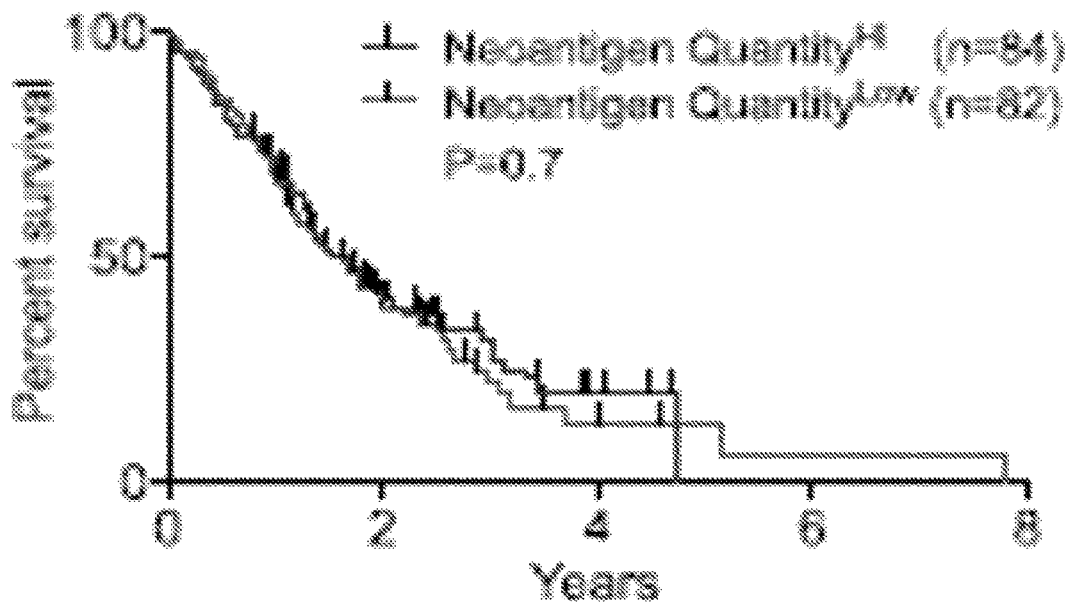
Fig. 54G2

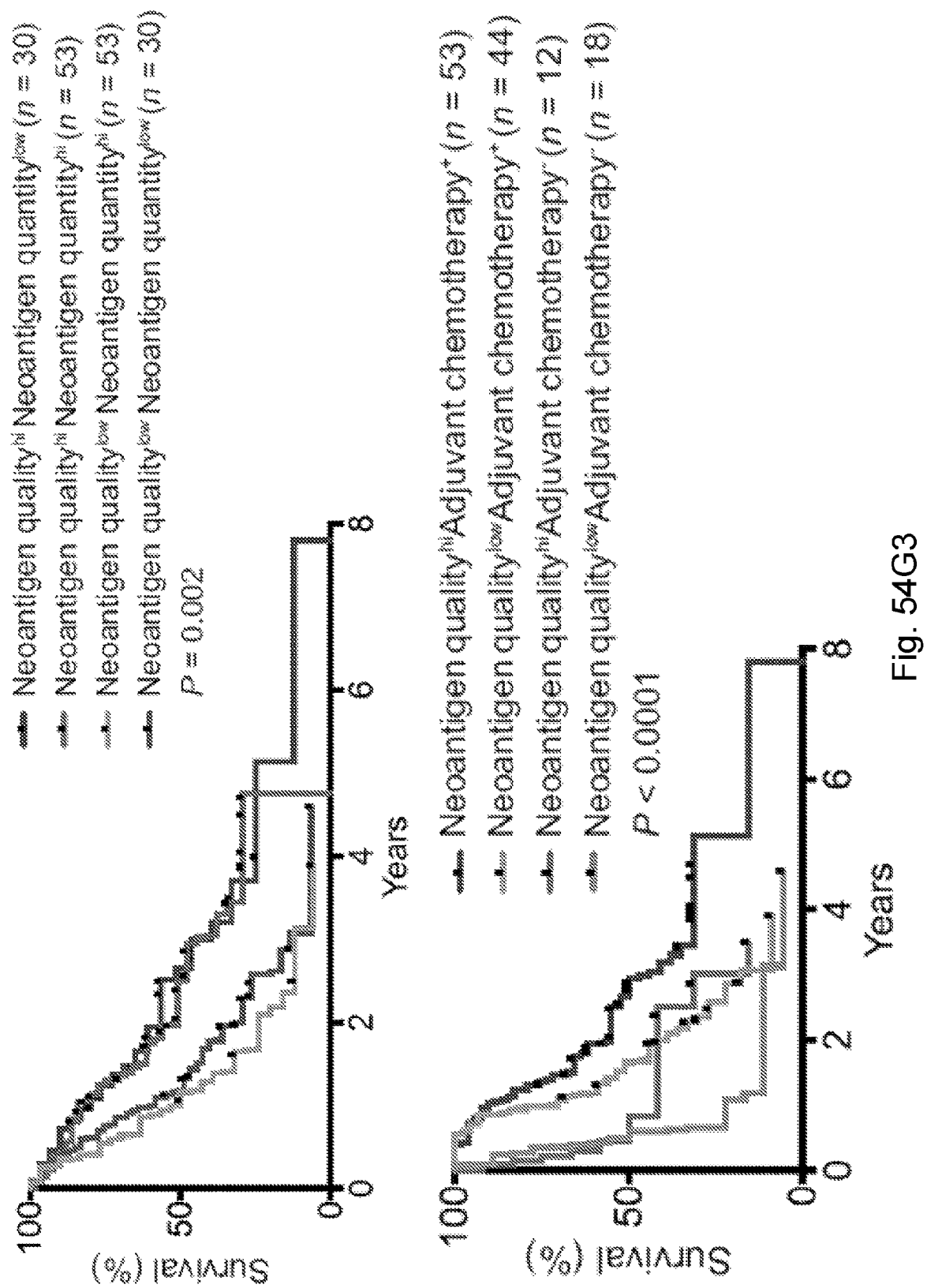
Fig. 54G3

| Variable | Univariate | | | Multivariate | | |
|---|---|---|---|---|---|---|
| | Hazard Ratio | 95% CI | P-Value | Hazard Ratio | 95% CI | P-Value |
| Adjuvant chemotherapy | 0.4 | 0.2–0.5 | 0.0001 | 0.4 | 0.2–0.7 | 0.001 |
| Pathologic stage | | | | | | |
| -Stage I | - | - | - | - | - | - |
| -Stage II | 2.5 | 0.9–7 | 0.07 | 3.7 | 0.9–15.9 | 0.07 |
| Stage III/IV | 6.8 | 1.9–24.8 | 0.004 | 12.7 | 1.1–146 | 0.04 |
| Margin | | | | | | |
| -R0 | - | - | - | - | - | - |
| -R1 | 2.3 | 1.4–3.7 | 0.0001 | 2.7 | 1.6–4.5 | 0.001 |
| -R2 | 3.6 | 1.6–8 | 0.001 | 0.9 | 0.09–9.5 | 0.9 |
| Neoantigen Quality | 0.4 | 0.3–0.64 | 0.0001 | 0.5 | 0.3–0.9 | 0.01 |

Fig. 54G4

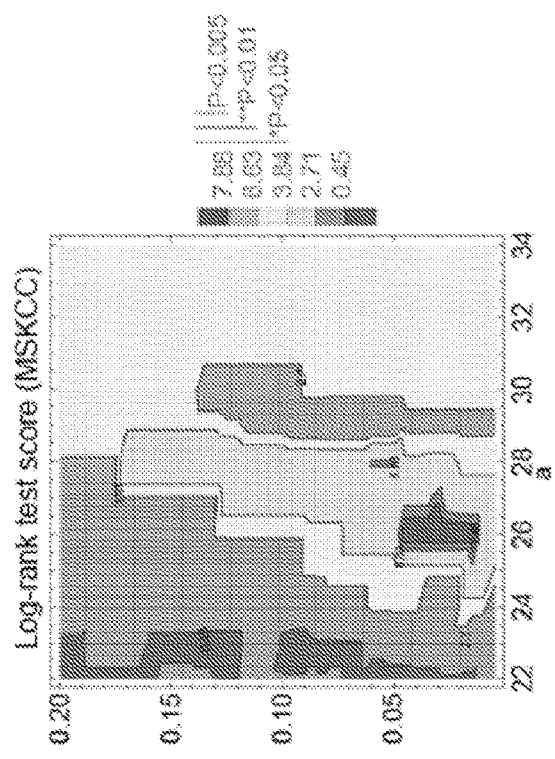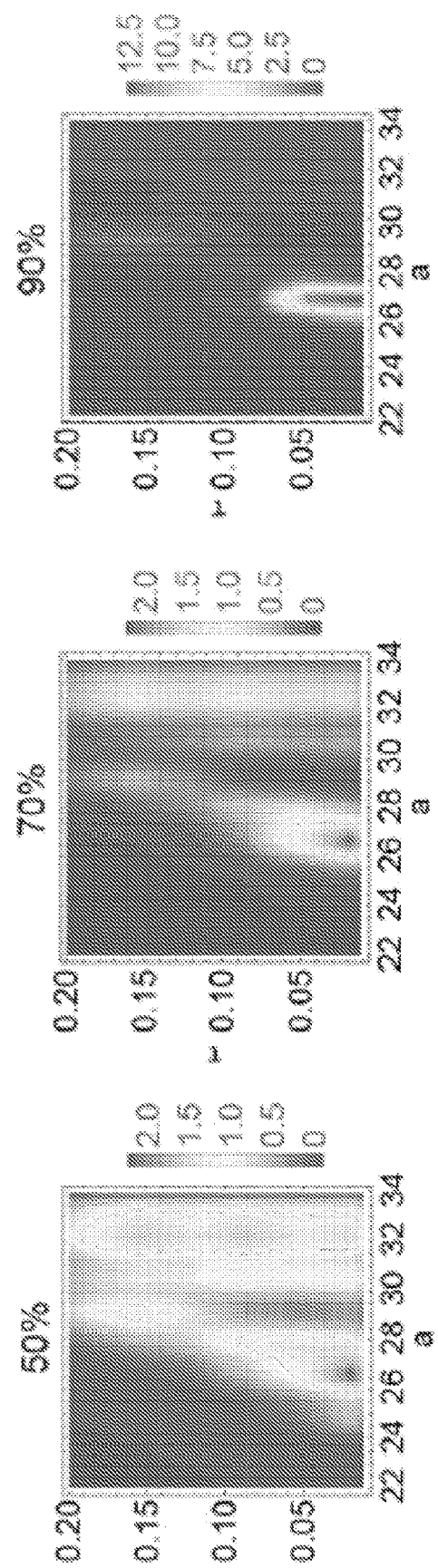
Fig. 54H1

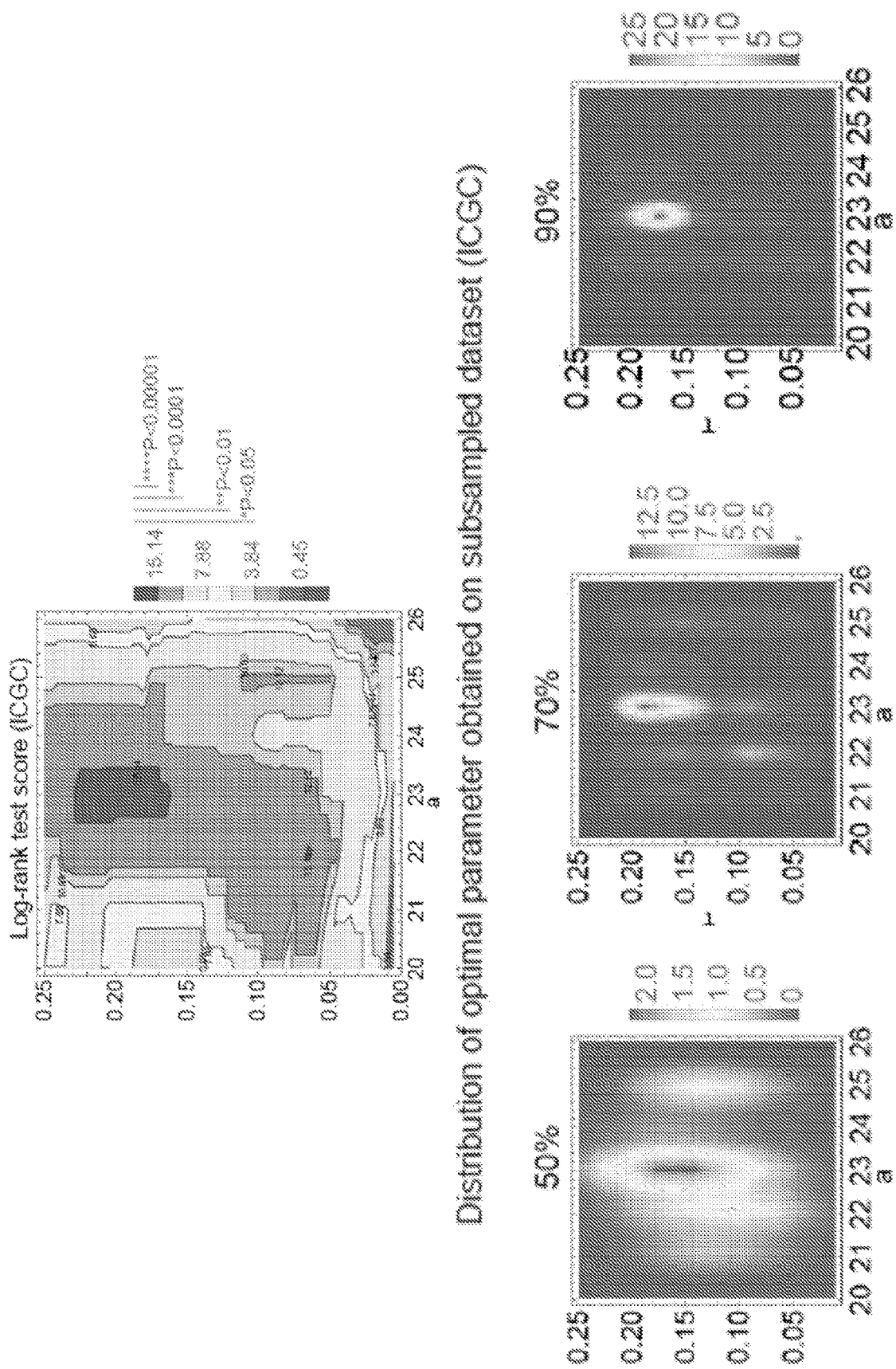
Fig. 54H2

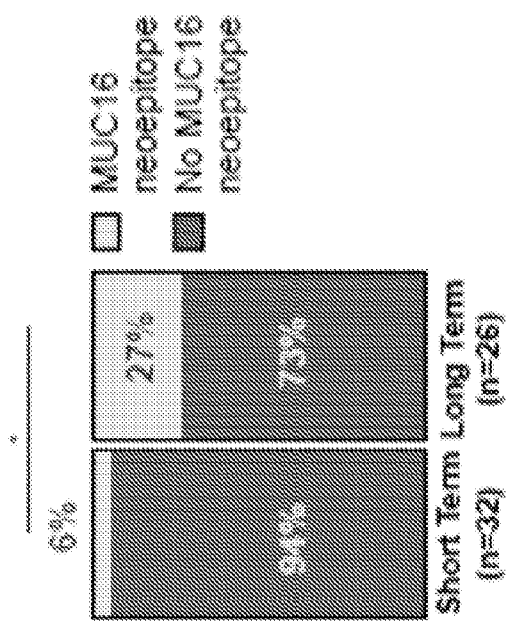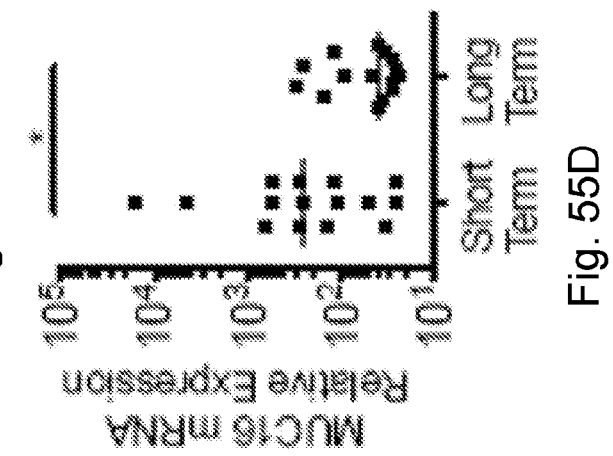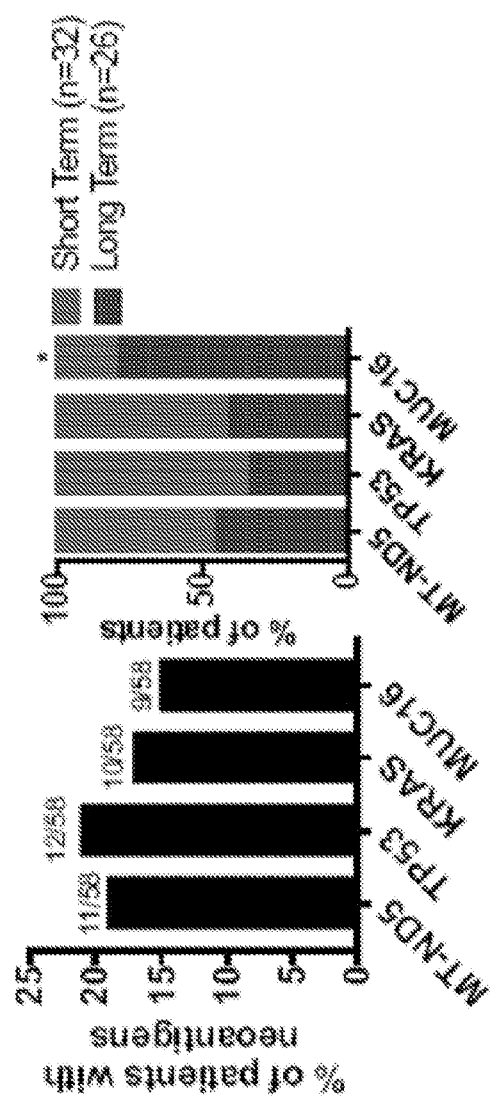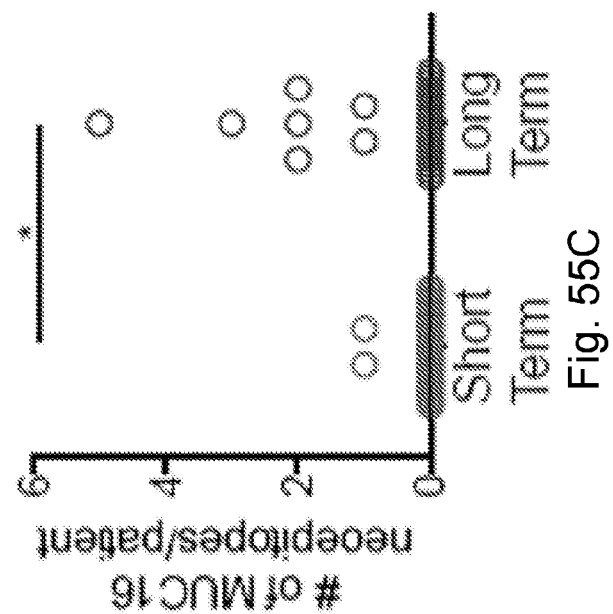
Fig. 55A
Fig. 55B
Fig. 55C
Fig. 55D

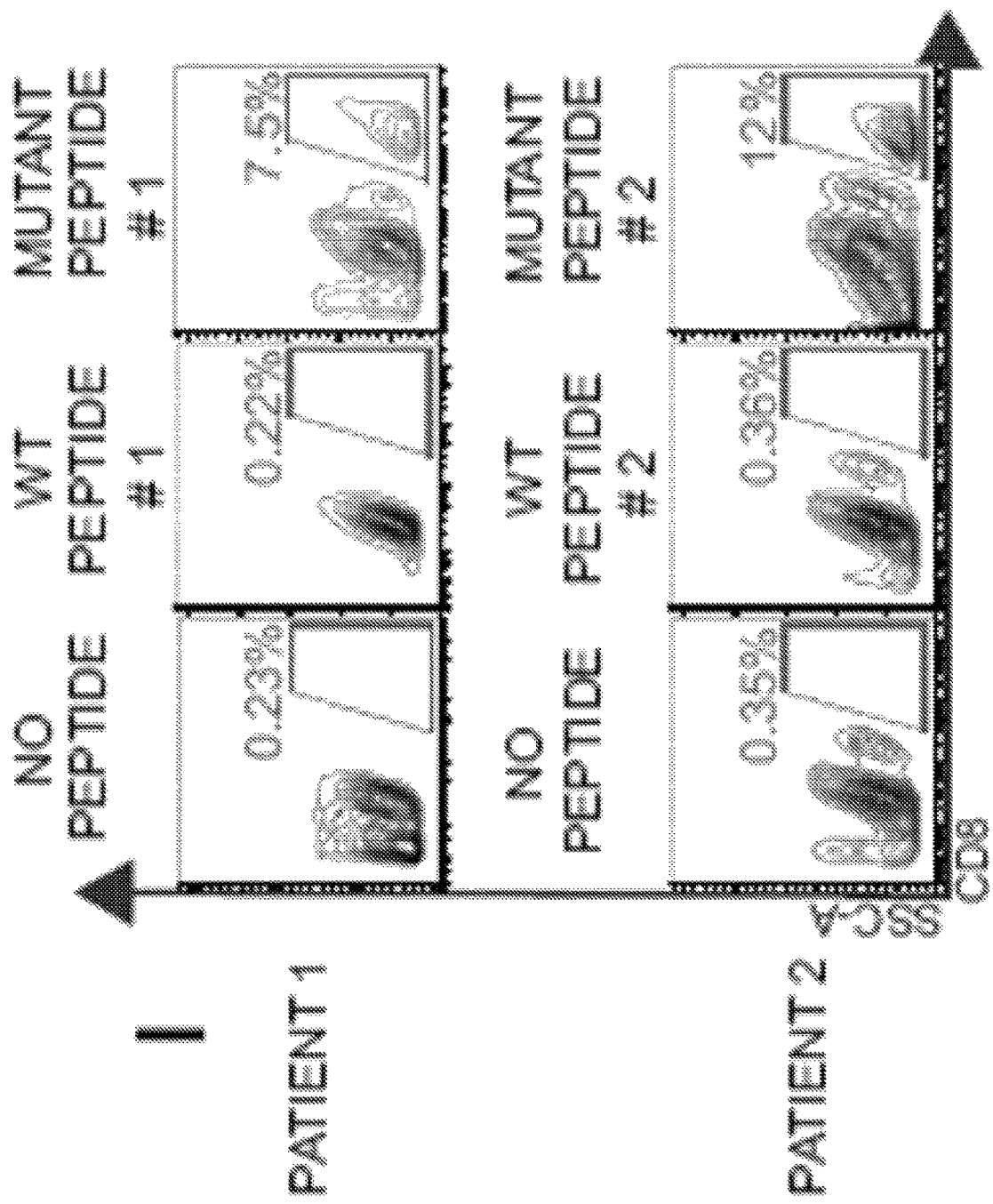
Fig. 55I1

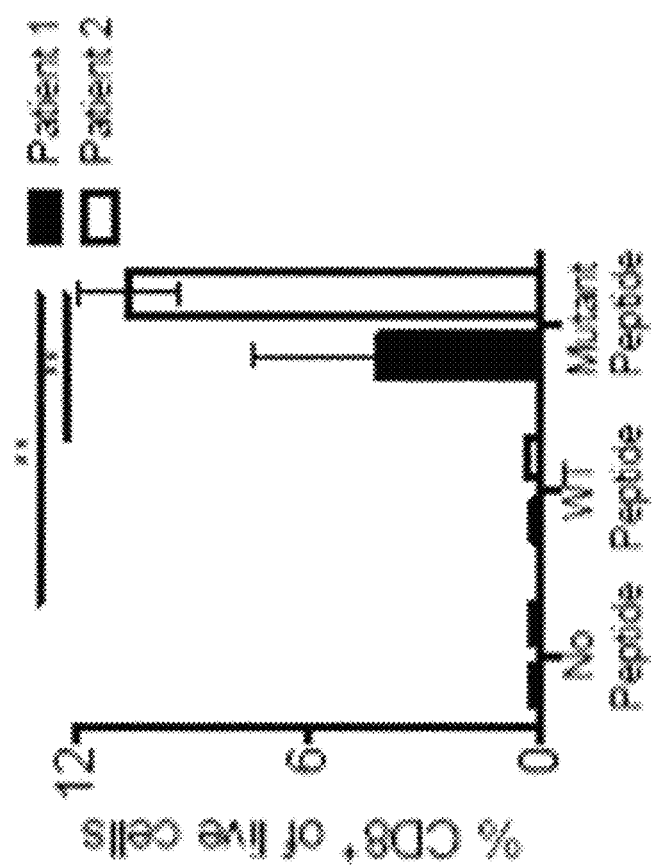
Fig. 55I2

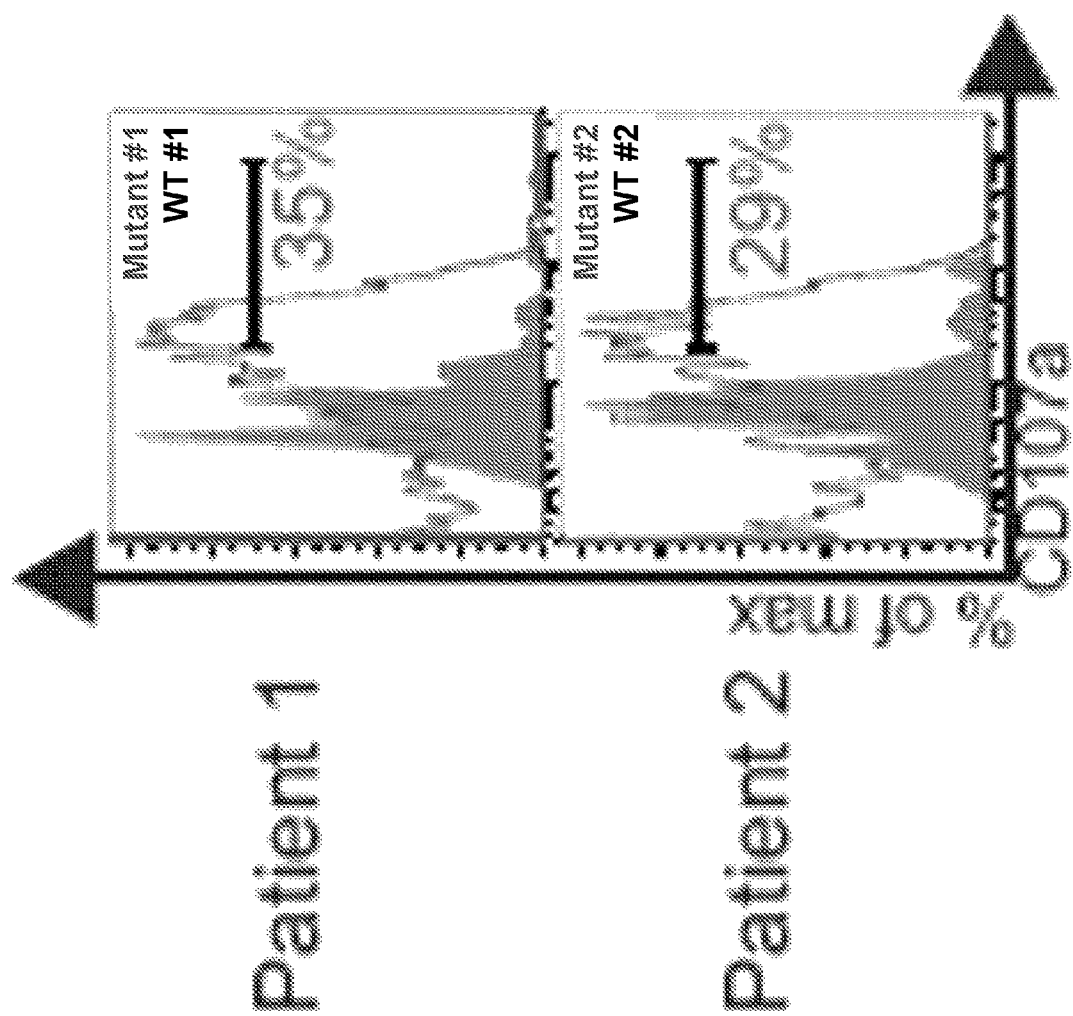
Fig. 55J1

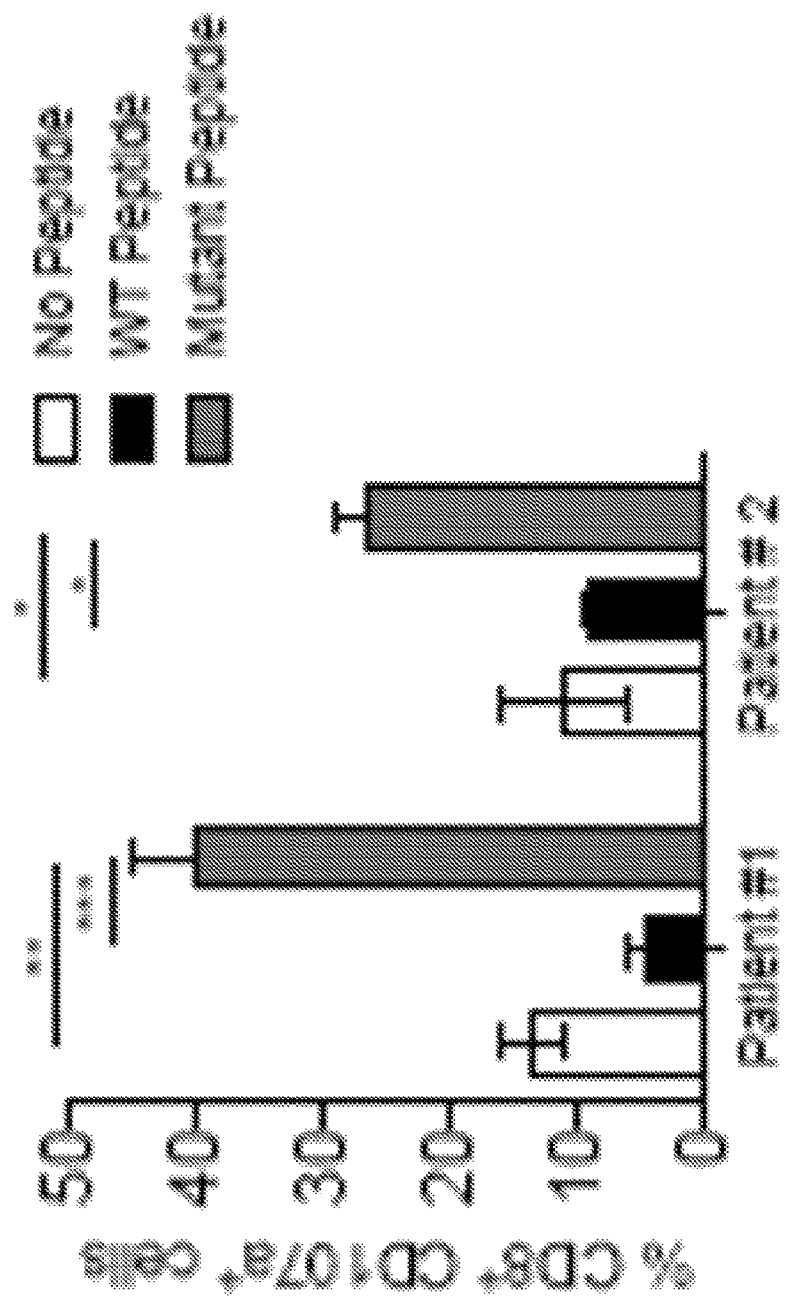
Fig. 55J2

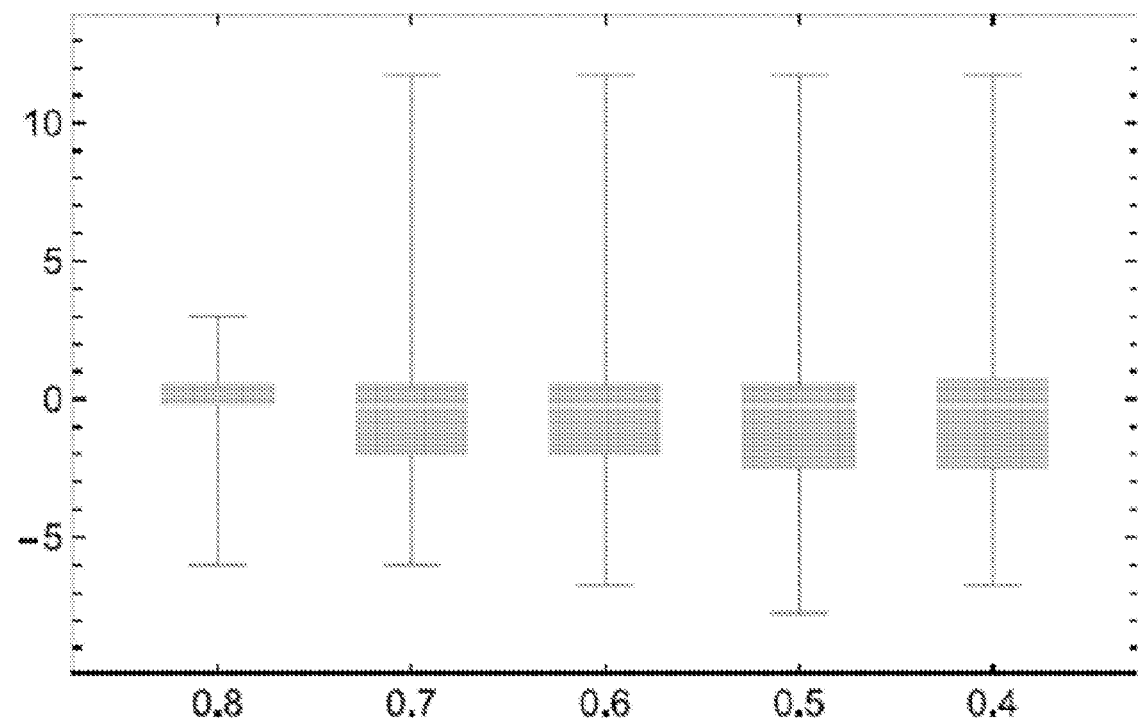
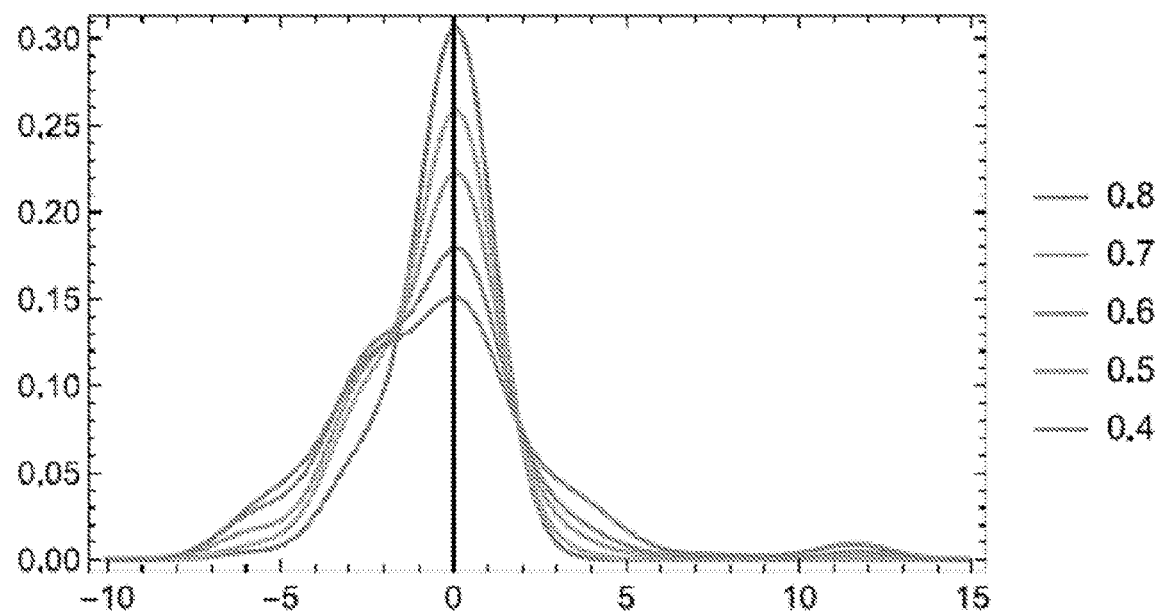
Fig. 56

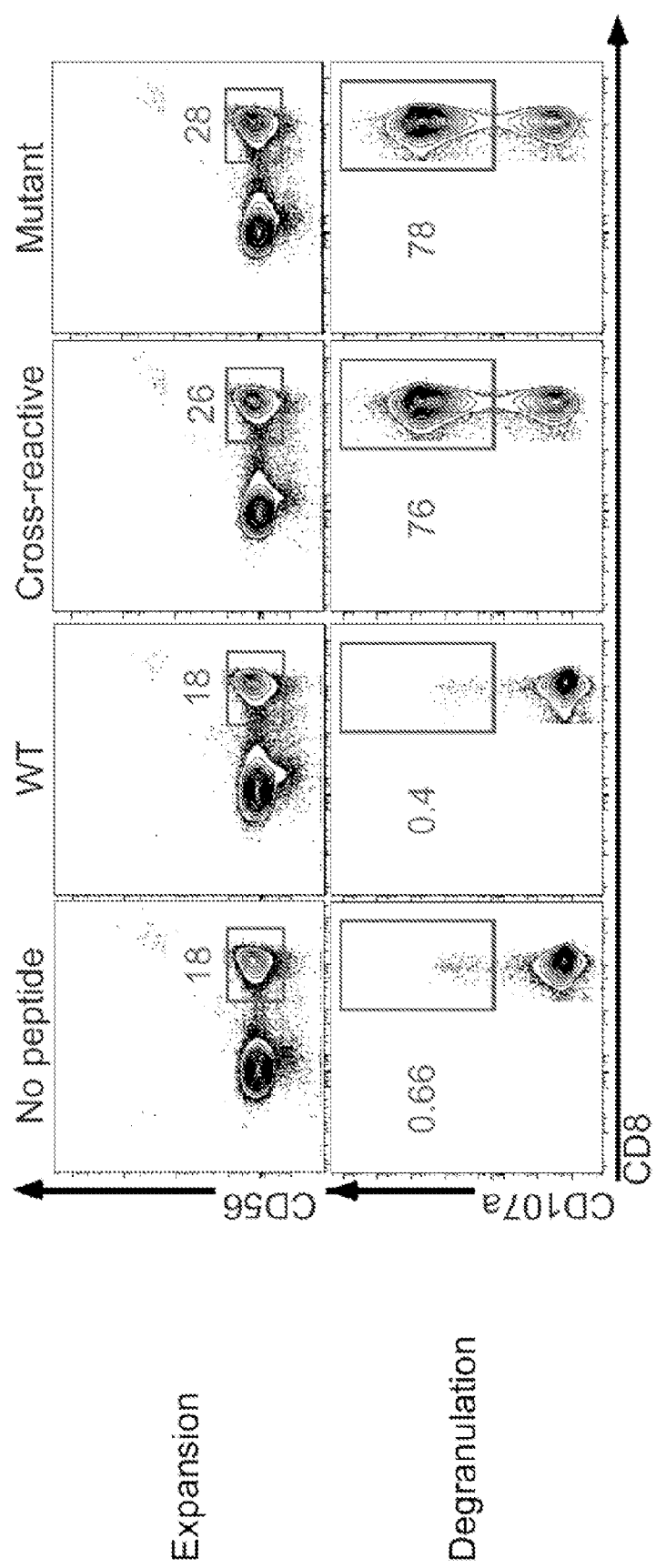
Fig. 69C1

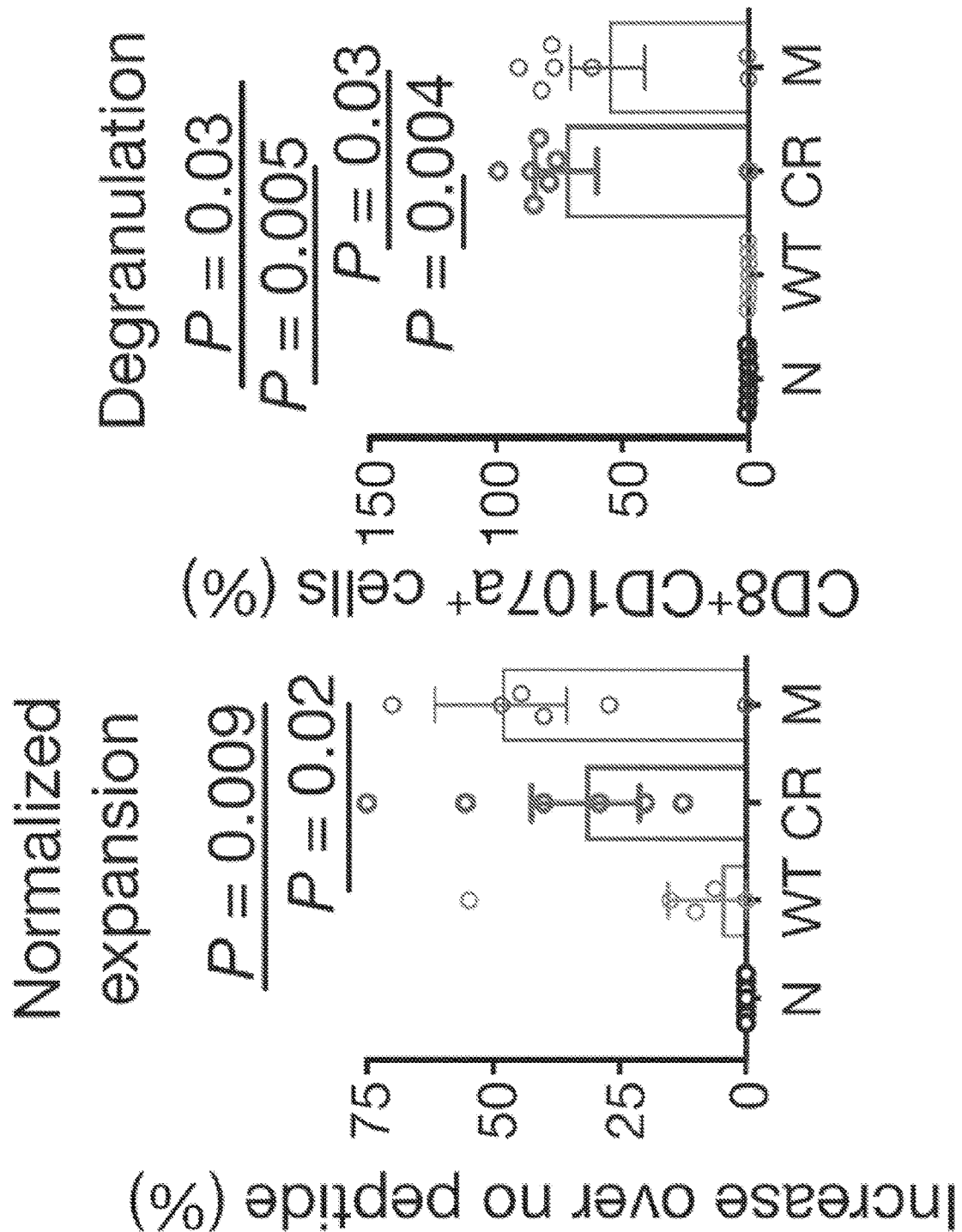
Fig. 69C2

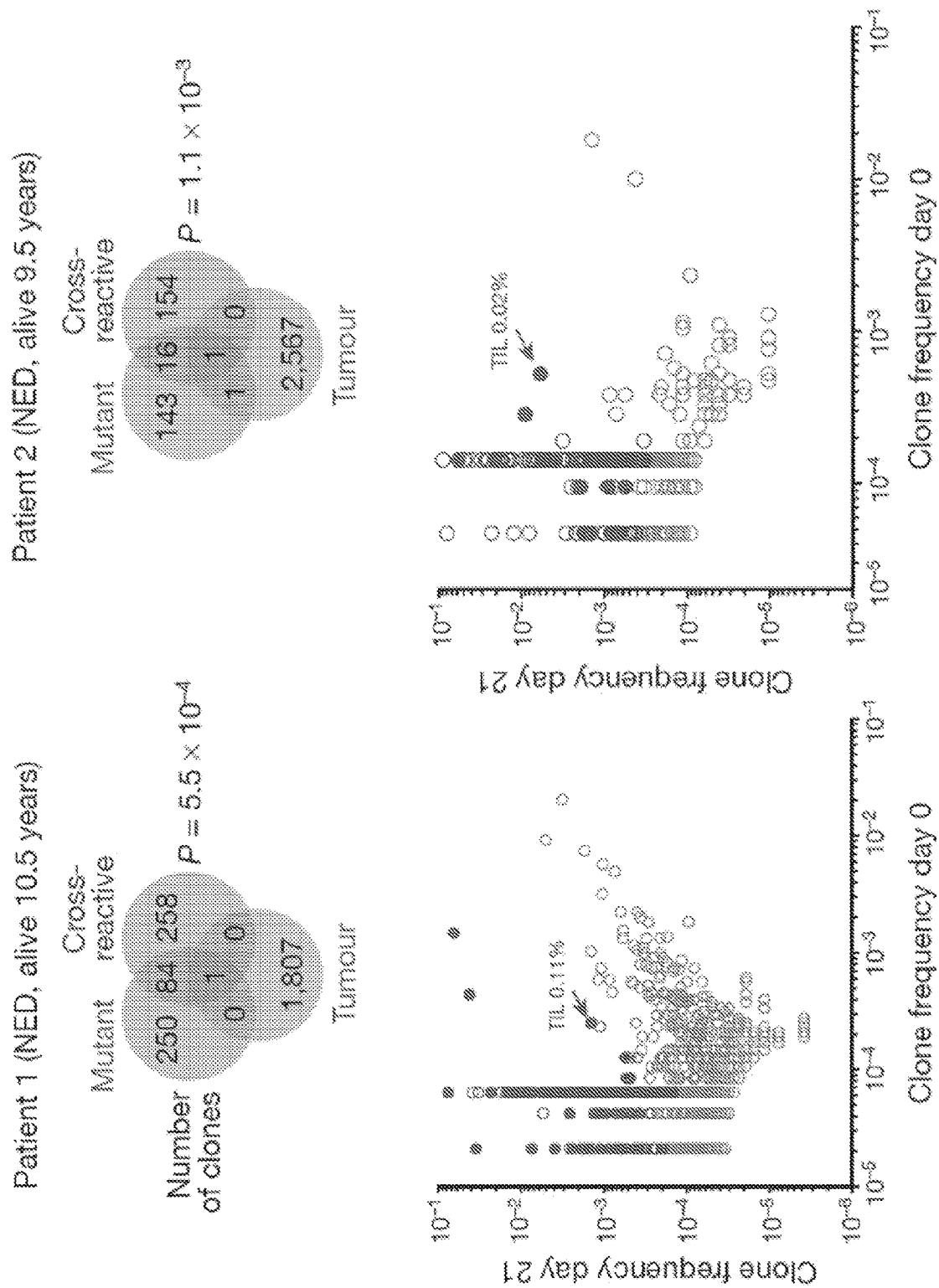
Fig. 69D1

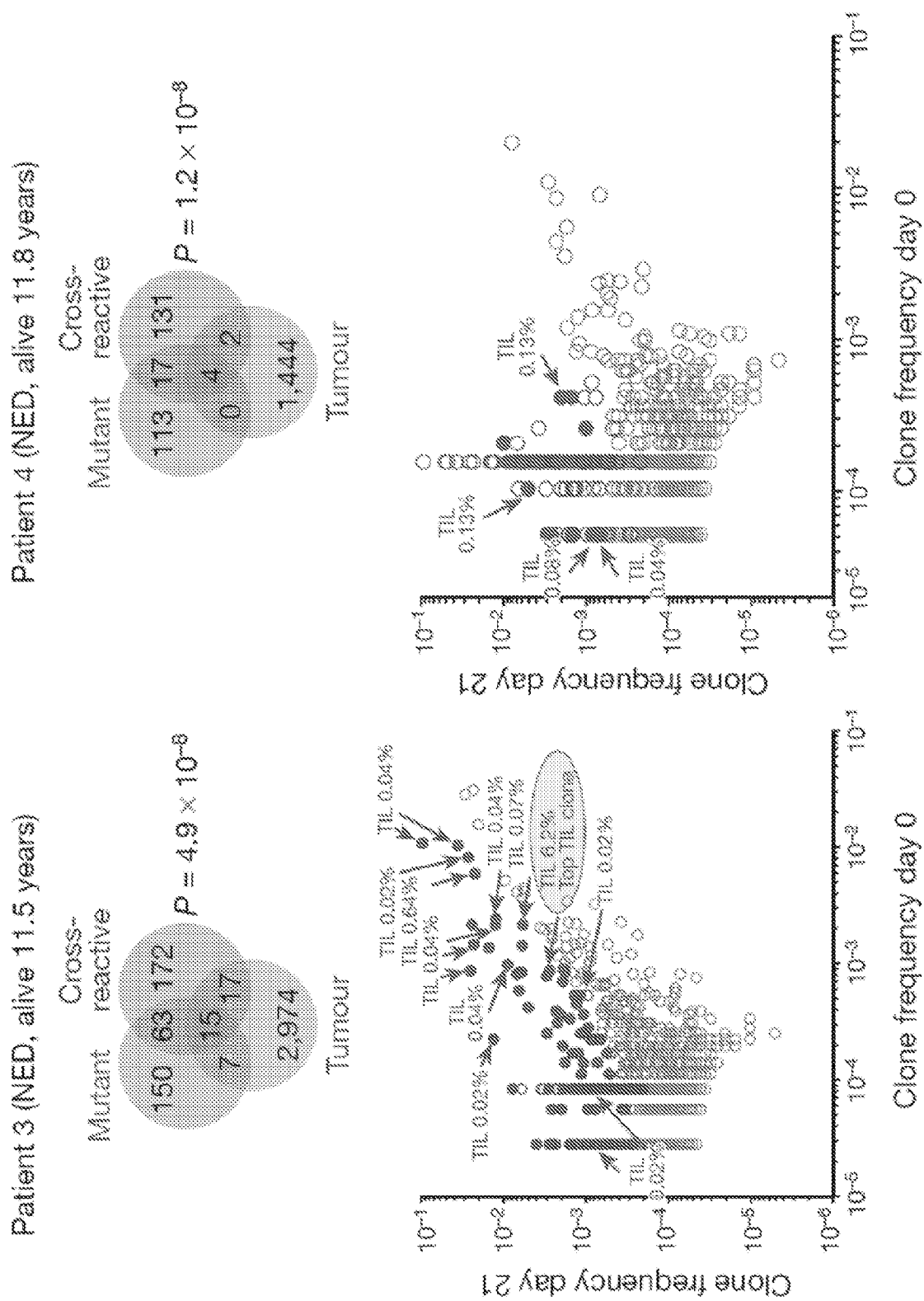
Fig. 69D2

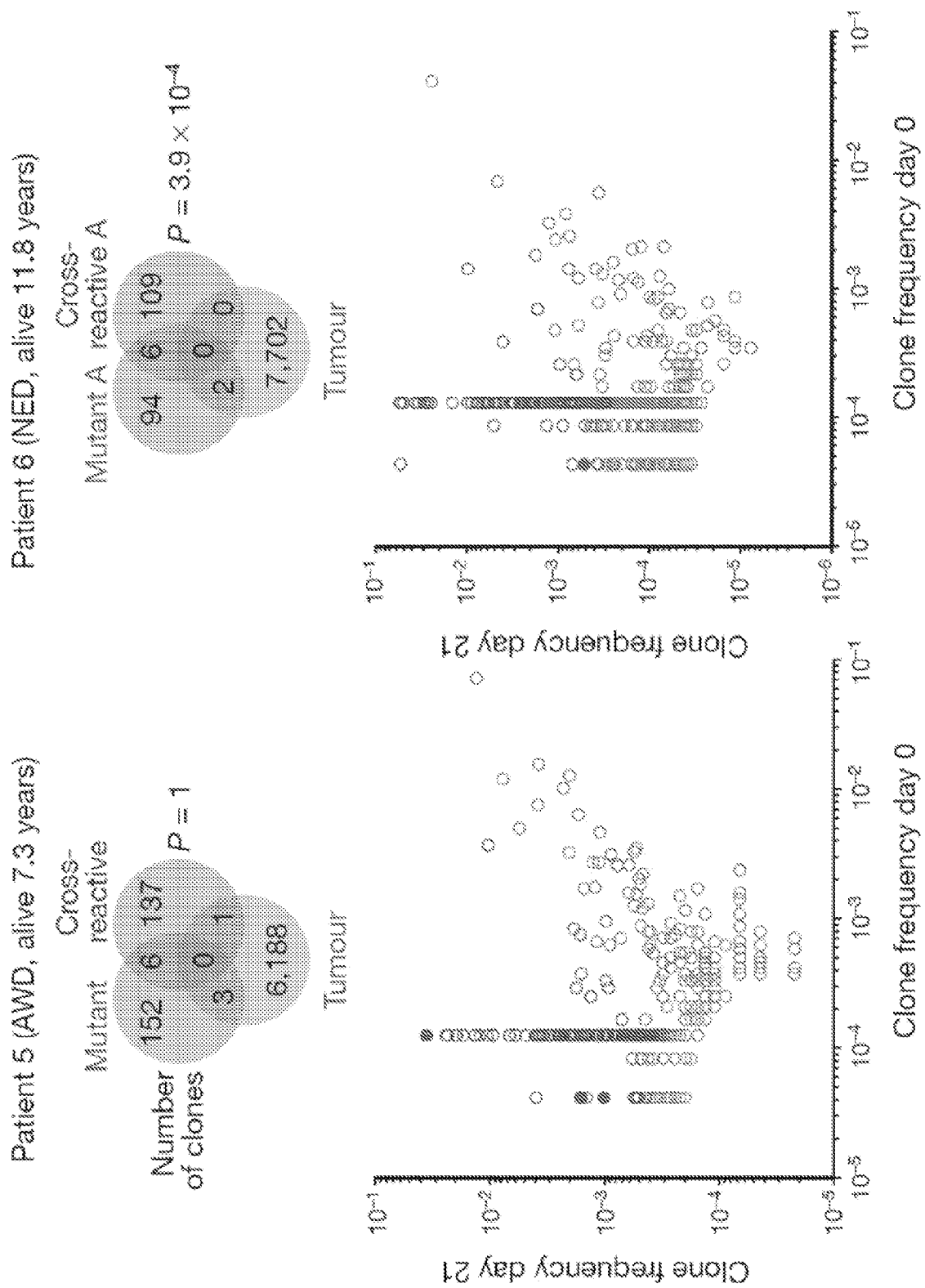
Fig. 69D3

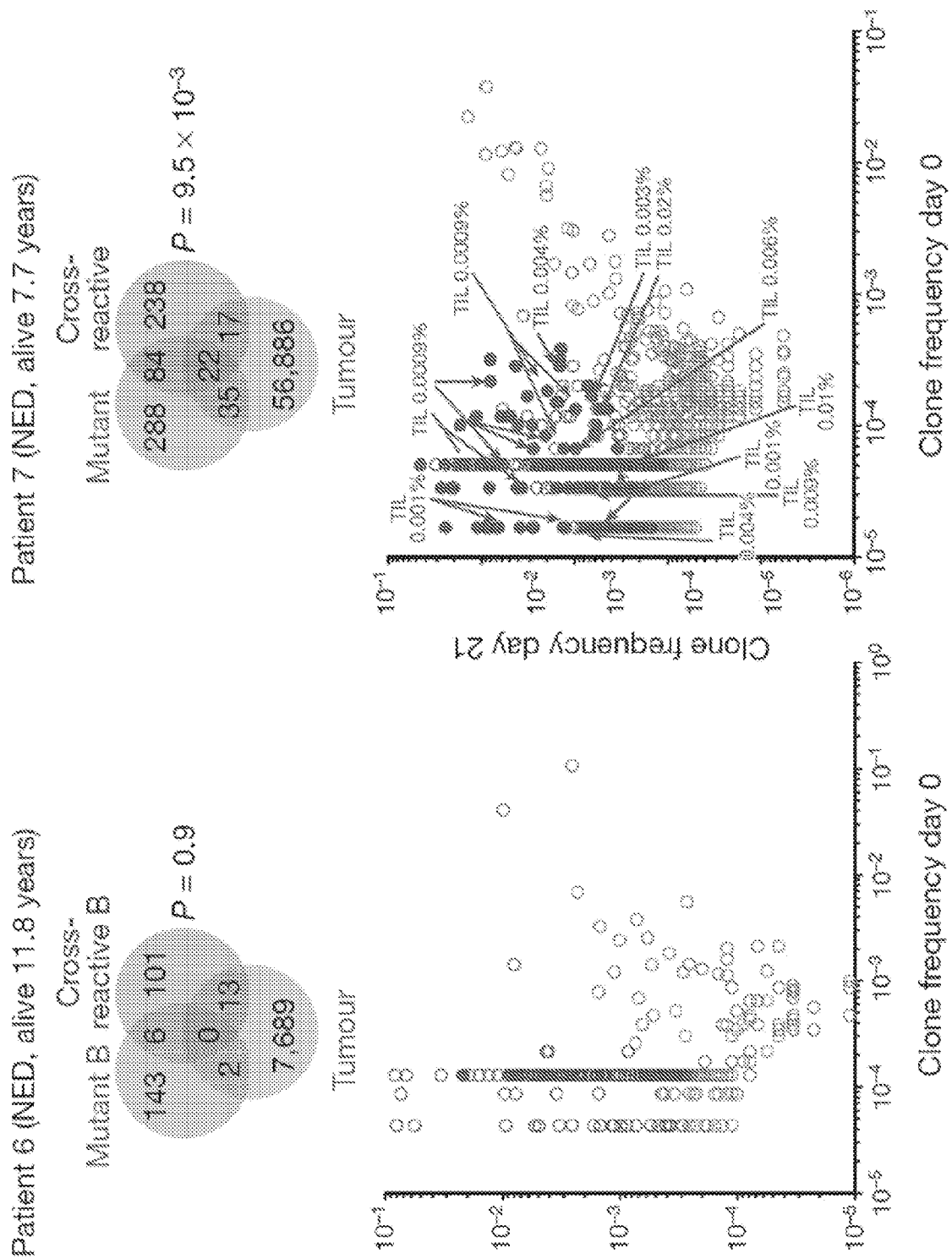
Fig. 69D4

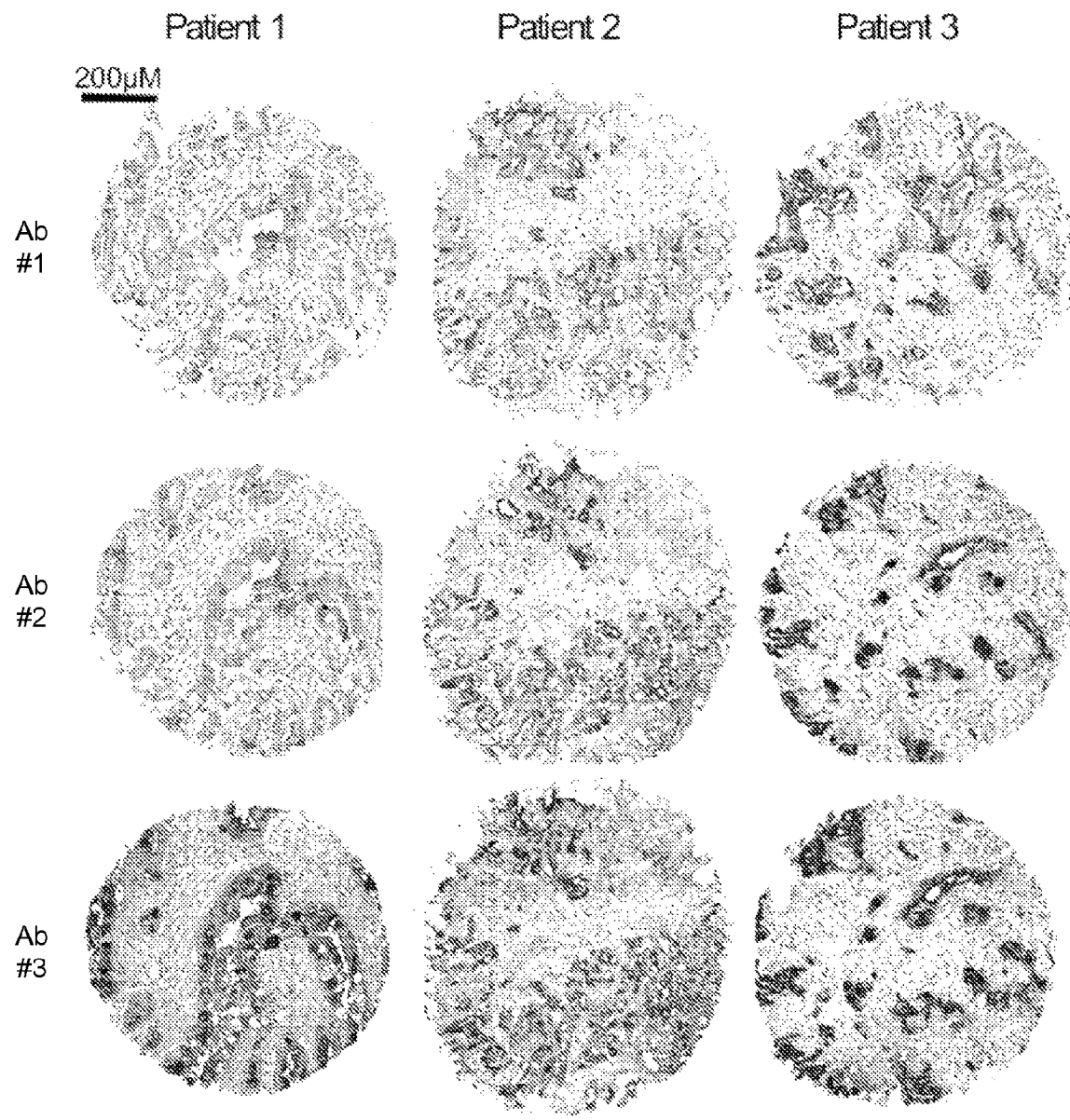
Fig. 70A1

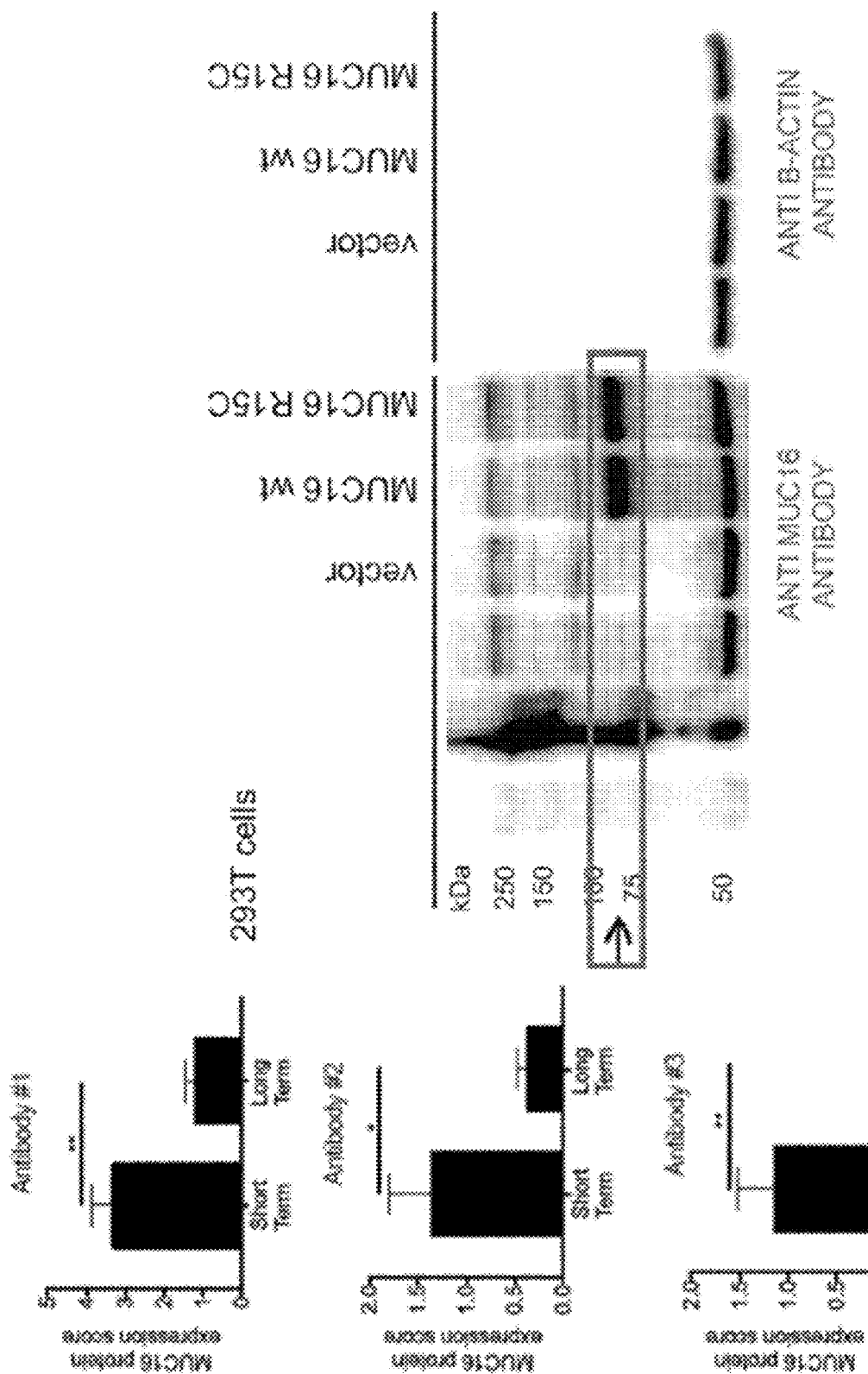
Fig. 70B1
Fig. 70A2

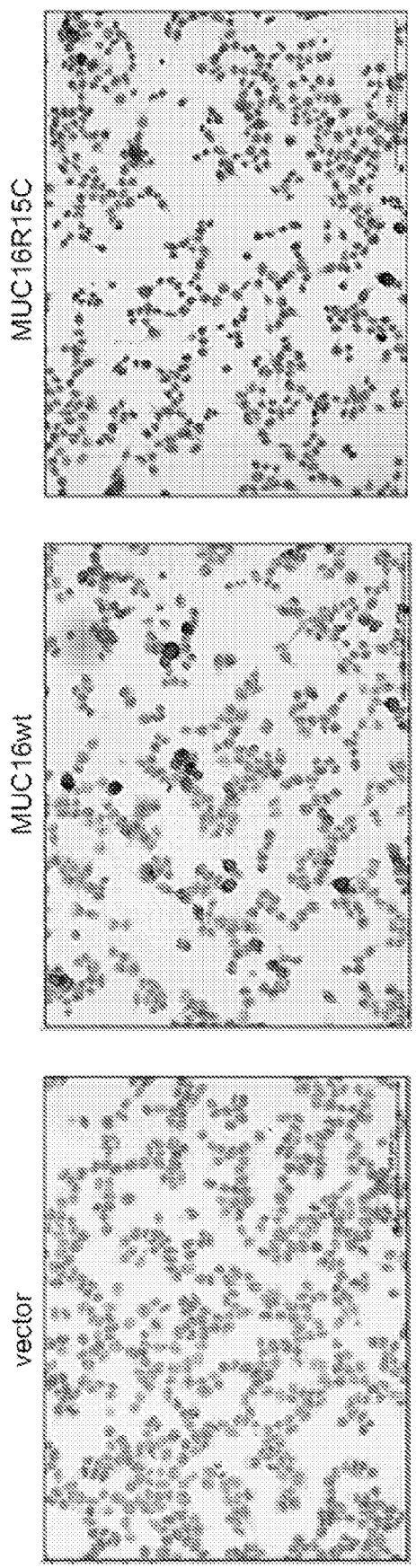
Fig. 70B2

SEQUENCE LISTING

```
<160> NUMBER OF SEQ ID NOS: 152

<210> SEQ ID NO 1
<211> LENGTH: 9
<212> TYPE: PRT
<213> ORGANISM: Artificial Sequence
<220> FEATURE:
<223> OTHER INFORMATION: Neoantigenic peptide

<400> SEQUENCE: 1

Val Met Lys His Leu Leu Ser Pro Leu
1               5

<210> SEQ ID NO 2
<211> LENGTH: 9
<212> TYPE: PRT
<213> ORGANISM: Artificial Sequence
<220> FEATURE:
<223> OTHER INFORMATION: Neoantigenic peptide

<400> SEQUENCE: 2

Met His His Pro Gly Ser Arg Lys Phe
1               5

<210> SEQ ID NO 3
<211> LENGTH: 9
<212> TYPE: PRT
<213> ORGANISM: Artificial Sequence
<220> FEATURE:
<223> OTHER INFORMATION: Neoantigen peptide

<400> SEQUENCE: 3

Asn Ser Thr Leu Ile Pro Thr Leu Ile
1               5

<210> SEQ ID NO 4
<211> LENGTH: 9
<212> TYPE: PRT
<213> ORGANISM: Artificial Sequence
<220> FEATURE:
<223> OTHER INFORMATION: Neoantigenic peptide

<400> SEQUENCE: 4

Ser Ser Ser Gly Val Asn Ser Thr Ile
1               5

<210> SEQ ID NO 5
<211> LENGTH: 9
<212> TYPE: PRT
<213> ORGANISM: Artificial Sequence
<220> FEATURE:
<223> OTHER INFORMATION: Neoantigenic peptide

<400> SEQUENCE: 5
```

```
Ser Thr Leu Ile Pro Thr Leu Ile Leu
1               5

<210> SEQ ID NO 6
<211> LENGTH: 9
<212> TYPE: PRT
<213> ORGANISM: Artificial Sequence
<220> FEATURE:
<223> OTHER INFORMATION: Neoantigenic peptide

<400> SEQUENCE: 6

Ala Glu Ala Ser Ser Ala Val Pro Thr
1               5

<210> SEQ ID NO 7
<211> LENGTH: 9
<212> TYPE: PRT
<213> ORGANISM: Artificial Sequence
<220> FEATURE:
<223> OTHER INFORMATION: Neoantigenic peptide

<400> SEQUENCE: 7

Glu Ala Ser Ser Ala Val Pro Thr Val
1               5

<210> SEQ ID NO 8
<211> LENGTH: 9
<212> TYPE: PRT
<213> ORGANISM: Artificial Sequence
<220> FEATURE:
<223> OTHER INFORMATION: Neoantigenic peptide

<400> SEQUENCE: 8

Ser Arg Ala Val Thr Ser Thr Thr Ile
1               5

<210> SEQ ID NO 9
<211> LENGTH: 9
<212> TYPE: PRT
<213> ORGANISM: Artificial Sequence
<220> FEATURE:
<223> OTHER INFORMATION: Neoantigenic peptide

<400> SEQUENCE: 9

Ser Thr Thr Ile Pro Ile Leu Thr Leu
1               5

<210> SEQ ID NO 10
<211> LENGTH: 9
<212> TYPE: PRT
<213> ORGANISM: Artificial Sequence
<220> FEATURE:
<223> OTHER INFORMATION: Neoantigenic peptide

<400> SEQUENCE: 10

Thr Ile Pro Ile Leu Thr Leu Ser Leu
1               5

<210> SEQ ID NO 11
<211> LENGTH: 9
<212> TYPE: PRT
<213> ORGANISM: Artificial Sequence
<220> FEATURE:
<223> OTHER INFORMATION: Neoantigenic peptide

<400> SEQUENCE: 11
```

```
Gly Leu Arg Lys Thr Asn Met Ser Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Neoantigenic peptide

<400> SEQUENCE: 12

Ser Met Pro Ala Asn Phe Glu Thr Ile
1               5

<210> SEQ ID NO 13
<211> LENGTH: 9
<212> TYPE: PRT
<213> ORGANISM: Artificial Sequence
<220> FEATURE:
<223> OTHER INFORMATION: Neoantigenic peptide

<400> SEQUENCE: 13

Ser Thr Val Arg Lys Ser Pro Trp Lys
1               5

<210> SEQ ID NO 14
<211> LENGTH: 9
<212> TYPE: PRT
<213> ORGANISM: Artificial Sequence
<220> FEATURE:
<223> OTHER INFORMATION: Neoantigenic peptide

<400> SEQUENCE: 14

Ser Thr Val Arg Lys Ser Pro Trp Lys
1               5

<210> SEQ ID NO 15
<211> LENGTH: 9
<212> TYPE: PRT
<213> ORGANISM: Artificial Sequence
<220> FEATURE:
<223> OTHER INFORMATION: Neoantigen peptide

<400> SEQUENCE: 15

Met Gly Lys Ser Thr His Thr Ser Met
1               5

<210> SEQ ID NO 16
<211> LENGTH: 9
<212> TYPE: PRT
<213> ORGANISM: Artificial Sequence
<220> FEATURE:
<223> OTHER INFORMATION: Neoantigen peptide

<400> SEQUENCE: 16

Ser Met Lys Ala Glu Arg Pro Pro Ala
1               5

<210> SEQ ID NO 17
<211> LENGTH: 9
<212> TYPE: PRT
<213> ORGANISM: Artificial Sequence
<220> FEATURE:
<223> OTHER INFORMATION: Neoantigen peptide

<400> SEQUENCE: 17

Thr Thr Ser Pro Ser Asn Thr Leu Val
```

```
<210> SEQ ID NO 18
<211> LENGTH: 9
<212> TYPE: PRT
<213> ORGANISM: Artificial Sequence
<220> FEATURE:
<223> OTHER INFORMATION: Neoantigen peptide

<400> SEQUENCE: 18

Ser Ser Ser Pro Thr Cys Ser Leu Met
1               5

<210> SEQ ID NO 19
<211> LENGTH: 9
<212> TYPE: PRT
<213> ORGANISM: Artificial Sequence
<220> FEATURE:
<223> OTHER INFORMATION: Neoantigenic peptide

<400> SEQUENCE: 19

Ala Pro Leu Gly Ala Pro Pro Pro Leu
1               5

<210> SEQ ID NO 20
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 20

Ala Ser Leu His His His His His Arg
1               5

<210> SEQ ID NO 21
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 21

Ala Thr Tyr His Phe His Phe Asn Leu
1               5

<210> SEQ ID NO 22
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 22

Asp Trp Pro Val Phe Pro Gly Leu Phe
1               5

<210> SEQ ID NO 23
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 23

Glu Ala Phe Thr Leu Lys Ala Thr Val
1               5
```

<210> SEQ ID NO 24
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 24

Glu Ala His His His Phe Pro Ser Leu
1               5

<210> SEQ ID NO 25
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 25

Phe Leu Asn Arg Trp Met Ala Asn Thr
1               5

<210> SEQ ID NO 26
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 26

Gly Ile Val Ser Trp Asp Thr Phe Leu
1               5

<210> SEQ ID NO 27
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 27

Gly Thr Pro Arg Ala Ala Thr Met Lys
1               5

<210> SEQ ID NO 28
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 28

His Trp Pro Glu Lys Glu Trp Pro Ile
1               5

<210> SEQ ID NO 29
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 29

Ile Leu Phe Asp Glu Ala Val Lys Leu
1               5

```
<210> SEQ ID NO 30
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 30

Ile Leu Ile Ala Cys Arg Leu Asn Lys
1               5

<210> SEQ ID NO 31
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 31

Ile Leu Pro Thr Cys Ser Pro Leu Val
1               5

<210> SEQ ID NO 32
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 32

Lys Pro Arg Phe Leu Val Gly Leu Trp
1               5

<210> SEQ ID NO 33
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 33

Lys Tyr Ile Ala Phe Cys Ile Asn Ile
1               5

<210> SEQ ID NO 34
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 34

Leu Phe His Gln Cys Leu Ser Ile Tyr
1               5

<210> SEQ ID NO 35
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 35

Leu Leu Leu Met Ser Thr Leu Gly Ile
1               5
```

```
<210> SEQ ID NO 36
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 36

Leu Leu Pro Pro Gln Asp Pro His Leu
1               5

<210> SEQ ID NO 37
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 37

Leu Gln Asp Phe Tyr Leu Gly Thr Tyr
1               5

<210> SEQ ID NO 38
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 38

Leu Thr Pro Pro Gln Ala Gln Glu Leu
1               5

<210> SEQ ID NO 39
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 39

Gln Thr Tyr Gln His Met Trp Asn Tyr
1               5

<210> SEQ ID NO 40
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 40

Arg Glu Phe Lys Phe Arg Val Ser Ala
1               5

<210> SEQ ID NO 41
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 41

Ser Thr Gly Phe Pro His Met Leu Phe
1               5

<210> SEQ ID NO 42
```

```
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 42

Thr Leu Val Gly His Gln Gly Pro Val
1               5

<210> SEQ ID NO 43
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 43

Val Asp Trp Phe Leu Asp Trp Leu Arg
1               5

<210> SEQ ID NO 44
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 44

Gly Gly Ala Pro His Phe Gly His Phe
1               5

<210> SEQ ID NO 45
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 45

Cys Tyr Tyr Glu Leu Asn Gln Cys Leu
1               5

<210> SEQ ID NO 46
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 46

Ala Tyr Pro Gln Tyr Val Ile Glu Tyr
1               5

<210> SEQ ID NO 47
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 47

His Leu Glu Thr His Asn Thr Asp Lys
1               5

<210> SEQ ID NO 48
<211> LENGTH: 9
```

```
<212> TYPE: PRT
<213> ORGANISM: Artificial Sequence
<220> FEATURE:
<223> OTHER INFORMATION: neoantigenic peptide

<400> SEQUENCE: 48

Ala Glu Glu Glu Glu Glu Val Val
1               5

<210> SEQ ID NO 49
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 49

Arg Gly Met Gln Cys Ala Ile Cys Lys
1               5

<210> SEQ ID NO 50
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 50

Met Pro Glu Asp Glu Tyr Met Val Tyr
1               5

<210> SEQ ID NO 51
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 51

Ser Ser Tyr Gly Arg Asn His Tyr Ile
1               5

<210> SEQ ID NO 52
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 52

Ala Met Asp Asp Leu Asp Thr Asp Met
1               5

<210> SEQ ID NO 53
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 53

Pro Thr Asp Pro Met Leu Gly Leu Ala
1               5

<210> SEQ ID NO 54
<211> LENGTH: 9
<212> TYPE: PRT
```

<213> ORGANISM: Artificial Sequence
<220> FEATURE:
<223> OTHER INFORMATION: neoantigenic peptide

<400> SEQUENCE: 54

Phe Ser Ser Asn Leu Pro Thr Tyr Tyr
1               5

<210> SEQ ID NO 55
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 55

Phe Ser Ser Asn Leu Pro Thr Tyr Tyr
1               5

<210> SEQ ID NO 56
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 56

Phe Arg His Ser Met Val Val Pro Tyr
1               5

<210> SEQ ID NO 57
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 57

Asn Leu Leu Gly Arg Asn Ser Phe Lys
1               5

<210> SEQ ID NO 58
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 58

Gly Leu Gly Phe Tyr Asn Asp Val Val
1               5

<210> SEQ ID NO 59
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 59

Ala Gln Thr His Glu Pro Arg Gln Trp
1               5

<210> SEQ ID NO 60
<211> LENGTH: 9
<212> TYPE: PRT
<213> ORGANISM: Artificial Sequence

```
<220> FEATURE:
<223> OTHER INFORMATION: neoantigenic peptide

<400> SEQUENCE: 60

Ser Thr His Pro Ser Leu Ser Gln Trp
1               5

<210> SEQ ID NO 61
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 61

Val Tyr Met Pro Pro Pro Arg Leu Leu
1               5

<210> SEQ ID NO 62
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 62

Asn His Asp Asp Asp Asp Val Glu Ile
1               5

<210> SEQ ID NO 63
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 63

Tyr Val Lys Ile Tyr Leu Leu Pro Tyr
1               5

<210> SEQ ID NO 64
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 64

Ser Tyr Gln Ser Thr Gly Asp Pro Lys
1               5

<210> SEQ ID NO 65
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 65

Arg Pro Arg Lys Ala Trp Ala Trp Cys
1               5

<210> SEQ ID NO 66
<211> LENGTH: 9
<212> TYPE: PRT
<213> ORGANISM: Artificial Sequence
<220> FEATURE:
```

```
<223> OTHER INFORMATION: neoantigenic peptide

<400> SEQUENCE: 66

Trp Val Leu His His Met Gly Gly Met
1               5

<210> SEQ ID NO 67
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 67

Leu Ala Gly Glu Trp Arg Glu Arg Leu
1               5

<210> SEQ ID NO 68
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 68

Thr Val Trp Pro Ser Leu Ala Pro Leu
1               5

<210> SEQ ID NO 69
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 69

Gln Glu Ala Ser Asn Lys His Ala Glu
1               5

<210> SEQ ID NO 70
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 70

Arg Arg Arg Leu Cys Ile Leu Arg Met
1               5

<210> SEQ ID NO 71
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 71

Val Arg Leu Gly Pro Val Lys Ser Ile
1               5

<210> SEQ ID NO 72
<211> LENGTH: 9
<212> TYPE: PRT
<213> ORGANISM: Artificial Sequence
<220> FEATURE:
<223> OTHER INFORMATION: neoantigenic peptide
```

```
<400> SEQUENCE: 72

Phe Phe Val Glu Lys Arg His Ala Phe
1               5

<210> SEQ ID NO 73
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 73

His Thr Ser Leu Arg Gly Phe Leu Tyr
1               5

<210> SEQ ID NO 74
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 74

Ser Leu Ala Glu Thr Lys Thr Leu Tyr
1               5

<210> SEQ ID NO 75
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 75

Thr Tyr Ala Pro Leu Phe Ile Trp Val
1               5

<210> SEQ ID NO 76
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 76

Ser Pro Ala Pro Glu Arg Cys Met Val
1               5

<210> SEQ ID NO 77
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 77

Glu Gln Leu Lys Leu Gly Ala Ile Phe
1               5

<210> SEQ ID NO 78
<211> LENGTH: 9
<212> TYPE: PRT
<213> ORGANISM: Artificial Sequence
<220> FEATURE:
<223> OTHER INFORMATION: neoantigenic peptide
```

```
<400> SEQUENCE: 78

Arg Pro Gln Gly Gln Arg Pro Ala Leu
1               5

<210> SEQ ID NO 79
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 79

Ala Pro Arg Gly Val Cys Tyr Gly Ala
1               5

<210> SEQ ID NO 80
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 80

Ala Pro Arg Gly Val Cys Tyr Gly Ala
1               5

<210> SEQ ID NO 81
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 81

Leu Ala Ala Pro Arg Gly Val Cys Tyr
1               5

<210> SEQ ID NO 82
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 82

Pro Pro Arg Tyr Ile Gly Ile Pro Ile
1               5

<210> SEQ ID NO 83
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 83

His Val Trp Leu Cys Asp Leu Pro Val
1               5

<210> SEQ ID NO 84
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 84
```

```
Gln Leu Tyr Met Asn Pro Lys Thr Trp
1               5

<210> SEQ ID NO 85
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 85

Lys Tyr Ser Asn Tyr Val Trp Pro Ile
1               5

<210> SEQ ID NO 86
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 86

Leu Pro Arg Gln Tyr Trp Glu Ala Leu
1               5

<210> SEQ ID NO 87
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 87

Val Leu Asn Gly Trp Leu Arg Ser Val
1               5

<210> SEQ ID NO 88
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 88

Tyr Leu Ala Leu Ala Ala Gln Cys Leu
1               5

<210> SEQ ID NO 89
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 89

Cys Pro Leu Pro Arg Pro Pro Pro Ile
1               5

<210> SEQ ID NO 90
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 90
```

Gly Ile Ile Cys Leu Asp Tyr Lys Leu
1               5

<210> SEQ ID NO 91
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 91

Thr Leu Gly Val Phe Cys Leu Gly Leu
1               5

<210> SEQ ID NO 92
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 92

Glu Arg Pro Cys His Arg Glu Pro Leu
1               5

<210> SEQ ID NO 93
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 93

Arg Leu Ala Leu Ser Thr Phe Glu Trp
1               5

<210> SEQ ID NO 94
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 94

Val Val Trp Ala Thr Lys Tyr Phe Leu
1               5

<210> SEQ ID NO 95
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 95

Asn Pro Glu Ala Met Cys Ser Asp Leu
1               5

<210> SEQ ID NO 96
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 96

Ile Pro Leu Glu Val Met Glu Pro Phe

```
1               5

<210> SEQ ID NO 97
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 97

Glu Glu Ala Phe Val Pro Ile Leu Tyr
1               5

<210> SEQ ID NO 98
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 98

His His His His His His Gln Ala Trp
1               5

<210> SEQ ID NO 99
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 99

Leu Val Trp Ser Leu Pro Cys Gly Phe
1               5

<210> SEQ ID NO 100
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 100

Met Pro Asp Val Val His Gln Ser Leu
1               5

<210> SEQ ID NO 101
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 101

Cys Arg Pro Gln Cys Cys Gln Ser Val
1               5

<210> SEQ ID NO 102
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 102

Met Thr Pro Ser Val Tyr Gly Gly Ala
1               5
```

<210> SEQ ID NO 103
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 103

Tyr Lys Leu Val Val Val Gly Ala Val
1               5

<210> SEQ ID NO 104
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 104

Tyr Lys Leu Val Val Val Gly Ala Val
1               5

<210> SEQ ID NO 105
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 105

Tyr Lys Leu Val Val Val Gly Ala Val
1               5

<210> SEQ ID NO 106
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 106

Ala Pro Ala Gln Pro Pro Met Leu Ala
1               5

<210> SEQ ID NO 107
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 107

Glu Pro Pro Pro Pro Pro Ser Pro Leu
1               5

<210> SEQ ID NO 108
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 108

Tyr Leu Trp Glu Asp Pro Val Cys Gly
1               5

```
<210> SEQ ID NO 109
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 109

Ser Phe Ala Asp Phe Glu Trp His Phe
1               5

<210> SEQ ID NO 110
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 110

Tyr Gln Gln Ser Asn Thr Trp Ser Leu
1               5

<210> SEQ ID NO 111
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 111

Ser Pro Gly Gly Trp Arg Ser Gly Trp
1               5

<210> SEQ ID NO 112
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 112

Arg Val Trp Asp Ile Val Pro Thr Leu
1               5

<210> SEQ ID NO 113
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 113

Met Leu Ala Ile Gly Cys Ala Leu Leu
1               5

<210> SEQ ID NO 114
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 114

Trp Glu Glu Glu Tyr Thr Val Trp Ile
1               5
```

```
<210> SEQ ID NO 115
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 115

Val Trp Pro Lys Lys Ile Asn Asn Ile
1               5

<210> SEQ ID NO 116
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 116

Trp Pro Gln Cys His Pro Glu Glu Ile
1               5

<210> SEQ ID NO 117
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 117

Gln Glu Phe Glu Asn Ile Lys Ser Tyr
1               5

<210> SEQ ID NO 118
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 118

Thr Met Asp Val Ala Thr Pro Ser Val
1               5

<210> SEQ ID NO 119
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 119

Leu Pro Leu His Leu Tyr Asp Thr Leu
1               5

<210> SEQ ID NO 120
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 120

Arg Pro Gly Gln Ser Pro Gly Gln Leu
1               5

<210> SEQ ID NO 121
```

```
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 121

Glu Leu Leu Asp Tyr Ile Arg Ala Val
1               5

<210> SEQ ID NO 122
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 122

Leu Pro Pro Ser Leu Gln Gly Ala Val
1               5

<210> SEQ ID NO 123
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 123

Phe Leu Thr Gln Pro Val Ala Pro Lys
1               5

<210> SEQ ID NO 124
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 124

Leu Ala Ser Ser Cys Gly Cys Thr Phe
1               5

<210> SEQ ID NO 125
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 125

Arg Pro Arg Gly Asp Asn Gly Tyr Thr
1               5

<210> SEQ ID NO 126
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 126

Gln Ala Met Tyr Asp Val Leu Thr Phe
1               5

<210> SEQ ID NO 127
<211> LENGTH: 9
```

```
<212> TYPE: PRT
<213> ORGANISM: Artificial Sequence
<220> FEATURE:
<223> OTHER INFORMATION: neoantigenic peptide

<400> SEQUENCE: 127

Leu Thr Ile Ser Gly Glu Cys Pro Lys
1               5

<210> SEQ ID NO 128
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 128

Ser Trp Lys Ser Pro Gly Trp Ser Phe
1               5

<210> SEQ ID NO 129
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 129

Arg Lys Arg Glu Glu Glu Glu Arg Trp
1               5

<210> SEQ ID NO 130
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 130

Asn His Leu Cys Phe Gly His Cys Phe
1               5

<210> SEQ ID NO 131
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 131

Tyr Val Tyr Ser Leu Tyr Trp Ser Ile
1               5

<210> SEQ ID NO 132
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 132

Met Val Leu Trp His Leu Pro Ala Val
1               5

<210> SEQ ID NO 133
<211> LENGTH: 9
<212> TYPE: PRT
```

<213> ORGANISM: Artificial Sequence
<220> FEATURE:
<223> OTHER INFORMATION: neoantigenic peptide

<400> SEQUENCE: 133

Phe Ser Val Ser Pro Glu Trp Ala Val
1               5

<210> SEQ ID NO 134
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 134

Gly Tyr Tyr Thr Leu Leu Asn Val Phe
1               5

<210> SEQ ID NO 135
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 135

Gln Ala Leu Ile Arg Pro Thr Thr Phe
1               5

<210> SEQ ID NO 136
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 136

Lys Gln Leu Pro Arg Ile Leu Glu Ala
1               5

<210> SEQ ID NO 137
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 137

Tyr Gln Gln Ala Leu Gly Lys Arg Phe
1               5

<210> SEQ ID NO 138
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 138

Gln Leu Ala Trp Val Pro Ser Pro Tyr
1               5

<210> SEQ ID NO 139
<211> LENGTH: 9
<212> TYPE: PRT
<213> ORGANISM: Artificial Sequence

```
<220> FEATURE:
<223> OTHER INFORMATION: neoantigenic peptide

<400> SEQUENCE: 139

His Ile Gln Asp Leu Tyr Thr Val Leu
1               5

<210> SEQ ID NO 140
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 140

Met Asn Arg Gly Arg Arg Ser Ser Leu
1               5

<210> SEQ ID NO 141
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 141

Tyr Ala Tyr Thr Phe Trp Thr Tyr Ile
1               5

<210> SEQ ID NO 142
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 142

Ser Glu Val Leu Gly Tyr Trp Ala Phe
1               5

<210> SEQ ID NO 143
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 143

Lys Pro Leu Leu Ser Gly Pro Trp Ala
1               5

<210> SEQ ID NO 144
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 144

Phe Asn Gly Asn Phe Leu Leu Ser Met
1               5

<210> SEQ ID NO 145
<211> LENGTH: 9
<212> TYPE: PRT
<213> ORGANISM: Artificial Sequence
<220> FEATURE:
```

```
<223> OTHER INFORMATION: neoantigenic peptide

<400> SEQUENCE: 145

Ala His Pro Asp Gly Ser Trp Thr Phe
1               5

<210> SEQ ID NO 146
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 146

Met Thr Thr Lys Ala Thr Ser Ser Met
1               5

<210> SEQ ID NO 147
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 147

Thr Leu Asp Tyr Lys Pro Val Thr Val
1               5

<210> SEQ ID NO 148
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 148

Gln Ile Lys Asn Lys Asn Lys Glu Ile
1               5

<210> SEQ ID NO 149
<211> LENGTH: 9
<212> TYPE: PRT
<213> ORGANISM: Artificial Sequence
<220> FEATURE:
<223> OTHER INFORMATION: neoantigenic peptide

<400> SEQUENCE: 149

Thr Leu Asp Tyr Lys Pro Val Thr Val
1               5

<210> SEQ ID NO 150
<211> LENGTH: 9
<212> TYPE: PRT
<213> ORGANISM: Artificial Sequence
<220> FEATURE:
<223> OTHER INFORMATION: wild type epitope

<400> SEQUENCE: 150

Pro Pro Ser Ala Arg Gly Gly Pro Leu
1               5

<210> SEQ ID NO 151
<211> LENGTH: 9
<212> TYPE: PRT
<213> ORGANISM: Artificial Sequence
<220> FEATURE:
<223> OTHER INFORMATION: neoantigenic peptide
```

```
<400> SEQUENCE: 151

Pro Pro Ser Ala Arg Arg Gly Pro Leu
1               5

<210> SEQ ID NO 152
<211> LENGTH: 15
<212> TYPE: PRT
<213> ORGANISM: Artificial Sequence
<220> FEATURE:
<223> OTHER INFORMATION: Human Herpes Virus 8

<400> SEQUENCE: 152

Pro Pro Ser Gly Gln Arg Gly Pro Val Ala Phe Arg Thr Arg Val
1               5                   10                  15
```

NEOANTIGENS AND USES THEREOF FOR TREATING CANCER

CROSS REFERENCE TO RELATED APPLICATIONS

This application claims priority to U.S. Provisional Patent Application No. 62/582,851 entitled "Systems and Methods for Predicting Tumor Response to Checkpoint Blockade Immunotherapy," filed Nov. 7, 2017, which is hereby incorporated by reference.

This application also claims priority to U.S. Provisional Patent Application No. 62/554,232 entitled "Neoantigens and Uses Thereof for Treating Cancer," filed Sep. 5, 2017, which is hereby incorporated by reference.

This application also claims priority to U.S. Provisional Patent Application No. 62/448,291 entitled "Neoantigens and Uses Thereof for Treating Cancer," filed Jan. 19, 2017, which is hereby incorporated by reference.

This application also claims priority to U.S. Provisional Patent Application No. 62/448,247 entitled "Neoantigens and Uses Thereof for Treating Cancer," filed Jan. 19, 2017, which is hereby incorporated by reference.

This application also claims priority to U.S. Provisional Patent Application No. 62/447,852 entitled "Neoantigen Fitness Model Predicts Tumor Response to CheckPoint Blockade Immunotherapy," filed Jan. 18, 2017, which is hereby incorporated by reference.

This application also claims priority to U.S. Provisional Patent Application No. 62/618,540 entitled "Neoantigens and Uses Thereof for Treating Cancer," filed Jan. 17, 2018, which is hereby incorporated by reference.

STATEMENT REGARDING FEDERALLY FUNDED RESEARCH

This invention was made with government support under R01DK097087-01 awarded by National Institute of Health, K12CA184746-01A1 awarded by National Cancer Institute, 1545935 awarded by National Science Foundation, and P30 CA08748 awarded by National Cancer Institute Cancer Center. The government has certain rights in this invention reference.

SEQUENCE LISTING

The instant application contains a Sequence Listing that has been submitted electronically in ASCII format and is hereby incorporated by reference in its entirety. The ASCII copy, created on Jan. 18, 2018, is named 104593-5011-WO_ST25.txt and is 30 kilobytes in size.

TECHNICAL FIELD

The present disclosure relates generally to systems and methods for determining a likelihood that a human subject afflicted with a cancer will be responsive to a treatment regimen, where the treatment regimen that comprises administering a checkpoint blockade immunotherapy directed to the cancer to the subject.

BACKGROUND

Pancreatic ductal adenocarcinoma (PDAC) will be diagnosed in approximately 53,000 patients in the United States in 2016, and an estimated 41,000 will die from its effects[1]. PDAC is one of the most lethal forms of cancer, less than 7% of PDAC patients survive 5 years after diagnosis[2]. A large proportion of patients present with advanced and metastatic disease at initial diagnosis and offered treatment options restricted to cytotoxic chemotherapies which extend life by no more than a few months[3]. Research aims to identify new therapeutic agents and effective combinations of existing therapies for PDAC patients have not yet significantly improved patient survival[4].

The immune system plays an important role in controlling and eradicating cancer. Nevertheless, in the setting of malignancy, multiple mechanisms of immune suppression can exist that prevent effective antitumor immunity. Antibody therapy directed against several negative immunologic regulators (checkpoints) is demonstrating significant success and is likely to be a major component of treatment for patients with a variety of malignancies. Immunologic checkpoint blockade with antibodies that target cytotoxic T lymphocyte-associated antigen 4 (CTLA-4) and the programmed cell death protein 1 pathway (PD-1/PD-L1) have demonstrated promise in a variety of malignancies. However, these immune checkpoint inhibitors have demonstrated limited impact on overall patient survival in PDAC[5]. A possible reason for this can be the relatively low mutational load observed in PDAC[6].

Checkpoint blockade immunotherapies enable the host immune system to recognize and destroy tumor cells. Recent clinical trials using immune checkpoint blocking antibodies, such as anti-cytotoxic T-lymphocyte-associated protein 4 (anti-CTLA4), or anti-programmed cell death protein-1 (anti-PD-1), have improved overall survival in many malignancies by disinhibiting the immune system. See Topalian et al., 2015, "Immune checkpoint blockade: a common denominator approach to cancer therapy," 2015, Cancer Cell 27, pp. 450-61. Their clinical activity depends on activated T-cell recognition of neoantigens, which are tumor-specific, mutated peptides presented on the surface of cancer cells. See Schumacher and Schreiber, 2015, "Neoantigens in cancer immunotherapy," Science 348, pp. 69-74; and Gubin et al., 2015, "Tumor neoantigens: building a framework for personalized cancer immunotherapy," J. Clin. Invest. pp. 3413-3421. How these underlying processes determine the success of immunotherapies has remained unclear. Furthermore, only a minority of patients achieves a durable clinical benefit, suggesting there may be genetic determinants of response.

De novo somatic mutations within coding regions can create neoantigens—novel protein epitopes specific to tumors, which MHC molecules present to the immune system and which may be recognized by T-cells as non-self. An elevated number of mutations or neoantigens has been linked to improved response to checkpoint blockade therapy in multiple malignancies. (See, Snyder et al., 2014, "Genetic Basis for Clinical Response to CTLA-4 Blockade in Melanoma," N. Engl. J. Med. 371, pp. 2189-2199; Van Allen et al., 2015, "Genomic correlates of response to CTLA-4 blockade in metastatic melanoma," Science 350, pp. 207-211, and Rizvi et al., 2015, "Mutational landscape determines sensitivity to PD-1 blockade in non-small cell lung cancer, Science 348, pp. 124-128). Hence, inferred neoantigen burden is a coarse-grained proxy for whether a tumor is likely to respond to therapy.

Other implicated biomarkers of response include T-cell receptor (TCR) repertoire profiles (leading to hypothesized roles for the microbiome (Vétizou et al., 2015, "Anticancer immunotherapy by CTLA-4 blockade relies on the gut microbiota," Science 350, pp. 1079-1084; and Zitvogel et al., 2016, "Microbiome and Anticancer Immunosurveillance," Cell 165, pp. 276-287), immune based microenvironment signatures (Snyder et al., 2014, "Genetic Basis for Clinical Response to CTLA-4 Blockade in Melanoma," N. Engl. J. Med. 371, pp. 2189-2199; de Henau et al., 2016 "Overcoming resistance to checkpoint blockade therapy by targeting PI3Kγ in myeloid cells," Nature 539, pp. 443-447) and tumor heterogeneity (McGranahan et al., 2016, "Clonal neoantigens elicit T cell immunoreactivity and sensitivity to immune checkpoint blockade," Science 351, pp. 1463-1469.

Despite high overall mutational load, a heterogeneous tumor may have immunogenic neoantigens present only in certain subclones. As a result, therapies targeting only a fraction of the tumor could disrupt clonal competitive balance and inadvertently stimulate growth of untargeted clones (Fisher et al., 2015, "The value of monitoring to control evolving populations," Proc. Natl. Acad. Sci. 112(4), pp. 1007-1012; and Anagnostu et al., 2016, "Evolution of neoantigen landscape during immune checkpoint blockade in non-small cell lung cancer," Cancer Discov., 7(3), pp. 264-276). Moreover, mass spectrometry based validation of neoantigens, already limited by sensitivity, does not sample all of the many relevant clones in heterogeneous tumors nor account for clonal variations across metastases (Purcell et al., "More than one reason to rethink the use of peptides in vaccine design," Nature Rev. Drug Discov. 6, pp. 404-414). Worldwide efforts are being undertaken to model neoantigens and quantify neoantigen features from genomic data, and a predictive neoantigen-based model for immunotherapy response is a highly sought-after goal.

Given the above background, what is needed in the art are systems and methods for determining the likely responsiveness of a human cancer subject to a checkpoint blockade immunotherapy regimen. Further, given the above background, there remains a need for developing novel therapies that improve the survival of PDAC patients.

SUMMARY

The present disclosure addresses the need in the art for systems and methods for determining the likely responsiveness of a human cancer subject to a checkpoint blockade immunotherapy regimen. Such a mathematical model using genomic data has the advantage of broad consideration of neoantigen space. The disclosed recognition potential fitness model of immune interactions is used to describe the evolutionary dynamics of cancer cell populations under checkpoint-blockade immunotherapy.

To calculate the recognition potential fitness model, sequencing reads (e.g., whole genome sequencing reads, exome sequencing reads, targeted sequencing reads, etc.) are obtained from samples from the subject representative of the cancer. A human leukocyte antigen (HLA) type and a plurality of clones is determined (e.g., from the sequencing reads). For each clone, an initial frequency $X_\alpha$ in the one or more samples is determined and a corresponding clone fitness score of the clone is computed, thereby computing clone fitness scores. Each such fitness score is computed by identifying neoantigens in the respective clone, computing a recognition potential for each neoantigen, and determining the corresponding clone fitness score of the respective clone as an aggregate of these recognition potentials. A total fitness, quantifying the likely responsiveness of the subject to the regimen, is then computed by summing the clone fitness scores across the plurality of clones.

As such, one aspect of the present disclosure provides a method for determining a likelihood that a human subject afflicted with a cancer will be responsive to a treatment regimen, where the treatment regimen comprises administering a checkpoint blockade immunotherapy directed to the cancer to the subject. In some embodiments, the checkpoint blockade immunotherapy comprises administering an anti-CTLA-4, anti-PD1, anti-PD-L1, anti-LAG3, anti-TIM-3, anti-GITR, anti-OX40, anti-CD40, anti-TIGIT, anti4-1BB, anti-B7-H3, anti-B7-H4, or anti-BTLA compound to the cancer subject. In some embodiments, the cancer is a carcinoma, a melanoma, a lymphoma/leukemia, a sarcoma, or a neuro-glial tumor. In some embodiments, the cancer is lung cancer, pancreatic cancer, colon cancer, stomach or esophagus cancer, breast cancer, ovary cancer, prostate cancer, or liver cancer.

In the present disclosure, a plurality of sequencing reads (e.g., whole genome sequencing reads, exome sequencing reads, targeted sequencing reads, etc.) is obtained from one or more samples from the human cancer subject that is representative of the cancer. In some embodiments, the plurality of sequencing reads exhibits an average read depth of less than 40. In some embodiments, the plurality of sequencing reads exhibits an average read depth of between 25 and 60.

In the method in accordance with the present disclosure, a human leukocyte antigen (HLA) type of the human cancer subject is determined. In some embodiments, the HLA type of the human cancer subject is determined from the plurality of sequencing reads. In some embodiments, the determining the HLA type of the human cancer subject is determined using a polymerase chain reaction using a biological sample from the cancer subject.

In the method in accordance with the present disclosure, a plurality of clones is determined from the plurality of sequencing reads. For each respective clone α in the plurality of clones, an initial frequency $X$, of the respective clone α in the one or more samples is determined.

In some embodiments, each clone α in the plurality of clones is uniquely defined by a unique set of somatic mutations (e.g., single nucleotide variant or an indel). In some embodiments, the plurality of clones is determined by a variant allele frequency of each respective somatic mutation in a plurality of somatic mutations determined from the whole-genome sequencing data.

In some embodiments, the plurality of clones is determined by identifying a plurality of inferred copy number variations using the whole-genome sequencing data.

In some embodiments, each clone α in the plurality of clones is uniquely defined by a unique set of somatic mutations. In such embodiments, the plurality of clones is determined by a combination of (i) a variant allele frequency of each respective somatic mutation in the plurality of somatic mutations determined from the whole-genome sequencing data and (ii) an identification of a plurality of inferred copy number variations using the whole-genome sequencing data (330).

In some embodiments, the plurality of clones consists of two clones (332). In some embodiments, the plurality of clones consists of between two clones and ten clones (334). In some embodiments, the initial frequency $X_\alpha$ of the respective clone α in the one or more samples is determined using the plurality of sequencing reads from the one or more samples from the human cancer subject (336).

In the method in accordance with the present disclosure, for each respective clone α in the plurality of clones, a corresponding clone fitness score of the respective clone is computed, thereby computing a plurality of clone fitness scores, each corresponding clone fitness score computed for a respective clone α by a first procedure.

In the first procedure, a plurality of neoantigens in the respective clone α is identified. In some embodiments, each neoantigen in the plurality of neoantigens of a clone in the plurality of clones is a nonamer peptide. In some embodiments, each neoantigen in the plurality of neoantigens of a clone in the plurality of clones is a peptide that is eight, nine, ten, or eleven residues in length. In certain embodiments each neoantigen in the plurality of neoantigens of a clone in the plurality of clones is a peptide that is 3-30 amino acids, e.g., about 3-5, about 5-15 (e.g., about 8-11, about 5-10, or about 10-15), about 15-20, about 20-25, or about 20-30 amino acids, in length. In certain embodiments, each neoantigen in the plurality of neoantigens of a clone in the plurality of clones is a peptide that is about 8-11 amino acids in length. In certain embodiments, each neoantigen in the plurality of neoantigens of a clone in the plurality of clones is a peptide that is about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 amino acids in length. In certain embodiments, each neoantigen in the plurality of neoantigens of a clone in the plurality of clones is a peptide that is at least about 3, at least about 5, or at least about 8 amino acids in length. In certain embodiments, each neoantigen in the plurality of neoantigens of a clone in the plurality of clones is a peptide is less than about 30, less than about 20, less than about 15, or less than about 10 amino acids in length.

In some embodiments, the method further comprises identifying a population of neoantigens present in the one or more samples by a procedure comprising: determining a plurality of somatic single nucleotide polymorphisms (SNPs) in the plurality of sequencing reads by comparison of the plurality of sequencing reads to a reference human genome, evaluating each respective somatic SNP in the plurality of SNPs as a neoantigen candidate by evaluation of a peptide encoded by a portion of one or more sequencing reads in the sequencing reads that includes the respective somatic SNP against a classifier that has been trained to predict peptide binding to class 1 MHC of the HLA type of the cancer subject, where a neoantigen candidate having a binding score below a threshold value is deemed to be a neoantigen in the population of neoantigens. Further, the identifying the plurality of neoantigens in the respective clone α comprises matching the SNPs in the respective clone α to respective neoantigens in the population of neoantigens. In some such embodiments, the threshold value is 500 nM.

Continuing with the method in accordance with the present disclosure, a recognition potential of each respective neoantigen in the plurality of neoantigens in the respective clone α is computed by a second procedure. In the second procedure, an amplitude A of the respective neoantigen is computed as a function of the relative major histocompatibility complex (MHC) affinity of the respective neoantigen and the wildtype counterpart of the respective neoantigen given the HLA type of the subject. In some such embodiments, the function of the relative class I MHC affinity of the respective neoantigen and the wildtype counterpart of the respective neoantigen given the HLA type of the human cancer subject is a ratio of the relative class I MHC affinity of the respective neoantigen and the wildtype counterpart of the respective neoantigen given the HLA type of the subject.

In some embodiments, the function of the relative class I MHC affinity of the respective neoantigen and the wildtype counterpart of the respective neoantigen given the HLA type of the subject is a ratio of: (1) a dissociation constant between the respective neoantigen and the class I MHC presented by the cancer subject given the HLA type of the cancer subject, and (2) a dissociation constant between the wildtype counterpart of the respective neoantigen and the class I MHC presented by the cancer subject given the HLA type of the cancer subject. In some such embodiments, the dissociation constant between the respective neoantigen and the class I MHC presented by the cancer subject is obtained as output from a first classifier upon inputting into the first classifier the amino acid sequence of the neoantigen. The dissociation constant between the wildtype counterpart of the respective neoantigen and the class I MHC presented by the cancer subject of the HLA type of the subject is obtained as output from the first classifier upon inputting into the first classifier the amino acid sequence of the respective wildtype counterpart of the neoantigen (e.g., the first classifier is specific to the HLA type of the cancer subject and has been trained with the respective class I MHC binding coefficient and sequence data of each peptide epitope in a plurality of epitopes presented by class I MHC in a training population having the HLA type of the subject).

Further, in the second procedure, a probability of T-cell receptor recognition R of the respective neoantigen is computed as a probability that the respective neoantigen binds one or more epitopes that are positively recognized by T-cells after class I MHC presentation.

In some such embodiments, the probability that the respective neoantigen binds one or more epitopes that are positively recognized by T-cells after class I MHC presentation is determined by a third procedure that comprises (a) selecting a respective epitope e from an epitope database IEDB, where the respective epitope e is positively recognized by T-cells after class I MHC presentation, (b) computing, for the respective epitope e, the probability $$Pr_{binding}(s, e) = \frac{1}{1 + e^{-k(|s,e|-a)}}$$

where, |s, e| is a sequence alignment score between the sequence of the respective neoantigen and the sequence of the respective epitope, and k and a are constants, (c) performing the selecting (a) and the computing (b) for each respective epitope e in a plurality of epitopes in the epitope database IEDB, thereby computing a plurality of probabilities $Pr_{binding}(s, e)$; and (d) computing the probability of T-cell receptor recognition R of the respective neoantigen as:

$$R = 1 - \Pi_{e \in IEDB}[1 - Pr_{binding}(s,e)],$$

where IEDB is the plurality of epitopes. In some such embodiments, |s, e| is computed as an alignment (e.g., gapless, or an alignment that allows gaps with suitable gap introduction and extension penalties) between the sequence of the respective neoantigen and the sequence of the respective epitope using an amino-acid similarity matrix. In some such embodiments, the amino-acid similarity matrix is a BLOSUM62 matrix. In some embodiments, for each patient (e.g., in a cohort), sequence alignments of IEDB sequences and the patient's neoantigen sequences is performed. In some embodiments, BLAST and a blastp program with BLOSUM62 matrix and a strong gap penalty −11 is used to prevent gapped alignments. In some embodiments, the gap extension cost is set to the default value −1. In some embodiments, a threshold on alignment E-values is not imposed and all alignments are considered. In some embodiments, alignment scores for these identified alignments are then computed with Biopython Bio.pairwise2 package.

In the second procedure, the recognition potential of the respective neoantigen is computed as a function (e.g., product) of the amplitude A of the respective neoantigen and the probability of T-cell receptor recognition R of the respective neoantigen.

In accordance with the present disclosure, the method further comprises determining the corresponding clone fitness score of the respective clone α as an aggregate of the neoantigen recognition potential across the plurality of neoantigens in the respective clone α. In some such embodiments, the aggregate of the neoantigen recognition potentials across the plurality of neoantigens in the respective clone α is computed as:

$$F_\alpha = - \max_{i \in \text{Clone } \alpha} (A_i \times R_i)$$

where i is an index iterating over each neoantigen in the plurality of neoantigens in the respective clone α.

In some such embodiments, the aggregate of the neoantigen recognition potentials across the plurality of neoantigens in the respective clone α is computed as a summation of the recognition potential of each respective neoantigen in the plurality of neoantigens. In some embodiments, the aggregate of the neoantigen recognition potentials across the plurality of neoantigens in the respective clone α is computed as a summation of the recognition potentials of a subset of the neoantigens in the plurality of neoantigens. In some embodiments, the subset of the neoantigens in the plurality of neoantigens constitutes a predetermined number of neoantigens in the plurality of neoantigens that have the top recognition potential for the respective clone α.

In some embodiments, the aggregate of the neoantigen recognition potentials across the plurality of neoantigens in the respective clone α is computed as a nonlinear combination of the recognition potential of all or a subset of the neoantigens in the plurality of neoantigens. In some such embodiments, the computing a total fitness for the one or more samples as a sum of the clone fitness scores across the plurality of clones is computed as:

$$n(\tau) = \Sigma_\alpha X_\alpha \exp(F_\alpha \tau),$$

where τ is a characteristic evolutionary time scale.

In accordance with the present disclosure, the method further comprises computing a total fitness for the one or more samples as a sum of the clone fitness scores across the plurality of clones, where each clone fitness score is weighted by the initial frequency $X_\alpha$ of the corresponding clone α, and the total fitness quantifies the likelihood that the human subject afflicted with the cancer will be responsive to the treatment regimen. In some such embodiments, the computing a total fitness for the one or more samples as a sum of the clone fitness scores across the plurality of clones is computed as:

$$n(\tau) = \Sigma_\alpha X_\alpha \exp(F_\alpha \tau),$$

where τ is a characteristic evolutionary time scale (374). In some such embodiments, τ is between 0.0 and 0.5. In some such embodiments, τ is 0.06. In some such embodiments, τ is 0.09. In some such embodiments, τ is between 0.01 and 1.0. In some such embodiments, a lower total fitness score is associated with (a) a higher likelihood that the cancer subject will be responsive to the immunotherapy and (b) a longer term survival of the cancer patient.

Another aspect of the present disclosure provides a method for identifying an immunotherapy for a cancer. In some embodiments of the method, a plurality of sequencing reads is obtained from one or more samples from a human cancer subject that is representative of the cancer. A human leukocyte antigen (HLA) type of the human cancer subject is determined from the plurality of sequencing reads. A plurality of clones is determined. For each respective clone α in the plurality of clones, an initial frequency $X_\alpha$ of the respective clone α in the one or more samples is determined from the plurality of sequencing reads. Further, for each respective clone α in the plurality of clones, a corresponding clone fitness score of the respective clone is computed, thereby computing a plurality of clone fitness scores, each corresponding clone fitness score computed for a respective clone α by a first procedure.

In the first procedure, a plurality of neoantigens in the respective clone α are identified.

A recognition potential of each respective neoantigen in the plurality of neoantigens in the respective clone α is then computed by a second procedure. In the second procedure, an amplitude A of the respective neoantigen as a function of the relative major histocompatibility complex (MHC) affinity of the respective neoantigen and the wildtype counterpart of the respective neoantigen given the HLA type of the subject is computed. Further, a probability of T-cell receptor recognition R of the respective neoantigen as a probability that the respective neoantigen binds one or more epitopes that are positively recognized by T-cells after class I MHC presentation is computed. The recognition potential of the respective neoantigen is computed as a function of (e.g., the product of) the amplitude A of the respective neoantigen and the probability of T-cell receptor recognition R of the respective neoantigen.

In the first procedure, the corresponding clone fitness score of the respective clone α is determined as an aggregate of the neoantigen recognition potentials across the plurality of neoantigens in the respective clone α.

In the disclosed first procedure, a first neoantigen is selected from a plurality of neoantigens for a respective clone α in the plurality of respective clones based upon the recognition potential of the first neoantigen as the immunotherapy for the cancer.

In some embodiments, the first procedure is repeated for a plurality of human cancer subjects across a plurality of HLA types and the first neoantigen is selected on the basis of the recognition potential of the first neoantigen across the plurality of HLA types.

In some embodiments, the first procedure is repeated for a plurality of human cancer subjects and the first neoantigen is selected on the basis of the recognition potential of the first neoantigen across the plurality of human cancer subject.

In some embodiments, the cancer is a carcinoma, a melanoma, a lymphoma/leukemia, a sarcoma, or a neuroglial tumor. In some embodiments, the cancer is lung cancer, pancreatic cancer, colon cancer, stomach or esophagus cancer, breast cancer, ovary cancer, prostate cancer, or liver cancer.

In some embodiments, each clone α in the plurality of clones is uniquely defined by a unique set of somatic mutations, and the plurality of clones is determined by a variant allele frequency of each respective somatic mutation in a plurality of somatic mutations determined from the whole-genome sequencing data. For instance, in some embodiments, the somatic mutation is a single nucleotide variant or an indel.

In some embodiments, the plurality of clones is determined by identifying a plurality of inferred copy number variations using the whole-genome sequencing data.

In some embodiments, each clone α in the plurality of clones is uniquely defined by a unique set of somatic mutations, and the plurality of clones is determined by a combination of (i) a variant allele frequency of each respective somatic mutation in the plurality of somatic mutations determined from the whole-genome sequencing data and (ii) an identification of a plurality of inferred copy number variations using the whole-genome sequencing data.

In some embodiments, the plurality of sequencing reads exhibits an average read depth of less than 40. In some embodiments, the plurality of sequencing reads exhibits an average read depth of between 25 and 60.

In some embodiments, each neoantigen in the plurality of neoantigens of a clone in the plurality of clones is a nonamer peptide. In some embodiments, each neoantigen in the plurality of neoantigens of a clone in the plurality of clones is a peptide that is eight, nine, ten, or eleven residues in length. In certain embodiments each neoantigen in the plurality of neoantigens of a clone in the plurality of clones is a peptide that is 3-30 amino acids, e.g., about 3-5, about 5-15 (e.g., about 8-11, about 5-10, or about 10-15), about 15-20, about 20-25, or about 20-30 amino acids, in length. In certain embodiments, each neoantigen in the plurality of neoantigens of a clone in the plurality of clones is a peptide that is about 8-11 amino acids in length. In certain embodiments, each neoantigen in the plurality of neoantigens of a clone in the plurality of clones is a peptide that is about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 amino acids in length. In certain embodiments, each neoantigen in the plurality of neoantigens of a clone in the plurality of clones is a peptide that is at least about 3, at least about 5, or at least about 8 amino acids in length. In certain embodiments, each neoantigen in the plurality of neoantigens of a clone in the plurality of clones is a peptide is less than about 30, less than about 20, less than about 15, or less than about 10 amino acids in length.

In some embodiments, the method further comprises identifying a population of neoantigens present in the one or more samples by a third procedure in which a plurality of somatic single nucleotide polymorphisms (SNPs) in the plurality of sequencing reads is determined by comparison of the plurality of sequencing reads to a reference human genome. In the third procedure, each respective somatic SNP in the plurality of SNPs is evaluated as a neoantigen candidate by evaluation of a peptide encoded by a portion of one or more sequencing reads in the sequencing reads that includes the respective somatic SNP against a classifier that has been trained to predict peptide binding to class 1 MHC of the HLA type of the cancer subject, where a neoantigen candidate having a binding score below a threshold value (e.g., 500 nM) is deemed to be a neoantigen in the population of neoantigens. Further, when this third procedure is used, the identifying the plurality of neoantigens in the respective clone α comprises matching the SNPs in the respective clone α to respective neoantigens in the population of neoantigens.

In some embodiments, the HLA type determination of the human cancer subject is made from the plurality of sequencing reads. In some embodiments, the HLA type determination of the human cancer subject is made using a polymerase chain reaction using a biological sample from the cancer subject.

In some embodiments, the plurality of clones consists of two clones. In some embodiments, the plurality of clones consists of between two clones and ten clones. In some embodiments, the initial frequency $X_\alpha$ of the respective clone α in the one or more samples is determined using the plurality of sequencing reads from the one or more samples from the human cancer subject.

In some embodiments, the function of the relative class I MHC affinity of the respective neoantigen and the wildtype counterpart of the respective neoantigen given the HLA type of the subject is a ratio of the relative class I MHC affinity of the respective neoantigen and the wildtype counterpart of the respective neoantigen given the HLA type of the subject.

In some embodiments, the function of the relative class I MHC affinity of the respective neoantigen and the wildtype counterpart of the respective neoantigen given the HLA type of the human cancer subject is a ratio of: (1) a dissociation constant between the respective neoantigen and the class I MHC presented by the cancer subject given the HLA type of the cancer subject, and (2) a dissociation constant between the wildtype counterpart of the respective neoantigen and the class I MHC presented by the cancer subject given the HLA type of the cancer subject. In some such embodiments, the dissociation constant between the respective neoantigen and the class I MHC presented by the cancer subject is obtained as output from a first classifier upon inputting into the first classifier the amino acid sequence of the neoantigen, and the dissociation constant between the wildtype counterpart of the respective neoantigen and the class I MHC presented by the cancer subject of the HLA type of the subject is obtained as output from the first classifier upon inputting into the first classifier the amino acid sequence of the respective wildtype counterpart of the neoantigen. In some such embodiments, the first classifier is specific to the HLA type of the cancer subject and has been trained with the respective class I MHC binding coefficient and sequence data of each peptide epitope in a plurality of epitopes presented by class I MHC in a training population having the HLA type of the subject.

In some embodiments, the probability that the respective neoantigen binds one or more epitopes that are positively recognized by T-cells after class I MHC presentation is determined by a third procedure that comprises (a) selecting a respective epitope e from an epitope database IEDB, where the respective epitope e is positively recognized by T-cells after class I MHC presentation, (b) computing, for the respective epitope e, the probability $$Pr_{binding}(s, e) = \frac{1}{1 + e^{-k(|s,e|-a)}}$$

where |s, e| is a sequence alignment score between the sequence of the respective neoantigen and the sequence of the respective epitope, and k and a are constants, and (c) performing the selecting (a) and the computing (b) for each respective epitope e in a plurality of epitopes in the epitope database IEDB, thereby computing a plurality of probabilities $Pr_{binding}(s, e)$, and (d) computing the probability of T-cell receptor recognition R of the respective neoantigen as:

$R = 1 - \Pi_{e \in IEDB}[1 - Pr_{binding}(s,e)]$, where IEDB the plurality of epitopes. In some such embodiments, a is set to 23 and k is set to 1. In some such embodiments, |s, e| is computed as an alignment (e.g., gapless, or an alignment that allows gaps with suitable gap introduction and extension penalties) between the sequence of the respective neoantigen and the sequence of the respective epitope using an amino-acid similarity matrix (e.g., a BLOSUM62 matrix).

In some embodiments, the first neoantigen from a plurality of neoantigens for a respective clone α in the plurality of respective clones is selected when it has a recognition potential that is lower than the recognition potential of other neoantigens in each plurality of neoantigens for each respective clone α in the plurality of respective clones of the subject.

The presently disclosed subject matter further provides neoantigens, methods for detecting neoantigens, uses of the neoantigens for identifying cancer subjects as candidates for an immunotherapy, and uses of the neoantigens for predicting responsiveness of cancer subjects to an immunotherapy. In addition, the presently disclosed subject matter provides a population of T cells that target one or more of the presently disclosed neoantigens, and vaccines comprising one or more of the presently disclosed neoantigens.

In one aspect, the presently disclosed subject matter provides a method for identifying a subject having a cancer as a candidate for treatment with an immunotherapy. In certain non-limiting embodiments, the method comprises (a) obtaining a biological sample from the subject; (b) measuring the number of neoantigens (neoantigen number) in the biological sample; and (c) measuring the homology between each of the neoantigen and a microbial epitope (neoantigen-microbial homology); wherein a neoantigen number higher than the median neoantigen number obtained from a population of subjects having the cancer and a neoantigen-microbial homology higher than the median neoantigen-microbial homology obtained from subjects having the cancer indicate that the subject is a candidate for an immunotherapy. In certain embodiments, the neoantigen-microbial homology is measured by calculating a recognition potential score between each neoantigen and microbial epitope.

In certain embodiments, the method for identifying a subject having a cancer as a candidate for treatment with an immunotherapy comprises: (a) measuring the number of neoantigens (neoantigen number) in a biological sample of the subject; and (b) measuring the number of activated T cells (activated T cell number) in a biological sample of the subject; wherein a neoantigen number higher than the median neoantigen number obtained from a population of subjects having the cancer and an activated T cell number higher than the median activated T cell number obtained from subjects having the cancer indicate that the subject is a candidate for an immunotherapy.

The presently disclosed subject matter further provides a method of predicting the responsiveness of a subject having a cancer to an immunotherapy. In certain embodiments, the method comprises: (a) obtaining a biological sample from the subject; (b) measuring the number of neoantigens (neoantigen number) in the biological sample; and (c) measuring the homology between each of the neoantigen and a microbial epitope (neoantigen-microbial homology); wherein a neoantigen number higher than the median neoantigen number obtained from a population of subjects having the cancer and a neoantigen-microbial homology higher than the median neoantigen-microbial homology obtained from subjects having the cancer indicate that the subject is likely to be responsive to an immunotherapy. In certain embodiments, the neoantigen-microbial homology is measured by calculating a recognition potential score between each neoantigen and microbial epitope.

In certain embodiments, the method of predicting the responsiveness of a subject having a cancer to an immunotherapy comprises: (a) measuring the number of neoantigens (neoantigen number) in a biological sample of the subject; and (b) measuring the number of activated T cells (activated T cell number) in a biological sample of the subject; wherein a neoantigen number higher than the median neoantigen number obtained from a population of subjects having the cancer and an activated T cell number higher than the median activated T cell number obtained from subjects having the cancer indicate that the subject is likely to be responsive to an immunotherapy.

In certain non-limiting embodiments, the subject's neoantigen number, the neoantigen-microbial homology, and activated T cell numbers are at least about 1%, at least about 2%, at least about 3%, at least about 4%, at least about 5%, at least about 6%, at least about 7%, at least about 8%, at least about 9%, at least about 10%, or at least about 20%, or at least about 30%, higher than the median values.

In certain embodiments, the activated T cells are T cells expressing one or more T cell activation marker. In certain embodiments, the one or more T cell activation marker is selected from the group consisting of CD3, CD8, PD-1, 4-1BB, CD69, CD107a, Granzyme B, and combinations thereof. In certain embodiments, the activated T cells are selected from the group consisting of $CD3^+CD8^+$ T cells, $CD3^+CD8^+Granzyme-B^+$ T cells, and polyclonal activated T cells.

In certain embodiments, the cancer is a solid tumor. In certain embodiments, the cancer is pancreatic cancer. In certain embodiments, the pancreatic cancer is pancreatic ductal adenocarcinoma (PDAC). In certain embodiments, the one or more neoantigen is selected from the neoantigenic peptides listed in Table 2.

The presently disclosed subject matter also provides a method for identifying a subject having pancreatic cancer as a candidate for treatment with an immunotherapy. In certain embodiments, the method comprises: (a) obtaining a biological sample from the subject; and (b) detecting one or more neoantigen of MUC16 in the biological sample; wherein the presence of one or more neoantigen of MUC16 in the biological sample indicates that the subject is a candidate for an immunotherapy. In certain embodiments, the method comprises detecting a plurality of neoantigens of MUC16. In certain embodiments, the one or more neoantigen is selected from the neoantigenic peptides listed in Table 1.

Additionally, the presently disclosed subject matter provides a method for predicting the responsiveness of a subject having pancreatic cancer to an immunotherapy. In certain embodiments, the method comprises: (a) obtaining a biological sample from the subject; and (b) detecting one or more neoantigen in MUC16 in the biological sample; wherein the presence of one or more neoantigen, and preferably a plurality of neoantigens, in MUC16 in the biological sample indicates that the subject is likely to be responsive to an immunotherapy. In certain embodiments, the method comprises detecting a plurality of neoantigens of MUC16. In certain embodiments, the one or more neoantigen is selected from the neoantigenic peptides listed in Table 1.

In certain embodiments, the neoantigen is a peptide, for example a peptide incorporated into a larger protein. In certain embodiments, the neoantigen is about 8 to 11 amino acids in length. In certain embodiments each neoantigen in the plurality of neoantigens of a clone in the plurality of clones is a peptide that is 3-30 amino acids, e.g., about 3-5, about 5-15 (e.g., about 8-11, about 5-10, or about 10-15), about 15-20, about 20-25, or about 20-30 amino acids, in length. In certain embodiments, each neoantigen in the plurality of neoantigens of a clone in the plurality of clones is a peptide that is about 8-11 amino acids in length. In certain embodiments, each neoantigen in the plurality of neoantigens of a clone in the plurality of clones is a peptide that is about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 amino acids in length. In certain embodiments, each neoantigen in the plurality of neoantigens of a clone in the plurality of clones is a peptide that is at least about 3, at least about 5, or at least about 8 amino acids in length. In certain embodiments, each neoantigen in the plurality of neoantigens of a clone in the plurality of clones is a peptide is less than about 30, less than about 20, less than about 15, or less than about 10 amino acids in length.

In certain embodiments, the neoantigen is identified by exome sequencing. In certain embodiments, the immunotherapy is selected from the group consisting of therapies comprising one or more immune checkpoint-blocking antibody, adoptive T cell therapies, and combinations thereof. In certain embodiments, the one or more immune checkpoint-blocking antibody is selected from the group consisting of anti-CTLA-4 antibodies, anti-PD-1 antibodies, anti-PD-L1 antibodies, anti-TIM3 antibodies, anti-LAG3 antibodies, anti-GITR antibodies, anti-OX40 antibodies, anti-CD40 antibodies, anti-TIGIT antibodies, and anti-4-1BB antibodies, anti-B7-H3 antibodies, anti-B7-H4 antibodies, anti-BTLA antibodies.

Furthermore, the presently disclosed subject matter provides a population of neoantigen-specific T cells. In certain embodiments, the T cells target one or more neoantigen in MUC16. In certain embodiments, the one or more neoantigen in MUC16 is selected from the neoantigenic peptides listed in Table 1. In certain embodiments, the T cells target one or more neoantigen associated with a cancer, said one or more neoantigen correlating with a neoantigen-microbial homology that is higher than the median neoantigen-microbial homology occurring in subjects with the cancer. In certain embodiments, the T cells target one or more neoantigen associated with a cancer, said neoantigen correlating with an activated T cell number that is higher than the median activated T cell number occurring in subjects with the cancer.

In certain embodiments, the T cells are selectively expanded to target the one or more neoantigen in MUC16. In certain embodiments, the one or more neoantigen in MUC16 is selected from the neoantigenic peptides listed in Table 1. In certain embodiments, the neoantigen to be targeted is selected based, at least in part, on predicted immunogenicity. In certain embodiments, a neoantigen may be selectively targeted based on one or more of the following: (i) homology to an epitope of a known pathogen or microbe; and/or (ii) ability to activate T cells, e.g. in an in vitro assay. In certain embodiments, the T cells are selectively expanded to target the one or more neoantigen associated with a cancer, said one or more neoantigen correlating with a neoantigen-microbial homology that is higher than the median neoantigen-microbial homology occurring in subjects with the cancer, where said neoantigen less frequently occurs in subjects with the cancer and having neoantigen-microbial homology at or less than the median value. In certain embodiments, the T cells are selectively expanded to target a neoantigen occurring in a subject with a cancer where said subject has an activated T cell number that is higher than the median activated T cell number of subjects with the cancer, where said neoantigen less frequently occurs in subjects with the cancer and having activated T cell numbers at or less than the median value.

In certain embodiments, the T cells comprise a recombinant antigen receptor that specifically binds to one or more neoantigen of MUC16. In certain embodiments, the one or more neoantigen of MUC16 is selected from the neoantigenic peptides listed in Table 1. In certain embodiments, the T cells comprise a recombinant antigen receptor that specifically binds to the one or more neoantigen associated with a cancer, said one or more neoantigen correlating with a neoantigen-microbial homology that is higher than the median neoantigen-microbial homology occurring in subjects with the cancer. In certain embodiments, the T cells comprise a recombinant antigen receptor that specifically binds to a neoantigen associated with a cancer, said neoantigen correlating with an activated T cell number that is higher than the median activated T cell number occurring in subjects with the cancer. In certain embodiments, the one or more neoantigen is selected from the neoantigenic peptides listed in Table 2.

In certain embodiments, the recombinant antigen receptor is a T cell receptor (TCR). In certain embodiments, the recombinant antigen receptor is a chimeric antigen receptor (CAR).

The presently disclosed subject further provides a vaccine comprising one or more neoantigen described herein or a polynucleotide encoding said neoantigen or a protein or peptide comprising said neoantigen. In certain embodiments, the vaccine comprises one or more neoantigen of MUC16, or a polynucleotide encoding said neoantigen or a protein or peptide comprising said neoantigen. In certain embodiments, the one or more neoantigen of MUC16 is selected from the neoantigenic peptides listed in Table 1. In certain embodiments, the vaccine is comprised in a vector. In certain embodiments, the vector is a viral vector. In certain embodiments, the polynucleotide is an RNA or a DNA.

The presently disclosed subject matter provides compositions comprising the T cell population described herein. The presently disclosed subject also provides compositions comprising the vaccine described herein. In certain embodiments, the composition is a pharmaceutical composition that comprises a pharmaceutically acceptable carrier.

The presently disclosed subject provides methods of treating pancreatic cancer. In certain embodiments, the method comprises administering to the subject the T cell population or the composition comprising the T cell population as described herein. In certain embodiments, the method comprises administering to the subject the vaccine or the composition comprising the vaccine as described herein.

BRIEF DESCRIPTION OF THE DRAWINGS

FIGS. 3A, 3B, 3C, 3D, 3E, and 3F collectively provide a flow chart of processes and features for determining a likelihood that a human subject afflicted with a cancer will be responsive to a treatment regimen that comprises administering a checkpoint blockade immunotherapy directed to the cancer to the subject, in accordance with some embodiments of the present disclosure.

curve 1102 represents low fitness tumors while curve 1104 represents high fitness tumors. Error bars represent standard error due to sample size and were calculated in GraphPad Prism 7 and are defined by the standard error of the Kaplan-Meier estimator using Greenwood's formula (Greenwood, 1926, "The natural duration of cancer. Rep Public Health and Related Subjects. 33). The p-values from log-rank test comparing the two KM curves are shown above each plot.

Figure 12:
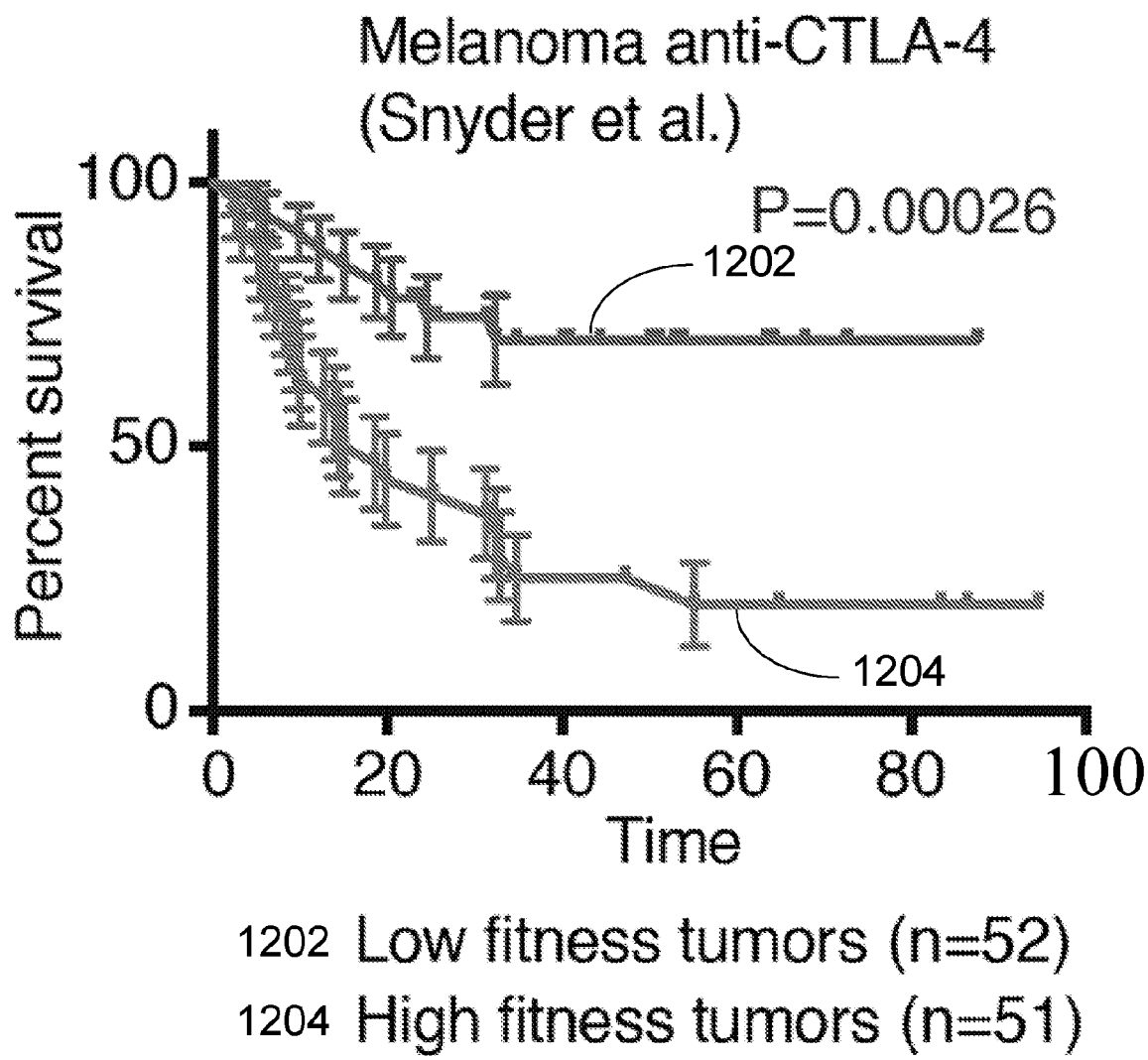

FIG. 12 illustrates how a disclosed neoantigen recognition potential fitness model is predictive of patient survival after checkpoint blockade immunotherapy. Kaplan-Meier survival curves are calculated across a melanoma patient dataset treated with anti-CTLA4 antibodies (See, Snyder et al., 2014, "Genetic Basis for Clinical Response to CTLA-4 Blockade in Melanoma," N. Engl. J. Med. 371, pp. 2189-2199). The samples are split in an unsupervised manner by the median value of their tumor's relative population size $n(\tau)=\Sigma_\alpha X_\alpha \exp(F_\alpha \tau)$, where $$F_\alpha = -\max_{i \in \text{Clone } \alpha}(A_i \times R_i).$$

Curve 1202 represents low fitness tumors while curve 1204 represents high fitness tumors. Error bars represent standard error due to sample size and were calculated in GraphPad Prism 7 and are defined by the standard error of the Kaplan-Meier estimator using Greenwood's formula (Greenwood, 1926, "The natural duration of cancer. Rep Public Health and Related Subjects. 33). The p-values from log-rank test comparing the two KM curves are shown above each plot.

Figure 13:
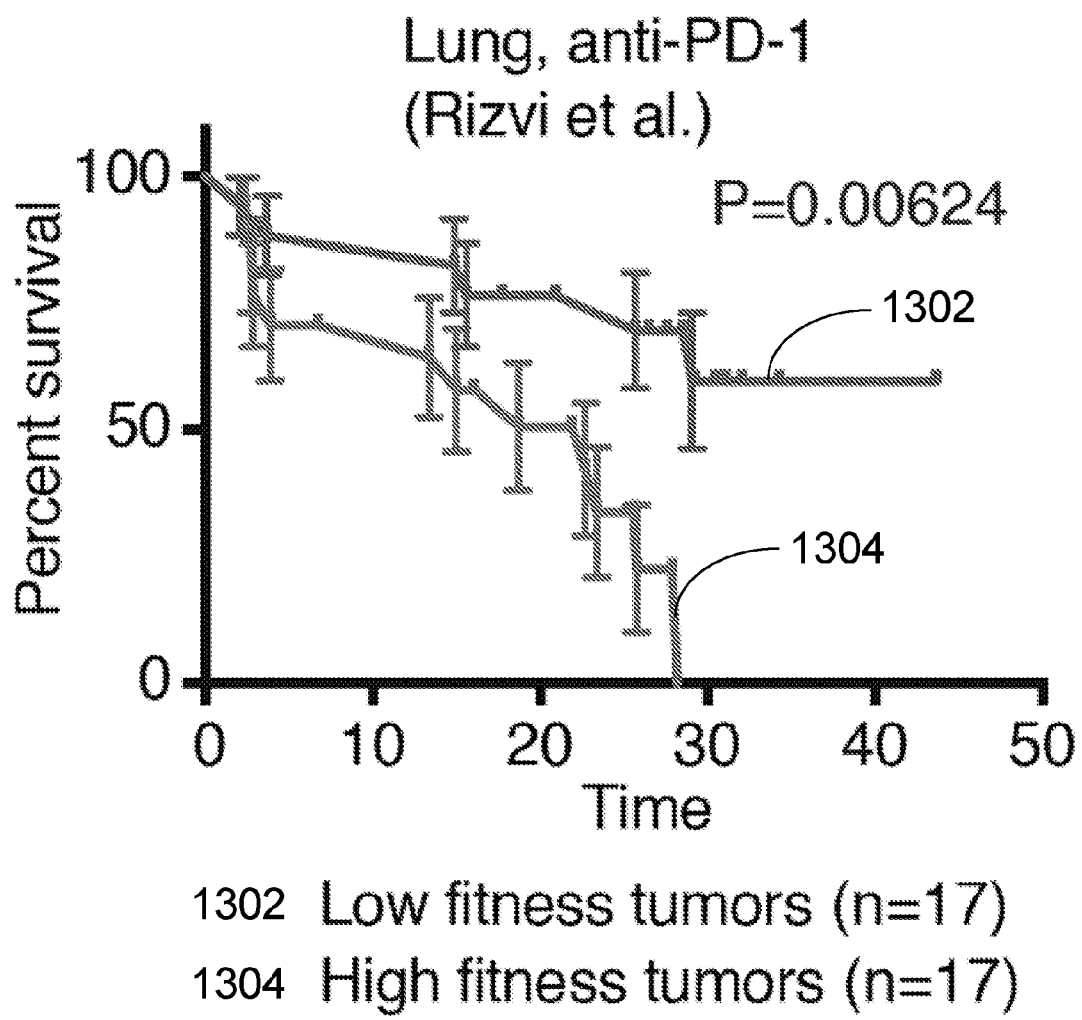

FIG. 13 illustrates how a disclosed neoantigen recognition potential fitness model is predictive of patient survival after checkpoint blockade immunotherapy. Kaplan-Meier survival curves are calculated across a melanoma patient dataset treated with anti-CTLA4 antibodies (Rizvi et al., 2015, "Mutational landscape determines sensitivity to PD-1 blockade in non-small cell lung cancer," Science 348, pp. 124-128). The samples are split in an unsupervised manner by the median value of their tumor's relative population size $n(\tau)=\Sigma_\alpha X_\alpha \exp(F_\alpha \tau)$, where $$F_\alpha = -\max_{i \in \text{Clone } \alpha}(A_i \times R_i).$$

curve 1302 represents low fitness tumors while curve 1304 represents high fitness tumors. Error bars represent standard error due to sample size and were calculated in GraphPad Prism 7 and are defined by the standard error of the Kaplan-Meier estimator using Greenwood's formula (Greenwood, 1926, "The natural duration of cancer. Rep Public Health and Related Subjects. 33). The p-values from log-rank test comparing the two KM curves are shown above each plot.

Figure 11:
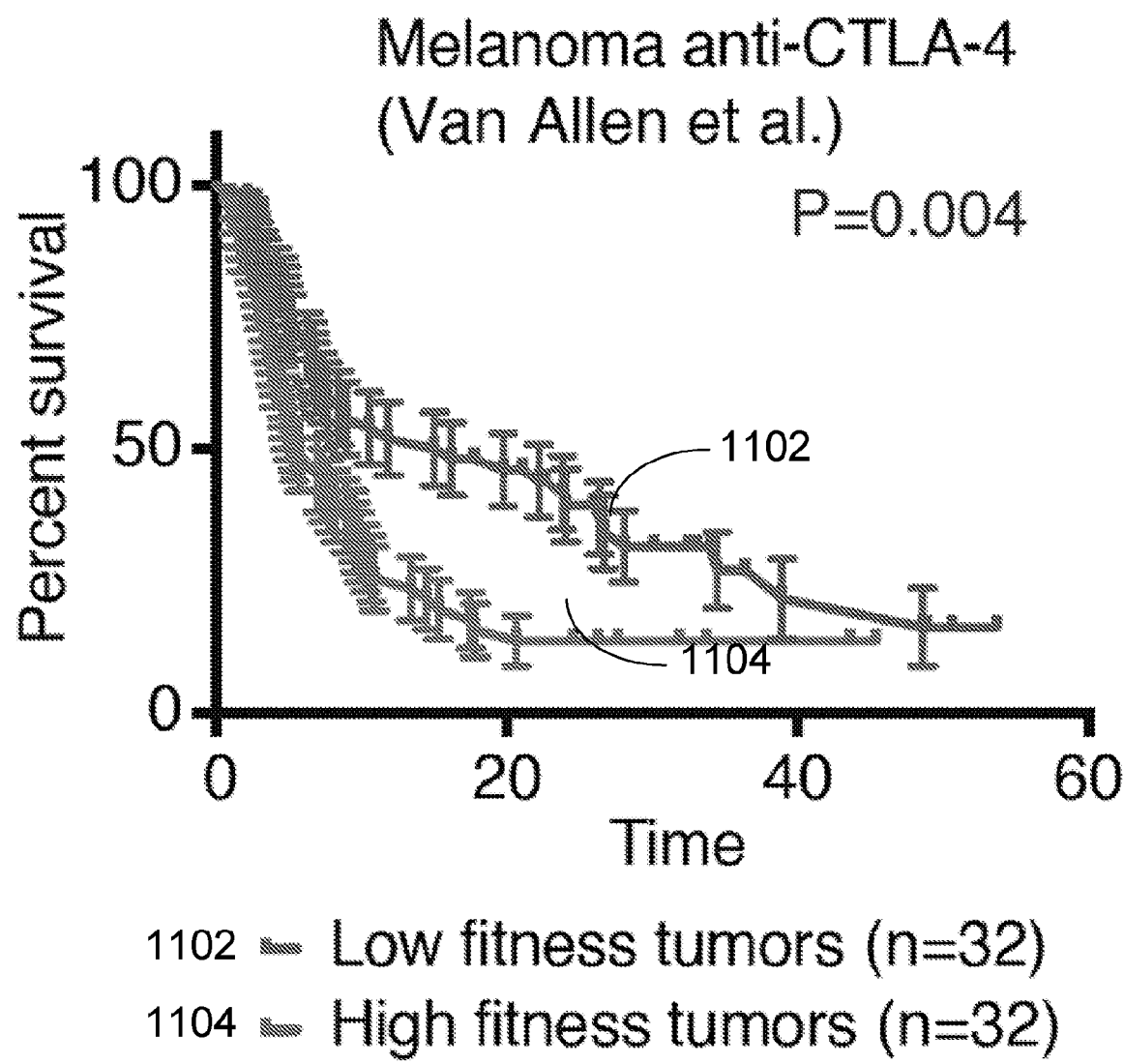
FIG. 11 illustrates how a disclosed neoantigen recognition potential fitness model is predictive of patient survival after checkpoint blockade immunotherapy. Kaplan-Meier survival curves are calculated across a melanoma patient dataset treated with anti-CTLA4 antibodies (Van Allen et al., 2015, "Genomic correlates of response to CTLA-4 blockade in metastatic melanoma," Science 350, pp. 207-211). The samples are split in an unsupervised manner by the median value of their tumor's relative population size $n(\tau)=\Sigma_\alpha X_\alpha \exp(F_\alpha \tau)$, where $$F_\alpha = - \max_{i \in \text{Clone } \alpha} (A_i \times R_i).$$
Figure 14:
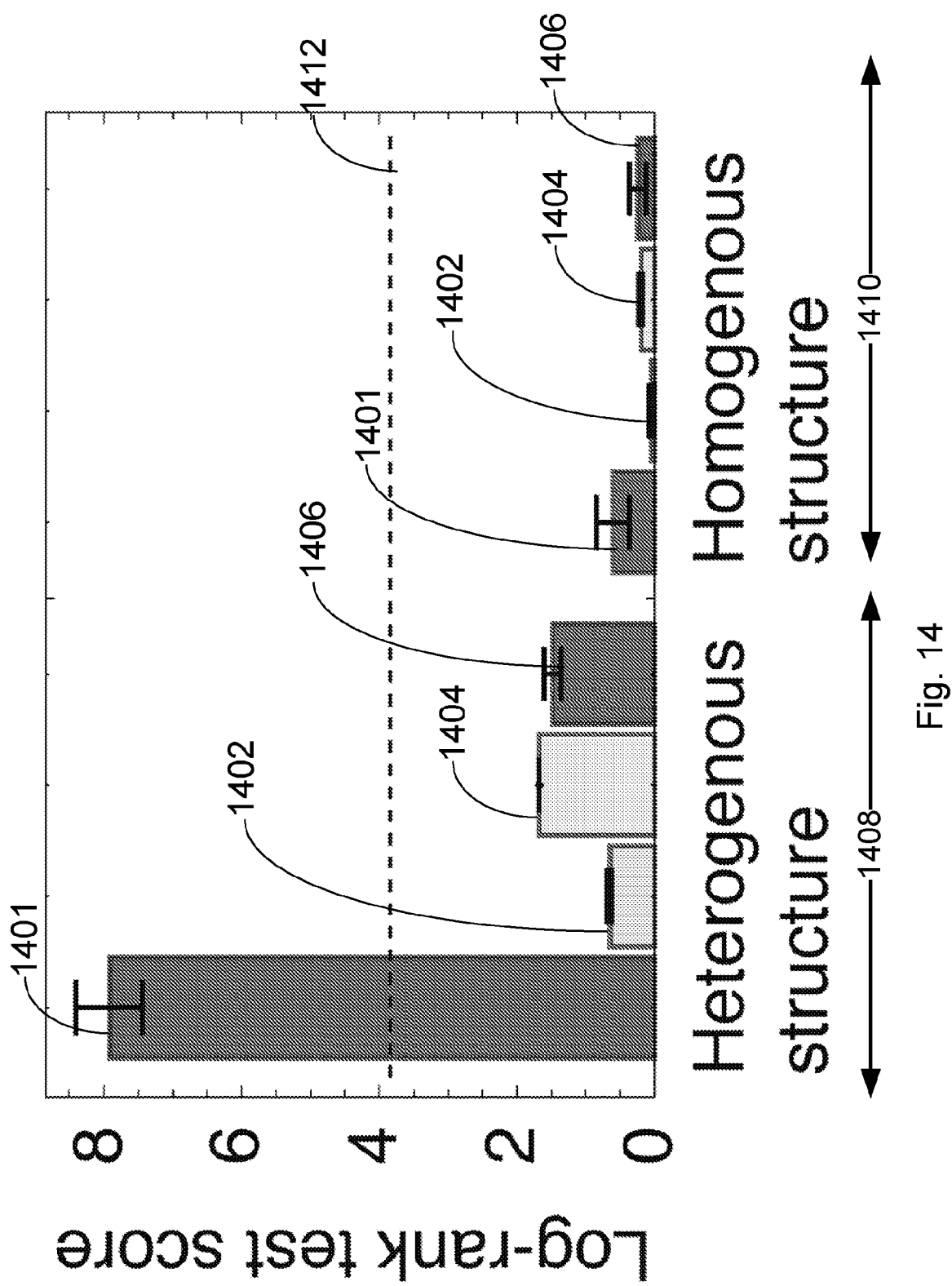

FIG. 14 illustrates the log-rank test score (higher is better) for the model of the Van Allen et al., 2015, "Genomic correlates of response to CTLA-4 blockade in metastatic melanoma," Science 350, pp. 207-211 cohort of FIG. 11, which accounts for removal of one feature of the model: full model (1401), an MHC-presentability only model in which the recognition factor is ignored and fitness is assumed to be determined only by MHC-amplitude of neoantigens in accordance with the equation $$n(\tau) = \sum_\alpha X_\alpha \exp\left[-\max_{i \in \text{Clone } \alpha} A_i \tau\right]$$

(1402) and a TCR-recognition only model in which the MHC-presentation factor is ignored and fitness is assumed to be determined only by TCR-recognition of neoantigens as given by $$n(\tau) = \sum_\alpha X_\alpha \exp\left[-\max_{i \in \text{Clone } \alpha} R_i \tau\right]$$

(1404). These values are compared with a tumors neoantigen burden, computed as a uniform fitness cost to each neoantigen, where for $L_\alpha$ the number of neoantigens in clone, this model is defined by $n(\tau)=\tau_\alpha X_\alpha \exp[-L_\alpha \tau]$ (1406), and the model is computed both over a tumor's clonal structure (heterogeneous, left 1408) and without taking heterogeneity into account, where for each of the MHC-presentability only model, the TCR-recognition only model, and the tumors neoantigen burden model, the homogenous structure equivalent is computed by assuming the tumor is strictly clonal with all neoantigens in the same clone at frequency 1 (homogenous, right 1410). The dashed line 1412 marks the score value corresponding to the significance threshold of 5%. The error bars are the standard deviation of log-rank test score acquired from the survival analysis with one sample removed from the cohort at a time (n=64).

Figure 15:
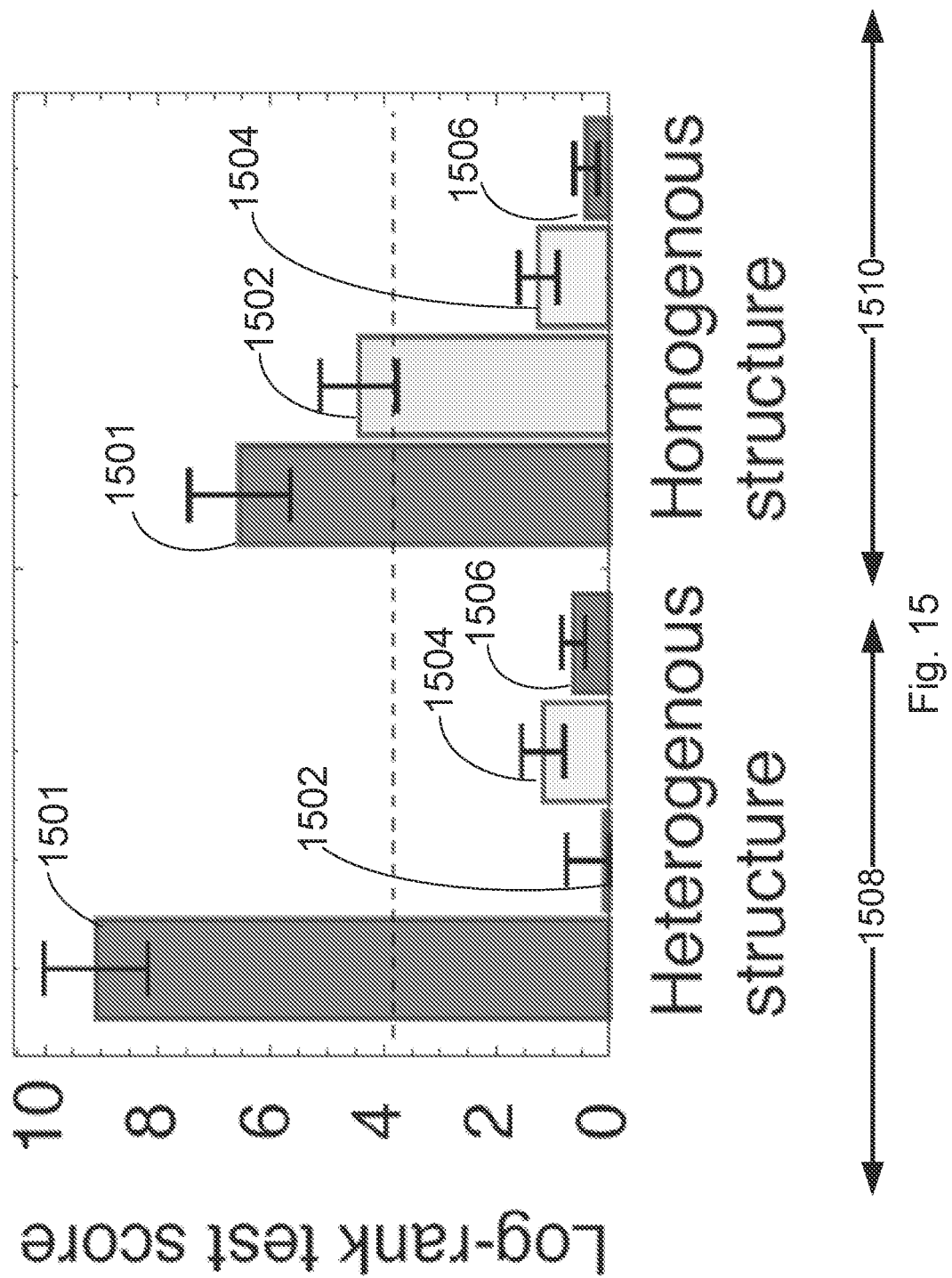

FIG. 15 illustrates the log-rank test score (higher is better) for the model of the Snyder et al., 2014, "Genetic Basis for Clinical Response to CTLA-4 Blockade in Melanoma," N. Engl. J. Med. 371, pp. 2189-2199 cohort of FIG. 12, which accounts for removal of one feature of the model: full model (1501), an MHC-presentability only model (1502) and a TCR-recognition only model (1504). These values are compared with a tumors neoantigen burden (1506), and the model is computed both over a tumor's clonal structure (clonal, left 1508) and without taking heterogeneity into account (homogenous, right 1510). The dashed line 1512 marks the score value corresponding to the significance threshold of 5%. The error bars are the standard deviation of log-rank test score acquired from the survival analysis with one sample removed from the cohort at a time (n=103).

Figure 16:
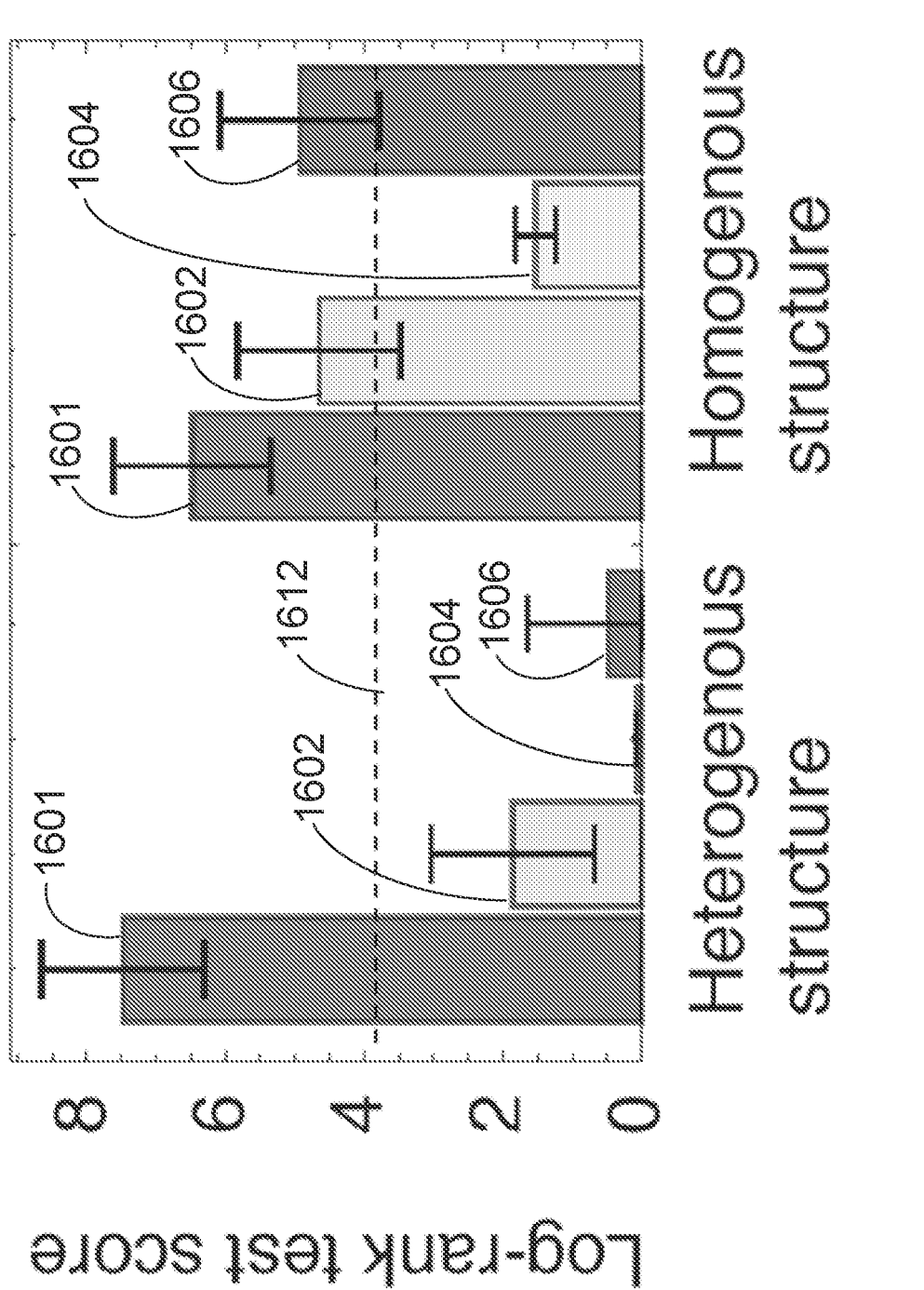

FIG. 16 illustrates the log-rank test score (higher is better) for the model of the Rizvi et al., 2015, "Mutational landscape determines sensitivity to PD-1 blockade in non-small cell lung cancer," Science 348, pp. 124-128 cohort of FIG. 13, which accounts for removal of one feature of the model: full model (1601), an MHC-presentability only model (1602) and a TCR-recognition only model (1604). These values are compared with a tumors neoantigen burden (1606), and the model is computed both over a tumor's clonal structure (clonal, left 1608) and without taking heterogeneity into account (homogenous, right 1610). The dashed line 1612 marks the score value corresponding to the significance threshold of 5%. The error bars are the standard deviation of log-rank test score acquired from the survival analysis with one sample removed from the cohort at a time (n=34).

FIG. 17 illustrates a survival landscape for Snyder et al., 2014, "Genetic Basis for Clinical Response to CTLA-4 Blockade in Melanoma," N. Engl. J. Med. 371, pp. 2189-2199 (A) and Rizvi et al., 2015, "Mutational landscape determines sensitivity to PD-1 blockade in non-small cell lung cancer, Science 348, pp. 124-128 (B) cohorts in accordance with an embodiment of the present disclosure.

Figure 18:
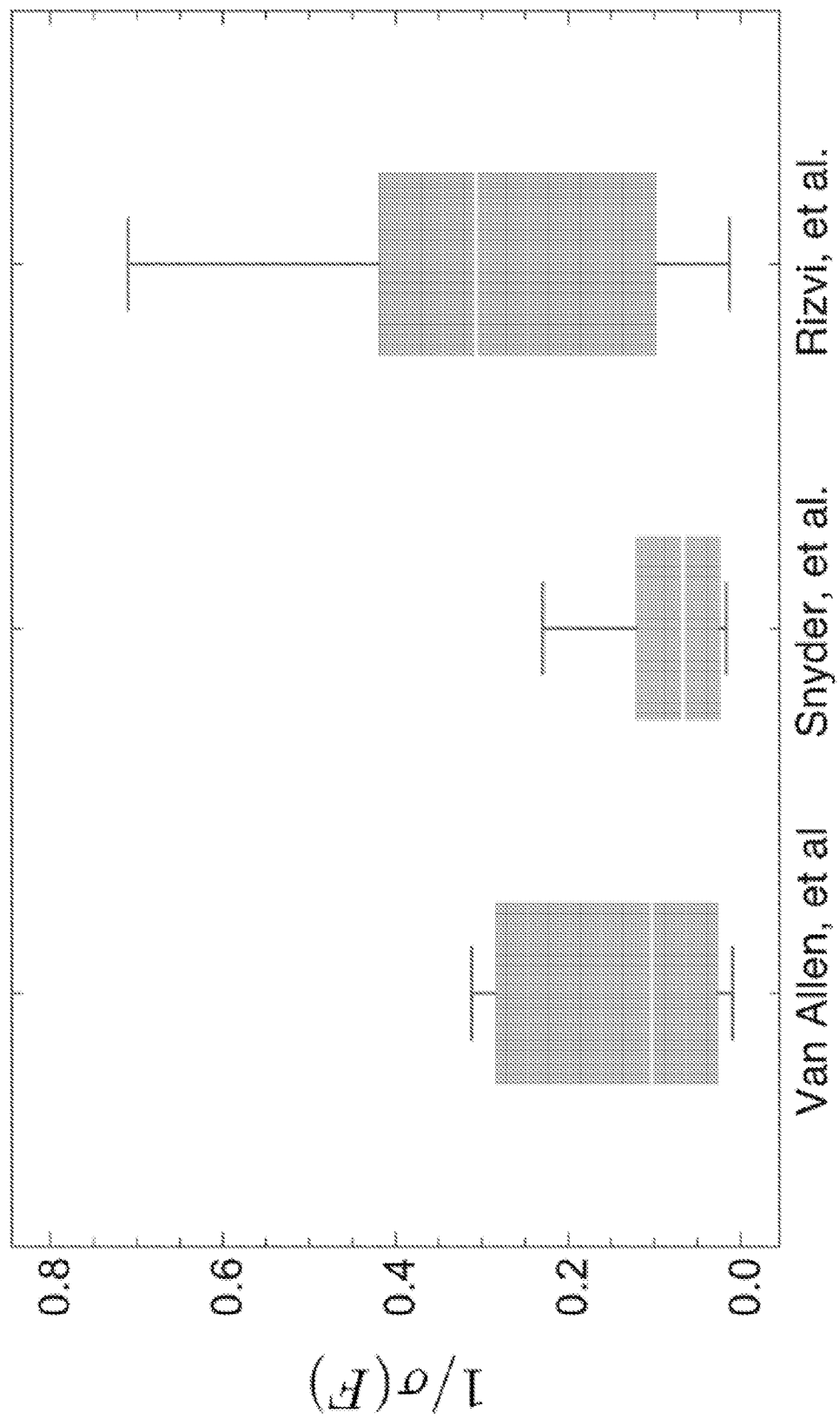

FIG. 18 illustrates the distribution of characteristic times scales of samples with clonal fitness heterogeneity for the three patient cohorts (Van Allen et al., 2015, "Genomic correlates of response to CTLA-4 blockade in metastatic melanoma," Science 350, pp. 207-211, Snyder et al., 2014, "Genetic Basis for Clinical Response to CTLA-4 Blockade in Melanoma," N. Engl. J. Med. 371, pp. 2189-2199, and Rizvi et al., 2015, "Mutational landscape determines sensitivity to PD-1 blockade in non-small cell lung cancer, Science 348, pp. 124-128). These distributions consistently define the interval for relevant time scales of $\tau$, in all datasets investigated $\tau \in [0,0.5]$, in accordance with an embodiment of the present disclosure.

Figure 19:
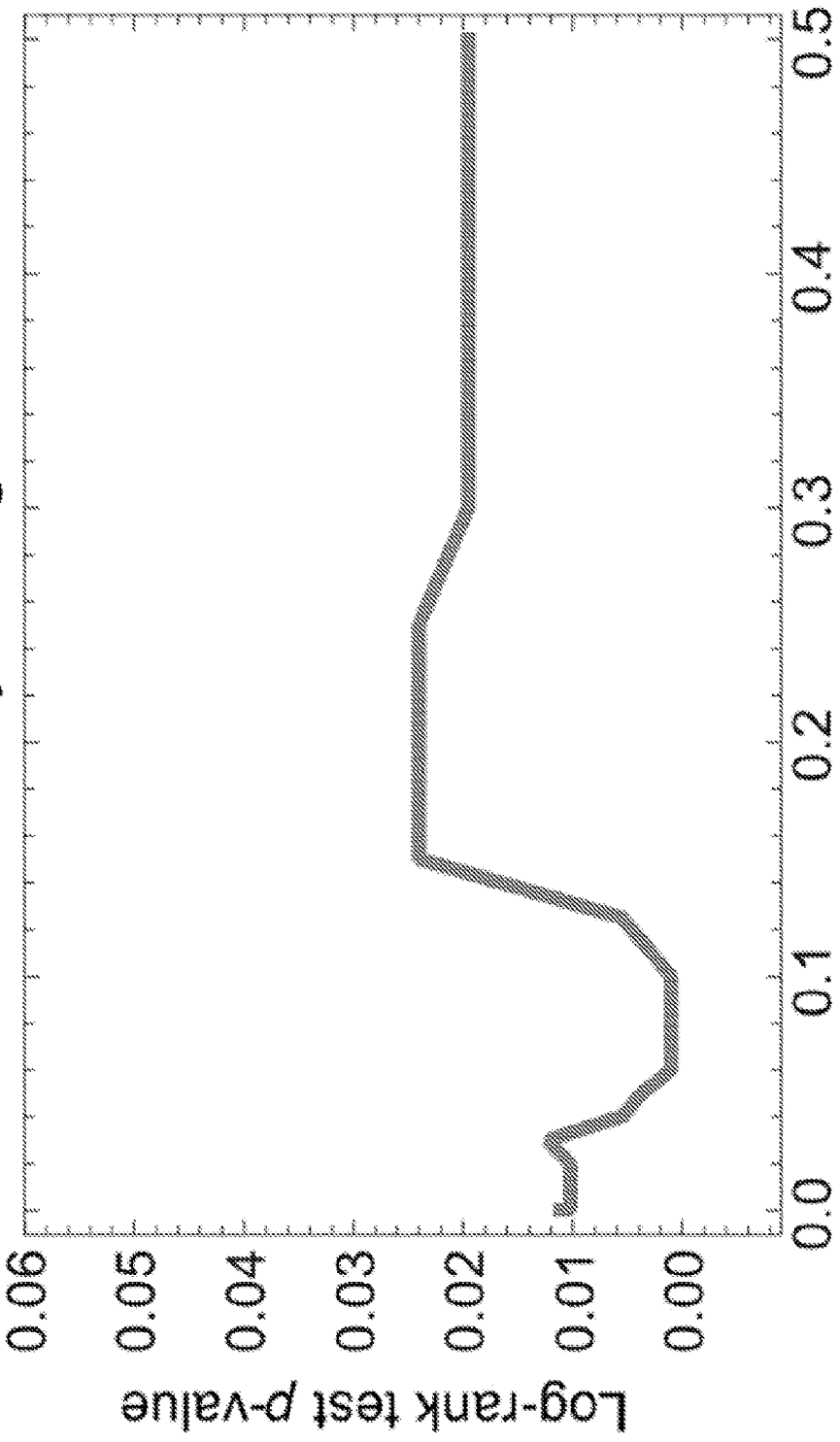

FIG. 19 illustrates significance of survival analysis reported as the result of the log-rank test on the Van Allen et al., 2015, "Genomic correlates of response to CTLA-4 blockade in metastatic melanoma," Science 350, pp. 207-211 dataset with sample split at a median value $n(\tau)$ plotted as a function of $\tau$, in accordance with an embodiment of the present disclosure. The chosen value of parameter $\tau=0.06$ and a broad surrounding interval gives highly significant sample segregation in the Van Allen et al., 2015, "Genomic correlates of response to CTLA-4 blockade in metastatic melanoma," Science 350, pp. 207-211 dataset.

Figure 20:
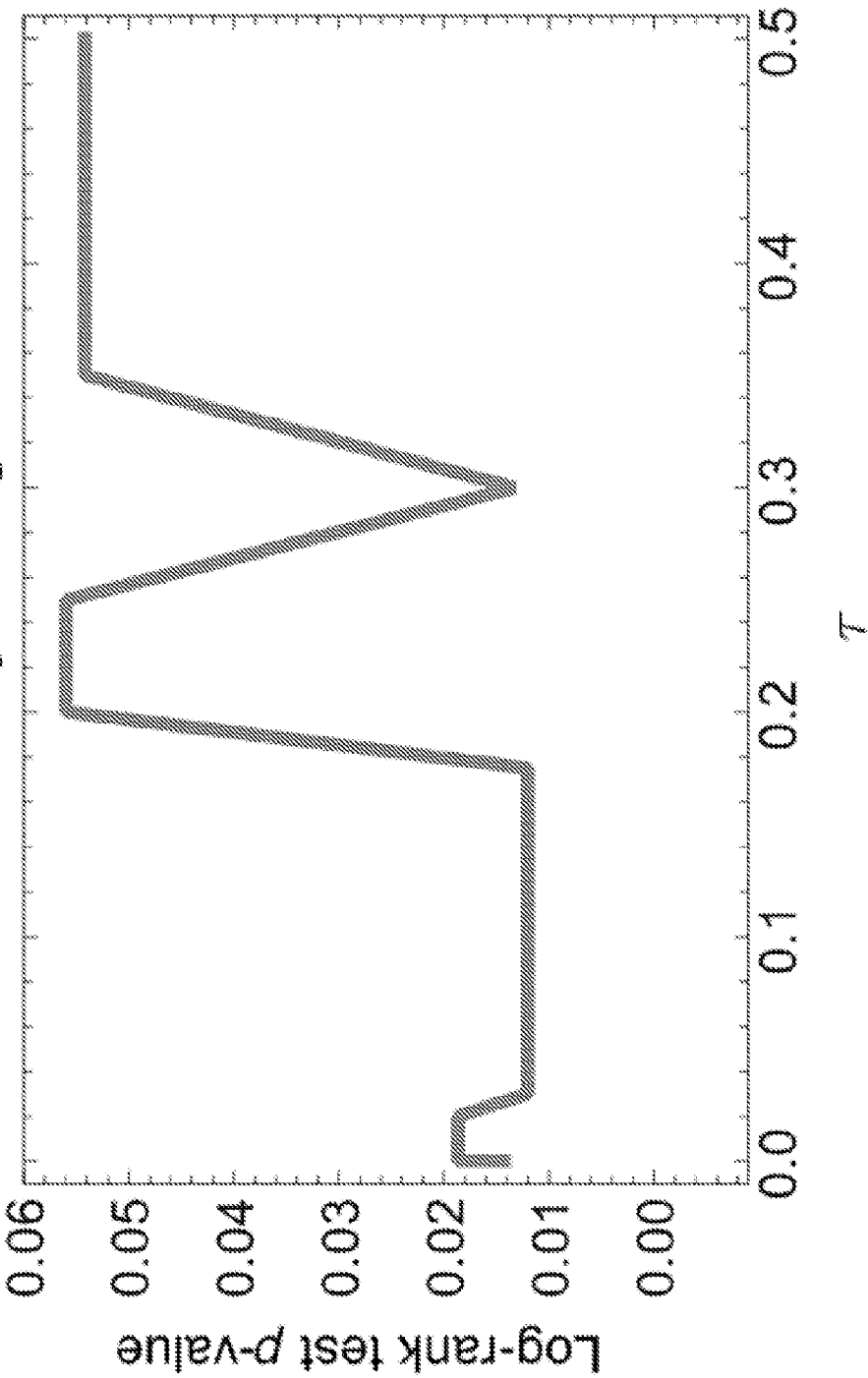

FIG. 20 illustrates significance of survival analysis reported as the result of the log-rank test on the Snyder et al., 2014, "Genetic Basis for Clinical Response to CTLA-4 Blockade in Melanoma," N. Engl. J. Med. 371, pp. 2189-2199 dataset with sample split at a median value $n(\tau)$ plotted as a function of $\tau$, in accordance with an embodiment of the present disclosure. The chosen value of parameter $r=0.06$ and a broad surrounding interval gives highly significant sample segregation in the Snyder et al., 2014, "Genetic Basis for Clinical Response to CTLA-4 Blockade in Melanoma," N. Engl. J. Med. 371, pp. 2189-2199 dataset.

Figure 21:
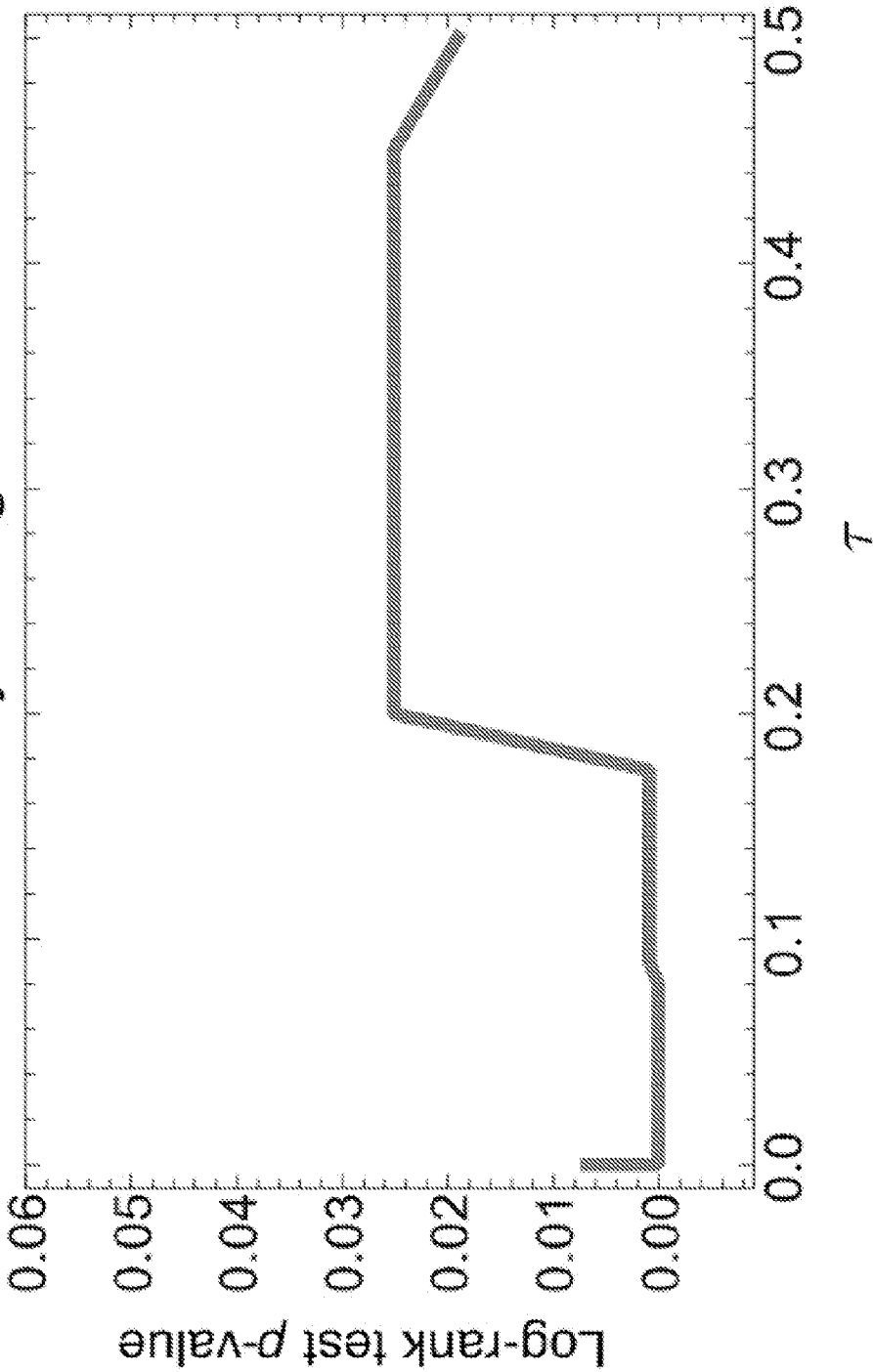

FIG. 21 illustrates significance of survival analysis reported as the result of the log-rank test on the Rizvi et al., 2015, "Mutational landscape determines sensitivity to PD-1 blockade in non-small cell lung cancer, Science 348, pp. 124-128 dataset with sample split at a median value $n(\tau)$ plotted as a function of $\tau$, in accordance with an embodiment of the present disclosure. The chosen value of parameter $r=0.06$ and a broad surrounding interval gives highly significant sample segregation in the Rizvi et al., 2015, "Mutational landscape determines sensitivity to PD-1 blockade in non-small cell lung cancer, Science 348, pp. 124-128 dataset.

Figure 22:
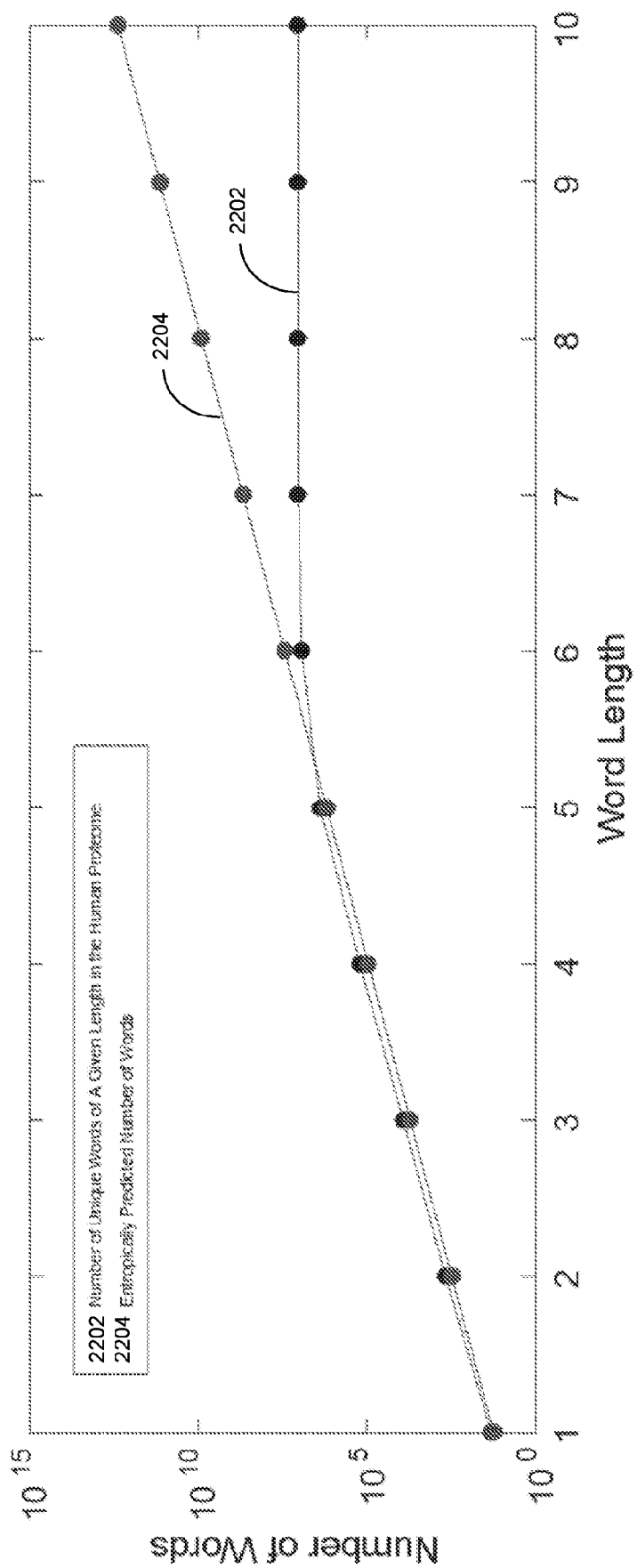

FIG. 22 illustrates how word usage in a proteome is exhausted between 5 and 6 letter words. Given the entropy of the genome, see Lehmann et al., 2016, "Fundamental amino acid mass distributions and entropy costs in proteomes," J. Theor. Biol. 410, pp. 119-124 (2016), hereby incorporated by reference, the expected number of words of a given length in the proteome is calculated as a function of word length. This is compared that to the number of unique words in the proteome of a given length. Between 5 and 6 letters the two curves diverge due to the finite size of the genome. By the time one reaches 9 letter nonamers (the length of a neoantigen) this divergence is of several orders of magnitude.

FIG. 23 illustrates the ranking of fitness models when accounting for tumor subclonal composition in which the ranking of fitness models evaluated for the Van Allen et al., 2015, "Genomic correlates of response to CTLA-4 blockade in metastatic melanoma," Science 350, pp. 207-211 (n=103) cohort in accordance with an embodiment of the present disclosure.

FIG. 24 illustrates the ranking of fitness models when accounting for tumor subclonal composition in which the ranking of fitness models evaluated for the Snyder et al., 2014, "Genetic Basis for Clinical Response to CTLA-4 Blockade in Melanoma," N. Engl. J. Med. 371, pp. 2189-2199 (n=64) cohort in accordance with an embodiment of the present disclosure.

FIG. 25 illustrates the ranking of fitness models when accounting for tumor subclonal composition in which the ranking of fitness models evaluated for the Rizvi et al., 2015, "Mutational landscape determines sensitivity to PD-1 blockade in non-small cell lung cancer, Science 348, pp. 124-128 (n=34) cohort in accordance with an embodiment of the present disclosure.

Figure 26:
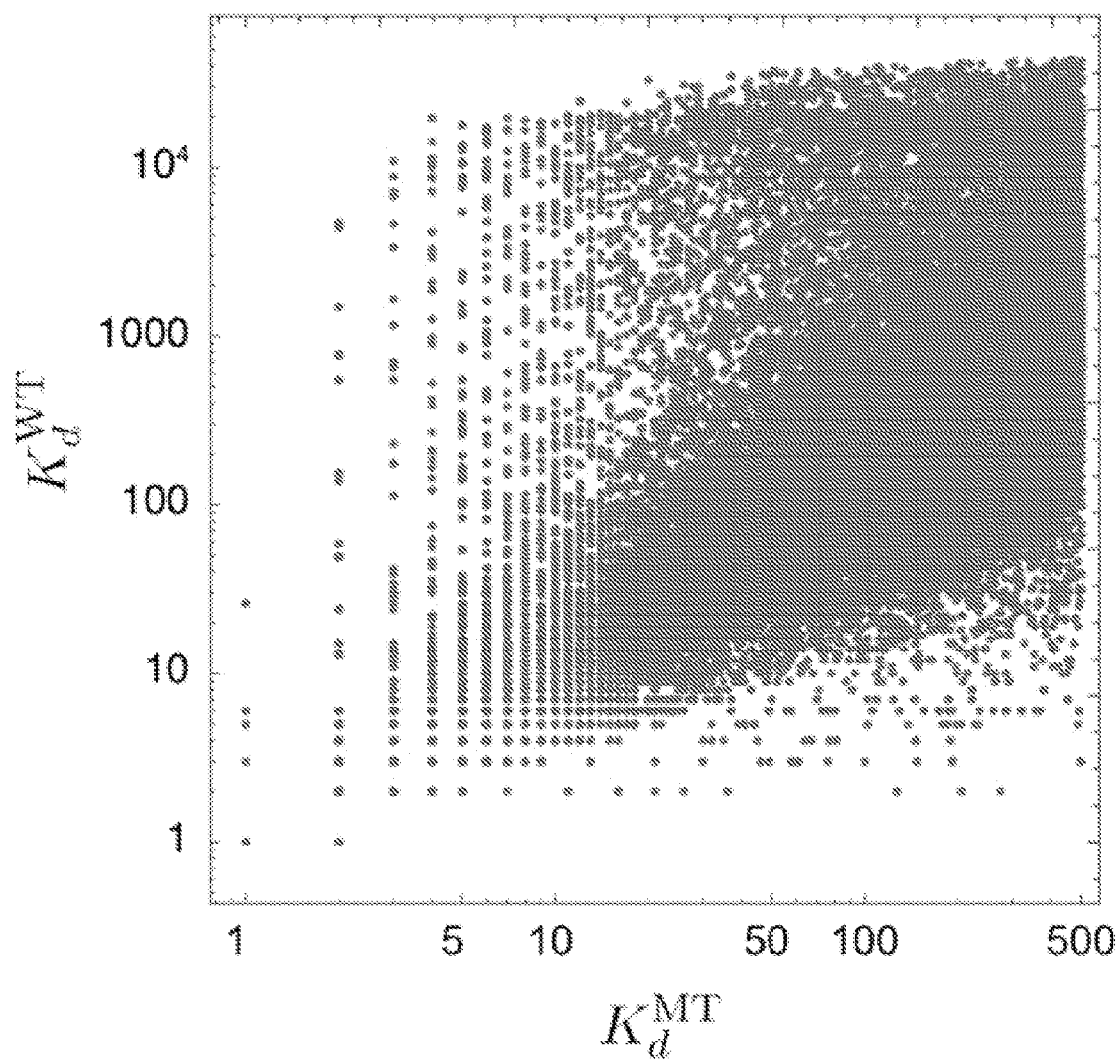

FIG. 26 illustrates inferred MHC binding affinities of mutant versus wildtype peptides in the Van Allen et al., 2015, "Genomic correlates of response to CTLA-4 blockade in metastatic melanoma," Science 350, pp. 207-211 dataset in accordance with an embodiment of the present disclosure.

Figure 27:
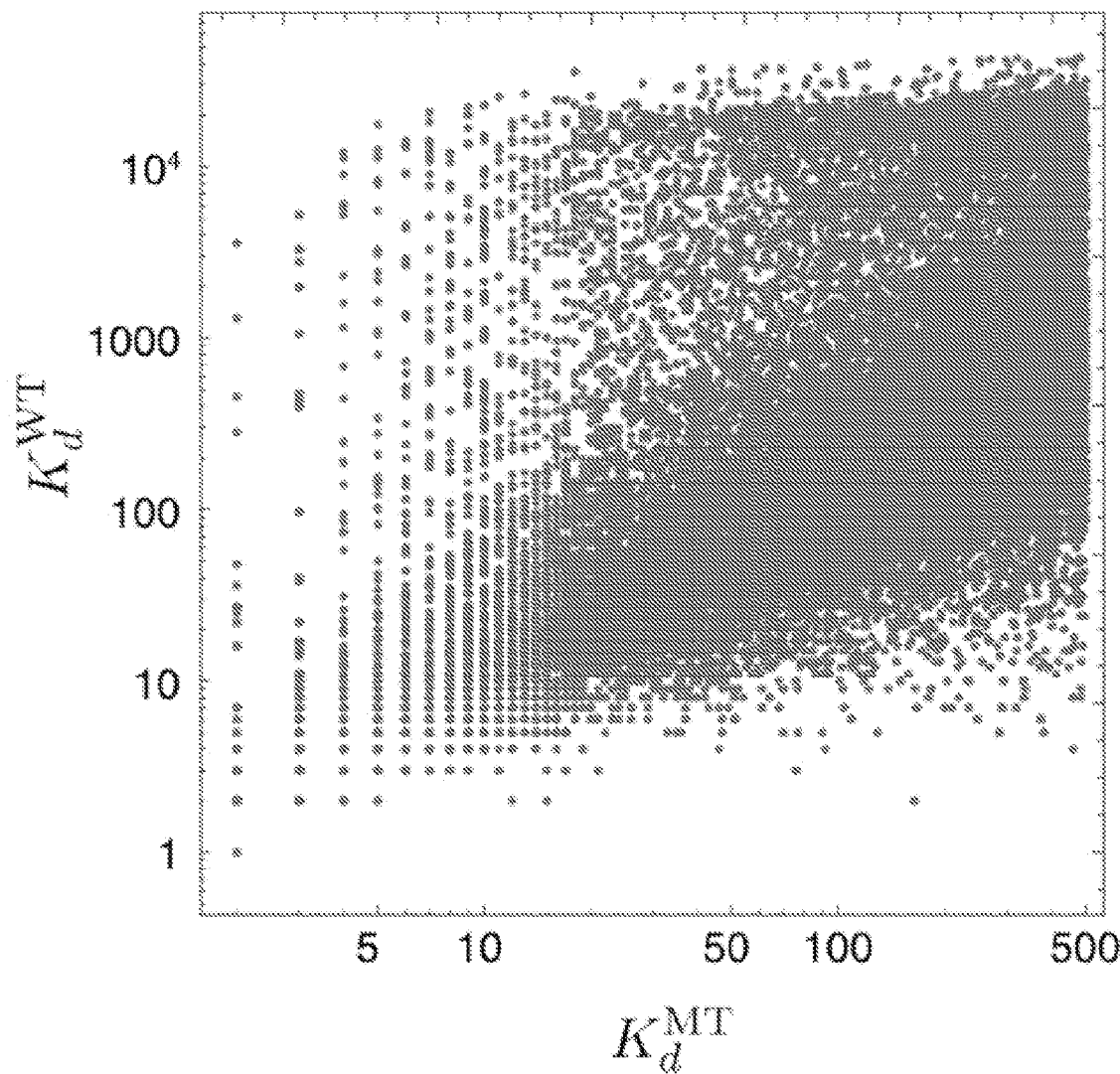

FIG. 27 illustrates inferred MHC binding affinities of mutant versus wildtype peptides in the Snyder et al., 2014, "Genetic Basis for Clinical Response to CTLA-4 Blockade in Melanoma," N. Engl. J. Med. 371, pp. 2189-2199 dataset in accordance with an embodiment of the present disclosure.

Figure 28:
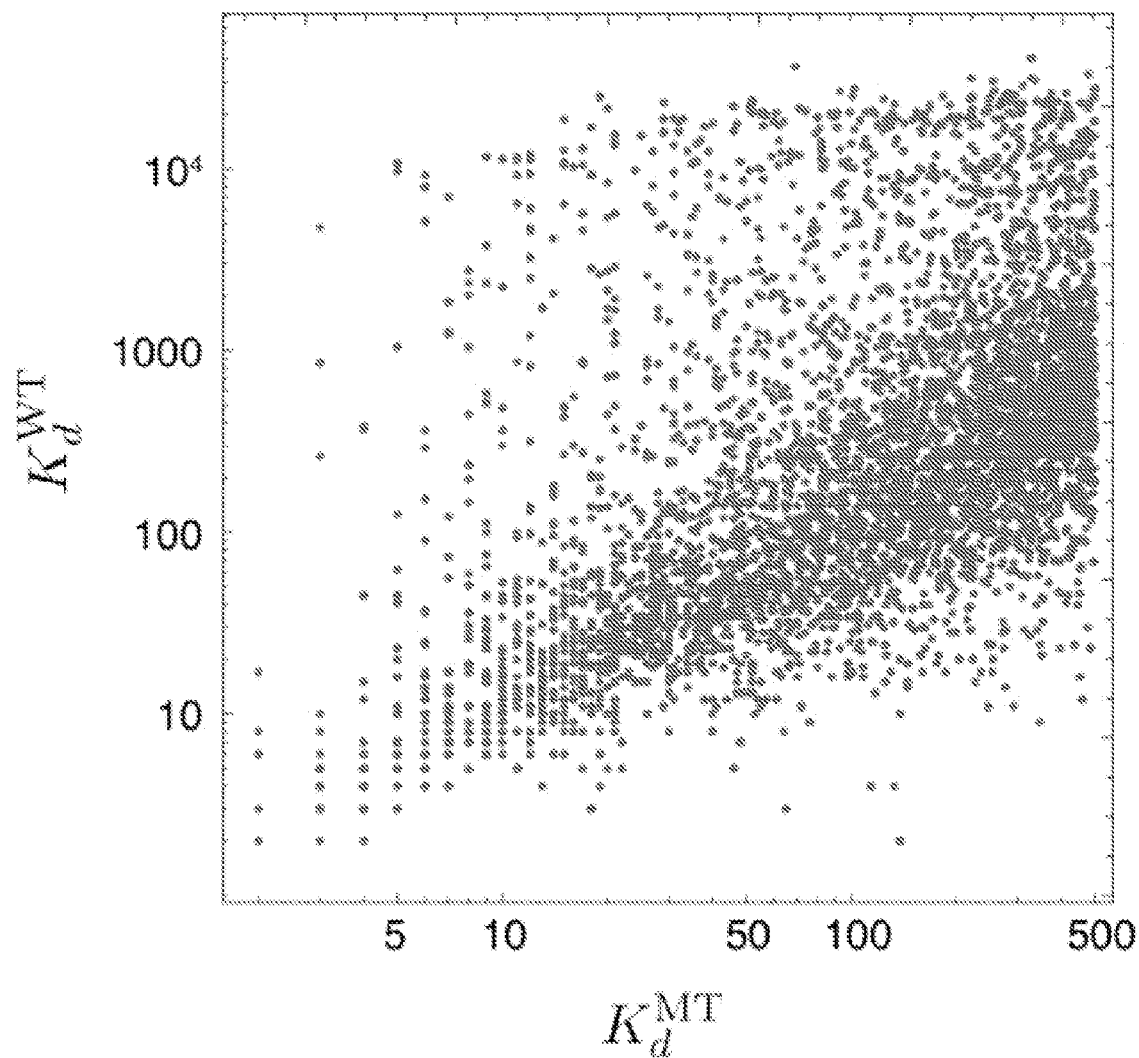

FIG. 28 illustrates inferred MHC binding affinities of mutant versus wildtype peptides in the Rizvi et al., 2015, "Mutational landscape determines sensitivity to PD-1 blockade in non-small cell lung cancer, Science 348, pp. 124-128 dataset in accordance with an embodiment of the present disclosure.

Figure 29:
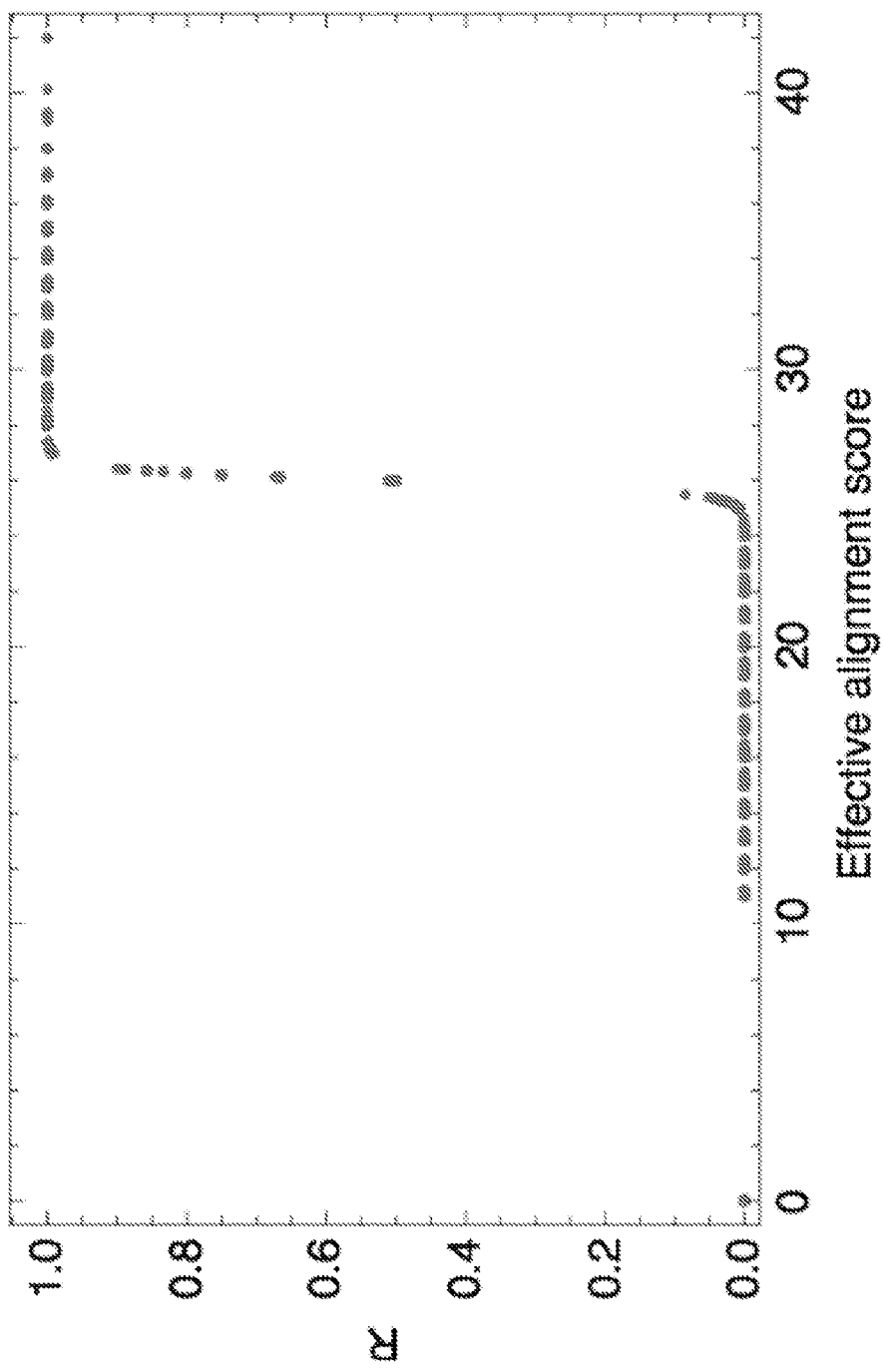

FIG. 29 illustrates alignments to IEDB epitopes in which the TCR recognition probability for a neoantigen is a sigmoidal function of the neoantigen's alignment scores with IEDB epitopes, here shown as evaluated for the set of neoantigens from Van Allen et al. cohort patients, using a consistent set of parameters in accordance with an embodiment of the present disclosure.

Figure 30A:
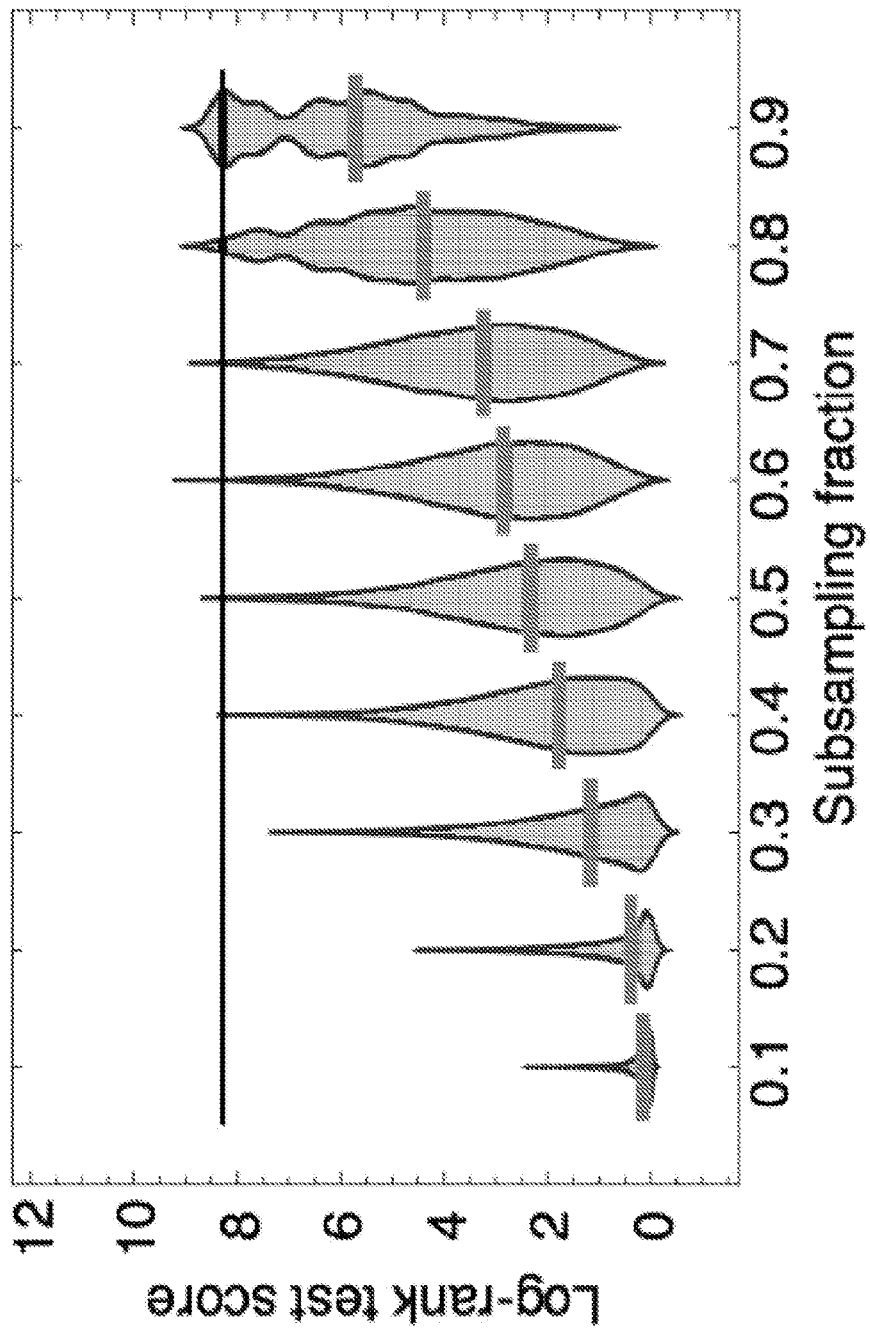
Figure 30B:
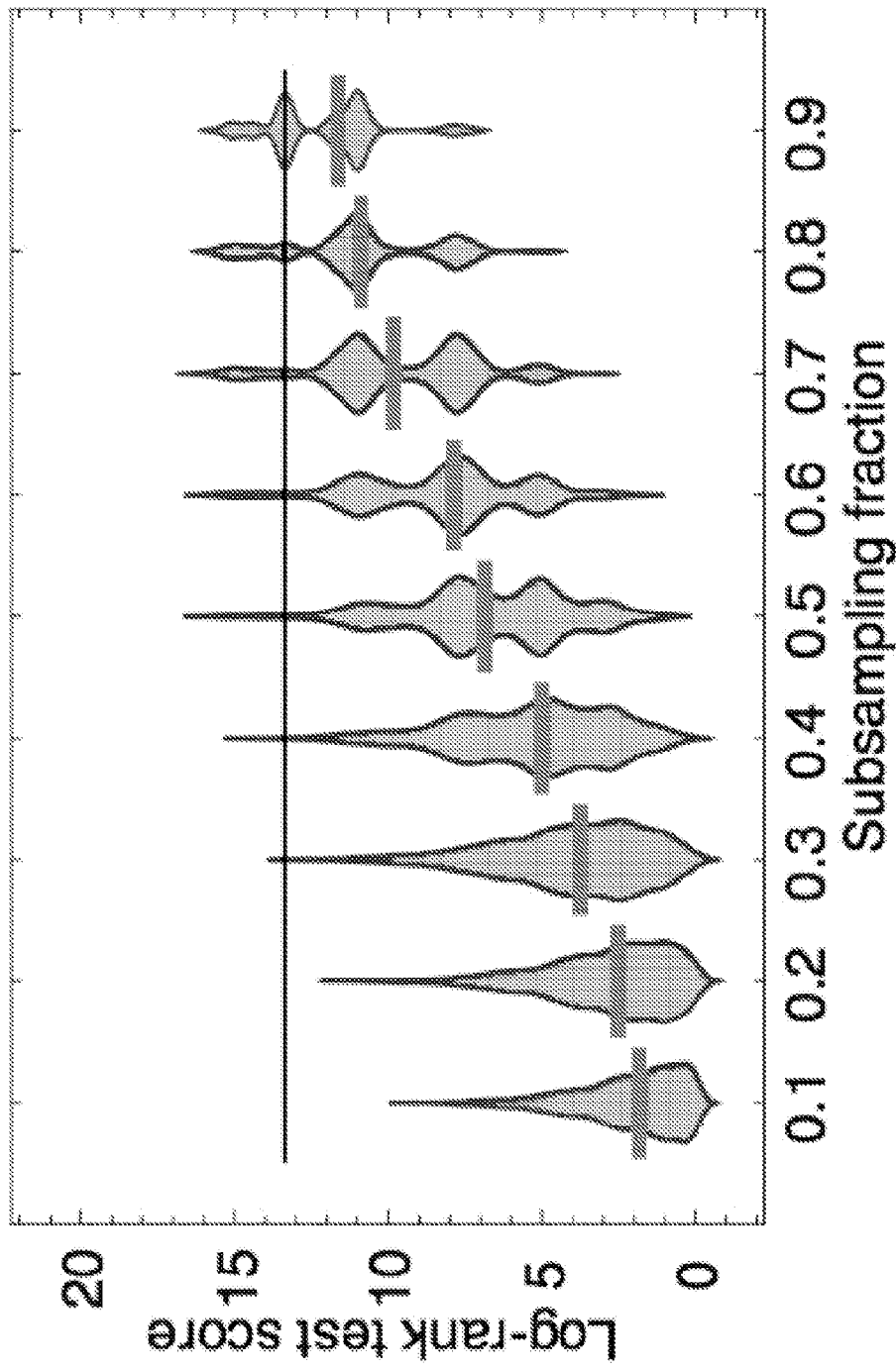
Figure 30C:
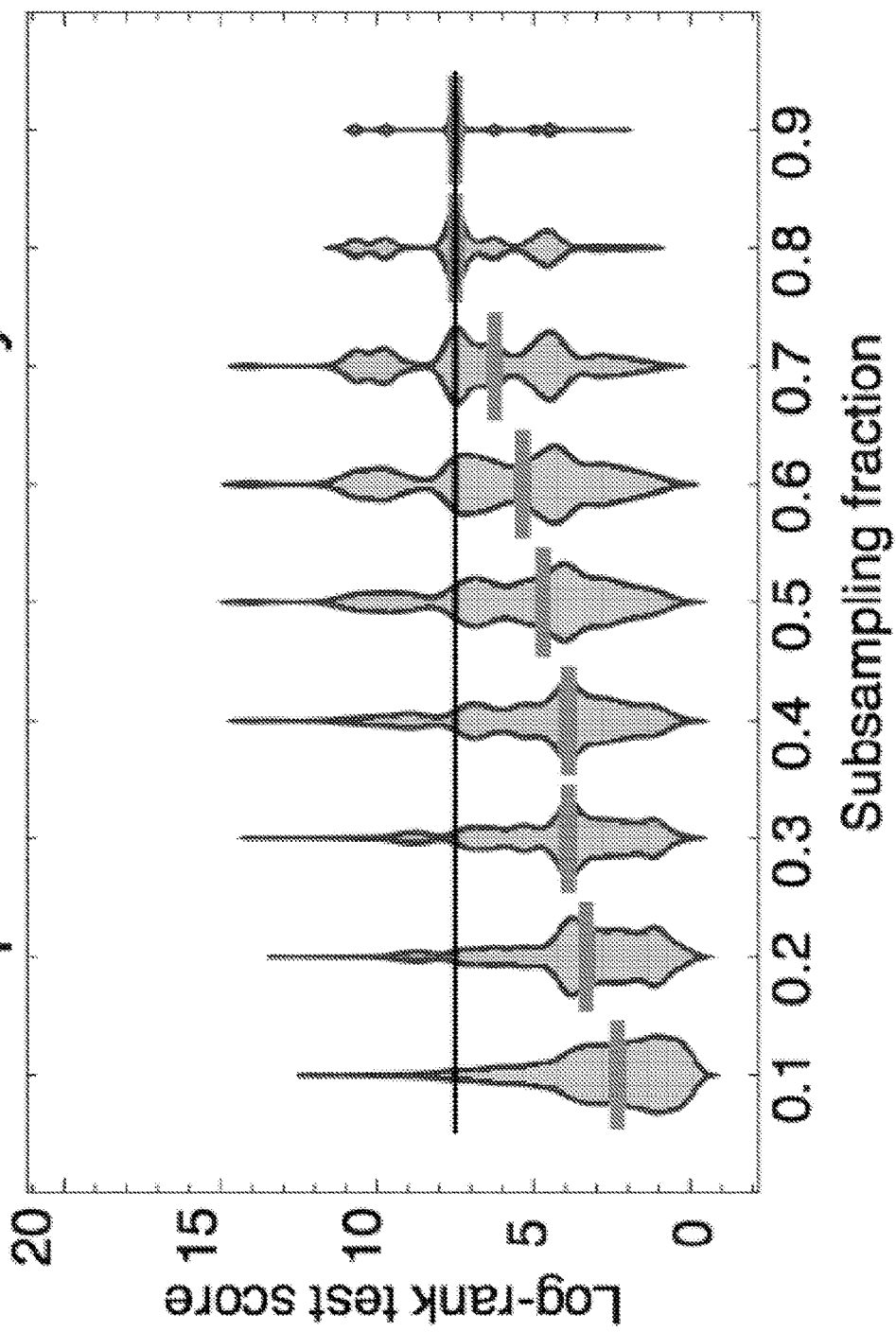
Figure 30D:
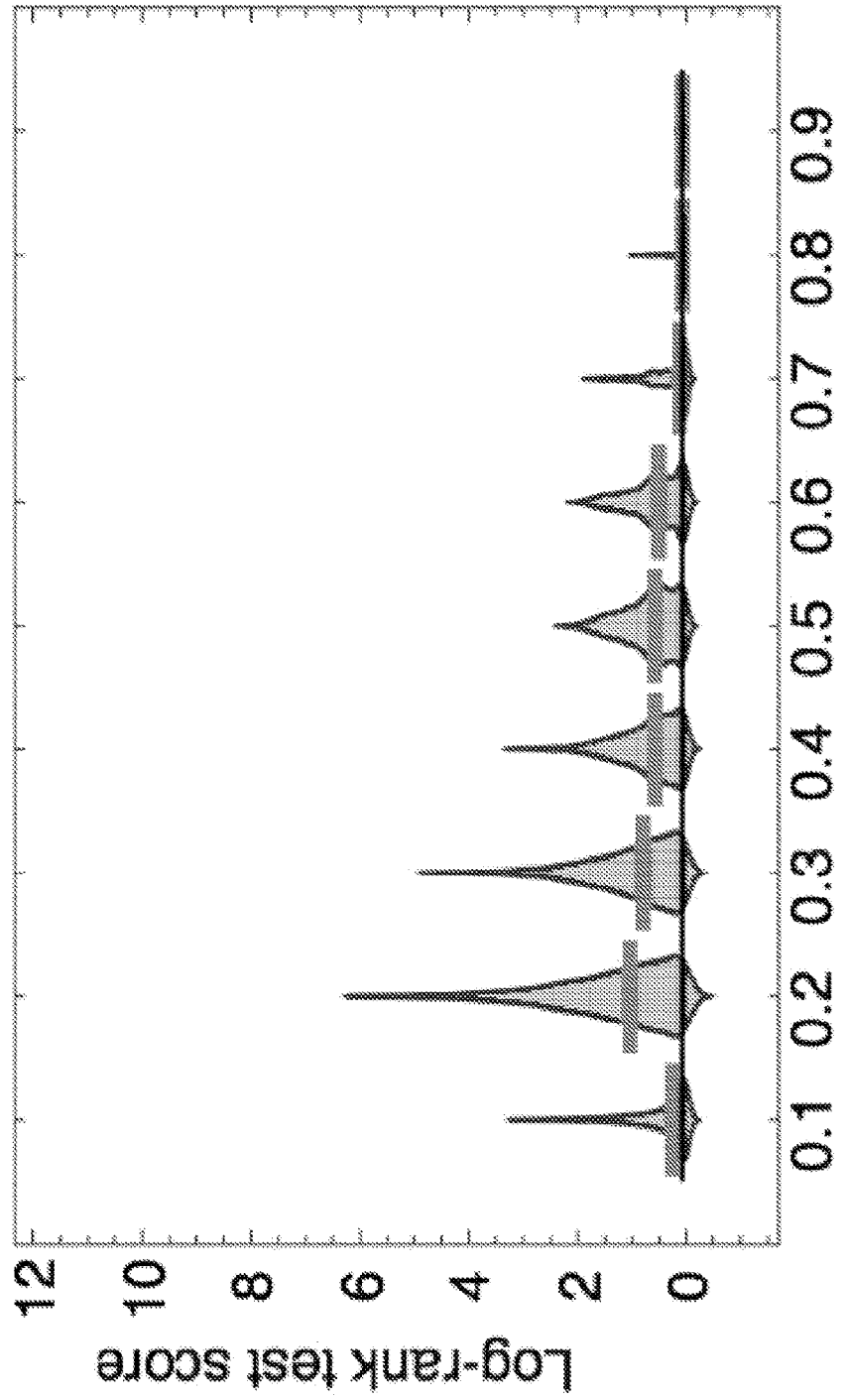
Figure 30E:
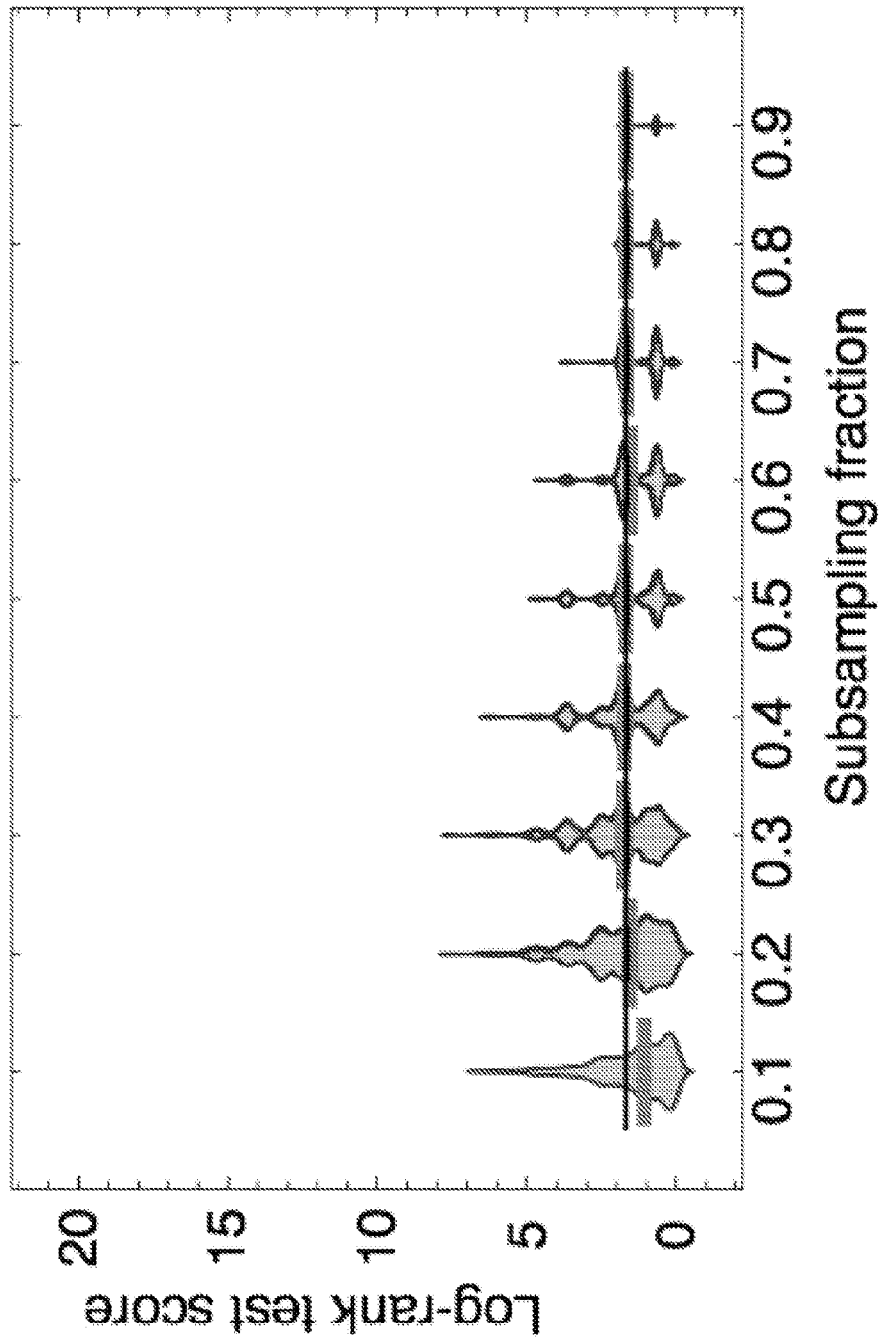
Figure 30F:
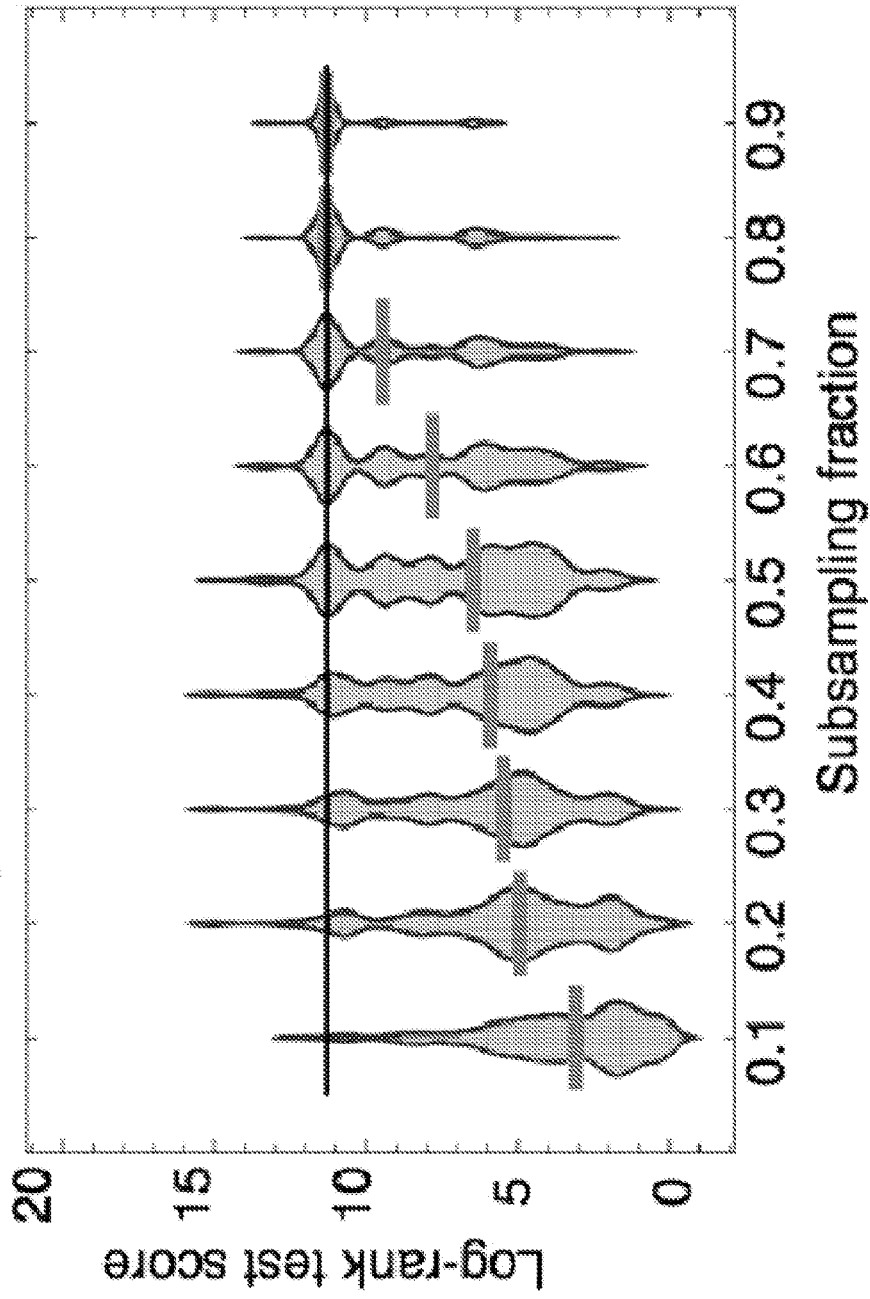

FIGS. 30A, 30B, 30C, 30D, 30E, and 30F illustrate the effect of IEDB sequence content on predictive power of neoantigen recognition potential fitness model. Predictions were performed using subsampled IEDB epitope sequences, with subsampling rate varying between 0.1 and 0.9. For each rate, 10,000 iterations were performed to obtain a distribution of log-rank test scores. The violin plots represent data density at a given value on a vertical axis (n=10,000). Solid black lines mark the log-rank test score of the prediction on the full set of epitope sequences and gray thick lines mark the median scores on subsampled data. FIGS. 30A, 30B, 30C, subsampling of the original set of IEDB sequences, supported by positive T-cell assays, shows that quality of predictions decreases with subsampling rate. Prediction quality is more robust in the Snyder et al. and Rizvi et al. datasets. FIGS. 30D, 30E, and 30F, analogous subsampling procedure was repeated on IEDB sequences not supported by positive T-cell assays. For Van Allen et al. and Snyder et al., model performance is substantially lowered.

Figure 31A:
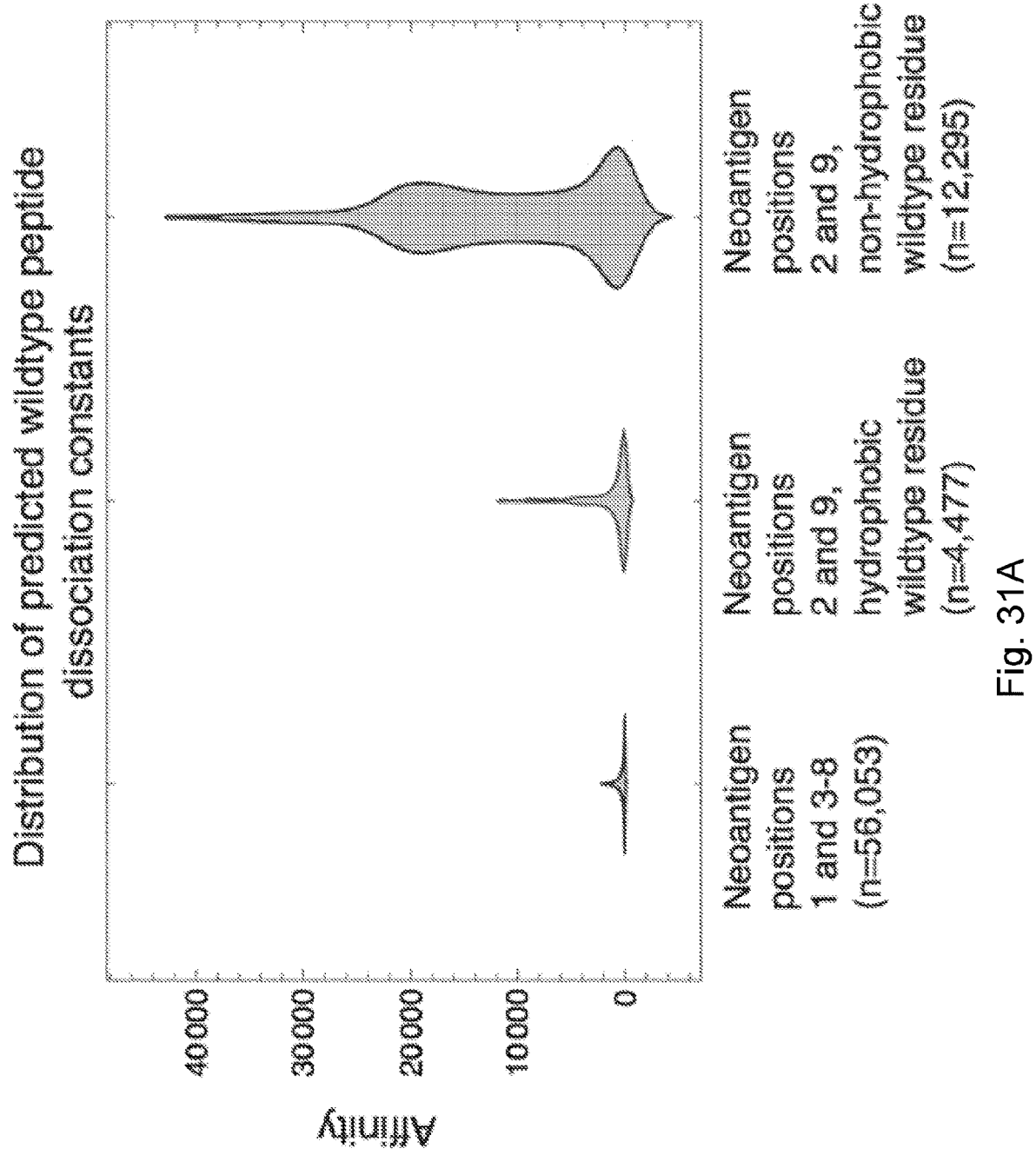
Figure 31C:
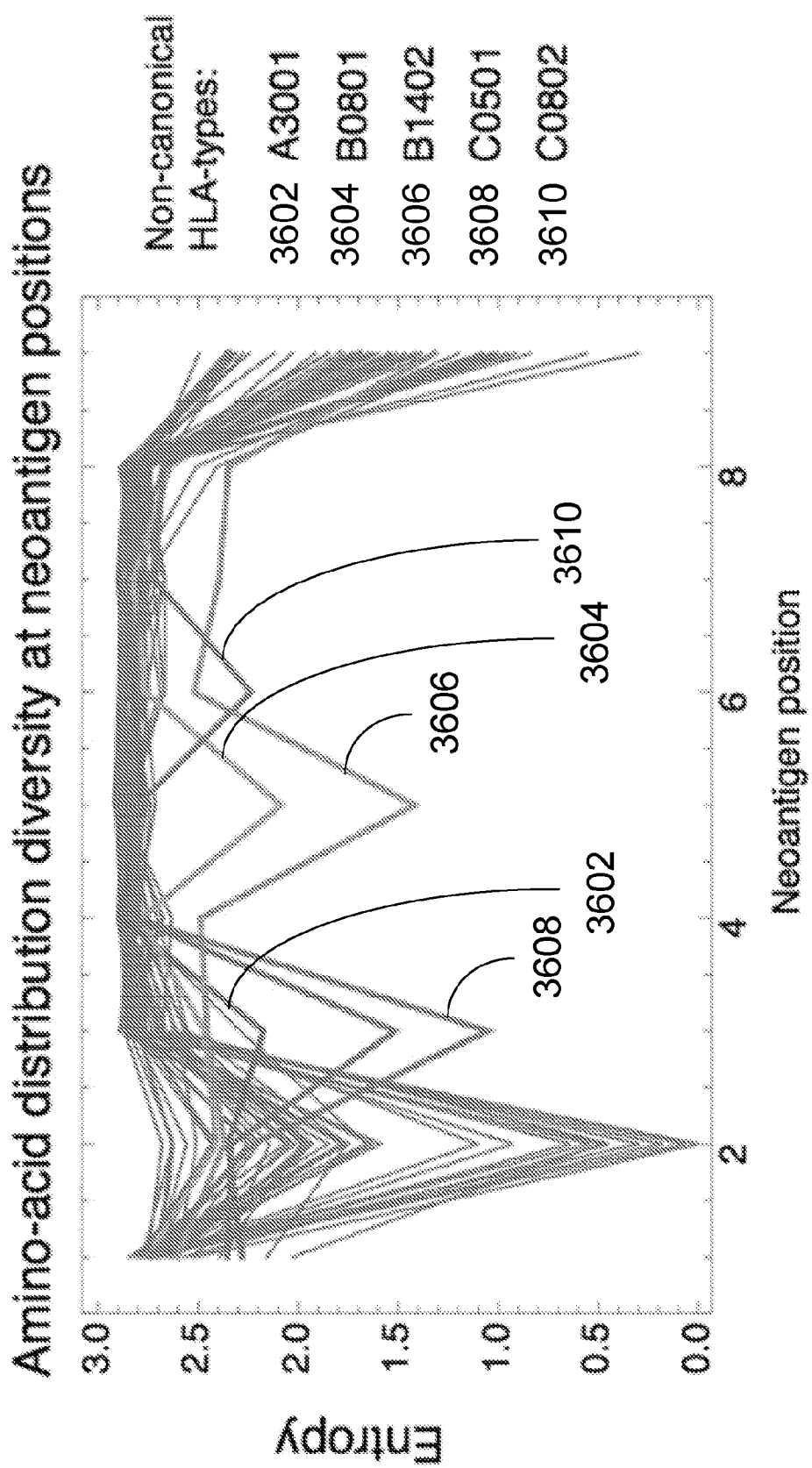

FIGS. 31A, 31B, and 31C illustrate how neoantigen residue positions 2 and 9 provide less predictive value. The violin plots represent data density at a given value on a vertical axis. In FIG. 31A, neoantigens coming from mutations at position 2 or 9 tend to have wildtype peptides with larger predicted affinities. In particular, this is magnified if the corresponding wildtype residue is non-hydrophobic. In FIG. 31B, those biases are reflected in a wider distribution of amplitudes $$n(\tau, \beta) = \sum_{\alpha} X_\alpha \exp\left[ \sum_{\substack{i \in \text{max} \\ \text{Clone } \alpha}} \frac{\exp(-\beta f_i)}{Z(\beta)} f_i \tau \right]$$

for wildtype peptides with non-hydrophobic residues at positions 2 and 9. FIG. 31C illustrates the Shannon entropy of amino acid diversity by position in neoantigens, shown for all distinct HLA-types and computed based on neoantigens across all datasets. Positions 2 and 9 have lower entropy than other residues. Other sites have the same entropy as the overall proteome (Lehmann et al., 2016, "Fundamental amino acid mass distributions and entropy costs in proteomes," J. Theor. Biol. 410, pp. 119-124) and are therefore unconstrained. Five HLA with non-canonical entropy profiles are singled out in the plot. These HLA types contributed only five informative neoantigens across all datasets and therefore are not treated differentially in the model.

FIGS. 32A, 32B, and 32C illustrate ranking of fitness models disregarding subclonal composition of tumors. Fitness models described in conjunction with FIGS. 23, 24, and 25 are evaluated without accounting for subclonal composition of tumors on the same three cohorts, Van Allen et al. (n=103), Snyder et al. (n=64) and Rizvi et al. (n=34). As in FIGS. 23, 24, and 24, parameters used for predictions and error bars for these parameters are reported. Parameter τ is not a free parameter when disregarding subclonal composition of tumors and is not reported. Log-rank test scores are reported for all models and the log-rank test p-value for models with significant patient segregation (p<0.05). The significant models are highlighted: models significant in a single cohort are shown with a solid line box, and models significant across two cohorts are shown with a dashed line box.

Figure 33A:
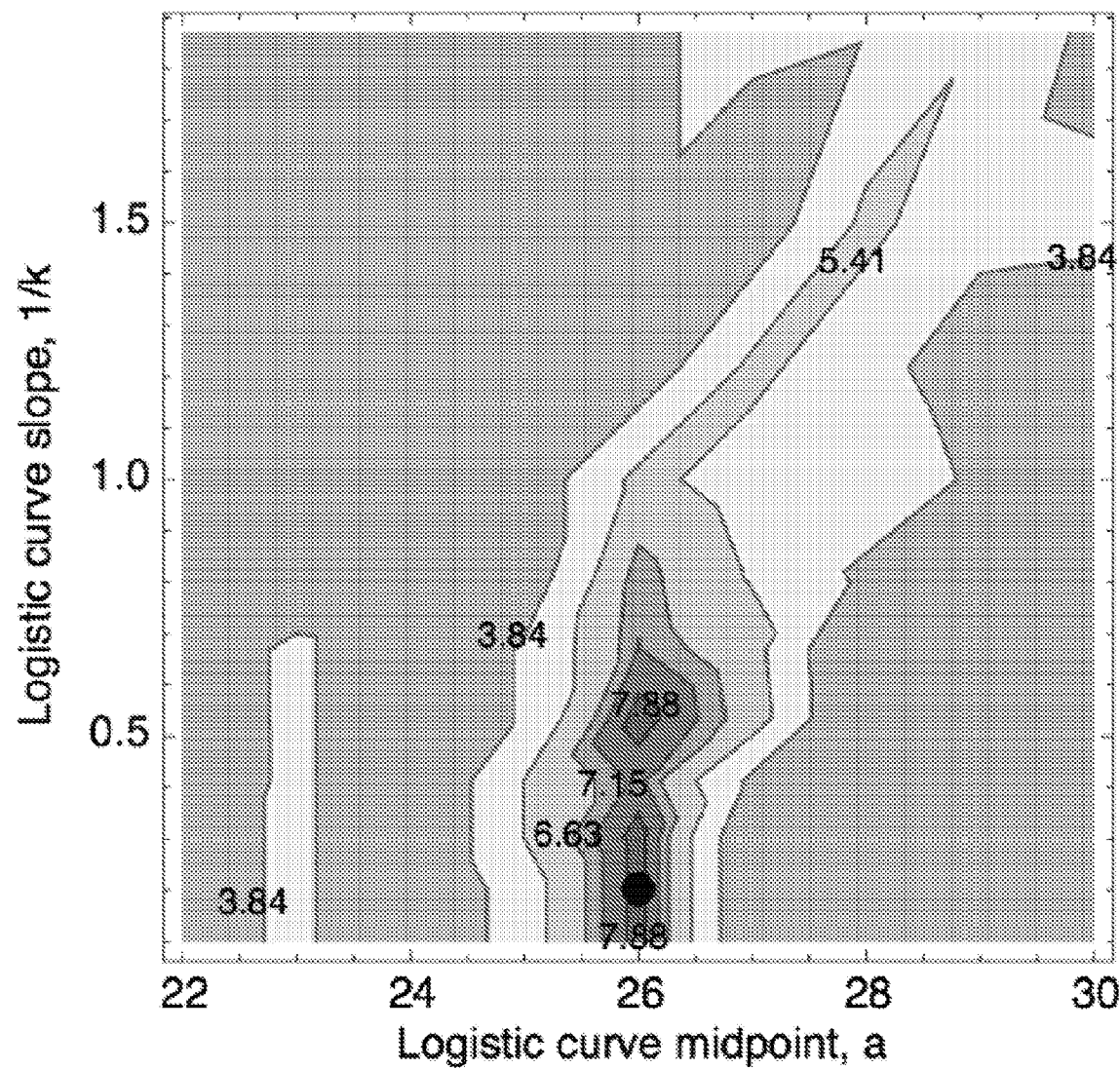
Figure 33B:
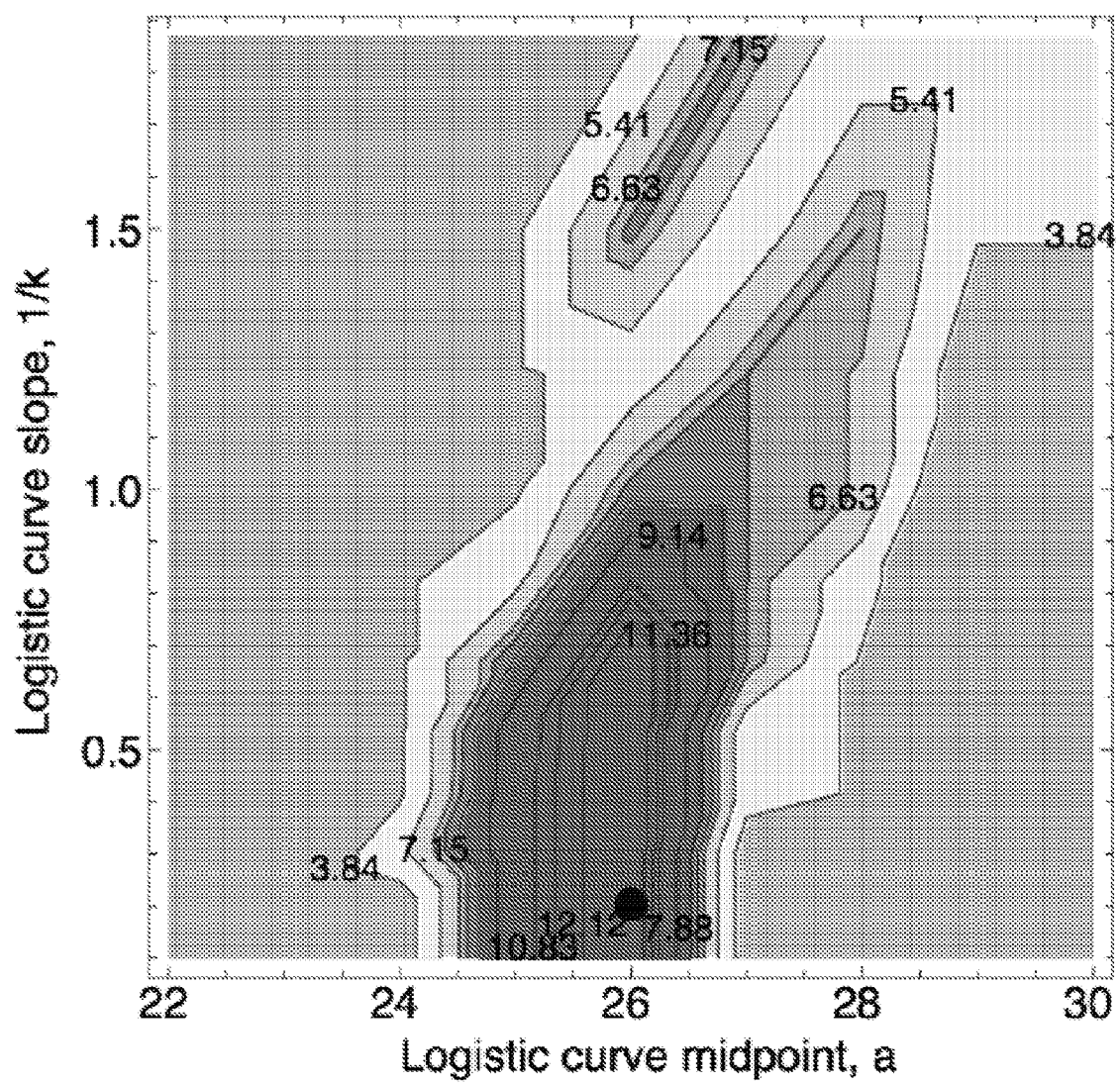
Figure 33C:
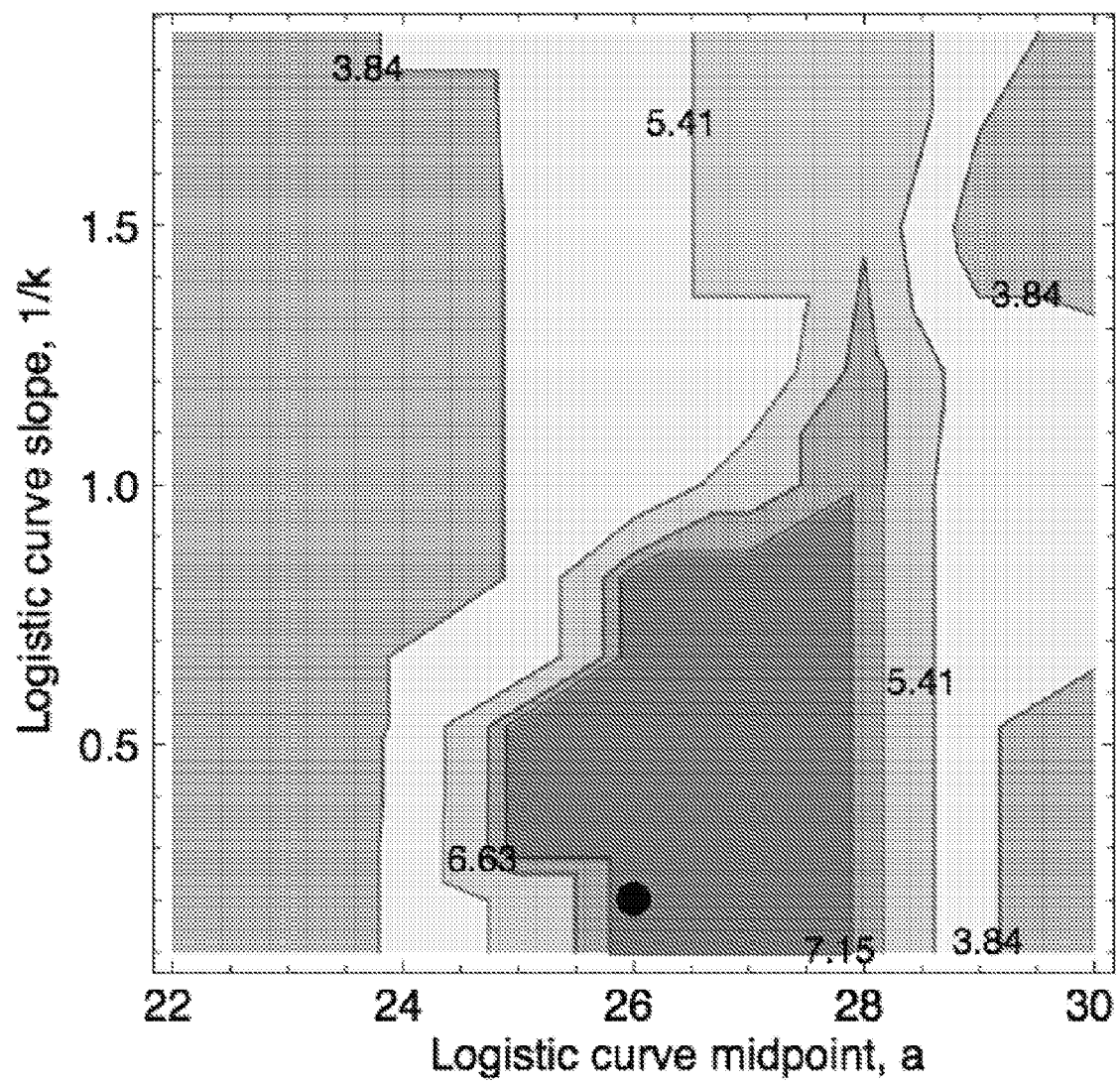
Figure 33D:
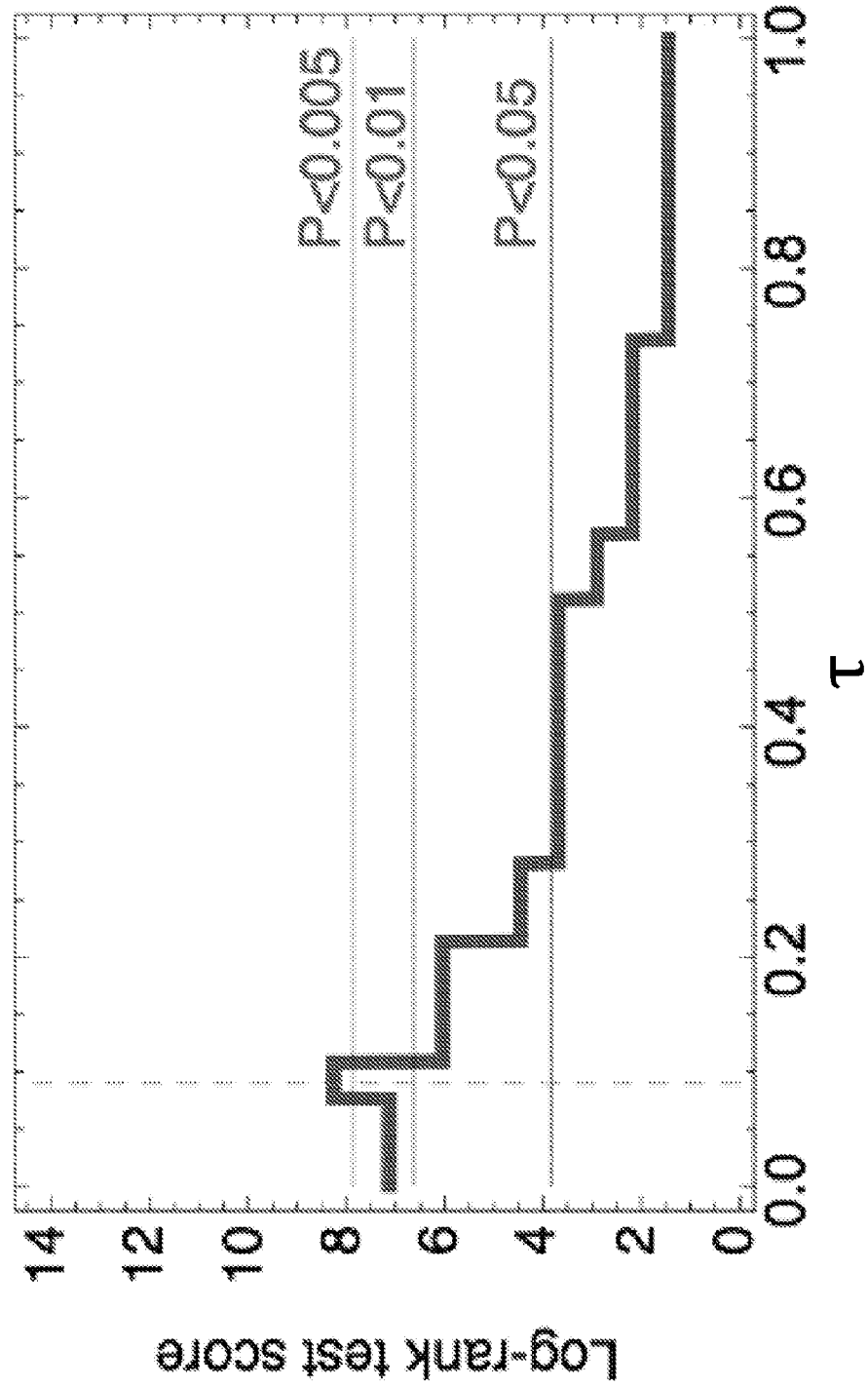
Figure 33E:
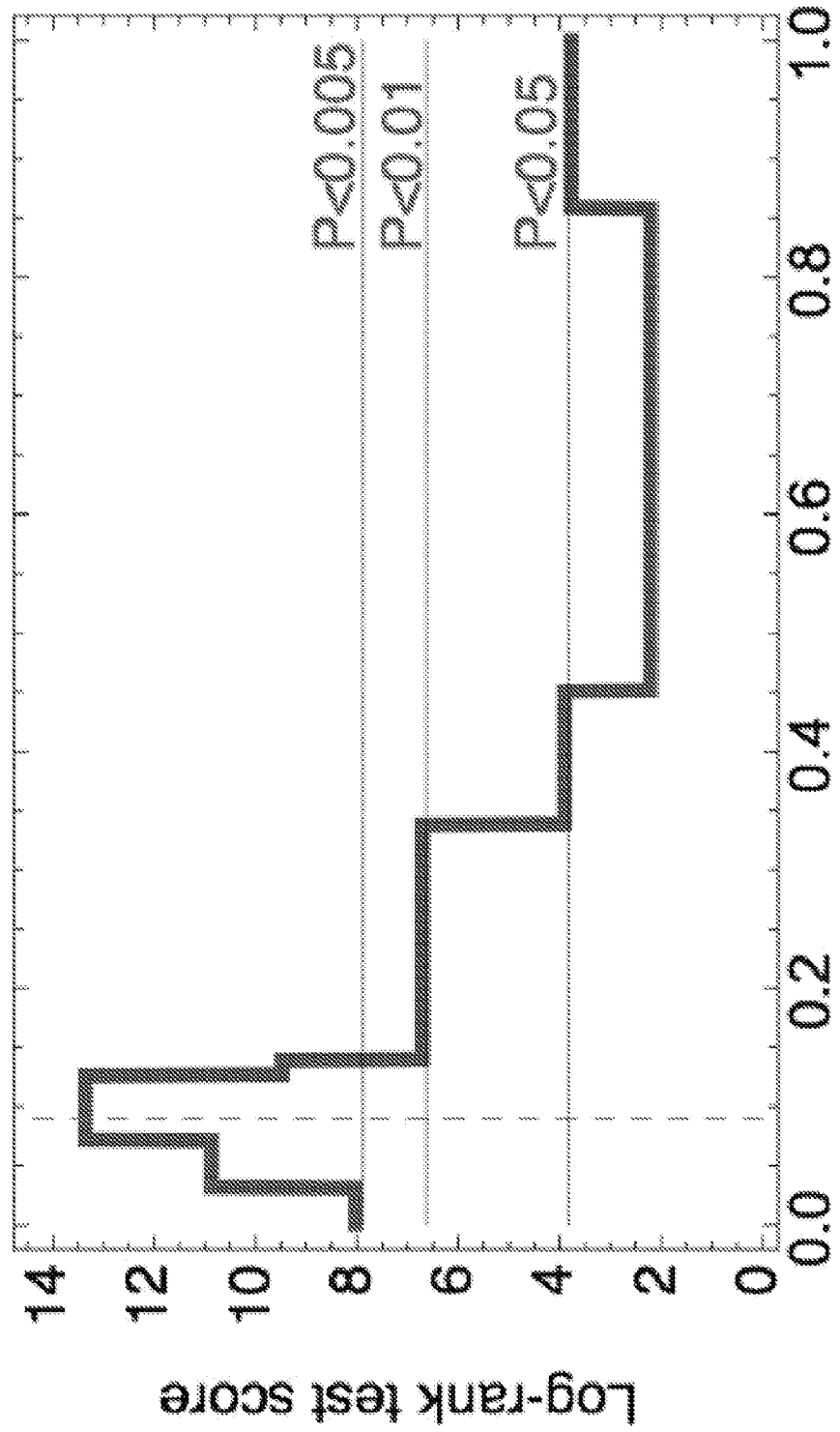
Figure 33F:
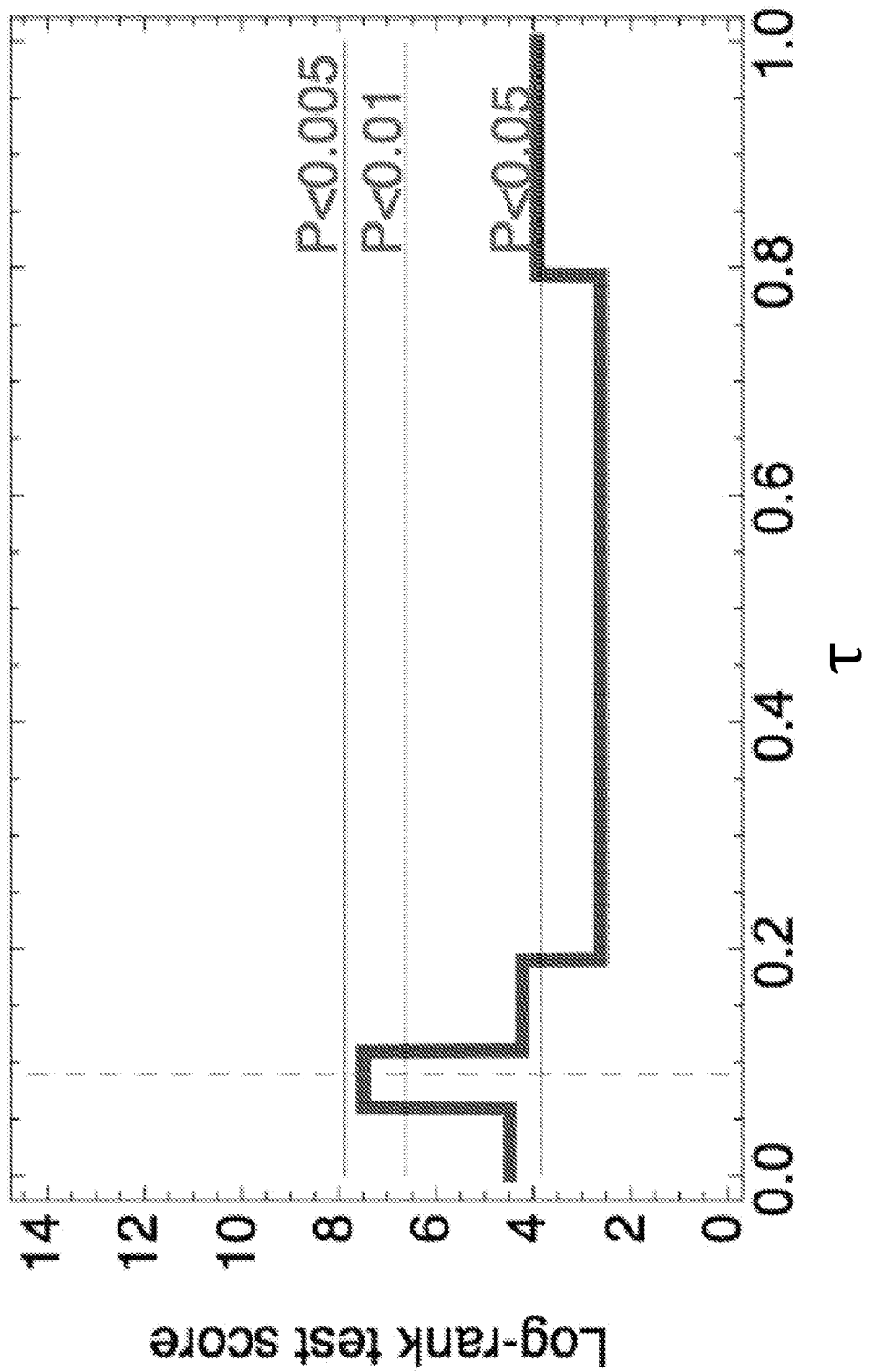

FIGS. 33A, 33B, 33C, 33D, 33E, and 33F illustrate survival analysis score landscape as a function of model parameters. In FIGS. 33A, 33B, and 33C, the landscape of log-rank test scores as the function of the parameters of the TCR binding model (a and l/k), shown for the consistent choice of τ=0.09, different shadings represent the significance level of the long-rank test. The regions of high scores are similar across all three datasets. The point corresponding to consistent parameters (a=26 and k=4.87) is marked by a black dot in each plot. In FIGS. 33D, 33E, and 33F, log-rank score for fitness model at consistent binding function parameters, plotted as a function of τ. Dashed vertical lines are at r=0.09, thin solid lines mark the score values corresponding to significance of 0.05, 0.01 and 0.005. (n=103 (FIGS. 33A and 33D), n=64 (FIGS. 33B and 33E), n=34 (FIGS. 33C and 33F)).

Figure 34A:
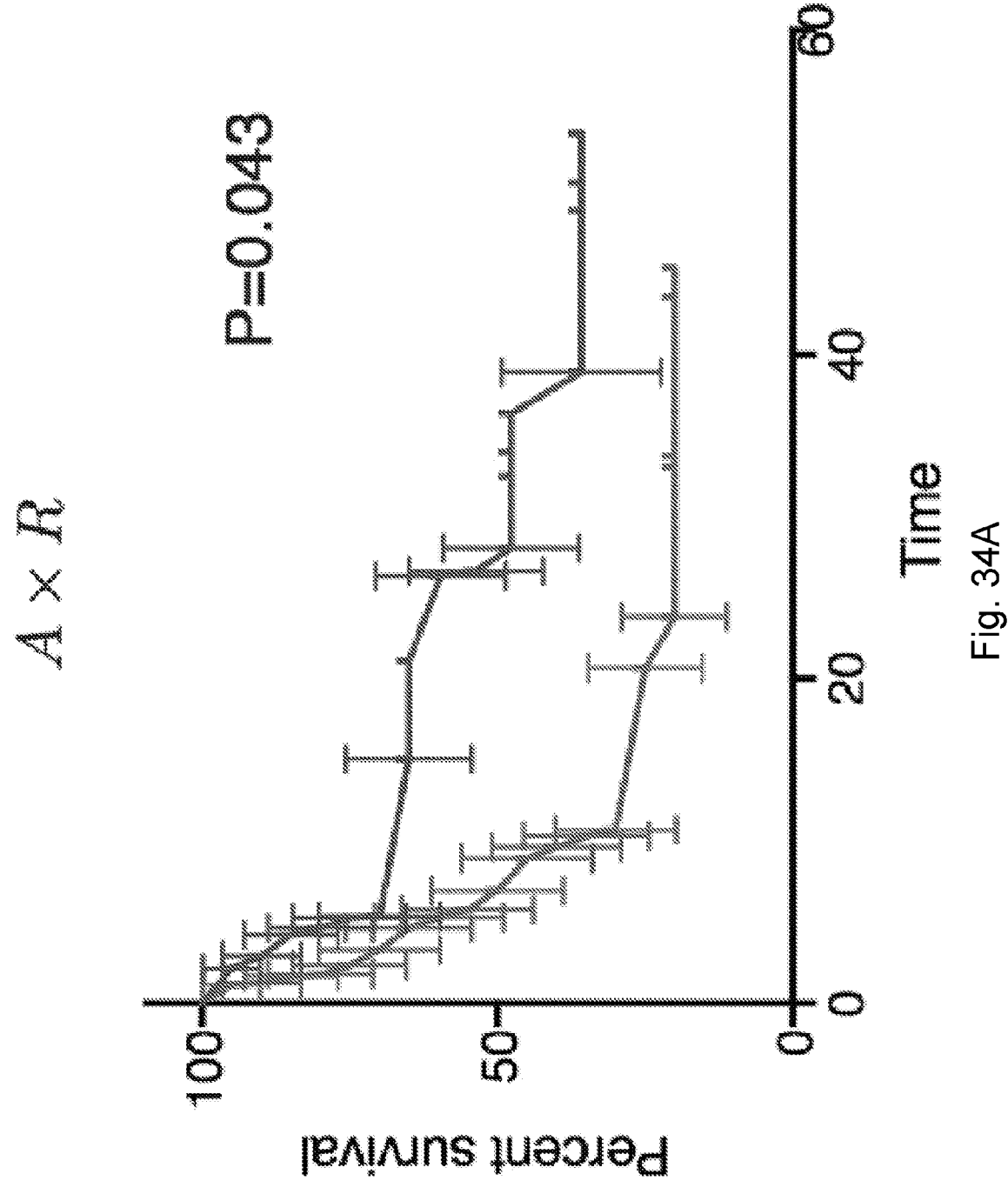
Figure 34B:
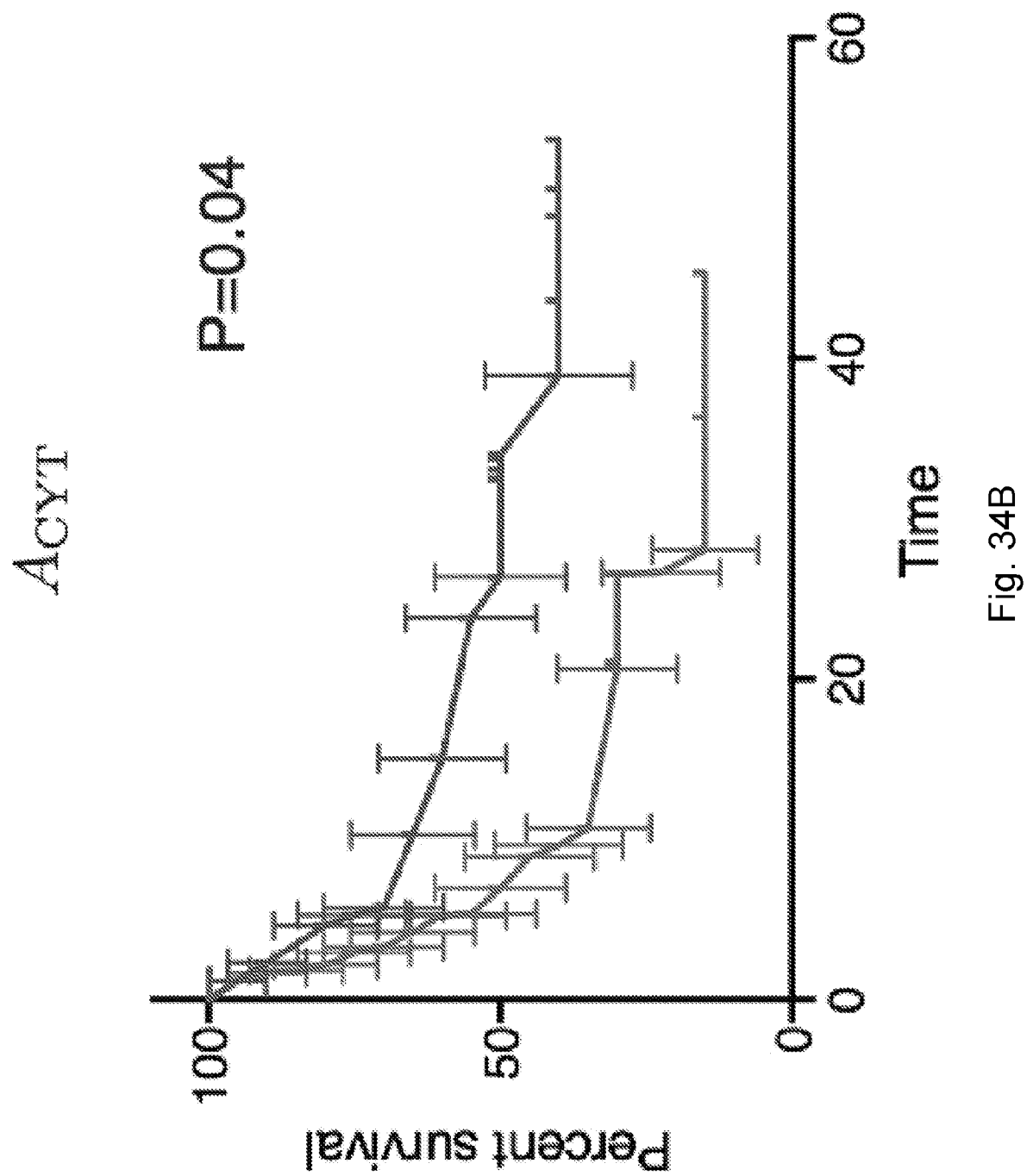
Figure 34C:
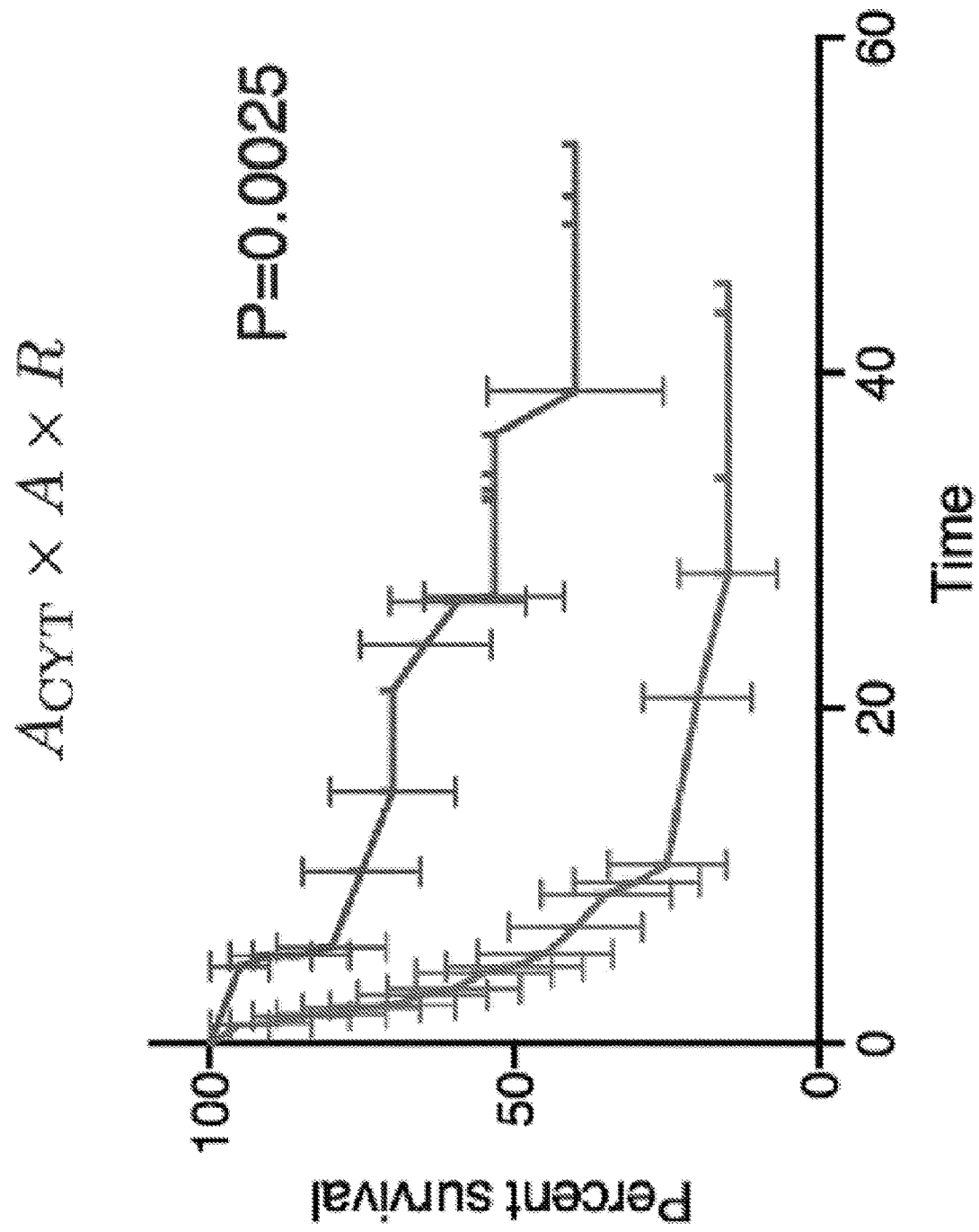

FIGS. 34A, 34B, and 34C illustrate how cytolytic score improves prediction quality. FIG. 34A illustrates a Kaplan-Meier curve of overall survival shown for the disclosed model applied to Van Allen et al. for n=40 patient subset with transcriptional data. Samples are split by the median value of their tumor's relative population size n(τ) from the equation:

$$n(\tau) = \tau_\alpha X_\alpha \exp(F_\alpha \tau),$$

Error bars represent standard error due to sample size. FIG. 34B illustrates that the model optimized for cytolytic score significantly separates patients as described in further detail in Example IV. FIG. 34C illustrates how inclusion of cytolytic score in the model improves prediction on 40 patient subset. The p-values from log-rank tests comparing the two KM curves are shown above each plot. In FIGS. 34A and 34C, consistent parameters are used to trained on the three cohorts (FIG. 31). In FIG. 34B, parameter τ is optimized.

Figure 35:
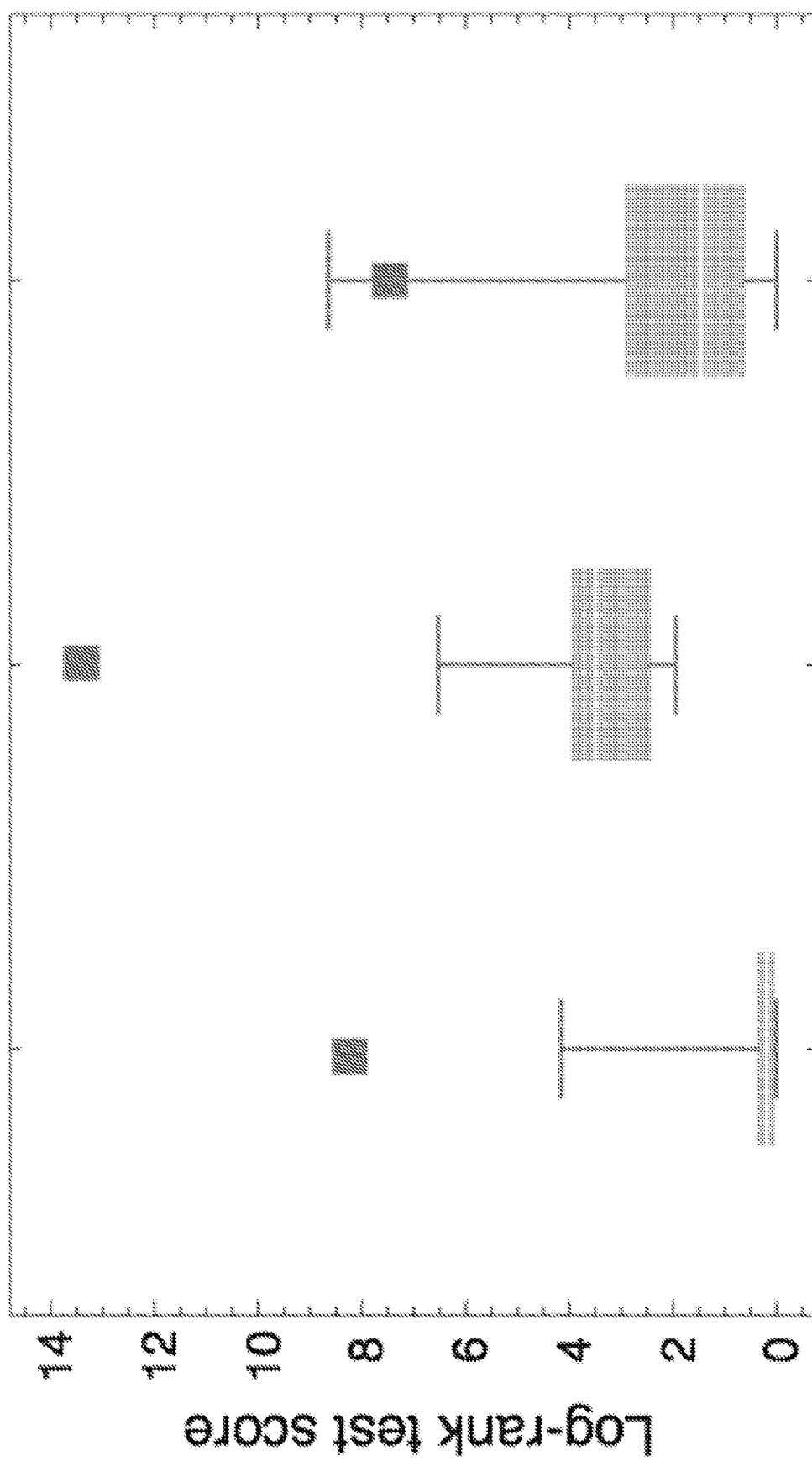

FIG. 35 illustrates how the reshuffling of patient HLA-types reduces predictive power of the disclosed neoantigen recognition potential fitness model. In each cohort, ten iterations of reshuffling patient HLA-types, followed by computational neoantigen prediction, recognition potential fitness model calculation and survival analysis is performed. The distribution of log-rank test scores is reported over these iterations: boxes mark 75% confidence intervals and whiskers mark the range of scores (n=10). The score values for the model on original data are marked with squares.

FIG. 36 illustrates a multivariate analysis with a Cox proportional hazards model that was performed to adjust for clinical covariates, while assessing for the predictive value of n(τ) values. In melanoma cohorts (Van Allen et al., n=103 and Snyder et al., n=64), stage, gender, and age were controlled for. Stage IIIC and IVa are combined together, as both of these stages had limited number of patients in either cohort. Stage IIIc/IVa serve as the reference in the table. In both the Van Allen et al. and Snyder et al. cohorts, n(τ) predictions are independently associated with overall survival after anti-CTLA4 therapy. In the lung cancer cohort (Rizvi et al., n=34), all patients are Stage IV, so we correct for age, gender, and number of pack years smoked, and continued to find that n(τ) predictions are independently associated with overall survival after anti-PD1 therapy.

FIG. 37 illustrates a script for computing neoantigen fitness scores (recognition potentials) for the Van Allen et al., Snyder et al., and Rizvi et al., datasets in accordance with an embodiment of the present disclosure.

FIGS. 38A, 38 B and 38C collectively illustrate the "main.py" python script that is called by the script of FIG. 37 in order to compute neoantigen fitness scores (recognition potentials) for the Van Allen et al., Snyder et al., and Rizvi et al., datasets in accordance with an embodiment of the present disclosure.

FIGS. 39A and 39B collectively illustrate the "aligner.py" python script that is called by the "main.py" script of FIG. 38 in order to compute neoantigen fitness scores (recognition potentials) for the Van Allen et al., Snyder et al., and Rizvi et al., datasets in accordance with an embodiment of the present disclosure.

Figure 40B:
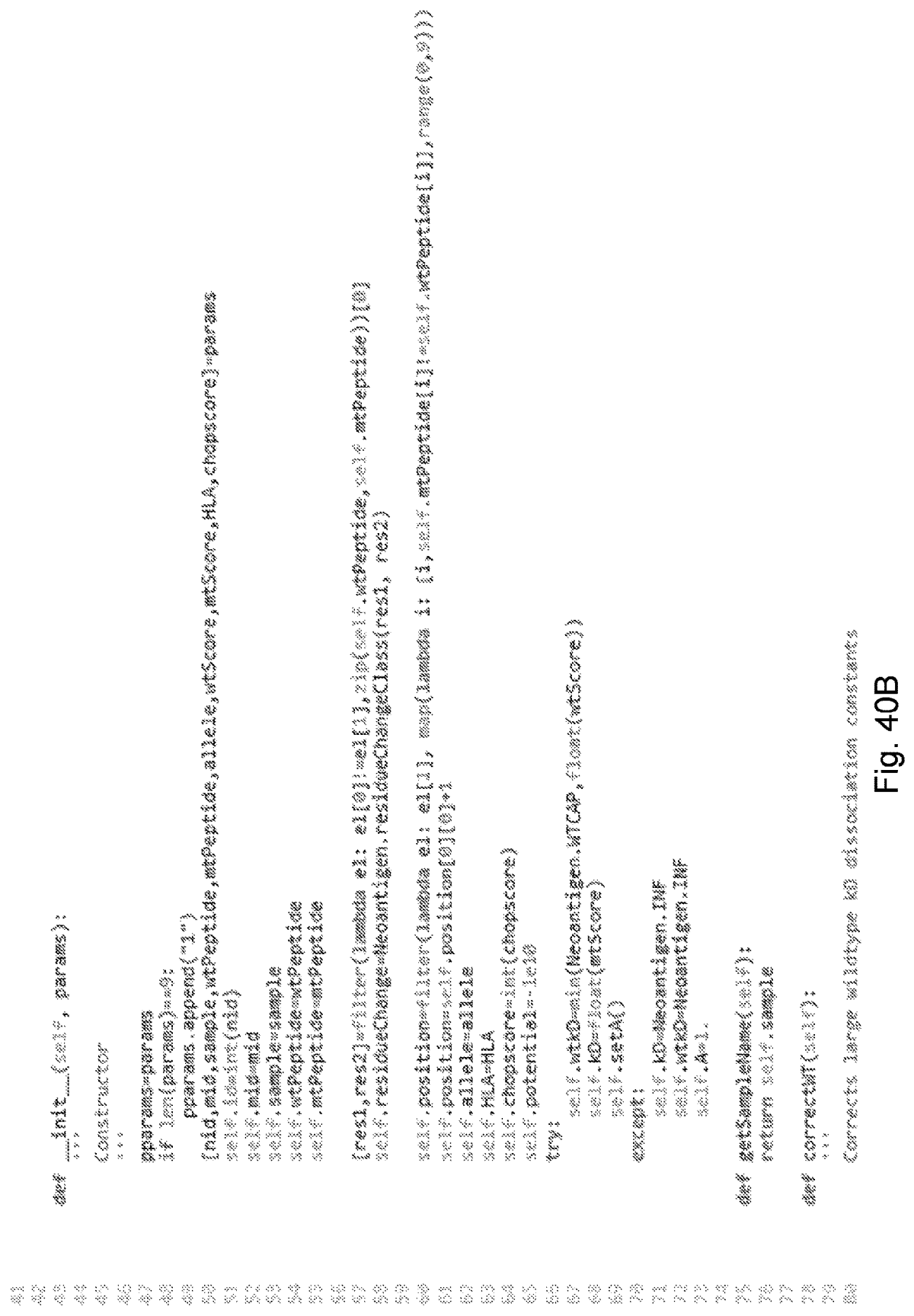

FIGS. 40A, 40B, and 40C collectively illustrate the "neoantigen.py" python script that is called by the "main.py" script of FIG. 38 in order to compute neoantigen fitness scores (recognition potentials) for the Van Allen et al., Snyder et al., and Rizvi et al., datasets in accordance with an embodiment of the present disclosure.

Figure 41A:
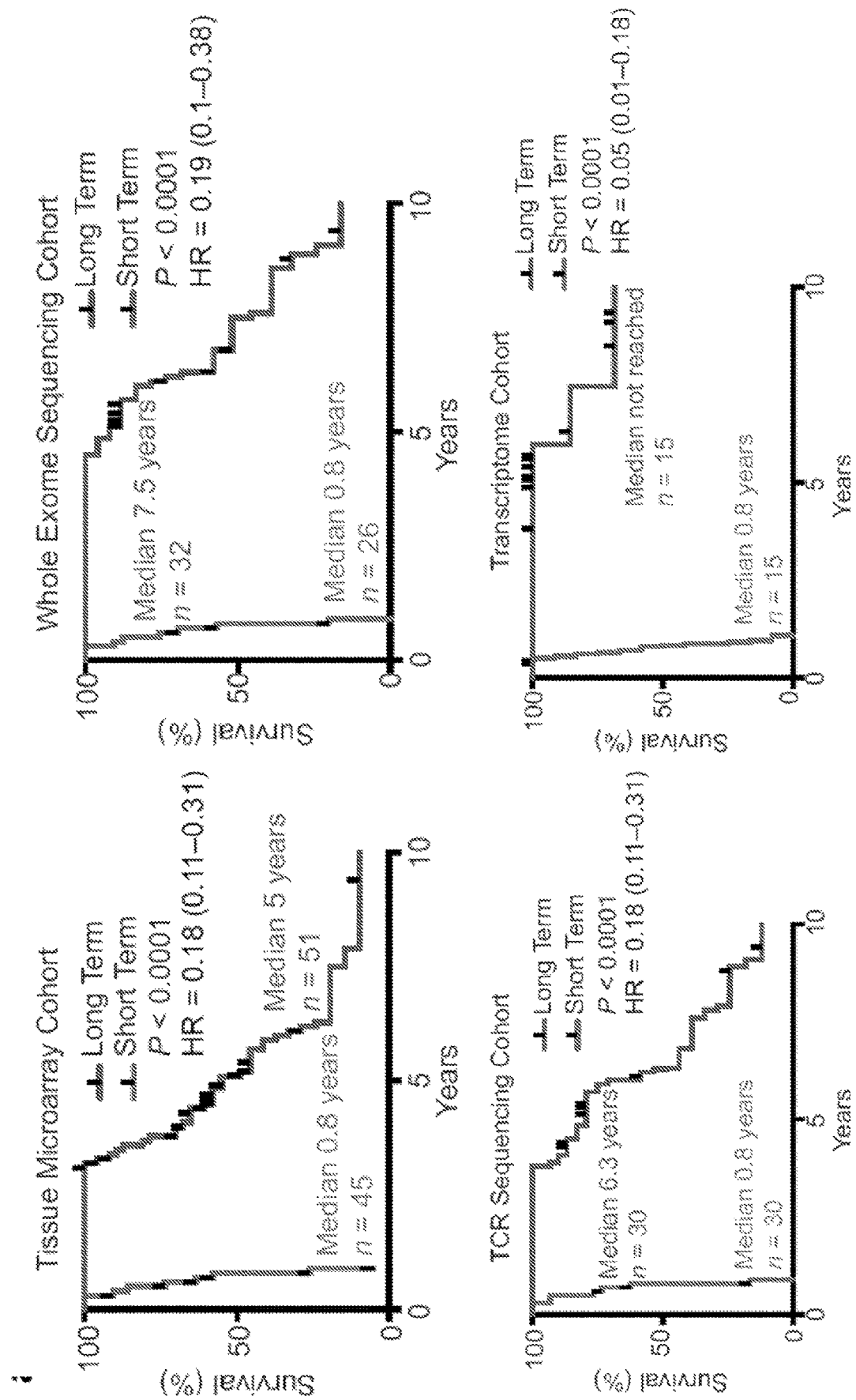
Figure 41B:
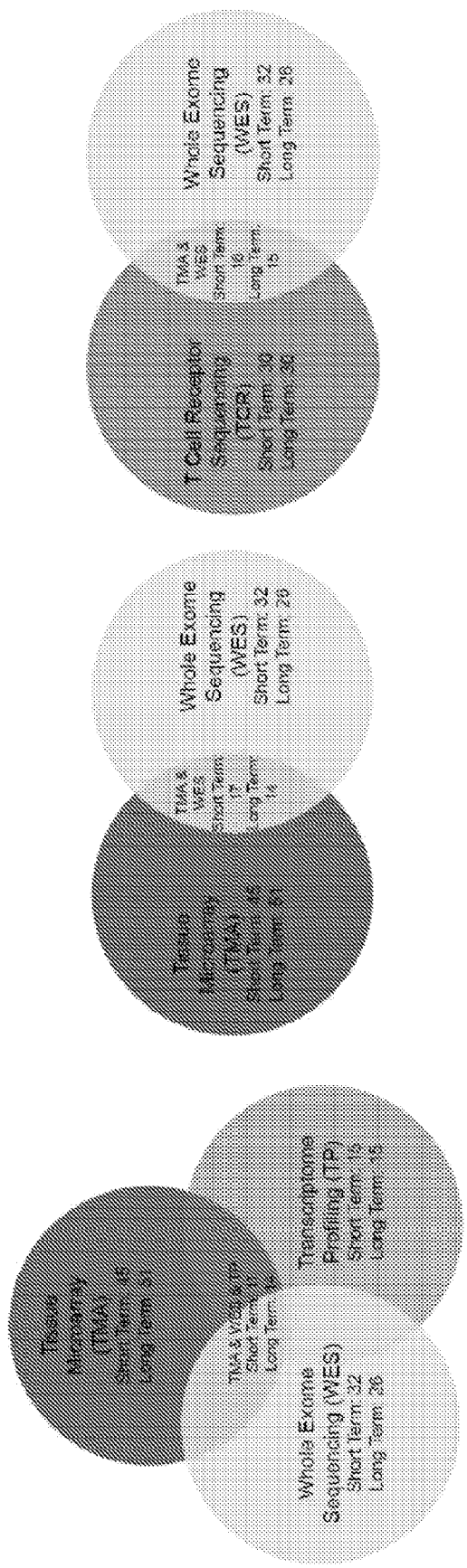

FIGS. 41A and 41B collectively depict overall Survival and patient overlap of short and long term survivors in tissue microarray, whole exome sequencing, TCR sequencing, and bulk tumor transcriptomic profiling cohorts.

FIGS. 42A, 42B, 42C, 42D, 42E, 42F, 42G, 42H, 42K, 42L, and 42M collectively present data showing that long term pancreatic cancer survivors displayed enhanced intratumoral T cell immunity. (A) Overall survival of short (>3 m, <1 yr) and long term (>3 yr) survivor cohorts. Composite images (B) and quantification (C, D, E) of multiplexed immunophenotyping. In (B), red rectangular sections are enlarged to 50×. CK19 stains tumor cells. Arrows indicate $CD3^+CD8^+Granzyme-B^+$ T cells. Data in (E) indicates log 2(cells/mm2). Highlighted boxes indicated significantly increased parameters in long term survivors. (F) Bulk tumor transcriptomic immune profiling. Ligands of PD-1 (PDL-1) and TIGIT (CD226) are also shown. (G) T cell frequency (top) and repertoire clonality (1=complete oligoclonality, 0=complete polyclonality, bottom) in tumor and matched adjacent non-tumor pancreatic tissue by quantitative TCR Vβ sequencing. (H) Percentage of tumor T cell clones unique to tumors, or shared with matched adjacent non-tumor pancreatic tissue by quantitative TCR Vβ sequencing. (I) Frequency of PD-1, CD69, CD45RA, and CD45RO expressing CD8+ T cells in blood, tumor draining lymph nodes (DLN), and tumor in unselected patients by flow cytometry. (J) Clonality of tumor T cell repertoire in short and long term survivors by quantitative TCR Vβ sequencing. All data represent values in individual patients. C, D, E represent median values of 3 cores per patient. Horizontal bars represent median values and are indicated in (C). In (I, bottom), data are mean±SEM, * and ** indicate comparisons between blood, DLN, and tumor. *P<0.05; P<0.01; *P<0.001; ****P<0.0001. (K-M) Depict overall survival of patients who did or did not receive adjuvant chemotherapy (adjuvant chemotherapy +/− respectively, top left), and of patients with tumors harboring greater or less than the median number of CD3-CD8Granzyme B triple positive cells (CD3-CD8-GranzymeB$^{Hi/Low}$ respectively, top right). Overall survival of all four groups shown in bottom. Table shows univariate and multivariate Cox regression analysis of clinicopathologic features, adjuvant chemotherapy, and CD3-CD8-GranzymeB density association with overall survival.

Figure 42B:
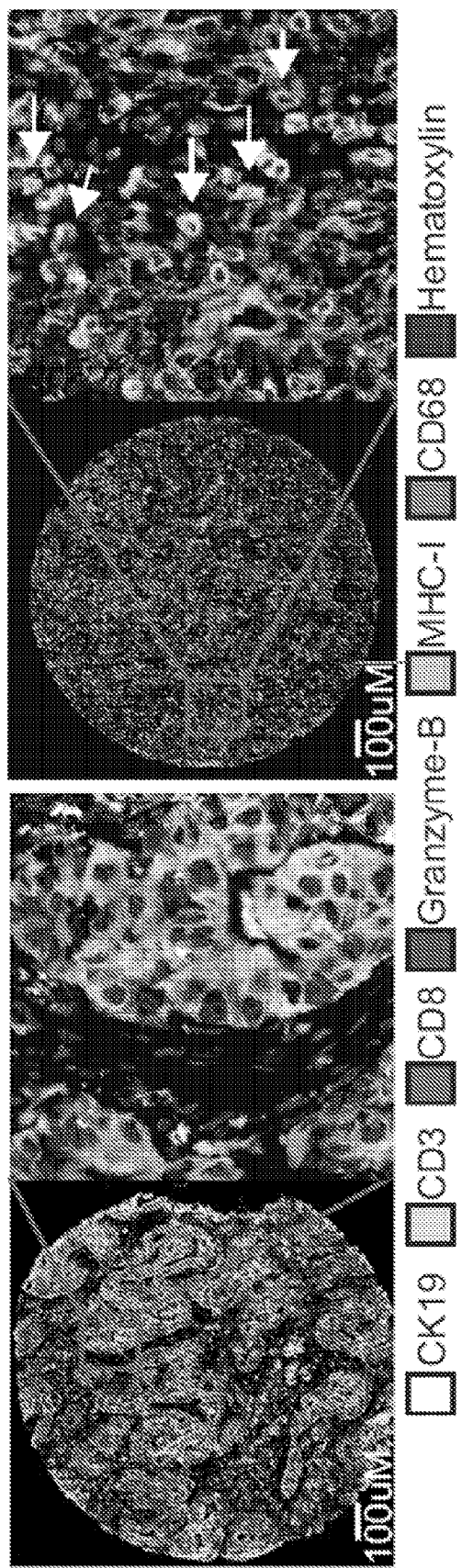
Figure 42C:
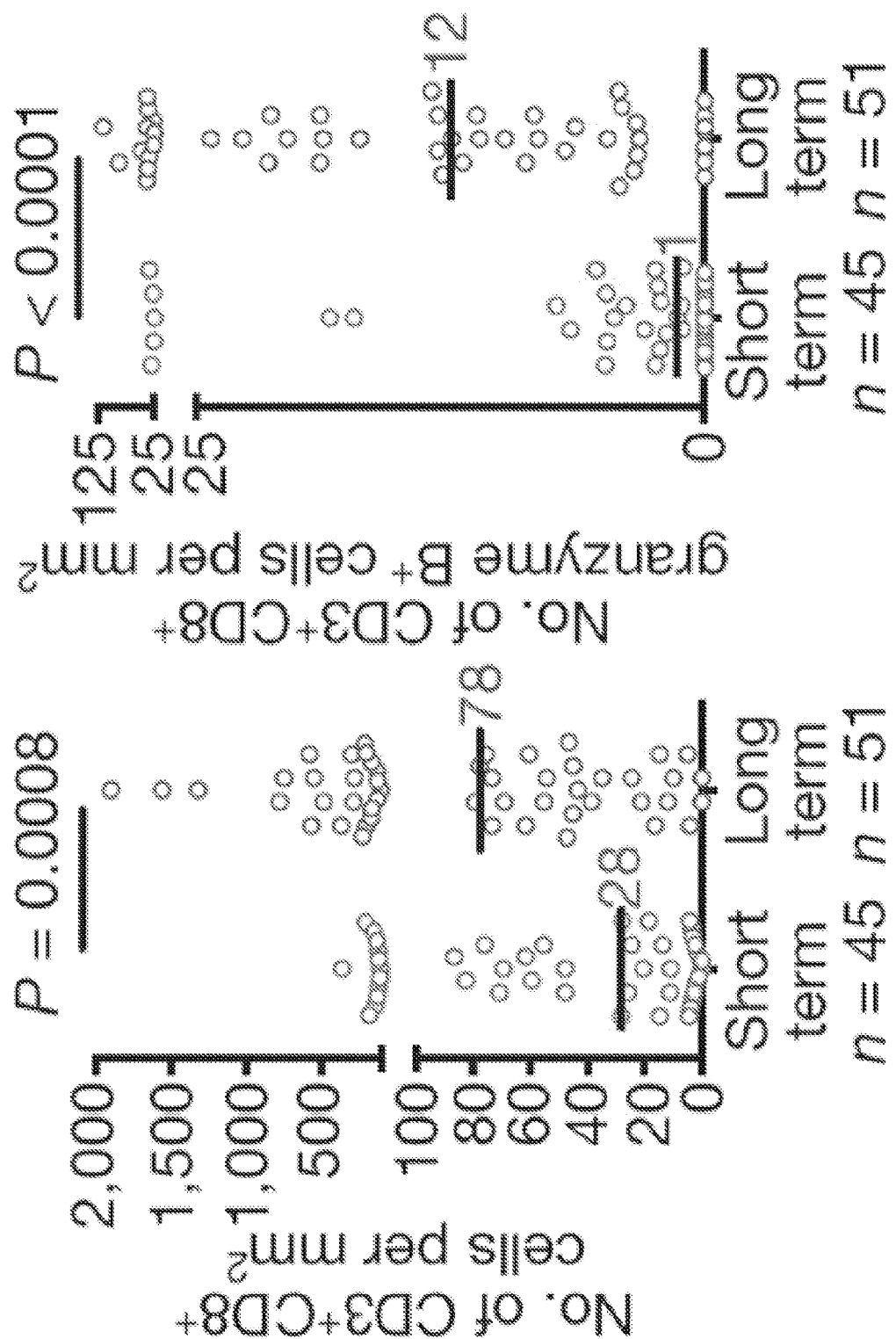
Figure 42D:
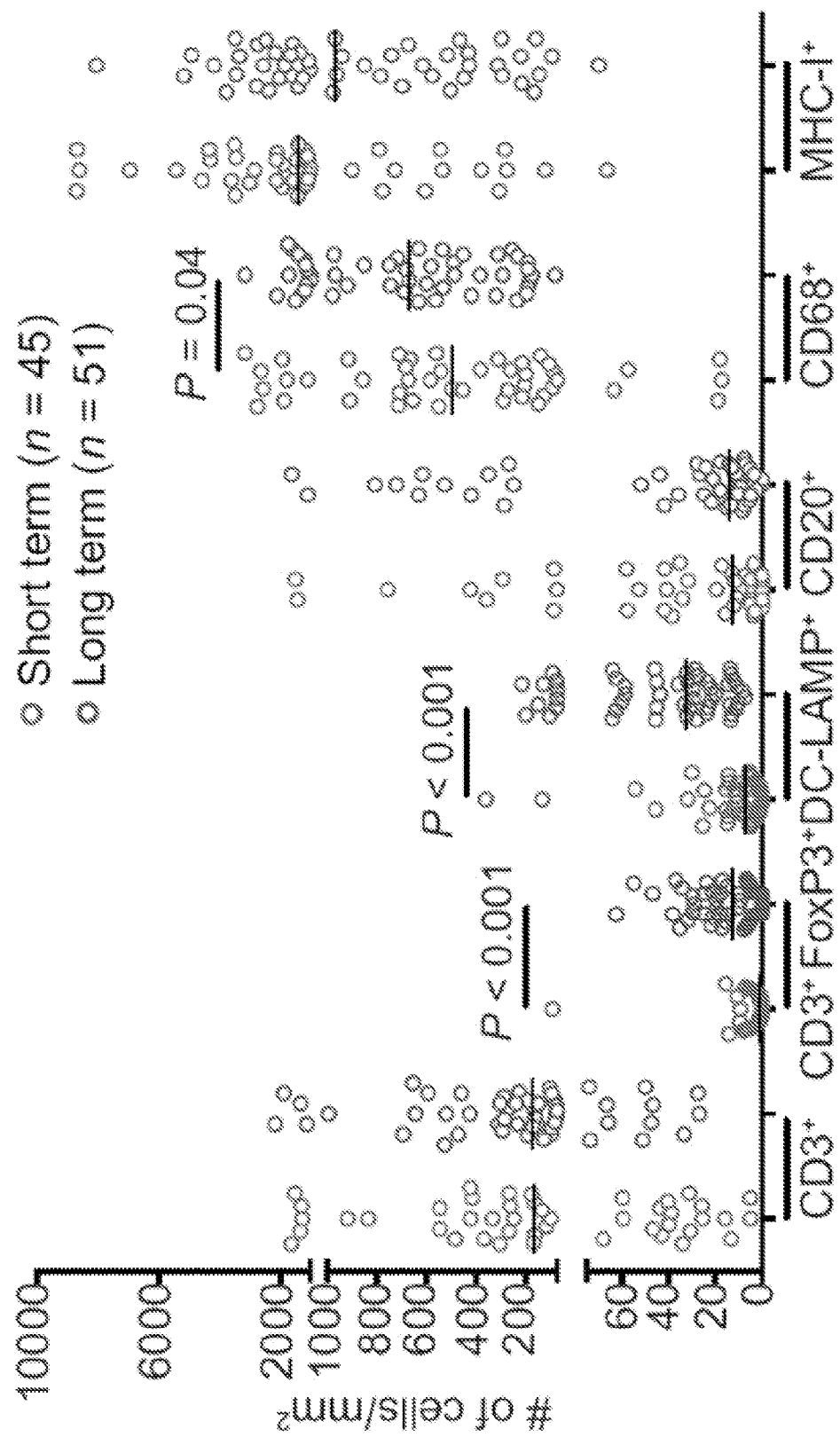
Figure 42E:
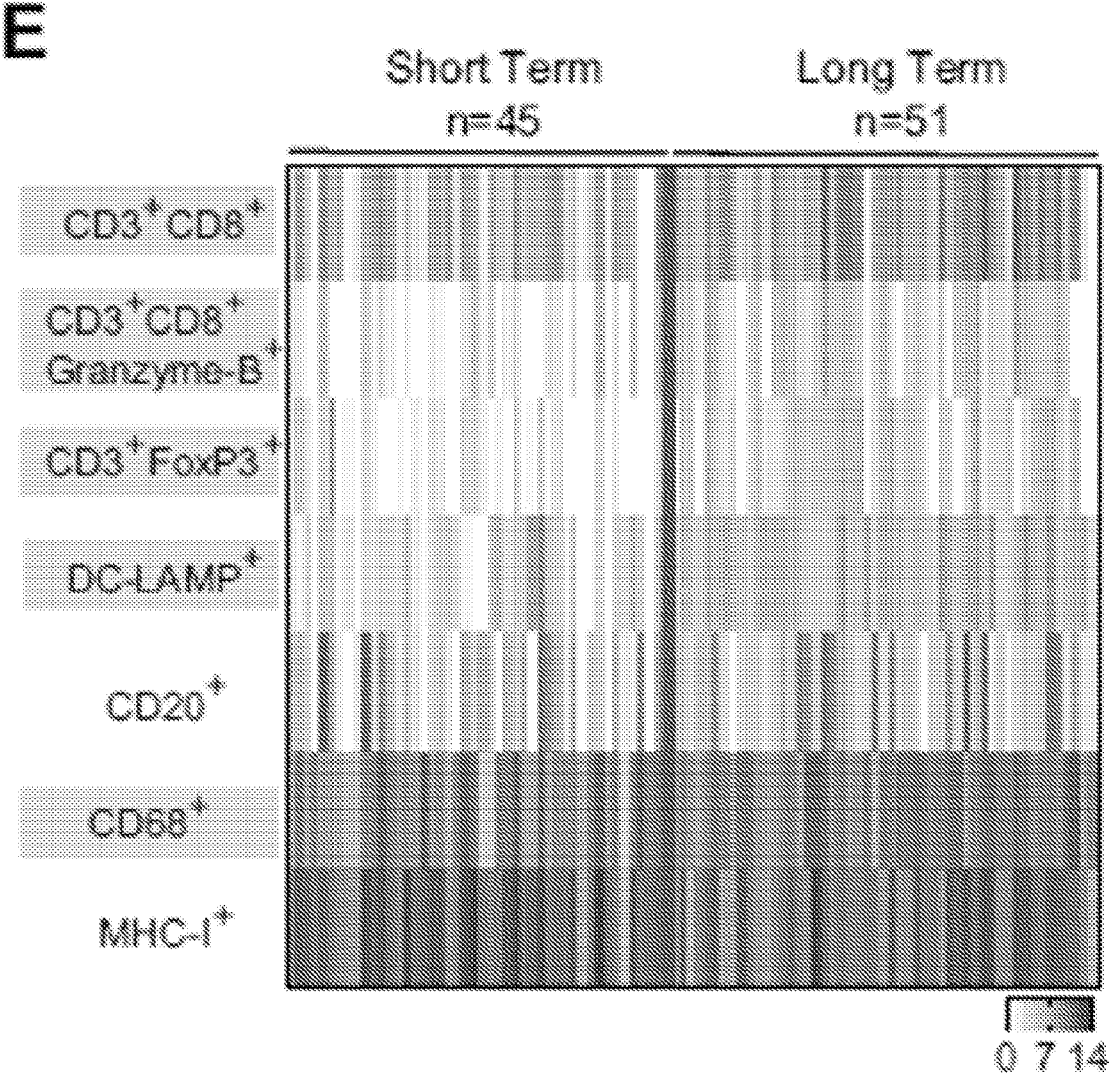
Figure 43A:
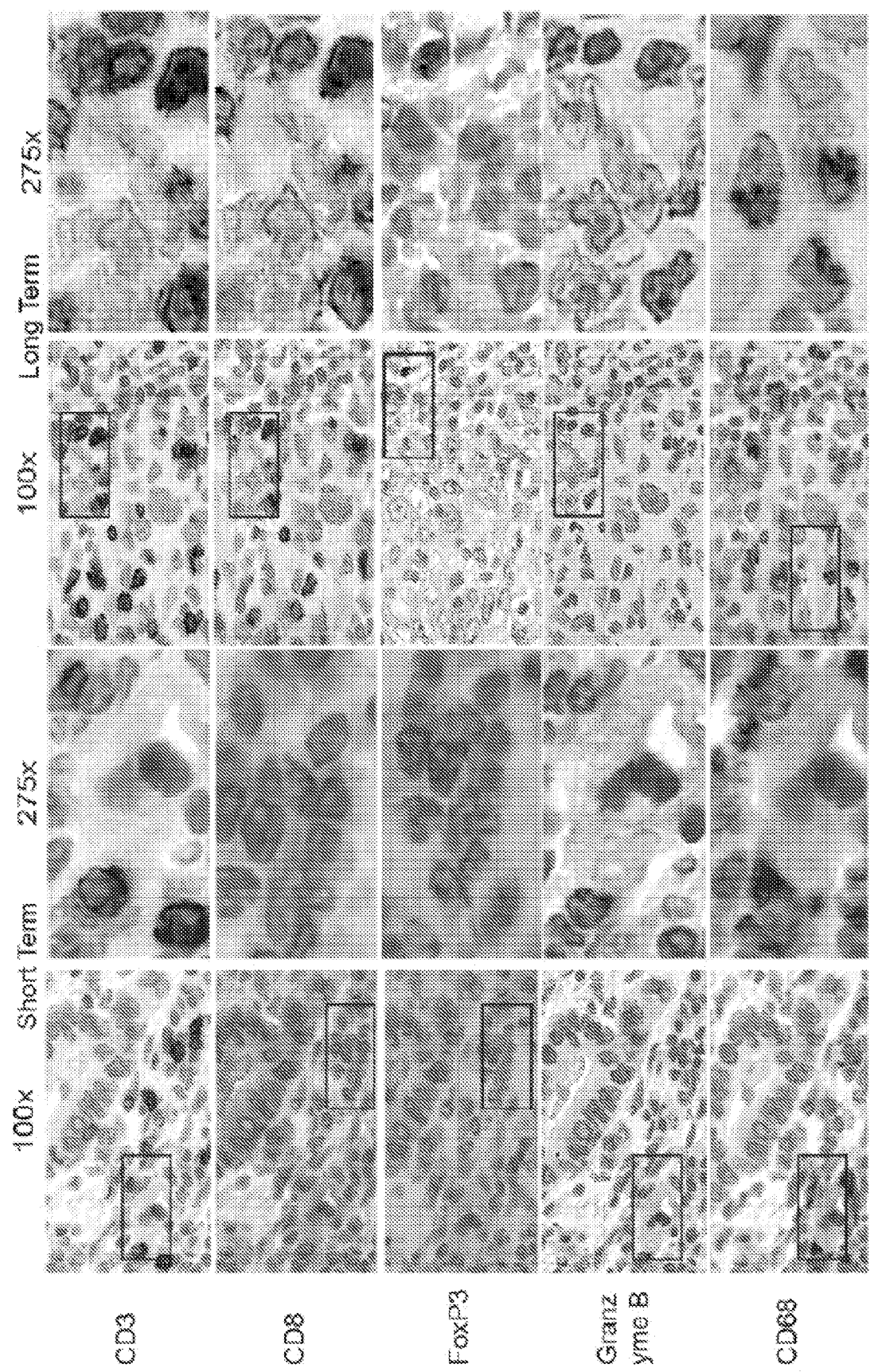
Figure 43B:
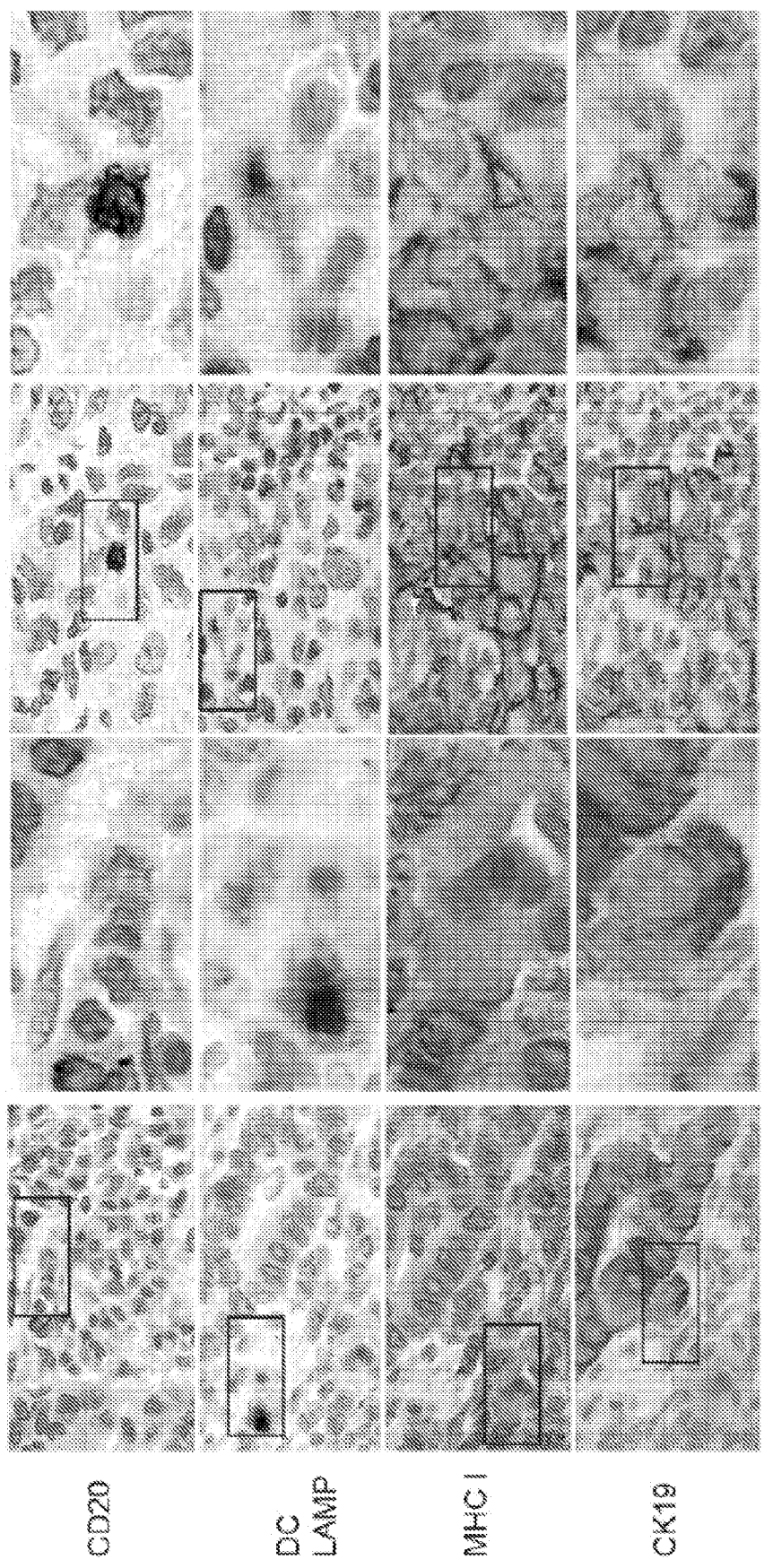

FIGS. 43A and 43B collectively depict representative sequential immunohistochemistical staining of a single short term and a single long term core tumor section. Sections bounded by black rectangles (100×) are magnified to 275× (right) for each core section. Merged images are shown in FIG. 42B.

Figure 44:
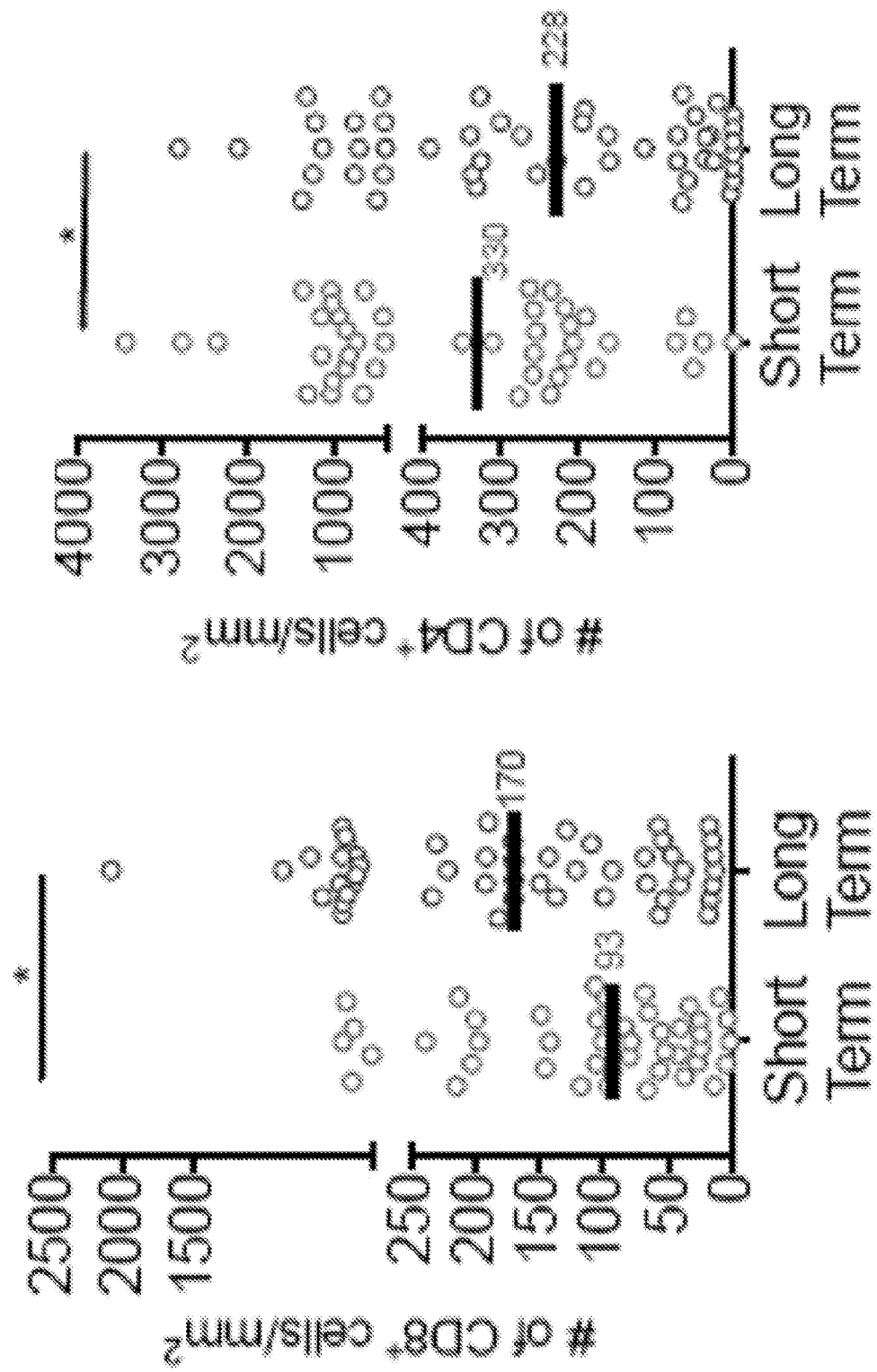

FIG. 44 depicts immunofluorescent quantification of CD8+ and CD4+ cells in tumor tissue microarray of short and long term survivors. Slides used above were cut from separate sections of the block as those used for sequential immunohistochemistry (FIG. 42B-42E). *P<0.05.

Figure 45:
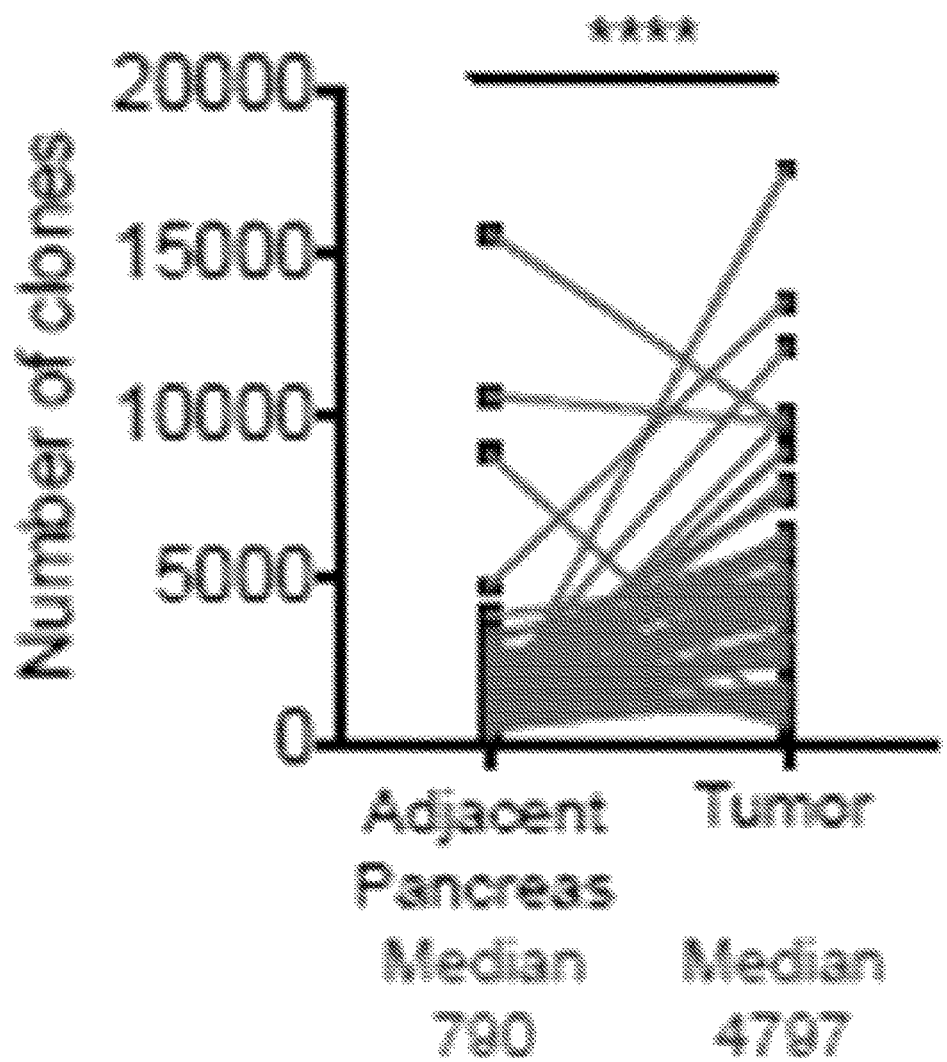
Figure 46A:
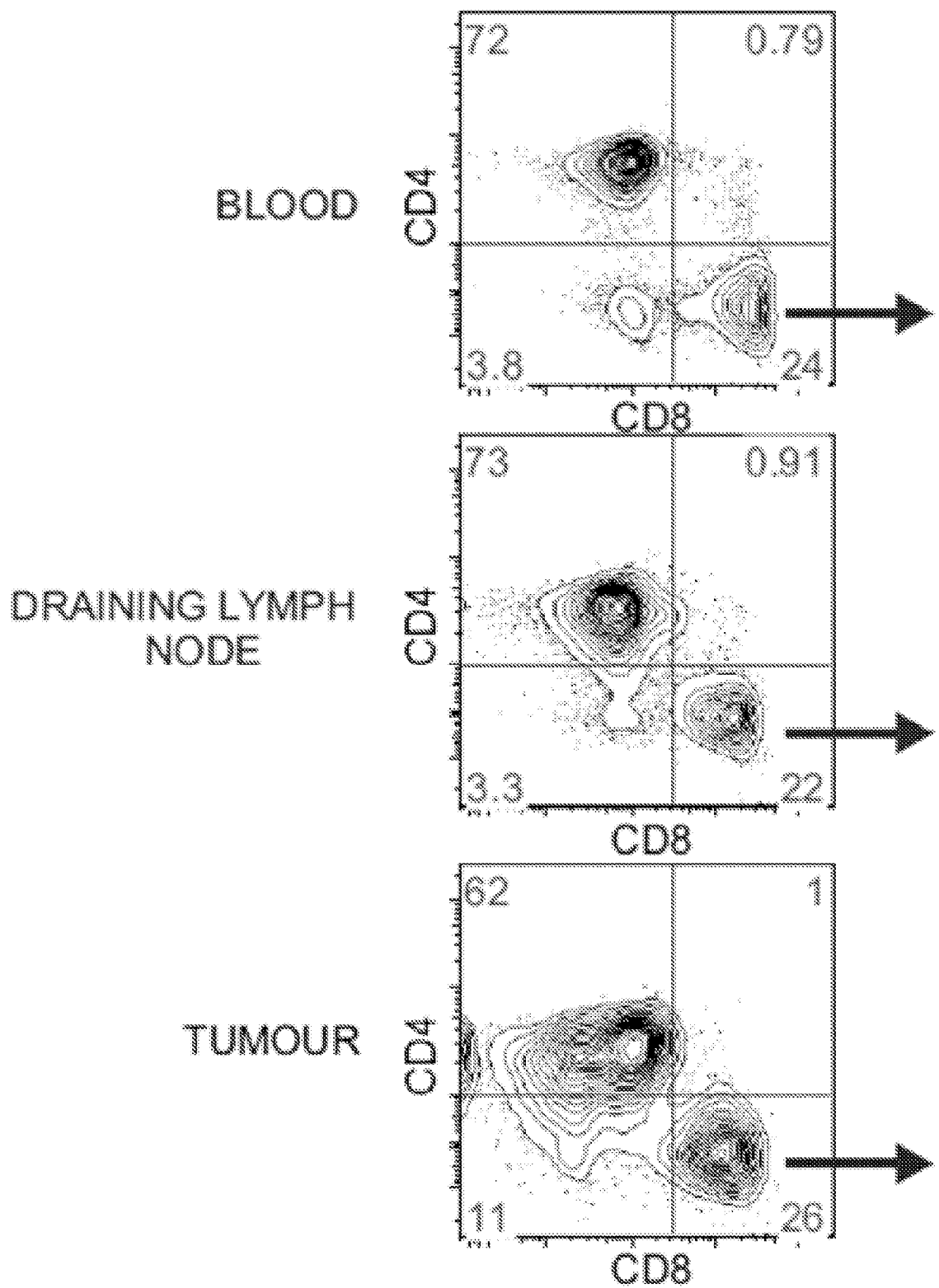
Figure 46B:
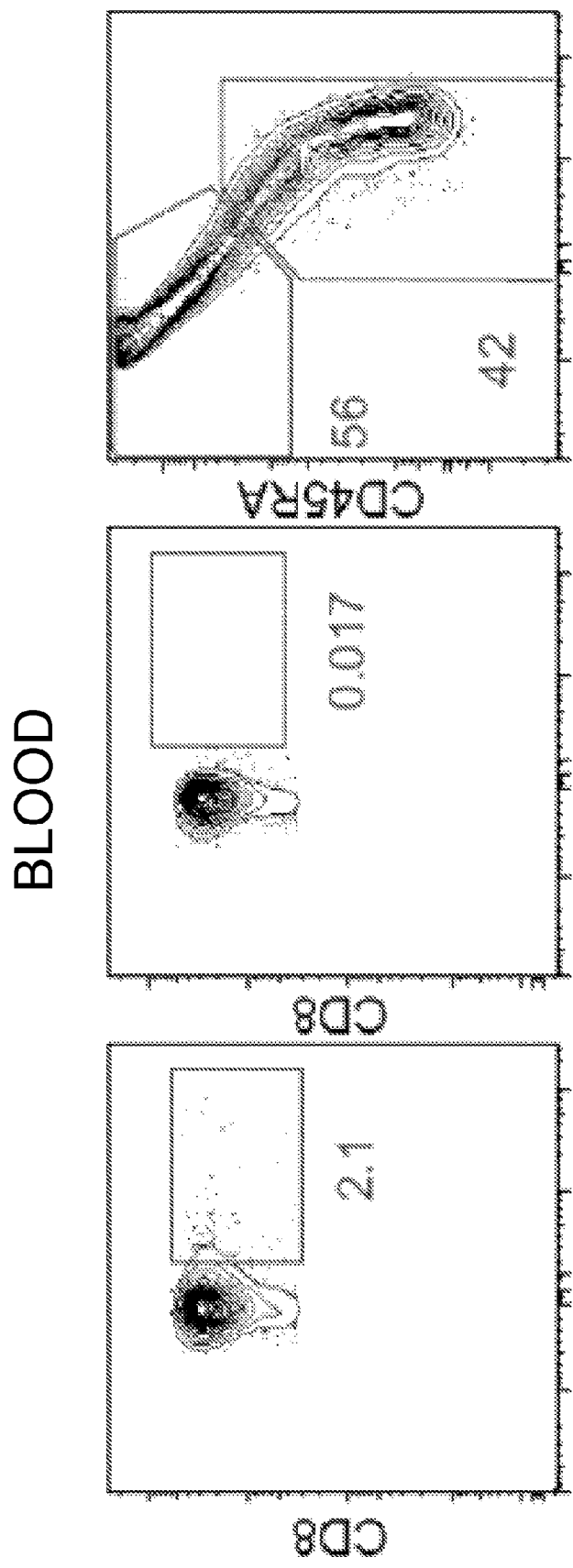
Figure 46C:
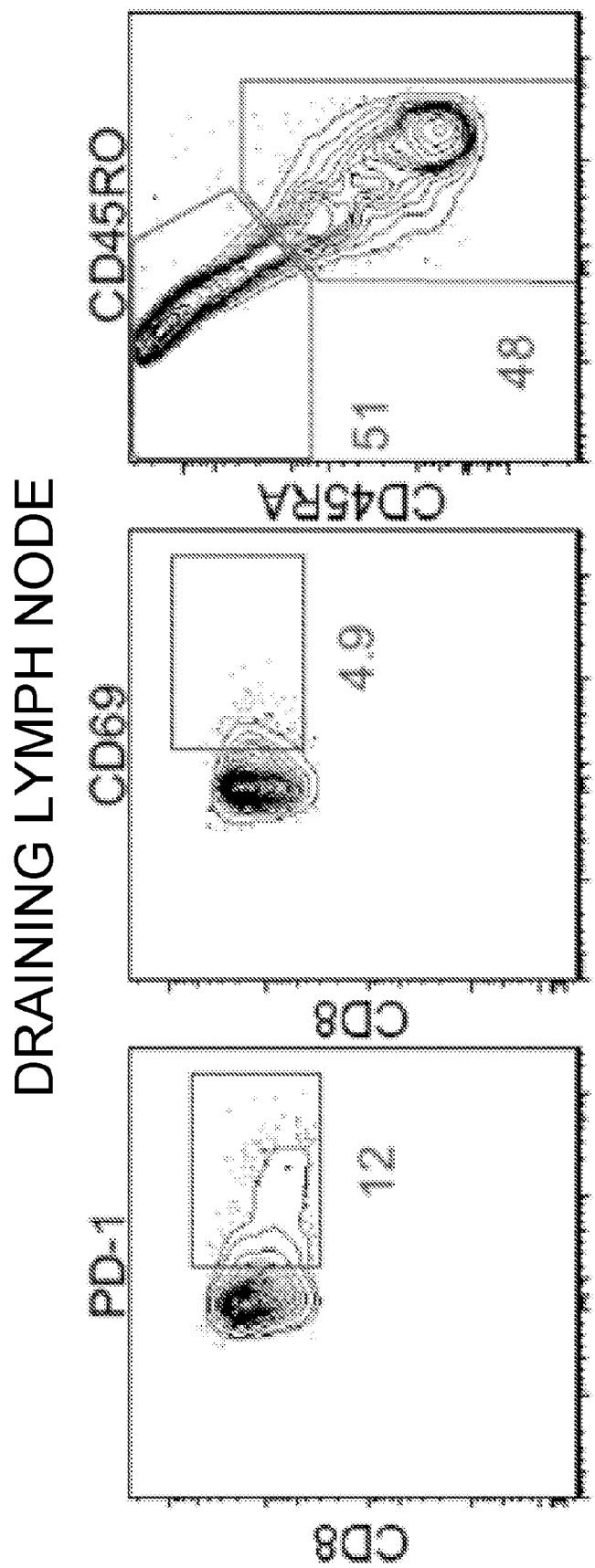
Figure 46D:
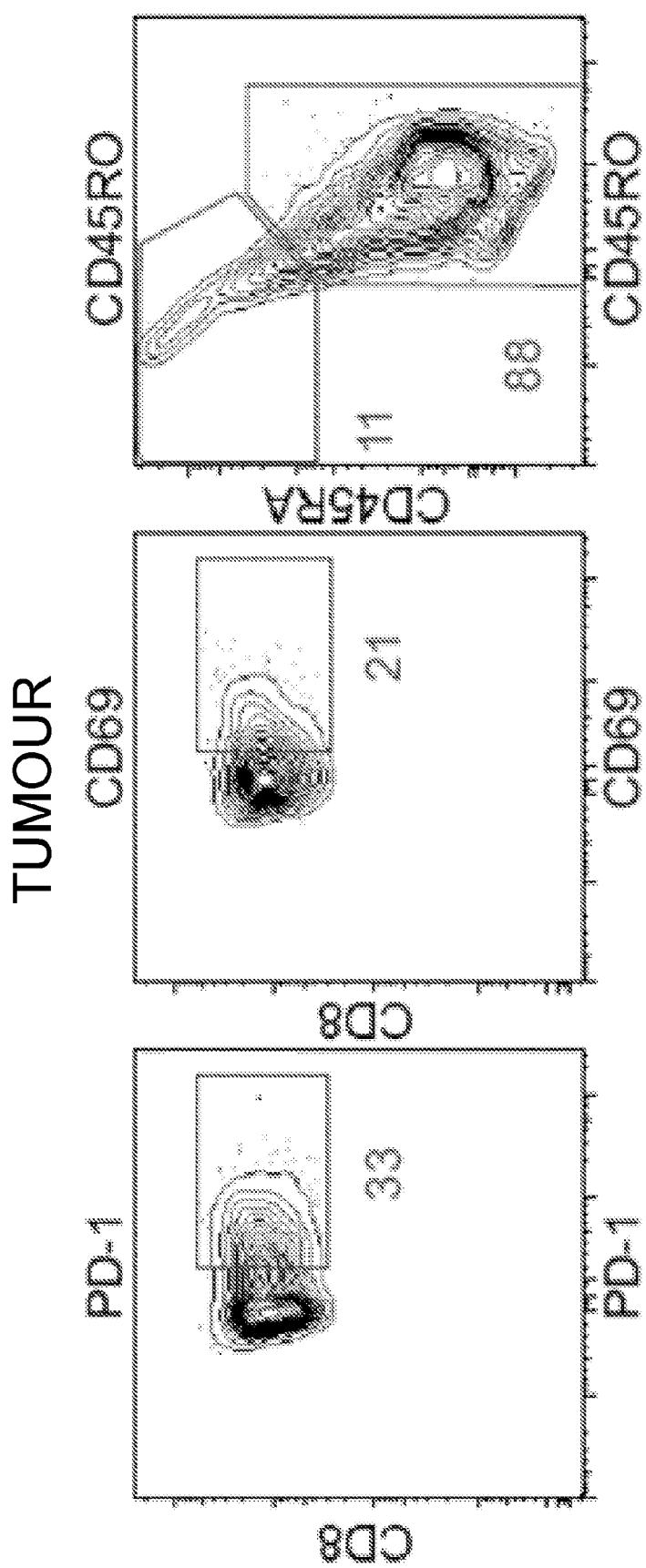

FIG. 45 depicts the number of T cell clones in matched tumor and adjacent non-tumor pancreatic tissue. ****P<0.0001.

FIGS. 46A-46D collectively depict a representative flow cytometric gating strategy to phenotype human T cells. Single cell suspensions from peripheral blood, tumor draining lymph nodes, and tumor tissue were subjected to flow cytometric analysis. First plot is pre-gated on live cells, followed by CD45+, and CD3+CD56− cells. Values indicate percentage of cells within the red boxes, and are gated based on isotype controls.

Figure 47:
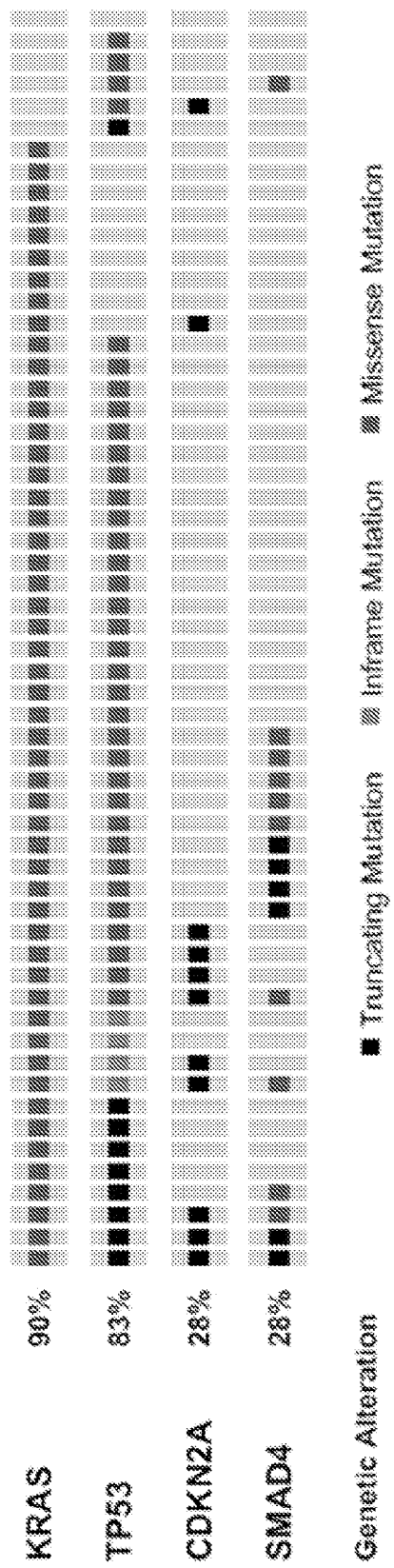

FIG. 47 depicts an oncoprint demonstrating the frequency of oncogenic driver gene mutations in the MSKCC PDAC cohort.

FIGS. 48A, 48B1, 48B2, and 48C collectively depict data showing that neoantigen quantity and cytotoxic CD8+ T cell infiltrate identified long term pancreatic cancer survivors. (A) Number of nonsynonymous, missense, and neoantigenic mutations per tumor. (B1-B2) Overall survival of patients with tumors harboring greater than the median number of neoantigens (NeoantigenHi), CD3-CD8 double positive cells (CD3-CD8Hi), CD3-CD8-Granzyme-B triple positive cells (CD3-CD8-Granzyme-BHi), or median polyclonality (PolyclonalHi), compared to all other patients (Rest). Neoantigens were determined using the MSKCC (left) and the pVAC-Seq (right) neoantigen prediction pipelines. (C) Unsupervised hierarchical clusters (cluster 1-4) of bulk tumor whole transcriptomic profiling in short and long term survivors (left). Each column represents a patient, each row a gene. Gene list available in methods. Overlap of NeoantigenHiCD8Hi, NeoantigenHiCD3-CD8-Granzyme-BHi, or all other tumors (Rest) with transcriptionally defined clusters (right). Each bar in (A) represents data from one patient's tumor. Mutations in (A), (B1-B2), and (C) were determined by whole exome sequencing. Polyclonality in (B1-B2) was calculated by quantitative TCR Vβ sequencing. Number of immune cells in (B1-B2) and (C) were quantified by immunophenotyping as the median of three cores per tumor in short and long term survivor tumor tissue microarrays. *P<0.05.

Figure 49A:
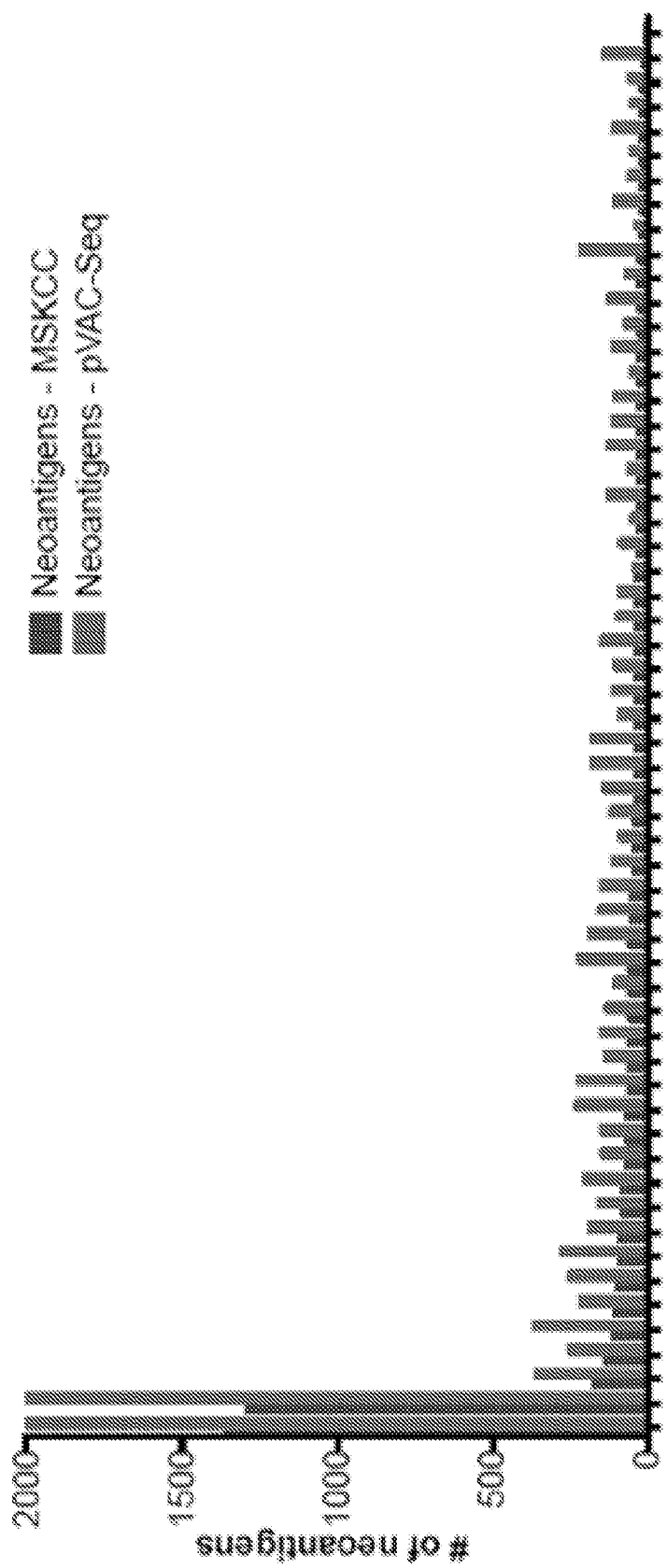
Figure 49B:
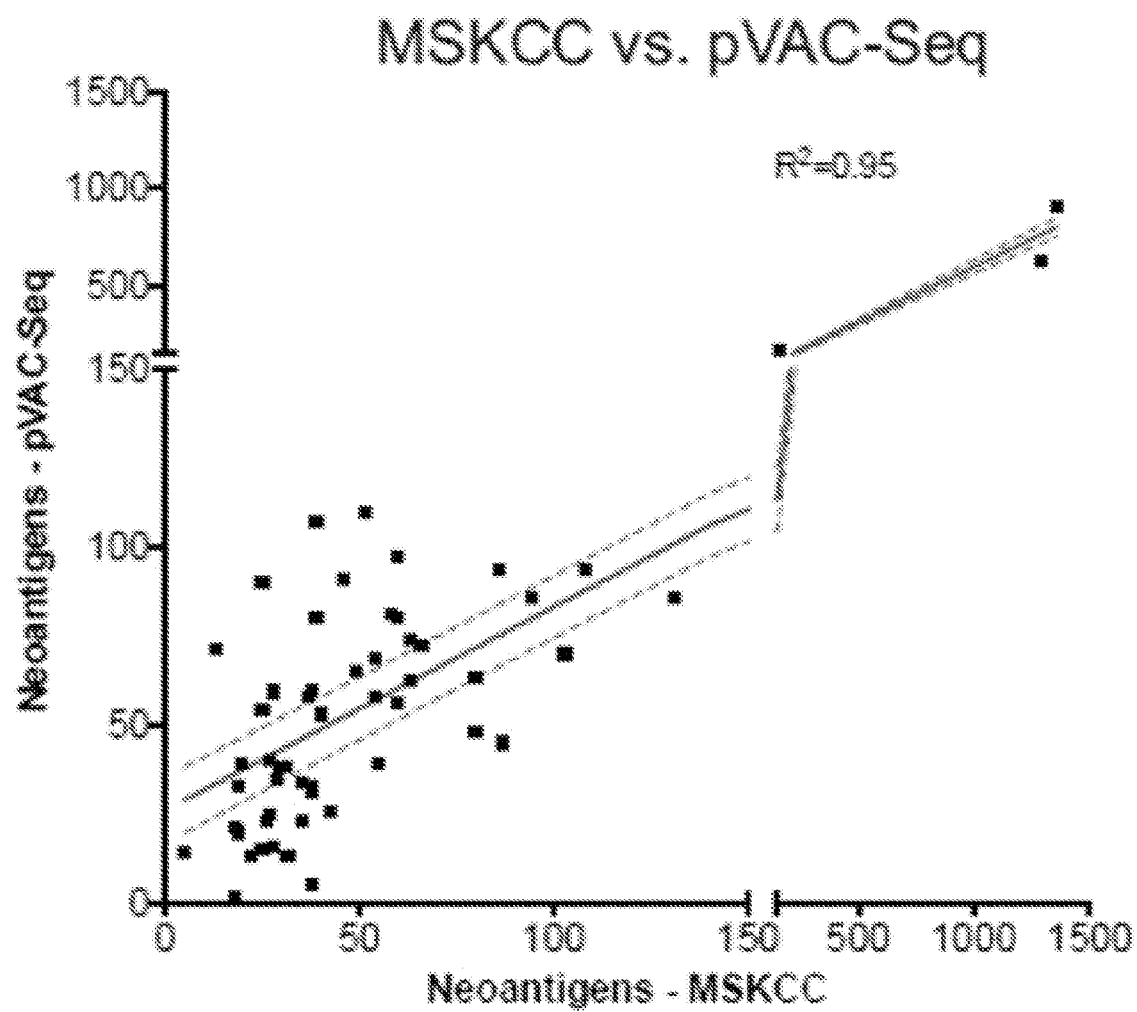

FIGS. 49A and 49B collectively depict number of neoantigens per tumor (n=58) as determined by the MSKCC and pVAC-Seq neoantigen calling pipelines (A). Tick marks on the x-axis correspond to individual tumors. Correlation matrix of neoantigens as determined by the MSKCC and pVAC-Seq neoantigen calling pipelines (B). Solid red line indicates line of best fit, dotted lines indicate 95% confidence intervals.

Figure 50A:
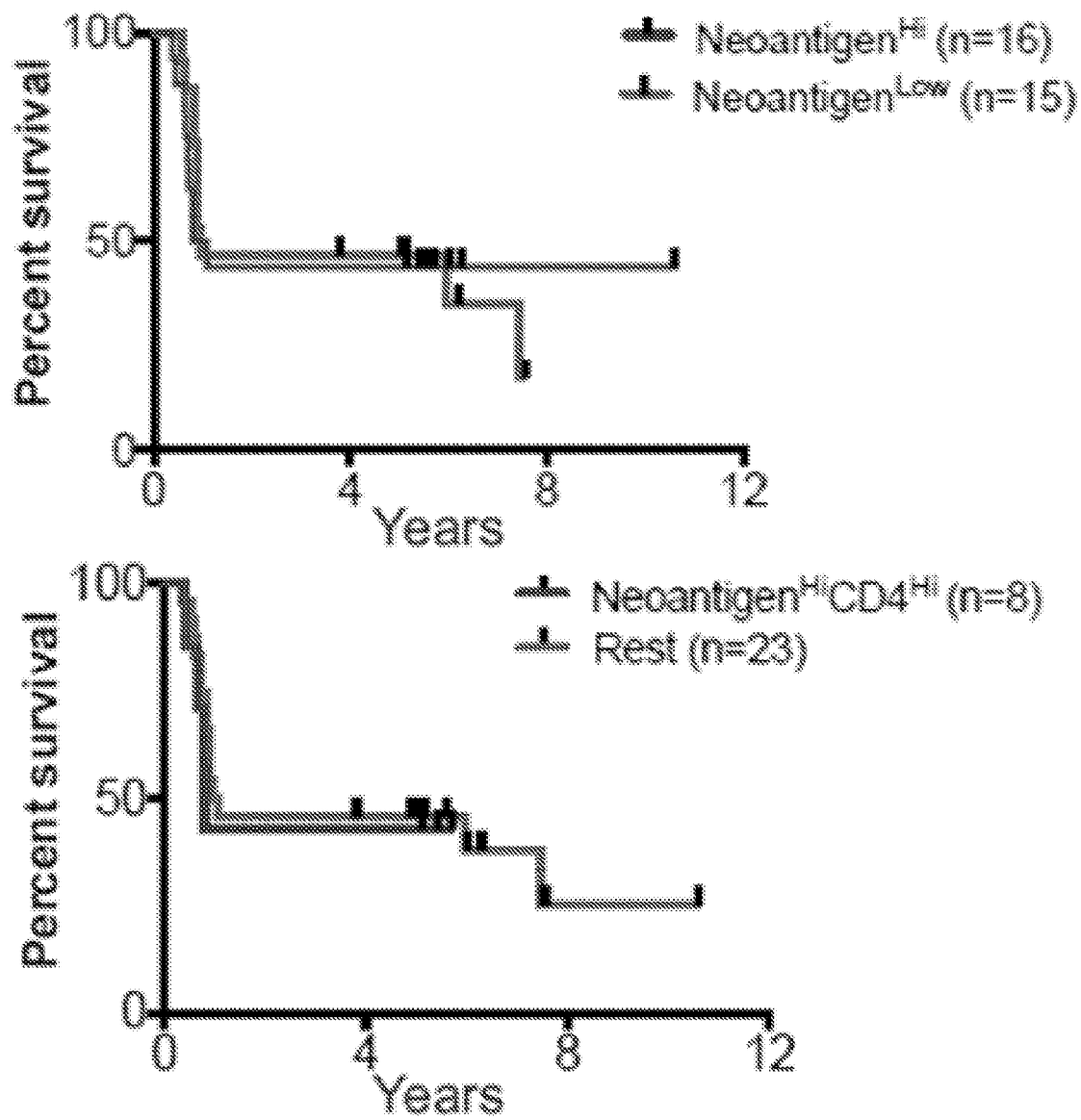
Figure 50B:
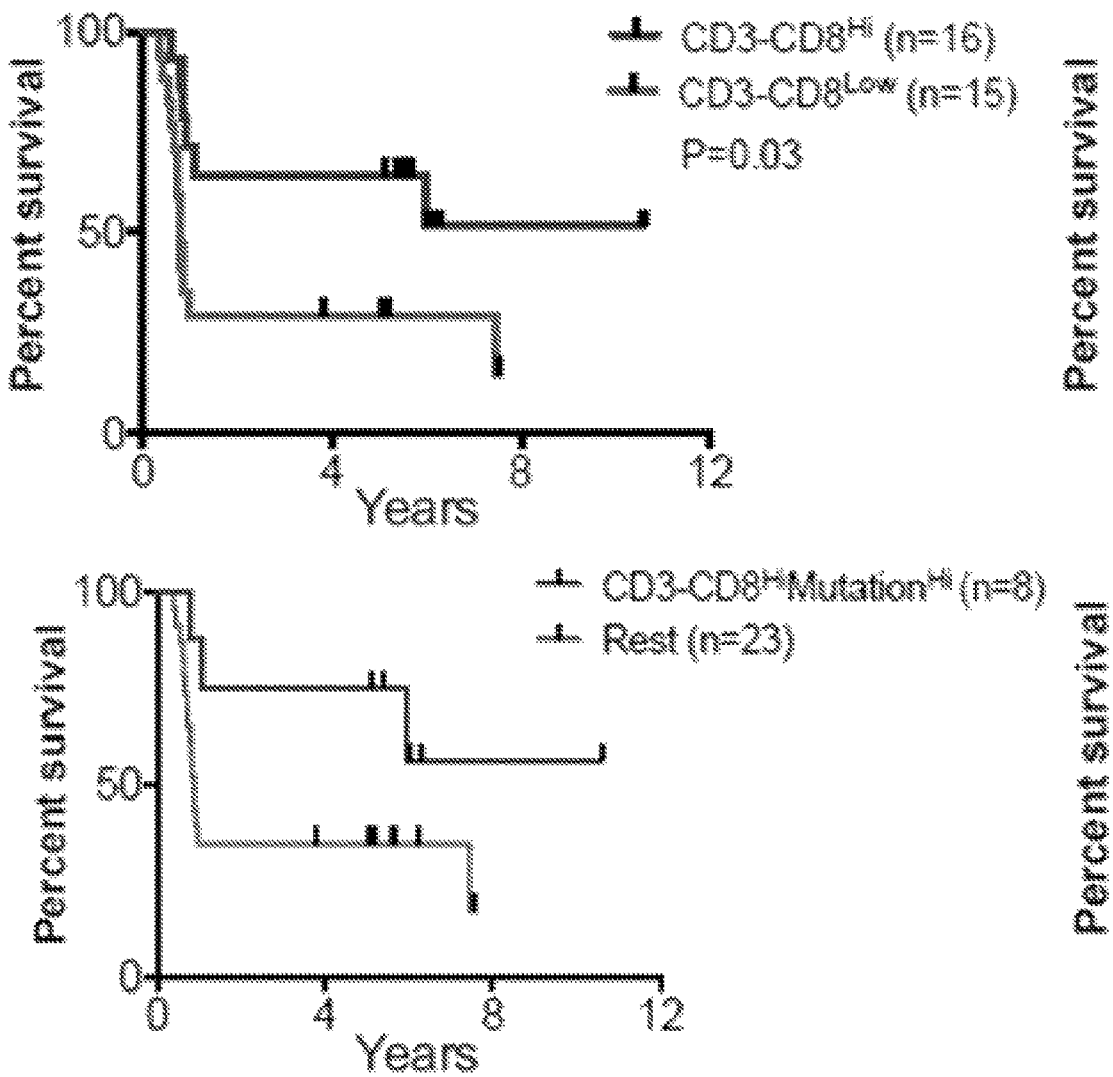
Figure 50C:
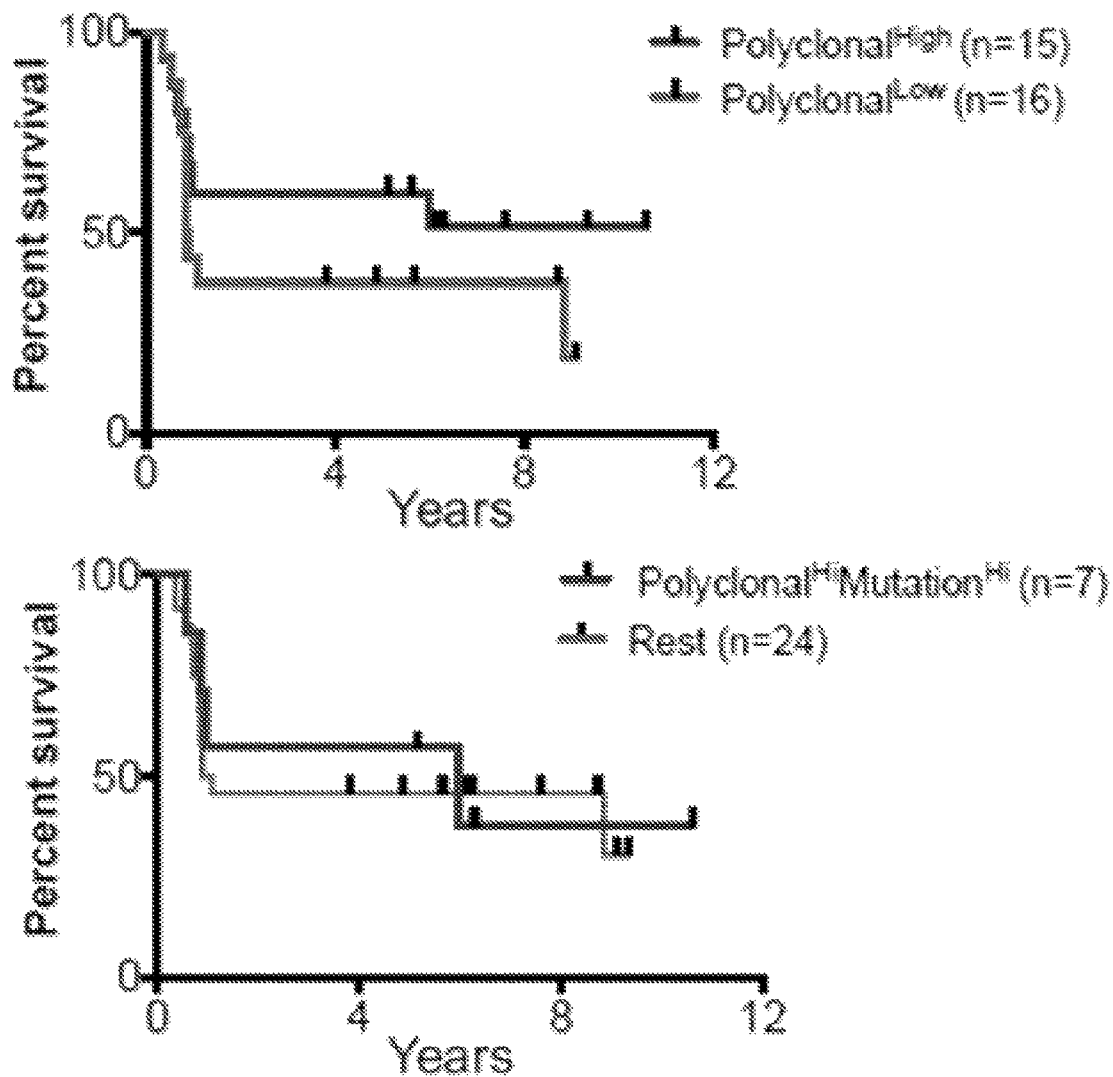

FIGS. 50A, 50B, and 50C collectively depict survival of patients relative to number of neoantigens. (A) depicts overall survival of patients with tumors harbouring more or fewer than the median number of neoantigens (neoantigen$^{hi/low}$) and CD4 single positive cells (CD4$^{hi/low}$) compared to all other patients (Rest). (B) depicts overall survival of patients with tumors harbouring CD3-CD8 double-positive cells (CD3-CD8$^{hi/low}$) compared to all other patients (Rest). (C) depicts overall survival of patients with tumors harbouring polyclonality (polyclonal$^{hi/low}$) and mutations (mutation$^{hi/low}$), compared to all other patients (Rest).

Figure 51:
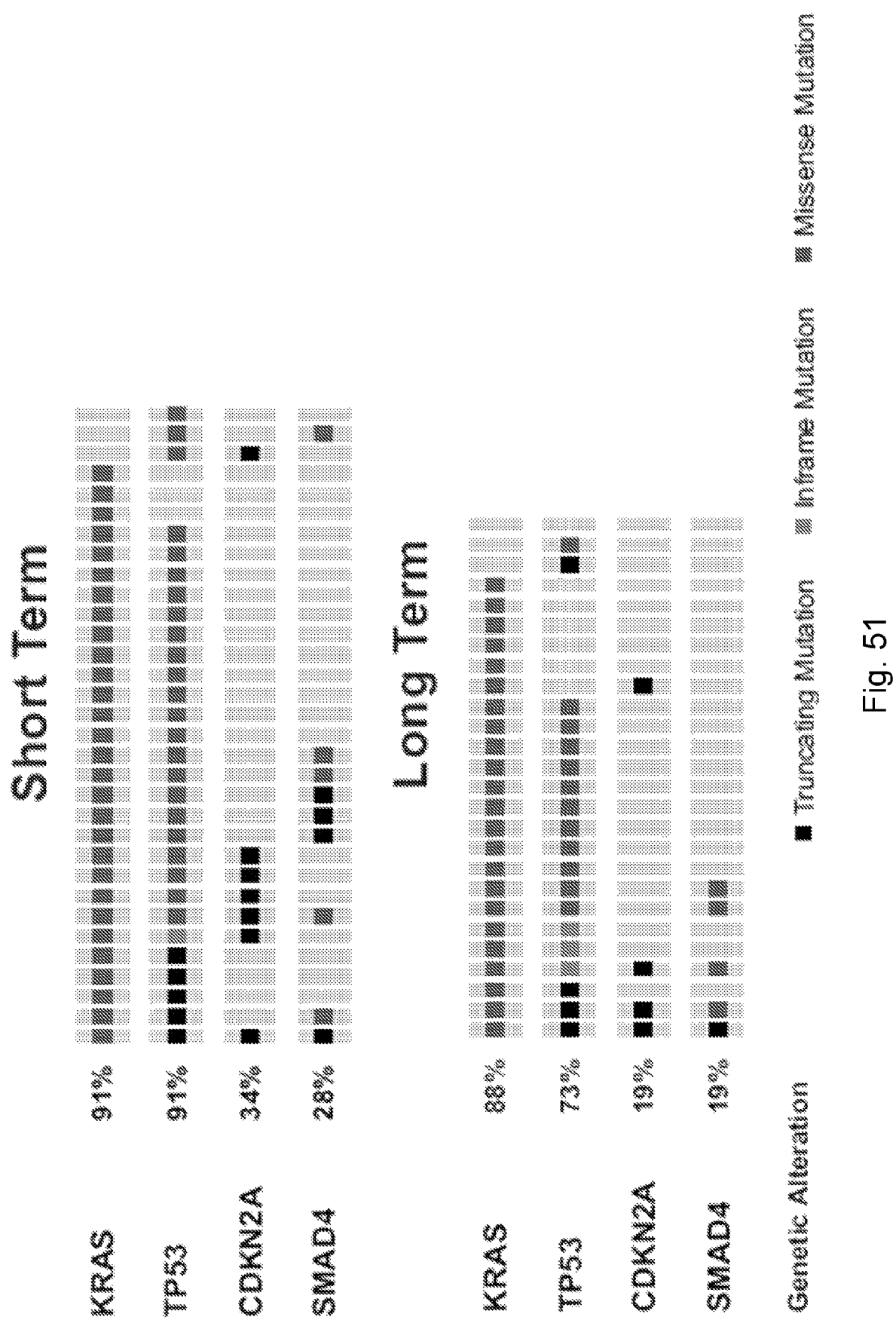

FIG. 51 depicts an oncoprint demonstrating the frequency of oncogenic driver mutations in short and long term tumors.

Figure 52:
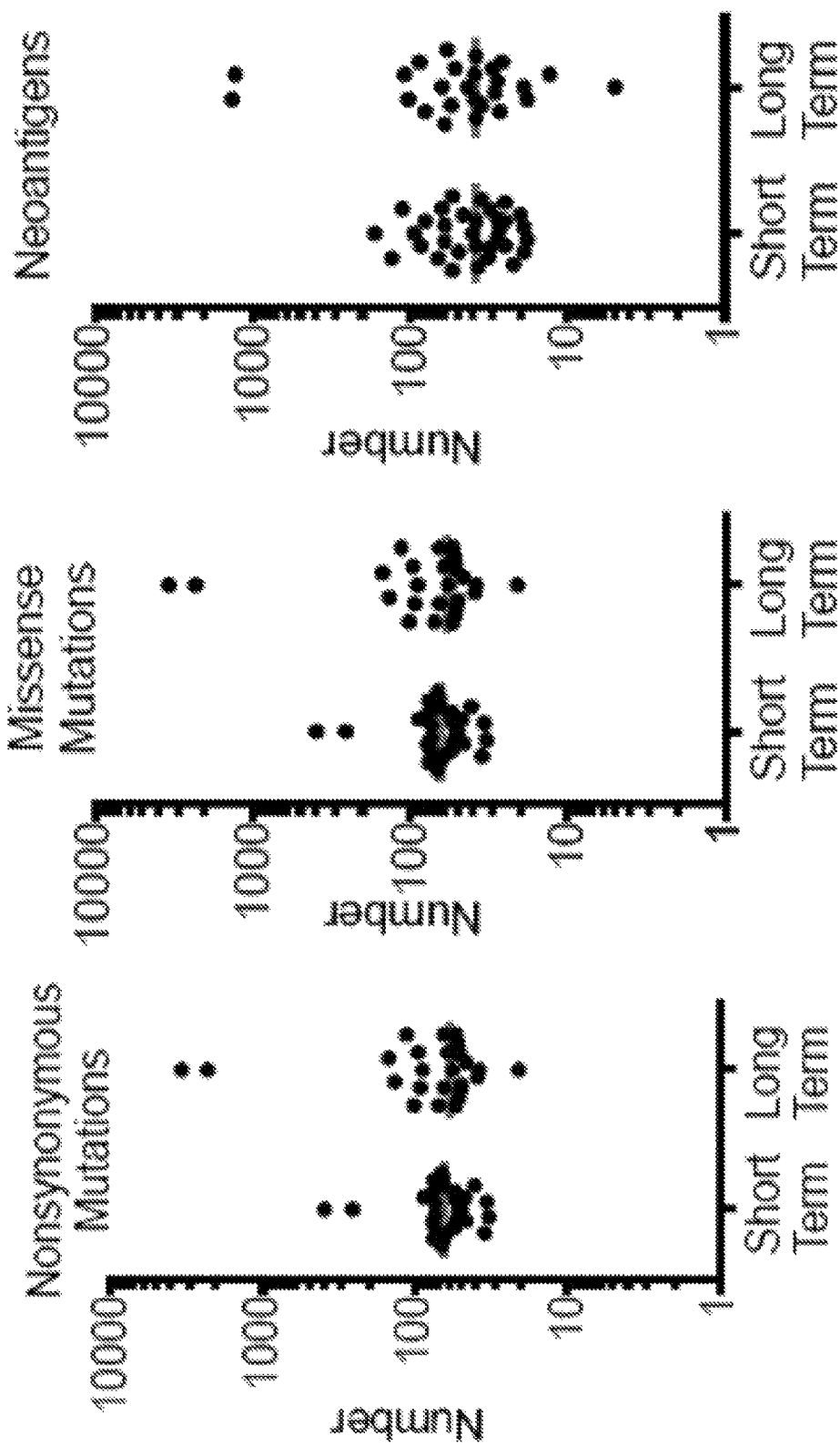

FIG. 52 depicts the number of nonsynonymous, missense, and immunogenic mutations (neoantigens) in short and long term PDAC tumors.

Figure 53:
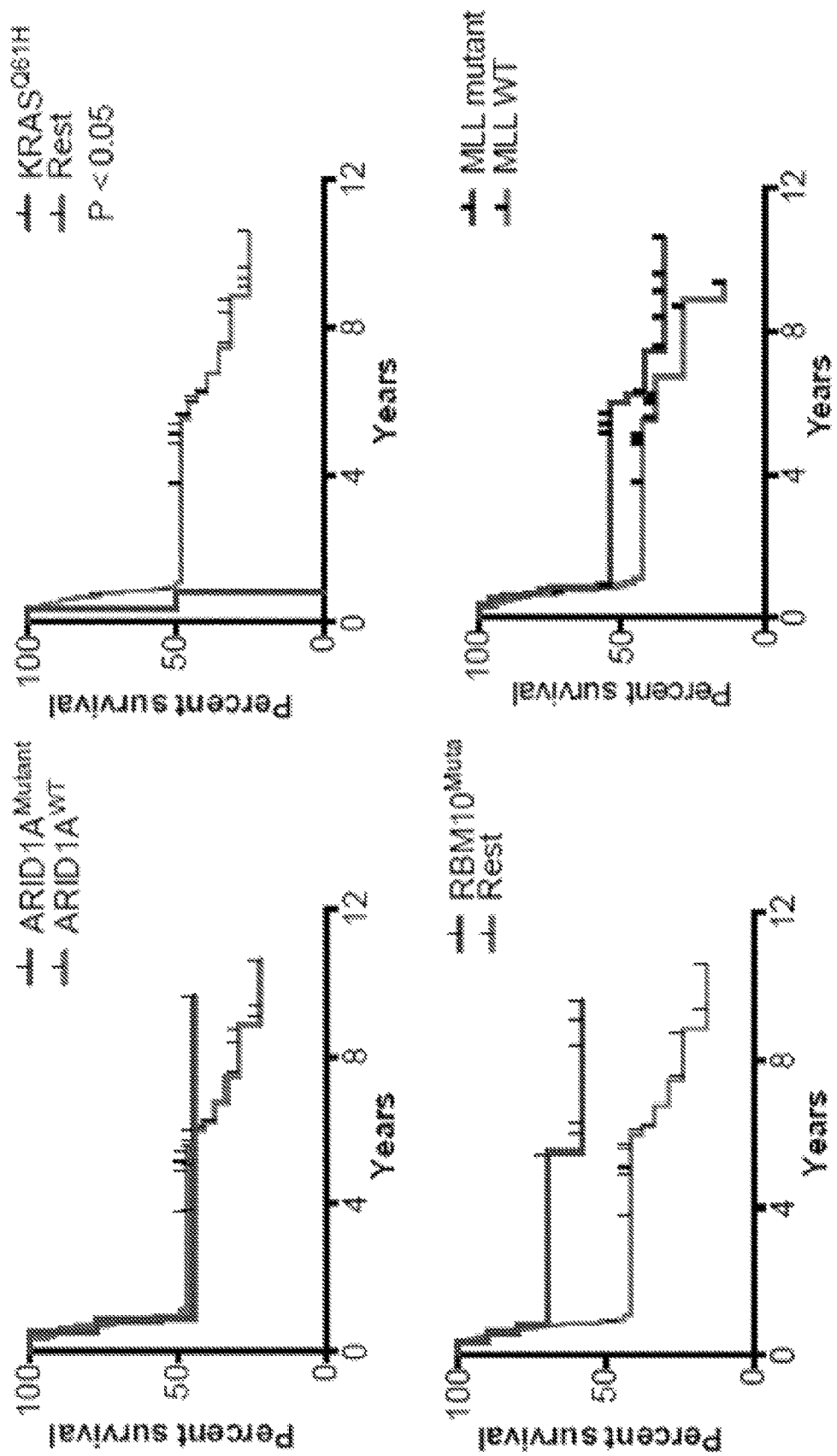

FIG. 53 depicts overall survival stratified by mutations in ARID1A, KRASQ61H, RBM10, and MLL related genes (MLL, MLL2, MLL3, MLL5) in accordance with an embodiment of the present disclosure.

FIGS. 54A, 54B, 54C, 54D, 54E1, 54E2, 54E3, 54F, 54G1, 54G2, 54G3, 54G4, 54H1, and 54H2 collectively depict neoantigens with microbial homology stratify long term pancreatic cancer survivors. (A) Schematic of neoantigen immune fitness models. Each circle represents a tumor clone in an evolutionary tree. Clones in both models are identical with respect to the number of mutations and neoantigens. Numbers represent hypothetical neoantigens gained in a successive tumor clone. Shades of red indicate immunogenicity of each clone, as ascribed by the two models, namely neoantigen quality (recognition potential model or quality model) or neoantigen quantity (neoantigen load model or quantity model). (B) Parameters defining the recognition potential score in the recognition potential model. In (a), amino acid sequences of a hypothetical wild type (WT) epitope, tumor neoepitope, and a homologous microbial epitope are shown. Yellow highlights the changing amino acid between the WT and tumor sequence as a consequence of a tumor specific mutation. The amino acids in red indicate homology between the tumor neoepitope and the microbial epitope. (C) Overall survival of patients in the MSKCC cohort whose tumors displayed high neoantigen recognition potential (recognition potential$^{Hi}$) compared to low neoantigen recognition potential (recognition potential$^{Low}$) to pathogenic epitopes (top). Overall survival of patients whose tumors displayed high neoantigen load (Neoantigen$^{Hi}$) compared to low neoantigen load (Neoantigen$^{Low}$) (bottom). (D) Distribution of high and low recognition potential neoantigens in Neoantigen$^{Hi}$ CD3-CD8$^{Hi}$ and Neoantigen$^{Hi}$ CD3-CD8-Granzyme-B$^{Hi}$ long term pancreatic cancer survivors compared to all other patients (Rest). **P<0.01. (E) Neoantigen quality is independently associated with long term survival. Overall survival of patients whose tumors displayed high compared to low neoantigen recognition potential (Neoantigen QualityHi/Low) to microbial epitopes (E1 top). Overall survival of patient who did or did not receive adjuvant chemotherapy (E2 top). Overall survival of all four groups is shown at the bottom. Neoantigen quality defined by neoantigen fitness modeling of sequence homology to microbial epitopes. Table shows univariate and multivariate Cox regression analysis of the associations of clinicopathologic features, adjuvant chemotherapy, and neoantigen quality with overall survival. Data include all patients in the whole exome sequencing MSKCC cohort. (F) Overall survival of patients in the ICGC cohort whose tumors displayed high neoantigen recognition potential (Neoantigen Quality$^{Hi}$) compared to low neoantigen recognition potential (Neoantigen Quality$^{Low}$) to pathogenic epitopes (top). Overall survival of patients whose tumors displayed high neoantigen load (Neoantigen Quantity$^{Hi}$) compared to low neoantigen load (Neoantigen Quantity$^{LOW}$) (bottom). (G1) Number of non-synonymous, missense, and neoantigenic mutations per patient in the ICGC cohort (n=166). (G2) Overall survival of patients whose tumors displayed high compared to low neoantigen recognition potential (Neoantigen QualityHi/Low) to microbial epitopes in the ICGC cohort (top). Overall survival of patients in the ICGC cohort stratified by adjuvant chemotherapy administration (bottom). (G3) Overall survival of all four groups. Neoantigen quality defined by neoantigen fitness modeling of sequence homology to microbial epitopes. Table shows univariate and multivariate Cox regression analysis of the associations of clinicopathologic features, adjuvant chemotherapy, and neoantigen quality with overall survival in the ICGC cohort. (H) depicts parameters of the neoantigen recognition potential fitness (quality model) for a, the MSKCC cohort b, and the ICGC cohort. (top) Log-rank test score landscape as a function of the model parameters, the horizontal alignment score displacement a, and the characterist time T, the significance of the score is denoted in the legend. (bottom) Two dimensional histograms showing distributions of optimal parameters obtained on subsampled datasets with 50, 70, and 80% of patients left, over 500 iterations of subsampling at each frequency.

FIGS. 55A, 55B, 55C, 55D, 55E, 55F, 55G, 55H, 55I1, 55I2, 55J1, 55J2, 55K, and 55L collectively depict MUC16 to be a neoantigen enriched immunogenic hotspot in long term pancreatic cancer survivors. (A) Frequency (left) and distribution (right) of patients with neoantigens. Genes harboring neoantigens in >15% of patients are indicated. (B) Frequency of patients with MUC16 neoantigens and (C) the number of MUC16 neoantigens per tumor. (D) Bulk tumor MUC16 mRNA and (E) quantified immunohistochemical protein expression. (F) MUC16 mutant allele frequency in non-hypermutated tumors with MUC16 mutations. (G) Frequency of patients with neoantigens in genes recurrently harboring neoantigens in >5% of patients in both MSKCC and ICGC cohorts. (H) Frequency of MUC16 neoantigens in MSKCC and ICGC cohorts. (I, J, K) Unique wild type (WT peptide 1,2) and mutant (Mutant peptide 1,2) MUC16 nonamers were generated for two long term PDAC survivors (Patients 1, 2) respectively based on in silico neoantigen predictions. Peripheral blood mononuclear cells were pulsed in vitro for 3 weeks and CD8$^+$ T cell expansion (I), CD107a expression (J), and TCR clonotyping (K) were determined. Data in (I, J) indicate n=2/group and are representative of two experiments with similar results. Venn diagrams in (K) indicate clonal overlap. (L) Peripheral blood mononuclear cells of healthy donors (neopeptide 1, 2–n=5; neopeptide 3–n=6) were stained with MUC16 neopeptide-MHC multimers based on in silico somatic neoantigen predictions in tumors of long term survivors. For each neopeptide, healthy donors were HLA-matched to alleles predicted to bind the neopeptide. HLA-matched irrelevant multimers (control multimer) were available for neoepitopes 1, and 2 and were used as controls. Data represent mean±SEM. *P<0.05, P<0.01, *P<0.001.

FIG. 56 depicts the recognition potential load fitness model parameter stability analysis. The boxplots (top) and the histograms (bottom) illustrate distributions of the difference between the optimal shift parameter obtained on the full dataset and the subsampled datasets, with frequencies 0.8, 0.7, 0.6, 0.5, and 0.4.

Figure 57:
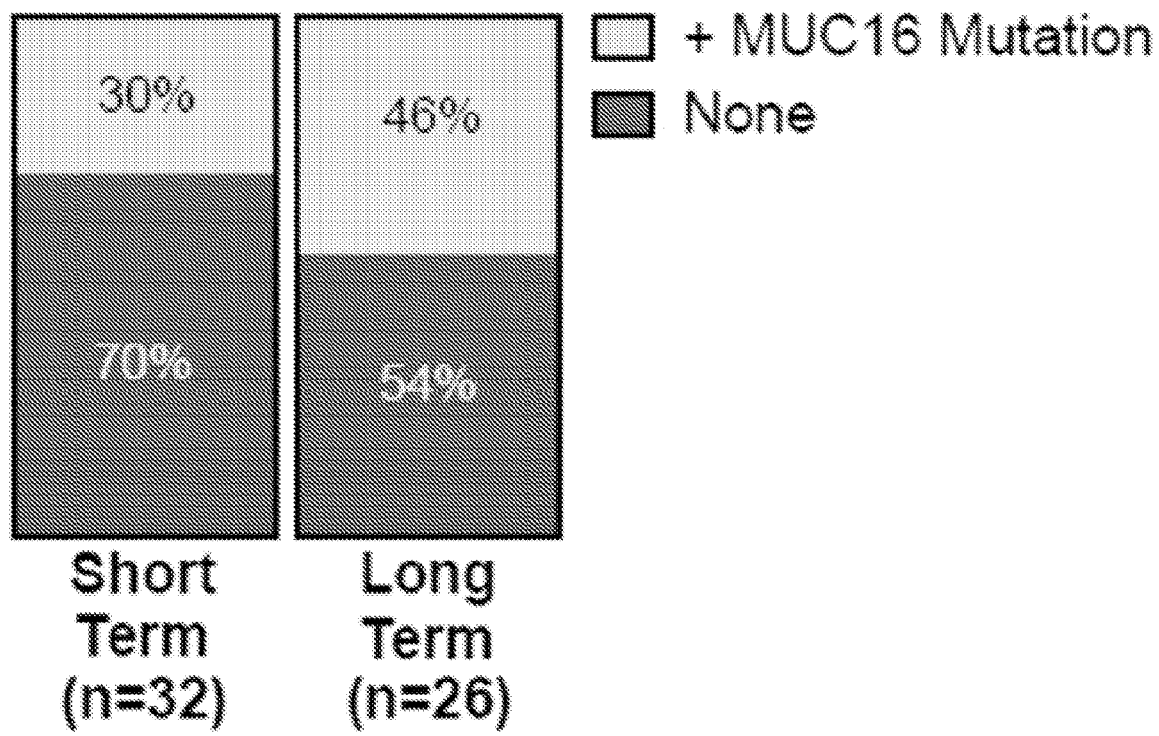

FIG. 57 depicts the frequency of MUC16 mutations in short and long term PDAC tumors.

Figure 58:
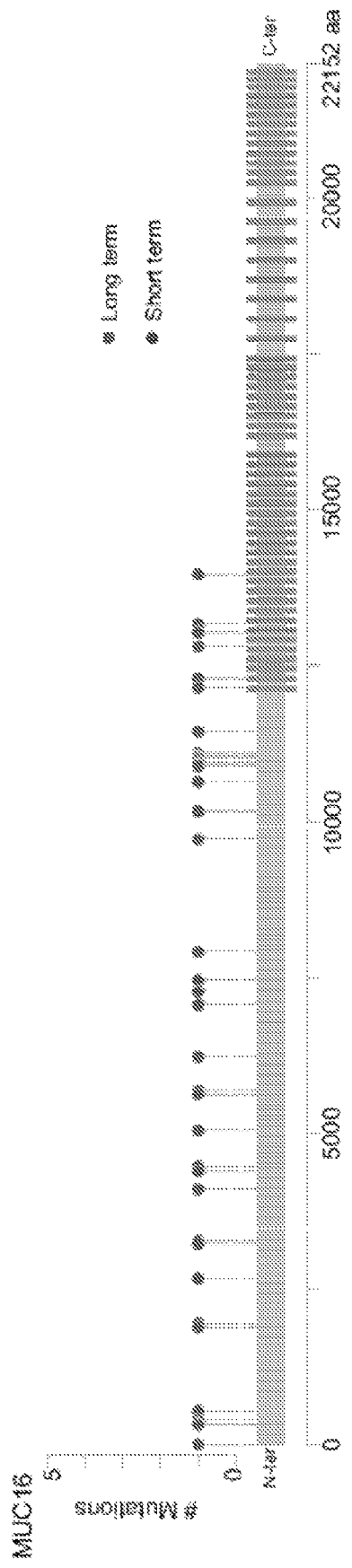

FIG. 58 depicts a lollipop plot showing location of MUC16 mutations in short and long term pancreatic cancer survivors.

Figure 59:
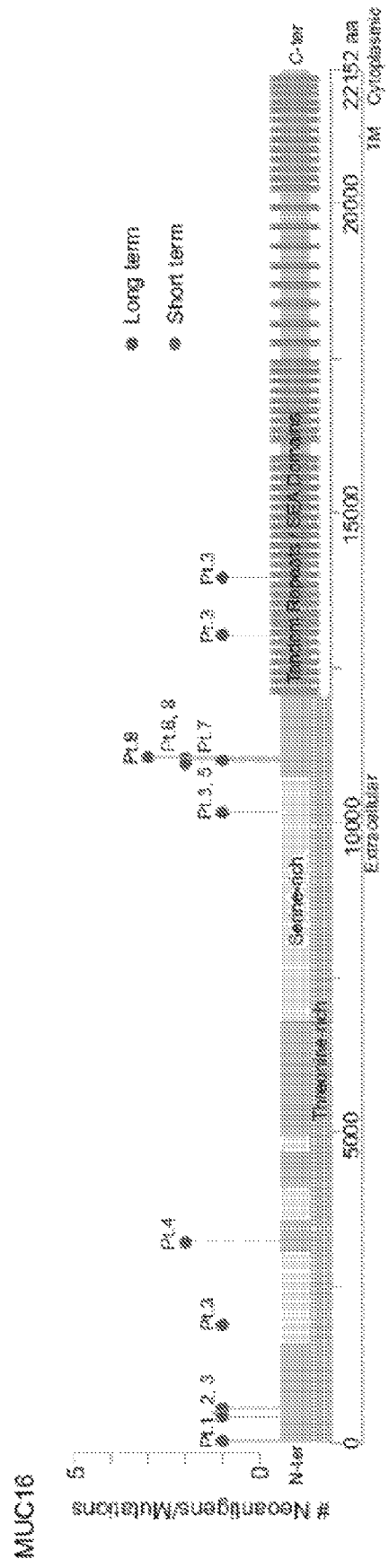

FIG. 59 depicts a lollipop plot showing location of MUC16 neoantigens in short and long term pancreatic cancer survivors.

Figure 60:
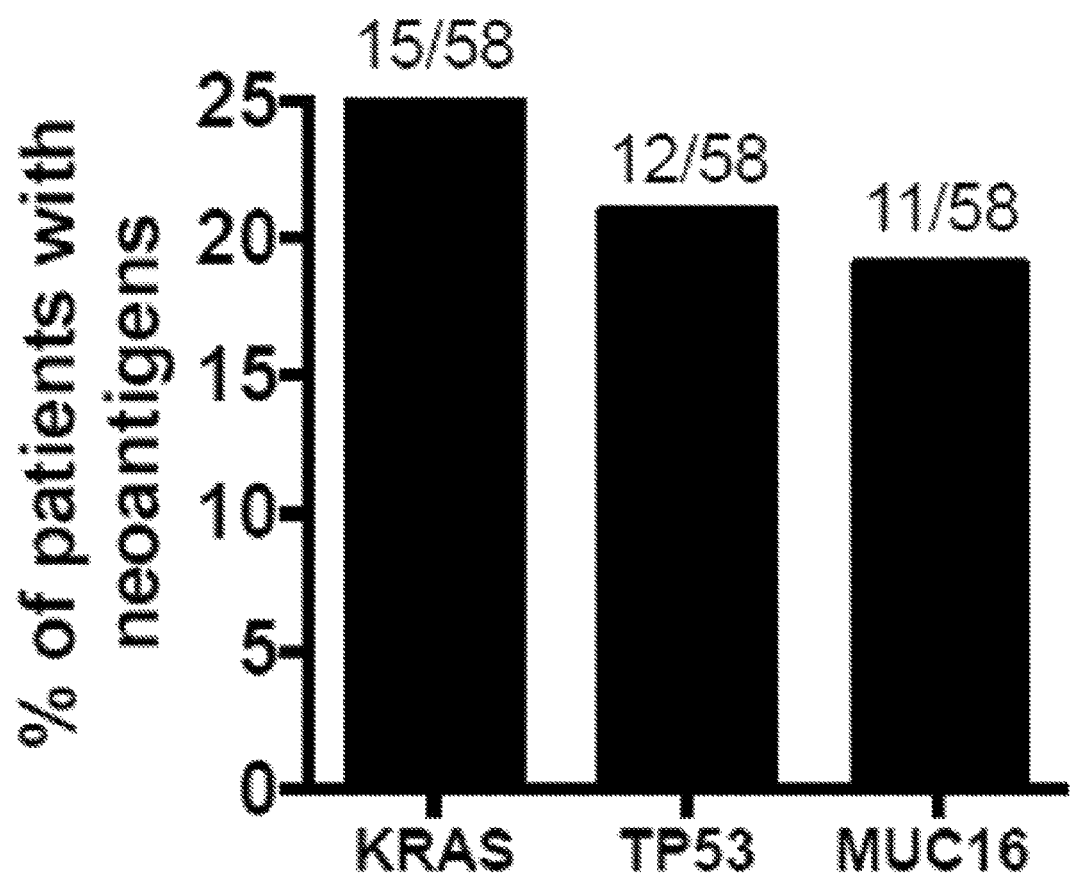

FIG. 60 depicts genes most frequently generating neoantigens as determined by pVACSeq. Frequency of patients and raw numbers are indicated.

Figure 61:
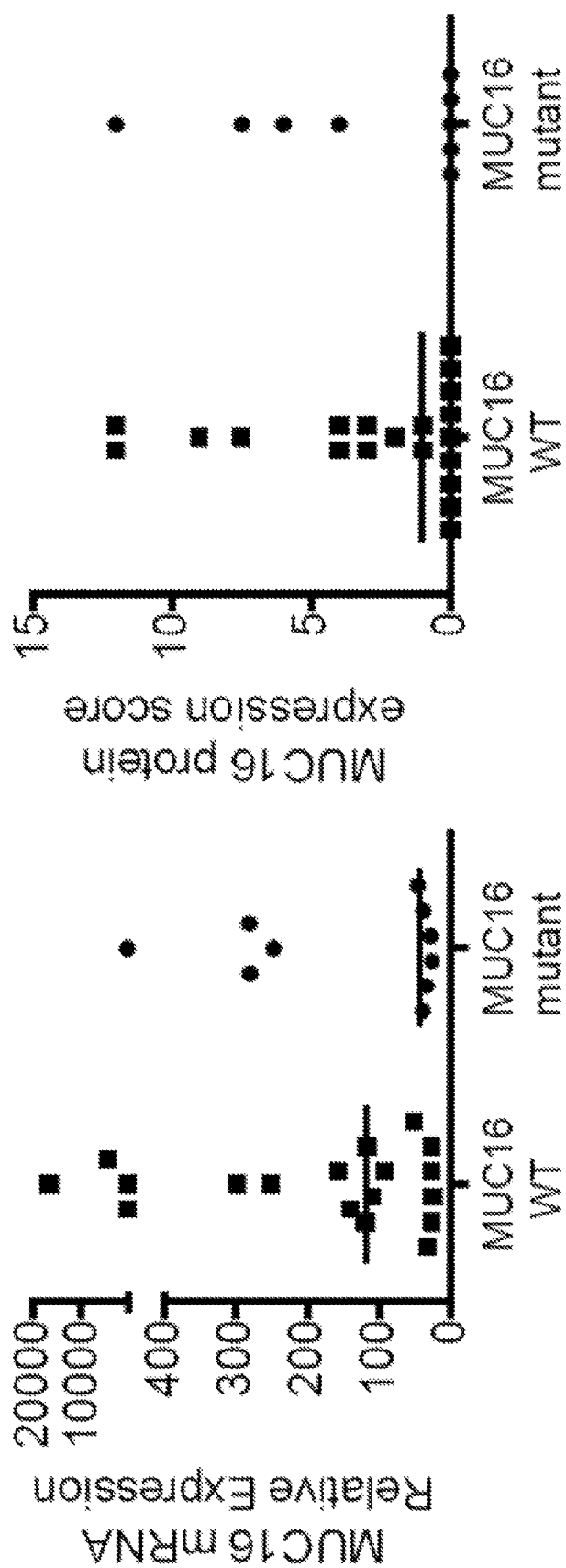

FIG. 61 depicts MUC16 mRNA and protein expression in MUC16 non-mutated (WT) and mutated (mutant) tumors.

Figure 62:
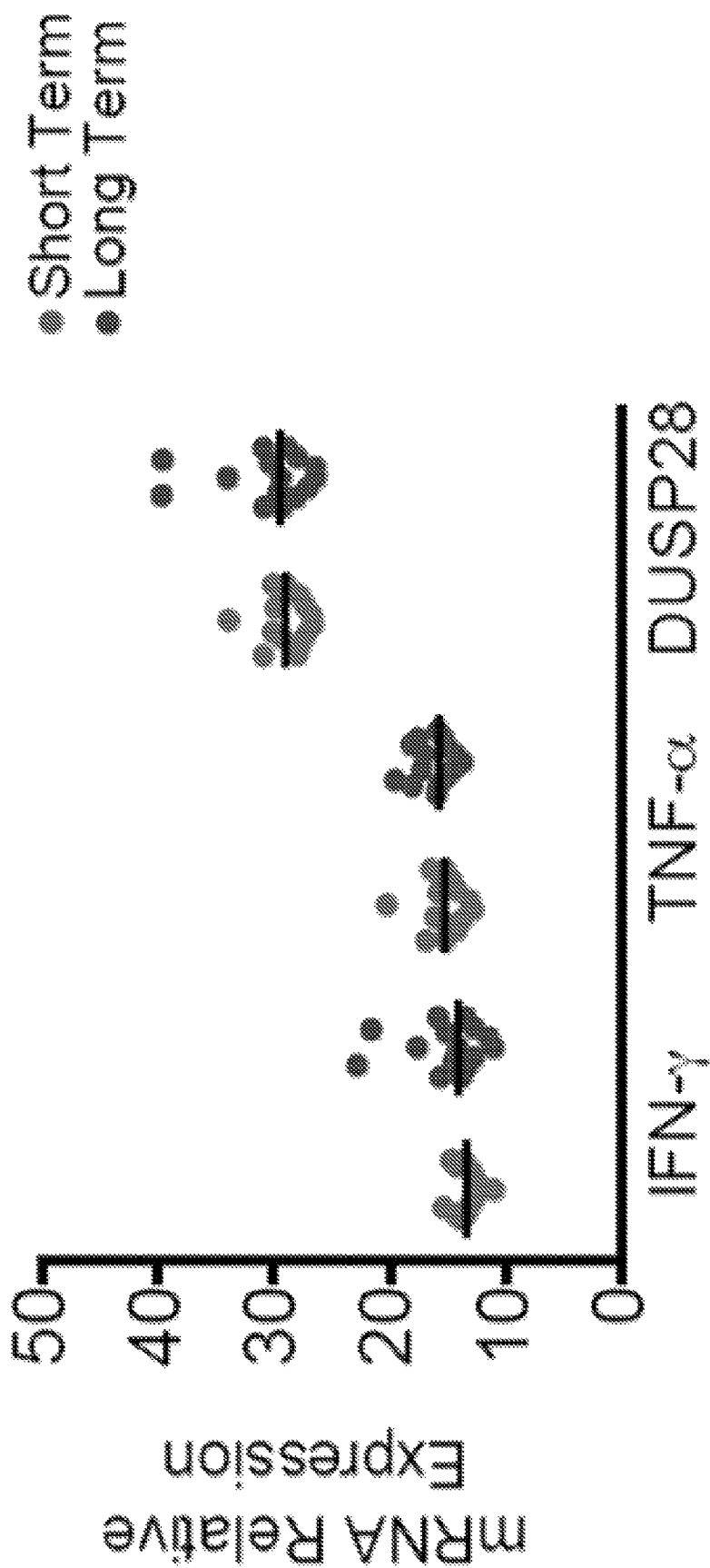

FIG. 62 depicts mRNA expression of transcriptional activators of MUC16.

Figure 63:
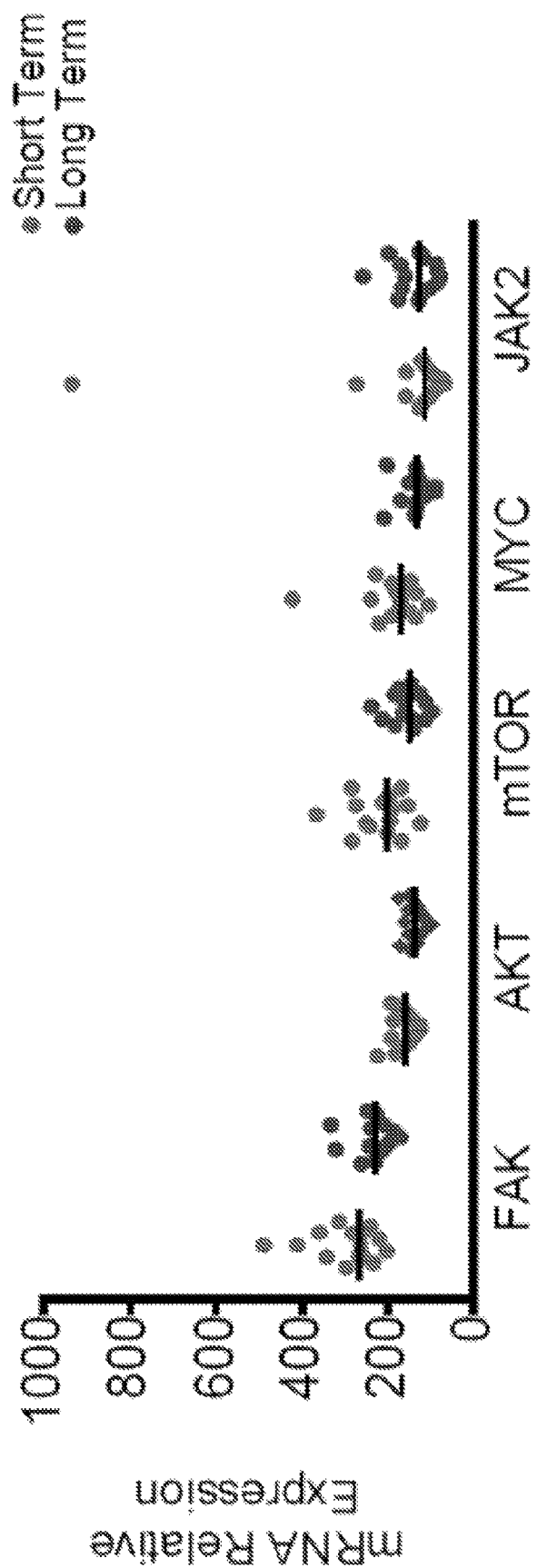

FIG. 63 depicts mRNA expression of mediators implicated in MUC16 dependent tumor progression in short and long term tumors.

Figure 64:
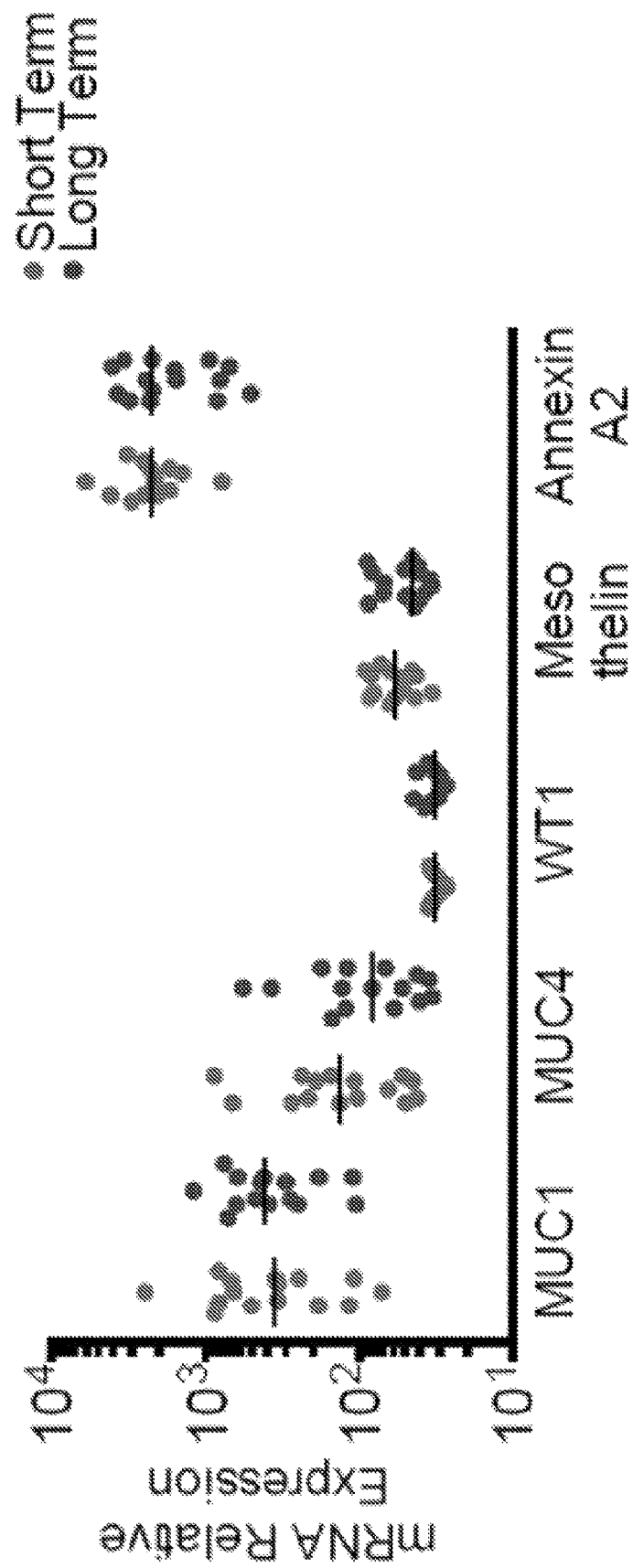

FIG. 64 depicts mRNA expression of tissue expression antigens MUC1, MUC4, WT1, mesothelin, and Annexin A2 in short and long term tumors.

Figure 65:
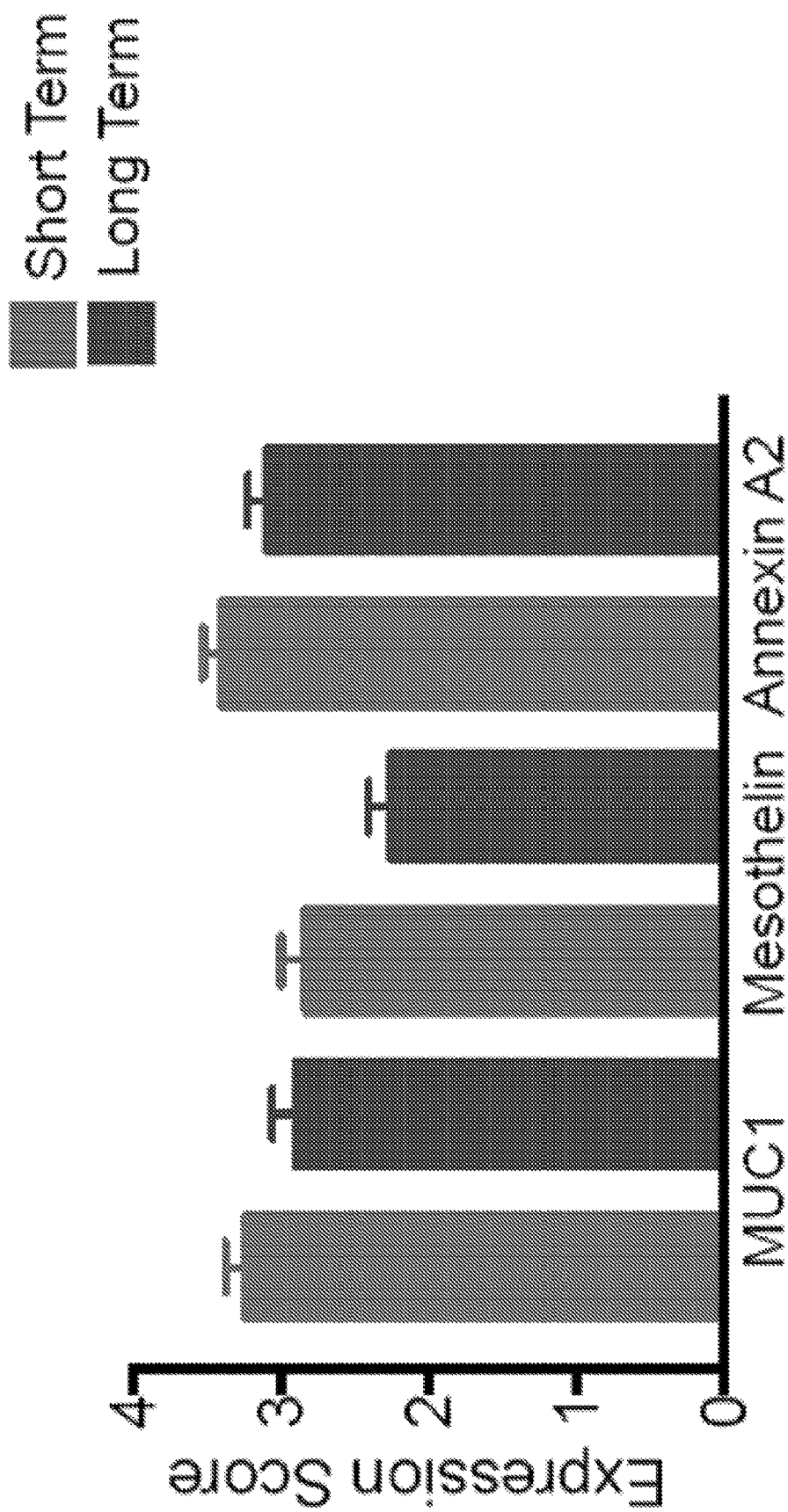

FIG. 65 depicts quantified protein expression of tissue expression antigens MUC1, mesothelin, and Annexin A2 in short and long term tumors. WT1 protein was undetectable in tumors of both short and long term survivors.

Figure 66:
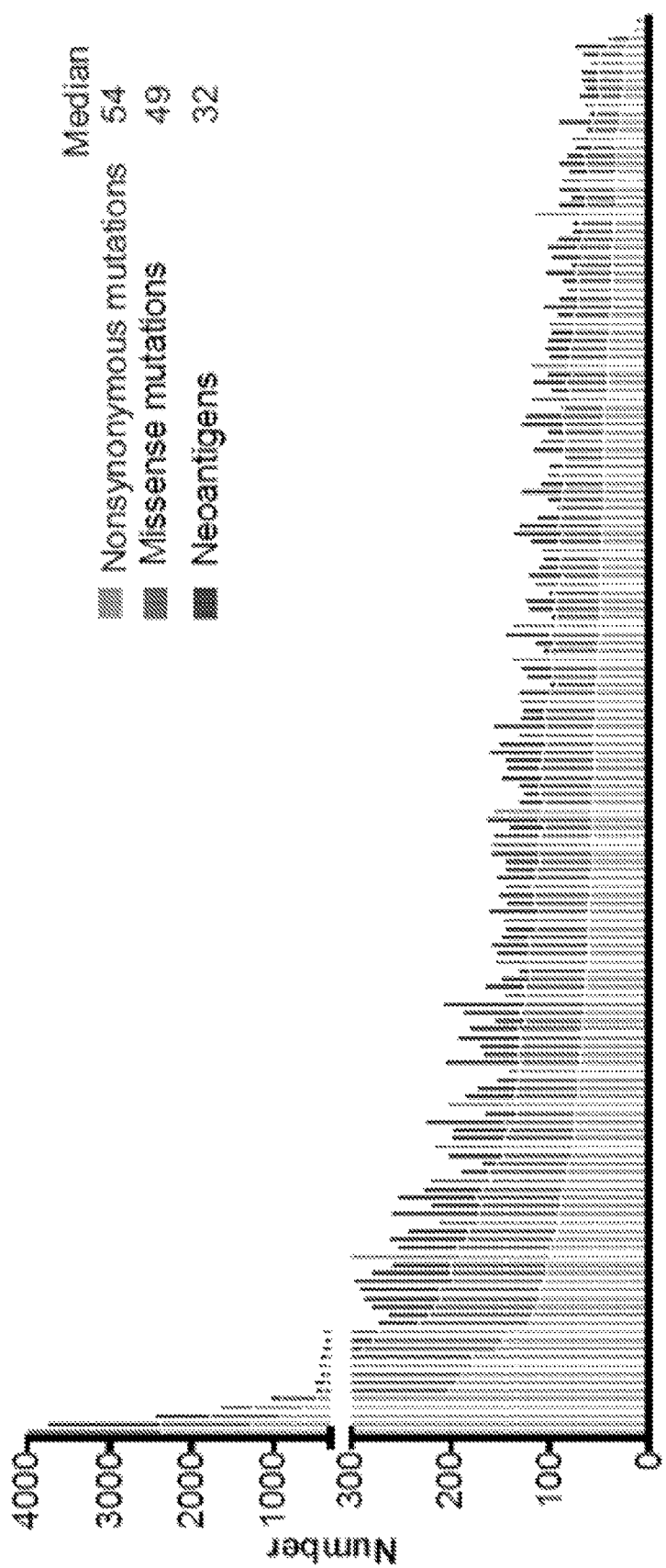

FIG. 66 depicts number of nonsynonymous, missense, and neoantigen mutations per patient in the ICGC cohort (n=169).

Figure 67A:
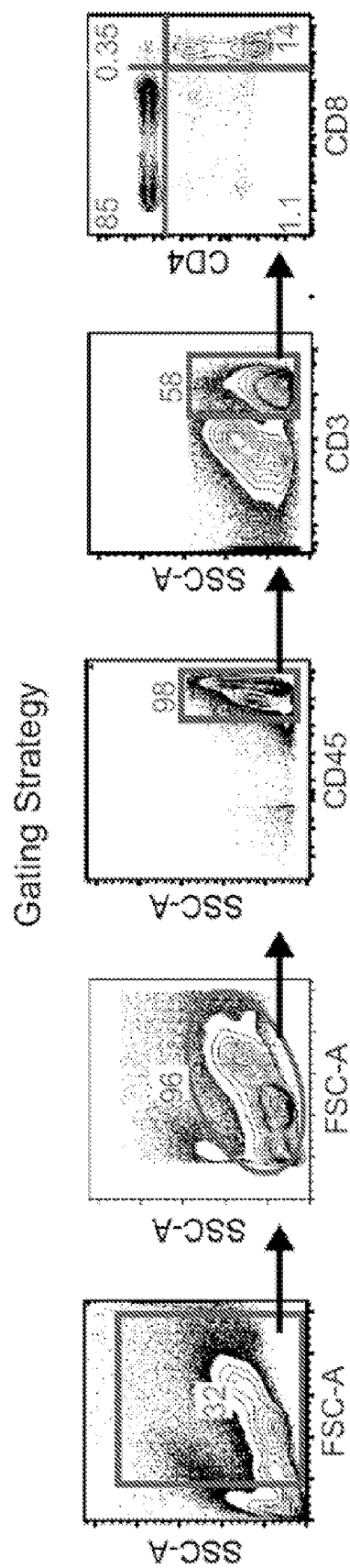
Figure 67B:
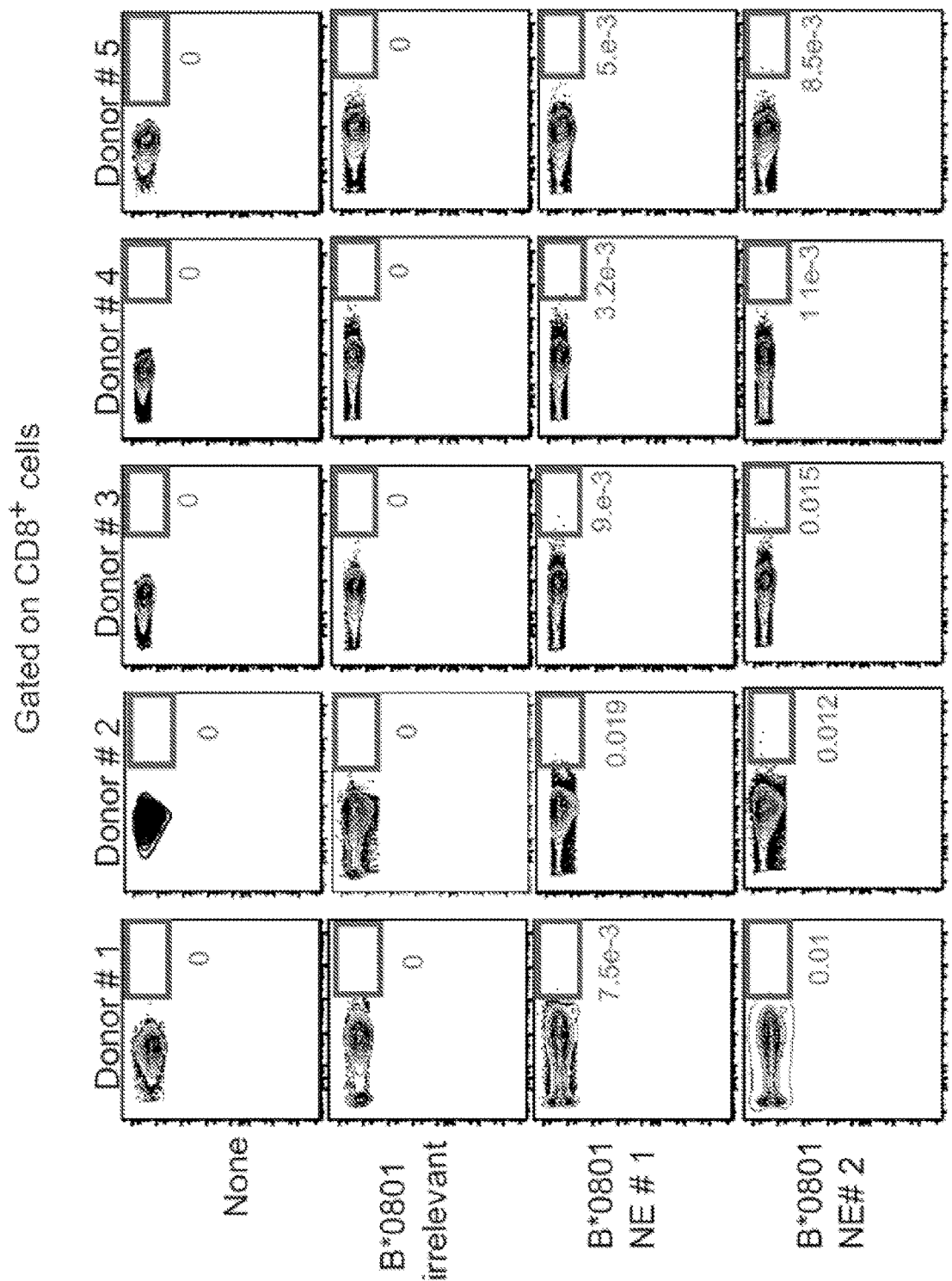

FIGS. 67A and 67B collectively depict representative gating strategy to identify CD8$^+$ T cells in peripheral blood of healthy donors (67A). Identification of CD8$^+$ T cells in healthy donors reactive to 2 unique MUC16 neoepitopes (NE #1, NE #2; NE=Neoepitope) predicted to bind to the B*0801 HLA-allele, using MUC16-neoepitope-HLA multimers (67B).

Figure 68:
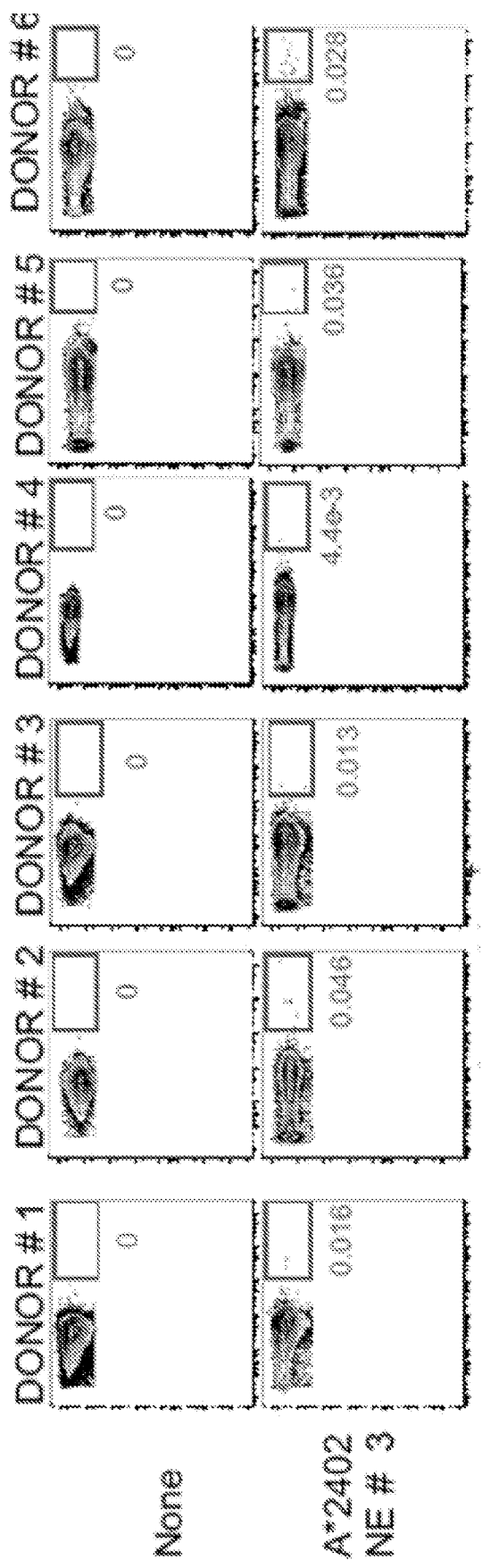

FIG. 68 depicts identification of CD8$^+$ T cells in healthy donors reactive to MUC16 neoepitopes (NE #3, NE=Neoepitope) predicted to bind to the A*2402 HLA-allele, using MUC16-neoepitope-HLA multimers.

FIGS. 69A, 69B, 69C1, 69C2, 69D1, 69D2, 69D3, and 69D4 collectively depict neoantigen and cross-reactive microbial peptide T cells detected in blood and tumours. (A) Left, gene expression in the presence (red) or absence (grey) of high-quality neoantigenic mutations. x axis, genes; shaded circles, biologically independent samples in individual patients (n=30). Right, median non-neoantigenic and neoantigenic expression. All high-quality neoantigenic genes with available mRNA expression are shown. (B) Metastatic propagation of all clones in the primary tumour stratified by neoantigen quality. Mutant allele frequencies in matched primary-metastatic tumours (left) and metastatic tumours alone (right) are shown in biologically independent samples in one patient. MAF, mutant allele frequency; M, metastasis; P, primary tumour. (C and D) Peripheral blood mononuclear cells (PBMCs) pulsed with no (N), wild-type control (WT), cross-reactive (CR), and high-quality neo (M) peptides (n=7). c, CD8+ T-cell expansion and degranulation. (D) Clonal overlap of expanded T-cell clones in (C) and archival tumours by TCR Vβ sequencing. Arrows indicate clones in archival primary tumours with rank frequencies. Venn diagrams show the number of T-cell clones expanding with mutant peptides, with cross-reactive peptides, their respective clonal overlap, and clonal overlap with archival primary tumours. Note the presence of clones recognizing both neopeptides and cross-reactive peptides in archival tumours. Years surviving after surgery are shown for each individual patient. AWD, alive with disease; NED, no evidence of disease. Horizontal bars indicate median values, error bars represent the s.e.m. n is the number of biologically independent samples in individual patients in (A) and (C). P values were determined using a two-tailed Student's t-test (A), a two-tailed Mann-Whitney U-test (B), a one-way analysis of variance (ANOVA) with Tukey's multiple comparison test (C) and as described in Example X (D).

FIGS. 70A1, 70A2, 70B1, 70B2, and 70C collectively show decreased MUC16 protein expression in long term survivors is not a consequence of differential antibody binding to neoantigenic MUC16 mutations. (A) representative immunohistochemical staining and quantification of MUC16 expression in tissue microarrays of short and long term pancreatic cancer survivors as assese using three independent anti MUC16 antibodies Ab #1-clone EPSISR23, purchased from Abcam; Ab #2-polyclonal, purchased from Abcam ab1333419; Ab #3-clone 4H11. (B) Western blot (B1) and immunocytochemistry (B2) of untransfected (−), empty vector (vector), MUC16 wild type (MUC16WT), and MUC16 mutant (MUC16 R15C) HEK293T cells. The top left blot was probed with anti MUC16 specific antibody (clone 4H11) and the right blot with anti b-actin. Red rectandly indicates MUC16 specific band. All bottom cells were probed with anti MUC16 antibody (clone 4H11). The inserted mutation was identical to a neoantigenic MUC16 mutation. (C) MUC16 immunohistochemistry on two long term pancreatic cancer survivors with MUC16 neoepitopes in primary resected tumors. Areas in rectangular low power fields are magnified on the right.

Figure 71:
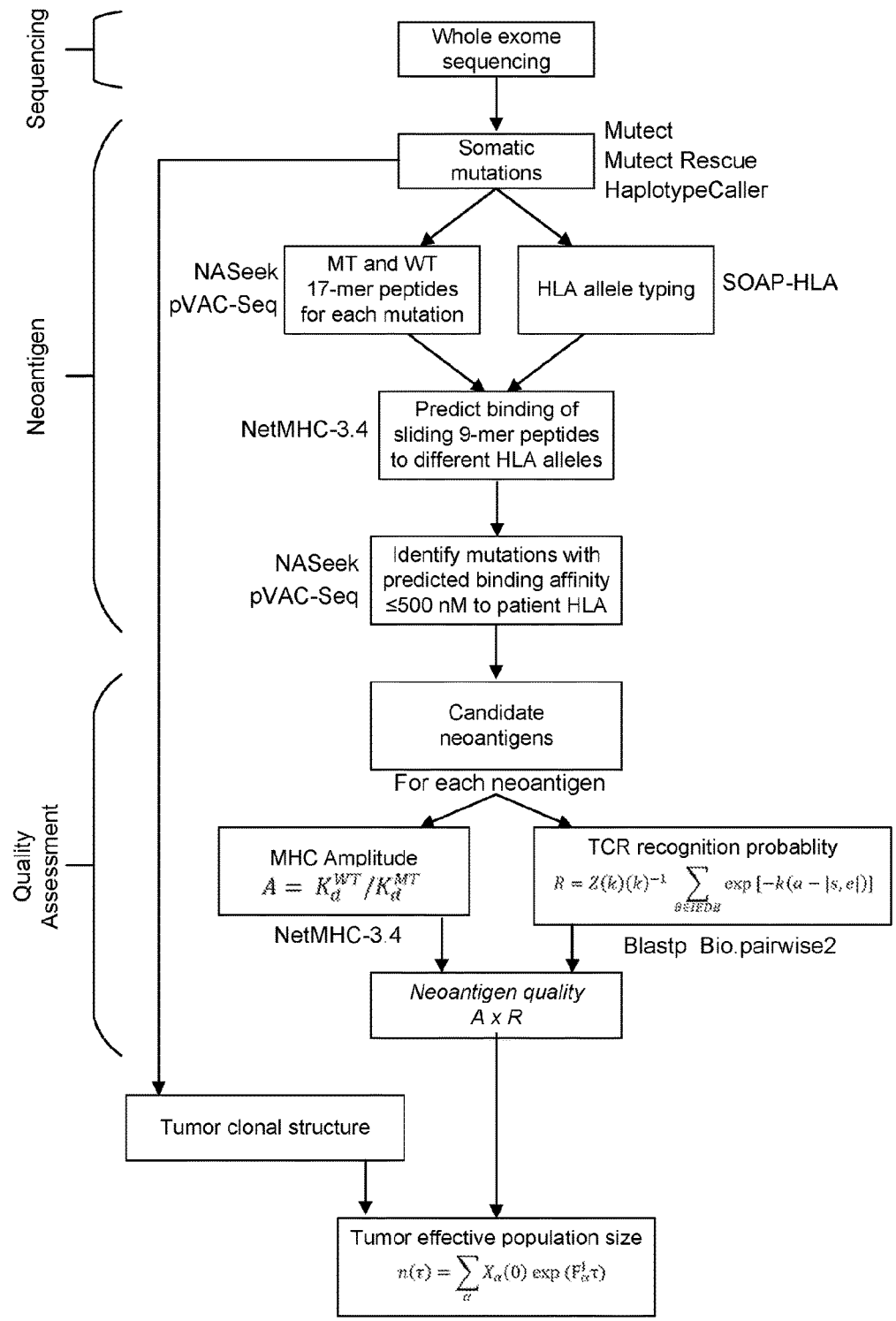

FIG. 71 depicts a comprehensive flowchart of neoantigen fitness modelling pipeline. Software programs utilized for each step are indicated in bold, colored text. Mathematical formulae for calculation of individual components of neoantigen quality are shown above and further defined in Methods. All software components of the pipeline are published and/or publically available.

Like reference numerals refer to corresponding parts throughout the several views of the drawings.

DETAILED DESCRIPTION

The presently disclosed subject matter provides strategies for improving cancer therapy (e.g., immunotherapy) by selection of particular patients to receive therapy based on the neoantigen portfolio of the patients (e.g., immunogenic hotspot (e.g., MUC16 for pancreatic cancer), neoantigen quantity and neoantigen immunogenicity). The presently disclosed subject matter also provides methods for predicting responsiveness of cancer patients to immunotherapy based on the patients' neoantigen portfolio. Furthermore, based on the fact that, at least in tumors with high mutational loads, the amount of DNA damage is sufficient for the immune system to perceive one or more neoantigens as foreign, it becomes of interest to stimulate neoantigen-specific T cell responses in cancer patients. The presently disclosed subject matter further provides vaccines comprising one or more neoantigen, and/or therapeutic T cell preparations comprising neoantigen-specific T cells.

The present disclosure further provides a recognition potential fitness model for tumors based on the immune interactions of dominant neoantigens predicts response to immunotherapy. The disclosed recognition potential fitness model associates each neoantigen with a fitness cost, which is termed the recognition potential of a neoantigen. The recognition potential of a neoantigen is the likelihood it is productively recognized by the TCR repertoire. It is defined by two components. The first is the amplitude A, which is given by the relative probability that a neoantigen will be presented by on class I major histocompatibility complex (MHC) and the relative probability that its wildtype counterpart will not be presented. The second component is the probability R that a presented neoantigen will be recognized by the TCR repertoire, which is inferred from its sequence homology to known antigens. For a given neoantigen their product defines its recognition potential, A×R. In some embodiments, this recognition potential is computed using the scripts illustrated in FIGS. 37 through 40 in accordance with the present disclosure.

Reference will now be made in detail to embodiments, examples of which are illustrated in the accompanying drawings. In the following detailed description, numerous specific details are set forth in order to provide a thorough understanding of the present disclosure. However, it will be apparent to one of ordinary skill in the art that the present disclosure may be practiced without these specific details. In other instances, well-known methods, procedures, components, circuits, and networks have not been described in detail so as not to unnecessarily obscure aspects of the embodiments.

1. Definitions

Unless defined otherwise, all technical and scientific terms used herein have the meaning commonly understood by a person skilled in the art to which this invention belongs. The following references provide one of ordinary skill in the art with a general definition of many of the terms used herein: Singleton et al., Dictionary of Microbiology and Molecular Biology (2nd ed. 1994); The Cambridge Dictionary of Science and Technology (Walker ed., 1988); The Glossary of Genetics, 5th Ed., R. Rieger et al. (eds.), Springer Verlag (1991); and Hale & Marham, The Harper Collins Dictionary of Biology (1991); Molecular Cloning: a Laboratory Manual 3rd edition, J. F. Sambrook and D. W. Russell, ed. Cold Spring Harbor Laboratory Press 2001; Recombinant Antibodies for Immunotherapy, Melvyn Little, ed. Cambridge University Press 2009; "Oligonucleotide Synthesis" (M. J. Gait, ed., 1984); "Animal Cell Culture" (R. I. Freshney, ed., 1987); "Methods in Enzymology" (Academic Press, Inc.); "Current Protocols in Molecular Biology" (F. M. Ausubel et al., eds., 1987, and periodic updates); "PCR: The Polymerase Chain Reaction", (Mullis et al., ed., 1994); "A Practical Guide to Molecular Cloning" (Perbal Bernard V., 1988); "Phage Display: A Laboratory Manual" (Barbas et al., 2001). The contents of these references and other references containing standard protocols, widely known to and relied upon by those of skill in the art, including manufacturers' instructions are hereby incorporated by reference as part of the presently disclosed subject matter. As used herein, the following terms have the meanings ascribed to them below, unless specified otherwise.

As used herein, the term "about" or "approximately" means within an acceptable error range for the particular value as determined by one of ordinary skill in the art, which will depend in part on how the value is measured or determined, i.e., the limitations of the measurement system. For example, "about" can mean within 3 or more than 3 standard deviations, per the practice in the art. Alternatively, "about" can mean a range of up to 20%, e.g., up to 10%, up to 5%, or up to 1% of a given value. Alternatively, particularly with respect to biological systems or processes, the term can mean within an order of magnitude, e.g., within 5-fold, or within 2-fold, of a value.

As used herein, the term "neoantigen", "neoepitope" or "neopeptide" refers to a tumor-specific antigen that arises from one or more tumor-specific mutation, which alters the amino acid sequence of genome encoded proteins.

As used herein, the term "neoantigen number" or "neoantigen burden" refers to the number of neoantigen(s) measured, detected or predicted in a sample (e.g., a biological sample from a subject). In certain embodiments, the neoantigen number is measured by using whole exome sequencing and in silico prediction.

As used herein, the term "mutation" refers to permanent change in the DNA sequence that makes up a gene. In certain embodiments, mutations range in size from a single DNA building block (DNA base) to a large segment of a chromosome. In certain embodiments, mutations can include missense mutations, frameshift mutations, duplications, insertions, nonsense mutation, deletions and repeat expansions. In certain embodiments, a missense mutation is a change in one DNA base pair that results in the substitution of one amino acid for another in the protein made by a gene. In certain embodiments, a nonsense mutation is also a change in one DNA base pair. Instead of substituting one amino acid for another, however, the altered DNA sequence prematurely signals the cell to stop building a protein. In certain embodiments, an insertion changes the number of DNA bases in a gene by adding a piece of DNA. In certain embodiments, a deletion changes the number of DNA bases by removing a piece of DNA. In certain embodiments, small deletions can remove one or a few base pairs within a gene, while larger deletions can remove an entire gene or several neighboring genes. In certain embodiments, a duplication consists of a piece of DNA that is abnormally copied one or more times. In certain embodiments, frameshift mutations occur when the addition or loss of DNA bases changes a gene's reading frame. A reading frame consists of groups of 3 bases that each code for one amino acid. In certain embodiments, a frameshift mutation shifts the grouping of these bases and changes the code for amino acids. In certain embodiments, insertions, deletions, and duplications can all be frameshift mutations. In certain embodiments, a repeat expansion is another type of mutation. In certain embodiments, nucleotide repeats are short DNA sequences that are repeated a number of times in a row. For example, a trinucleotide repeat is made up of 3-base-pair sequences, and a tetranucleotide repeat is made up of 4-base-pair sequences. In certain embodiments, a repeat expansion is a mutation that increases the number of times that the short DNA sequence is repeated.

As used herein, the "median" value (e.g., median neoantigen number, median neoantigen-microbial homology— e.g., median cross-reactivity score, median recognition potential score, or median activated T cell number—refers to the median value obtained from a population of subjects having a cancer (e.g., pancreatic cancer, e.g., PDAC). The median values may be previously determined reference values, or may be contemporaneously determined values.

As used herein, the term "cell population" refers to a group of at least two cells expressing similar or different phenotypes. In non-limiting examples, a cell population can include at least about 10, at least about 100, at least about 200, at least about 300, at least about 400, at least about 500, at least about 600, at least about 700, at least about 800, at least about 900, or at least about 1000 cells expressing similar or different phenotypes.

As used herein, the terms "antibody" and "antibodies" refer to antigen-binding proteins of the immune system. As used herein, the term "antibody" includes whole, full length antibodies having an antigen-binding region, and any fragment thereof in which the "antigen-binding portion" or "antigen-binding region" is retained, or single chains, for example, single chain variable fragment (scFv), thereof. The term "antibody" means not only intact antibody molecules, but also fragments of antibody molecules that retain immunogen-binding ability. Such fragments are also well known in the art and are regularly employed both in vitro and in vivo. Accordingly, as used herein, the term "antibody" means not only intact immunoglobulin molecules but also the well-known active fragments F(ab')2, and Fab. F(ab')2, and Fab fragments that lack the Fc fragment of intact antibody, clear more rapidly from the circulation, and can have less non-specific tissue binding of an intact antibody (Wahl et al., J. Nucl. Med. 24:316-325 (1983). In certain embodiments, an antibody is a glycoprotein comprising at least two heavy (H) chains and two light (L) chains interconnected by disulfide bonds. Each heavy chain is comprised of a heavy chain variable region (abbreviated herein as $V_H$) and a heavy chain constant ($C_H$) region. The heavy chain constant region is comprised of three domains, $C_H 1$, $C_H 2$ and $C_H 3$. Each light chain is comprised of a light chain variable region (abbreviated herein as $V_L$) and a light chain constant $C_L$ region. The light chain constant region is comprised of one domain, $C_L$. The $V_H$ and $V_L$ regions can be further sub-divided into regions of hypervariability, termed complementarity determining regions (CDR), interspersed with regions that are more conserved, termed framework regions (FR). Each VH and $V_L$ is composed of three CDRs and four FRs arranged from amino-terminus to carboxy-terminus in the following order: FR1, CDR1, FR2, CDR2, FR3, CDR3, FR4. The variable regions of the heavy and light chains contain a binding domain that interacts with an antigen. The constant regions of the antibodies can mediate the binding of the immunoglobulin to host tissues or factors, including various cells of the immune system (e.g., effector cells) and the first component (C1 q) of the classical complement system.

The term "antigen-binding portion", "antigen-binding fragment", or "antigen-binding region" of an antibody, as used herein, refers to that region or portion of an antibody that binds to the antigen and which confers antigen specificity to the antibody; fragments of antigen-binding proteins. It has been shown that the antigen-binding function of an antibody can be performed by fragments of a full-length antibody. Examples of antigen-binding portions encompassed within the term "antibody fragments" of an antibody include a Fab fragment, a monovalent fragment consisting of the $V_L$, $V_H$, $C_L$ and $C_H 1$ domains; a F(ab)2 fragment, a bivalent fragment comprising two Fab fragments linked by a disulfide bridge at the hinge region; a Fd fragment consisting of the $V_H$ and CH1 domains; a Fv fragment consisting of the $V_L$ and $V_H$ domains of a single arm of an antibody;

a dAb fragment (Ward et al., 1989 Nature 341:544-546), which consists of a $V_H$ domain; and an isolated complementarity determining region (CDR).

As used herein, the term "single-chain variable fragment" or "scFv" is a fusion protein of the variable regions of the heavy ($V_H$) and light chains ($V_L$) of an immunoglobulin (e.g., mouse or human) covalently linked to form a $V_H$::$V_L$ heterodimer. The heavy ($V_H$) and light chains ($V_L$) are either joined directly or joined by a peptide-encoding linker (e.g., 10, 15, 20, 25 amino acids), which connects the N-terminus of the $V_H$ with the C-terminus of the $V_L$, or the C-terminus of the $V_H$ with the N-terminus of the $V_L$. The linker is usually rich in glycine for flexibility, as well as serine or threonine for solubility. Despite removal of the constant regions and the introduction of a linker, scFv proteins retain the specificity of the original immunoglobulin. Single chain Fv polypeptide antibodies can be expressed from a nucleic acid comprising $V_H$- and $V_L$-encoding sequences as described by Huston et al. (Proc. Nat. Acad. Sci. USA, 85:5879-5883, 1988). See, also, U.S. Pat. Nos. 5,091,513, 5,132,405 and 4,956,778; and U.S. Patent Publication Nos. 20050196754 and 20050196754. Antagonistic scFvs having inhibitory activity have been described (see, e.g., Zhao et al. Hyrbidoma (Larchmt) 2008 27(6):455-51; Peter et al., J Cachexia Sarcopenia Muscle 2012 Aug. 12; Shieh et al., J Imunol 2009 183(4):2277-85; Giomarelli et al., Thromb Haemost 2007 97(6):955-63; Fife eta., J Clin Invst 2006 116(8):2252-61; Brocks et al., Immunotechnology 1997 3(3):173-84; Mooscaner et al., Ther Immunol 1995 2(10: 31-40). Agonistic scFvs having stimulatory activity have been described (see, e.g., Peter et al., J Bio Chem 2003 25278(38):36740-7; Xie et al., Nat Biotech 1997 15(8):768-71; Ledbetter et al., Crit Rev Immunol 1997 17(5-6): 427-55; Ho et al., BioChim Biophys Acta 2003 1638(3):257-66).

As used herein, "F(ab)" refers to a fragment of an antibody structure that binds to an antigen but is monovalent and does not have a Fc portion, for example, an antibody digested by the enzyme papain yields two F(ab) fragments and an Fc fragment (e.g., a heavy (H) chain constant region; Fc region that does not bind to an antigen).

As used herein, "F(ab')$_2$" refers to an antibody fragment generated by pepsin digestion of whole IgG antibodies, wherein this fragment has two antigen binding (ab') (bivalent) regions, wherein each (ab') region comprises two separate amino acid chains, a part of a H chain and a light (L) chain linked by an S—S bond for binding an antigen and where the remaining H chain portions are linked together. A "F(ab')$_2$" fragment can be split into two individual Fab' fragments.

As used herein, the term "antigen-binding protein" refers to a protein or polypeptide that comprises an antigen-binding region or antigen-binding portion, that is, has a strong affinity to another molecule to which it binds. Antigen-binding proteins encompass antibodies, chimeric antigen receptors (CARs) and fusion proteins.

As used herein, the term "treating" or "treatment" refers to clinical intervention in an attempt to alter the disease course of the individual or cell being treated, and can be performed either for prophylaxis or during the course of clinical pathology. Therapeutic effects of treatment include, without limitation, preventing occurrence or recurrence of disease, alleviation of symptoms, diminishment of any direct or indirect pathological consequences of the disease, preventing metastases, decreasing the rate of disease progression, amelioration or palliation of the disease state, and remission or improved prognosis. By preventing progression of a disease or disorder, a treatment can prevent deterioration due to a disorder in an affected or diagnosed subject or a subject suspected of having the disorder, but also a treatment may prevent the onset of the disorder or a symptom of the disorder in a subject at risk for the disorder or suspected of having the disorder.

As used herein, the term "subject" refers to any animal (e.g., a mammal), including, but not limited to, humans, and non-human animals (including, but not limited to, non-human primates, dogs, cats, rodents, horses, cows, pigs, mice, rats, hamsters, rabbits, and the like (e.g., which is to be the recipient of a particular treatment, or from whom cells are harvested). In certain embodiments, the subject is a human.

As used herein, an "effective amount" or "therapeutically effective amount" is an amount sufficient to affect a beneficial or desired clinical result upon treatment. An effective amount can be administered to a subject in one or more doses. In terms of treatment, an effective amount is an amount that is sufficient to palliate, ameliorate, stabilize, reverse or slow the progression of the disease, or otherwise reduce the pathological consequences of the disease. The effective amount is generally determined by the physician on a case-by-case basis and is within the skill of one in the art. Several factors are typically taken into account when determining an appropriate dosage to achieve an effective amount. These factors include age, sex and weight of the subject, the condition being treated, the severity of the condition and the form and effective concentration of the immunoresponsive cells administered.

As used herein, the term "response" or "responsiveness" refers to an alteration in a subject's condition that occurs as a result of or correlates with treatment. In certain embodiments, a response is a beneficial response. In certain embodiments, a beneficial response can include stabilization of the condition (e.g., prevention or delay of deterioration expected or typically observed to occur absent the treatment), amelioration (e.g., reduction in frequency and/or intensity) of one or more symptoms of the condition, and/or improvement in the prospects for cure of the condition, etc. In certain embodiments, "response" can refer to response of an organism, an organ, a tissue, a cell, or a cell component or in vitro system. In certain embodiments, a response is a clinical response. In certain embodiments, presence, extent, and/or nature of response can be measured and/or characterized according to particular criteria. In certain embodiments, such criteria can include clinical criteria and/or objective criteria. In certain embodiments, techniques for assessing response can include, but are not limited to, clinical examination, positron emission tomography, chest X-ray CT scan, MRI, ultrasound, endoscopy, laparoscopy, presence or level of a particular marker in a sample, cytology, and/or histology. Where a response of interest is a response of a tumor to a therapy, ones skilled in the art will be aware of a variety of established techniques for assessing such response, including, for example, for determining tumor burden, tumor size, tumor stage, etc. The likelihood of a subject having predictive features identified herein (e.g., one or more MUC16 neoantigen, number of neoantigens, number of activated T cells) exhibiting a particular response is relative to a similarly situated second subject (e.g., a second subject having the same type cancer, optionally the same type of cancer with similar characteristics (e.g. stage and/or location/distribution)) or group of subjects that lack one or more predictive feature.

As used herein, the term "sample" refers to a biological sample obtained or derived from a source of interest, as described herein. In certain embodiments, a source of interest comprises an organism, such as an animal or human. In certain embodiments, a biological sample is a biological tissue or fluid. Non-limiting biological samples include bone marrow, blood, blood cells, ascites, (tissue or fine needle) biopsy samples, cell-containing body fluids, free floating nucleic acids, sputum, saliva, urine, cerebrospinal fluid, peritoneal fluid, pleural fluid, feces, lymph, gynecological fluids, swabs (e.g., skin swabs, vaginal swabs, oral swabs, and nasal swabs), washings or lavages such as a ductal lavages or broncheoalveolar lavages, aspirates, scrapings, specimens (e.g., bone marrow specimens, tissue biopsy specimens, and surgical specimens), feces, other body fluids, secretions, and/or excretions, and cells therefrom, etc.

As used herein, the term "substantially" refers to the qualitative condition of exhibiting total or near-total extent or degree of a characteristic or property of interest. One of ordinary skill in the art will understand that biological and chemical phenomena rarely, if ever, go to completion and/or proceed to completeness or achieve or avoid an absolute result. The term "substantially" is therefore used herein to capture the potential lack of completeness inherent in many biological and chemical phenomena.

As used herein, the term "vaccine" refers to a composition for generating immunity for the prophylaxis and/or treatment of diseases (e.g., neoplasia/tumor). In certain embodiments, vaccines are medicaments that comprise antigens and are intended to be used in humans or animals for generating specific defense and protective substance by vaccination.

It will also be understood that, although the terms first, second, etc. may be used herein to describe various elements, these elements should not be limited by these terms. These terms are only used to distinguish one element from another. For example, a first subject could be termed a second subject, and, similarly, a second subject could be termed a first subject, without departing from the scope of the present disclosure. The first subject and the second subject are both subjects, but they are not the same subject. Furthermore, the terms "subject," "user," and "patient" are used interchangeably herein.

The terminology used in the present disclosure is for the purpose of describing particular embodiments only and is not intended to be limiting of the invention. As used in the description of the invention and the appended claims, the singular forms "a", "an" and "the" are intended to include the plural forms as well, unless the context clearly indicates otherwise. It will also be understood that the term "and/or" as used herein refers to and encompasses any and all possible combinations of one or more of the associated listed items. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

As used herein, the term "if" may be construed to mean "when" or "upon" or "in response to determining" or "in response to detecting," depending on the context. Similarly, the phrase "if it is determined" or "if [a stated condition or event] is detected" may be construed to mean "upon determining" or "in response to determining" or "upon detecting [the stated condition or event]" or "in response to detecting [the stated condition or event]," depending on the context.

2. Neoantigens

The presently disclosed subject matter provides identification of neoantigens in subjects having cancer, e.g., pancreatic cancer (e.g., pancreatic ductal adenocarcinoma (PDAC)).

2.1 Neoantigens

Neoantigen is a tumor-specific antigen that arises from one or more tumor-specific mutation. In certain embodiments, the neoantigen is a tumor-specific antigen that arises from a tumor-specific mutation. In certain embodiments, a neoantigen is not expressed by healthy cells (e.g., non-tumor cells or non-cancer cells) in a subject.

Many antigens expressed by cancer cells are self-antigens which are selectively expressed or overexpressed on the cancer cells. These self-antigens are difficult to target with immunotherapy because they require overcoming both central tolerance (whereby autoreactive T cells are deleted in the thymus during development) and peripheral tolerance (whereby mature T cells are suppressed by regulatory mechanisms). Targeting neoantigens can abrogate these tolerance mechanisms. In certain embodiments, a neoantigen is recognized by cells of the immune system of a subject (e.g., T cells) as "non-self". Neoantigens are not recognized as "self-antigens" by immune system, T cells that are capable of targeting neoantigens are not subject to central and peripheral tolerance mechanisms to the same extent as T cells which recognize self-antigens.

In certain embodiments, the tumor-specific mutation that results in a neoantigen is a somatic mutation. Somatic mutations comprise DNA alterations in non-germline cells and commonly occur in cancer cells. Certain somatic mutations in cancer cells result in the expression of neoantigens, that in certain embodiments, transform a stretch of amino acids from being recognized as "self" to "non-self". Human tumors without a viral etiology can accumulate tens to hundreds of fold somatic mutations in tumor genes during neoplastic transformation, and some of these somatic mutations can occur in protein-coding regions and result in the formation of neoantigens. The exome is the protein-encoding part of the genome. Based on the mutations present within the protein-encoding part of the genome (i.e., the exome) of an individual tumor, potential neoantigens can be predicted for the individual tumor. In certain embodiments, whole exome sequencing is performed in a biological sample (e.g., a tumor sample) obtained from a subject having cancer.

In certain embodiments, a neoantigen is a neoantigenic peptide comprising a tumor specific mutation. The neoantigenic peptide can be a peptide that is incorporated into a larger protein. In certain embodiments, a neoantigenic peptide is a series of residues, typically L-amino acids, connected one to the other, typically by peptide bonds between the α-amino and carboxyl groups of adjacent amino acids. A neoantigenic peptide can be a variety of lengths, either in their neutral (uncharged) forms or in forms which are salts, and either free of modifications such as glycosylation, side chain oxidation, or phosphorylation.

In certain embodiments, the size of the neoantigenic peptide is about 3-30 amino acids, e.g., about 3-5, about 5-15 (e.g., about 8-11, about 5-10, or about 10-15), about 15-20, about 20-25, or about 20-30 amino acids, in length. In certain embodiments, the neoantigenic peptide is about 8-11 amino acids in length. In certain embodiments, the neoantigenic peptide is about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 amino acids in length. In certain embodiments, the neoantigenic peptide is at least about 3, at least about 5, or at least about 8 amino acids in length. In certain embodiments, the neoantigenic peptide is less than about 30, less than about 20, less than about 15, or less than about 10 amino acids in length.

In certain embodiments, a neoantigenic peptide is selected from the neoantigenic peptides listed in Table 1.

TABLE 1

| NEOANTIGENIC PEPTIDE[A] | GENE THE NEOANTIGENIC PEPTIDE IS LOCATED | MUTANT ALLELE[B] IN MUC16 |
|---|---|---|
| vmKhllspl (SEQ ID NO: 1) | MUC16 | B0801 |
| mHhpgsrkf (SEQ ID NO: 2) | MUC16 | C0701 |
| nstLiptli (SEQ ID NO: 3) | MUC16 | A6802 |
| sssgvnstI (SEQ ID NO: 4) | MUC16 | A6802 |
| stLiptlil (SEQ ID NO: 5) | MUC16 | A6802 |
| aeassAvpt (SEQ ID NO: 6) | MUC16 | B4501 |
| eassAvptv (SEQ ID NO: 7) | MUC16 | C1203 |

TABLE 1-continued

| NEOANTIGENIC PEPTIDE[A] | GENE THE NEOANTIGENIC PEPTIDE IS LOCATED | MUTANT ALLELE[B] IN MUC16 |
|---|---|---|
| sravtsttI (SEQ ID NO: 8) | MUC16 | C0602 |
| sttipiltL (SEQ ID NO: 9) | MUC16 | C1402 |
| tipiltLsl (SEQ ID NO: 10) | MUC16 | C1402 |
| gLrktnmsl (SEQ ID NO: 11) | MUC16 | B0702 |
| smpanfetI (SEQ ID NO: 12) | MUC16 | A2402 |
| stvrKspwk (SEQ ID NO: 13) | MUC16 | A0301 |
| stvrKspwk (SEQ ID NO: 14) | MUC16 | A1101 |
| mgKsthtsm (SEQ ID NO: 15) | MUC16 | B0801 |
| smkAerppa (SEQ ID NO: 16) | MUC16 | B0801 |
| ttspsNtlv (SEQ ID NO: 17) | MUC16 | C0701 |
| sssptCslm (SEQ ID NO: 18) | MUC16 | C1502 |

[A]the capitalized letter represents the changed amino acid between the WT and mutated sequences
[B]"MT allele" represents the HLA allele predicted to bind the mutated neopeptide In certain embodiments, a neoantigenic peptide is selected from the neoantigenic peptides listed in Table 2.

TABLE 2

| NEOANTIGENIC PEPTIDE | GENE THE NEOANTIGENIC PEPTIDE IS LOCATED | ALIGNMENT SCORE | S-TAU[C] |
|---|---|---|---|
| APLGAPPPL (SEQ ID NO: 19) | FBRS | 29 | 0.690625 |
| ASLHHHHR (SEQ ID NO: 20) | CACNA1B | 24 | 0.987118 |
| ATYHFHFNL (SEQ ID NO: 21) | COL6A5 | 25 | 0.955964 |
| DWPVFPGLF (SEQ ID NO: 22) | HDAC3 | 27 | 0.772377 |
| EAFTLKATV (SEQ ID NO: 23) | PZP | 26 | 0.920519 |
| EAHHHFPSL (SEQ ID NO: 24) | TTLL3 | 29 | 0.843503 |
| FLNRWMANT (SEQ ID NO: 25) | AADACL2 | 28 | 0.920174 |
| GIVSWDTFL (SEQ ID NO: 26) | ELMO1 | 28 | 0.646096 |
| GTPRAATMK (SEQ ID NO: 27) | PRKAR1B | 18 | 0.999997 |
| HWPEKEWPI (SEQ ID NO: 28) | N/A | 22 | 0.982173 |
| ILFDEAVKL (SEQ ID NO: 29) | IQCA1 | 20 | 0.973993 |
| ILIACRLNK (SEQ ID NO: 30) | LRPPRC | 21 | 0.679058 |
| ILPTCSPLV (SEQ ID NO: 31) | LRP4 | 27 | 0.419822 |
| KPRFLVGLW (SEQ ID NO: 32) | IGFN1 | 27 | 0.872717 |
| KYIAFCINI (SEQ ID NO: 33) | S1PR3 | 26 | 0.691118 |
| LFHQCLSIY (SEQ ID NO: 34) | C5orf42 | 31 | 0.006421 |
| LLLMSTLGI (SEQ ID NO: 35) | KLRD1 | 32 | 0.565677 |
| LLPPQDPHL (SEQ ID NO: 36) | PCDHB15 | 24 | 0.679058 |

TABLE 2-continued

| NEOANTIGENIC PEPTIDE | GENE THE NEOANTIGENIC PEPTIDE IS LOCATED | ALIGNMENT SCORE | S-TAU[c] |
|---|---|---|---|
| LQDFYLGTY (SEQ ID NO: 37) | SLC15A5 | 29 | 0.652087 |
| LTPPQAQEL (SEQ ID NO: 38) | #N/A | 25 | 0.811812 |
| QTYQHMWNY (SEQ ID NO: 39) | GRIK5 | 34 | 0.973993 |
| REFKFRVSA (SEQ ID NO: 40) | PCDHB16 | 18 | 0.99305 |
| STGFPHMLF (SEQ ID NO: 41) | CSNK2B-LY6G5B-1181 | 22 | 0.953153 |
| TLVGHQGPV (SEQ ID NO: 42) | TRAF7 | 21 | 0.459383 |
| VDWFLDWLR (SEQ ID NO: 43) | SLC1A6 | 28 | 0.811812 |
| GGAPHFGHF (SEQ ID NO: 44) | ZNRF1 | 17 | 0.904809 |
| CYYELNQCL (SEQ ID NO: 45) | ZNF430 | 26 | 0.48456 |
| AYPQYVIEY (SEQ ID NO: 46) | ZC3HAV1 | 26 | 0.994797 |
| HLETHNTDK (SEQ ID NO: 47) | ZBTB17 | 24 | 0.964887 |
| AEEEEEVV (SEQ ID NO: 48) | WWC1 | 26 | 0.806188 |
| RGMQCAICK (SEQ ID NO: 49) | WDR59 | 26 | 0.833236 |
| MPEDEYMVY (SEQ ID NO: 50) | VTN | 17 | 0.946362 |
| SSYGRNHYI (SEQ ID NO: 51) | VCPIP1 | 25 | 0.976041 |
| AMDDLDTDM (SEQ ID NO: 52) | UTRN | 27 | 0.45028 |
| PTDPMLGLA (SEQ ID NO: 53) | TSPAN10 | 24 | 0.935737 |
| FSSNLPTYY (SEQ ID NO: 54) | TPTE | 27 | 0.571614 |
| FSSNLPTYY (SEQ ID NO: 55) | TPTE | 27 | 0.571614 |
| FRHSMVVPY (SEQ ID NO: 56) | TP53 | 23 | 0.920174 |
| NLLGRNSFK (SEQ ID NO: 57) | TP53 | 36 | 0.771043 |
| GLGFYNDVV (SEQ ID NO: 58) | TNFRSF4 | 23 | 0.45028 |
| AQTHEPRQW (SEQ ID NO: 59) | TMEM132C | 26 | 0.887438 |
| STHPSLSQW (SEQ ID NO: 60) | TGOLN2 | 27 | 0.677777 |
| VYMPPPRLL (SEQ ID NO: 61) | TENM2 | 23 | 0.902688 |
| NHDDDDVEI (SEQ ID NO: 62) | TADA2B | 32 | 0.18872 |
| YVKIYLLPY (SEQ ID NO: 63) | SYT9 | 28 | 0.904809 |
| SYQSTGDPK (SEQ ID NO: 64) | SVIL | 24 | 0.732722 |
| RPRKAWAWC (SEQ ID NO: 65) | SUOX | 26 | 0.679058 |
| WVLHHMGGM (SEQ ID NO: 66) | SRP54 | 30 | 0.18872 |
| LAGEWRERL (SEQ ID NO: 67) | SPTBN2 | 16 | 0.646096 |
| TVWPSLAPL (SEQ ID NO: 68) | SPEG | 23 | 0.955964 |
| QEASNKHAE (SEQ ID NO: 69) | SMC2 | 27 | 0.970774 |
| RRRLCILRM (SEQ ID NO: 70) | SMAD4 | 22 | 0.872717 |
| VRLGPVKSI (SEQ ID NO: 71) | SETX | 28 | 0.964887 |
| FFVEKRHAF (SEQ ID NO: 72) | SCAND3 | 24 | 0.994797 |
| HTSLRGFLY (SEQ ID NO: 73) | SBK2 | 26 | 0.419822 |

TABLE 2-continued

| NEOANTIGENIC PEPTIDE | GENE THE NEOANTIGENIC PEPTIDE IS LOCATED | ALIGNMENT SCORE | S-TAU[c] |
|---|---|---|---|
| SLAETKTLY (SEQ ID NO: 74) | SARDH | 17 | 0.99983 |
| TYAPLFIWV (SEQ ID NO: 75) | RXFP1 | 27 | 0.691118 |
| SPAPERCMV (SEQ ID NO: 76) | RTL1 | 26 | 0.872717 |
| EQLKLGAIF (SEQ ID NO: 77) | RNGTT | 23 | 0.907671 |
| RPQGQRPAL (SEQ ID NO: 78) | RNF5 | 26 | 0.771676 |
| APRGVCYGA (SEQ ID NO: 79) | RETSAT | 24 | 0.973993 |
| APRGVCYGA (SEQ ID NO: 80) | RETSAT | 24 | 0.772377 |
| LAAPRGVCY (SEQ ID NO: 81) | RETSAT | 24 | 0.955964 |
| PPRYIGIPI (SEQ ID NO: 82) | RAPGEF2 | 25 | 0.48456 |
| HVWLCDLPV (SEQ ID NO: 83) | RABGGTA | 30 | 0.772377 |
| QLYMNPKTW (SEQ ID NO: 84) | PYGL | 31 | 0.946362 |
| KYSNYVWPI (SEQ ID NO: 85) | PRSS50 | 26 | 0.419822 |
| LPRQYWEAL (SEQ ID NO: 86) | POLRMT | 27 | 0.771676 |
| VLNGWLRSV (SEQ ID NO: 87) | PNPLA6 | 28 | 0.780199 |
| YLALAAQCL (SEQ ID NO: 88) | PLEKHH3 | 28 | 0.48456 |
| CPLPRPPPI (SEQ ID NO: 89) | PCDH15 | 28 | 0.970774 |
| GIICLDYKL (SEQ ID NO: 90) | OR2A14 | 24 | 0.998936 |
| TLGVFCLGL (SEQ ID NO: 91) | OLR1 | 32 | 0.909408 |
| ERPCHREPL (SEQ ID NO: 92) | OBSCN | 24 | 0.971063 |
| RLALSTFEW (SEQ ID NO: 93) | NLRP12 | 26 | 0.403676 |
| VVWATKYFL (SEQ ID NO: 94) | NCEH1 | 25 | 0.920174 |
| NPEAMCSDL (SEQ ID NO: 95) | MYRIP | 25 | 0.679058 |
| IPLEVMEPF (SEQ ID NO: 96) | MORC1 | 26 | 0.728968 |
| EEAFVPILY (SEQ ID NO: 97) | MLK4 | 24 | 0.887438 |
| HHHHHHQAW (SEQ ID NO: 98) | MAFB | 28 | 0.459383 |
| LVWSLPCGF (SEQ ID NO: 99) | LBR | 29 | 0.45028 |
| MPDVVHQSL (SEQ ID NO: 100) | L3MBTL1 | 30 | 0.971063 |
| CRPQCCQSV (SEQ ID NO: 101) | KRTAP4-7 | 28 | 0.677777 |
| MTPSVYGGA (SEQ ID NO: 102) | KRT20 | 25 | 0.982173 |
| YKLVVVGAV (SEQ ID NO: 103) | KRAS | 24 | 0.690625 |
| YKLVVVGAV (SEQ ID NO: 104) | KRAS | 24 | 0.891553 |
| YKLVVVGAV (SEQ ID NO: 105) | KRAS | 24 | 0.811812 |
| APAQPPMLA (SEQ ID NO: 106) | KMT2D | 24 | 0.732722 |
| EPPPPPSPL (SEQ ID NO: 107) | KMT2D | 22 | 0.946362 |
| YLWEDPVCG (SEQ ID NO: 108) | KIF26A | 25 | 0.780199 |
| SFADFEWHF (SEQ ID NO: 109) | KIF22 | 26 | 0.909408 |
| YQQSNTWSL (SEQ ID NO: 110) | KIAA1407 | 30 | 0.891553 |
| SPGGWRSGW (SEQ ID NO: 111) | ITPKB | 32 | 0.403676 |

TABLE 2-continued

| NEOANTIGENIC PEPTIDE | GENE THE NEOANTIGENIC PEPTIDE IS LOCATED | ALIGNMENT SCORE | S-TAU[c] |
|---|---|---|---|
| RVWDIVPTL (SEQ ID NO: 112) | ILVBL | 37 | 0.945017 |
| MLAIGCALL (SEQ ID NO: 113) | IL6R | 29 | 0.652087 |
| WEEEYTVWI (SEQ ID NO: 114) | IFFO1 | 29 | 0.893521 |
| VWPKKINNI (SEQ ID NO: 115) | HYDIN | 24 | 0.987118 |
| WPQCHPEEI (SEQ ID NO: 116) | HN1 | 36 | 0.971063 |
| QEFENIKSY (SEQ ID NO: 117) | HIVEP1 | 23 | 0.708595 |
| TMDVATPSV (SEQ ID NO: 118) | HERC2 | 26 | 0.853911 |
| LPLHLYDTL (SEQ ID NO: 119) | HECTD1 | 23 | 0.893521 |
| RPGQSPGQL (SEQ ID NO: 120) | HAND1 | 29 | 0.780199 |
| ELLDYIRAV (SEQ ID NO: 121) | GRM8 | 25 | 0.833236 |
| LPPSLQGAV (SEQ ID NO: 122) | GPR179 | 26 | 0.970774 |
| FLTQPVAPK (SEQ ID NO: 123) | FGD3 | 24 | 0.806188 |
| LASSCGCTF (SEQ ID NO: 124) | FCGBP | 24 | 0.843503 |
| RPRGDNGYT (SEQ ID NO: 125) | FBN1 | 19 | 0.987118 |
| QAMYDVLTF (SEQ ID NO: 126) | FAT3 | 29 | 0.45028 |
| LTISGECPK (SEQ ID NO: 127) | FAM83H | 21 | 0.45028 |
| SWKSPGWSF (SEQ ID NO: 128) | FAM124B | 26 | 0.902688 |
| RKREEEERW (SEQ ID NO: 129) | EFHD1 | 27 | 0.691118 |
| NHLCFGHCF (SEQ ID NO: 130) | DAND5 | 28 | 0.907671 |
| YVYSLYWSI (SEQ ID NO: 131) | CNGA1 | 29 | 0.000624 |
| MVLWHLPAV (SEQ ID NO: 132) | CLCF1 | 29 | 0.18872 |
| FSVSPEWAV (SEQ ID NO: 133) | CDHR2 | 22 | 0.891553 |
| GYYTLLNVF (SEQ ID NO: 134) | CACNA1A | 26 | 0.883775 |
| QALIRPTTF (SEQ ID NO: 135) | C18orf8 | 27 | 0.976041 |
| KQLPRILEA (SEQ ID NO: 136) | C17orf100 | 18 | 0.677777 |
| YQQALGKRF (SEQ ID NO: 137) | C16orf78 | 21 | 0.920519 |
| QLAWVPSPY (SEQ ID NO: 138) | AUTS2 | 27 | 0.953153 |
| HIQDLYTVL (SEQ ID NO: 139) | ATP6V0A2 | 28 | 0.883775 |
| MNRGRRSSL (SEQ ID NO: 140) | ARID4A | 25 | 0.982173 |
| YAYTFWTYI (SEQ ID NO: 141) | APEX1 | 28 | 0.888813 |
| SEVLGYWAF (SEQ ID NO: 142) | ADRA1A | 27 | 0.99305 |
| KPLLSGPWA (SEQ ID NO: 143) | ADAMTS5 | 27 | 0.780199 |
| FNGNFLLSM (SEQ ID NO: 144) | ADAMTS20 | 22 | 0.907671 |
| AHPDGSWTF (SEQ ID NO: 145) | ABT1 | 30 | 0.972244 |

[c]this parameter is a metric of the whole tumor, not just the neoantigen

Neoantigens may vary in different subjects, e.g., different subjects may have different combinations of neoantigens, also referred to as "neoantigen signatures". For example, each subject may have a unique neoantigen signature. In certain embodiments, a neoantigen signature is a combination of one or more neoantigen listed in Tables 1 and 2.

The presently disclosed subject matter also provides compositions comprising one or more presently disclosed neoantigen. In certain embodiments, the compositions are pharmaceutical compositions comprising pharmaceutically acceptable carriers. In certain embodiments, the composition comprises two or more neoantigens. The two or more can be linked, e.g., by any biochemical strategy to link two proteins.

2.2 Detection of Neoantigens

Cancers can be screened to detect neoantigens using any of a variety of known technologies. In certain embodiments, neoantigens or expression thereof is detected at the nucleic acid level (e.g., in DNA or RNA). In certain embodiments, neoantigens or expression thereof is detected at the protein level (e.g., in a sample comprising polypeptides from cancer cells, which sample can be or comprise polypeptide complexes or other higher order structures including but not limited to cells, tissues, or organs).

In certain embodiments, a neoantigen is detected by the method selected from the group consisting of whole exome sequencing, immunoassay, microarray, genome sequencing, RNA sequencing, ELISA, Western Transfer, DNA or RNA sequencing, mass spectrometry, and combinations thereof. In certain embodiments, one or more neoantigen is detected by whole exome sequencing. In certain embodiments, one or more neoantigen is detected by the immunogenicity analysis method of somatic mutations described in Snyder et al. *Engl J Med* 371, 2189-2199 (2014). In certain embodiments, one or more neoantigen is detected by the pVAC-Seq method described in Hndal et al., *Genome Med* (2016); 8:11. In certain embodiments, one or more neoantigen is detected by the in silico neoantigen prediction pipeline method described in Rizvi et al., *Science* 348, 124-128 (2015). In certain embodiments, one or more neoantigen is detected by any of the methods described in WO2015/103037 and WO2016/081947.

3. Uses of Neoantigens for Patient Selection for and Responsiveness Prediction to Immunotherapies The neoantigens of the presently disclosed subject matter can be used to identify cancer subjects as candidates for immunotherapies, and to predict responsiveness of cancer subjects to immunotherapies. In certain embodiments, the presently disclosed subject matter provides methods of identifying subjects (e.g., cancer subjects) as candidates for treatment with an immunotherapy (hereinafter "the patient selection method"). In certain embodiments, the presently disclosed subject matter provides methods of predicting the responsiveness of subjects (e.g., cancer subjects) to an immunotherapy (hereinafter "the responsiveness prediction method").

3.1 MUC16 as Immunogenic Hotspot

As used herein, the term "immunogenic hotspot" refers to a genetic locus that is enriched with neoantigens (e.g., a genetic locus that frequently generates neoantigens). The immunogenic hotspot can vary depending on the type of disease (e.g., tumor). Detecting one or more neoantigen of an immunogenic hotspot can be used to identify cancer subjects as candidates for immunotherapies, and to predict responsiveness of cancer subjects to immunotherapies. Furthermore, immunotherapies (e.g., vaccines, T cells (including modified T cells, e.g., T cells comprising a T cell receptor (TCR) or a chimeric antigen receptor (CAR)) targeting one or more neoantigen of an immunogenic hotspot can be used for neoantigen-directed therapies, e.g., cancer therapies. In certain embodiments, MUC16 is an immunogenic hotspot for pancreatic cancer, more specifically, for pancreatic ductal adenocarcinoma (PDAC). In certain embodiments, MUC16 is an immunogenic hotspot for checkpoint blockade refractory tumor (e.g., PDAC).

MUC16-neoantigen specific T cell immunity induces immunoediting of MUC16-expressing clones in primary tumors, curtails the development of metastases, and prolongs survival, given the cell-autonomous roles of MUC16 in promoting metastases.

In certain non-limiting embodiments, the patient selection method comprises obtaining a biological sample from the subject, and detecting one or more neoantigen of MUC16 in the biological sample, wherein the presence of one or more neoantigen of MUC16 in the biological sample indicates that the subject is a candidate for an immunotherapy.

In certain non-limiting embodiments, the responsiveness prediction method comprises obtaining a biological sample from the subject, and detecting one or more neoantigen of MUC16 in the biological sample, wherein the presence of one or more neoantigen of MUC16 in the biological sample indicates that the subject is likely to be responsive to an immunotherapy.

In certain embodiments, the patient selection method and responsiveness prediction method comprise detecting a plurality of neoantigens of MUC16. In certain embodiments, the methods comprise detecting one or more of the neoantigenic peptides listed in Table 1. In certain embodiments, the methods comprise detecting one or more of the neoantigenic peptides having the amino acid sequences set forth in SEQ ID NOS: 1-18.

In certain embodiments, the subject has pancreatic cancer. In certain embodiments, the pancreatic cancer is pancreatic ductal adenocacinma (PDAC).

In some embodiments, neoantigens of MUC16 are detected by any of the methods for detecting neoantigens, e.g., those described in Section 2.2. In certain embodiments, the neoantigens of MUC16 are detected by whole exome sequencing the biological sample. In certain embodiments, the neoantigens of MUC16 are detected by the immunogenicity analysis method of somatic mutations described in Snyder et al. *Engl J Med* 371, 2189-2199 (2014). In certain embodiments, the neoantigens of MUC16 are detected by the pVAC-Seq method described in Hndal et al., *Genome Med* (2016); 8:11. In certain embodiments, the neoantigens of MUC16 are detected by the in silico neoantigen prediction pipeline described in Rizvi et al., 2015, *Science* 348, 124-128. In certain embodiments, the neoantigens of MUC16 are detected by any of the methods described in WO2015/103037 and WO2016/081947.

3.2 Neoantigen Quantity and Neoantigen Immunogenicity

In certain embodiments, the patient selection method and responsiveness prediction method relate to the quantity of the neoantigens (e.g., the number of neoantigens (hereinafter "neoantigen number") in the subject. In certain embodiments, the neoantigen number includes but is not limited to MUC16 neoantigens.

In some embodiments, neoantigen number is measured by any methods for detecting neoantigens, e.g., those described in Section 2.2. In certain embodiments, the neoantigen number is measured by whole exome sequencing the biological sample. In certain embodiments, the neoantigen number is measured by the immunogenicity analysis method of somatic mutations described in Snyder et al., 204, *Engl J Med* 371, 2189-2199. In certain embodiments, the neoantigen number is measured by the pVAC-Seq method described in Hndal et al., 2016, *Genome Med* 8, 11. In certain embodiments, the neoantigen number is measured by the in silico neoantigen prediction pipeline described in Rizvi et al., 2015 *Science* 348, 124-128. In certain embodiments, the neoantigen number is measured by any of the methods described in WO2015/103037 and WO2016/081947.

The neoantigen number obtained from a population of subjects having the cancer may vary depending on the type of the cancer, therapy (e.g., immunotherapy, chemotherapy), the caner histology, and/or the site of disease (tumor). In certain embodiments, the median neoantigen number obtained from a population of subjects having cancer is between 10 and 10,000, between 10 and 50, between 30 and 50, between 30 and 40, between 50 and 100, between 100 and 200, between 200 and 300, between 300 and 400, between 400 and 500, between 500 and 600, between 600 and 700, between 700 and 800, between 800 and 900, between 900 and 1,000, between 1,000 and 2,000, between 2,000 and 3,000, between 3,000 and 4,000, between 4,000 and 5,000, between 5,000 and 6,000, between 6,000 and 7,000, between 7,000 and 8,000, between 8,000 and 9,000, or between 9,000 and 10,000. In certain embodiments, the median neoantigen number obtained from a population of subjects having cancer is about 40. In certain embodiments, the median neoantigen number obtained from a population of subjects having cancer is about 38. In certain embodiments, the cancer is pancreatic cancer, e.g., PDAC.

The neoantigens can be located in any genes in a subject. In certain embodiments, the neoantigen is located in MUC16. In certain embodiments, the neoantigen is located in any of the genes listed in Table 2.

In certain embodiments, the patient selection method and responsiveness prediction method relate to the quantity of the neoantigens and the immunogenicity of the neoantigens (hereinafter "neoantigen immunogenicity") in the subject. In certain embodiments, the patient selection method and responsiveness prediction method comprise assessing the neoantigen immunogenicity. Immunogenicity is the ability of a particular substance, such as an antigen (e.g., a neoantigen), to induce or stimulate an immune response in the cells expressing such antigen. In certain embodiments, assessing the neoantigen immunogenicity comprises measuring one or more surrogate for the neoantigen immunogenicity.

In certain embodiments, the surrogate is the homology between a neoantigen and a microbial epitope (hereinafter "neoantigen-microbial homology").

In certain non-limiting embodiments, the patient selection method comprises obtaining a biological sample from the subject, measuring the neoantigen number in the biological sample; and measuring the homology between each of the neoantigen and a microbial epitope (neoantigen-microbial homology), where a neoantigen number higher than the median neoantigen number obtained from a population of subjects having the cancer (e.g., referred to as "neoantigen number$^{high}$") and a neoantigen-microbial homology higher than the median neoantigen-microbial homology obtained from subjects having the cancer (e.g., referred to as "neoantigen-microbial homology$^{high}$") indicate that the subject is a candidate for an immunotherapy.

In certain non-limiting embodiments, the responsiveness prediction method comprises obtaining a biological sample from the subject, measuring the neoantigen number in the biological sample, and measuring the neoantigen-microbial homology, where a neoantigen number higher than the median neoantigen number obtained from a population of subjects having the cancer (e.g., referred to as "neoantigen number$^{high}$") and a neoantigen-microbial homology higher than the median neoantigen-microbial homology obtained from subjects having the cancer (e.g., referred to as "neoantigen-microbial homology$^{high}$") indicate that the subject is likely to be responsive to an immunotherapy.

In certain embodiments, the surrogate is the number of activated T cells (hereinafter "activated T cell number"). The immune system plays an important role in controlling and eradicating cancer. The number and frequency of the activated T cells present in the tumor can affect the fraction of tumor cells eventually killed in vitro. Therefore, the baseline infiltration by activated T cells in the tumor can have important prognostic implications for solid tumors.

In certain non-limiting embodiments, the subject's neoantigen number, the neoantigen-microbial homology, and activated T cell numbers are at least about 1%, at least about 2%, at least about 3%, at least about 4%, at least about 5%, at least about 6%, at least about 7%, at least about 8%, at least about 9%, at least about 10%, or at least about 20%, or at least about 30%, higher than the median values.

In certain embodiments, the one or more neoantigen is selected from the neoantigenic peptides listed in Tables 1 and 2.

In certain embodiments, activated T cells are T cells expressing one or more T cell activation marker. Non-limiting examples of T cell activation markers include CD3, CD8, PD-1, 4-1BB, CD69, CD107a, and Granzyme B. In certain embodiments, the activated T cells are selected from the group consisting of CD3$^+$CD8$^+$ T cells, CD3$^+$CD8$^+$ Granzyme-B$^+$ T cells, polyclonal activated T cells, and combinations thereof.

In certain non-limiting embodiments, the patient selection method comprises measuring the neoantigen number in a biological sample of the subject, and measuring the number of activated T cells (hereinafter "activated T cell number") in a biological sample of the subject. In such embodiments, a neoantigen number higher than the median neoantigen number obtained from a population of subjects having the cancer (e.g., referred to as "neoantigen number$^{high}$") and an activated T cell number higher than the median activated T cell number obtained from subjects having the cancer (e.g., referred to as "activated T cell number$^{high}$") indicate that the subject is a candidate for an immunotherapy.

In certain non-limiting embodiments, the responsiveness prediction method comprises measuring the neoantigen number in a biological sample of the subject; and measuring the activated T cell number a biological sample of the subject. In such embodiments, a neoantigen number higher than the median neoantigen number obtained from a population of subjects having the cancer (e.g., referred to as "neoantigen number$^{high}$") and an activated T cell number higher than the median activated T cell number obtained from subjects having the cancer (e.g., referred to as "activated T cell number$^{high}$") indicate that the subject is likely to be responsive to an immunotherapy.

The patient selection method and responsiveness prediction method further comprise obtaining one or more biological sample from the subject. The biological sample used to measure the neoantigen number, the biological sample used to measure the neoantigen-microbial homology, and the biological sample used to measure the activated T cell numbers can be the same or different. In certain embodiments, the biological sample can be a tumor tissue. In certain embodiments, the biological sample is a blood sample.

In certain embodiments, the neoantigen-microbial homology is measured by calculating a recognition potential (cross reactivity) score between each neoantigen and microbial epitope. As used herein, the terms "cross reactivity" and "recognition potential" are used interchangeably. In certain embodiments, calculating a recognition potential score between each neoantigen and microbial epitope is performed by a recognition potential model. As used herein the terms "recognition potential model," "neoantigen recognition potential model," and "cross reactivity model" are used interchangeably. In certain embodiments, the neoantigen recognition potential model comprises measuring sequence alignment scores for each neoantigen to a microbial epitope (e.g., with positive immune assays from the Immune Epitope Database). The neoantigen recognition potential model can also comprise scaling the alignment scores to binding probability of a T cell to cross reacting microbial epitope by fitting a sigmoid function. In some embodiments, the binding probabilities are amplified by relative wild type ("WT") and neoantigenic peptide ("Mutant"). A neoantigen recognition potential score for a given neoantigen is a function of the alignment score and the amplitude, $K_d^{WT}/K_d^{Mutant}$. In some embodiments, the calculation of a recognition potential score for a neoantigen is done using any of the fitness models disclosed in Luksza et al., 2017, "A neoantigen fitness model predicts tumour response to checkpoint blockade immunotherapy," Nature 551, 517-520. In some embodiments, the calculation of a recognition potential score for a neoantigen is done using any of the fitness models disclosed in Luksza et al., 2017, "A neoantigen fitness model predicts tumour response to checkpoint blockade immunotherapy," Nature 551, 517-520. In some embodiments, the calculation of a recognition potential score for a neoantigen is done in accordance with any of the models disclosed below in conjunction with blocks 346 through 358 of FIG. 3.

In certain embodiments, the neoantigen-microbial homology$^{high}$ neoantigen is a cross-reactivity score$^{high}$ neoantigen, e.g., a neoantigen having a recognition potential score (e.g., calculated by i) a recognition potential model described above, ii) any of the fitness models disclosed in Luksza et al., 2017, "A neoantigen fitness model predicts tumour response to checkpoint blockade immunotherapy," Nature 551, 517-520, and/or iii) any of the models disclosed below in conjunction with blocks 346 through 358 of FIG. 3) higher than the median recognition potential obtained from a population of subjects with the cancer. The median recognition potential score obtained from a population of subjects having the cancer may vary depending on the type of the cancer, the type of therapy (e.g., immunotherapy, chemotherapy), the caner histology, and/or presence/absence of neoantigens. In certain embodiments, the median recognition potential score (e.g., calculated by i) a neoantigen recognition potential model described above, ii) any of the fitness models disclosed in Luksza et al., 2017, "A neoantigen fitness model predicts tumour response to checkpoint blockade immunotherapy," Nature 551, 517-520, and/or iii) any of the models disclosed below in conjunction with blocks 346 through 358 of FIG. 3) obtained from a population of subjects having a cancer is between about 0 and 1, between about 0 and 0.5, between about 0 and 0.1, between about 0.1 and 0.2, between about 0.2 and 0.3, between about 0.3 and 0.4, between about 0.4 and 0.5, between about 0.5 and 1, between about 0.5 and 0.6, between about 0.6 and 0.7, between about 0.7 and 0.8, between about 0.8 and 0.9, or between about 0.9 and 0.1. In certain embodiments, the median neoantigen number (e.g., calculated by i) a recognition potential model described above, ii) any of the fitness models disclosed in Luksza et al., 2017, "A neoantigen fitness model predicts tumour response to checkpoint blockade immunotherapy," Nature 551, 517-520, and/or iii) any of the models disclosed below in conjunction with blocks 346 through 358 of FIG. 3) obtained from a population of subjects having cancer is about 0.8. In certain embodiments, the median neoantigen number (e.g., calculated by i) a recognition potential model described above, ii) any of the fitness models disclosed in Luksza et al., 2017, "A neoantigen fitness model predicts tumour response to checkpoint blockade immunotherapy," Nature 551, 517-520, and/or iii) any of the models disclosed below in conjunction with blocks 346 through 358 of FIG. 3) obtained from a population of subjects having cancer is about 0.9. In certain embodiments, the cancer is pancreatic cancer, e.g., PDAC.

In some embodiments, the median activated T cell number obtained from subjects having the cancer varies depending on the type of the cancer, the type of therapy (e.g., immunotherapy, chemotherapy), the caner histology, presence/absence of ongoing immune response, and/or presence/absence of neoantigens. In certain embodiments, the median activated T cell number obtained from a population of subjects having a cancer is between 0 and 2,000 cells/mm$^2$, between 0 and 10 cells/mm$^2$, between 10 and 20 cells/mm$^2$, between 20 and 30 cells/mm$^2$, between 30 and 40 cells/mm$^2$, between 40 and 50 cells/mm$^2$, between 10 and 50 cells/mm$^2$, between 50 and 100 cells/mm$^2$, between 50 and 60 cells/mm$^2$, between 60 and 70 cells/mm$^2$, between 70 and 80 cells/mm$^2$, between 80 and 90 cells/mm$^2$, between 90 and 100 cells/mm$^2$, between 100 and 200 cells/mm$^2$, between 200 and 500 cells/mm$^2$, between 500 and 1,000 cells/mm$^2$, between 1,000 and 1,500 cells/mm$^2$, or between 1,500 and 2,000 cells/mm$^2$. In certain embodiments, the median activated T cell number obtained from a population of subjects having a cancer is about 60 cells/mm$^2$. In certain embodiments, the median activated T cell number obtained from a population of subjects having a cancer is about 58 cells/mm$^2$. In certain embodiments, the cancer is pancreatic cancer, e.g., PDAC.

In some embodiments, the cancer is a solid tumor. In some embodiments, the cancer is a liquid tumor. Non-limiting examples of solid tumor include pancreatic cancer, gastric cancer, bile duct cancer (e.g., cholangiocarcinoma), liver cancer, colorectal cancer, melanoma, lung cancer, and breast cancer. Non-limiting examples of liquid tumor include acute leukemia and chronic leukemia. In certain embodiments, the cancer is pancreatic cancer. In certain embodiments, the pancreatic cancer is pancreatic ductal adenocacinma (PDAC).

3.3. Immunotherapy

Immunotherapies that boost the ability of endogenous T cells to destroy cancer cells have demonstrated therapeutic efficacy in a variety of human malignancies. However, some cancer patients have resistance to certain immunotherapies. The presently disclosed subject matter provides methods for identifying cancer patients who would be candidates and/or who would likely to respond to an immunotherapy.

Non-limiting examples of immunotherapies include therapies comprising one or more immune checkpoint blocking antibody, adoptive T cell therapies, non-checkpoint blocking antibody based immunotherapies, small molecule inhibitors, cancer vaccines, and combinations thereof.

Non-limiting examples of immune checkpoint blocking antibodies include antibodies against CTLA cytotoxic T-lymphocyte antigen 4 (anti-CTLA4 antibodies), antibodies against programmed death 1 (anti-PD-1 antibodies), antibodies against Programmed death-ligand 1 (anti-PD-L1 antibodies), antibodies against lymphocyte activation gene-3 (anti-LAG3 antibodies), antibodies against T cell immunoglobulin and mucin domain-containing protein 3 (anti-TIM-3 antibodies), antibodies against glucocorticoid-induced TNFR-related protein (GITR), antibodies against OX40, antibodies against CD40, antibodies against T cell immunoreceptor with Ig and ITIM domains (TIGIT), antibodies against 4-1BB, antibodies against B7 homolog 3 (anti-B7-H3 antibodies), antibodies against B7 homolog 4 (anti-B7-H4 antibodies), and antibodies against B- and T-lymphocyte attenuator (anti-BTLA antibodies).

Adoptive T cell therapy involves the isolation and ex vivo expansion of tumor specific T cells to achieve greater number of T cells. The tumor specific T cells are infused into cancer patients to give their immune system the ability to overwhelm remaining tumor via T cells which can attack and kill cancer. Non-limiting examples of adoptive T cell therapy include tumor-infiltrating lymphocyte (TIL) cell therapies, therapies comprising engineered or modified T cells, e.g., T cells engineered or modified with T cell receptor (TCR-transduced T cells), or T cells engineered or modified with chimeric antigen receptor (CAR-transduced T cells). These engineered or modified T cells recognize specific antigens associated with the cancers and attack cancers.

4. Therapeutic Uses of the Neoantigens

In some embodiments, the neoantigens of the present disclosure, or identified using the methods of the present disclosure, are used for vaccine therapy and/or adoptive T cell therapies.

4.1 Vaccines

Neoantigens can be an attractive source of targets for vaccine therapy. Neoantigen-based cancer vaccine can induce more robust and specific anti-tumor T-cell responses compared with conventional shared-antigen-targeted vaccine. Certain genetic loci, also known as immunogenic hotspots, can be preferentially enriched for neoantigens in specific tumors that display great T cell infiltration and adaptive immune activation. Vaccine targeting tumor-specific immunogenic hotspot generated neoantigen can induce robust and specific anti-tumor T cell response against the tumor cell. The vaccine can be used along or in combination with other cancer treatment, e.g., immunotherapy.

In one aspect, the present disclosure provides a vaccine comprising one or more of the presently disclosed neoantigens, or a polynucleotide encoding the neoantigen, or a protein or peptide comprising the neoantigen. In some embodiments, the neoantigen is selected based, at least in part, on predicted immunogenicity, for example, in silico. In some embodiments, the predicted immunogenicity is analyzed using computational algorithms for MHC class I and class II binding as well as use of tandem minigene libraries for class II epitope screening. In addition, in some embodiments, neoantigen specific T cell assays are used to differentiate true immunogenic neoepitopes from putative ones (see Kvistborg et. al., 2016, J. ImmunoTherapy of Cancer 4:22 for detailed review). In some embodiments, any methods and tools known in the art are used to predict immunogenicity of a neoantigen. For example, in some embodiments, the Immune Epitope Database (IEDB) T Cell Epitope-MHC Binding Prediction Tool disclosed in Brown et. al. 2010, Nucleic Acids Res. January; 38 (Database issue):D854-62) is used to predict the binding of neoantigen to autologous HLA-A encoded MHC proteins. In certain embodiments, immunogenicity analysis strategy and tools disclosed in WO2015/103037 are used in accordance with the disclosed subject matter, and the content of the forgoing patent is incorporated herein by reference in its entirety. In certain embodiments, a neoantigen is selectively targeted based on one or more of the following: (i) homology to an epitope of a known pathogen or microbe and/or (ii) ability to activate T cells, e.g. in an in vitro assay.

In another aspect, the present disclosure provides a vaccine comprising one or more neoantigens identified using any of the neoantigen identification methods disclosed herein.

In certain embodiments, the vaccine comprises one or more neoantigen of MUC16, or a polynucleotide encoding said neoantigen or a protein or peptide comprising said neoantigen. In certain embodiments, the one or more neoantigen of MUC16 is selected from the neoantigenic peptides listed in Table 1. In certain embodiments, the vaccine comprises one or more neoantigen associated with a cancer, the one or more neoantigen correlating with a neoantigen-microbial homology that is higher than the median neoantigen-microbial homology occurring in subjects with the cancer, or a polynucleotide encoding the neoantigen or a protein or peptide comprising the neoantigen. In certain embodiments, the vaccine comprises one or more neoantigen associated with a cancer, the neoantigen correlating with an activated T cell number that is higher than the median activated T cell number occurring in subjects with a cancer, or a polynucleotide encoding the neoantigen or a protein or peptide comprising the neoantigen.

In certain embodiments, the vaccine comprises a neoantigen that occurs in a subject with a cancer, where this subject has an activated T cell number that is higher than the median activated T cell number of a population of subjects with the cancer. In certain embodiments, the neoantigen less frequently occurs in subjects with the cancer and having activated T cell numbers at or less than the median activated T cell number.

In some embodiments, the number of different neoantigens in the vaccine varies, for example, in some embodiments the vaccine comprises 2, 3, 4, 5, 6, 7, 8, 9, 10 or more different neoantigens. In some embodiments, the neoantigens of a given vaccine are linked, e.g., by any biochemical strategy to link two proteins. In some embodiments, the neoantigens of a given vaccine are not linked.

In certain embodiments, the vaccine comprises one or more polynucleotides. In some embodiments, the one or more polynucleotides are RNA, DNA, or a mixture thereof. In certain embodiments, the vaccine is in the form of DNA or RNA vaccines relating to neoantigens. In some embodiments, the one or more neoantigen are delivered via a bacterial or viral vector containing DNA or RNA sequences that encode one or more neoantigen.

Non-limiting examples of vaccines of the present disclosure include tumor cell vaccines, antigen vaccines, and dendritic cell vaccines, RNA vaccines, and DNA vaccines. Tumor cell vaccines are made from cancer cells removed from the patient. In some such embodiments, the cells are altered (and killed) to make them more likely to be attacked by the immune system and then injected back into the patient. In some embodiments, the tumor cell vaccines are autologous, e.g., the vaccine is made from killed tumor cells taken from the same person who receives the vaccine. In some embodiments, the tumor cell vaccines are allogeneic, e.g., the cells for the vaccine come from someone other than the patient being treated.

In some embodiments, the vaccine is an antigen presenting cell vaccine, e.g., a dendritic cell vaccine. Dendritic cells are special immune cells in the body that help the immune system recognize cancer cells. They break down cancer cells into smaller pieces (including antigens), and then hold out these antigens so T cells can see them. The T cells then start an immune reaction against any cells in the body that contain these antigens.

In some embodiments, the antigen presenting cell such as a dendritic cell is pulsed or loaded with the neoantigen, or genetically modified (via DNA or RNA transfer) to express one or more neoantigen (see, e.g., Butterfield, 2015, BMJ. 22, 350; and Palucka, 2013, Immunity 39, 38-48). In certain embodiments, the dendritic cell is genetically modified to express one or more neoantigen peptide. In some embodiments, any suitable method known in the art is used for preparing dendritic cell vaccines of the present disclosure. For example, in some embodiments, immune cells are removed from the patient's blood and exposed to cancer cells or cancer antigens, as well as to other chemicals that turn the immune cells into dendritic cells and help them grow. The dendritic cells are then injected back into the patient, where they can cause an immune response to cancer cells in the body.

Furthermore, the presently disclosed subject matter provides methods for treating pancreatic cancer in a subject. In certain embodiments, the method comprises administering to the subject a presently disclosed vaccine.

In certain embodiments, the vaccination is therapeutic vaccination, administered to a subject who has pancreatic cancer. In certain embodiments, the vaccination is prophylactic vaccination, administered to a subject who can be at risk of developing pancreatic cancer. In certain embodiments, the vaccine is administered to a subject who has previously had cancer and in whom there is a risk of the cancer recurring.

Vaccines can be administered in any suitable way as known in the art. In certain embodiments, the vaccine is delivered using a vector delivery system. In some embodiments, the vector delivery system is viral, bacterial or makes use of liposomes. In certain embodiments, a listeria vaccine or electroporation is used to deliver the vaccine.

The presently disclosed subject matter further provides a composition comprising a presently disclosed vaccine. In certain embodiments, the composition is a pharmaceutical composition. In some embodiments, the pharmaceutical composition further comprises a pharmaceutically acceptable carrier, diluent or excipient.

In certain embodiments, the vaccine leads to generation of an immune response in a subject. In some embodiments, the immune response is humoral and/or cell-mediated immunity, for example the stimulation of antibody production, or the stimulation of cytotoxic or killer cells, which can recognize and destroy (or otherwise eliminate) cells (e. g., tumor cells) expressing antigens (e.g., neoantigen) corresponding to the antigens in the vaccine on their surface. In some embodiments, inducing or stimulating an immune response includes all types of immune responses and mechanisms for stimulating them. In certain embodiments, the induced immune response comprises expansion and/or activation of Cytotoxic T Lymphocytes (CTLs). In certain embodiments, the induced immune response comprises expansion and/or activation of $CD8^+$ T cells. In certain embodiments, the induced immune response comprises expansion and/or activation of helper $CD4^+$ T Cells. In some embodiments, the extent of an immune response is assessed by production of cytokines, including, but not limited to, IL-2, IFN-γ, and/or TNFα.

4.2 Adoptive T-Cell Therapy

In some embodiments of the present disclosure, the neoantigens of the present disclosure are used in adoptive T cell therapy. The presently disclosed subject matter provides a population of T cells that target one or more of the presently disclosed neoantigens. In some embodiments, the neoantigen are selected based, at least in part, on predicted immunogenicity, for example, in silico. In some embodiments, the predicted immunogenicity is analyzed using computational algorithms for MHC class I and class II binding as well as use of tandem minigene libraries for class II epitope screening. In addition, or alternatively, in some embodiments neoantigen specific T cell assays are used to differentiate true immunogenic neoepitopes from putative ones (see, Kvistborg et. al., 2016, J. ImmunoTherapy of Cancer 4:22 for a detailed review). In some embodiments, any methods and tools known in the art are used to predict immunogenicity of a neoantigen. For example, in some embodiments the Immune Epitope Database (IEDB) T Cell Epitope-MHC Binding Prediction Tool disclosed in Brown et. al., 2010, Nucleic Acids Res. 38 (Database issue): D854-62 is used to predict the binding of neoantigen to autologous HLA-A encoded MHC proteins. In certain embodiments, immunogenicity analysis strategy and tools disclosed in WO2015/103037 are used in accordance with the disclosed subject matter, and the content of the forgoing patent is incorporated herein by reference in its entirety. In certain embodiments, a neoantigen is selectively targeted based on one or more of the following: (i) homology to an epitope of a known pathogen or microbe; and/or (ii) ability to activate T cells, e.g. in an in vitro assay.

In certain embodiments, the population of T cells target one or more neoantigen of MUC16. In certain embodiments, the one or more neoantigen of MUC16 is selected from the neoantigenic peptides listed in Table 1. In certain embodiments, the population of T cells target one or more neoantigen associated with a cancer, the one or more neoantigen correlating with a neoantigen-microbial homology that is higher than the median neoantigen-microbial homology occurring in subjects with the cancer. In certain embodiments, the population of T cells target one or more neoantigen associated with a cancer, the neoantigen correlating with an activated T cell number that is higher than the median activated T cell number occurring in subjects with the cancer. In certain embodiments, the neoantigen comprised in the vaccine occurs in a subject with a cancer, where the subject has an activated T cell number that is higher than the median activated T cell number of a population of subjects with the cancer. In certain embodiments, the neoantigen occurs less frequently in subjects with the cancer and having activated T cell numbers at or less than the median activated T cell number.

In certain embodiments, the T cells are selectively expanded to target the one or more neoantigen. T cells are lymphocytes that mature in the thymus and are chiefly responsible for cell-mediated immunity. T cells are involved in the adaptive immune system. In some embodiments, the T cells of the presently disclosed subject matter are any type of T cells, including, but not limited to, helper T cells, cytotoxic T cells, memory T cells (including central memory T cells, stem-cell-like memory T cells (or stem-like memory T cells), and two types of effector memory T cells: e.g., $T_{EM}$ cells and $T_{EMRA}$ cells, regulatory T cells (also known as suppressor T cells), natural killer T cells, mucosal associated invariant T cells, and γδ T cells. Cytotoxic T cells (CTL or killer T cells) are a subset of T lymphocytes capable of inducing the death of infected somatic or tumor cells.

In certain embodiments, the T cells that specifically target one or more neoantigen are engineered or modified T cells. In certain embodiments, the engineered T cells comprise a recombinant antigen receptor that specifically targets or binds to one or more of the presently disclose neoantigens. In certain embodiments, the recombinant antigen receptor specifically targets one or more neoantigen of MUC16. In certain embodiments, the recombinant antigen receptor specifically targets one or more neoantigen associated with a cancer, the one or more neoantigen correlating with a neoantigen-microbial homology that is higher than the median neoantigen-microbial homology occurring in subjects with the cancer. In certain embodiments, the recombinant antigen receptor specifically targets one or more neoantigen associated with a cancer, the neoantigen correlating with an activated T cell number that is higher than the median activated T cell number occurring in subjects with the cancer. In certain embodiments, the recombinant antigen receptor is a chimeric antigen receptor (CAR). In certain embodiments, the recombinant antigen receptor is a T cell receptor (TCR). In certain embodiments, the CAR comprises an extracellular antigen-binding domain that specifically binds to one or more neoantigen, a transmembrane domain, and an intracellular signaling domain. CARs can activate the T-cell in response to recognition by the extracellular antigen-binding domain of its target. When T cells express such a CAR, they recognize and kill cells that express one or more neoantigen.

Affinity-enhanced TCRs are generated by identifying a T cell clone from which the TCR α and β chains with the desired target specificity are cloned. The candidate TCR then undergoes PCR directed mutagenesis at the complimentary determining regions ("CDR") of the α and β chains. The mutations in each CDR region are screened to select for mutants with enhanced affinity over the native TCR. Once completed, lead candidates are cloned into vectors to allow functional testing in T cells expressing the affinity-enhanced TCR.

In certain embodiments, the T cell population is enriched with T cells that are specific to one or more neoantigen, e.g., having an increased number of T cells that target one or more neoantigen. Therefore, the T cell population differs from a naturally occurring T cell population, in that the percentage or proportion of T cells that target a neoantigen is increased.

In certain embodiments, the T cell population comprises at least about 10%, about 20%, about 30%, about 40%, about 50%, about 60%, about 70%, about 80%, about 90%, about 95%, or about 100% T cells that target one or more neoantigen. In certain embodiments, the T cell population comprises no more than about 5%, about 10%, about 15%, about 20%, about 25%, about 30%, about 35%, about 40%, about 45%, or about 50% T cells that do not target one or more neoantigen.

In certain embodiments, the T cell population is generated from T cells isolated from a subject with cancer. In one non-limiting example, the T cell population is generated from T cells in a biological sample isolated from a subject with cancer. In some embodiments, the biological sample is a tumor sample, a peripheral blood sample, or a sample from a tissue of the subject. In certain embodiments, the T cell population is generated from a biological sample in which the one or more neoantigen is identified or detected.

The presently disclosed subject matter further provides a composition comprising such T cell populations as described herein. In certain embodiments, the composition is a pharmaceutical composition that comprises a pharmaceutically acceptable carrier. Furthermore, the presently disclosed subject matter provides a method of treating cancer in a subject, comprising administering to the subject a composition comprising such T cell population as described herein. In some embodiments, the cancer is any of the cancers enumerated in the present disclosure. In some embodiments the cancer is pancreatic cancer. In certain embodiments, the composition comprises a population of T cells that target one or more neoantigen of MUC16. In certain embodiments, the one or more neoantigen of MUC16 is selected from the neoantigenic peptides listed in Table 1.

In some embodiments, the methods are used in vitro, ex vivo or in vivo, for example, either for in situ treatment or for ex vivo treatment followed by the administration of the treated cells to the subject. In certain embodiments, the T cell population or composition is reinfused into the subject, for example following T cell isolation and expansion to target the one or more MUC16 neoantigen.

5. Further Uses of Neoantigen Fitness Models for Determining a Likelihood that a Human Subject Afflicted with a Cancer Will be Responsive to a Treatment Regimen that Comprises Administering a Checkpoint Blockade Immunotherapy and/or for Identifying an Immunotherapy for a Cancer 5.1 Heterogeneous Tumor Evolution To describe the evolution of a heterogeneous tumor, its fitness is evaluated as a weighted average over dominant neoantigens in the tumor's subclones. The disclosed neoantigen recognition potential model predicts survival in anti-CTLA4 treated melanoma patients (Snyder et al., 2014, "Genetic Basis for Clinical Response to CTLA-4 Blockade in Melanoma," N. Engl. J. Med. 371, pp. 2189-2199; and Van Allen et al., 2015, "Genomic correlates of response to CTLA-4 blockade in metastatic melanoma," Science 350, pp. 207-211, each of which is hereby incorporated by reference) and anti-PD1 treated lung cancer patients (Rizvi et al., 2015, "Mutational landscape determines sensitivity to PD-1 blockade in non-small cell lung cancer, Science 348, pp. 124-128, which is hereby incorporated by reference). Importantly, in some embodiments, low-fitness neoantigens identified by the systems and methods of the present disclosure are leveraged for developing novel immunotherapies as disclosed below and as discussed in the sections above. In a broader context, the present disclosure reveals evolutionary similarities between cancers and fast-evolving pathogens (Luksza and Lassig, 2014, "Predictive fitness model for influenza, Nature 507, pp. 57-61; Wang et al., 2015, "Manipulating the selection forces during affinity maturation to generate cross-reactive HIV antibodies," Cell 160, pp. 785-797; and Nourmohammad et al., 2016, "Host-pathogen coevolution and the emergence of broadly neutralizing antibodies in chronic infections," PLoS Genet 12, e1006171, each of which is hereby incorporated by reference).

Figure 1:
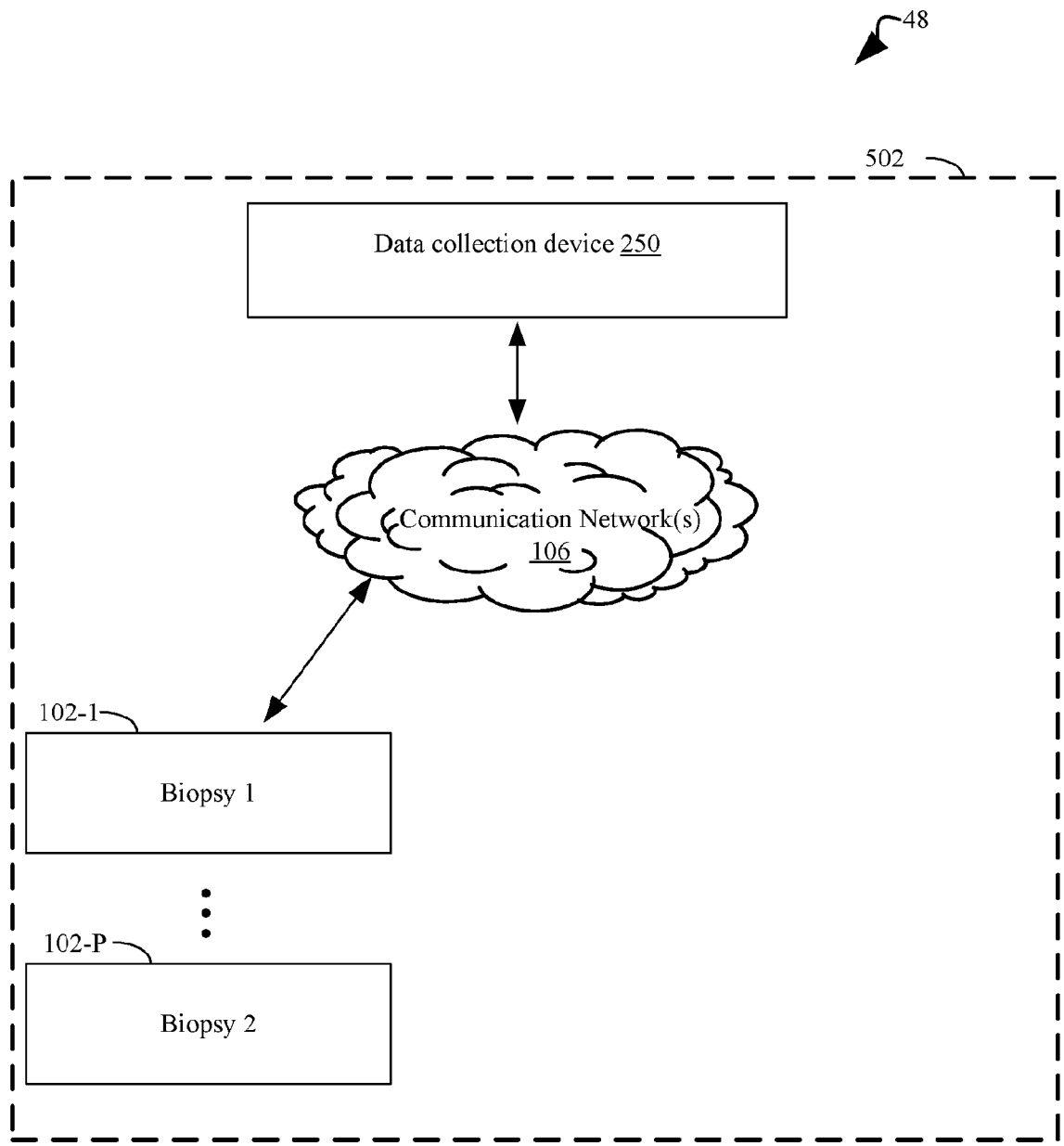
FIG. 1 illustrates an exemplary system topology for determining a likelihood that a human subject afflicted with a cancer will be responsive to a treatment regimen that comprises administering a checkpoint blockade immunotherapy directed to the cancer to the subject, in accordance with an embodiment of the present disclosure.
Figure 2:
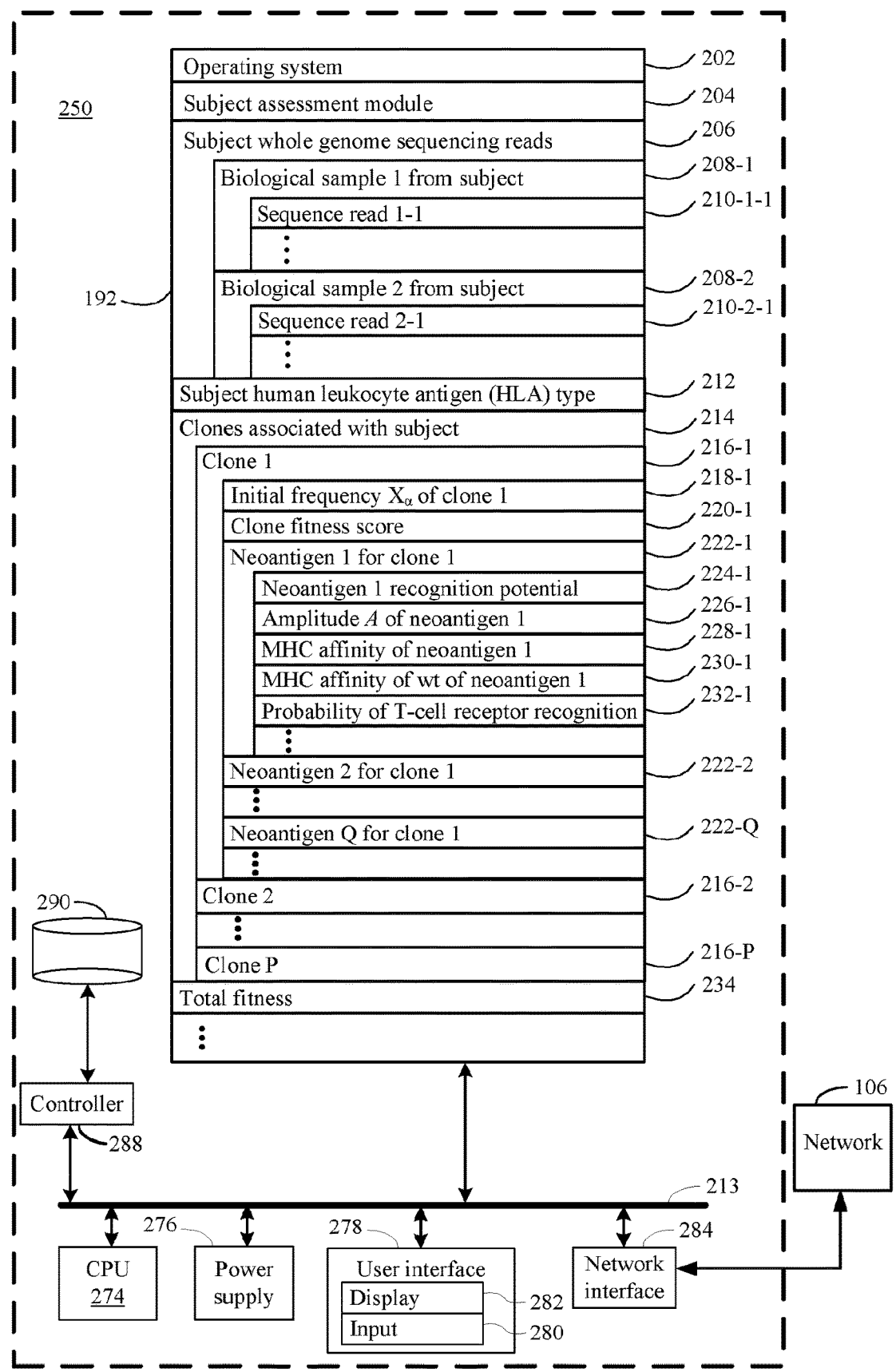
FIG. 2 illustrates a device for determining a likelihood that a human subject afflicted with a cancer will be responsive to a treatment regimen that comprises administering a checkpoint blockade immunotherapy directed to the cancer to the subject in accordance with an embodiment of the present disclosure.

5.2 Example Systems for Determining a Likelihood that a Human Subject Afflicted with a Cancer Will be Responsive to a Treatment Regimen and/or for Identifying an Immunotherapy for a Cancer Using a Neoantigen Fitness Model One aspect of the present disclosure relies upon the acquisition of a data set comprising a plurality of sequence reads (e.g., whole genome sequencing reads, exome sequencing reads, targeted sequencing reads, etc.) of a subject. FIG. 1 illustrates an example of an integrated system 502 for the acquisition of such data, and FIG. 2 provides more details of such a system 502. The integrated system 502 obtains sequencing data (e.g., whole genome sequencing reads, exome sequencing reads, targeted sequencing reads, etc.) from one or more samples 102 from a human cancer subject that is representative of the cancer, one or more glucose monitors 102, and a data collection device 250.

A detailed description of a data collection device 250 for determining a likelihood that a human subject afflicted with a cancer will be responsive to a treatment regimen (e.g., a treatment regimen comprising administering a checkpoint blockade immunotherapy directed to the cancer to the subject in accordance with the present disclosure) and/or for identifying an immunotherapy for a cancer using a neoantigen fitness model is described in conjunction with FIGS. 1 and 2. As such, FIGS. 1 and 2 collectively illustrate the topology of the system in accordance with the present disclosure. In the topology, there is a data collection device 250 for determining a likelihood that a human subject afflicted with a cancer will be responsive to a treatment regimen and/or for identifying an immunotherapy for a cancer using a neoantigen fitness model.

Referring to FIG. 2, the data collection device 250 determines a likelihood that a human subject afflicted with a cancer will be responsive to a treatment regimen and/or for identifying an immunotherapy for a cancer using a neoantigen fitness model. To do this, the data collection device 250, receives sequencing reads (e.g., whole genome sequencing reads, exome sequencing reads, targeted sequencing reads, etc.) originating from one or more biological samples (e.g., biopsies) 102 of a subject. In some embodiments, the data collection device 250 receives such data directly from nucleic acid sequencers. For instance, in some embodiments the data collection device 250 receives this data wirelessly through radio-frequency signals. In some embodiments such signals are in accordance with an 802.11 (WiFi), Bluetooth, or ZigBee standard. In some embodiments, the data collection device 250 receives such data directly. In some embodiments the data collection device 250 receives this data across a communications networks.

Examples of networks 106 include, but are not limited to, the World Wide Web (WWW), an intranet and/or a wireless network, such as a cellular telephone network, a wireless local area network (LAN) and/or a metropolitan area network (MAN), and other devices by wireless communication. The wireless communication optionally uses any of a plurality of communications standards, protocols and technologies, including but not limited to Global System for Mobile Communications (GSM), Enhanced Data GSM Environment (EDGE), high-speed downlink packet access (HSDPA), high-speed uplink packet access (HSUPA), Evolution, Data-Only (EV-DO), HSPA, HSPA+, Dual-Cell HSPA (DC-HSPDA), long term evolution (LTE), near field communication (NFC), wideband code division multiple access (W-CDMA), code division multiple access (CDMA), time division multiple access (TDMA), Bluetooth, Wireless Fidelity (Wi-Fi) (e.g., IEEE 802.11a, IEEE 802.11ac, IEEE 802.11ax, IEEE 802.11b, IEEE 802.11g and/or IEEE 802.11n), voice over Internet Protocol (VoIP), Wi-MAX, a protocol for e-mail (e.g., Internet message access protocol (IMAP) and/or post office protocol (POP)), instant messaging (e.g., extensible messaging and presence protocol (XMPP), Session Initiation Protocol for Instant Messaging and Presence Leveraging Extensions (SIMPLE), Instant Messaging and Presence Service (IMPS)), and/or Short Message Service (SMS), or any other suitable communication protocol, including communication protocols not yet developed as of the filing date of the present disclosure.

Of course, other topologies of the system 48 of FIG. 1 are possible. For instance, rather than relying on a communications network 106, information may be sent directly to the data collection device 250. Further, the data collection device 250 may constitute a portable electronic device, a server computer, or in fact constitute several computers that are linked together in a network or be a virtual machine in a cloud computing context. As such, the exemplary topology shown in FIG. 1 merely serves to describe the features of an embodiment of the present disclosure in a manner that will be readily understood to one of skill in the art.

Referring to FIG. 2, in typical embodiments, the data collection device 250 comprises one or more computers. For purposes of illustration in FIG. 2, the data collection device 250 is represented as a single computer that includes all of the functionality for determining a likelihood that a human subject afflicted with a cancer will be responsive to a treatment regimen and/or for identifying an immunotherapy for a cancer using a neoantigen fitness model. However, the disclosure is not so limited. In some embodiments, the functionality for determining a likelihood that a human subject afflicted with a cancer will be responsive to a treatment regimen and/or for identifying an immunotherapy for a cancer using a neoantigen fitness model is spread across any number of networked computers and/or resides on each of several networked computers and/or is hosted on one or more virtual machines at a remote location accessible across the communications network 106. One of skill in the art will appreciate that any of a wide array of different computer topologies are used for the application and all such topologies are within the scope of the present disclosure.

Turning to FIG. 2 with the foregoing in mind, an exemplary data collection device 250 for determining a likelihood that a human subject afflicted with a cancer will be responsive to a treatment regimen and/or for identifying an immunotherapy for a cancer using a neoantigen fitness model comprises one or more processing units (CPU's) 274, a network or other communications interface 284, a memory 192 (e.g., random access memory), one or more magnetic disk storage and/or persistent devices 290 optionally accessed by one or more controllers 288, one or more communication busses 213 for interconnecting the aforementioned components, a user interface 278, the user interface 278 including a display 282 and input 280 (e.g., keyboard, keypad, touch screen), and a power supply 276 for powering the aforementioned components. In some embodiments, the input 280 is a touch-sensitive display, such as a touch-sensitive surface. In some embodiments, the user interface 278 includes one or more soft keyboard embodiments. The soft keyboard embodiments may include standard (QWERTY) and/or non-standard configurations of symbols on the displayed icons. In some embodiments, data in memory 192 is seamlessly shared with non-volatile memory 290 using known computing techniques such as caching. In some embodiments, memory 192 and/or memory 290 includes mass storage that is remotely located with respect to the central processing unit(s) 274. In other words, some data stored in memory 192 and/or memory 290 may in fact be hosted on computers that are external to the data collection device 250 but that can be electronically accessed by the data collection device 250 over an Internet, intranet, or other form of network or electronic cable (illustrated as element 106 in FIG. 2) using network interface 284.

In some embodiments, the memory 192 of the data collection device 250 for determining a likelihood that a human subject afflicted with a cancer will be responsive to a treatment regimen and/or for identifying an immunotherapy for a cancer using a neoantigen fitness model stores:
an operating system 202 that includes procedures for handling various basic system services;
a subject assessment module 204;
whole genome sequencing reads 206 for the subject, the whole genome sequencing reads comprising, for each biological sample 208 from the subject, a plurality of sequence reads 210;
a human leukocyte antigen (HLA) type of the subject 212;
a plurality of clones 214 associated with a subject, and, for each respective clone 216 in the plurality of clones 214, an initial frequency $X_\alpha$ 218 of the clone 216, a clone fitness score 220, and a plurality of neoantigens 222 of the clone 216, each such neoantigen 222 including a neoantigen recognition potential 224, an amplitude A 226, an optional MHC affinity 228, and optional MHC affinity of the wildtype sequence corresponding to the neoantigen 230, and a probability of T-cell receptor recognition 232; and
a total fitness 234 of the cancer.

In some embodiments, the subject assessment module 204 is accessible within any browser (phone, tablet, laptop/desktop). In some embodiments the subject assessment module 204 runs on native device frameworks, and is available for download onto the data collection device 250 running an operating system 202 such as Android or iOS.

In some implementations, one or more of the above identified data elements or modules of the data collection device 250 for determining a likelihood that a human subject afflicted with a cancer will be responsive to a treatment regimen and/or for identifying an immunotherapy for a cancer using a neoantigen fitness model are stored in one or more of the previously described memory devices, and correspond to a set of instructions for performing a function described above. The above-identified data, modules or programs (e.g., sets of instructions) need not be implemented as separate software programs, procedures or modules, and thus various subsets of these modules may be combined or otherwise re-arranged in various implementations. In some implementations, the memory 192 and/or 290 optionally stores a subset of the modules and data structures identified above. Furthermore, in some embodiments the memory 192 and/or 290 stores additional modules and data structures not described above. Further still, in some embodiments, the data collection device 250 stores data for determining a likelihood that a human subject afflicted with a cancer will be responsive to a treatment regimen and/or for identifying an immunotherapy for a cancer using a neoantigen fitness model for two or more subjects, five or more subjects, one hundred or more subjects, or 1000 or more subjects.

In some embodiments, a data collection device 250 for determining a likelihood that a human subject afflicted with a cancer will be responsive to a treatment regimen and/or for identifying an immunotherapy for a cancer using a neoantigen fitness model is a smart phone (e.g., an iPHONE), laptop, tablet computer, desktop computer, or other form of electronic device (e.g., a gaming console). In some embodiments, the data collection device 250 is not mobile. In some embodiments, the data collection device 250 is mobile.

It should be appreciated that the data collection device 250 illustrated in FIG. 2 is only one example of a multi-function device that may be used for determining a likelihood that a human subject afflicted with a cancer will be responsive to a treatment regimen and/or for identifying an immunotherapy for a cancer using a neoantigen fitness model, and that the data collection device 250 optionally has more or fewer components than shown, optionally combines two or more components, or optionally has a different configuration or arrangement of the components. The various components shown in FIG. 2 are implemented in hardware, software, firmware, or a combination thereof, including one or more signal processing and/or application specific integrated circuits.

RF (radio frequency) circuitry of network interface 284 receives and sends RF signals, also called electromagnetic signals. In some embodiments, the sequencing reads 206 and HLA type 212 and/or other data is received using this RF circuitry from one or more devices such as nucleic acid sequencers. In some embodiments, the RF circuitry 108 converts electrical signals to/from electromagnetic signals and communicates with communications networks and other communications devices via the electromagnetic signals. The RF circuitry 284 optionally includes well-known circuitry for performing these functions, including but not limited to an antenna system, an RF transceiver, one or more amplifiers, a tuner, one or more oscillators, a digital signal processor, a CODEC chipset, a subscriber identity module (SIM) card, memory, and so forth. RF circuitry 284 optionally communicates with the communication network 106. In some embodiments, the circuitry 284 does not include RF circuitry and, in fact, is connected to the network 106 through one or more hard wires (e.g., an optical cable, a coaxial cable, or the like).

In some embodiments, the power supply 276 optionally includes a power management system, one or more power sources (e.g., battery, alternating current (AC)), a recharging system, a power failure detection circuit, a power converter or inverter, a power status indicator (e.g., a light-emitting diode (LED)) and any other components associated with the generation, management and distribution of power in portable devices.

As illustrated in FIG. 2, the data collection device 250 preferably comprises an operating system 202 that includes procedures for handling various basic system services. The operating system 202 (e.g., iOS, DARWIN, RTXC, LINUX, UNIX, OS X, WINDOWS, or an embedded operating system such as VxWorks) includes various software components and/or drivers for controlling and managing general system tasks (e.g., memory management, storage device control, power management, etc.) and facilitates communication between various hardware and software components.

In some embodiments the data collection device 250 is a smart phone. In other embodiments, the data collection device 250 is not a smart phone but rather is a tablet computer, desktop computer, emergency vehicle computer, or other form or wired or wireless networked device. In some embodiments, the data collection device 250 has any or all of the circuitry, hardware components, and software components found in the data collection device 250 depicted in FIG. 2. In the interest of brevity and clarity, only a few of the possible components of the data collection device 250 are shown in order to better emphasize the additional software modules that are installed on the data collection device 250.

While the system 48 disclosed in FIG. 1 can work standalone, in some embodiments it can also be linked with electronic medical records to exchange information in any way.

5.3 Example Methods for Determining a Likelihood that a Human Subject Afflicted with a Cancer Will be Responsive to a Treatment Regimen Now that details of a system 48 for determining a likelihood that a human subject afflicted with a cancer will be responsive to a treatment regimen (e.g., where the treatment regimen comprises administering a checkpoint blockade immunotherapy directed to the cancer to the subject) and/or for identifying an immunotherapy for a cancer using a neoantigen fitness model have been disclosed, details regarding a flow chart of processes and features of the system, in accordance with an embodiment of the present disclosure, are disclosed with reference to FIGS. 3A through 3F. In some embodiments, such processes and features of the system are carried out by the subject assessment module 204 illustrated in FIG. 2.

Block 302. Referring to block 302 of FIG. 3A, one aspect of the present disclosure provides systems and method for determining a likelihood that a human subject afflicted with a cancer will be responsive to a treatment regimen (e.g., that comprises administering a checkpoint blockade immunotherapy directed to the cancer to the subject) and/or for identifying an immunotherapy for a cancer using a neoantigen fitness model is provided.

In some embodiments, the checkpoint blockade immunotherapy comprises administering an anti-CTLA-4, anti-PD1 or anti-PD-L1 compound to the cancer subject. See Jantscheff et al., 2016, 76(14) "Anti-PD-1, Anti-PD-L1 and Anti-CTLA-4 checkpoint inhibitor treatment leads to different responses in syngeneic tumor models," Cancer Research, 76(14), DOI: 10.1158/1538-7445.AM2016-3216, which is hereby incorporated by reference for disclosure on Anti-PD-1, Anti-PD-L1 and Anti-CTLA-4 checkpoint inhibitors. In some embodiments, the checkpoint blockade immunotherapy comprises administering one or more antibodies or other compounds against lymphocyte activation gene-3 (anti-LAG3 compounds), one or more antibodies or other compounds against T cell immunoglobulin and mucin domain-containing protein 3 (anti-TIM-3 compounds), one or more antibodies or other compounds against glucocorticoid-induced TNFR-related protein (anti-GITR compounds), one or more antibodies or other compounds against OX40 (anti-OX40 compounds), one or more antibodies or other compounds against CD40 (anti-CD40 compounds), one or more antibodies or other compounds against T cell immunoreceptor with Ig and ITIM domains (anti-TIGIT compounds), one or more antibodies or other compounds against 4-1BB (anti4-1BB compounds), one or more antibodies or other compounds against B7 homolog 3 (anti-B7-H3 compounds), one or more antibodies or other compounds against B7 homolog 4 (anti-B7-H4 compounds), or one or more antibodies or other compounds against B- and T-lymphocyte attenuator (anti-BTLA compounds). In some embodiments, the checkpoint blockade immunotherapy comprises administering an anti-CTLA-4, anti-PD1, anti-PD-L1, anti-LAG3, anti-TIM-3, anti-GITR, anti-OX40, anti-CD40, anti-TIGIT, anti4-1BB, anti-B7-H3, anti-B7-H4, or anti-BTLA compound to the cancer subject (304).

In some embodiments, the cancer is a carcinoma, a melanoma, a lymphoma/leukemia, a sarcoma, or a neuroglial tumor (308). In some embodiments, the cancer is lung cancer, pancreatic cancer, colon cancer, stomach or esophagus cancer, breast cancer, ovary cancer, prostate cancer, or liver cancer (310). In some embodiments, the cancer is a solid tumor. In some embodiments, the cancer is a liquid tumor. Non-limiting examples of solid tumor include pancreatic cancer, gastric cancer, bile duct cancer (e.g., cholangiocarcinoma), liver cancer, colorectal cancer, melanoma, lung cancer, and breast cancer. Non-limiting examples of liquid tumor include acute leukemia and chronic leukemia. In certain embodiments, the cancer is pancreatic cancer. In certain embodiments, the pancreatic cancer is pancreatic ductal adenocacinma (PDAC).

Block 312. Referring to block 312 of FIG. 3A, a plurality of sequencing reads 210 (e.g., whole genome sequencing reads, exome sequencing reads, targeted sequencing reads, etc.) is obtained from one or more biological samples 208 from the human cancer subject that is representative of the cancer. In certain embodiments, a biological sample 208 is a biological tissue or fluid. Non-limiting biological samples 208 include bone marrow, blood, blood cells, ascites, (tissue or fine needle) biopsy samples, cell-containing body fluids, free floating nucleic acids, sputum, saliva, urine, cerebrospinal fluid, peritoneal fluid, pleural fluid, feces, lymph, gynecological fluids, swabs (e.g., skin swabs, vaginal swabs, oral swabs, and nasal swabs), washings or lavages such as a ductal lavages or broncheoalveolar lavages, aspirates, scrapings, specimens (e.g., bone marrow specimens, tissue biopsy specimens, and surgical specimens), feces, other body fluids, secretions, and/or excretions, and cells therefrom, etc.

In some embodiments, the plurality of sequencing reads is whole genome sequencing reads that collectively exhibit an average read depth of less than 200, less than 100, less than 50, less than 40, or less than 20 (314). In some embodiments, the plurality of sequencing reads are whole genome sequencing reads that collectively exhibit an average read depth of between 25 and 60 (316).

In some embodiments, the plurality of sequencing reads encompasses a subset of the genome of the subject and not the rest of the genome of the subject. In some such embodiments, the plurality of sequencing reads exhibits an average read depth of less than 200, less than 100, less than 50, less than 40, or less than 20 across this subset of the genome of the subject. In some embodiments, the plurality of sequencing reads exhibits an average read depth of between 25 and 60 across this subset of the genome of the subject. In some embodiments, the plurality of sequencing reads comprises whole genome sequencing reads. In some embodiments, the plurality of sequencing reads comprises exome sequencing reads. In some embodiments, the plurality of sequencing reads comprises targeted sequencing reads.

In some embodiments, the subset of the genome is between one percent and ten percent of a single chromosome of the subject, between five percent and fifteen percent of a single chromosome of the subject, between ten percent and twenty percent of a single chromosome of the subject, between fifteen percent and thirty percent of a single chromosome of the subject, between twenty-five percent and fifty percent of a single chromosome of the subject, between forty-five percent and seventy-five percent of a single chromosome of the subject, or between seventy percent and one hundred percent of a single chromosome of the subject.

In some embodiments, the subset of the genome is between one percent and ten percent of a two or more chromosomes of the subject, between five percent and fifteen percent of two or more chromosomes of the subject, between ten percent and twenty percent of two or more chromosomes of the subject, between fifteen percent and thirty percent of two or more chromosomes of the subject, between twenty-five percent and fifty percent of two or more chromosomes of the subject, between forty-five percent and seventy-five percent of two or more chromosomes of the subject, or between seventy percent and one hundred percent of two or more chromosomes of the subject.

In some embodiments, the subset of the genome is between one percent and ten percent of the genome of the subject, between five percent and fifteen percent of the genome of the subject, between ten percent and twenty percent of the genome of the subject, between fifteen percent and thirty percent of the genome of the subject, between twenty-five percent and fifty percent of the genome of the subject, between forty-five percent and seventy-five percent of the genome of the subject, or between seventy percent and one ninety-nine percent of the genome of the subject.

Block 318. Referring to block 318 of FIG. 3A, a human leukocyte antigen (HLA) type of the human cancer subject is determined. In some such embodiments, the HLA type of the human cancer subject is determined from the plurality of sequencing reads (320). In some embodiments, the determining the HLA type of the human cancer subject is determined using a polymerase chain reaction using a biological sample from the cancer subject (322). In some such embodiments, HLA typing is performed using the sequence reads 210 by either low to intermediate resolution polymerase chain reaction-sequence-specific primer (PCR-SSP) method or by high-resolution SeCore HLA sequence-based typing method (HLA-SBT) (INVITROGEN). In some embodiments ATHLATES is used for HLA typing and confirmation. See Liu and Duffy et al., 2013, "ATHLATES: accurate typing of human leukocyte antigen through exome sequencing," Nucleic Acids Res 41:e142, which is hereby incorporated by reference Block 324. Referring to block 324 of FIG. 3B, a plurality of clones is determined from the plurality of sequencing reads 210. In some embodiments, the raw sequence reads 210 are processed in order to identify the plurality of clones 216. For instance, in some embodiments, raw sequence data reads 210 are aligned to a reference human genome (e.g., hg19) using an alignment tool such as the Burrows-Wheeler Alignment tool. Base-quality score recalibration, and duplicate-read removal is performed. In some embodiments, this recalibration excludes germline variants, annotation of mutations, and indels as described in Snyder et al, 2014, "Genetic Basis for Clinical Response to CTLA-4 Blockade in Melanoma," N. Engl. J. Med. 371, 2189-2199, which is hereby incorporated by reference. In some embodiments, local realignment and quality score recalibration are conducted using the Genome Analysis Toolkit (GATK) according to GATK best practices. See, DePristo et al., 2011, "A framework for variation discovery and genotyping using next-generation DNA sequencing data," Nature Genet. 43, pp. 491-498; and Van der Auwera et al, 2013, "From FastQ Data to High-Confidence Variant Calls: The Genome Analysis Toolkit Best Practices Pipeline," Curr. Prot. in Bioinformatics 43, 11.10.1-11.10.33 each of which is hereby incorporated by reference. Further, sequence alignment and mutation identification is performed. In some embodiments, sequence alignment and mutation identification is performed using FASTQ files that are processed to remove any adapter sequences at the end of the reads. In some embodiments, adapter sequences are removed using cutadapt (v1.6). See Martin, 2011, "Cutadapt removes adapter sequences from high-throughput sequencing reads," EMBnet.journal 17, pp. 10-12, which is hereby incorporated by reference. Then, resulting files are mapped using a mapping software such as the BWA mapper (bwa mem v0.7.12), (see Li and Durbin, 2009, "Fast and accurate short read alignment with Burrows-Wheeler Transform," Bioinformatics 25, pp. 1754-1760, which is hereby incorporated by reference). In some such embodiments, the resulting files (e.g. SAM files) are sorted, and read group tags added using the PICARD tools. After sorting in coordinate order, the BAMs are processed with a tool such as PICARD MarkDuplicates. Realignment and recalibration is then carried out in some embodiments, (e.g., with a first realignment using the InDel realigner followed by base quality value recalibration with the Base-QRecalibrator). Once realignment and recalibration have been performed, mutation callers are then used to identify single nucleotide variants. Exemplary mutation callers that can be used include, but are not limited to, Mutect 1.1.4, Somatic Sniper 1.0.4, Varscan 2.3.7, and Strelka 1.013). See Wei et al, 2015, "MAC: identifying and correcting annotation for multi-nucleotide variations, BMC Genomics 16, p. 569; Snyder and Chan, 2015, "Immunogenic peptide discovery in cancer genomes," Curr Opin Genet Dev 30, pp. 7-16; Nielsen et al., 2003, "Reliable prediction of T-cell epitopes using neural networks with novel sequence representations," Protein Sci 12, pp. 1007-1017; and Shen and Seshan, 2016, "FACETS: allele-specific copy number and clonal heterogeneity analysis tool for high-throughput DNA sequencing," Nucleic Acids Res. 44, e131, each of which is incorporated by reference.

In some embodiments, SNVs with an allele read count of less than 4 or with corresponding normal coverage of less than 7 reads are filtered out. In some embodiments, SNVs with an allele read count of less than 7, of less than 5, or of less than 3 or with corresponding normal coverage of less than 12 reads, less than 8 reads, or less than 5 reads are filtered out. See, for example, Riaz et al., 2016, "Recurrent SERPINB3 and SERPINB4 mutations in patients who respond to anti-CTLA4 immunotherapy," Nat. Genet. 48, 1327-1329, which is hereby incorporated by reference.

In some embodiments, the assignment of a somatic mutation to a neoantigen is estimated using a bioinformatics tool such as NASeek. See Snyder et al., 2014, "Genetic Basis for Clinical Response to CTLA-4 Blockade in Melanoma," N. Engl. J. Med. 371, pp. 2189-2199, which is hereby incorporated by reference. NASeek is a computational algorithm that first translates all mutations in exomes to strings of 17 amino acids, for both the wildtype and mutated sequences, with the amino acid resulting from the mutation centrally situated. Secondly, it evaluates putative MHC Class I binding for both wildtype and mutant nonamers using a sliding window method using NetMHC3.4 (on the Internet cbs.dtu.dk/services/NetMHC-3.4/) (see Andreatta and Nielsen, 2016, "Gapped sequence alignment using artificial neural networks: application to the MHC class I system,"

Bioinformatics 32, pp. 511-517, which is hereby incorporated by reference) for patient-specific HLA types, to generate predicted binding affinities for both peptides. NASeek finally assesses for similarity between nonamers that predicted to be presented by patient-specific MHC Class I. In some embodiments, all nonamers with binding scores below 500 nM are defined as neoantigens. In some embodiments, all nonamers with binding scores below 250 nM are defined as neoantigens. In some embodiments, all nonamers with binding scores below 800 nM are defined as neoantigens.

In some embodiments, the plurality of clones is 2 or more clones 216, 3 or more clones 216, 4 or more clones 216, 5 or more clones 216, 10 or more clones 216 or 100 or more clones 216. For each respective clone α in the plurality of clones, an initial frequency $X_\alpha$ 218 of the respective clone α 216 in the one or more samples 208 is determined.

In some such embodiments, tumor clones 214 are reconstructed using the PhyloWGS software package. See Deshwar et al., 2015, "PhyloWGS: reconstructing subclonal composition and evolution from whole-genome sequencing of tumors," Genome Biol. 16, p. 35, which is hereby incorporated by reference. The trees estimate the nested clonal structure of the tumor and the frequency of each clone, $X_\alpha$. The differences between the high scoring trees are marginal on some datasets, concerning only peripheral clones and small differences in frequency estimates. In some embodiments, the predicted relative size of a cancer population n(τ) is computed as an averaged prediction over 5 trees with the highest likelihood score, weighting their contribution proportionally to their likelihood. In some embodiments, the predicted relative size of a cancer population n(τ) is predicted as an averaged prediction over 5 or more trees, 10 or more trees, 15 or more trees, or 20 or more trees with the highest likelihood score.

In some such embodiments, to identify tumor clones, input data for the clone determining algorithm is extracted from exome sequencing data: (1) mutation reads obtained from the sequencing reads 210 processed in accordance with the pipeline described above and (2) allele-specific copy-number variant data, obtained with a program such as FACETS v0.5.0. See, Shen and Seshan, 2015, "FACETS: allele-specific copy number and clonal heterogeneity analysis tool for high-throughput DNA sequencing," Nucleic Acids Res. 44, e131, which is hereby incorporated by reference. FACETS clusters mutations into clones by the frequency of their sequence reads 210 and infers possible nesting of clones (ancestral relations) between pairs of clones. Intuitively, an ancestral clone needs to have higher frequency then its derived clone. From this information PhyloWGS reconstructs high likelihood tumor geneological trees.

In some embodiments, each clone α 216 in the plurality of clones is uniquely defined by a unique set of somatic mutations (e.g., single nucleotide variant or an indel). In some embodiments, the plurality of clones is determined by a variant allele frequency of each respective somatic mutation in a plurality of somatic mutations determined from the whole-genome sequencing data (326).

In some embodiments, the plurality of clones is determined by identifying a plurality of inferred copy number variations using the whole-genome sequencing data (328).

In some embodiments, each clone α in the plurality of clones is uniquely defined by a unique set of somatic mutations. In some embodiments, the plurality of clones is determined by a combination of (i) a variant allele frequency of each respective somatic mutation in the plurality of somatic mutations determined from the whole-genome sequencing data and (ii) an identification of a plurality of inferred copy number variations using the whole-genome sequencing data (330).

In some embodiments, the plurality of clones consists of two clones (332). In some embodiments, the plurality of clones consists of between two clones and ten clones (334). In some embodiments, the plurality of clones comprises two or more clones, three or more clones, four or more clones, five or more clones, six or move clones, between 3 and 20 clones, or between 5 and 1000 clones.

In some embodiments, the initial frequency $X_\alpha$ of the respective clone α in the one or more samples is determined using the plurality of sequencing reads from the one or more samples from the human cancer subject (336). In some embodiments, the initial clone α frequency is inferred from the sequence reads 210 using techniques disclosed in Deshwar et al., 2015, "PhyloWGS: reconstructing subclonal composition and evolution from whole-genome sequencing of tumors," Genome Biol. 16, p. 35, which is hereby incorporated by reference.

Block 338. Referring to block 338 of FIG. 3C, for each respective clone α 216 in the plurality of clones, a corresponding clone fitness score 220 of the respective clone 216 is computed, thereby computing a plurality of clone fitness scores, each corresponding clone fitness score computed for a respective clone α by a first procedure.

In the first procedure, a plurality of neoantigens 222 in the respective clone α 216 is identified (340). Methods for identifying neoantigens in accordance with some embodiments of the disclosure are described above and in Example I. Moreover, in some embodiments, neoantigens are determined by whole exome sequencing, immunoassay, microarray, genome sequencing, RNA sequencing, ELISA, Western Transfer, DNA sequencing, mass spectrometry, or combinations thereof. In some embodiments, a neoantigen is detected by the method described in Snyder et al., 2014, "Genetic Basis for Clinical Response to CTLA-4 Blockade in Melanoma," N. Engl. J. Med. 371, pp. 2189-2199; or Rizvi et al., 2015, *Science* 348, pp. 124-128, each of which is hereby incorporated by reference.

In some embodiments, each neoantigen 222 in the plurality of neoantigens of a clone 216 in the plurality of clones is a nonamer peptide (342). In some embodiments, each neoantigen in the plurality of neoantigens of a clone in the plurality of clones is a peptide that is eight, nine, ten, or eleven residues in length (344). In some embodiments, at least one neoantigen is a neoantigen listed in Table 1 or Table 2. In some embodiments, at least one neoantigen is from MUC16 or a gene listed in Table 2.

In some embodiments, the method further comprises identifying a population of neoantigens present in the one or more samples by a third procedure comprising: determining a plurality of somatic single nucleotide polymorphisms (SNPs) in the plurality of sequencing reads by comparison of the plurality of sequencing reads (e.g., whole genome sequencing reads, exome sequencing reads, targeted sequencing reads, etc.) to a reference human genome, and evaluating each respective somatic SNP in the plurality of SNPs as a neoantigen candidate by evaluation of a peptide encoded by a portion of one or more sequencing reads in the sequencing reads that includes the respective somatic SNP against a classifier that has been trained to predict peptide binding to class 1 MHC of the HLA type of the cancer subject, where a neoantigen candidate having a binding score below a threshold value is deemed to be a neoantigen in the population of neoantigens. Further, the identifying the plurality of neoantigens in the respective clone α comprises matching the SNPs in the respective clone α to respective neoantigens in the population of neoantigens. In some such embodiments, the threshold value is 500 nM. In some such embodiments, the threshold value is 1000 nM, 900 nM, 800 nM, 700 nM, 600 nM, 500 nM, 400 nM, 300 nM, 200 nM, or 100 nM. In some such embodiments, the threshold value is 1000 nM or less, 900 nM or less, 800 nM or less, 700 nM or less, 600 nM or less, 500 nM or less, 400 nM or less, 300 nM or less, 200 nM or less, or 100 nM or less.

Continuing with the first procedure, a recognition potential fitness potential of each respective neoantigen in the plurality of neoantigens in the respective clone α is computed by a second procedure (346).

Computing an amplitude. In the second procedure, an amplitude A of the respective neoantigen is computed as a function of the relative major histocompatibility complex (MHC) affinity between the respective wildtype and the mutant peptide (neoantigen) given the HLA type of the subject (348). In other words, the amplitude, A, is the ratio of the relative probability that a neoantigen is bound on class I MHC times the relative probability that a neoantigen's wildtype counterpart is not bound. In some embodiments, the amplitude $A=(P_U^{WT}/P_B^{WT}) \times (P_B^{MT}/P_U^{MT})$ where $P_B^{MT}$ is the binding probability of a neoantigen, $P_B^{WT}$ is the binding probability of its wildtype counterpart, and $P_U^{WT}=1-P_B^{WT}$ and $P_U^{MT}=1-P_B^{MT}$. As a result, the amplitude, A, rewards cases where the discrimination energy between a mutant and wildtype peptide by the same class I MHC molecule (i.e. the same HLA allele) is large (Storma, 2013, Quantitative Biol. 1, p 115), while the mutant binding energy is kept low. The r parameter effectively sets this energy scale for dominant neoantigens in a dine when R=1. Assuming similar concentrations for mutant and wildtype peptides, the amplitude is the ratio of wildtype to mutant dissociation constants:

$$A=K_d^{WT}/K_d^{MT}.$$

Negative thymic selection on TCRs is not absolute, but rather "prunes" the repertoire recognizing the self proteome (Yu et al., 2015, Immunity 42, p. 929; and Legoux et al., 2015, Immunity 43, p. 896). The amplitude A is therefore used as a proxy for the availability of TCRs in the repertoire to recognize a neoantigen. Neoantigens differ from their wildtype peptides by only a single mutation. Given the uniqueness of nonamer sequence in the self-proteome due to finite genome size (SI) it is highly improbable that the mutant peptide would have another 8-mer match in the human proteome, so only the comparison with the respective wildtype peptide is taken into account in some embodiments. We verified that the above is the case for 92% of al neoantigens, with the remainder largely emanating from gene families with many paralogs. The amplitude can be interpreted as a multiplicity of receptors available to cross-reactively recognize a neoantigen.

In some embodiments, neoantigens with mutations on positions 2 and 9, are excluded. In such embodiments, a high value of amplitude means the wildtype also likely already has hydrophobic residues at the anchor position and could be presented. Since neoantigens differ from their wildtype peptides by a single mutation, and given the uniqueness of nonamer sequences in the proteome, the self-nonamer in the genome with the greatest similarity to a neoantigen is likely to be its wildtype peptide. See, for example, Example II below. This implies that a high amplitude usually stands for a self peptide not likely to be abundantly presented by the MHC. Therefore, as its immunogenicity is not mitigated by a homologous self-peptide, the mutant peptide with high affinity is likely to be novel to T-cells.

In some embodiments, the function of the relative class I MHC affinity of the respective neoantigen and the wildtype counterpart of the respective neoantigen given the HLA type of the human cancer subject is a ratio of the relative class I MHC affinity of the respective neoantigen and the wildtype counterpart of the respective neoantigen given the HLA type of the subject (350).

In some such embodiments, the MHC presentation is quantified, as amplitude A, using the relative MHC affinity between the wildtype peptide and mutant neoantigen, a ratio used to analyze computational neoantigen predictions. See Hundal et al., 2016, "pVAC-Seq: A genome-guided in silico approach to identifying tumor neoantigens," Genome Med. 8, 1-11, which is hereby incorporated by reference. The relative MHC affinity rewards mutant neoantigens with strong mutant affinities compared to wildtype. Without intending to be limited to any particular theory, it is posited that the wildtype peptides presented by MHC are potentially subject to tolerance and hence, due to homology, their mutant counterparts may be as well, compromising their immunogenicity.

In some such embodiments, the function of the relative class I MHC affinity of the respective neoantigen and the wildtype counterpart of the respective neoantigen given the HLA type of the subject is a ratio of: (1) a dissociation constant between the respective neoantigen and the class I MHC presented by the cancer subject given the HLA type of the cancer subject, and (2) a dissociation constant between the wildtype counterpart of the respective neoantigen and the class I MHC presented by the cancer subject given the HLA type of the cancer subject (352).

In some such embodiments, the dissociation constant between the respective neoantigen and the class I MHC presented by the cancer subject is obtained as output from a first classifier upon inputting into the first classifier the amino acid sequence of the neoantigen. The dissociation constant between the wildtype counterpart of the respective neoantigen and the class I MHC presented by the cancer subject of the HLA type of the subject is obtained as output from the first classifier upon inputting into the first classifier the amino acid sequence of the respective wildtype counterpart of the neoantigen (e.g., the first classifier is specific to the HLA type of the cancer subject and has been trained with the respective class I MHC binding coefficient and sequence data of each peptide epitope in a plurality of epitopes presented by class I MHC in a training population having the HLA type of the subject) (354).

In some embodiments amplitude A is computed as set forth in Example III. In some embodiments amplitude A is computed by any of the methods disclosed in Luksza et al., 2017, "A neoantigen fitness model predicts tumour response to checkpoint blockade immunotherapy," Nature 551, 517-520.

Despite their differing only by a single mutation, inferred binding affinities for these peptides can be substantially different (FIGS. 26-28). FIGS. 26-28 provide inferred MHC binding affinities of mutant versus wildtype peptides. Neoantigens used in this study are 9-residue long peptides affinities predicted to be less than 500 nM by NetMHC3.4 (Andreatta Nielsen, 2016, "Gapped sequence alignment using artificial neural networks: application to the MHC class I system," Bioinformatics 32, pp. 511-517. Predicted affinities are plotted of mutant peptides, designated $K_d^{MT}$, versus the predicted dissociation affinities of the wildtype peptides, which generated them, designated $K_d^{MT}$. A single point mutation can lead to predicted dissociation constant difference of up to four orders of magnitude.

Moreover, unlike considering solely mutant or wildtype affinities, the amplitude has consistent predictive value within the disclosed model (FIGS. 23-25). In FIGS. 23-25, ranking of fitness models when accounting for tumor sub-clonal composition is provided, in which fitness models evaluated for the three cohorts, Van Allen et al. (n=103), Snyder et al., 2014, "Genetic Basis for Clinical Response to CTLA-4 Blockade in Melanoma," N. Engl. J. Med. 371, pp. 2189-2199 (n=64) and Rizvi et al., 2015, "Mutational landscape determines sensitivity to PD-1 blockade in non-small cell lung cancer, Science 348, pp. 124-128 (n=34) are ranked. The survival prediction of full recognition potential fitness model:

$$F_\alpha = - \max_{i \in \text{Clone } \alpha} (A_i \times R_i)$$

is compared with alternative models: (1) models that eliminate one of the features of the full model, namely A-only model:

$$F_\alpha = - \max_{i \in \text{Clone } \alpha} (A_i)$$

and R-only model:

$$F_\alpha = - \max_{i \in \text{Clone } \alpha} (R_i)$$

models wildtype dissociation constant:

$$F_\alpha = - \max_{i \in \text{Clone } \alpha} K_d^{WT}{}_i (\times R_i),$$

and without mutant dissociation constant:

$$F_\alpha = - \max_{i \in \text{Clone } \alpha} \frac{1}{K_d^{MT}{}_i} (\times R_i),$$

neoantigen load model:

$$F_\alpha = -L_\alpha$$

an additive neoantigen fitness model which uniformly summates fitness contributions of neoantigens in a clone. Additionally, the model is compared in which alignments to IEDB epitopes are evaluated only on position 3-8, a model that does not implement any filtering of neoantigens on position 2&9, and a model where the R component is evaluated on IEDB assays without positive validation. Finally, an alternative predictive criterion is tested by using the average fitness over tumor clones instead of $n(\tau)$ to separate patients in survival analysis:

$$n(\tau) = \exp[F_\tau].$$

For each model, parameters used for predictions and error bars for these parameters are reported. The predictive power of all models is assessed with survival analysis, separating patients into equal size groups by the median value of $n(\tau)$ or the median value of the average fitness F within the cohort. A logrank test is used, the results of this comparison are reported in FIGS. 23, 24, and 25. To assign error bars to fluctuations of the log-rank test score a leave-one-out analysis is performed. That is, the survival analysis is repeated for each dataset after leaving out one sample in a cohort and compute standard deviation of the test statistic over all leave-one-out iterations. A fitness model is deemed predictive in some embodiments if it gives patient segregation of highly significant scores in all datasets with the same consistent set of parameters. Only the full neoantigen recognition potential fitness model meets these criteria. The results are highly significant when patient segregation is based on $n(\tau)$ values. The average fitness criterion the equation $$\langle F \rangle = \sum_\alpha X_\alpha F_\alpha$$

marginally meets the above requirements for predictiveness, but with smaller significance (FIGS. 23, 24, and 25). The log-rank test scores is reported for all models and the logrank test p-value for models with significant patient segregation (p<0.05).

Without intending to be limited to any particular theory, an interpretation of the above observation that amplitude has consistent predictive value within the disclosed model is that the amplitude is related to the quantity of TCRs available to recognize the neoantigen. A neoantigen needs to have low dissociation constant (i.e. high binding affinity) to be presented and generate a TCR response. However, if the wildtype peptide also has a low dissociation constant, tolerance mechanisms could have removed wildtype peptide specific TCRs. Due to cross-reactivity, the quantity of mutant specific TCRs could be reduced.

Computing a probability of T-cell receptor recognition R. Referring to block 356 of FIG. 3D, in the second procedure, a probability of T-cell receptor recognition R of the respective neoantigen is computed as a probability that the respective neoantigen binds one or more epitopes that are positively recognized by T-cells after class I MHC presentation (356). As such, for TCR-recognition, in some such embodiments, recognition potential of neoantigens is modeled with positive, class I restricted T-cell antigens from the Immune Epitope Database (IEDB). See, Vita, R. et al., 2014, "The immune epitope database (IEDB) 3.0., Nucleic Acids Res. 43, D405-D412, which is hereby incorporated by reference. In such embodiments, preexisting host immunity due to this epitope set is not assumed. Rather it is posited that high-scoring neoantigens are more "non-self" As TCRs have intrinsic biases in their generation probability and can recognize large classes of peptides via cross reactivity (Murugan et al., 2012, "Statistical inference of the generation probability of T-cell receptors from sequence repertoires," Proc. Natl. Acad. Sci. 109, pp. 16161-16166; and Birnbaum et al., 2014, "Deconstructing the peptide-MHC specificity of T cell recognition," Cell 157, pp. 1073-1087), such neoantigens would be more likely recognized. In some such embodiments, a thermodynamic model is used to estimate this probability that a given TCR binds a tumor neoantigen. See Berg et al., 1987, "Selection of DNA binding sites by regulatory proteins: Statistical-mechanical theory and application to operators and promoters.," J. Mol. Biol. 193, pp. 723-743, which is hereby incorporated by reference. For a given neoantigen 222 with peptide sequence s and Epitope Database and Analysis Resource (IEDB) (see Vita et al., 2014, "The immune epitope database (IEDB) 3.0," Nucleic Acids Res. 43, D405-D412, which is hereby incorporated by reference), epitope with sequence e, the alignment score between s and e estimates the binding free energy between s and a TCR that recognizes e. Under this assumption, each mutation that changes a residue in e into a corresponding residue in s in their alignment will increase the binding energy between s and the TCR recognizing epitope e proportional to the alignment mismatch cost. In some embodiments analysis is restricted to linear epitopes from human infectious diseases that are positively recognized by T-cells after class I MHC presentation. In some embodiments a set of epitopes from the Immune Epitope Database (IEDB), a repository of over 120,000 immune epitopes, is utilized (Vita et al., 2014, "The immune epitope database (IEDB) 3.0.," Nucleic Acids Res. 43, D405-D412). IEDB is a collection of epitope-specific experimental assays—the nature of which can be accessed by various fields (www.iedb.org). Every T cell assay reflects the binding of an epitope-specific TCR to an experimentally tested antigen (Vita et al., 2014, "The immune epitope database (IEDB) 3.0.," Nucleic Acids Res. 43, D405-D412). In this case analysis was restricted to linear epitopes from human infectious diseases studies presented by class I MHC molecules for which there were positive T cell assays. For negative controls, epitopes associated with assays satisfying all of the above fields were downloaded, except we did not restrict for positive assays. We then excluded those for which we assigned positive by IEDB to create a negative assay list.

In such an approach, it is assumed that a neoantigen predicted to cross-react with a TCR from this pool of immunogenic epitopes is a neoantigen more likely to be immunogenic itself, as members of the T-cell receptor repertoire both recognize a high number of presented antigens (Mason, 1999, "A very high level of crossreactivity is an essential feature of the T-cell receptor," Immunology Today 19, pp. 395-404; and Sewell, 2012, "Why must T cells be cross-reactive?," Nature Rev. Immunol. 12, pp. 669-677) and have intrinsic biases in their generation probabilities. See, Murugan et al., 2012, "Statistical inference of the generation probability of T-cell receptors from sequence repertoires," Proc. Natl. Acad. Sci. 109, pp. 16161-16166.

The probability a neoantigen is bound by a TCR is given by a nonlinear logistic dependence on sequence alignment scores to the epitope set. This model does not require full 9-amino acid identity of the neoantigen and epitope sequences for recognition. In some embodiments, the total TCR-recognition probability, R, is defined as the probability that neoantigen s is recognized by at least one TCR corresponding to an IEDB epitope.

In some such embodiments, the probability that the respective neoantigen binds one or more epitopes that are positively recognized by T-cells after class I MHC presentation is determined by a third procedure that comprises (a) selecting a respective epitope e from an epitope database IEDB, where the respective epitope e is positively recognized by T-cells after class I MHC presentation, (b) computing, for the respective epitope e, the probability $$Pr_{binding}(s, e) = \frac{1}{1 + e^{-k(|s,e|-a)}}$$

where, |s, e| is a sequence alignment score between the sequence of the respective neoantigen and the sequence of the respective epitope, and k and a are constants; (c) performing the selecting (a) and the computing (b) for each respective epitope e in a plurality of epitopes in the epitope database IEDB, thereby computing a plurality of probabilities $Pr_{binding}(s, e)$; and (d) computing the probability of T-cell receptor recognition R of the respective neoantigen as:

$$R = 1 - \Pi_{e \in IEDB}[1 - Pr_{binding}(s,e)],$$

where IEDB is the plurality of epitopes (358). In some such embodiments, the IEDB database is collated as set forth in Example IV.

In some such embodiments, |s, e| is computed as an alignment (e.g., gapless, or an alignment that allows gaps with suitable gap introduction and extension penalties) between the sequence of the respective neoantigen and the sequence of the respective epitope using an amino-acid similarity matrix. In some such embodiments, the amino-acid similarity matrix is a BLOSUM62 matrix. In alternative embodiments, a different amino-acid similarity matrix is used. For instance, in some embodiments, a Blocks Substitutions Matrix (BLOSUM) BLOSUM45 matrix, BLOSUM50 matrix, BLOSUM52 matrix, BLOSUM60 matrix, BLOSUM80 matrix, BLOSUM90 matrix, a Percent Accepted Mutation (PAM) 250 matrix, a PAM200 matrix, a PAM160 matrix, a PAM120 matrix, a PAM100 matrix, or a Gonnet substitution matrix is used. In some embodiments, a matrix disclosed in Pearson, 2013, "Selecting the Right Similarity-Scoring Matrix," Curr Protoc. Bioinformatics, 43: 3.51-3.5.9, ed. Baxevanis et al., which is hereby incorporated by reference, is used.

In some embodiments, rather than a sequence alignment, a binding energy constant between the neoantigen and receptor is computed using three-dimensional models of the neoantigen and the receptor and an applicable force field such as CHARMM, AMBER GROMACS, or NAMD software packages. See generally Adcock & McCammon, 2006, Chemical Reviews, 106, 1589, which is hereby incorporated by reference.

In some embodiments, any of the techniques disclosed for computing R in Luksza et al., 2017, "A neoantigen fitness model predicts tumour response to checkpoint blockade immunotherapy," Nature 551, 517-520, is used.

In some embodiments, a multistate thermodynamic model is used to define R. In this model, sequence similarities are treated as a proxy for binding energies. To assess sequence similarity between a neoantigen with peptide sequence s and an IEDB epitope e, an alignment (e.g., gapless, or an alignment that allows gaps with suitable gap introduction and extension penalties) between the two sequences is computed with a BLOSUM62 amino-acid similarity matrix (or an equivalent alignment matrix) (See, Henikoff and Henikoff, 1992, "Amino acid substitution matrices from protein blocks.," Proc. Natl. Acad. Sci. USA 89, pp. 10915-10919) and we denote their alignment scores as |s, e|. Given these sequence similarities, for a given neoantigen with peptide sequence s, the probability that it is bound by a TCR specific to some epitope e is computed from the IEDB pool as $$R = Z(k)^{-1} \sum_{e \in IEDB} \exp[-k(a - |s, e|)],$$

where a represents the horizontal displacement of the binding curve, k sets the steepness of the curve at a, and $$Z(k) = 1 + \sum_{e \in IEDB} \exp[-k(a - |s, e|)]$$

is the partition function over the unbound state and all bound states. In the model, k functions as an inverse temperature and $a-|s, e|$ functions as a binding energy. These parameters define the shape of the sigmoid function (FIG. 29) and, along with the characteristic time scale r, are free parameters to be fit in our model. In some such embodiments, the IEDB database is collated as set forth in Example V.

In some embodiments, the parameters which give consistently informative predictions across all three datasets are $a=26$ and $k=4.87$. The logistic function is therefore a strongly nonlinear function of the effective alignment score, $\log(\Sigma_{e \in IEDB} \exp[-k (a-|s, e|)])$. The average alignment length corresponding to score 26 is 6.8 for neoantigens in our datasets, but the effective alignment score is occasionally increased by multiple contributions of shorter alignments. Under the interpretation where, for a sufficiently presented neoantigen, A represents the multiplicity of available TCRs and R represents an intrinsic probability of recognition, A×R represents the effective size of the overall TCR response. We present it as a core quantity that can be modulated by additional environmental factors such as the T-cell infiltration as discussed in Example IV below.

In some embodiments, the probability that the respective neoantigen binds one or more epitopes that are positively recognized by T-cells after class I MHC presentation is computed as:

$$R = Z(k)^{-1} \sum_{e \in D} \exp[-k(a-|s, e|)],$$

where a is a number that represents a horizontal displacement of a binding curve for the respective neoantigen, k is a number that sets the steepness of the binding curve at a, Z(k) is a partition function over the unbound state and all bound states of the respective neoantigen of the form $$1 + \sum_{e \in D} \exp[-k(a-|s, e|)]$$

where D is a plurality of epitopes, each respective epitope e is an epitope from the plurality of epitopes that is positively recognized by T-cells after class I MHC presentation, and $|s, e|$ is a measure of affinity between the respective neoantigen s and the respective epitope e. In some such embodiments, a is set to 26 and k is set to 4.87. In some such embodiments, the measure of affinity $|s, e|$ is computed as a sequence alignment between the sequence of the respective neoantigen s and the sequence of the respective epitope e using an amino-acid similarity matrix. For instance, in some such embodiments, the amino-acid similarity matrix is a Blocks Substitutions Matrix (BLOSUM) BLOSUM45 matrix, BLOSUM50 matrix, BLOSUM52 matrix, BLOSUM60 matrix, BLOSUM80 matrix, BLOSUM90 matrix, a Percent Accepted Mutation (PAM) 250 matrix, a PAM200 matrix, a PAM160 matrix, a PAM120 matrix, a PAM100 matrix, or a Gonnet substitution matrix. In some embodiments, the plurality of epitopes comprises a public database of epitopes that have been recognized by human T-cells from any human, or combination of humans, in a population of humans. In some embodiments, the public database is the immune epitope database 3.0 or equivalent. See, Vita, R. et al., 2015, "The immune epitope database (IEDB) 3.0," Nucleic Acids Res. 43, D405-D412, which is hereby incorporated by reference. In some alternative embodiments, the plurality of epitopes consists of epitopes that have been recognized by human T-cells from the human subject. In some embodiments, the plurality of epitopes comprises 1000 epitopes. In some embodiments, the plurality of epitopes comprises 10,000 epitopes. In some embodiments, the plurality of epitopes comprises 100,000 epitopes. In some embodiments, the plurality of epitopes comprises $1 \times 10^6$ epitopes.

In some embodiments, the probability that the respective neoantigen binds one or more epitopes that are positively recognized by T-cells after class I MHC presentation is computed as:

$$R = Z(k)^{-1} \sum_{t \in F} \exp[-k(a-|s, t|)],$$

where a is a number that represents a horizontal displacement of a binding curve for the respective neoantigen, k is a number that sets the steepness of the binding curve at a, Z(k) is a partition function over the unbound state and all bound states of the respective neoantigen of the form $$1 + \sum_{t \in F} \exp[-k(a-|s, t|)]$$

where F is a plurality of T-cell receptor sequences, each respective T-cell receptor t is a T-cell receptor from the plurality of T-cell receptor sequences F, and $|s, t|$ is a measure of affinity between the respective neoantigen s and the respective T-cell receptor t. In some such embodiments, the plurality of T-cell receptors is a database of T-cell receptors drawn from a population of humans. In alternative embodiments, the plurality of T-cell receptors is drawn exclusively from the subject. In some embodiments, the plurality of T-cell receptors comprises 1000 T-cell receptors. In some embodiments, the plurality of T-cell receptors comprises 10,000 T-cell receptors. In some embodiments, the plurality of T-cell receptors comprises 100,000 T-cell receptors. In some embodiments the plurality of T-cell receptors comprises $1 \times 10^6$ T-cell receptors.

Figure 3A:
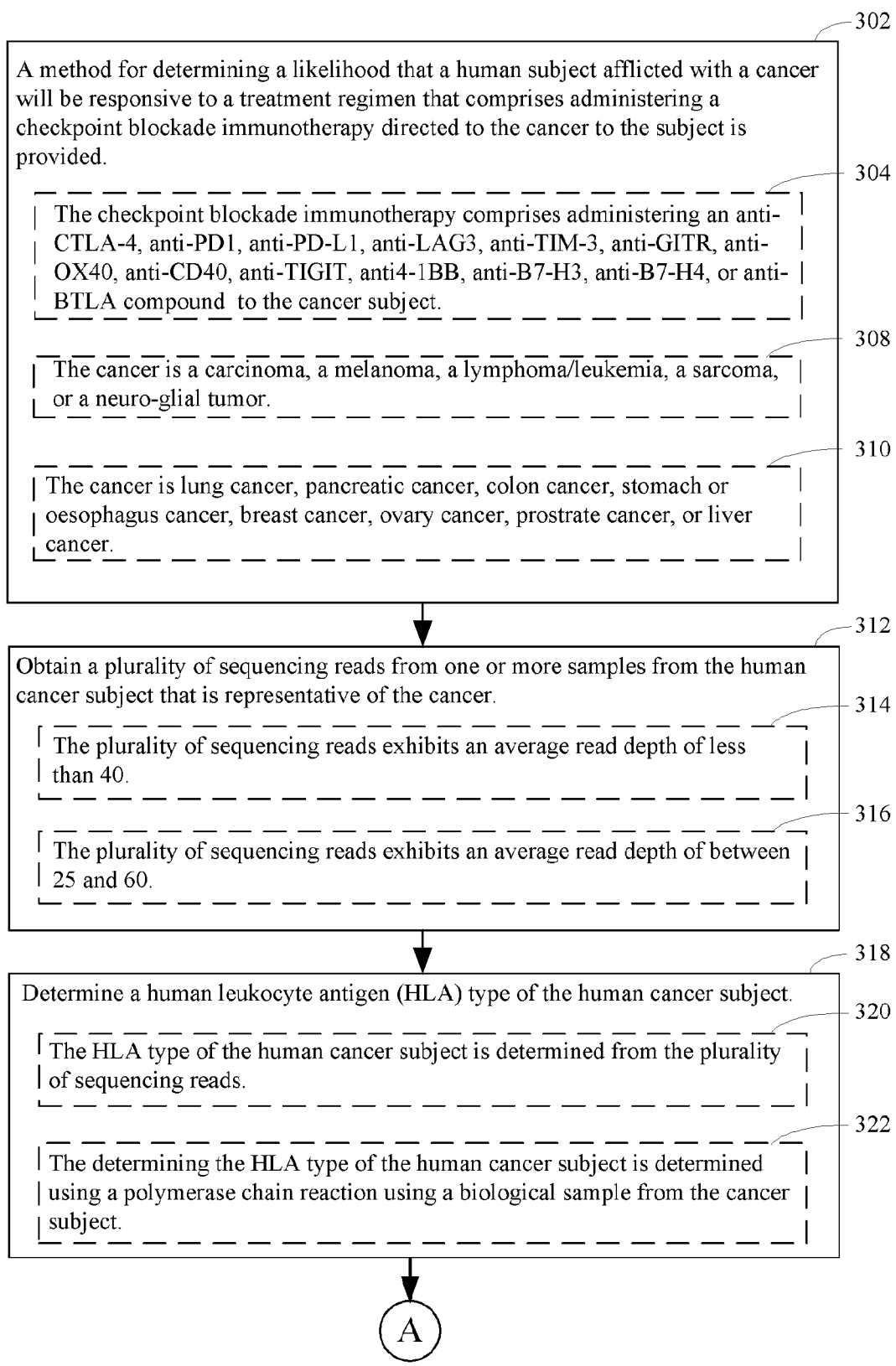
Figure 3B:
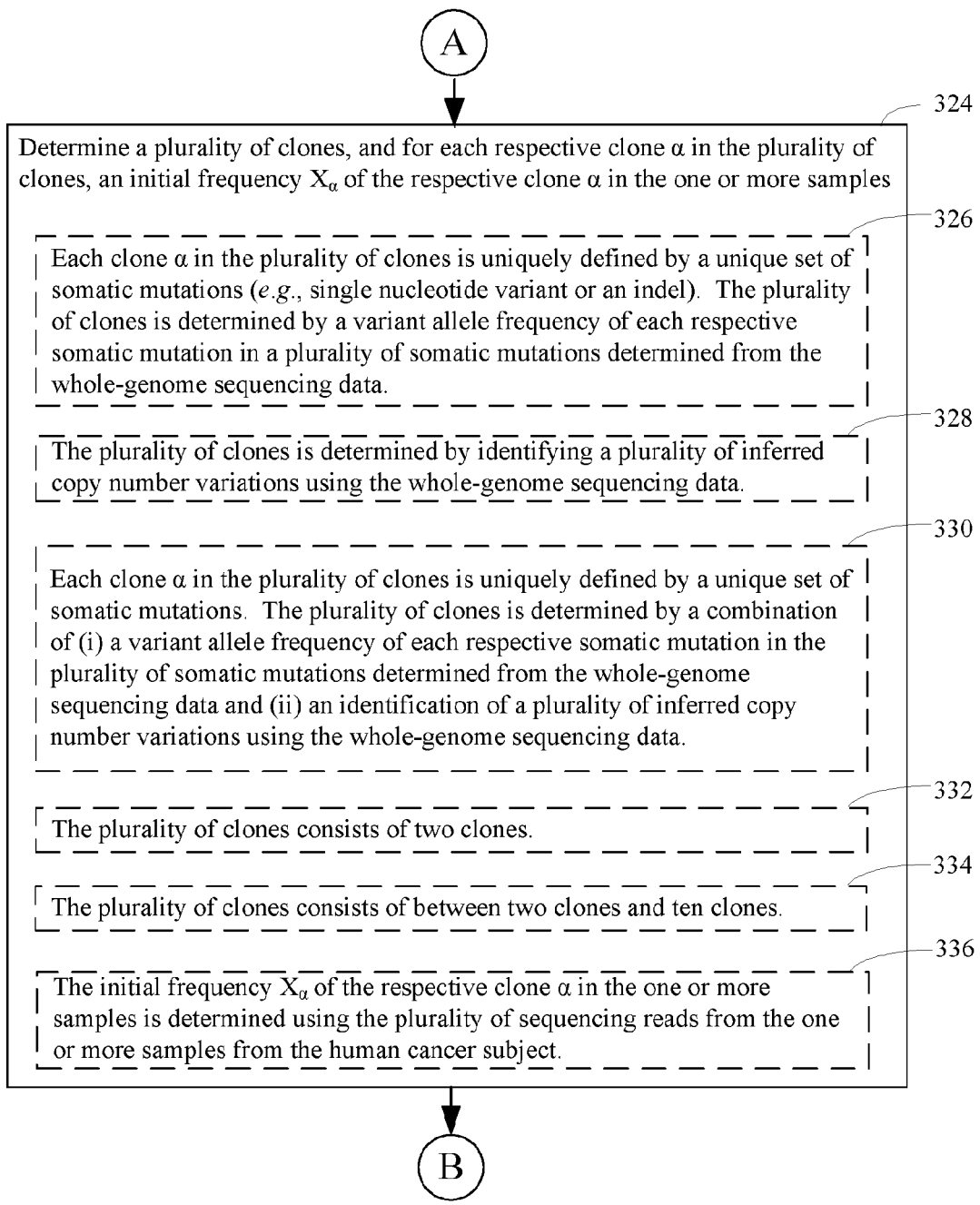
Figure 3E:
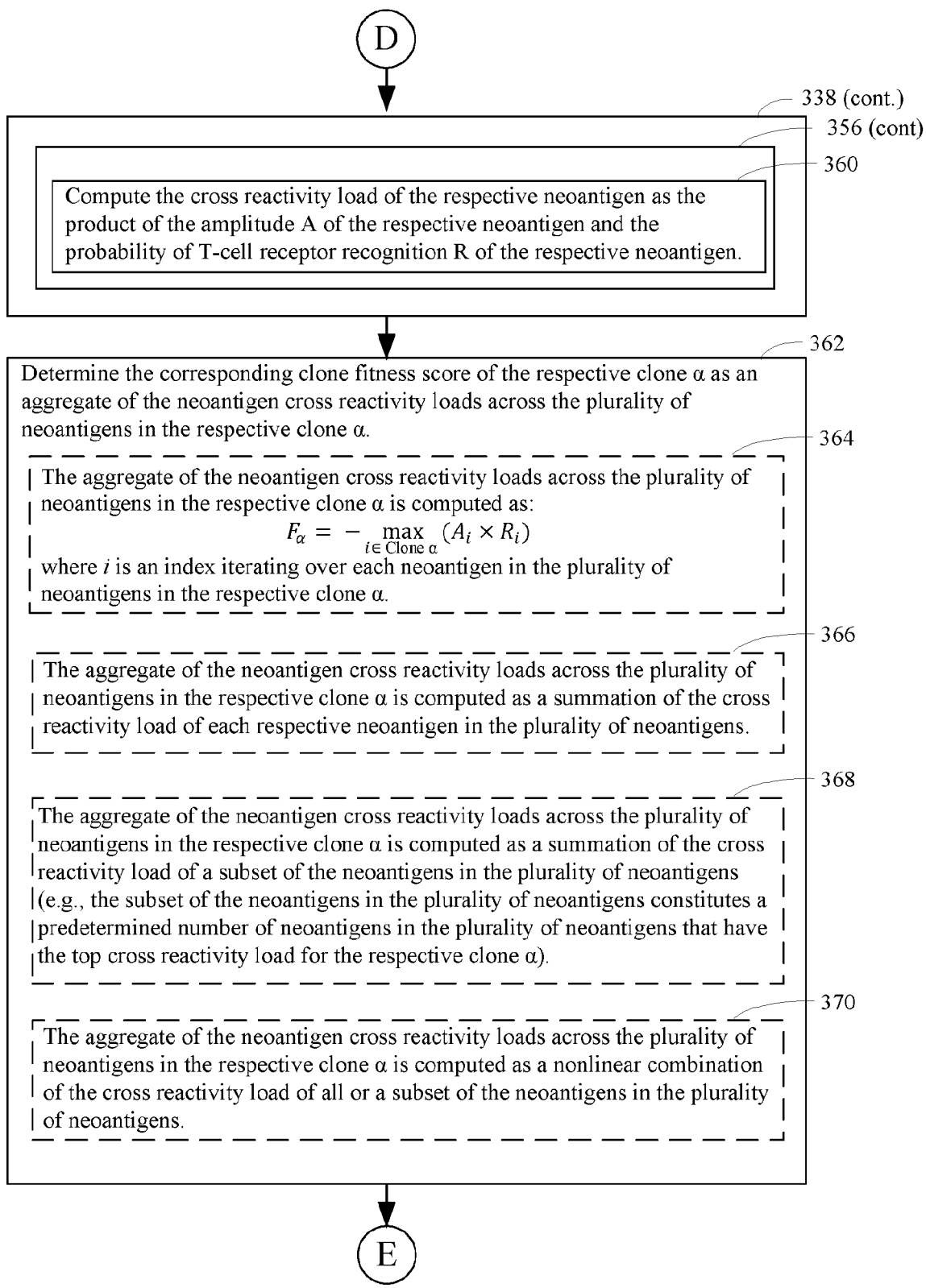
Figure 4:
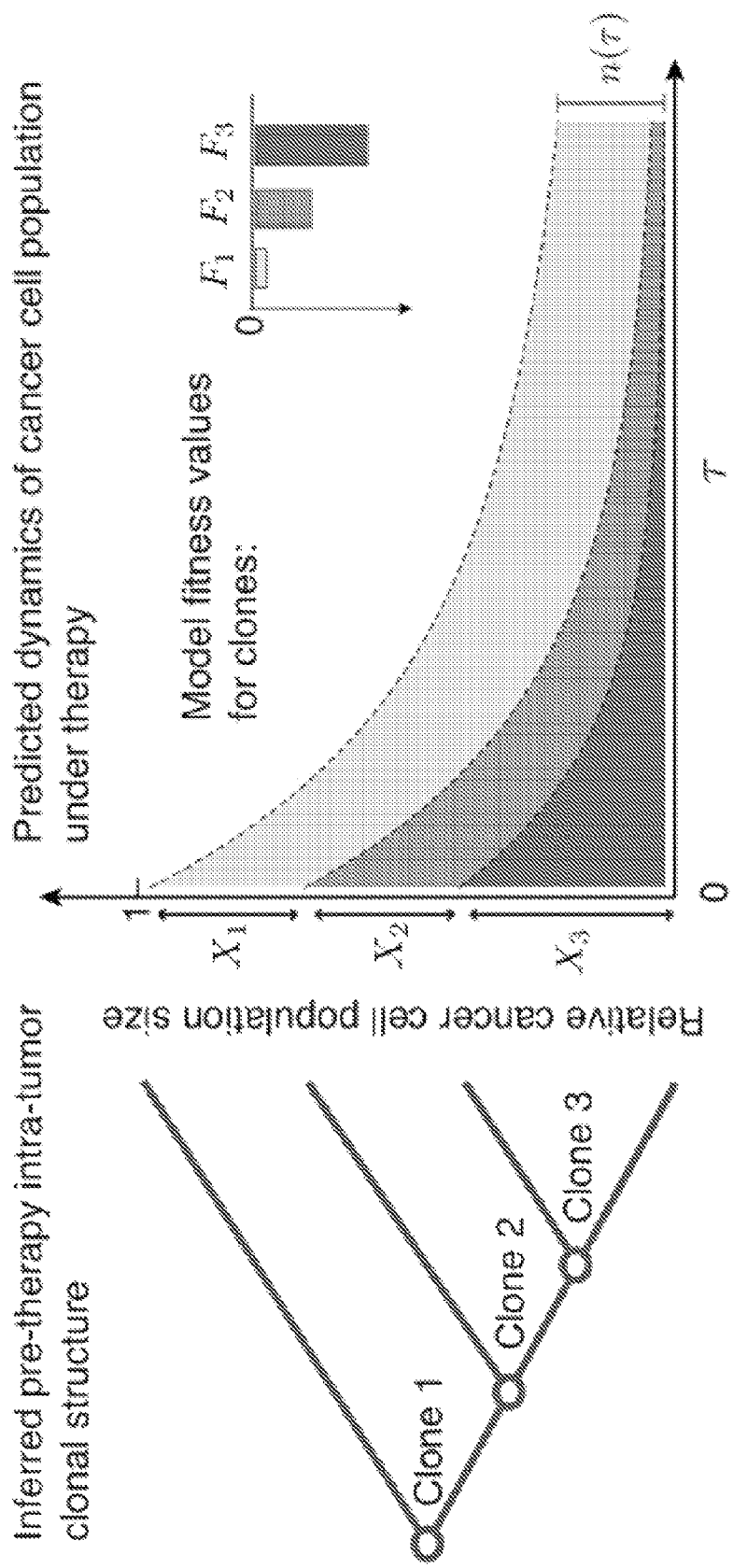
FIG. 4 illustrates evolutionary tumor dynamics under strong immune selection and a neoantigen recognition potential fitness model based on immune interactions. In the left panel, clones are inferred from a tumor's genealogical tree. The value $n(\tau)$, the future effective size of the cancer cell population, relative to its size at the start of therapy is predicted using the equation $n(\tau)=\Sigma_\alpha X_\alpha \exp(F_\alpha \tau)$, by evolving clones under the model over a fixed time-scale, $\tau$. Application of therapy can decrease fitness of clones depending on their neoantigens. Clones with strongly negative fitness have greater loss of population size than more fit ones. In the right panel, the disclosed model accounts for the presence of dominant neoantigens within a clone, $\alpha$, by modeling presentation and recognition of inferred neoantigens, assigning fitness to a clone, $F_\alpha$.

Referring to block 360 of FIG. 3E, in the second procedure, the recognition potential of the respective neoantigen is computed as a function of (i) the amplitude A of the respective neoantigen and (ii) the probability of T-cell receptor recognition R of the respective neoantigen. As used herein, the term is used broadly to mean any linear or nonlinear function of (i) the amplitude A of the respective neoantigen and (ii) the probability of T-cell receptor recognition R of the respective neoantigen. Such a function may further include additional variables or constants in addition to (i) the amplitude A of the respective neoantigen and (ii) the probability of T-cell receptor recognition R of the respective neoantigen. Checkpoint blockade exposes cancer cells to strong immune pressure on their neoantigens and thereby reduces their reproductive success. The fitness of a cancer cell in a genetic clone α is its expected replication rate, i.e.

$$\frac{dN_\alpha}{d\tau} = F_\alpha N_\alpha$$

where $N_\alpha$ is the population size of clone α and $F_\alpha$ is that clone's fitness. Checkpoint-blockade immunotherapy introduces a strong selection challenge, which is expected to overshadow pre-therapy fitness effects in a productive response. For a given clone α the dynamics of its absolute size are hence given by $N_\alpha(\tau)=N_\alpha(0)\exp(F_\alpha\tau)$, and the total cancer cell population size is computed as a sum over its clones:

$$N(\tau)=\Sigma_\alpha N_\alpha(\tau)=\Sigma_\alpha N_\alpha(0)\exp(F_\alpha\tau).$$

The absolute size $N(\tau)$ is an effective population size, the number of cells estimates to have generated the observed clonal diversity. In some embodiments, the measure of survival used is the evolved relative population size $n(\tau)=N(\tau)/N(0)$, which compares the predicted evolved population size after a characteristic dimensionless time scale of evolution τ to the initial pretreatment effective size N(0), the assumption being that successful responders to therapy will have their future effective cancer cell population size more strongly suppressed. The initial clone α frequency is denoted $X_\alpha=N_\alpha(0)/N(0)$, these frequencies are inferred from bulk exome reads from a tumor sample. See Deshwar et al., 2015, "PhyloWGS: reconstructing subclonal composition and evolution from whole-genome sequencing of tumors," Genome Biol. 16, p. 35, which is hereby incorporated by reference. Hence, to compute $n(\tau)$ only estimates of the initial frequencies and fitness values for each clone are required, as shown in the following equation:

$$n(\tau)=\Sigma_\alpha X_\alpha \exp(F_\alpha\tau),$$

the absolute population size measurements are not needed. The hypothesis that due to the unleashing of a T-cell mediated immune response by checkpoint-blockade immunotherapy, the deleterious effects due to recognition of neoantigens are a dominant effect, and tumors with the greatest degree of selective immune challenge are better responders to therapy. In the above equation, the predicted relative size $n(\tau)$ of a cancer cell population in a tumor is computed as a weighted sum over its genetic clones, where $F_\alpha$ is the fitness and $X_\alpha$ is the initial frequency of clone α and τ is a characteristic evolutionary time scale. For each such model defined, its homogenous structure equivalent can be defined by assuming the tumor is strictly clonal with all neoantigens in the same clone at frequency 1.

Without intending to be limited to any particular theory, intuitively, patients with less immunologically fit tumors will have more significant population size reductions and, hence, improved response to therapy.

In accordance with block 360 of FIG. 3E, the disclosed approach quantifies two factors that determine immunogenicity of a neoantigen: an amplitude determined by MHC-presentation, A 226, and the probability of TCR-recognition, R 232. The product of these two factors, A×R, is labeled the neoantigen recognition potential 224 of the neoantigen. In some embodiments, this recognition potential is computed using the scripts illustrated in FIGS. 37 through 40 in accordance with the present disclosure. In some embodiments, the subject assessment module 204 includes the scripts illustrated in FIGS. 37 through 40 in accordance with the present disclosure or equivalents thereof.

Figure 5:
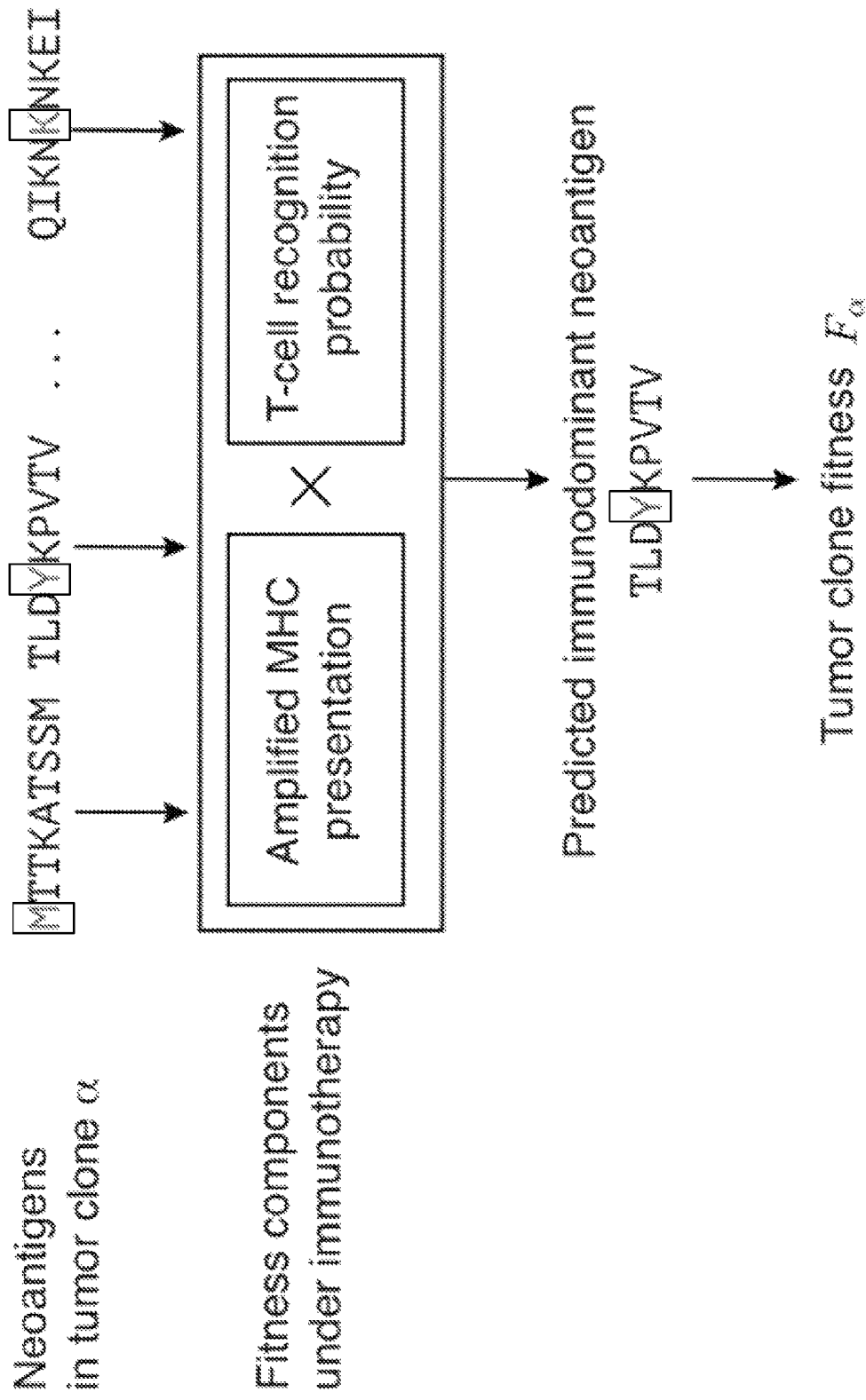
FIG. 5 illustrates a neoantigen recognition potential fitness model based on immune interactions that accounts for the presence of dominant neoantigens within a clone, $\alpha$, by modeling the presentation and recognition of inferred neoantigens and assigning a fitness to a clone, $F_\alpha$ in accordance with some embodiments of the present disclosure.

Block 362. Referring to block 362, the first procedure continues by determining the corresponding clone fitness score 220 of the respective clone α 216 as an aggregate of the neoantigen recognition potential 224 across the plurality of neoantigens 222 in the respective clone α. Next, as illustrated in FIG. 5, the total fitness $F_\alpha$ 234 for cancer cells in a tumor clone is computed by aggregating over the fitness scores 220 due to its neoantigens 222. Specifically, the fitness is modeled for a given clone α by the recognition potential of the immunodominant neoantigen:

$$F_\alpha = -\max_{i \in Clone\ \alpha}(A_i \times R_i)$$

where index i iterates over all neoantigens 222 in clone α 216. That is, in such embodiments, the fitness of a given clone α is modeled by the recognition potential of the immunodominant neoantigen. Taking the best score within a clone is consistent with the notions of heterologous immunity and immunodominance—that a small set of antigens drive the immune response, whereas summing over neoantigens would imply a more uniform distribution of contributions. In such embodiments, the full form of the predicted relative cancer cell population size is given by $$n(\tau) = \sum_\alpha X_\alpha \exp\left[-\max_{i \in Clone\ \alpha}(A_i \times R_i)\tau\right].$$

In some embodiments, a more general model for aggregating neoantigen fitness effects within a clone is used:

$$n(\tau, \beta) = \sum_\alpha X_\alpha \exp\left[\sum_{\substack{max \\ i \in Clone\ \alpha}} \frac{\exp(-\beta f_i)}{Z(\beta)} f_i \tau\right].$$

where $f_i=A_i \times R_i$ and $Z(\beta)=\Sigma_{i \in Clone\ \alpha}\exp(-\beta f_i)$. In addition to the above equation for $n(\tau)$, which corresponds to the limit $\beta \to \infty$, we show the case where $\beta=0$ (uniform summation over all neoantigens (FIGS. 23-25). In that sense the above equation for $n(\tau, \beta)$ represents a general mathematical framework for weighing neoantigen contributions, with weights reflecting the probability of their productive recognition. The choice of β could be informed by additional data sources or defined in a clone specific manner, and it would then become an additional model parameter (or parameters). Taking the highest score within a clone as in the above equation for $n(\tau)$ is consistent with notions of immunodominance—that a relatively small set of antigens drive the immune response.

In some embodiments, the aggregate of the neoantigen recognition potentials across the plurality of neoantigens in the respective clone α is computed as a summation of the recognition potential of each respective neoantigen in the plurality of neoantigens in accordance with the general model for fitness of the clone (216):

$$F_\alpha = -\underset{i \in Clone\ \alpha}{Ag}(A_i \times R_i)$$

where Ag is an aggregation function over recognition potential fitness effects of neoantigens within a clone, such as a summation over all neoantigens in the clone (FIG. 3E, 366), a predetermined subset of the neoantigens in the clone (FIG. 3E, 368), or a nonlinear combination of the neoantigens in the clone (FIG. 3E, 370). For instance, in some embodiments, the subset of the neoantigens in the plurality of neoantigens constitutes a predetermined number of neoantigens in the plurality of neoantigens that have the top recognition potential for the respective clone α (e.g., the top two neoantigens, the top three neoantigens, the top four neoantigens, etc. In some embodiments, the aggregate of the neoantigen recognition potentials across the plurality of neoantigens in the respective clone α is computed as a nonlinear combination of the recognition potential of all or a subset of the neoantigens in the plurality of neoantigens (370).

In some embodiments, the aggregate of the neoantigen recognition potentials across the plurality of neoantigens in the respective clone α is computed by any of the methods disclosed in Luksza et al., 2017, "A neoantigen fitness model predicts tumour response to checkpoint blockade immunotherapy," Nature 551, 517-520.

Block 372. Referring to block 372 of FIG. 3F, a total fitness 234 for the one or more samples is computed as a sum of the clone fitness scores 220 across the plurality of clones, where each clone fitness score 220 is weighted by the initial frequency $X_\alpha$ 218 of the corresponding clone α, and the total fitness 234 quantifies the likelihood that the human subject afflicted with the cancer will be responsive to the treatment regimen. In some such embodiments, the computation of the total fitness 234 for the one or more samples 208 is a sum of the clone fitness scores 220 across the plurality of clones 216. Accordingly, in some embodiments total fitness 234 is computed as n(τ), the predicted future size of a cancer cell population in a tumor relative to its effective size at the start of therapy as a weighted sum over its genetic clones:

$$n(\tau) = \tau_\alpha X_\alpha \exp(F_\alpha \tau),$$

where τ is a characteristic evolutionary time scale, $X_\alpha$ is the initial frequency $X_\alpha$ 218 of the corresponding clone α, $F_\alpha$ is the clone fitness score 220 of the corresponding clone α, and the summation of this equation is across all clones 216 identified in the one or more biological samples 208 (FIG. 3F, 374). In some such embodiments, τ is between 0.0 and 0.5. In some such embodiments, τ is 0.06. In some such embodiments, a lower total fitness score is associated with (a) a higher likelihood that the cancer subject will be responsive to the immunotherapy and (b) a longer term survival of the cancer patient (FIG. 3F, 374).

5.4 Example Methods for Identifying an Immunotherapy for a Cancer

Another aspect of the present disclosure provides methods for identifying an immunotherapy for a cancer. In some embodiments, the cancer is a solid tumor. In some embodiments the cancer is a liquid tumor. Non-limiting examples of solid tumors include pancreatic cancer, gastric cancer, bile duct cancer (e.g., cholangiocarcinoma), liver cancer, colorectal cancer, melanoma, lung cancer, and breast cancer. Non-limiting examples of liquid tumors include acute leukemia and chronic leukemia.

In the disclosed methods, a plurality of sequencing reads 210 (e.g., whole genome sequencing reads, exome sequencing reads, targeted sequencing reads, etc.) is obtained from one or more biological samples 208 from a human cancer subject that is representative of the cancer. A human leukocyte antigen (HLA) type of the human cancer subject 212 is determined from the plurality of sequencing reads. A plurality of clones 216 is determined (e.g., from the sequencing reads). For each respective clone α 216 in the plurality of clones, an initial frequency $X_\alpha$ 218 of the respective clone α in the one or more samples is determined from the plurality of sequencing reads. Further, for each respective clone α in the plurality of clones, a corresponding clone fitness score 220 of the respective clone is computed, thereby computing a plurality of clone fitness scores, each corresponding clone fitness score computed for a respective clone α by a first procedure.

In the first procedure, a plurality of neoantigens 222 in the respective clone α are identified. For instance, in some embodiments this is done using the sequence reads 210 as follows. Raw sequence data reads are aligned to a reference human genome (e.g., hg19) using an alignment tool such as the Burrows-Wheeler Alignment tool. In some embodiments, base-quality score recalibration, and duplicate-read removal is performed, with exclusion of germline variants, annotation of mutations, and indels as described in Snyder et al., 2014 "Genetic Basis for Clinical Response to CTLA-4 Blockade in Melanoma," N. Engl. J. Med. 371, pp. 2189-2199, which is hereby incorporated by reference. Local realignment and quality score recalibration are conducted using, for example the Genome Analysis Toolkit (GATK) according to GATK best practices. See DePristo et al., 2011, "A framework for variation discovery and genotyping using next-generation DNA sequencing data," Nature Genet. 43, 491-498; and Van der Auwera et al., 2013, "From FastQ Data to High-Confidence Variant Calls: The Genome Analysis Toolkit Best Practices Pipeline," Curr. Prot. in Bioinformatics 43, 11.10.1-11.10.33, each of which is hereby incorporated by reference. For sequence alignment and mutation identification, adapter sequences at the end of the reads are removed. In some embodiments this is done using cutadapt (v1.6). Martin, 2011, "Cutadapt removes adapter sequences from high-throughput sequencing reads," EMBnet. journal 17, pp. 10-12, which is hereby incorporated by reference. In some embodiments, the files were then mapped using the BWA mapper (bwa mem v0.7.12) (Li and Durbin, 2009, "Fast and accurate short read alignment with Burrows-Wheeler Transform," Bioinformatics 25, pp. 1754-1760, hereby incorporated by reference), the SAM files sorted, and read group tags added using the PICARD tools. After sorting in coordinate order, the BAMs are processed with PICARD MarkDuplicates. First realignment was carried out using the InDel realigner followed by base quality value recalibration with the BaseQRecalibrator. Next, mutations callers are used to identify single nucleotide variants (SNVs). Exemplary base callers that are used in some embodiments are a combination of four different mutation callers (Mutect 1.1.4, Somatic Sniper 1.0.4, Varscan 2.3.7, and Strelka 1.013).[33-36]. See Wei et al, 2015, "MAC: identifying and correcting annotation for multi-nucleotide variations, BMC Genomics 16, p. 569; Snyder and Chan, 2015, "Immunogenic peptide discovery in cancer genomes," Curr Opin Genet Dev 30, pp. 7-16; Nielsen et al., 2003, "Reliable prediction of T-cell epitopes using neural networks with novel sequence representations," Protein Sci 12, pp. 1007-1017; and Shen and Seshan, 2016, "FACETS: allele-specific copy number and clonal heterogeneity analysis tool for high-throughput DNA sequencing," Nucleic Acids Res. 44, e131, each of which is incorporated by reference. In some embodiments SNVs with an allele read count of less than four or with corresponding normal coverage of less than 7 reads were filtered out in accordance with the criteria set forth in Riaz et al., 2016, "Recurrent SERPINB3 and SERPINB4 mutations in patients who respond to anti-CTLA4 immunotherapy," *Nat. Genet.* 48, pp. 1327-1329, which is hereby incorporated by reference. In some embodiments, the assignment of a somatic mutation to a neoantigen is estimated using a previously described bioinformatics tool called NASeek. See Snyder et al., 2014, "Genetic Basis for Clinical Response to CTLA-4 Blockade in Melanoma," N. Engl. J.

Med. 371, pp. 2189-2199, which is hereby incorporated by reference. NASeek is a computational algorithm that first translates all mutations in exomes to strings of 17 amino acids, for both the wildtype and mutated sequences, with the amino acid resulting from the mutation centrally situated. Secondly, it evaluates putative MHC Class I binding for both wildtype and mutant nonamers using a sliding window method using NetMHC3.4 (See Andreatta and Nielsen, 2016, "Gapped sequence alignment using artificial neural networks: application to the MHC class I system," Bioinformatics 32, pp. 511-517, hereby incorporated by reference) for patient-specific HLA types, to generate predicted binding affinities for both peptides. NASeek finally assesses for similarity between nonamers that predicted to be presented by patient-specific MHC Class I. In some embodiments all nonamers with binding scores below 500 nM are defined as neoantigens.

Next, a recognition potential 224 of each respective neoantigen 222 in the plurality of neoantigens in the respective clone $\alpha$ 216 is then computed by a second procedure. In the second procedure, an amplitude A 226 of the respective neoantigen as a function of the relative major histocompatibility complex (MHC) affinity of the respective neoantigen and the wildtype counterpart of the respective neoantigen given the HLA type of the subject is computed. Further, a probability of T-cell receptor recognition R 232 of the respective neoantigen as a probability that the respective neoantigen binds one or more epitopes that are positively recognized by T-cells after class I MHC presentation is computed. In some embodiments, the recognition potential 224 of the respective neoantigen 222 is computed as the product of the amplitude A 226 of the respective neoantigen and the probability of T-cell receptor recognition R 232 of the respective neoantigen.

In the first procedure, the corresponding clone fitness score 220 of the respective clone $\alpha$ is determined as an aggregate of the neoantigen recognition potentials across the plurality of neoantigens in the respective clone $\alpha$.

In the disclosed first procedure, a first neoantigen 222 is selected from a plurality of neoantigens for a respective clone $\alpha$ 216 in the plurality of respective clones based upon the recognition potential 224 of the first neoantigen 222 as the immunotherapy for the cancer.

In some embodiments, the first procedure is repeated for a plurality of human cancer subjects across a plurality of HLA types and the first neoantigen 222 is selected on the basis of the recognition potential of the first neoantigen 222 across the plurality of HLA types.

In some embodiments, the first procedure is repeated for a plurality of human cancer subjects and the first neoantigen 222 is selected on the basis of the recognition potential of the first neoantigen 222 across the plurality of human cancer subject.

In some embodiments, the cancer is a carcinoma, a melanoma, a lymphoma/leukemia, a sarcoma, or a neuroglial tumor. In some embodiments, the cancer is lung cancer, pancreatic cancer, colon cancer, stomach or esophagus cancer, breast cancer, ovary cancer, prostate cancer, or liver cancer.

In some embodiments, each clone $\alpha$ 216 in the plurality of clones is uniquely defined by a unique set of somatic mutations, and the plurality of clones is determined by a variant allele frequency of each respective somatic mutation in a plurality of somatic mutations determined from the whole-genome sequencing data. For instance, in some embodiments, the somatic mutation is a single nucleotide variant or an indel.

In some embodiments, the plurality of clones is determined by identifying a plurality of inferred copy number variations using the whole-genome sequencing data.

In some embodiments, each clone $\alpha$ 216 in the plurality of clones is uniquely defined by a unique set of somatic mutations, and the plurality of clones is determined by a combination of (i) a variant allele frequency of each respective somatic mutation in the plurality of somatic mutations determined from the whole-genome sequencing data and (ii) an identification of a plurality of inferred copy number variations using the whole-genome sequencing data.

In some embodiments, the plurality of sequencing reads (e.g., whole genome sequencing reads, exome sequencing reads, targeted sequencing reads, etc.) exhibits an average read depth of less than 40. In some embodiments, the plurality of sequencing reads exhibits an average read depth of between 25 and 60.

In some embodiments, the plurality of sequencing reads encompasses a subset of the genome of the subject and not the rest of the genome of the subject. In some such embodiments, the plurality of sequencing reads encompass exhibits an average read depth of less than 200, less than 100, less than 50, less than 40, or less than 20 across this subset of the genome of the subject. In some embodiments, the plurality of whole genome sequencing reads exhibits an average read depth of between 25 and 60 across this subset of the genome of the subject. In some embodiments, the plurality of sequencing reads comprises whole genome sequencing reads. In some embodiments, the plurality of sequencing reads comprises exome sequencing reads. In some embodiments, the plurality of sequencing reads comprises targeted sequencing reads.

In some embodiments, the subset of the genome is between one percent and ten percent of a single chromosome of the subject, between five percent and fifteen percent of a single chromosome of the subject, between ten percent and twenty percent of a single chromosome of the subject, between fifteen percent and thirty percent of a single chromosome of the subject, between twenty-five percent and fifty percent of a single chromosome of the subject, between forty-five percent and seventy-five percent of a single chromosome of the subject, or between seventy percent and one hundred percent of a single chromosome of the subject.

In some embodiments, the subset of the genome is between one percent and ten percent of a two or more chromosomes of the subject, between five percent and fifteen percent of two or more chromosomes of the subject, between ten percent and twenty percent of two or more chromosomes of the subject, between fifteen percent and thirty percent of two or more chromosomes of the subject, between twenty-five percent and fifty percent of two or more chromosomes of the subject, between forty-five percent and seventy-five percent of two or more chromosomes of the subject, or between seventy percent and one hundred percent of two or more chromosomes of the subject.

In some embodiments, the subset of the genome is between one percent and ten percent of the genome of the subject, between five percent and fifteen percent of the genome of the subject, between ten percent and twenty percent of the genome of the subject, between fifteen percent and thirty percent of the genome of the subject, between twenty-five percent and fifty percent of the genome of the subject, between forty-five percent and seventy-five percent of the genome of the subject, or between seventy percent and one ninety-nine percent of the genome of the subject.

In some embodiments, each neoantigen 222 in the plurality of neoantigens of a clone 216 in the plurality of clones is a nonamer peptide. In some embodiments, each neoantigen 222 in the plurality of neoantigens of a clone 216 in the plurality of clones is a peptide that is eight, nine, ten, or eleven residues in length. In certain embodiments each neoantigen in the plurality of neoantigens of a clone in the plurality of clones is a peptide that is 3-30 amino acids, e.g., about 3-5, about 5-15 (e.g., about 8-11, about 5-10, or about 10-15), about 15-20, about 20-25, or about 20-30 amino acids, in length. In certain embodiments, each neoantigen in the plurality of neoantigens of a clone in the plurality of clones is a peptide that is about 8-11 amino acids in length. In certain embodiments, each neoantigen in the plurality of neoantigens of a clone in the plurality of clones is a peptide that is about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 25, about 26, about 27, about 28, about 29, or about 30 amino acids in length. In certain embodiments, each neoantigen in the plurality of neoantigens of a clone in the plurality of clones is a peptide that is at least about 3, at least about 5, or at least about 8 amino acids in length. In certain embodiments, each neoantigen in the plurality of neoantigens of a clone in the plurality of clones is a peptide is less than about 30, less than about 20, less than about 15, or less than about 10 amino acids in length.

In some embodiments, the method further comprises identifying a population of neoantigens present in the one or more samples by a third procedure in which a plurality of somatic single nucleotide polymorphisms (SNPs) in the plurality of sequencing reads is determined by comparison of the plurality of sequencing reads to a reference human genome. In the third procedure, each respective somatic SNP in the plurality of SNPs is evaluated as a neoantigen 222 candidate by evaluation of a peptide encoded by a portion of one or more sequencing reads in the sequencing reads that includes the respective somatic SNP against a classifier that has been trained to predict peptide binding to class 1 MHC of the HLA type of the cancer subject, where a neoantigen 222 candidate having a binding score below a threshold value (e.g., 500 nM) is deemed to be a neoantigen 222 in the population of neoantigens. Further, when this third procedure is used, the identifying the plurality of neoantigens in the respective clone α 216 comprises matching the SNPs in the respective clone α 216 to respective neoantigens in the population of neoantigens.

In some embodiments, the HLA type determination of the human cancer subject is made from the plurality of sequencing reads. In some embodiments, the HLA type determination of the human cancer subject is made using a polymerase chain reaction using a biological sample from the cancer subject.

In some embodiments, the plurality of clones consists of two clones. In some embodiments, the plurality of clones consists of between two clones and ten clones. In some embodiments, the initial frequency $X_\alpha$ 218 of the respective clone α in the one or more samples is determined using the plurality of sequencing reads from the one or more samples from the human cancer subject.

In some embodiments, the function of the relative class I MHC affinity of the respective neoantigen 222 and the wildtype counterpart of the respective neoantigen 222 given the HLA type of the subject is a ratio of the relative class I MHC affinity of the respective neoantigen 222 and the wildtype counterpart of the respective neoantigen 222 given the HLA type of the subject.

In some embodiments, the function of the relative class I MHC affinity of the respective neoantigen 222 and the wildtype counterpart of the respective neoantigen 222 given the HLA type of the human cancer subject is a ratio of: (1) a dissociation constant between the respective neoantigen 222 and the class I MHC presented by the cancer subject given the HLA type of the cancer subject, and (2) a dissociation constant between the wildtype counterpart of the respective neoantigen 222 and the class I MHC presented by the cancer subject given the HLA type of the cancer subject. In some such embodiments, the dissociation constant between the respective neoantigen 222 and the class I MHC presented by the cancer subject is obtained as output from a first classifier upon inputting into the first classifier the amino acid sequence of the neoantigen 222, and the dissociation constant between the wildtype counterpart of the respective neoantigen 222 and the class I MHC presented by the cancer subject of the HLA type of the subject is obtained as output from the first classifier upon inputting into the first classifier the amino acid sequence of the respective wildtype counterpart of the neoantigen 222. In some such embodiments, the first classifier is specific to the HLA type of the cancer subject and has been trained with the respective class I MHC binding coefficient and sequence data of each peptide epitope in a plurality of epitopes presented by class I MHC in a training population having the HLA type of the subject.

In some embodiments, the probability that the respective neoantigen 222 binds one or more epitopes that are positively recognized by T-cells after class I MHC presentation is determined by a third procedure that comprises (a) selecting a respective epitope e from an epitope database IEDB, where the respective epitope e is positively recognized by T-cells after class I MHC presentation, (b) computing, for the respective epitope e, the probability $$Pr_{binding}(s, e) = \frac{1}{1 + e^{-k(|s,e|-a)}}$$

where |s, e| is a sequence alignment score between the sequence of the respective neoantigen 222 and the sequence of the respective epitope, and k and a are constants, and (c) performing the selecting (a) and the computing (b) for each respective epitope e in a plurality of epitopes in the epitope database IEDB, thereby computing a plurality of probabilities $Pr_{binding}(s, e)$, and (d) computing the probability of T-cell receptor recognition R of the respective neoantigen 222 as:

$$R = 1 - \Pi_{e \in IEDB}[1 - Pr_{binding}(s, e)],$$

where IEDB the plurality of epitopes. In some such embodiments, a is set to 23 and k is set to 1. In some such embodiments, |s, e| is computed as an alignment (e.g., gapless, or an alignment that allows gaps with suitable gap introduction and extension penalties) between the sequence of the respective neoantigen 222 and the sequence of the respective epitope using an amino-acid similarity matrix (e.g., a BLOSUM62 matrix).

In some embodiments, the first neoantigen 222 from a plurality of neoantigens for a respective clone α 216 in the plurality of respective clones is selected when it has a recognition potential 224 that is lower than the recognition potential of other neoantigens in each plurality of neoantigens for each respective clone α 216 in the plurality of respective clones of the subject.

EXEMPLIFICATION

Example I

Computational identification of neoantigens. Neoantigens from the three datasets were inferred using a consistent pipeline established at Memorial Sloan Kettering Cancer Center. Raw sequence data reads were aligned to the reference human genome (hg19) using the Burrows-Wheeler Alignment tool. Base-quality score recalibration, and duplicate-read removal were performed, with exclusion of germline variants, annotation of mutations, and indels as previously described. See Snyder et al, 2014, "Genetic Basis for Clinical Response to CTLA-4 Blockade in Melanoma," N. Engl. J. Med. 371, 2189-2199, which is hereby incorporated by reference. Local realignment and quality score recalibration were conducted using the Genome Analysis Toolkit (GATK) according to GATK best practices. See, DePristo et al., 2011, "A framework for variation discovery and genotyping using next-generation DNA sequencing data," Nature Genet. 43, pp. 491-498; and Van der Auwera et al, 2013, "From FastQ Data to High-Confidence Variant Calls: The Genome Analysis Toolkit Best Practices Pipeline," Curr. Prot. in Bioinformatics 43, 11.10.1-11.10.33 each of which is hereby incorporated by reference. For sequence alignment and mutation identification, the FASTQ files were processed to remove any adapter sequences at the end of the reads using cutadapt (v1.6). See Martin, 2011, "Cutadapt removes adapter sequences from high-throughput sequencing reads," EMBnet. journal 17, pp. 10-12, which is hereby incorporated by reference. The files were then mapped using the BWA mapper (bwa mem v0.7.12), (see Li and Durbin, 2009, "Fast and accurate short read alignment with Burrows-Wheeler Transform," Bioinformatics 25, pp. 1754-1760, which is hereby incorporated by reference) the SAM files sorted, and read group tags added using the PICARD tools. After sorting in coordinate order, the BAM's were processed with PICARD MarkDuplicates. First realignment was carried out using the InDel realigner followed by base quality value recalibration with the BaseQRecalibrator.

A combination of four different mutation callers (Mutect 1.1.4, Somatic Sniper 1.0.4, Varscan 2.3.7, and Strelka 1.013) were used to identify single nucleotide variants (SNVs). See Wei et al, 2015, "MAC: identifying and correcting annotation for multi-nucleotide variations, BMC Genomics 16, p. 569; Snyder and Chan, 2015, "Immunogenic peptide discovery in cancer genomes," Curr Opin Genet Dev 30, pp. 7-16; Nielsen et al., 2003, "Reliable prediction of T-cell epitopes using neural networks with novel sequence representations," Protein Sci 12, pp. 1007-1017; and Shen and Seshan, 2016, "FACETS: allele-specific copy number and clonal heterogeneity analysis tool for high-throughput DNA sequencing," Nucleic Acids Res. 44, e131, each of which is incorporated by reference. As previously described, SNVs with an allele read count of less than 4 or with corresponding normal coverage of less than 7 reads were filtered out. See Riaz et al., 2016, "Recurrent SERPINB3 and SERPINB4 mutations in patients who respond to anti-CTLA4 immunotherapy," Nat. Genet. 48, 1327-1329, which is hereby incorporated by reference.

The assignment of a somatic mutation to a neoantigen was estimated using a previously described bioinformatics tool called NASeek. See Snyder et al., 2014, "Genetic Basis for Clinical Response to CTLA-4 Blockade in Melanoma," N. Engl. J. Med. 371, pp. 2189-2199, which is hereby incorporated by reference. NASeek is a computational algorithm that first translates all mutations in exomes to strings of 17 amino acids, for both the wildtype and mutated sequences, with the amino acid resulting from the mutation centrally situated. Secondly, it evaluates putative MHC Class I binding for both wildtype and mutant nonamers using a sliding window method using NetMHC3.4 (on the Internet cbs.dtu.dk/services/NetMHC-3.4/) (see Andreatta and Nielsen, 2016, "Gapped sequence alignment using artificial neural networks: application to the MHC class I system," Bioinformatics 32, pp. 511-517, which is hereby incorporated by reference) for patient-specific HLA types, to generate predicted binding affinities for both peptides. Prediction values are given in nM $IC_{50}$ values and are trained on nonamer peptides like those used in the disclosed analysis. NASeek finally assesses for similarity between nonamers that are predicted to be presented by patient-specific MHC Class I. All nonamers with inferred affinities below 500 nM are defined as neoantigens.

Clonal tree construction. Tumor clones are reconstructed using the PhyloWGS software package. See, Deshwar et al., 2015, "PhyloWGS: reconstructing subclonal composition and evolution from whole-genome sequencing of tumors," Genome Biol. 16, 35, which is hereby incorporated by reference. The input data for the algorithm is extracted from exome sequencing data: (1) mutation reads obtained with the pipeline described above, and (2) allele-specific copy-number variant data, obtained with FACETS v0.5.0. Shen and Seshan, 2016, "FACETS: allele-specific copy number and clonal heterogeneity analysis tool for high-throughput DNA sequencing," Nucleic Acids Res. 44, e131. The package clusters mutations into clones by the frequency of their reads and it infers possible nesting of clones (ancestral relations) between pairs of clones. Intuitively, an ancestral clone needs to have higher frequency then its derived clone. From this information PhyloWGS reconstructs high likelihood tumor geneological trees.

In accordance with the present disclosure, the predicted relative size $n(\tau)$ of a cancer cell population in a tumor as a weighted sum over its genetic clones is calculated as:

$$n(\tau) = \Sigma_\alpha X_\alpha \exp(F_\alpha \tau),$$

where $F_\alpha$ is the fitness and $X_\alpha$ is the initial frequency of clone $\alpha$ and $\tau$ is a characteristic evolutionary time scale. The disclosed fitness model:

$$F_\alpha = -\max_{i \in Clone\ \alpha} (A_i \times R_i),$$

where index i iterates over all neoantigens in clone $\alpha$ was applied to three datasets: two melanoma patient cohorts treated with anti-CTLA4 (Snyder et al., 2014, "Genetic Basis for Clinical Response to CTLA-4 Blockade in Melanoma," N. Engl. J. Med. 371, pp. 2189-2199; and Van Allen et al., 2015, "Genomic correlates of response to CTLA-4 blockade in metastatic melanoma," Science 350, pp. 207-211, each of which is hereby incorporated by reference) and one lung tumor cohort treated with anti-PD1 (Rizvi et al., 2015, "Mutational landscape determines sensitivity to PD-1 blockade in non-small cell lung cancer, Science 348, pp. 124-128, which is hereby incorporated by reference).

Figure 6:
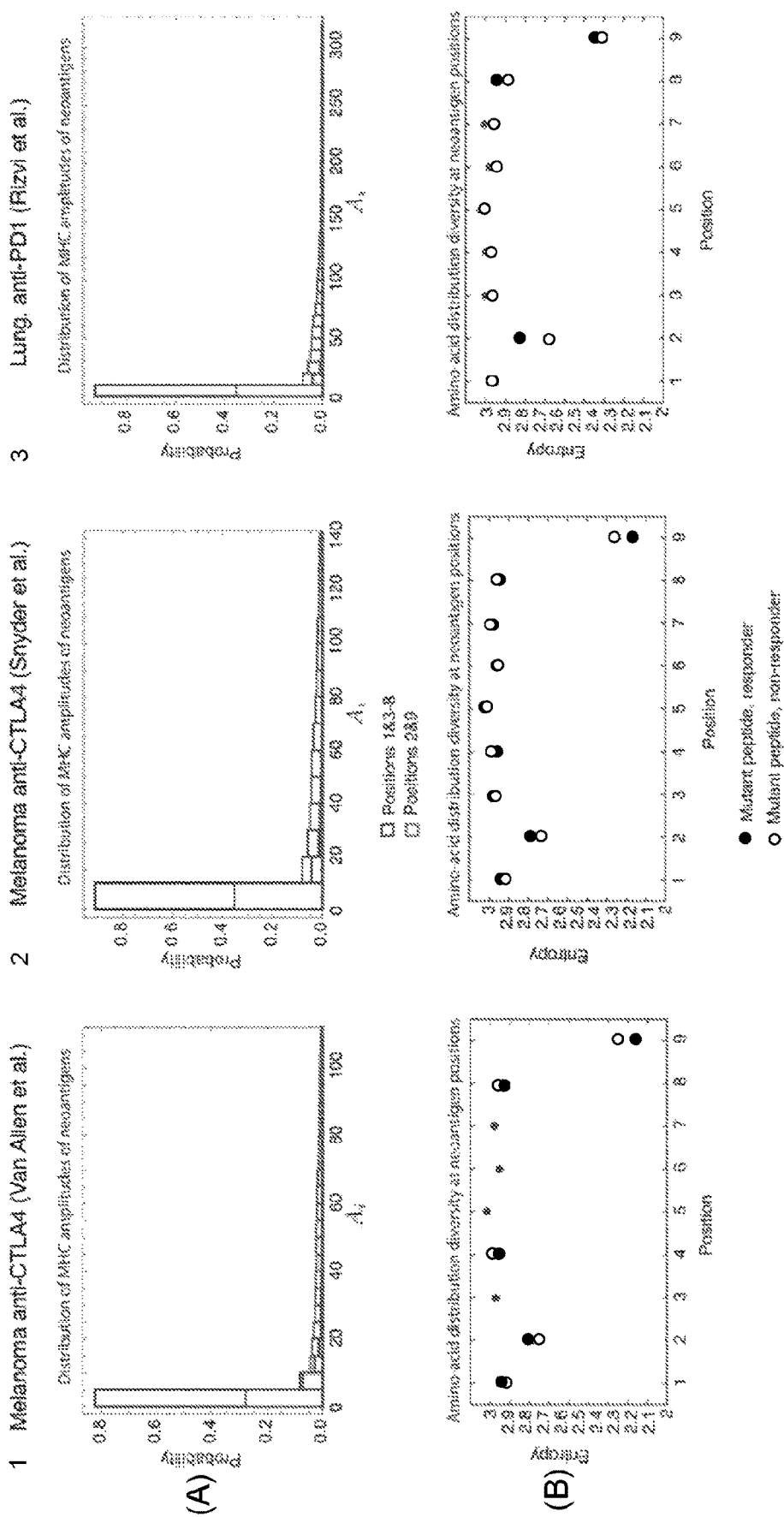
FIG. 6 illustrates (A) how positions 2 and 9 in neoantigens are of less predictive value in some embodiments of the present disclosure, with neoantigens with mutations at anchor residues at position 2 and 9 have highly diverging amplitude values and are of less overall predictive value than neoantigens at other positions; and (B) how patients classified in studies as responders are marked with solid circles and non-responders are marked with hollow circles. Positions 2 and 9 are highly constrained by a bias to be hydrophobic. Their Shannon entropy is lower than that of other residues, across all three datasets regardless of classification of their neoantigens in those datasets. Other residue sites have the same entropy as the overall proteome (Lehmann et al., 2016, "Fundamental amino acid mass distributions and entropy costs in proteomes," J. Theor. Biol. 410, pp. 119-124, which is hereby incorporated by reference) and are therefore unconstrained.

Efficiency is assessed using overall survival of patients from the beginning of immunotherapy. Neoantigen amino-acid anchor positions, 2 and 9, for the majority of HLA types, are constrained as reflected by non-informative MHC affinity amplitudes illustrated in FIG. 6(A). As illustrated in FIG. 6 (B), positions 2 and 9 are highly constrained by a bias to be hydrophobic. As illustrated in FIG. 31, neoantigens have decreased amino-acid diversity at these positions. See also, Lehman et al., 2016, "Fundamental amino acid mass distributions and entropy costs in proteomes," J. Theor. Biol. 410, pp. 119-124, which is hereby incorporated by reference. In FIG. 31, the violin plots represent data density at a given value on a vertical axis. FIG. 31A illustrates that neoantigens coming from mutations at position 2 or 9 tend to have wildtype peptides with larger predicted affinities. In particular, this is magnified if the corresponding wildtype residue is non-hydrophobic. FIG. 31B illustrates that those biases are reflected in a wider distribution of amplitudes for wildtype peptides with non-hydrophobic residues at positions 2 and 9. FIG. 31C illustrates that the Shannon entropy of amino acid diversity by position in neoantigens, shown for all distinct HLA-types and computed based on neoantigens across all datasets. Positions 2 and 9 have lower entropy than other residues. Other sites have the same entropy as the overall proteome (Lehmann et al., 2016, "Fundamental amino acid mass distributions and entropy costs in proteomes." J. Theor. Biol. 410, pp. 119-124) and are therefore unconstrained. Five HLA with non-canonical entropy profiles are singled out in the plot. These HLA types contributed only five informative neoantigens across all datasets and therefore are not treated differentially in our model. Hence, neoantigens with mutations at positions 2 and 9 were excluded from predictions with the model in this example. Amino-acid diversity on remaining positions is unconstrained as illustrated in FIG. 6B.

Amino acid diversity at $i^{th}$ position in a neoantigen is defined as $e^{H_i}$, where $H_i$ is Shannon entropy of amino acid usage at this position, i.e.

$$H_i = -\Sigma_{j=1}^{20}(a_{ij})\log(f(a_{ij})),$$

where $f(a_{ij})$ is frequency of the i-th position in all neoantigens in a group. Inferred neoantigens are nonamers, so i ranges in value from 1 to 9. The diversity of neoantigens at a given site were compared to the values found in the human proteome in Lehman et al., 2016, "Fundamental amino acid mass distributions and entropy costs in proteomes," J. Theor. Biol. 410, pp. 119-124, which is hereby incorporated by reference. To calculate the expected number of words in the proteome the frequency of amino acids from Lehman, et al is utilized. The entropy associated with the frequency of amino acids in the human genome is computed as:

$$H(a) = -\Sigma_{j=1}^{20} f(a_1)\log(f(a_j)),$$

where $f(a_j)$ is the frequency of the j-th amino acid in the human genome. The expected number of words of length n is therefore $e^{nH(a)}$. This value is compared to the observed number of words of length n in the reference proteome for GRCh38.p7 using an entropy of 2.90 (Lehman et al., 2016, "Fundamental amino acid mass distributions and entropy costs in proteomes," J. Theor. Biol. 410, pp. 119-124). Finite genome size exhausts word usage between 5 and 6-mers. By 9-mer length words the ratio of observed to expected words is approximately 0.000052.

R, the recognition potential 224 of a neoantigen with a TCR-pool defined as the probability that a neoantigen cross-reacts with at least one TCR corresponding to a known immunogenic epitope:

$$R = 1 - \prod_{e \in IEDB} [1 - Pr_{binding}(s, e)]$$

where s is the peptide sequence of the neoantigen and e is a set of epitopes of the neoantigen given by the Immune Epitope Database and Analysis Resource. See Vita et al., 2014, "The immune epitope database (IEDB) 3.0," Nucleic Acids Res. 43, D405-D412, which is hereby incorporated by reference. The probability that a TCR for a given epitope binds a given neoantigen is defined by a two-state thermodynamic model with logistic shape. In this model sequence alignment is used as a proxy for binding energy. To assess homology between a neoantigen with peptide sequence s and an IEDB epitope e, we compute an alignment (e.g., gapless, or an alignment that allows gaps with suitable gap introduction and extension penalties) between the two sequences with a BLOSUM62 amino-acid similarity matrix. See Berg and von Hippel, 1987, "Selection of DNA binding sites by regulatory proteins: Statistical-mechanical theory and application to operators and promoters," J. Mol. Biol. 193, pp. 723-743, which is hereby incorporated by reference. For an alignment score, |s, e|, the binding probability is computed as $$Pr_{binding}(s, e) = \frac{1}{1 + e^{-k(|s,e|-a)}},$$

where a represents the horizontal displacement of the binding curve (midpoint) and k sets the steepness of the curve at a. Model parameters a and k of the logistic binding function describes the probability of binding between neoantigens and epitope-specific TCRs.

Figure 7:
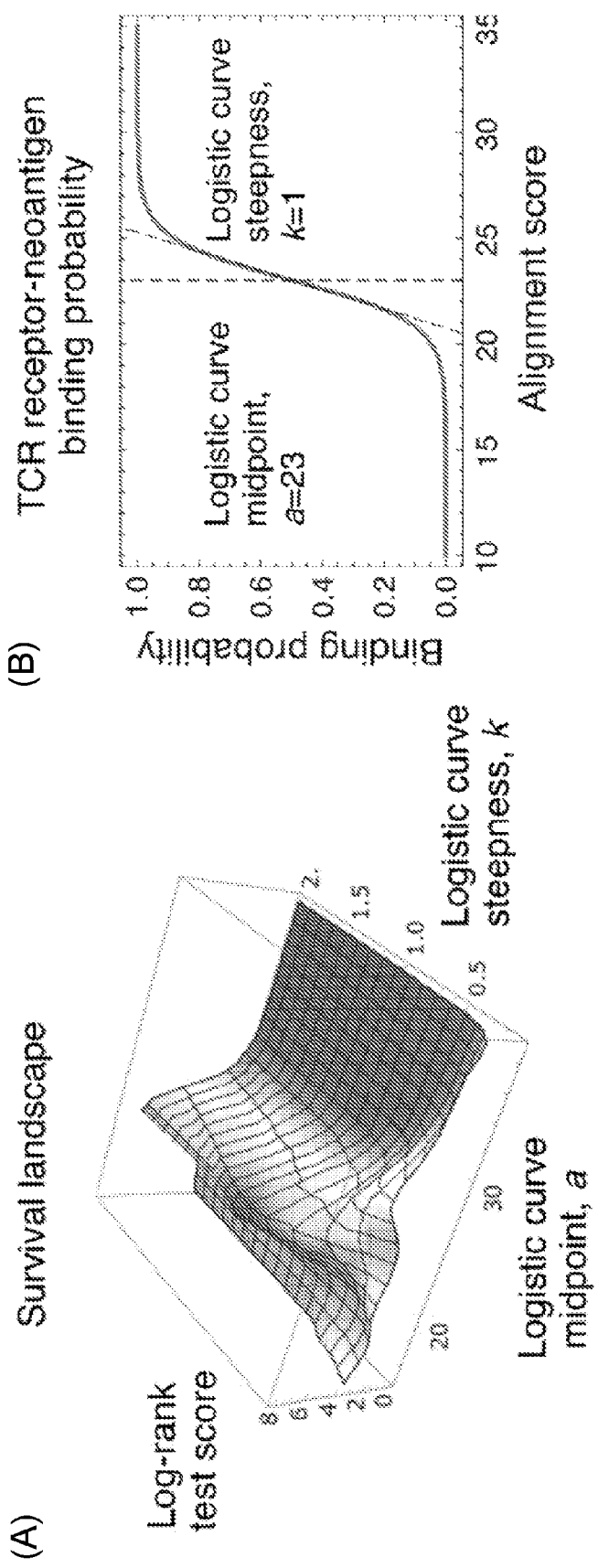
FIG. 7 illustrates survival landscape as a function of TCR binding model by illustrating (A) the landscape is a contour plot of log-rank test scores in survival analysis with patient data split by median relative population size ($n(\tau)=\tau_\alpha X_\alpha \exp(F_\alpha \tau)$). The locally smoothed landscape is plotted for the Van Allen et al., 2015, "Genomic correlates of response to CTLA-4 blockade in metastatic melanoma," Science 350, pp. 207-211 dataset as a function of the model parameters for the logistic curve midpoint (a) and steepness (k) and (B) a logistic binding curve at inferred midpoint and steepness parameters used across all three datasets from parameters in Van Allen et al., 2015, "Genomic correlates of response to CTLA-4 blockade in metastatic melanoma," Science 350, pp. 207-211. The curve represents the binding probability of a neoantigen to a T-cell receptor associated with an IEDB epitope as a function of its alignment score to that epitope, in accordance with an embodiment of the present disclosure.

To choose model parameters a and k for this equation, in some embodiments the log-rank-test scores of patient segregation as a function of these parameters was investigated. The survival analysis is performed by splitting patient cohort into high and low fitness groups by the median cohort value of $n(\tau)$, the predicted relative cancer cell population size at a characteristic time $\tau$ (we discuss the choice of $\tau$ below). The survival score landscapes (FIG. 7 and FIG. 17) appear to be consistent between the datasets, with an optimal value of parameter a around 23 and parameter k living on a trivial axis above value 1, suggesting strong nonlinear fitness dependence on the sequence alignment score. Parameters that optimize the log-rank-test score in the largest dataset in the study, the melanoma anti-CTLA4 cohort from Van Allen et al., 2015, "Genomic correlates of response to CTLA-4 blockade in metastatic melanoma," *Science* 350, pp. 207-211, hereby incorporated by reference were chosen.

Parameter $\tau$, a characteristic evolutionary time scale for a patient cohort, is a finite value at which cancer populations from tumors are expected to have responded to therapy Intuitively, this is the time at which samples are expected to have a resolved heterogeneity, with their highest fitness clone dominating the evolutionary dynamics. In other words, the parameter $\tau$ in the equation:

$$n(\tau) = \sum_\alpha X_\alpha \exp(F_\alpha \tau)$$

sets the characteristic time scale of response to therapy. At this time, clones with dominant neoantigens having amplitudes larger than $1/\tau$ will have been suppressed. In some embodiments, to estimate $\tau$, in the survival analysis the samples are split by the median cohort value $n(\tau)$ at a specified time scale $\tau$. Intuitively, this time should be set to a finite value at which the tumors are expected to have responded to therapy. At this value of $\tau$ the clonal heterogeneity of tumors is supposed to have decreased, with the highest fitness clone dominating in the population. For one tumor this time scale is inversely proportional to the standard deviation of intra-tumor fitness (i.e. of the order of $1/\sigma(F)$), where $$\sigma^2(F) = \sum_\alpha X_\alpha F_\alpha^2 - \left(\sum_\alpha X_\alpha F_\alpha\right)^2$$

In each cohort the interval of characteristic times of heterogeneous samples was determined. See, FIGS. 11, 12, and 13, the dependence of the prediction power on $\tau$ was tested by performing log-rank tests. See, FIGS. 14, 15, and 16. The optimal values of $\tau$ in each cohort belonged to a relatively wide interval. The consistent broadness of these intervals suggests low sensitivity of predictive power on $\tau$. Moreover, the parameter intervals giving highly significant patient segregation were also consistent between the cohorts.

Heterogeneous samples were selected with criterion $e^{H_F} \geq 2$, where $H_F$ is clonal fitness entropy defined as $$H_F = -\sum_\beta Y_\beta \log Y_\beta,$$

where the frequencies of clones with the same fitness are added together and denoted as $Y_\beta$. The index $\beta$ then refers to all clones with a given fitness.

Turning to FIG. 17, the survival landscape is defined by the log-rank test score as a function of the model parameters for the logistic curve shape, e.g. the midpoint (a) and steepness (k). The locally smoothed landscape is plotted for the FIG. 17 (A) Snyder et al., 2014, "Genetic Basis for Clinical Response to CTLA-4 Blockade in Melanoma," N. Engl. J. Med. 371, pp. 2189-2199, and FIG. 17 (B) Rizvi et al., 2015, "Mutational landscape determines sensitivity to PD-1 blockade in non-small cell lung cancer, Science 348, pp. 124-128, datasets. An X marks the optimal parameters from Van Allen et al., 2015, "Genomic correlates of response to CTLA-4 blockade in metastatic melanoma," Science 350, pp. 207-211., a=23 and k=1 (cf. FIG. 7), which are used to derive survival curves for these two datasets and are at high score regions of the landscapes.

In some embodiments, the survival log-rank test score is maximized to fit the binding curve parameters to the data on the largest dataset for Van Allen et al. (Van Allen et al., 2015, "Genomic correlates of response to CTLA-4 blockade in metastatic melanoma," Science 350, 207-211, which is hereby incorporated by reference) (103 metastatic patients). The same parameters are then used for validation in the two smaller datasets from Snyder et al., 2014, "Genetic Basis for Clinical Response to CTLA-4 Blockade in Melanoma," N. Engl. J. Med. 371, pp. 2189-2199, and Rizvi et al., 2015, "Mutational landscape determines sensitivity to PD-1 blockade in non-small cell lung cancer, Science 348, pp. 124-128, (64 and 34 patients respectively). See FIG. 7 and FIGS. 18-21. The parameters from Van Allen et al., yield consistently high survival log-rank scores in all three datasets. When using these logistic function parameters in all three datasets, the binding probability of 0.5 is obtained by alignments of average length of 6.55 amino acids; it is 6.98 amino acids for binding probability above 0.95.

Figure 8:
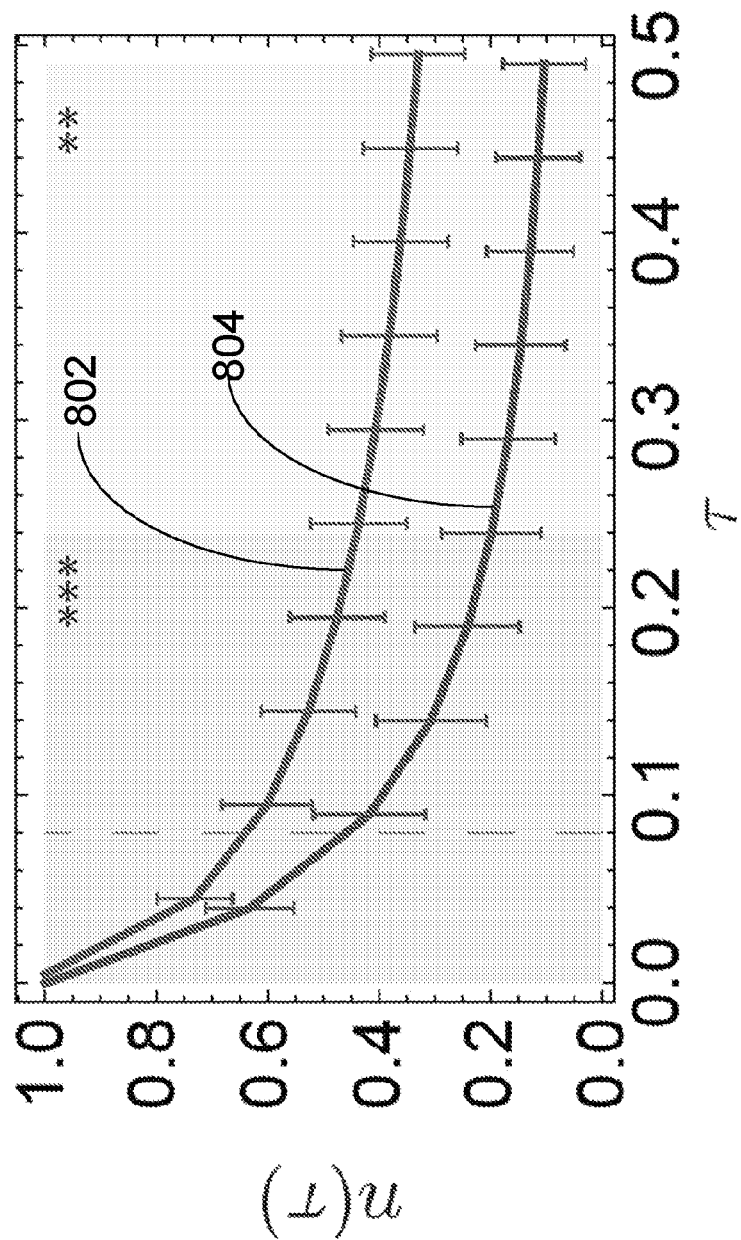
FIG. 8 illustrates distribution of predicted relative population size $n(\tau)$ for responders and non-responders at consistent parameters across the Van Allen et al., 2015, "Genomic correlates of response to CTLA-4 blockade in metastatic melanoma," Science 350, pp. 207-211 cohort. Responders and non-responders are as defined in Van Allen et al. Error bars are 95% confidence intervals around the population average. The dashed line indicates the consistent time scale $\tau=0.09$ used for patient survival predictions. The significance of the separation of the two groups was computed with Kolmogorov-Smirnov test, the p-value at $\tau=0.09$ is 0.0016. Background shading represents significance of separation of the two groups as a continuous function of $\tau$ (p<0.01, *p<0.001) in accordance with an embodiment of the present disclosure.
Figure 9:
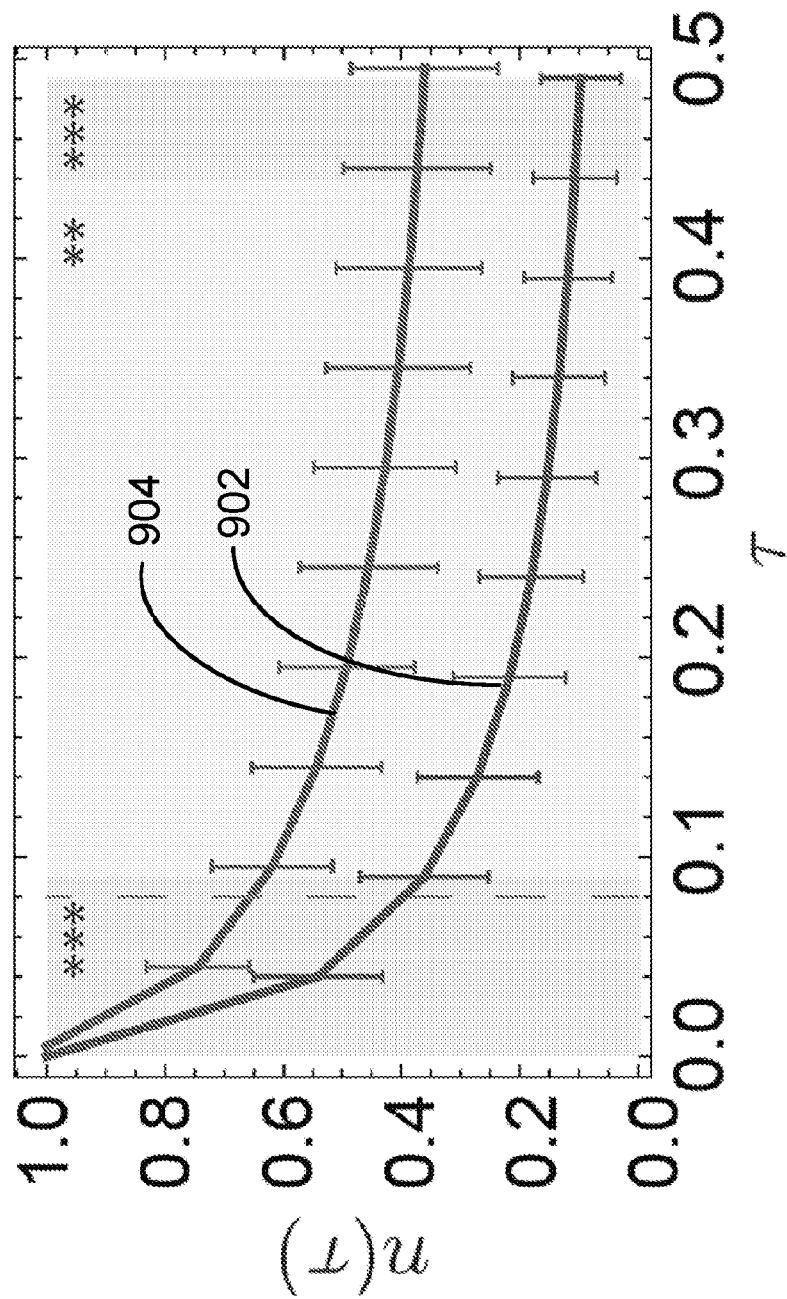
FIG. 9 illustrates distribution of predicted relative population size $n(\tau)$ for responders and non-responders at consistent parameters across the Snyder et al., 2014, "Genetic Basis for Clinical Response to CTLA-4 Blockade in Melanoma," N. Engl. J. Med. 371, pp. 2189-2199 cohort. Responders and non-responders are as defined in Synder et al. Error bars are 95% confidence intervals around the population average. The dashed line indicates the consistent choice of $\tau=0.09$ used for patient survival predictions. The significance of the separation of the two groups was computed with Kolmogorov-Smirnov test, the p-value at $\tau=0.09$ is 0.00084. Background shading represents significance of separation of the two groups as a continuous function of $\tau$ (p<0.01, *p<0.001) in accordance with an embodiment of the present disclosure.
Figure 10:
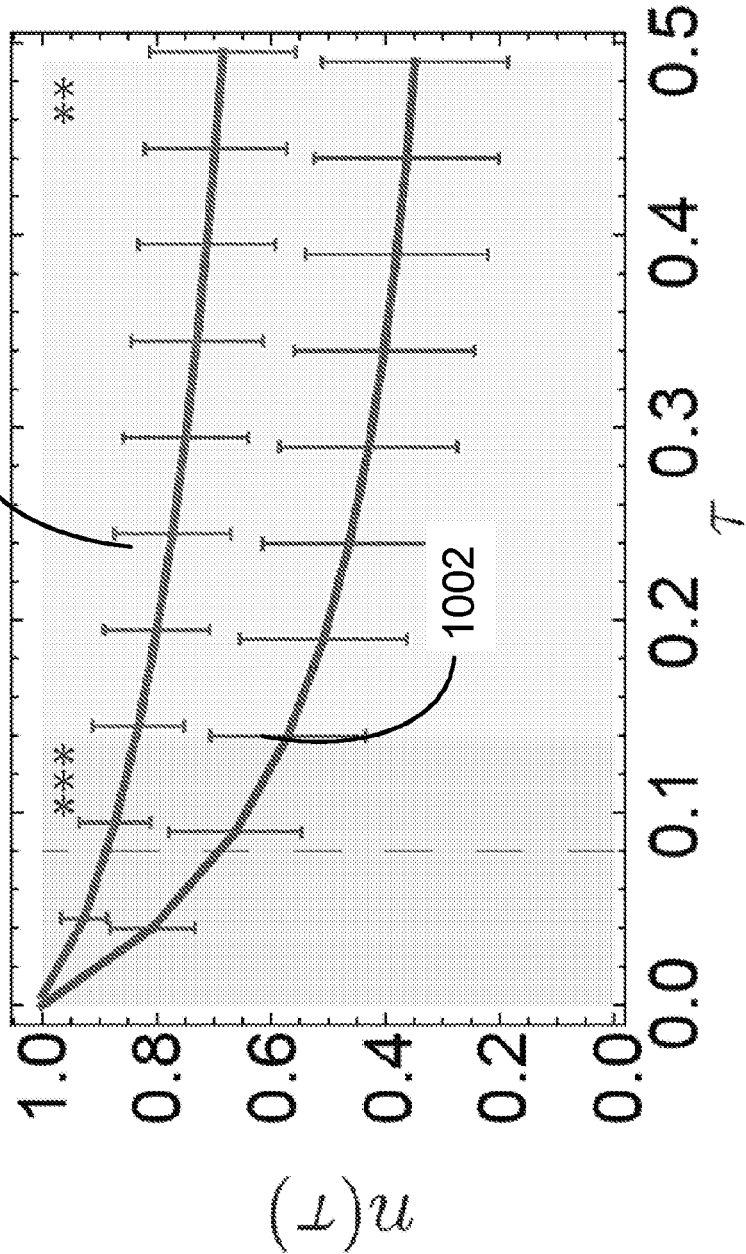
FIG. 10 illustrates distribution of predicted relative population size $n(\tau)$ for responders and non-responders at consistent parameters across the Rizvi et al., 2015, "Mutational landscape determines sensitivity to PD-1 blockade in non-small cell lung cancer," Science 348, pp. 124-128 cohort. Responders and non-responders are as defined in Synder et al. Error bars are 95% confidence intervals around the population average. The dashed line indicates the consistent choice of $\tau=0.09$ used for patient survival predictions. The significance of the separation of the two groups was computed with Kolmogorov-Smirnov test, the p-value at $\tau=0.09$ is 0.00071. Background shading represents significance of separation of the two groups as a continuous function of $\tau$(p<0.01, *p<0.001) in accordance with an embodiment of the present disclosure.

The predicted evolutionary dynamics of tumors naturally separates long- and short-term survivors (therapy responders and non-responders) in the datasets, using patient classifications defined in the original studies, as illustrated in FIGS. 8, 9, and 10. Long-term survivors (patients with survival time longer than two years in the Van Allen et al. and Snyder et al., 2014, "Genetic Basis for Clinical Response to CTLA-4 Blockade in Melanoma," N. Engl. J. Med. 371, pp. 2189-2199 datasets, and one year in Rizvi et al., 2015, "Mutational landscape determines sensitivity to PD-1 blockade in non-small cell lung cancer, Science 348, pp. 124-128 dataset) are predicted to have faster decreasing relative population sizes $n(\tau)$ across a broad ranges of $\tau$ values. The fitness of a cancer cell in a genetic clone $\alpha$ is its expected replication rate, i.e.

$$\frac{dN_\alpha}{d\tau} = F_\alpha N_\alpha$$

where $N_\alpha$ is the population size of clone $\alpha$. Checkpoint-blockade immunotherapy introduces a strong selection challenge, which is expected to overshadow pre-therapy fitness effects in a productive response. For a given clone $\alpha$ the dynamics of its absolute size are hence given by $N_\alpha(t) = N_\alpha(0) \exp(F_\alpha \tau)$, and the total cancer cell population size is computed as a sum over its clones:

$$N(\tau) = \Sigma_\alpha N_\alpha(\tau) = \Sigma_\alpha N_\alpha(0) \exp(F_\alpha \tau).$$

As the diagnostic of survival the relative population size $n(\tau) = N(\tau)/N(0)$ is used, which compares the predicted evolved population size after a characteristic time scale of evolution r (discussed below) to the initial pretreatment size $N(0)$. The initial clone $\alpha$ frequency is denoted $X_\alpha = N_\alpha(0)/N(0)$, these frequencies are inferred from bulk exome reads from a tumor sample. See Deshwar et al., 2015, "PhyloWGS: reconstructing subclonal composition and evolution from whole-genome sequencing of tumors," Genome Biol. 16, p. 35, which is hereby incorporated by reference. Hence, to compute $n(\tau)$ only estimates of the initial frequencies and fitness values for each clone are required, as shown in the following equation $$n(\tau) = \Sigma_\alpha X_\alpha \exp(F_\alpha \tau),$$

Thus, the absolute population size measurements are not needed. In this equation, and, referring to FIG. 4, the predicted relative size $n(\tau)$ of a cancer cell population in a tumor is computed as a weighted sum over its genetic clones, where $F_\alpha$ is the fitness and $X_\alpha$ is the initial frequency of clone $\alpha$ and $\tau$ is a characteristic evolutionary time scale. For each such model defined, its homogenous structure equivalent can be defined by assuming the tumor is strictly clonal with all neoantigens in the same clone at frequency 1.

Moreover, the neoantigen recognition potential fitness model $$F_\alpha = -\max_{i \in Clone\ \alpha}(A_i \times R_i),$$

results in highly significant separation of patients in survival analysis of all three datasets (FIGS. 11-16). The median value of $n(\tau)$ was used to separate patients into high and low predicted response groups. Using the median as opposed to an optimized threshold (See, Snyder et al., 2014, "Genetic Basis for Clinical Response to CTLA-4 Blockade in Melanoma," N. Engl. J. Med. 371, pp. 2189-2199; Van Allen et al., 2015, "Genomic correlates of response to CTLA-4 blockade in metastatic melanoma," Science 350, pp. 207-211; and McGranahan et al., 2016, "Clonal neoantigens elicit T cell immunoreactivity and sensitivity to immune checkpoint blockade," Science 351, pp. 1463-1469, each of which is hereby incorporated by reference) prevents over-fitting and allows for robust validation. Log-rank test p-values are p=0.04 for the Van Allen et al. (FIG. 11), p=0.0026 for Snyder et al., 2014, "Genetic Basis for Clinical Response to CTLA-4 Blockade in Melanoma," N. Engl. J. Med. 371, pp. 2189-2199 (FIG. 12), and p=0.00624 for Rizvi et al., 2015, "Mutational landscape determines sensitivity to PD-1 blockade in non-small cell lung cancer, Science 348, pp. 124-128 (FIG. 13). For comparison, a model considering only total neoantigen burden, is significant only for Rizvi et al., 2015, "Mutational landscape determines sensitivity to PD-1 blockade in non-small cell lung cancer, Science 348, pp. 124-128 (p=0.007), when also using unsupervised median partitioning of patients. An alternative neoantigen load model that only accounts for clonal structure was also used. Again, only the Rizvi et al., 2015, "Mutational landscape determines sensitivity to PD-1 blockade in non-small cell lung cancer," Science 348, pp. 124-128 cohort has a significant patient survival separation (p=0.03).

Parameter training. In some embodiments, the model has two other free parameters: the midpoint and steepness defining R. In some embodiments, these parameters are inferred by maximizing the survival log-rank test score on independent training data. In some embodiments, to choose model parameters a and k in the equation:

$$R = Z(k)^{-1} \sum_{e \in IEDB} \exp[-k(a - |s, e|)],$$

and the characteristic time $\tau$ at which the prediction is evaluated in the equations:

$$F_\alpha = \max_{i \in Clone\ \alpha} (A_i \times R_i)$$

$$n(\tau) = \sum_\alpha X_\alpha \exp\left[-\max_{i \in Clone\ \alpha}(A_i \times R_i)\tau\right]$$

the parameters that maximize log-rank-test scores of survival analysis on patient cohorts are identified. The survival analysis is performed by splitting patient cohort by the median value of $n(\tau)$ into high and low fitness groups. For each of the three cohorts, a parameter training is performed on independent data: the melanoma cohorts are used to train parameters for each other by using the maximal score of one to define parameters for the other, and both melanoma cohorts and maximization of their total log-rank test score is used to train parameters for the lung cohort. To infer consistent parameters between all datasets, the total log-rank test score over the three cohorts is maximized.

For a given training the optimal parameters $\hat{\Theta} = [\alpha, k, \tau]$ is computed, as an average $\hat{\Theta} = \langle \hat{\Theta} \rangle$, over a distribution $w(\Theta)$ defined by the log-rank test score landscape on this set $$w(\Theta) = Z^{-1}(\lambda)\exp[\lambda(S_{max} - S(\Theta))],$$

where $Z(\lambda)$ is the probability distribution normalization constant, $S(\Theta)$ is the value of the log-rank test score with parameters $\Theta$, and $S_{max}$ is the maximal score value obtained over all possible parameters. The weight parameter $\lambda$ is chosen such that the total statistical weight of the suboptimal parameter region is less than 0.01, the suboptimal scores are those less than $\max(3.841, S_{max}-2)$ (where 3.841 is the score value corresponding to 5% significance level of the log-rank test score). Using a smooth local neighborhood of parameters around the optimal values prevents over-fitting on a potentially rugged score landscape. For each individual parameter, the error bars reported in FIGS. 23-25, and FIGS. 32A, 32B, and 32C are computed as standard deviation using marginalized probability distribution w(0) for this parameter.

The survival score landscape, as illustrated in FIG. 33, are consistent between the datasets. The optimal value of parameter a, the midpoint of the logistic binding function, is around 26 and parameter k, the steepness of the logistic function, lives on a trivial axis above value 4, suggesting strong nonlinear fitness dependence on the sequence alignment score.

We use the Snyder melanoma cohort with 64 patients to train parameters for the 103 metastatic patients in the Van Allen cohort and vice versa; we use the total score of both melanoma cohorts to train parameters for the smaller lung cancer cohort from Rizvi et al. with 34 patients (Methods). For each cohort, significant stratification of patients is obtained: log-rank test p-values are p=0.0049 for the Van Allen et al., p=0.0026 for Snyder et al., and p=0.0062 for Rizvi et al. (FIGS. 23-25). The parameters thereby obtained are consistent between datasets and mutually included within each other's error bars (FIGS. 23-25). A joint optimization of the cumulative log-rank test score of the three cohorts was further performed, obtaining a single set of parameters with predictions highly stable around these values (FIG. 33). The alignment threshold parameter is consistently set to 26 (FIGS. 23-25), which in the datasets is obtained by alignments of average length of 6.8 amino-acids, just above the length of peptide motifs one would expect the TCR repertoire to discriminate. There are approximately 108 unique T-cell receptors in a given human (Arstila et al., 1999, "A direct estimate of the human αβ T cell receptor diversity," Science 286, pp. 958-961), and, moreover, the genome wide entropy of amino acid usage is approximately 2.9023. Therefore, one expects the length, L, of words TCRs can typically discriminate to be given by $10^8 \approx e^{2.901}$ on average (as opposed to say $20^L$ if one assumed uniform genome amino acid usage). Solving for this length yields $L \approx 6.35$. The slope parameter is set to 4.87 defining a strongly nonlinear dependence on alignment score, with the recognition probability dropping below 0.01 for score 25 and reaching above 0.99 at score 27 (FIG. 29). The r parameter is set to 0.09, meaning clones with amplitudes larger than 11.1 are, on average, suppressed at prediction time. At these consistent parameters, separation of patients does not change for Van Allen et al. and Rizvi et al. (log-rank score increases by less than 1 unit, p=0.004 for Van Allen et al. and p=0.0062 for Rizvi et al.), and it improves to p=0.00026 for Snyder et al. (FIGS. 11-16). Patient segregation by $n(\tau)$ evaluated at infinitesimally small r (equivalent to average tumor fitness over clones) is also significant (FIGS. 23-25, and 33), suggesting predictive power depends more on the model's ability to capture immune interactions than the duration of evolutionary projections. The performance of the model deteriorates when we disrupt the biological relevance of input data. When using the IEDB epitopes not supported by positive T-cell assays, the model loses predictive ability in both melanoma cohorts (FIGS. 23-25, and 30A-30F). Similarly, the model generally does not give significant patient separations when using neoantigens derived with randomized patient HLA types (FIG. 35, Example VI). The success of the disclosed model strongly depends on the joint contribution of A and R in the equation:

$$F_\alpha = -\max_{i \in Clone\ \alpha}(A_i \times R_i)$$

Partial models with only one component were constructed and the same training and validation procedure was repeated, with survival analysis separating patients in equal size groups as in the full model (FIGS. 11-16, and 23-25). In all datasets, partial models have lower log-rank scores than the full model and neither A nor R-only models result in significant segregation for any cohort. We also compare our full model with a neoantigen load model, which assigns a uniform fitness cost to each neoantigen. This model does not significantly separate patients by median in either cohort (FIGS. 11-16, and 23-25).

Model components. The success of the disclosed neoantigen recognition potential fitness model depends on the joint contribution of two fitness components, the MHC presentation amplitude A and TCR recognition probability R in the equation:

$$F_\alpha = -\max_{i \in Clone\ \alpha}(A_i \times R_i)$$

where index i iterates over all neoantigens in respective clone α.

MHC amplitude A. The amplitude due to the dissociation constant between a neoantigen and its wildtype peptide is defined as:

$$S = K_D^{WT}/K_D^{MT}.$$

This is an approximate form derived with the use of equilibrium kinetics, where the concentration of peptide bound to MHC is given by their individual concentrations and inferred binding constant $K_D$, derived from NetMHC. See, Andreatta et al., 2016, "Gapped sequence alignment using artificial neural networks: application to the MHC class I system, Bioinformatics 32, pp. 511-517, which is hereby incorporated by reference. The underlying dependencies are:

$$A = [MHC:neoantigen]^{MT}/[MHC:neoantigen]^{WT}$$
$$= (K_D^{WT}[MHC]^{MT}[neoantigen]^{MT})/$$
$$(K_D^{MT}[MHC]^{WT}[neoantigen]^{WT}),$$

where $[MHC:neoantigen]^{MT}$ is the concentration of the mutant form of the neoantigen to MHC, with the WT superscript representing the same quantity for the wild-type peptide. The above quantity is assumed to be dominated by the ratio of dissociation constants which derives the formula for A in the equation $A=K_D^{WT}/K_D^{MT}$. A standard cutoff, $K_D^{MT}<500$ nM, for the inferred mutant dissociation constant is used. See, Andreatta et al., 2016, "Gapped sequence alignment using artificial neural networks: application to the MHC class I system, Bioinformatics 32, pp. 511-517, which is hereby incorporated by reference.

The predictive power of amplitude A, as illustrated in FIGS. 11-16, can be related to the fact that this quantity reflects the relative concentration of mutant to wildtype peptide and therefore the likelihood that the mutant peptide would be presented versus its wildtype peptide. As neoantigens with mutations on positions 2 and 9, are excluded, a high value of amplitude means the wildtype also likely already has hydrophobic residues at the anchor position and could be presented. Since neoantigens differ from their wildtype peptides by a single mutation, and given the uniqueness of nonamer sequences in the proteome, as illustrated in FIG. 22, the self-nonamer in the genome with the greatest similarity to a neoantigen is likely to be its wildtype peptide. This was verified to be the case for 92% of all neoantigens, with the remainder largely emanating from gene families with many paralogs (Example II), implying a high amplitude usually stands for a self peptide not likely to be abundantly presented by the MHC. Therefore, as its immunogenicity is not mitigated by a homologous self-peptide, the mutant peptide with high affinity is likely to be novel to T-cells.

TCR-recognition. R is modeled as the recognition potential 224 of a neoantigen with a TCR-pool defined as the probability that a neoantigen cross-reacts with at least one TCR corresponding to a known immunogenic epitope. The recognition potential 224 of neoantigen is profiled in silico with a set of epitopes given by the Immune Epitope Database and Analysis Resource (IEDB). See Vita et al., 2014, "The immune epitope database (IEDB) 3.0," Nucleic Acids Res. 43, D405-D412, which is hereby incorporated by reference. Only IEDB epitopes that are positively recognized by T-cells after class I MHC presentation are used on the basis that a neoantigen that is predicted to cross-react with a TCR from this pool of immunogenic epitopes is a neoantigen more likely to be immunogenic itself.

The probability that a TCR for a given epitope binds a given neoantigen is defined by a two-state thermodynamic model with logistic shape. In this model we use sequence alignment as a proxy for binding energy. See Berg and von Hippel, 1987, "Selection of DNA binding sites by regulatory proteins: Statistical-mechanical theory and application to operators and promoters, J. Mol. Biol. 193, pp. 723-743, which is hereby incorporated by reference.

To assess homology between a neoantigen with peptide sequence s and an IEDB epitope e, an alignment (e.g., gapless, or an alignment that allows gaps with suitable gap introduction and extension penalties) between the two sequences is computed with a BLOSUM62 amino-acid similarity matrix. See Henikoff and Henikoff, 1992, "Amino acid substitution matrices from protein blocks," Proc. Natl. Acad. Sci. USA 89, pp. 10915-10919, which is hereby incorporated by reference. For an alignment score, |s, e|, the binding probability is computed as $$Pr_{binding}(s, e) = \frac{1}{1 + e^{-k(|s,e|-a)}},$$

where a represents the horizontal displacement of the binding curve and k sets the steepness of the curve at a. These are two free parameters to be fit in the model. The parameters that are used in predictions in the instant example are a=23 and k=1; these parameters give binding probability $Pr_{binding}$ (s, e)=0.5 at alignment score |s, e|=23; the probability drops to below 0.05 at |s, e|=20 and reaches value of above 0.95 at |s, e|=26. See FIG. 7. The corresponding alignment score span of 6 is close to the average identity match score in the BLOSUM62 matrix (5.64). The average alignment length corresponding to score 26 is 6.98 amino acids in the datasets and it is 6.55 for binding probability 0.5. The logistic function is therefore a strongly nonlinear function of the alignment score, where a mismatch on 1-2 positions can decide about lack of binding between the neoantigen and the epitope specific TCR.

For a given neoantigen s we calculate the probability it is recognized by a TCR within a repertoire as the probability it cross-reacts with at least one IEDB epitope:

$$R = 1 - \Pi_{e \in IEDB}[1 - Pr_{binding}(s,e)].$$

The model $$F_\alpha = -\max_{i \in Clone\ \alpha}(A_i \times R_i)$$

is decomposed by removing each of the components one at a time (FIGS. 14, 15, and 16). The MHC-only model, achieved by fixing $R_i=1$, results in consistently worse segregation of patients (not significant in Snyder et al., 2014, "Genetic Basis for Clinical Response to CTLA-4 Blockade in Melanoma," N. Engl. J. Med. 371, pp. 2189-2199, decreased significance in Van Allen, et. al, and Rizvi et al., 2015, "Mutational landscape determines sensitivity to PD-1 blockade in non-small cell lung cancer, Science 348, pp. 124-128, p=0.033 and p=0.013 respectively). The TCR-recognition-only model, achieved by fixing $A_i=1$, does not result in a significant segregation in any cohort.

It is of interest to assess the clonal structure of a tumor when trying to identify dominant neoantigens. The importance of tumor clonal structure in our identification of dominant neoantigens. In all data sets, the full clonal model performs significantly better than an alternative model assuming homogenous tumor structure (FIGS. 11-16). Clonality appears less crucial in partial models, which have either marginal or no statistical significance (FIGS. 11-16, 32A, 32B, and 32C). Moreover, the full model is predictive independent of other clinical correlates (Proportional Hazard model, FIG. 36).

The disclosed framework allows for straightforward incorporation of information about the tumor's microenvironment. For the cohort from Van Allen et al., gene expression data is available on 40 patients and local cytolytic activity is significantly associated with benefit (p=0.04, Example IV, below), as also observed in the original study by Van Allen et al., 2015, "Genomic correlates of response to CTLA-4 blockade in metastatic melanoma," Science 350, pp. 207-211. As a proof of principle, cytolytic score (Rooney et al., 2015, "Molecular and genetic properties of tumors associated with local immune cytolytic activity," Cell 160, pp. 48-61) was incorporated as an amplitude multiplying the T-cell recognition probability. Its inclusion improves predictions on these 40 patients, as assessed with survival analysis, (p=0.043 and p=0.0025 respectively, FIG. 34).

In a broader context, the model suggests strong similarities in the evolution of cancers and fast-evolving pathogens. In both systems, immune interactions govern the dynamics of a genetically heterogeneous population; fitness models can predict important aspects of these dynamics, as recently shown for human influenza A. See, Luksza and Lassig, 2014, "Predictive fitness model for influenza," Nature 507, pp. 57-61, which is hereby incorporated by reference. Yet there are important differences. Influenza evolution is determined by antigenic similarity with previous strains in the same lineage whereas cancer cells acquire somatic mutations in a large set of proteins. Hence, their immune interactions are distributed in a larger and less homogenous antigenic space. The fitness effects of these interactions have a specific interpretation: they capture neoantigen "non-selfness." The model formalizes what makes a tumor immunologically different from its hosts, analogously to models for innate recognition of non-self nucleic acids. See, Tanne et al., 2015, Distinguishing the immunostimulatory properties of noncoding RNAs expressed in cancer cells.," Proc. Natl. Acad. Sci. USA 112, pp. 5154-15159, which is hereby incorporated by reference.

The disclosed approach naturally extends to other fitness effects, such as positive selection due to acquisition of driver mutations, the impact of additional components in the microenvironment, or the hypothesized role of the microbiome. See, Vétizou et al., 2015, "Anticancer immunotherapy by CTLA-4 blockade relies on the gut microbiota." Science 350, pp. 1079-1084; and Dubin et al., 2016, "Intestinal microbiome analyses identify melanoma patients at risk for checkpoint-blockade-induced colitis." Nat. Commun. 7, p. 10391 (2016). Further advances in predicting proteosomal processing (Abelin et al., 2017, Mass spectrometry profiling of HLA-associated peptidomes in mono-allelic cells enables more accurate epitope prediction." Immunity 46, pp. 315-326) and stability (Strønen et al., 2016, "Targeting of cancer neoantigens with donor-derived T cell receptor repertoires," Science 352, pp. 1337-1341) of neoantigen-MHC binding could improve predictions. The disclosed approach is also useful in studies on acquired resistance to therapy. Moreover, this insight may be crucial for understanding when cross-reactivity with self-peptides may result in side effects. See Johnson et al. 2016, "Fulminant myocarditis with combination immune checkpoint blockade, New Engl. J. Med. 375, pp. 1749-1755; and Hofmann et al., 2016, "Cutaneous, gastrointestinal, hepatic, endocrine, and renal side-effects of anti-PD-1 therapy," European J. Cancer 60, 190-209, each of which is hereby incorporated by reference. Because the proposed neoantigen recognition potential fitness model is based on specific interactions underlying the presentation and recognition of neoantigens, it may also inform the choice of therapeutic targets for tumor vaccine design.

Example II

Identification of closest nonamers in human proteome to neoantigens. This example illustrates identification of closest nonamers in human proteome to neoantigens. The wildtype (WT, 9 matches) and mismatched type (MT, 8 matches, 1 mismatch) 9-mer peptides to all proteins in the current human reference genome (GRCh38.p7) with at least 8 out of 9 matches and no gaps (allowing only mismatches) were mapped using LAST (version 819) (see Kielbasa et al., 2011, "Adaptive seeds tame genomic sequence comparison," Genome Res. 21, pp. 487-493, which is hereby incorporated by reference) with the following parameters:

lastal-f   BlastTab-j1-r2-q1-e15-y2-m100000000-14-L4-P0 where 9-mer mapping with at most one mismatch is guaranteed to have a matching 4-mer word.

One expects the mutated peptide to only map to the same location as the wildtype peptide, wildtype mapping exactly (9 matches) and MT mapping with one mismatch (8 matches). The expected case is that the wildtype peptide maps to the proteome exactly and the MT peptide maps to the proteome with one mismatch and only to the loci wildtype peptide maps to.

This rule can be violated in the following cases, sorted from the most to the least severe:

1. WT peptide does not map to the proteome exactly. Some possible reasons are: a difference in the reference assemblies used for mutation calling and peptide mapping, a germline mutation mistakenly identified as somatic, or a difference between the patient genome and the reference genome used for alignments.

2. WT peptide maps to the proteome exactly (9 matches), MT peptide maps to the proteome exactly (9 matches) but to a different locus.

3. WT peptide maps to the proteome exactly, MT peptide maps to the proteome with one mismatch; however, MT peptide maps with one mismatch to the subjects WT does not map exactly.

4. WT peptide maps to the proteome exactly, MT peptide maps to the proteome with one mismatch; however, MT peptide maps with one mismatch to a different locus on the gene WT maps to.

Each peptide was examined for the worst possible scenario, going from category 1 to 4 in the list. Category 1 indicates a difference in the reference genome. Categories 2-4 typically are due to mutations that occur in repetitive gene families with many paralogs. Once a peptide was identified as belonging to any category, it was excluded from further considerations. In this way, the numbers of peptides in each category add up to the total number of peptides. Below is a summary for the different datasets utilized in this study:

Van Allen, et al., 2015, "Genomic correlates of response to CTLA-4 blockade in metastatic melanoma, Science 350, pp. 207-211, hereby incorporated by reference:
  39373 total peptides,
  (category 1)
    42 WT unmapped, leaving 39331
    36783 expected peptides (93.42%),
  (category 2) 387 have 9 matches in MT,
  (category 3) 2076 have other alignments, and
  (category 4) 85 have other alignments to the same subject;

Snyder, et al., 2014, "Genetic Basis for Clinical Response to CTLA-4 Blockade in Melanoma, N. Engl. J. Med. 371, pp. 2189-2199, hereby incorporated by reference:
  29781 total peptides,
  (category 1)
    35 WT unmapped, leaving 29746
    27674 expected peptides (92.93%),
  (category 2) 361 have 9 matches in MT,
  (category 3) 1644 have other alignments, and
  (category 4) 67 have other alignments to the same subject; and Rizvi, et al., 2015, "Mutational landscape determines sensitivity to PD-1 blockade in non-small cell lung cancer," Science 348, pp. 124-128 (2015), hereby incorporated by reference:
  5581 total peptides,
  (category 1)
    6 WT unmapped, leaving 5575
    5125 expected peptides (91.83%),
  (category 2) 105 have 9 matches in MT,
  (category 3) 323 have other alignments, and
  (category 4) 22 have other alignments to the same subject.

Example III

In some embodiments, amplitude A is computed as follows. MHC-binding probabilities are derived from the dissociation constants, which are themselves estimated from computationally predicted binding affinities, as justified in the present disclosure. Affinities are inferred for each peptide sequence and patient HLA type (Andreatta and Nielsen, 2016, Bioinformatics 32, p. 511); all mutant peptide sequences considered as neoantigens meet a standard 500 nM cutoff for their affinities. NetMHC 3.4 occasionally predicts affinities with very high values where training may be limited, and creating small denominators that can inflate the amplitude. In melanoma and lung cancer a high mutational burden inflates the frequency of such events. As a remedy, a pseudocount, $\varepsilon$, is introduced so that, for both mutant and wildtype peptides $P_U/P_B \rightarrow (P_U+\varepsilon)/(P_B+\varepsilon)$. In this case the new dissociation constant divided by peptide concentration becomes $$\frac{K_d/[L] + \varepsilon(1+K_d/[L])}{1+\varepsilon(1+K_d/[L])} \approx \frac{K_d/[L]}{1+\varepsilon K_d/[L]}$$

for small $\varepsilon$, where $K_d$ was the original dissociation constant and [L] is the peptide concentration. Consequently $1/\varepsilon$ sets a scale at which dissociation constants are not reliable for large $K_d$ at a given concentration. To fix these scales, it is noted that assays to determine dissociation constants for peptide-MHC binding are typically performed at 0.1-1 nM where the ligand concentration is typically small compared to the dissociation constant. See, Paul, 2013, J. Immunl. 191, p. 5831. In this regime, affinities can be interpreted as dissociation constants and 3687 nM is the outer range of predictability for the assays upon which NetMHC 3.4 is trained at no more that unit peptide concentrations. $\varepsilon/[L]$ is therefore chosen to be 0.0003≈1/3687 across datasets.

In embodiments where the affinity is less than 500 nM for the mutant peptide this correction is only relevant for the wildtype peptides. The corrected amplitude then becomes:

$$A \approx \frac{K_d^{WT}}{K_d^{MT}} \cdot \frac{1}{1+(\varepsilon/[L]) \cdot K_d^{WT}}$$

The amplitude in this form, combined with the TCR-recognition term, has a high predictive value for patient survival predictions (FIGS. 8-10), consistently over the three patient cohorts, which is not the case of either the mutant or wildtype dissociation constants on their own. FIGS. 23-25).

Example IV

Inclusion of Microenvironment and Proteosomal Processing in the Neoantigen Recognition Potential Fitness Model. The role of the microenvironment in the likelihood of productive T-cell recognition of tumor neoantigens can be incorporated in a natural manner into the disclosed modeling framework. We utilize the cytolytic score (CYT), the geometric mean of the transcript per kilobase million of perforin and granzyme (Rooney et al., 2015, "Molecular and genetic properties of tumors associated with local immune cytolytic activity," Cell 160, pp. 48-61. We do so for the 40 patients from the Van Allen, et al., anti-CTLA4 melanoma dataset, which have matched genome and transcriptome sequencing and where CYT had shown predictive value. For this set we also derive the CD8 T-cell fraction using CIBERSORT. See, Newman et al., 2015, "Robust enumeration of cell subsets from tissue expression profiles. Nature Methods 12, pp. 453-457). The two values have a Pearson correlation coefficient of 0.938. Given their encapsulation of similar information we used CYT as it had previously been show to give significant segregation of patient benefit. See Van Allen, et al., 2015, "Genomic correlates of response to CTLA-4 blockade in metastatic melanoma," Science 350, pp. 207-211. The score provides an additional amplitude $A_{CYT}$ and the recognition potential becomes $A_{CYT} \times A \times R$. Therefore, the cytolytic score amplifies the recognition potential by the degree of cytolytic activity. We attempted to include proteosomal processing into our model as an additional criterion, as evaluated with NetCHOP. See, Nielsen et al, 2005, "The role of the proteasome in generating cytotoxic T cell epitopes: Insights obtained from improved predictions of proteasomal cleavage," Immunogenetics 57, pp. 33-41. We tested this procedure on the Rizvi et al. cohort; however, the imposed stronger filtering of neoantigens leads to the loss of predictive power of the model.

Example V

IEDB sequences. The predictive value of R depends on the input set of IEDB sequences. In some embodiments, the set used in the disclosed analysis contained 2552 unique epitopes. We tested how the predictions depend on the content and size of the dataset by performing iterative subsampling of IEDB sequences at frequencies varying from 10% to 90% of the total set size. We repeated the survival analysis and log-rank test score evaluation (FIGS. 31-36). For all three datasets removal of sequences has on average a negative impact on their predictive power, which monotonically decreases with the subsampling rate. In the Van Allen et al. cohort median performance was below significance already at 70% subsampling and lower, and for Snyder et al. and Rizvi et al. at 20% and lower. To investigate the biological input associated with the set of curated IEDB sequences that we use, we also evaluated the R component using an alternative set of IEDB sequences, coming from T-cell assays that did not have a positive validation. This is a larger set of 4657 sequences. In the two melanoma datasets, the predictions have gotten worse, not giving significant separation of patients in the survival analysis. This effect was also not due to the different sequence set size—subsampling of sequences did not improve the outcome. While in the Rizvi et al. dataset the predictions were still significant, this significance was not supported by consistency between all three datasets which is observed on the IEDB sequence set with positive assays.

Example VI

Alternative fitness models. The full neoantigen recognition potential fitness model $$n(\tau) = \sum_\alpha X_\alpha \exp\left[-\max_{i \in Clone\ \alpha}(A_i \times R_i)\tau\right].$$

is compared to alternative models using model decompositions, where only one component is used $$F_\alpha = -\max_{i \in Clone\ \alpha}(A_i),$$

$$F_\alpha = -\max_{i \in Clone\ \alpha}(R_i).$$

Further, the amplitude $$A = K_d^{WT} \times \frac{1}{K_d^{MT}}$$

is decomposed and various variants of the model tested, with and without the R component, $$F_\alpha = -\max_{i \in Clone\ \alpha} K_{d_i}^{WT}(\times R_i),$$

$$F_\alpha = -\max_{i \in Clone\ \alpha} \frac{1}{K_{d_i}^{MT}}(\times R_i).$$

How informative the alignments contributing to the $R_i$ components are is investigated and a model where alignments are restricted to the 6 residues in-between anchor positions, on positions 3-8, is also tested. The loss of predictive power of a model that does not implement any filtering of neoantigens mutated on position 2 and 9 is also demonstrated (see FIG. 31). The problem of choosing the neoantigen aggregating function is reduced to that of model selection. A model where fitness is defined by the total effect of all neoantigens in the clone (which is the limit case of $\beta=0$ in the equation:

$$n(\tau, \beta) = \sum_\alpha X_\alpha \exp\left[\sum_{\substack{max \\ i \in Clone\ \alpha}} \frac{\exp(-\beta f_i)}{Z(\beta)} f_i \tau\right].$$

is also tested as:

$$F_\alpha = -\sum_{i \in Clone\ \alpha} A_i \times R_i.$$

Finally, a fitness model is formulated that associates a constant fitness cost with each neoantigen, $$F_\alpha = -L_\alpha,$$

where $L_\alpha$ is the number of neoantigens in clone $\alpha$, referred to as the neoantigen load of clone $\alpha$.

Example VII

Homogenous structure models. For each fitness model, its homogenous structure equivalent can be defined, which assumes a tumor is strictly clonal with all neoantigens in the same clone at frequency 1. In a homogenous model the population size is thus modeled by an exponential, $$n(\tau) = \exp[F\tau],$$

where F is the fitness function of the homogenous tumor. Since in this model tumors show a constant decay over time, ranking of $n(\tau)$ values for patients is defined only by fitness and does not depend on $\tau$. Therefore, $\tau$ is not a free parameter in these models when optimizing log-rank test score in survival analysis.

Example VIII

Average fitness. The average fitness of clones was also investigated:

$$\langle F \rangle = \sum_\alpha X_\alpha F_\alpha,$$

as a predictive marker for patients and an alternative to n(τ). The average fitness reflects the rate at which the tumor cell population is decreasing in size at the beginning of therapy. For the purpose of patient ranking, it is equivalent to n(τ) at infinitesimally small values of the time parameter τ. This is a lower complexity model because τ is not a free parameter. However, this measure is less robust to outliers—small clones with very low fitness can dominate the average fitness, while the evolutionary projection in n(τ) removes such effects.

Example IX

Comparison with Thresholded Neoantigen Load.

In the disclosed survival analysis, a standard, non-optimized partitioning of patients into two equally sized groups by the median value of n(τ) was used. This approach allows for unbiased comparison of models, and assigns a stringent predictive value. The disclosed results do not contradict the earlier reported predictive quality of neoantigen load. Consistent with Snyder et al., a significant split at a threshold value of 100 neoantigens or less is observed. This threshold classifies more than 70% of the patients in a long-term surviving group; separation by total neoantigen load is not significant at lower fractional partitions, including the median. In Van Allen et al., survival analysis was not originally presented and we did not see a significant separation of patients at any possible splitting by a neoantigen load threshold. Finally, the significant separation for the Rizvi et al. cohort is observed for the range a 32-50% range of partitions, including by the median (FIGS. 11-16, and 23-25). It is worth noting that for this cohort we use previously unpublished overall survival data, which differs from the progression free survival data used by the original study (Rizvi, et al. 2015, "Mutational landscape determines sensitivity to PD-1 blockade in non-small cell lung cancer," Science 348, 124-128). In all cohorts, the disclosed neoantigen recognition potential fitness model and partitioning based on n(τ) measure give significant separations at a larger range of partitions: 40-60% for the Van Allen et al. cohort, above 40% for the Snyder et al. cohort and 47-80% for the Rizvi et al. cohort.

Example X

Introduction

PDAC represents a class of solid tumors that has remained largely refractory to checkpoint immunotherapy. Although T cell immunity has been linked to this rare outcome[7-10], the relevant tumor antigens remain unknown. Immune checkpoint blockade can amplify spontaneous T cell recognition of neoantigens that arise in cancer-specific mutations[11,12], and elicit responses in heavily mutated tumors[13-15]. However, it is unclear if primary checkpoint blockade resistance in tumors with fewer mutations occurs due to diminished endogenous T cell reactivity to neoantigens.

Results

Figure 42A:
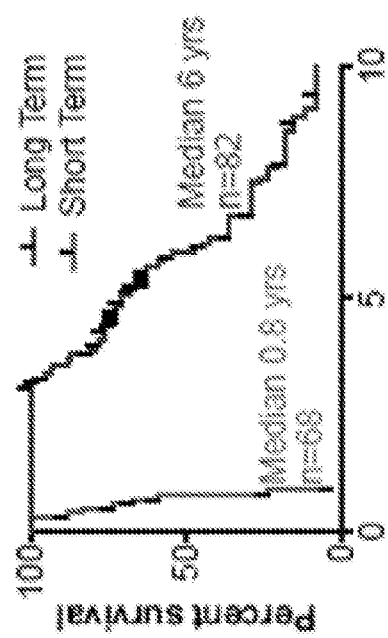

To define the significance of neoantigens in these patients, stage-matched cohorts of treatment-naïve, surgically resected, rare long term survivors (median survival 6 years) was compare to short term survivors with more typical poor outcome (median survival 0.8 years) (FIG. 42A, Tables 3-6, FIGS. 41A and 41B).

TABLE 3

Clinicopathologic characteristics of patients in tissue microarray cohort.

| Variable | Short Term (n = 45) n (%) | Long Term (n = 51) n (%) | P-value |
|---|---|---|---|
| Gender | | | |
| Male | 24 (53) | 26 (51) | NS |
| Female | 21 (47) | 25 (49) | |
| Age | | | |
| Median (Range) | 78 (54-91) | 74 (38-95) | NS |
| Tumor Location | | | |
| Head | 32 (71) | 37 (73) | NS |
| Body/Tail | 13 (29) | 14 (27) | |
| Procedure | | | |
| Distal Pancreatectomy | 13 (29) | 13 (25) | NS |
| Pancreaticoduodenectomy | 31 (69) | 37 (73) | |
| Total Pancreatectomy | 1 (2) | 1 (2) | |
| Pathological Stage | | | |
| I | 0 (0) | 2 (4) | NS |
| II | 38 (84) | 47 (92) | |
| III | 4 (9) | 2 (4) | |
| IV* | 3 (7) | 0 (0) | |
| pT | | | |
| 1 | 0 (0) | 0 (0) | NS |
| 2 | 0 (0) | 2 (4) | |
| 3 | 42 (96) | 47 (92) | |
| 4 | 3 (4) | 2 (4) | |
| pN | | | |
| 0 | 11 (24) | 21 (41) | NS |
| 1 | 34 (76) | 30 (59) | |
| pM | | | |
| 0 | 42 (93) | 51 (100) | NS |
| 1* | 3 (7) | 0 (0) | |
| Margin | | | |
| Positive | 8 (18) | 2 (4) | 0.03 |
| Negative | 37 (82) | 49 (96) | |
| Adjuvant Treatment | | | |
| Yes | 24 (53) | 42 (82) | 0.0077 |
| No | 20 (45) | 9 (18) | |
| Unknown | 1 (2) | 0 (0) | |

*One patient had liver metastasis noted on final pathology. One patient had distal pancreatectomy and metastasis to small bowel/mesentery. One patient had splenic metastasis.

TABLE 4

Clinicopathologic characteristics of patients 829 in transcriptome profiling cohort.

| Variable | Short Term (n = 15) n (%) | Long Term (n = 15) n (%) | P-value |
|---|---|---|---|
| Gender | | | |
| Male | 8 (53) | 5 (33) | NS |
| Female | 7 (47) | 10 (67) | |
| Age | | | |
| Median (Range) | 76 (54-84) | 65 (51-95) | NS |
| Tumor Location | | | |
| Head | 10 (67) | 12 (80) | NS |
| Body/Tail | 5 (33) | 3 (20) | |

TABLE 4-continued

Clinicopathologic characteristics of patients 829 in transcriptome profiling cohort.

| Variable | Short Term (n = 15) n (%) | Long Term (n = 15) n (%) | P-value |
|---|---|---|---|
| Procedure | | | |
| Distal Pancreatectomy | 5 (33) | 3 (20) | NS |
| Pancreaticoduodenectomy | 10 (67) | 12 (80) | |
| Pathological Stage | | | |
| I | 1 (0) | 0 (0) | NS |
| II | 12 (80) | 14 (93) | |
| III | 1 (7) | 1 (7) | |
| IV* | 2 (13) | 0 (0) | |
| pT | | | |
| 1 | 0 (0) | 0 (0) | NS |
| 2 | 0 (0) | 0 (0) | |
| 3 | 13 (87) | 14 (93) | |
| 4 | 2 (13) | 1 (7) | |
| pN | | | |
| 0 | 5 (33) | 6 (40) | NS |
| 1 | 10 (67) | 9 (60) | |
| pM | | | |
| 0 | 13 (87) | 15 (100) | NS |
| 1* | 2 (13) | 0 (0) | |
| Margin | | | |
| Positive | 4 (27) | 1 (7) | NS |
| Negative | 11 (73) | 14 (93) | |
| Adjuvant Treatment | | | |
| Yes | 10 (67) | 13 (87) | NS |
| No | 4 (26) | 2 (13) | |
| Unknown | 1 (7) | 0 (0) | |

*One patient had distal pancreatectomy and metastasis to small bowel/mesentery. One patient had liver metastasis noted on final pathology.

TABLE 5

Clinicopathologic characteristics 836 of patients in TCR sequencing cohort

| Variable | Short Term (n = 30) n (%) | LT (n = 30) n (%) | P-value |
|---|---|---|---|
| Gender | | | |
| Male | 17 (57) | 12 (40) | NS |
| Female | 13 (43) | 18 (60) | |
| Age | | | |
| Median (Range) | 73 (45-91) | 75 (54-95) | NS |
| Tumor Location | | | |
| Head | 17 (57) | 23 (77) | NS |
| Body/Tail | 13 (43) | 7 (23) | |
| Procedure | | | |
| Distal Pancreatectomy | 13 (43) | 7 (23) | NS |
| Pancreaticoduodenectomy | 17 (57) | 23 (77) | |
| Pathological Stage | | | |
| I | 0 (0) | 2 (7) | NS |
| II | 26 (87) | 27 (90) | |
| III | 1 (3) | 1 (3) | |
| IV* | 3 (10) | 0 (0) | |
| pT | | | |
| 1 | 0 (0) | 2 (7) | NS |
| 2 | 0 (0) | 0 (0) | |
| 3 | 28 (93) | 27 (90) | |
| 4 | 2 (7) | 1 (3) | |
| pN | | | |
| 0 | 14 (47) | 17 (57) | NS |
| 1 | 16 (53) | 13 (43) | |
| pM | | | |
| 0 | 28 (93) | 30 (100) | NS |
| 1* | 2 (7) | 0 (0) | |
| Margin | | | |
| Positive | 1 (3) | 2 (7) | NS |
| Negative | 29 (97) | 28 (93) | |
| Adjuvant Treatment | | | |
| Yes | 18 (60) | 26 (86) | NS |
| No | 9 (30) | 2 (7) | |
| Unknown | 3 (10) | 2 (7) | |

*One patient had liver metastasis noted on final pathology. One patient had distal pancreatectomy and metastasis to small bowel/mesentery.

TABLE 6

Clinicopathologic characteristics of patients 843 in whole exome sequencing cohort.

| Variable | Short Term (n = 32) n (%) | Long Term (n = 26) n (%) | P-value |
|---|---|---|---|
| Gender | | | |
| Male | 15 (47) | 8 (31) | NS |
| Female | 17 (53) | 18 (69) | |
| Age | | | |
| Median (Range) | 73 (48-91) | 75 (51-95) | NS |
| Tumor Location | | | |
| Head | 18 (56) | 21 (81) | NS |
| Body/Tail | 14 (44) | 5 (19) | |
| Procedure | | | |
| Distal Pancreatectomy | 13 (41) | 5 (19) | NS |
| Pancreaticoduodenectomy | 19 (59) | 21 (81) | |
| Pathological Stage | | | |
| I | 0 (0) | 1 (4) | NS |
| II | 28 (88) | 24 (92) | |
| III | 1 (3) | 1 (4) | |
| IV* | 3 (9) | 0 (0) | |
| pT | | | |
| 1 | 0 (0) | 1 (4) | NS |
| 2 | 0 (0) | 0 (0) | |
| 3 | 29 (91) | 24 (92) | |
| 4 | 3 (9) | 1 (4) | |
| pN | | | |
| 0 | 9 (28) | 11 (42) | NS |
| 1 | 23 (72) | 15 (58) | |
| pM | | | |
| 1 | 30 (94) | 26 (100) | NS |
| 0* | 2 (6) | 0 (0) | |
| Margin | | | |
| Positive | 5 (16) | 3 (12) | NS |
| Negative | 27 (84) | 23 (88) | |

TABLE 6-continued

Clinicopathologic characteristics of patients 843 in whole exome sequencing cohort.

| Variable | Short Term (n = 32) n (%) | Long Term (n = 26) n (%) | P-value |
|---|---|---|---|
| Adjuvant Treatment | | | |
| Yes | 22 (63) | 24 (92) | NS |
| No | 9 (28) | 2 (8) | |
| Unknown | 1 (9) | 0 (0) | |

*One patient had a distal pancreatectomy and metastasis to small bowel mesentery. One patient had liver metastasis noted on final pathology.

TABLE 7

Clinicopathologic characteristics of patients in matched primary and metastatic tumor cohort

| Variable | MUC16 Neoantigenic (n = 2), n (%) | Non-MUC16 Neoantigenic (n = 2), n (%) | P-value |
|---|---|---|---|
| Gender | | | |
| Male | 0 (0) | 1 (50) | NS |
| Female | 2 (100) | 1 (50) | |
| Age | | | |
| Median (Range) | 71 (57-85) | 52 (50-54) | NS |
| Pathological Stage | | | |
| I | 0 (0) | 0 (0) | NS |
| II | 0 (0) | 0 (0) | |
| III | 1 (50) | 0 (0) | |
| IV | 1 (50) | 2 (100) | |
| Chemotherapy | | | |
| Yes | 2 (100) | 1 (50) | NS |
| No | 0 (0) | 1 (50) | |

TABLE 8

Clinicopathologic characteristics of very long term pancreatic cancer survivors.

| Variable | Long Term (n = 7) n (%) |
|---|---|
| Gender | |
| Male | 1 (14) |
| Female | 6 (86) |
| Age | |
| Median (Range) | 73 (60-88) |
| Tumor Location | |
| Head | 4 (57) |
| Body/Tail | 3 (43) |
| Procedure | |
| Distal Pancreatectomy | 3 (43) |
| Pancreaticoduodenectomy | 4 (57) |
| Pathological Stage | |
| I | 1 (14) |
| II | 6 (86) |
| III | 0 (0) |
| IV | 0 (0) |
| pT | |
| 1 | 1 (14) |
| 2 | 0 (0) |
| 3 | 6 (86) |
| 4 | 0 (0) |
| pN | |
| 0 | 5 (71) |
| 1 | 2 (29) |
| pM | |
| 0 | 7 (100) |
| 1 | 0 (0) |
| Margin | |
| Positive | 1 (14) |
| Negative | 6 (86) |
| Adjuvant Treatment | |
| Yes | 7 (100) |
| No | 0 (0) |
| Unknown | 0 (0) |

| Recurrence and Survival | Recurrence | Survival (years) |
|---|---|---|
| Patient 1 | No | 10.5 |
| Patient 2 | No | 9.5 |
| Patient 3 | No | 11.5 |
| Patient 4 | No | 11.8 |
| Patient 5 | Yes | 7.3 |
| Patient 6 | Yes | 11.8 |
| Patient 7 | No | 7.7 |

Figure 42G:
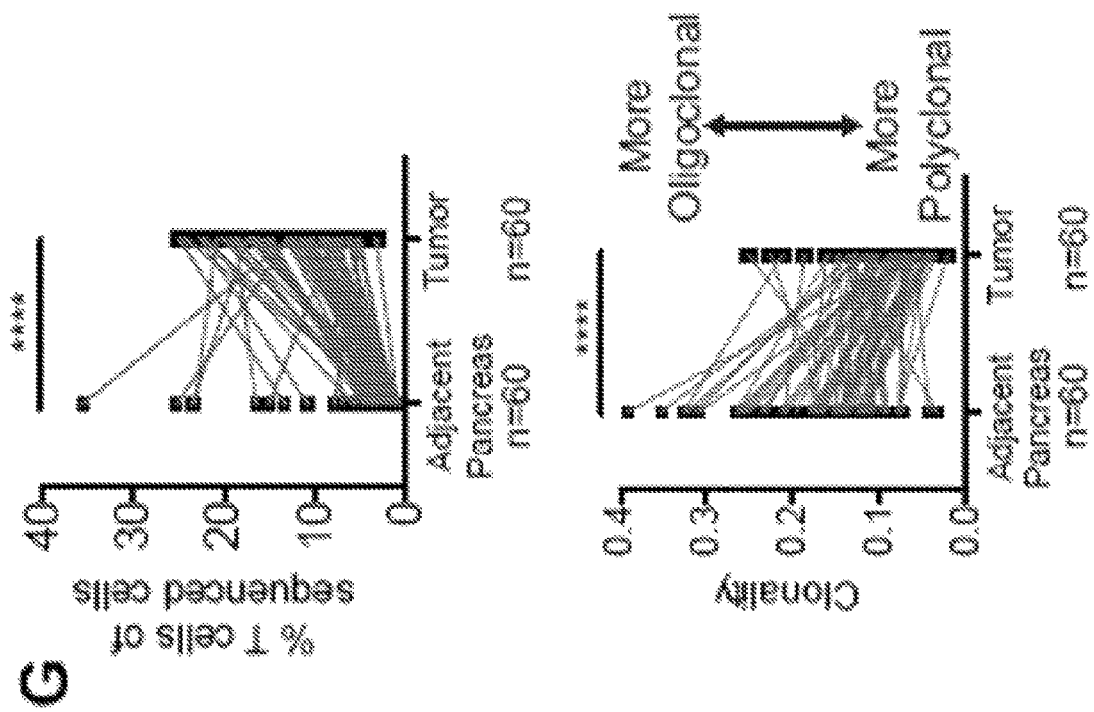
Figure 42F:
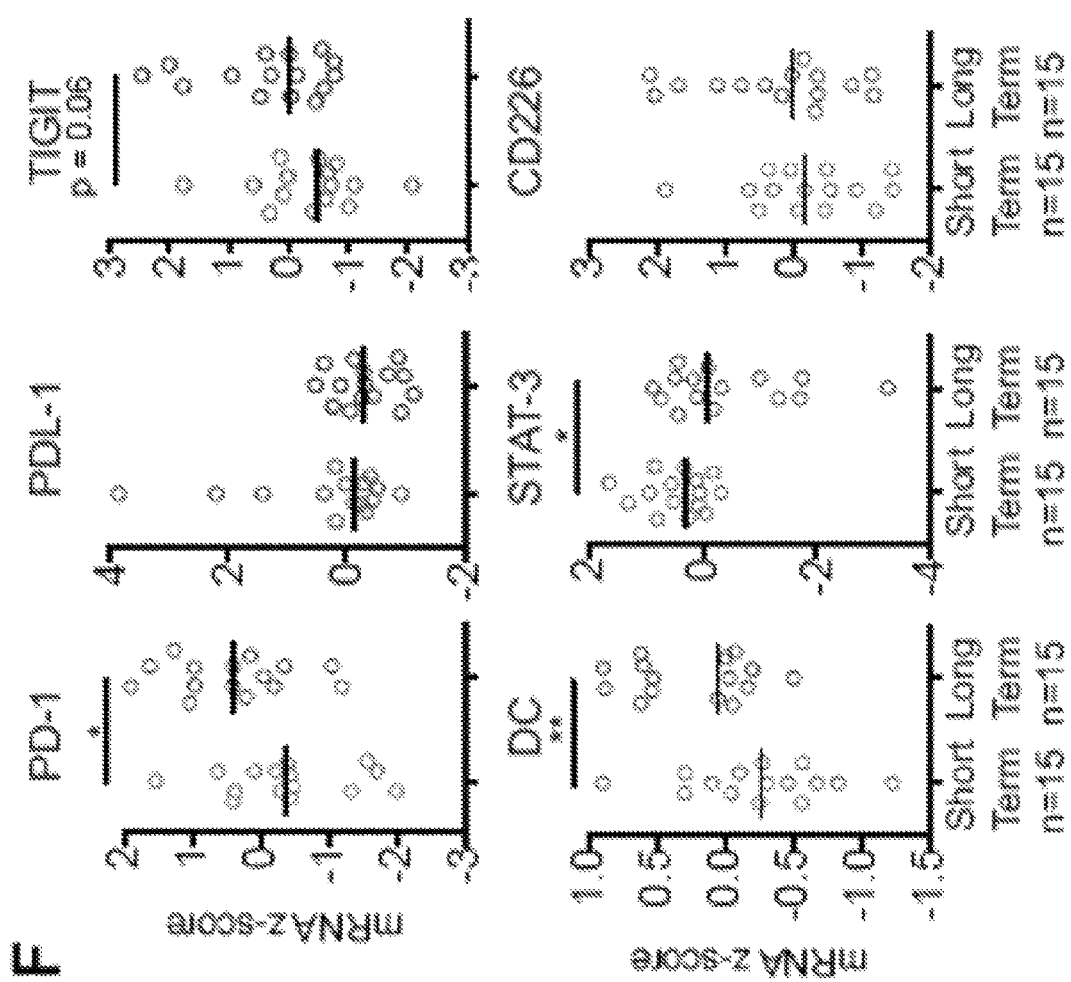
Figure 42H:
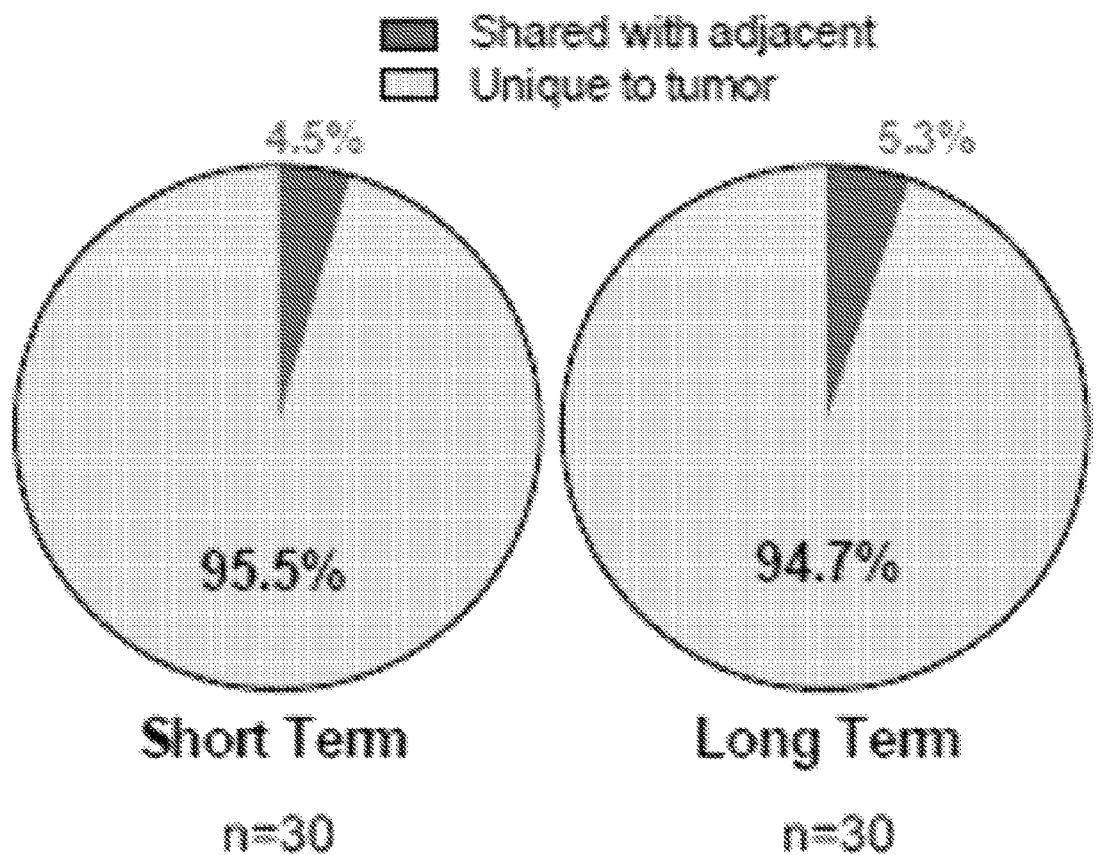
Figure 42I:
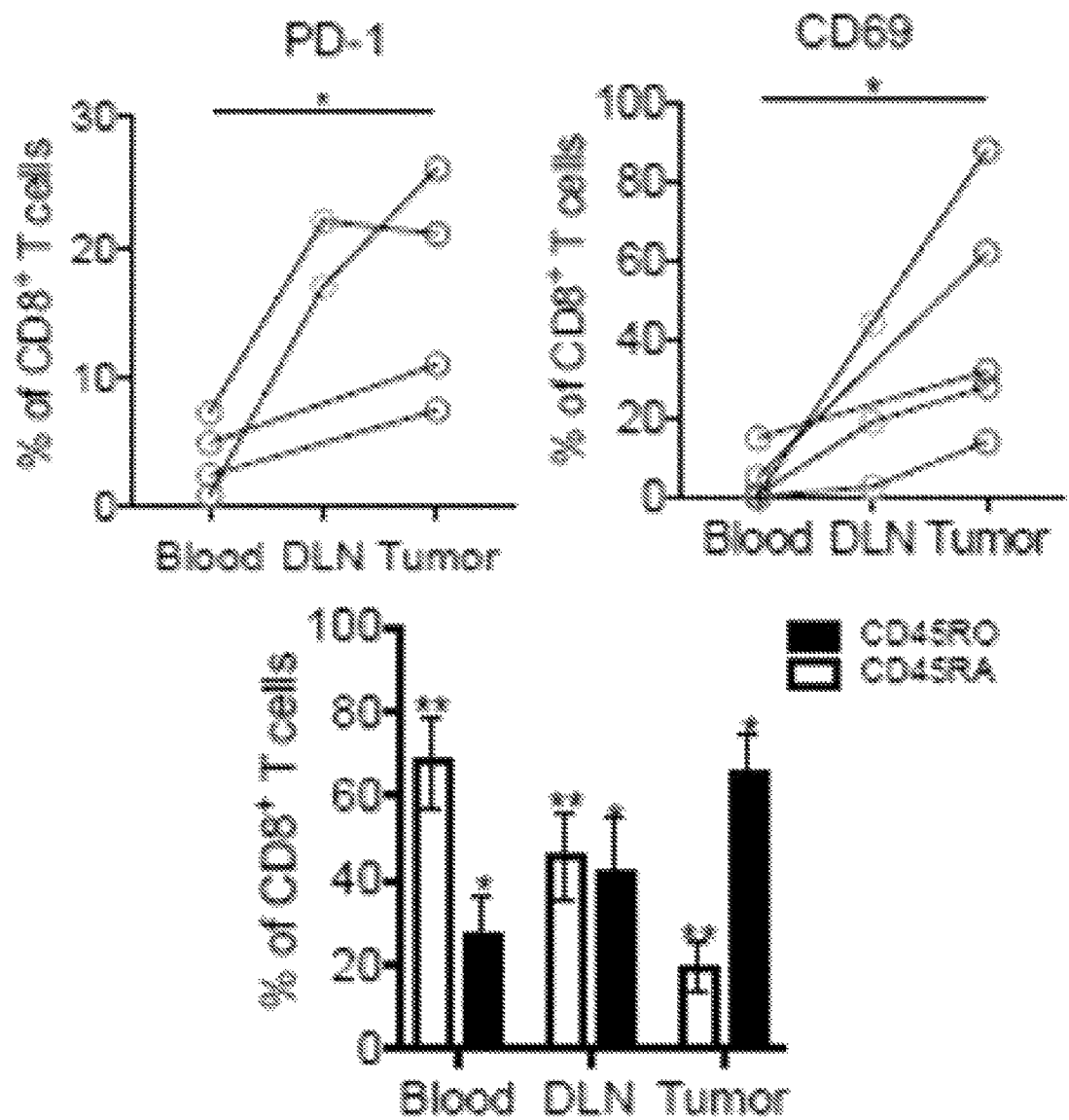
Figure 42J:
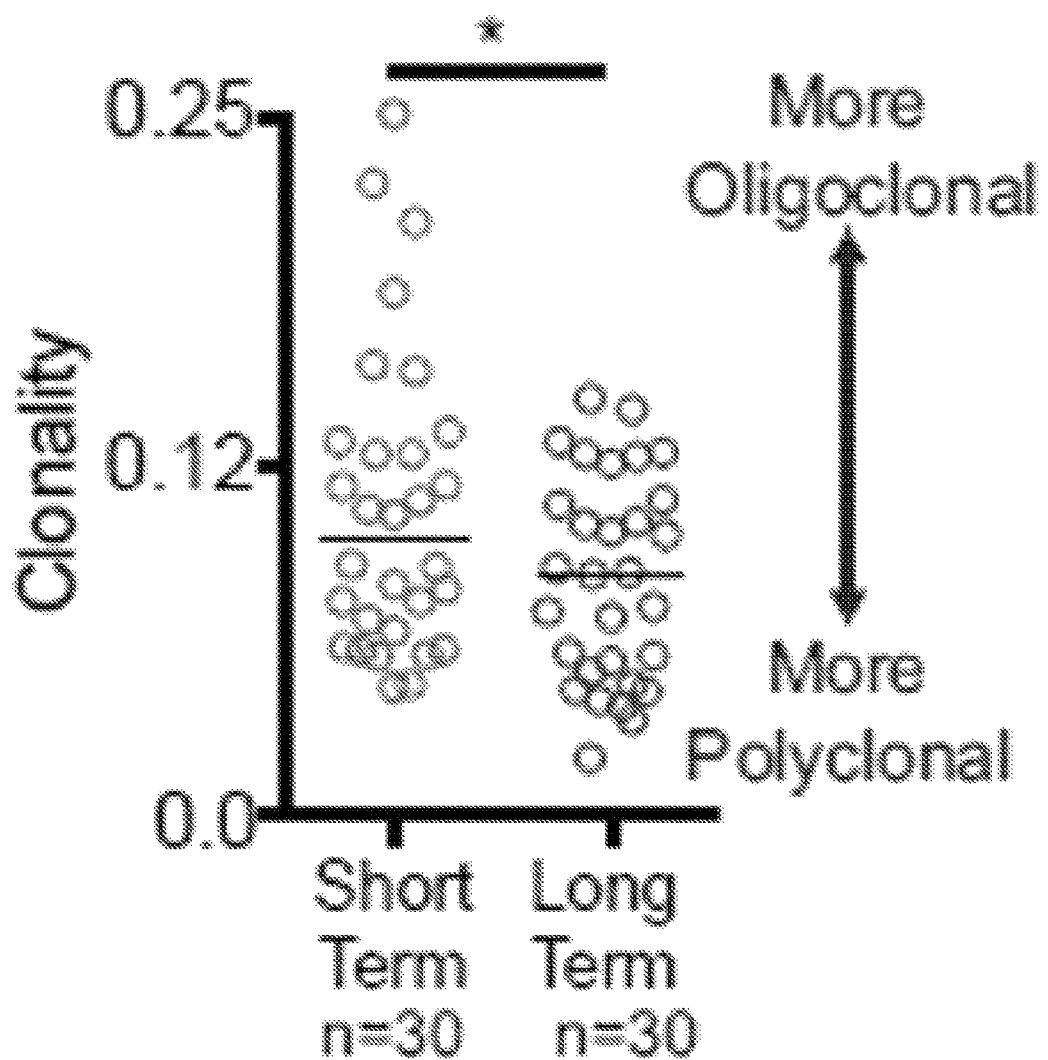
Figure 42K:
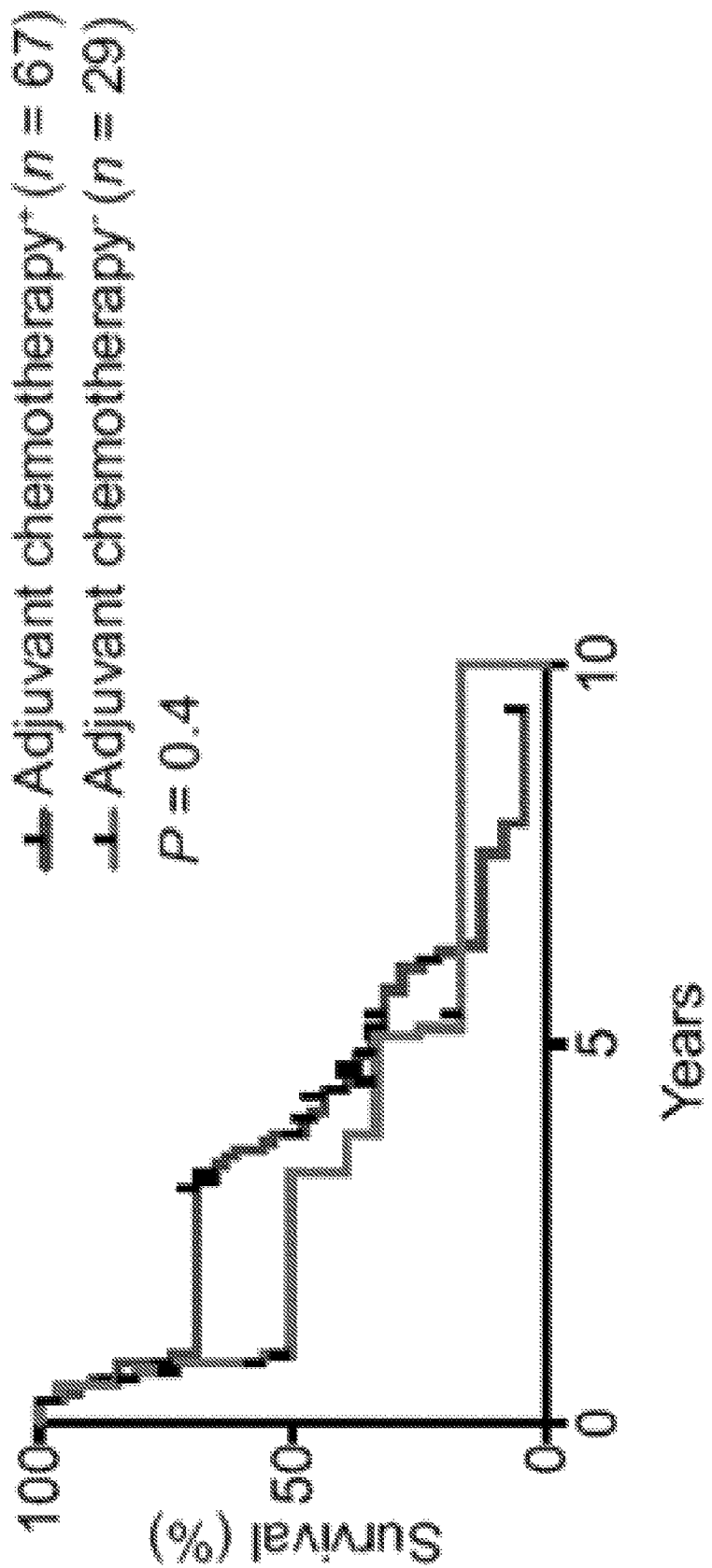
Figure 42L:
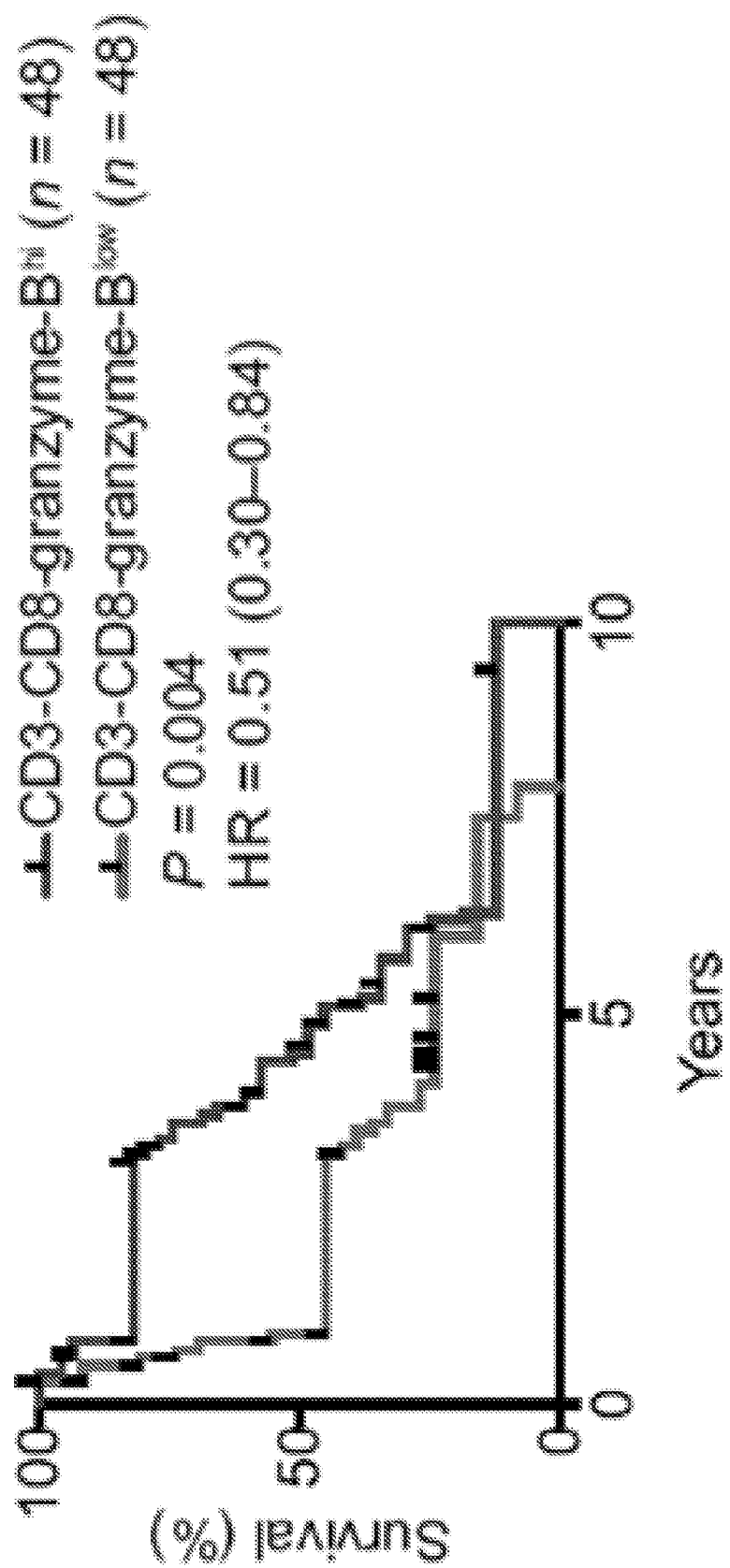
Figure 42M:
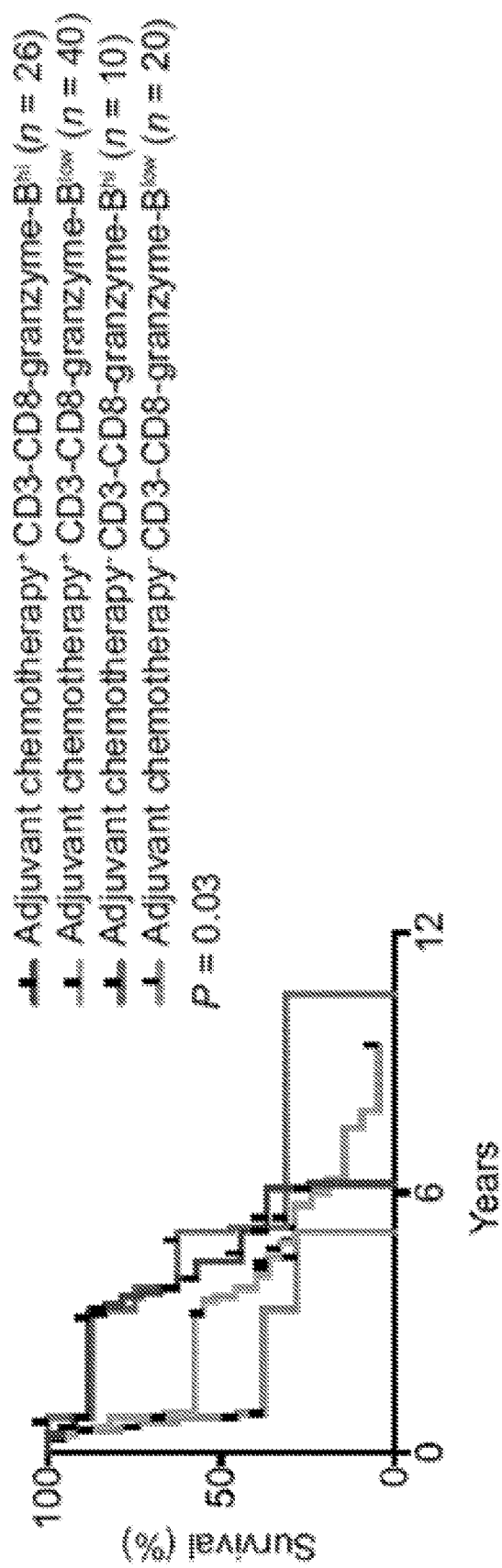

In Using 9-parameter immunophenotyping with multiplexed immunohistochemical consecutive staining on single slides[16] in tissue microarrays (TMAs), it was found greater densities of CD3+CD8+ T cells (3-fold), cytolytic CD3+CD8+Granzyme-B+ cells (12-fold), DC-LAMP+ mature dendritic cells, FoxP3+ regulatory T cells, and CD68+ macrophages in tumors of long term survivors, yet no differences in CD20+ B cells and MHC-I+ cells (FIGS. 42B-42E, FIG. 43). Consistently, immunofluorescent phenotyping also revealed that CD8+ T cells were increased and conversely, CD4+ T cells were decreased in tumors of long term survivors (FIG. 44). Tumor transcriptomic profiling revealed an immunogenic microenvironment in tumors of long term survivors, with upregulation of molecular markers of dendritic cells[17] and antigen reactivityl[8-20] (PD-1 and TIGIT), with downregulation of immunosuppressive markers (STAT3[21-22]) (FIG. 42F). T cell receptor (TCR) Vβ-chain sequencing demonstrated that intratumoral T cells were increased 5-fold compared to matched adjacent non-tumor pancreatic tissue (11.6% vs. 2.2%), and displayed a markedly polyclonal repertoire (FIG. 42G, FIG. 45). Strikingly, >94% of intratumoral T cell clones were unique to tumors, consistent with tumor specificity (FIG. 42H). In order to further address intratumoral T cell specificity, flow cytometry on freshly isolated intratumoral T cells in unselected patients revealed upregulation of activation and memory markers compared to T cells in matched draining lymph nodes and blood (FIG. 42I, FIG. 46). Finally, tumors of long term survivors exhibited greater TCR repertoire diversity compared to tumors of short term survivors (FIG. 42J). Importantly, the association of activated CD8+ T cells and survival was independent of clinicopathologic factors and adjuvant chemotherapy (FIG. 42K). Collectively, these data identify an activated, polyclonal, tumor-specific T cell infiltrate in tumors of long term survivors, implying differential antigenic targets.

Figure 48A:
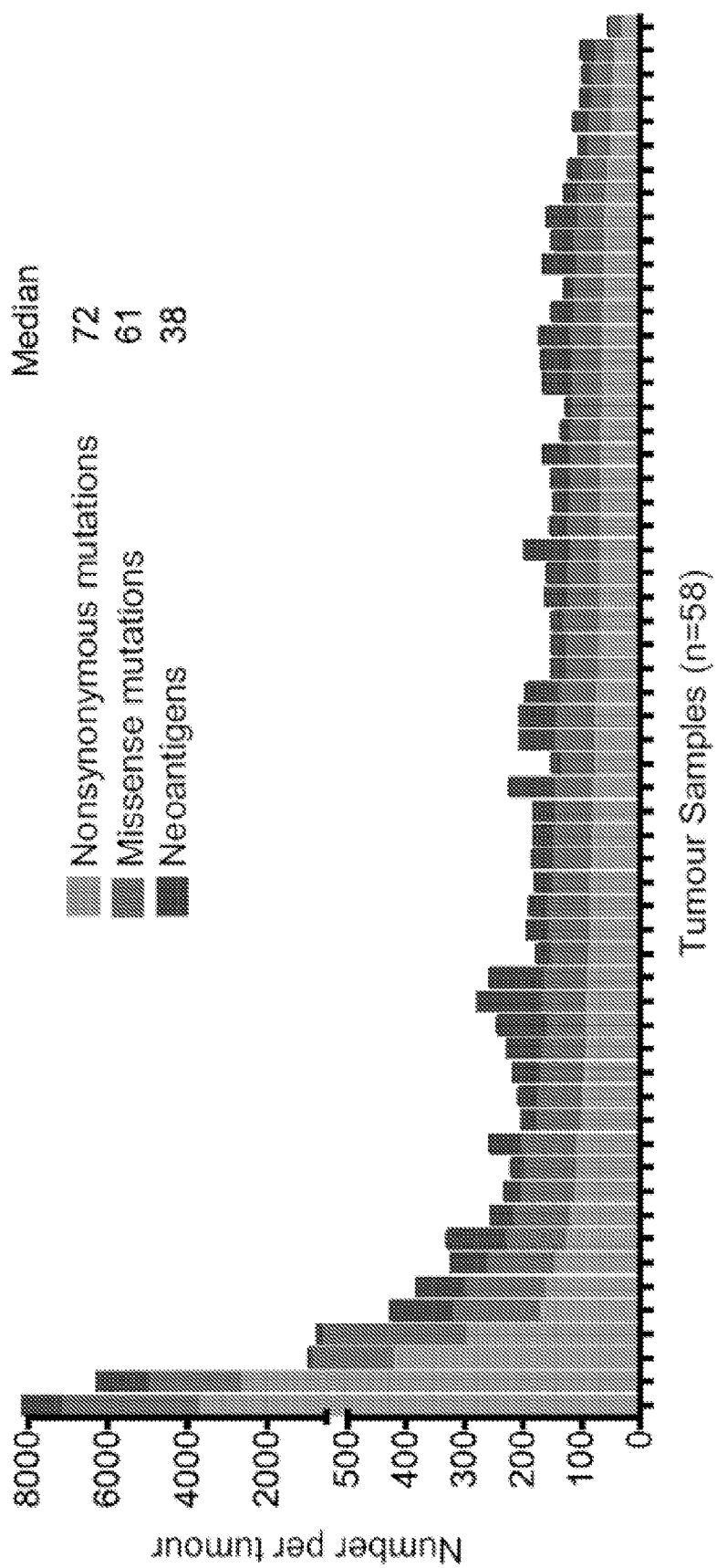
Figure 48C:
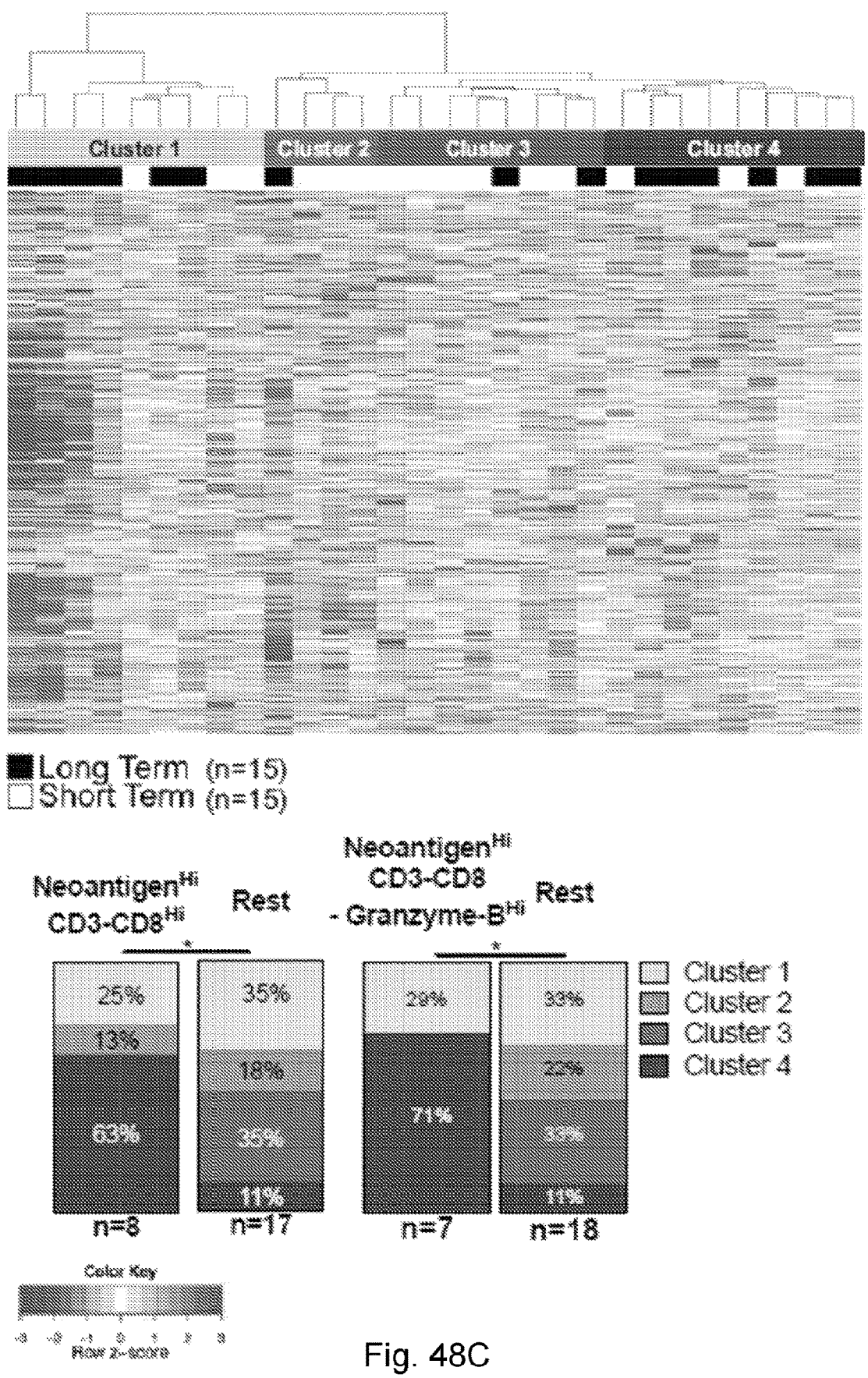

It has been posited that PDACs infrequently harbor neoantigens owing to a relatively low somatic mutational prevalence[12]. However, these estimates have been confounded by stromal contamination, as more recent sequencing efforts utilizing techniques to maximize tumor DNA capture have identified a higher burden of somatic mutations[23,24]. To determine the true neoantigen frequency in PDACs, whole exome sequencing on macrodissected tumor islands was performed, enabling isolation of DNA from specimens characterized by a high proportion of tumor cells (FIG. 47)[24,25]. Utilizing a previously developed pipeline for neoantigen prediction[13,14], a median of 61 missense mutations with 38 predicted neoantigens per tumor were detected (FIG. 48A). Remarkably, patients with the highest predicted neoantigen number and either the greatest $CD3^+CD8^+$, $CD3^+CD8^+Granzyme-B^+$, or polyclonal T cell repertoire, but not $CD4^+$ T cell infiltrates, exhibited the longest survival (median survival not reached). These findings were corroborated using a second, independent, neoantigen prediction algorithm pVAC-Seq[26] (FIG. 48B, FIG. 49). It was observed that no survival differences in patients are stratified by highest mutational load combined with either the highest $CD3^+CD8^+$ infiltrates or repertoire clonality (FIG. 50). It was also found that there is no differences in the two cohorts in predicted neoantigen quantity, driver or nonsynonymous mutation frequency, or associations of unique mutations with improved outcome (FIGS. 49-53)[24,27]. As an orthogonal test of these findings, unsupervised hierarchical clustering of bulk tumor transcriptomic profiling demonstrated that tumors harboring the highest activated T cell infiltrates and predicted neoantigen number segregated to unique clusters (FIG. 48C). Together, these data suggest that neoantigen immunogenicity/quality, and not purely quantity, modulate T cell responses and impact outcome in long term survivors.

Figure 69A:
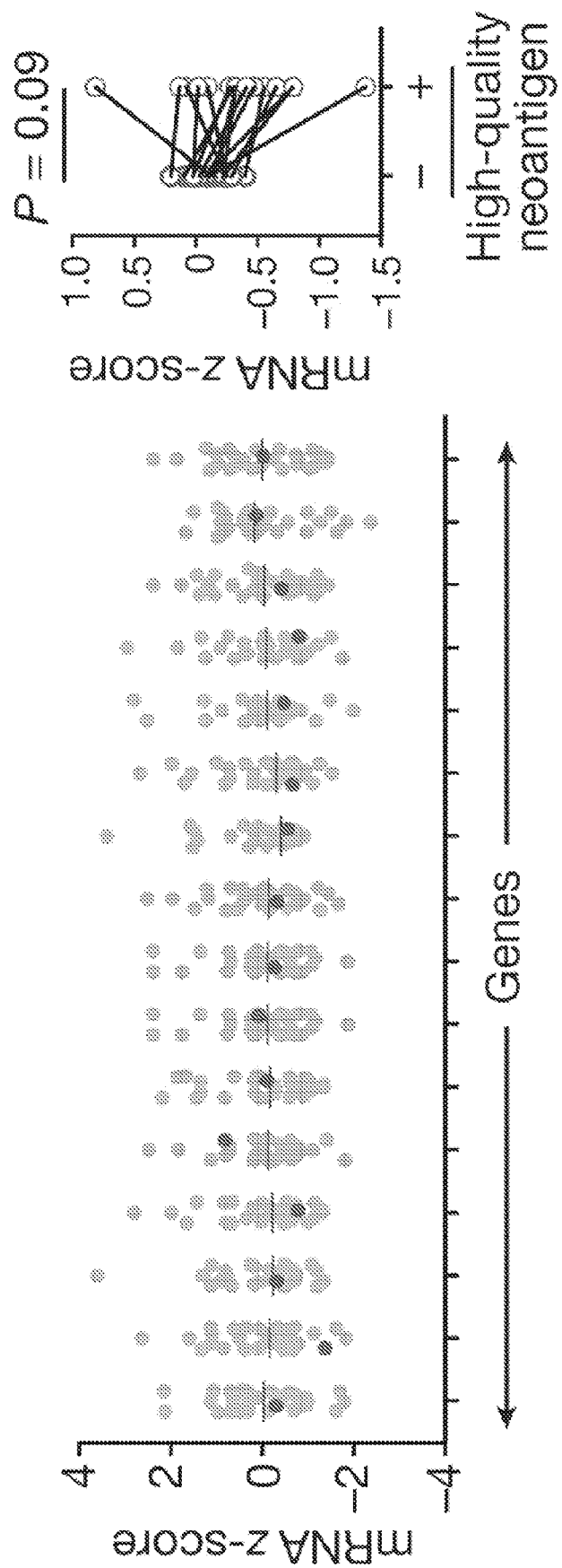
Figure 69B:
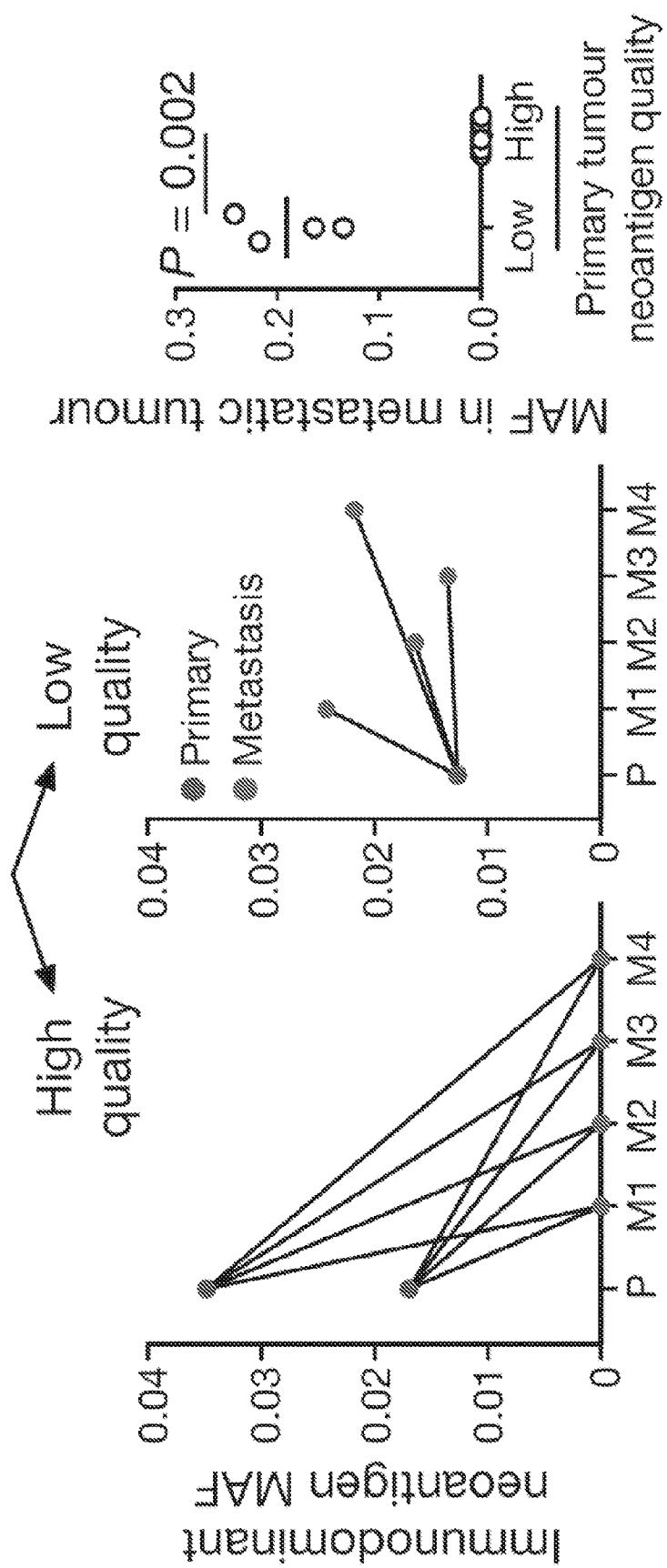
Figure 70C:
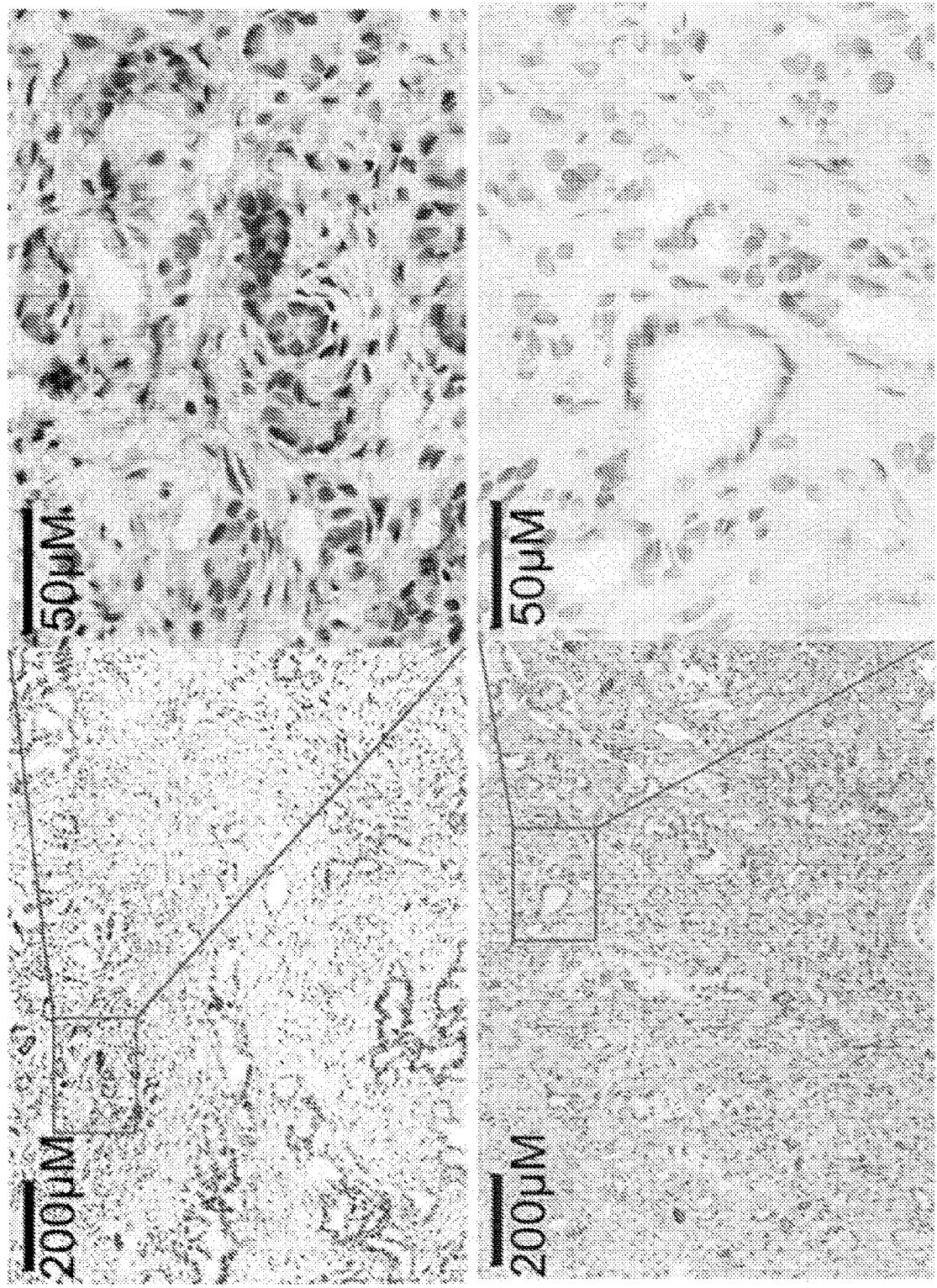

Indeed, recent data has shown that T cell-recognized neoantigens can be selectively lost from the tumor cell population either by mutant allelic loss or overall reduced gene expression. Consistently, genes with high quality neoantigens evidenced a modest trend to lower mRNA expression compared to gene expression in the absence of high quality neoantigens (FIG. 69A). To further explore this possibility of in vivo high quality neoantigen immunoediting, neoantigen clonal dynamics was examined on primary to metastatic tumor progression in one patient obtained through rapid autopsy. Of the three clones in the primary tumor, both clones with high quality neoantigens were lost in multiple metastatic samples, in contrast to the clone with a low quality neoantigen which was propagated to multiple metastatic sites (FIG. 69B, Table 7). These findings suggest differential immune fitness of clones bearing high versus low quality neoantigens within the same primary tumor.

We next sought to detect in vivo T cell responses to high quality neoantigens. We identified 7 very long term PDAC survivors (median OS 10.5 years) that normally account for <2% of all PDAC patients (Table 8) and pulsed their peripheral blood mononuclear cells with antigens predicted by the quality model. Remarkably, we observed selective $CD8^+$ T cell expansion and degranulation to neopeptides and cross reactive peptides but not WT peptides, with identical clones that significantly expanded with both neopeptides and cross reactive peptides in all patients (FIGS. 69C and 69D). Strikingly, in 5 of 7 patients, we identified neoantigen and microbial cross reactive peripheral T cell clones that 191 were also present in their respective archival primary tumors. Patient 3, alive and disease free 12 years after primary tumor removal illustrated the most extreme instance—15 neoantigen and microbial cross reactive T cell clones that persisted in the peripheral blood were found in the primary tumor, including the top T cell clone at an intratumoral rank frequency of 6.2% (FIG. 69D). These results support the idea that the quality model identifies bonafide neoantigens targeted by T cells and that tumor-infiltrating T cells can recognize both cancer neoantigens and homologous non-cancer microbial antigens.

Figure 54A:
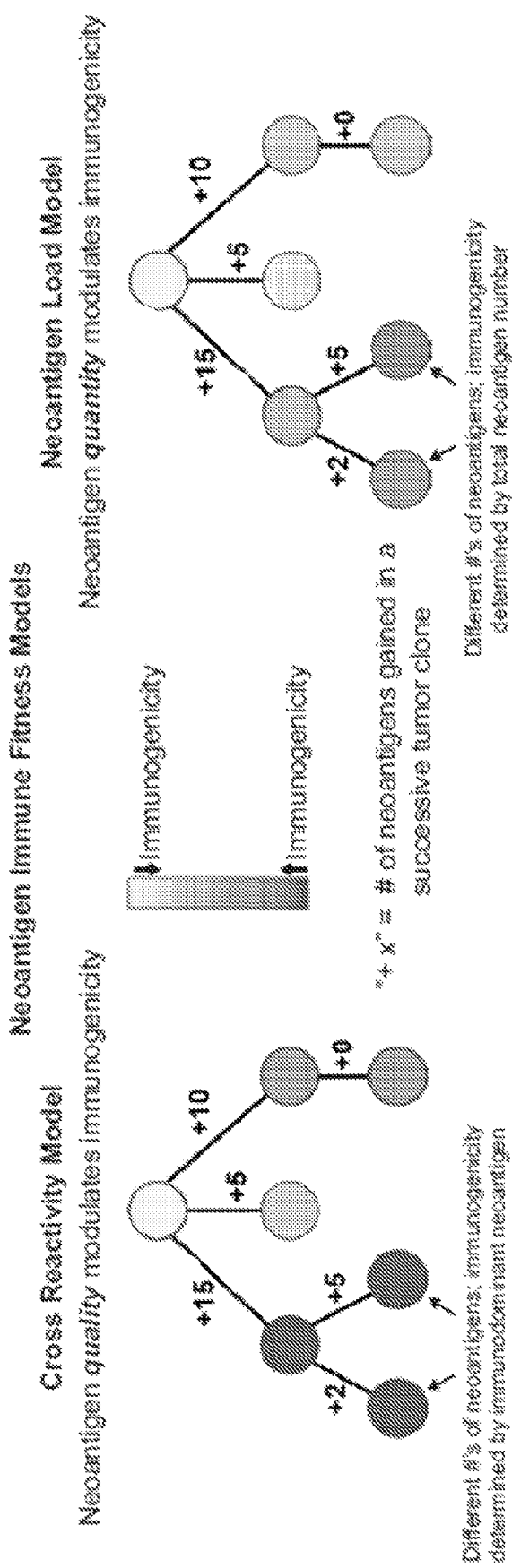
Figure 54B:
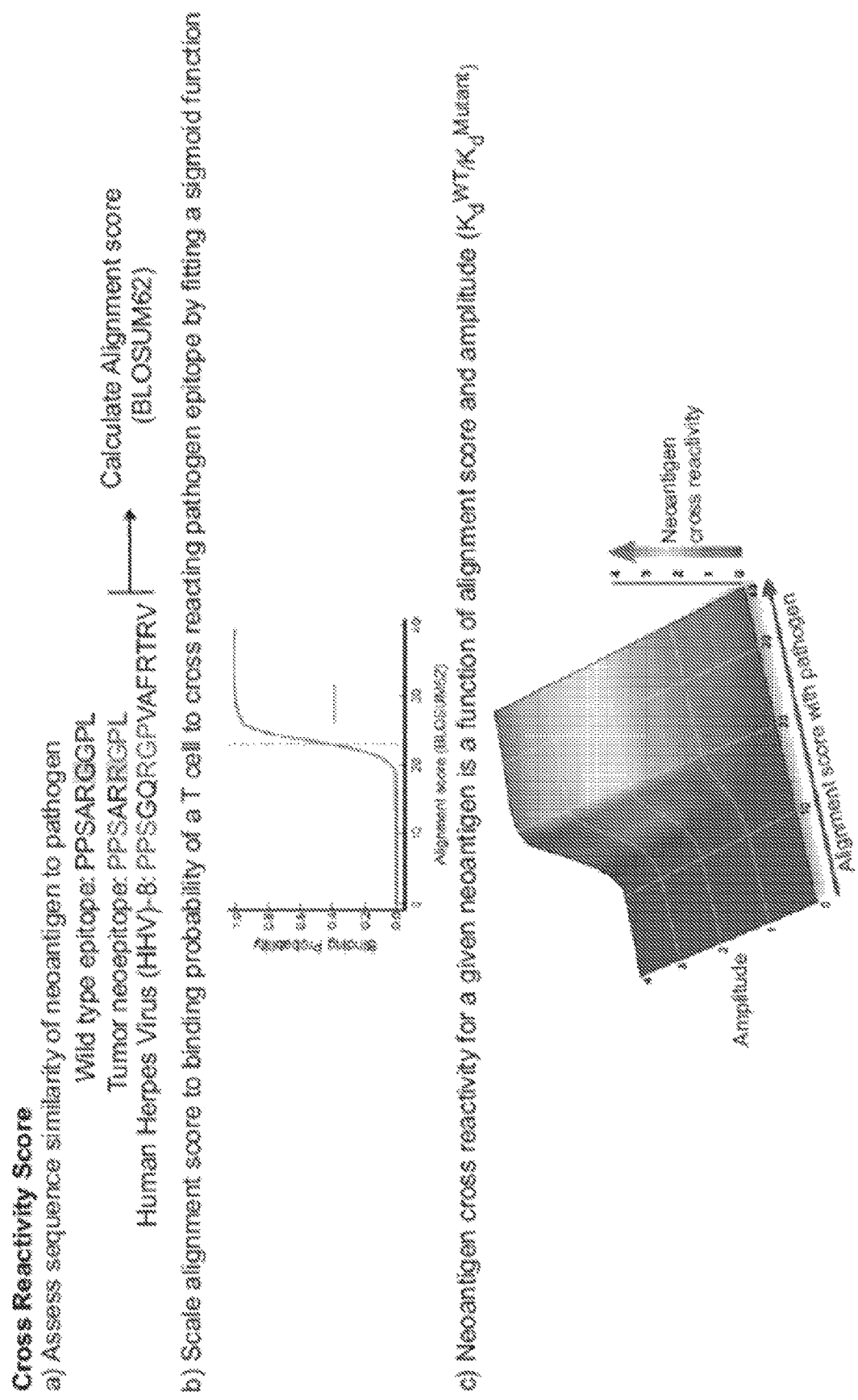
Figure 54C:
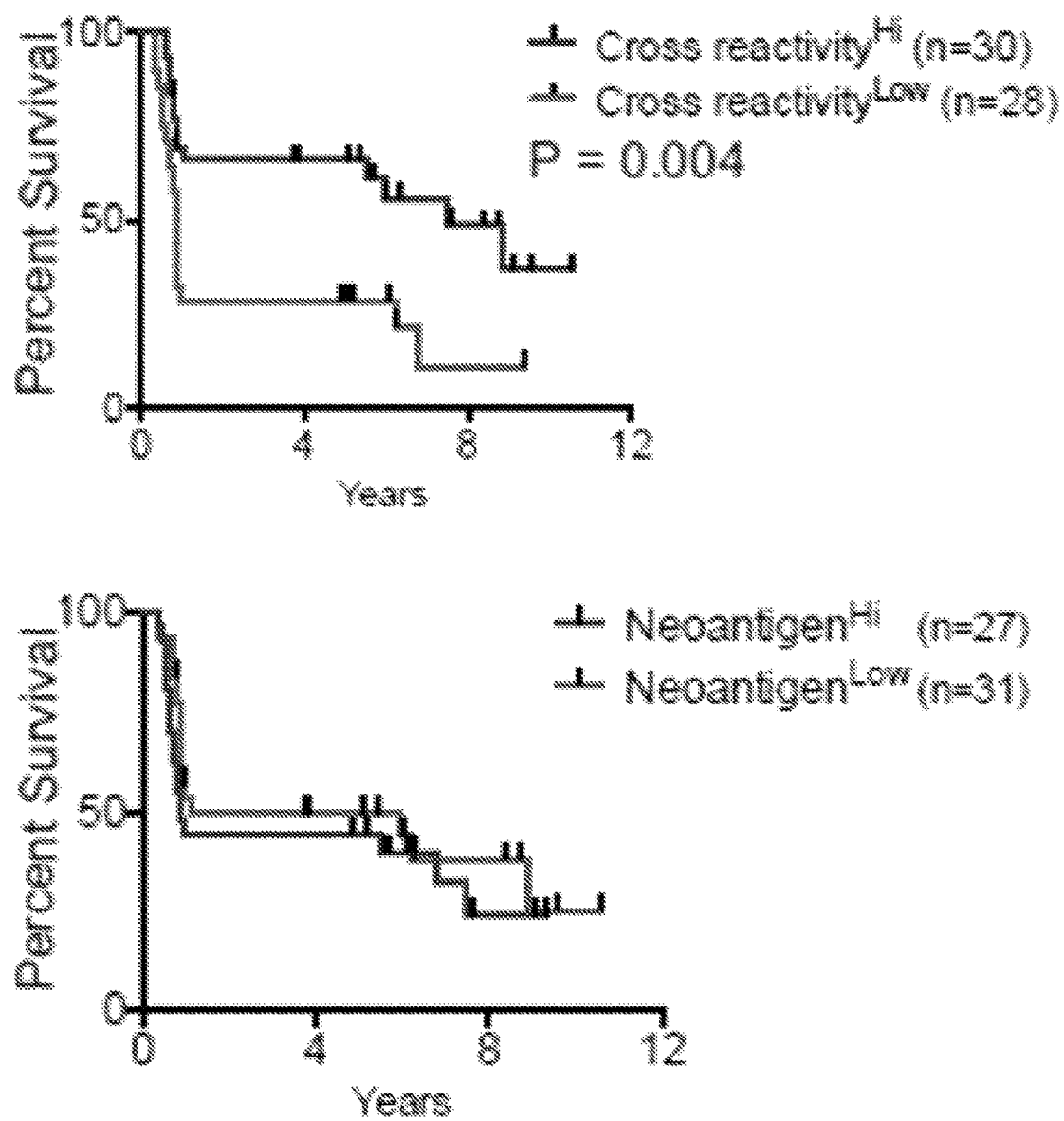
Figure 54D:
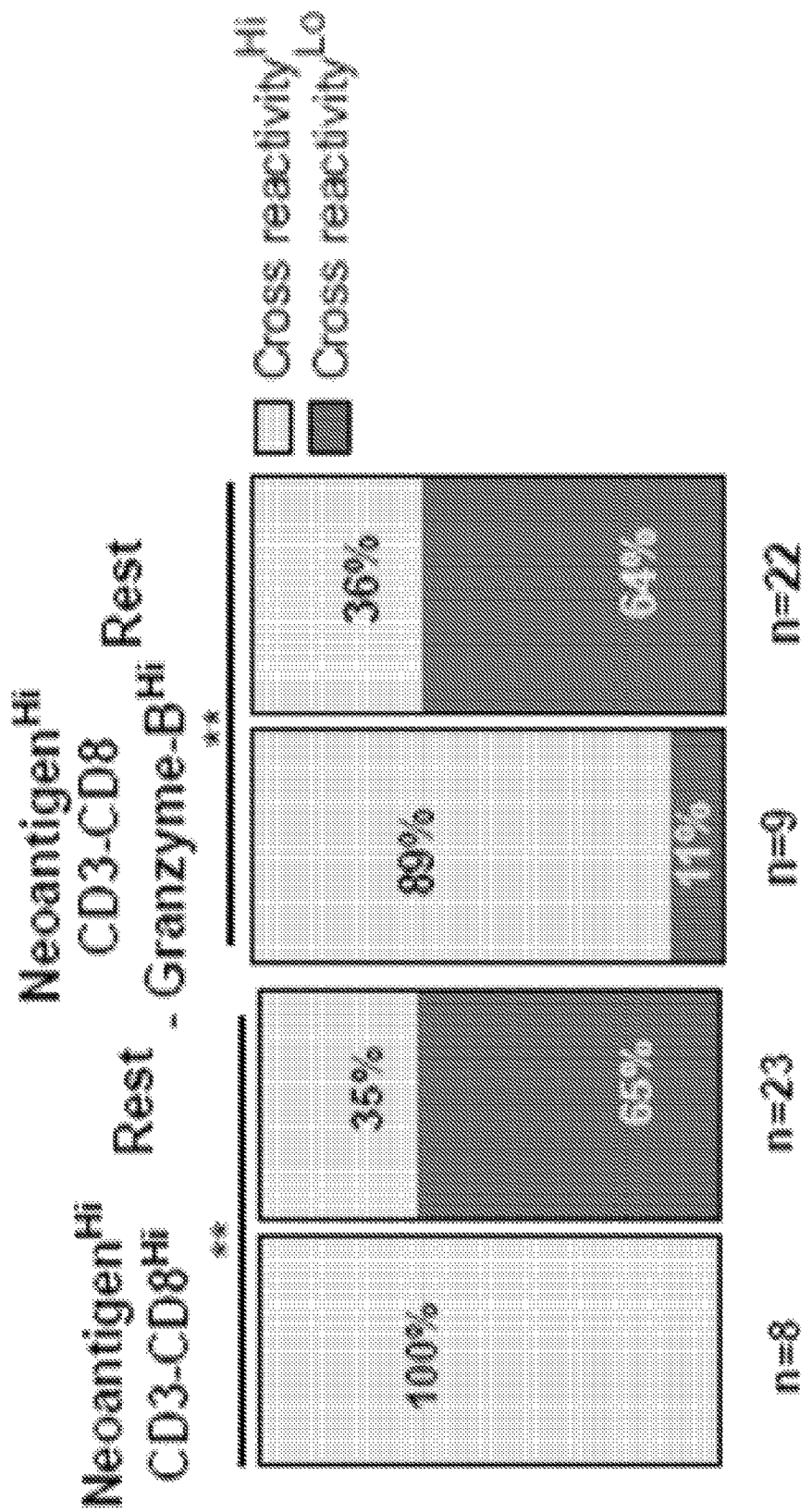
Figure 54F:
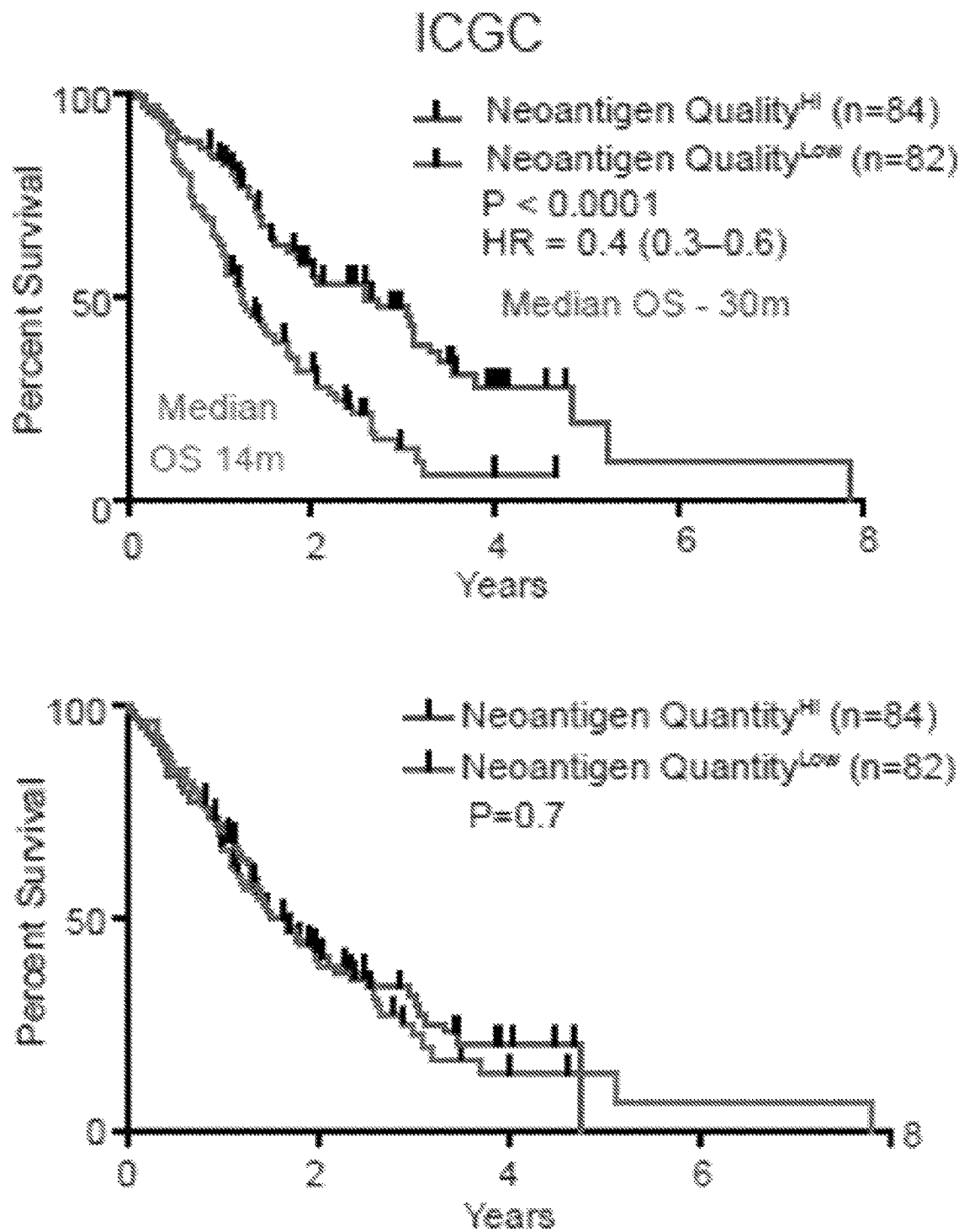

Next, neoantigen qualities that modulate differential immunogenicity was investigated. The theory of molecular mimicry postulates that TCRs generated against pathogens can cross react against non-pathogenic antigens, including tumor antigens. Cross reactivity between microbial and self-antigens has been documented in autoimmune diseases[28]. Although early experimental evidence suggests that cross reactivity between microbial and tumor antigens can stimulate immunosurveillance, this conclusion remains speculative[29]. It was hypothesized that neoantigen homology to microbial epitopes recognized by the human TCR repertoire would serve as a surrogate for differential neoantigen immunogenicity or "non-selfness". Furthermore, it was theorized that enhanced immunogenicity would impart a negative evolutionary fitness cost to tumor cell clones expressing these neoantigens, thereby inducing immunoediting of these clones. To test this hypothesis, two fitness models were developed: a neoantigen-microbial epitope recognition potential model (also interchangeably termed herein a cross reactivity model), inspired by recent methods predicting human influenza viral evolution for vaccine selection[30] and as further disclosed in Łuksza et al., 2017, "A neoantigen fitness model predicts tumour response to checkpoint blockade immunotherapy," Nature 551, 517-520, and a neoantigen load model, based on neoantigen number (FIG. 54A). For the recognition potential model model, sequence alignment scores were derived for each neoepitope to microbial epitopes with positive immune assays from the Immune Epitope Database (IEDB), and assigned a non-linear sigmoid dependence of alignment scores to TCR binding probability based on a two-state thermodynamic model. These binding probabilities were amplified by relative wild type and mutant peptide-MI-IC affinities to calculate recognition potential scores for every neoepitope (FIG. 54B). The neoantigen with the maximum recognition potential score within a clone was defined as the immunodominant neoantigen. For the neoantigen load model, the neoantigen score equaled the total number of neoantigens within a clone. Finally, the clonal tree structure for each tumor based on mutant allele frequencies[31] was recreated, and weighted contributions of each tumor clone to total immunogenicity in each model were summated. Of the resulting fitness functions, the recognition potential model significantly stratified short and long term survivors whereas the neoantigen load model did not (FIG. 54C, FIG. 56, FIG. 54E). These findings were further confirmed by testing a larger cohort of patients unselected by survival (International Cancer Genome Consortium (ICGC); n=166). Consistent with the MSKCC cohort, neoantigen quality but not quantity, was strongly prognostic of survival independent of confounding variables (FIG. 54F, FIG. 54G), with a stable associate with survival in subsampled datasets in both cohorts (FIG. 54H). Notably, nearly all tumors with the highest neoantigen load in combination with the most abundant $CD8^+$ T cell infiltrates harbored neoantigens with homology to microbial epitopes (FIG. 54D). Hence, enhanced neoantigen homology to microbial epitopes can modulate immunogenicity, immunoselection, and outcome in long term survivors.

Figure 55E:
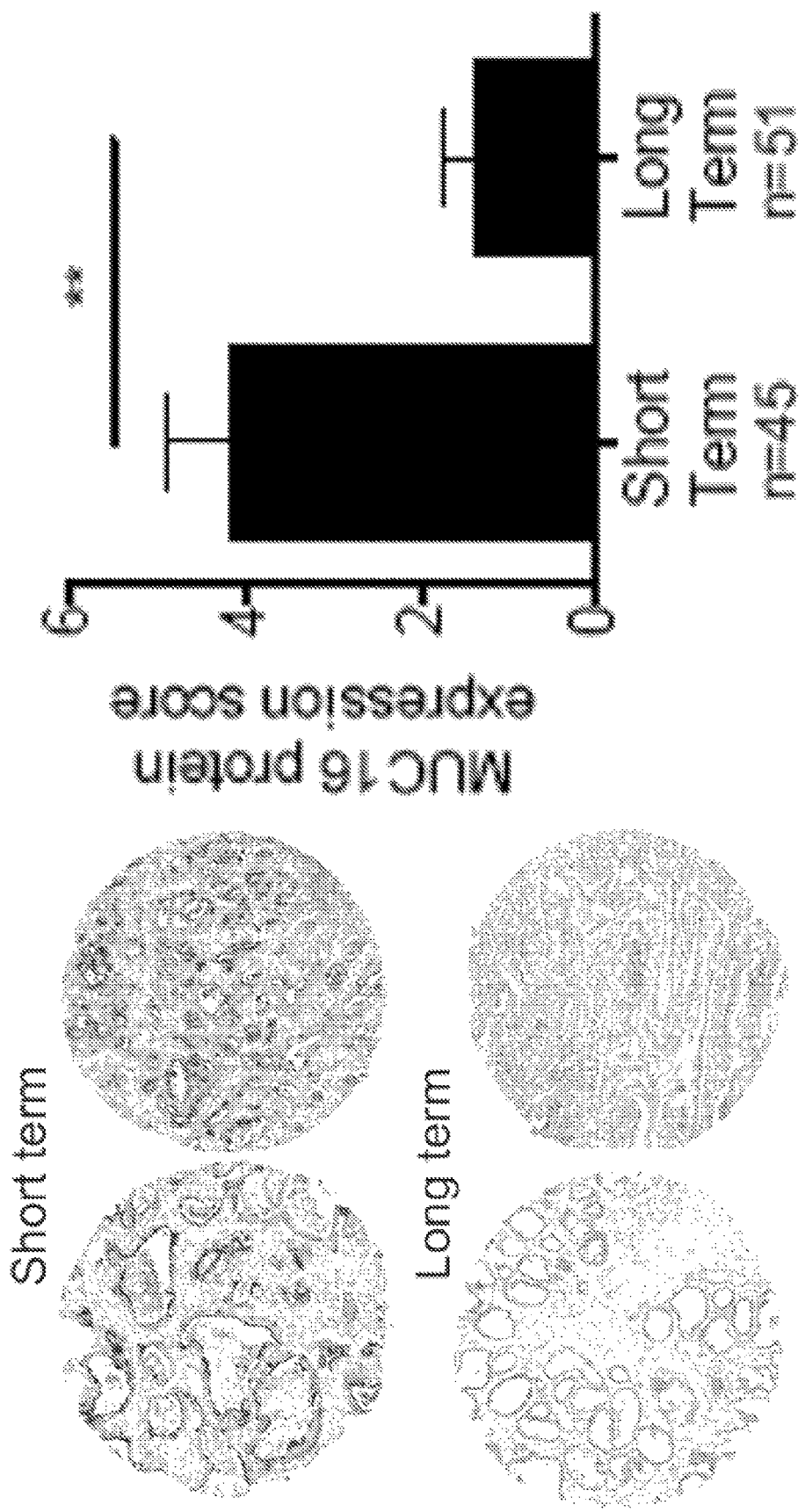
Figure 55F:
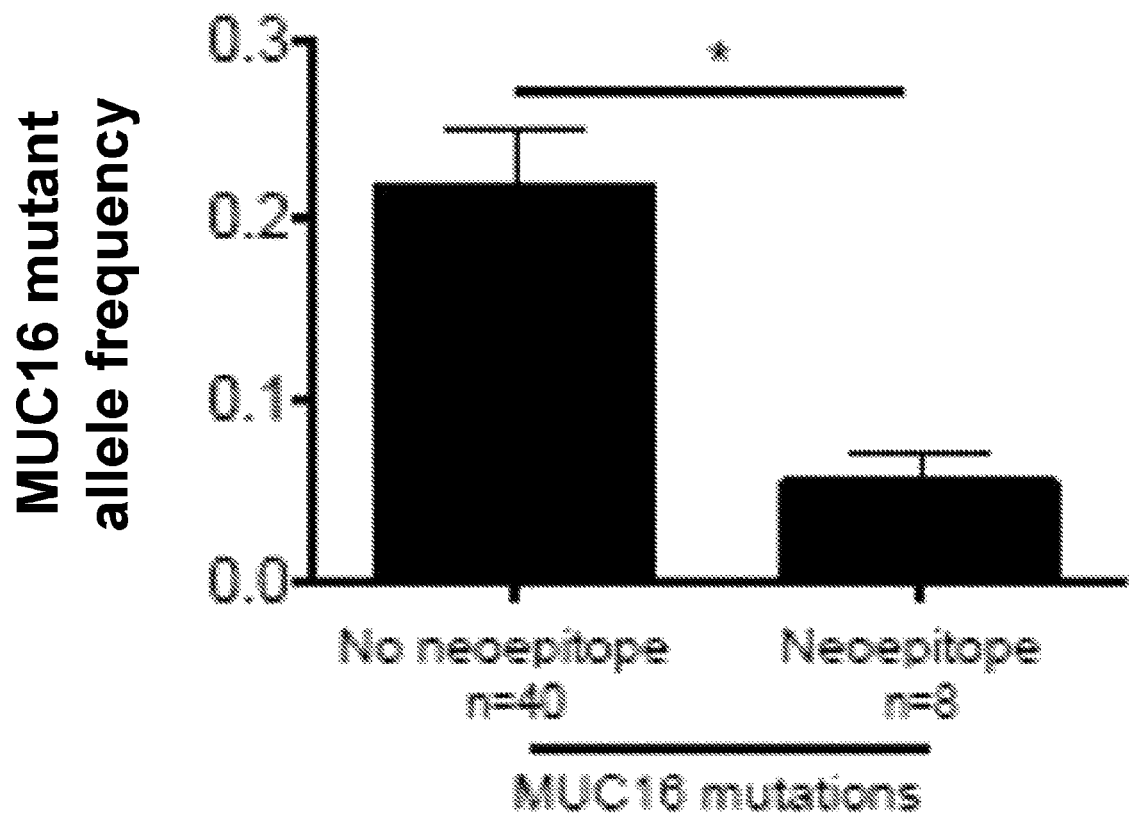

Although neoantigen formation is stochastic and private[12], the above outlined data suggested that unique neoantigen qualities might mediate preferential targeting. Therefore, further exploration was done on whether select genetic loci or "immunogenic hotspots" were preferentially enriched for neoantigens. Thresholds were applied to permit sufficient power to detect differences between patients with and without neoantigens in any given gene, and performed locus filtering. Four loci harboring neoantigens were detected in >15% of all patients, with one locus preferentially enriched in long term survivors—the tumor antigen MUC16, a common ovarian cancer biomarker (CA125), and an established target for T cell immunotherapy[32] (FIG. 55A). In tumors of long term survivors, a 4-fold higher MUC16 neoantigen frequency (27% vs. 6%) and multiple MUC16 neoantigens were found in the same tumor (maximum 5) whereas non-antigenic MUC16 mutation frequency was no different (FIGS. 55B-55C, FIGS. 57-59). Only one patient with MUC16 neoantigens had a hypermutated phenotype (>500 mutations), and exclusion of this patient did not alter the results (FIG. 55C). Consistently, the pVAC-Seq pipeline identified MUC16 as the most common genetic locus generating neoantigens, following the most frequently mutated oncogenes in PDAC (KRAS, TP53) (FIG. 60). In support of possible in vivo anti-MUC16 immune responses, MUC16 was the most differentially expressed gene in the two cohorts, with long term survivors evidencing significantly lower mRNA (6.6-fold), protein, and mutant allele frequency in non-hypermutated tumors (4-fold) (FIGS. 55D-55F). It was found no evidence of non-immunogenic MUC16 mutations altering RNA or protein expression. Furthermore, there were no differences in the two cohorts in cell autonomous regulators of MUC16 expression, mediators of MUC16 dependent effects on tumor progression, or expression of other mucins, and tumor antigens (FIGS. 61-65)[33-37]. One potential interpretation of these findings is MUC16-neoantigen specific T cell immunity induces immunoediting of MUC16-expressing clones in primary tumors, curtails the development of metastases, and prolongs survival, given the cell-autonomous roles of MUC16 in promoting metastases[34,36-38]. This hypothesis is consistent with recent evidence of possible neoantigen immunoediting demonstrated by overall reduced gene expression and mutant allelic loss in the setting of T cell neoantigen reactivity. Notably, MUC16 expression was low yet not absent in tumors of long term survivors, indicating antigen availability (FIG. 70). Consistent with possible MUC16 immunoediting, MUC16 neoantigens in primary tumors had complete neoantigenic mutational loss in matched metastases (n=10) in contrast to MUC16 non-neoantigenic mutations that demonstrated mutation enrichment on metastatic progression (Table 7). MUC16 was also the only locus recurrently harboring neoantigens in both MSKCC and ICGC cohorts, outside of genes expected to do so based on high mutation frequency (oncogenes-KRAS, TP53; largest human gene-TTN). Although the propensity to generate MUC16 neoantigens may be related to its large size, we did not detect trends towards neoantigen formation based on gene size alone across cohorts or pipelines. Our results are also consistent with recent findings demonstrating that MHC-I-restricted peptides derived from selective regions of the human genome. Hence MUC16 is a candidate immunogenic hotspot.

We next stimulated peripheral blood from 2 long term survivors (both disease-free 8 years following surgery) with predicted MUC16 neoantigens to identify in vivo MUC16-neoantigen specific T cell immunity. In both patients, we observed CD8+ T cell expansion and degranulation, with expanded clones also detected in archival surgically resected primary tumors. We confirmed peripheral blood CD8+ T cell recognition of 2 additional MUC16 neoantigen-MHC complexes using peptide-MHC multimers in HLA-matched healthy donors (FIG. 67), consistent with binding of putative MUC16 neoantigens by the human TCR repertoire. Hence we present evidence of in vivo T cell reactivity to neoantigens in the tumor antigen MUC16, with lasting MUC16-specific T cell immunity in PDAC survivors.

Figure 55G:
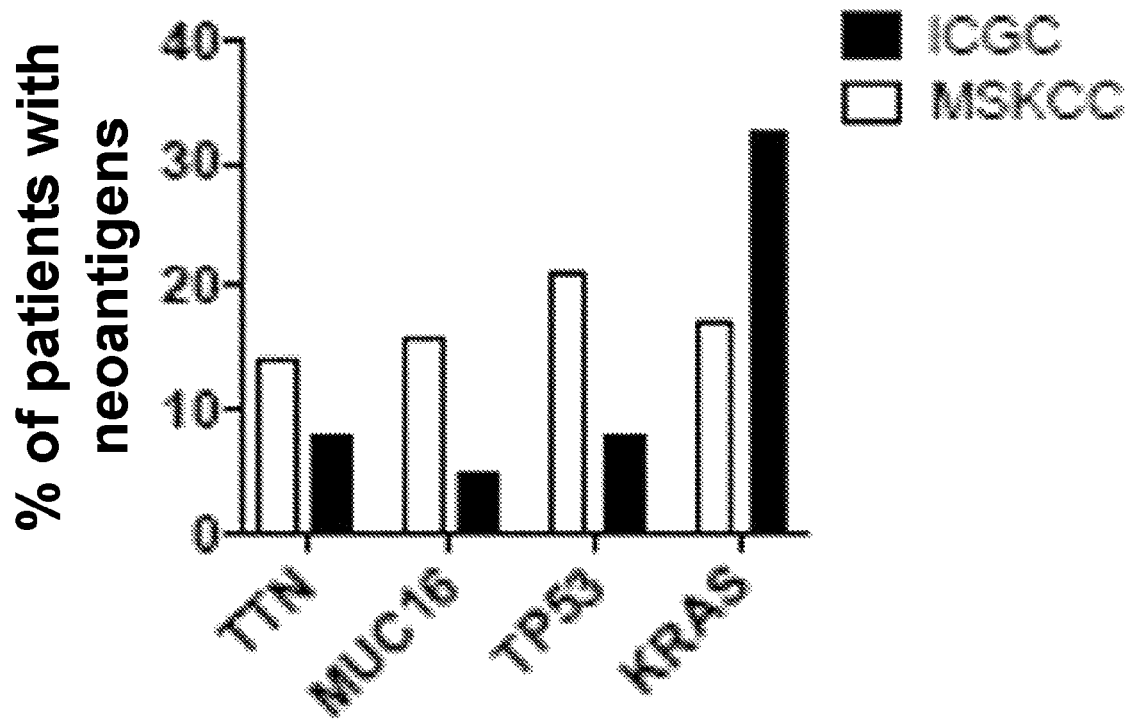
Figure 55H:
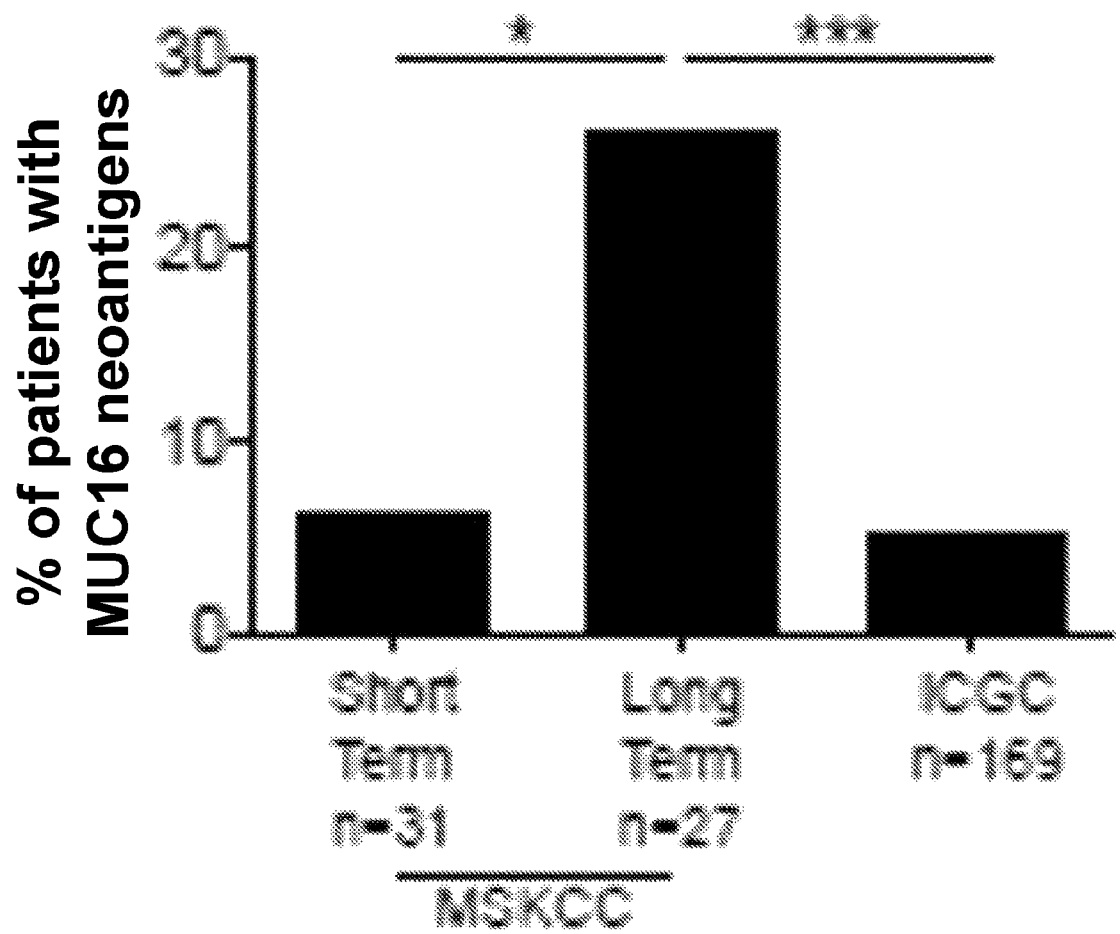

It is important to highlight that MUC16 expression was low yet not absent in tumors of long term survivors, supporting expression of MUC16 neoantigens. To further examine if MUC16 is an immunogenic hotspot in PDAC, neoantigens in a larger set of surgically resected PDAC unselected by survival (International Cancer Genome Consortium, n=169) were predicted[25]. MUC16 was the only locus recurrently harboring neoantigens in both cohorts, outside of genes expected to do so (mutated oncogenic driver genes-KRAS, TP53; largest human gene-TTN) (FIGS. 55G, 55H, 66). Although the propensity to generate neoantigens in MUC16 can be related to its large size, a general trend towards preferential neoantigen formation in genes based on size alone, either across cohorts or pipelines, was not detected. These results are also consistent with recent findings demonstrating that MHC-I restricted peptides derive from selective regions of the human genome[39]. These data suggest that MUC16 is a candidate immunogenic hotspot in PDAC.

Figure 55K:
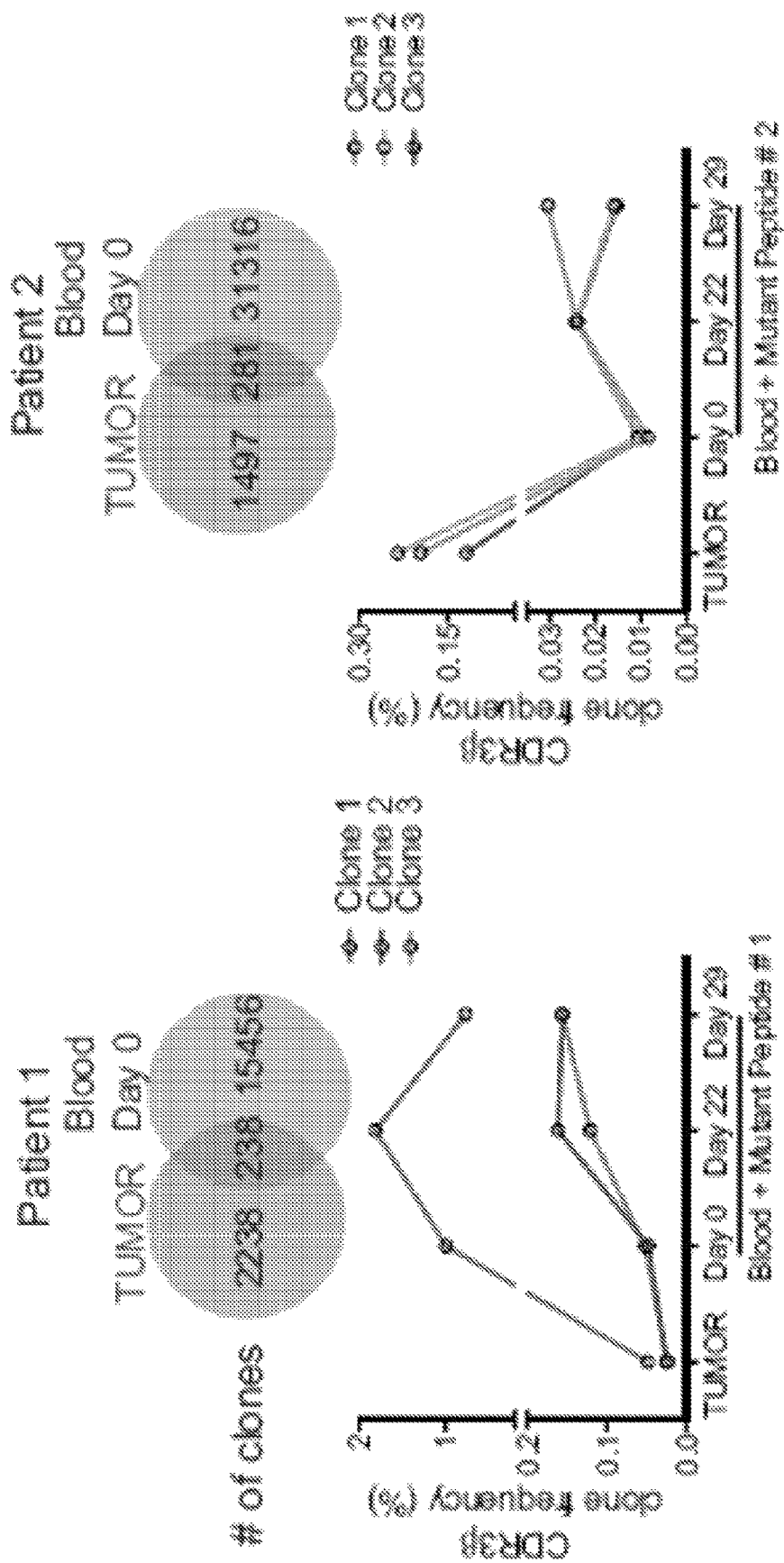
Figure 55L:
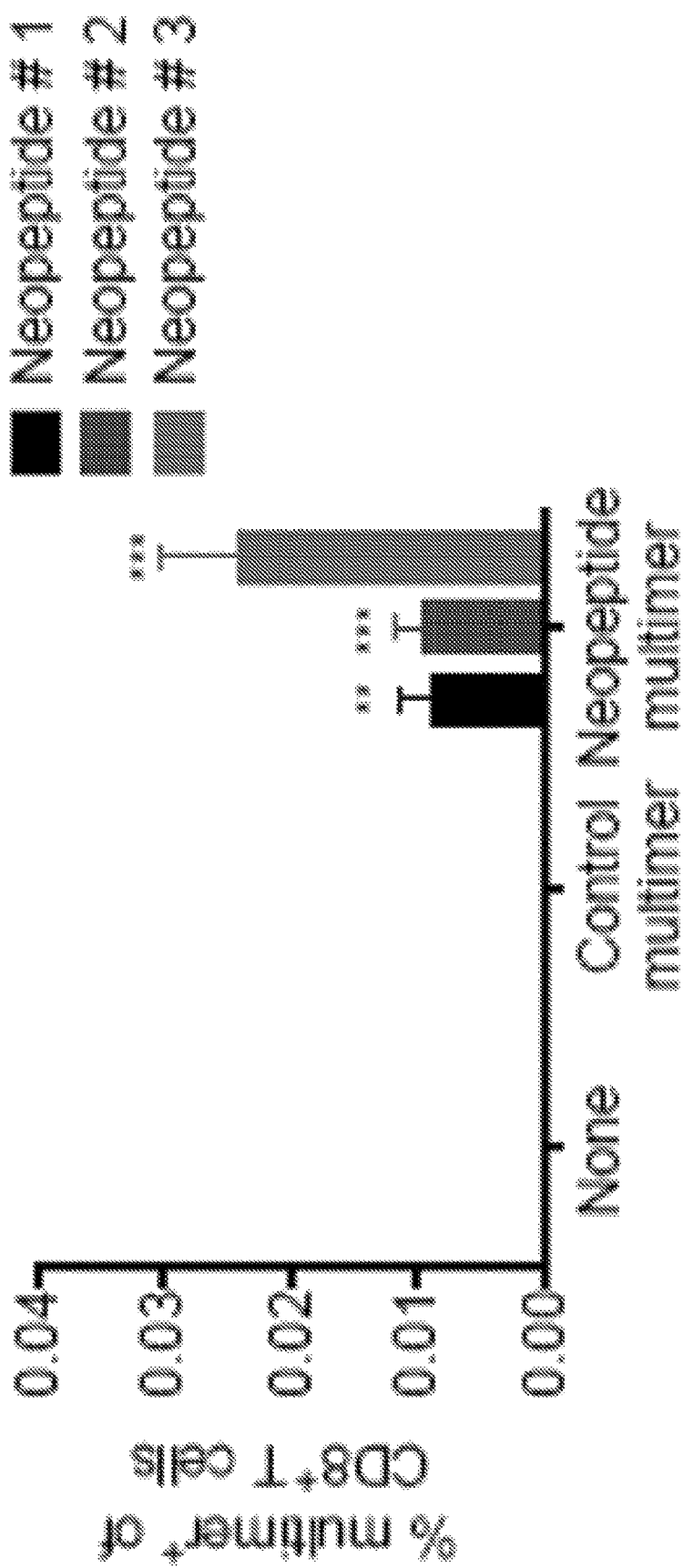

To identify the presence of in vivo MUC16-neoantigen specific T cell immunity in long term survivors, peripheral blood from 2 long term survivors (both disease-free 8 years following surgery) with predicted MUC16 neoantigens was stimulated. In both patients, over 30-fold CD8+ T cell expansion, and degranulation, with polyclonal T cell expansion selectively to mutant but not wild type MUC16 nonamers were observed. Remarkably, in both patients, expanding clones in the peripheral blood (defined by unique TCR Vβ sequences) were also detected in their respective archival primary tumors that were surgically resected 8 years prior, suggesting persistent MUC16-specific anti-tumor T cell immunity (FIGS. 55I-55K). Additionally, for 3 predicted MUC16 neoantigens, peripheral blood CD8+ T cell recognition of neoantigen-MHC complexes using peptide-MHC multimers in HLA-matched healthy donors were confirmed (FIG. 55L, 67, 68), consistent with binding of predicted MUC16 neoantigens by the human TCR repertoire. Hence, the study presented evidence of in vivo T cell reactivity against mutational neoantigens in the tumor antigen MUC16, with long-lasting MUC16-specific T cell immunity in long term PDAC survivors.

Materials and Methods

Patient Samples

MSKCC PDAC cohort: All tissues were collected at Memorial Sloan Kettering Cancer Center under institutional review board protocols. Informed consent was obtained on all patients. All tumor samples were surgically resected primary pancreatic ductal adenocarcinomas. Patients treated with neoadjuvant therapy were excluded. All tumors were subjected to pathologic re-review and histologic confirmation by two expert PDAC pathologists prior to analyses. Long term survivors were defined as patients with overall survival >3 years from surgery, short term survivors as patients with survival >3 m and <1 year from surgery to exclude perioperative mortalities.

ICGC cohort: Clinical characteristics of the ICGC cohort have been previously described[25].

Tissue Microarray

Tissue microarrays were constructed from tumor and adjacent non-tumor cores from formalin-fixed, paraffin embedded tissue blocks in short (n=45 tumors, 5 normals) and long term (n=51 tumors, 5 normals) survivors. Histology sections were reviewed by two expert PDAC pathologists and the most representative areas were selected and marked on H&E slides. 1 mm diameter cores were sampled from three different tumor regions per patient using an automated TMA Grand Master (Perkin Elmer, USA). Five µm sections were prepared from TMA blocks for immunohistochemistry.

Immunohistochemistry

Human specific antibodies to MUC16 (clone OCT125, dilution 1:130), WT1 (clone CAN-R9 (IHC)-56-2, dilution 1:30), and Annexin A2 (ab54771, 5 ug/ml) were purchased from Abcam (MA, USA), antibodies to MUC1 (clone M695, dilution 1:100), and Mesothelin (clone 5B2, dilution 1:50) were purchased from Vector laboratories (CA, USA). Immunohistochemistry was performed using standard techniques. MUC16 expression was scored as described[41]. For each core, a cumulative MUC16 expression score was calculated as the product of a score for the frequency of tumor cells expressing MUC16 (0-25%=1; 26-50%=2; 51-75%=3; 76-100%=4) and a score for the intensity of staining (0=negative; 1=weak; 2=moderate; 3=strong). The mean expression score across triplicate cores is reported as the final score for each patient.

Multiplexed consecutive immunohistochemistry on the same slide was performed as described[16]. Tissue microarray (TMA) slides were baked overnight at 37° C. Then, paraffin was removed using xylene and tissue rehydrated prior to incubation in antigen retrieval solution at 95° C. for 45 minutes (pH 9 Target Retrieval Solution, Dako). After endogenous peroxydase inhibition and FcR blocking, Granzyme B was stained with anti-Granzyme B monoclonal antibody (clone GrB-7, Dako) for 1 hour at room temperature. After signal amplification with an HRP labeled polymer (Dako), the revelation was done using 3-Amino-9-ethylcarbazole (AEC, Vector Laboratories). Then slides were immersed in hematoxylin, rinsed in distilled water and mounted in aqueous-based mounting median (glycergel, Dako). After imaging using whole slide scanner, the slides were subjected to the Multiplexed Immunohistochemical Consecutive Staining on Single Slide protocol (MICSSS)[34] and stained for T cells (CD3, clone 2GV6, Ventana and CD8, clone C8/144b, Dako), regulatory T cells (FoxP3, clone 236A/E7, Abcam), B cells (CD20, clone L26, Dako), macrophages (CD68, clone KP1, Dako), mature dendritic cells (DC-LAMP, clone 1010E1. 01, Novus Biologicals)], MHC class I (HLA-ABC, clone EMR8-5, Abcam) and tumor cells (CK19, clone EP1580Y, Abcam).

Immunofluorescence

For CD4, FoxP3, and CK19 staining, sections first were incubated with anti-CD4 (Ventana, cat #790-4423, 0.5 ug/ml) for 5 hours, followed by 60 minutes incubation with biotinylated goat anti-rabbit IgG (Vector, cat #PK6101) at 1:200 dilution. The detection was performed with Streptavidin-HRP D (part of DABMap kit, Ventana Medical Systems), followed by incubation with Tyramide Alexa 488 (Invitrogen, cat #T20922) prepared according to manufacturer instruction with predetermined dilutions. Next, slides were incubated with anti-FoxP3 (Abcam, cat #ab20034, 5 ug/ml) for 4 hours, followed by 60 minutes incubation with biotinylated horse anti-mouse IgG (Vector Labs, cat #MKB-22258) at 1:200 dilution. The detection was performed with Streptavidin-HRP D (part of DABMap kit, Ventana Medical Systems), followed by incubation with Tyramide Alexa Fluor 568 (Invitrogen, cat #T20914) prepared according to manufacturer instruction with predetermined dilutions. Finally, sections were incubated with anti-CK19 (Abcam, cat #ab52625, 1 ug/ml) for 5 hours, followed by 60 minutes incubation with biotinylated goat anti-rabbit IgG (Vector, cat #PK6101) at 1:200 dilution. The detection was performed with Streptavidin-HRP D (part of DABMap kit, Ventana Medical Systems), followed by incubation with Tyramide Alexa 647 (Invitrogen, cat #T20936) prepared according to manufacturer instruction with predetermined dilutions. After staining slides were counterstained with DAPI (Sigma Aldrich, cat #D9542, 5 ug/ml) for 10 min and coverslipped with Mowiol.

For CD3, CD8, and CK19 staining, slides first were incubated with anti-CD3 (DAKO, cat #A0452, 1.2 ug/ml) for 4 hours, followed by 60 minutes incubation with biotinylated goat anti-rabbit IgG (Vector Labs, cat #PK6101) at 1:200 dilution. The detection was performed with Streptavidin-HRP D (part of DABMap kit, Ventana Medical Systems), followed by incubation with Tyramide Alexa 488 (Invitrogen, cat #T20922) prepared according to manufacturer instruction with predetermined dilutions. Next, slides were incubated with anti-CD8 (Ventana, cat #790-4460, 0.35 ug/ml) for 5 hours, followed by 60 minutes incubation with biotinylated goat anti-rabbit IgG (Vector, cat #PK6101) at 1:200 dilution. The detection was performed with Streptavidin-HRP D (part of DABMap kit, Ventana Medical Systems), followed by incubation with Tyramide Alexa Fluor 568 (Invitrogen, cat #T20914) prepared according to manufacturer instruction with predetermined dilutions. Finally, sections were incubated with anti-CK19 (Abcam, cat #ab52625, 1 ug/ml) for 5 hours, followed by 60 minutes incubation with biotinylated goat anti-rabbit IgG (Vector, cat #PK6101) at 1:200 dilution. The detection was performed with Streptavidin-HRP D (part of DABMap kit, Ventana Medical Systems), followed by incubation with Tyramide Alexa 647 (Invitrogen, cat #T20936) prepared according to manufacturer instruction with predetermined dilutions. After staining slides were counterstained with DAPI (Sigma Aldrich, cat #D9542, 5 ug/ml) for 10 min and coverslipped with Mowiol.

Digital Image Processing and Analysis

Tissue microarrays (TMAs) for each immunohistochemical stain were individually digitally scanned using Pannoramic Flash (3DHistech, Budapest, Hungary) with a 40×/0.95NA objective. Images registration and alignment was performed using Image J (NIH, Bethesda, Md.). ROIs were drawn for each core of one scan then transferred to others using CaseViewer (3DHistech). Each region from each scan was exported as tiff images at full resolution (0.243 µm/pixel). Images of the same core from multiple scans were stacked together and aligned using Linear Stack Alignment with SIFT algorithm from FIJI/ImageJ (NIH, Bethesda, Md.). Once aligned, the RGB images were color deconvoluted to separate AEC and hematoxylin stainings and converted into 8-bit pseudo-fluorescent images. Individual immunohistochemical targets were sequentially assigned to fluorescent channels and subsequently merged. Hematoxylin staining was used to segment and count the number of nucleated cells in the core. After processing the images using background subtraction and median filter, staining was thresholded and split using Biovoxxel Watershed Irregular Features plugin. ROIs were drawn around each cell and matched to the signals from all other AEC stainings to count the number of positive cells for each staining. Total tissue area was measured by setting a very low threshold for hematoxylin images. For quantification, all nucleated cells were identified, followed by an intensity-based threshold determination of each target to identify positive cells. Triplicate cores were quantified followed by determination of the median number of cells per square mm of tissue (Image J, NIH, Bethesda Md.). Quantification of cells detected using immunofluorescence was performed in a similar fashion.

Nucleic Acid Extraction

10 μm slides were cut from OCT embedded frozen tumor and matched normal tissues. Sections were brought to containers with 70% ethanol for OCT removal. Following OCT removal, specimens were dissected for subsequent DNA and RNA extraction. For whole exome sequencing, tumor islands of ≥70% cellularity were macrodissected based on expert PDAC pathologic review, and DNA was extracted using the DNA Easy kit. Total RNA from Fresh Frozen OCT embedded tissues was extracted using TRIzol RNA Isolation Reagents (cat #15596-026, Life Technologies).

Transcriptome Analysis

Extracted RNA was qualified on Agilent BioAnalyzer and quantified by fluorometry (Ribogreen). Preparation of RNA for whole transcriptome expression analysis was done using the WT Pico Reagent Kit (Affymetrix, CA, USA). Reverse transcription was initiated at the poly-A tail as well as throughout the entire length of RNA to capture both coding and multiple forms of non-coding RNA. RNA amplification was achieved using low-cycle PCR followed by linear amplification using T7 in vitro transcription (IVT) technology. The cRNA was then converted to biotinylated sense strand DNA hybridization targets. Prepared target was hybridized to GeneChip® Human Transcriptome Array 2.0 (Affymetrix, CA, USA). Wash and scan was done using the GeneChip® Hybridization, Wash and Stain Kit using a Fluidics Station 450/250. Arrays were scanned using the GeneChip® Scanner 3000. Data analysis for the array was done using Affymetrix Expression Console™ Software (SST-RMA algorithm to summarize the signal from array probesets). Unsupervised hierarchical clustering was performed using Ward linkage and Euclidean distance (R, v 3.3.0). Clusters were defined using a probe set variance cutoff of 0.3. A dendritic cell signature was defined as previously described, using the genes CCL13, CCL17, CCL22, PPFIBP2, NPR1, HSD11B1, and CD209/DC-SIGN[17].

T Cell Receptor Vβ Sequencing

Frozen tumor (short term n=30, long term n=30) and paired non-tumor adjacent pancreas tissue (short term n=30, long term n=30) samples were processed (Adaptive Biotechnologies, Seattle, USA). Genomic DNA was extracted according to the manufacturer's instructions (QIAsymphony, Qiagen, Germany). The quantity and quality of extracted DNA was verified prior to sequencing. Using a standard quantity of input DNA, the TCR VD CDR3 regions were amplified and sequenced using the survey multiplexed PCR ImmunoSeq assay. The ImmunoSeq platform combines multiplex PCR with high throughput sequencing to selectively amplify the rearranged complementarity determining region 3 (CDR3) of the TCR, producing fragments sufficiently long to identify the VDJ region spanning each unique CDR3. 45 forward primers specific for TCR Vβ gene segments and 13 reverse primers specific to TCR Jβ gene segments were used (Adaptive Biotechnologies). Read lengths of 156 bp were obtained using the Illumina HiSeq System. The ImmunoSeq assay allows for quantitative assessment of both total and unique TCRs in a sample, as it uses a complete synthetic repertoire of TCRs to establish an amplification baseline and adjust the assay chemistry to correct for primer bias. Barcoded, spiked-in synthetic templates were also used to measure and correct for sequencing coverage and residual PCR bias. Output data were then filtered and clustered using the relative frequency ratio between similar clones and a modified nearest-neighbour algorithm, to merge closely related sequences and remove PCR and sequencing errors. The number of rearranged TCRs per diploid genome in the input material (total number of T cells) was estimated as previously described[37]. Data were analyzed using the ImmunoSeq analyzer tool. The frequency of T cells was determined as the total number of T cells per total number of sequenced cells in the input material. A T cell clone was defined as a T cell with a unique TCR CDR3 amino acid sequence. Clonality was defined as (1-normalized entropy). Normalized entropy was calculated as the Shannon entropy divided by the logarithm of the number of unique productive (exonic) TCR sequences. Shannon entropy equals the clonal abundance of all productive TCR sequences in the input material. For in vitro stimulated cells, clones with identical amino acid sequences detected in all four compartments, that expanded on day 22 compared to day 0 (fold change>2, ≥5 templates) are indicated. Data analysis was performed using Adaptive Biotechnologies ImmunoSeq Analyzer (Analyses 3.0, Seattle, Wash.).

Whole Exome Sequencing

For all MSKCC PDAC patients, 500 ng of genomic DNA was fragmented to a target size of 150 to 200 bp on the Covaris LE220 system. Barcoded libraries (Kapa Biosystems) were subjected to exon capture by hybridization using the SureSelect Human All Exon 51 MB V4 kit (Agilent). DNA libraries were subsequently sequenced on a HiSeq 4000 (Illumina) in a Paired End 100/100, using the TruSeq SBS Kit v3 (Illumina) with a target coverage of 150× for tumor samples and 70× for matched normal (MSKCC Center for Molecular Oncology). Sequence data were demultiplexed using CASAVA, and after removal of adapter sequences using cutadapt (v(1.6) reads were aligned to the reference human genome (hg19) using the Burrows-Wheeler Alignment tool (bwa mem v0.7.12). Duplicate-read removal, InDel realignment and Base Quality Score Recalibration were performed using the Genome Analysis Toolkit (GATK) according to GATK best practices, as previously described[13]. Variants were identified on processed data using mutect, mutect rescue (SNPs) and haplotype caller (insertions/deletions) (FIG. 71). A mean unique sequence coverage of 167.45× was achieved for tumor samples and 84.75× for normal samples. All MUC16 mutations were manually reviewed by 3 investigators using the Integrated Genomics Viewer (IGV) v2.3.72. Whole genome and whole exome sequencing for ICGC[25] patients has been previously described. For all ICGC samples, BAM files were re-processed and mutations identified as per the above outlined MSKCC protocol.

HLA Typing

HLA typing for PDAC patients was performed in silico using the tool Short Oligonucleotide Analysis Package-HLA (SOAP).

Immunogenicity Predictions of Somatic Mutations

MSKCC Pipeline: Immunogenicity of somatic mutations was estimated using a previously described bioinformatics tool called NASeek3. Briefly, NASeek is a computational algorithm that first translates all mutations in exomes to strings of 17 amino acids, for both the wild type and mutated sequences, with the amino acid resulting from the mutation centrally situated. Secondly, it evaluates putative MHC Class I binding for both wild type and mutant nonamers using a sliding window method using NetMHC3.4 for patient-specific HLA types, to generate predicted binding affinities for both peptides. NASeek finally assesses for similarity between nonamers that were predicted to be presented by patient-specific MHC Class I. All mutations with binding scores below 500 nM are defined as neoantigens. As the MSKCC pipeline was, on average, more stringent with respect to the number of neoantigens identified (in comparison to the pVAC-Seq pipeline below), all neoantigen predictions were performed with the MSKCC pipeline unless otherwise specified.

pVAC-Seq Pipeline: The pVAC-Seq pipeline[26] was used with the NetMHCpan binding strength predictor[43] to identify neoantigens (<500 nM binding strength). As recommended there, the variant effect predictor from Ensembl[44] was used to annotate variants for downstream processing by pVAC-Seq.

Neoantigen Fitness Modeling

The fitness of a clone is defined as $$\frac{dN_\alpha}{dt} = F_\alpha N_\alpha$$

where $N_\alpha$ is the effective population size of tumor clone $\alpha$, $F_\alpha$ is the fitness function of clone $\alpha$. The effective population size is the size of a clone estimated from a tumors phylogenetic tree[31].

Fitness due to neoantigen recognition potential (interchangeably referreed to herein as cross reactivity) is defined as $F_\alpha = -C_\alpha$, where $$C_\alpha = \max_{i \in Clone\ a} (A_i^{MHC} \times R_i),$$

that is, within a clone $\alpha$, the maximal product of the amplitude $A_i^{MHC}$ and the recognition potential (cross reactivity) probability $R_i$ for a neoantigen $n_1$, is probability that neoantigen $n_i$ will be recognized by a T-Cell receptor.

Fitness in the neoantigen load hypothesis is defined as $F_\alpha = -L_\alpha$, where $L_\alpha$ is the number of neoantigens in clone $\alpha$.

For a given neoantigen $n_i$, the recognition potential (cross reactivity) probability $R_i$ was calculated as the probability that neoantigen $n_i$ would be recognized by at least one T cell receptor specific to a microbial epitope e:

$$R_i = 1 - \prod_{e \in IEDB} (1 - Pr_{binding}(n_i, e)),$$

where $Pr_{binding}(n_i, e)$ estimates the binding probability of neoantigen $n_i$ to a T cell receptor specific to epitope e. Epitopes e were derived from the Immune Epitope Database, restricting the search to all human, infectious disease derived, class-I restricted targets with positive immune assays. The probability of a neoantigen $n_i$ eliciting recognition potential (cross reactivity) is modeled by its alignment to a validated IEDB epitope e via a logistic function of the alignment score between the two peptides, $|n_i, e|$, using the BLOSUM62 alignment matrix:

$$Pr_{binding}(n_i, e) = 1/(1 + e^{-k(|n_i, e| - e_0)}),$$

where $e_0$ represents the horizontal displacement of the binding curve and k sets the slope of the curve at $e_0$. These are two free parameters to be fit in our model.

The amplitude due to relative MHC dissociation constants between a neoantigen and its wildtype counterpart is $A_i^{MHC} \approx K_d^{WT}/K_d^{Mutant}$. The standard cutoff for $K_d^{Mutant}$ was used, the mutant dissociation constant, used in the literature, that is $K_d^{Mutant} < 500$ nM.

For all cases, the neoantigen load without clonal phylogeny was computed, which was the standard benchmark, and the neoantigen load with clonal phylogeny, by taking into account the effective size of clones in which neoantigens were contained. Our results were also compared to using the wild type cross reactivity alone, in which case our MHC amplitude was one, and the cross reactivity without clonality, which essentially just scores the best neoantigen across the tumor.

The predicted relative reduction in effective total tumor population size at time τ is therefore $$S(\tau) = \frac{N(\tau)}{N(0)} = \sum_\alpha X_\alpha(0) \exp(F_\alpha \tau)$$

where $N(0) = \Sigma_\alpha N_\alpha(0)$ is the initial total effective population size of all clones within the tumor, and $X_\alpha(0) = N_\alpha(0)/N(0)$ is frequency of clone $\alpha$. The parameter τ=0.05, and is a time-scale fixed across all datasets which empirically corresponds to the time after which the signal from the model degrades. Now S(τ) is calculated for each sample. Samples were split by the median value of the cohort, with samples below this value designated as a low fitness group, and those above as a high fitness group. Then survival for high versus low fitness groups were compared. Values for the shift parameter that optimized survival were calculated. To test the stability of this choice, the optimal value for subsampled datasets was derived, with subsampling frequencies of 0.8, 0.7, 0.6, 0.5 and 0.4. The optimal value of the parameter obtained on the full dataset, $e_0$=27, was within the standard deviation of the median optimal values for all subsampling frequencies (FIG. 56).

Finally, Monte-Carlo cross-validation was performed by randomly dividing the dataset into 50-50 partitions. In each case the optimal parameter was derived on one side of the partition (the training set), and then the p-value was determined between survival curves on the other 50% of samples (the validation set). The procedure was repeated 5000 times and gave the median p-value of 0.05.

In Vitro T Cell Assays

Fresh blood was collected from two PDAC long term survivors whose tumors were identified based on whole exome sequencing and in silico prediction to harbor MUC16 neoantigens. Peripheral-blood mononuclear cells were isolated by density centrifugation over Ficoll-Paque Plus (GE Healthcare). Peptides were generated for MUC16 neoantigens and the corresponding WT nonamers (Peptide 2.0, VA, USA). In vitro peptide stimulation was performed as described with minor modifications 3. Briefly, 2×10⁶ PBMCs were cultured with mutant or WT peptides (10 ug/ml) on day 1. Il-2 (10 U/ml) and IL-15 (long/ml) were added on day 2 and every subsequent 2-3 days. Mutant and WT peptides were added to respective cultures on days 7, and day 14 for second and third rounds of restimulation. On day 21 and 29, cells were restimulated in the presence of Brefeldin A and Golgiplug (BD Bioscience) for 6 hours and cells were subsequently stained as per manufacturer's instructions.

Flow Cytometry

Fresh blood and tumor samples from 6 individual patients undergoing elective surgery at Memorial Hospital were collected. Informed consent was obtained according to a Memorial Hospital Institutional Review Board approved protocol. Blood was drawn at the time of surgery, and peripheral-blood mononuclear cells were isolated by density centrifugation over Ficoll-Paque Plus (GE Healthcare). Tumor and draining lymph node tissues were processed immediately after removal from the patient and single-cell suspensions were prepared. To assess if T cells bind in silico predicted neoantigen-HLA complexes, T cells of peripheral blood mononuclear cells (PBMCs) from HLA-specific healthy donors (Precision For Medicine, Frederick, Md.) were assessed for binding to MUC16-neoantigen-MHC multimers. MUC16-MHC-FITC multimers were designed to HLA-B0801, A1101, A2402, and A0301 (Immudex, Copenhagen, Denmark) with nonamer peptide sequences derived based on mutated MUC16 sequences identified on whole exome sequencing that were in-silico predicted to be immunogenic. Single cell PBMC suspensions were surface stained for anti-human CD45, CD3, CD56, CD8, CD4, CD107a, and MHC-multimers according to manufacturer's instructions. Human-specific antibodies used in all flow cytometric phenotyping included CD45 (clone HI30, BioLegend), CD3 (clone OKT3, BioLegend), CD4 (clone SK3, BD Biosciences), CD8 (clone SK1, BioLegend), CD56 (clone α159, BD Biosciences), CD69 (clone FN50, BD Biosciences), CD19 (clone SJ25C1, BD Biosciences), PD1 (clone MIH4, BD Biosciences), CD45RA (clone HI100, BD Biosciences), CD45 RO (clone UCHL1, BD Biosciences) and CD107a (clone H4A3, BD Biosciences). Flow cytometry was performed on an LSRFortessa (BD Biosciences) and data were analyzed using FlowJo Software (Tree Star).

Statistics

Comparisons between two groups were performed using unpaired two-tailed Mann-Whitney test (unpaired samples), paired two-tailed Mann Whitney test (paired samples), and two-tailed students t-test (normally distributed parameters). Multiple samples were compared using Kruskal-Wallis test (non-grouped) and ANOVA with Tukey's post-test for multiple comparisons (grouped). Survival curves were compared using log-rank test (Mantel-Cox). Categorical variables were compared using chi-square test. All comparison groups had equivalent variances. $P<0.05$ was considered to be statistically significant.

Discussion

The current study in this Example X includes genomic, molecular, and cellular immunoprofiling with neoantigen discovery in rare long term survivors of pancreatic ductal adenocarcinoma (PDAC) (n=82, median survival 6 years), a lethal, checkpoint blockade refractory cancer with few predicted neoantigens[12]. Compared to short term survivors with poor outcome, greater cytolytic, polyclonal T cell infiltrates and adaptive immune activation in tumors of long term survivors were detected. Using whole exome sequencing and in silico prediction, it was found that tumors with the highest neoantigen number and the most abundant intratumoral cytolytic T cell infiltrates stratified patients with the longest survival (median survival not reached). To understand the specific neoantigen qualities in long term survivors, a neoantigen immunogenicity fitness model was developed, integrating clonal genealogy, epitope homology, and T cell receptor affinity. A model conferring greater immunogenicity to dominant neoantigens with homology to microbial epitopes identified long term survivors, whereas a model ascribing greater immunogenicity to increasing neoantigen number did not. Consistent with long term survivors harboring immunogenic neoantigens, it was found that long term survivors were 4 times more likely to harbor neoantigens at the MUC16 locus encoding the tumor antigen CA125. Finally, it was detected that evidence of an anti-MUC16 immune response in tumors of long term survivors with subsequent long-lasting MUC16 neoantigen-specific T cell immunity in peripheral blood, identifying MUC16 as a candidate immunogenic hotspot. The data suggest that even in tumors with fewer mutations such as PDAC, neoantigens can influence protective immunity, with immunodominant neoantigens identified by adaptive immune fitness and immunogenic hotspots. Therefore, clarification of factors determining neoantigen immunogenicity and detection of immunogenic hotspots can facilitate focused therapeutic targeting of neoantigens and inform application of future checkpoint blockade immunotherapies The results shed novel insight into the heterogeneous immunobiology of presumed poorly immunogenic and checkpoint blockade refractory tumors such as PDAC, demonstrating that neoantigens can be dominant T cell targets in subsets of long term survivors. It is proposed that neoantigen quality, and not merely quantity, modulate immunogenicity, clonal fitness, and immunoselection during tumor evolution, with neoantigens in immunogenic residues such as MUC16 emerging as apparent hotspots. It is noteworthy that our results do not invoke associations of pre-existing microbial and anti-tumor immunity in long term survivors; instead, our data suggest that microbial homology can serve as an effective surrogate for immunogenic neoantigen qualities. The data presented herein suggest that neoantigen-specific immunity gained during primary tumor outgrowth can be associated with decreased relapse and prolonged survival, comparable to classical murine studies of prior tumor exposure protecting against tumor rechallenge[35]. These findings have implications for cancer immunotherapy. Specifically, they provide a rationale for development of immunotherapeutic strategies to harness neoantigen-specific immunity in the treatment of checkpoint blockade refractory cancers, and immunogenic hotspot discovery for directed neoantigen targeting.

For further information, see Balachandran, V P et al., *Nature*, 551(7681):512-16 (2017), the content of which is expressly incorporated herein by reference in its entirety, for all purposes.

REFERENCES CITED AND ALTERNATIVE EMBODIMENTS

1. Siegel, R. L., Miller, K. D. & Jemal, A. *Cancer Statistics* 65, 5-29 (2015).
2. Kleeff, J. et al. Pancreatic cancer, *Nature Publishing Group* 2, 16022 (2016).
3. Hidalgo, M. Pancreatic cancer, *The New England Journal of Medicine* 362, 1605-1617 (2010).
4. Valsecchi, M. E., Diaz-Canton, E., de la Vega, M. & Littman, S. J., "Recent treatment advances and novel therapies in pancreas cancer: a review," *Journal of Gastrointestinal Cancer* 45, 190-201 (2014).

5. Royal, R. E. et al, "Phase 2 trial of single agent Ipilimumab (anti-CTLA-4) for locally advanced or metastatic pancreatic adenocarcinoma," *Journal of Immunotherapy* 33, 828-833 (2010).
6. Bailey, P. et al., "Genomic analyses identify molecular subtypes of pancreatic cancer," *Nature* 531, 47-52 (2016).
7. Ryschich, E. et al., "Control of T-cell-mediated immune response by HLA class I in human pancreatic carcinoma," *Clin Cancer Res* 11, 498-504 (2005).
8. Ino, Y. et al., "Immune cell infiltration as an indicator of the immune microenvironment of pancreatic cancer," *Br J Cancer* 108, 914-923 (2013).
9. Hiraoka, N. et al., "Intratumoral tertiary lymphoid organ is a favourable prognosticator in patients with pancreatic cancer," *Br J Cancer* 112, 1782-1790 (2015).
10. Dal Molin, M. et al., "Very Long-term Survival Following Resection for Pancreatic Cancer Is Not Explained by Commonly Mutated Genes: Results of Whole-Exome Sequencing Analysis," *Clin Cancer Res* 21, 1944-1950 (2015).
11. Gubin, M. M. et al., "Checkpoint blockade cancer immunotherapy targets tumour-specific mutant antigens," *Nature* 515, 577-581 (2014).
12. Schumacher, T. N. & Schreiber, R D., "Neoantigens in cancer immunotherapy," Science 348, 69-74 (2015).
13. Snyder, A. et al. "Genetic basis for clinical response to CTLA-4 blockade in melanoma," N Engl J Med 371, 2189-2199 (2014).
14. Rizvi, N. A. et al., "Cancer immunology. Mutational landscape determines sensitivity to PD-1 blockade in non-small cell lung cancer," Science 348, 124-128 (2015).
15. Van Allen, E. M. et al., "Genomic correlates of response to CTLA-4 blockade in metastatic melanoma," Science 350, 207-211 (2015).
16. Remark, R., Merghoub, T. & Grabe, N, "In-depth tissue profiling using multiplexed immunohistochemical consecutive staining on single slide," Science (2016).
17. Bindea, G. et al., "Spatiotemporal Dynamics of Intratumoral Immune Cells Reveal the Immune Landscape in Human Cancer," *Immunity* 39, 782-795 (2013).
18. Gros, A. et al., "PD-1 identifies the patient-specific CD8$^+$ tumor-reactive repertoire infiltrating human tumors," *The Journal of Clinical Investigation* 124, 2246-2259 (2014).
19. Gros, A. et al., "Prospective identification of neoantigen-specific lymphocytes in the peripheral blood of melanoma patients," *Nat Med* 22, 433-438 (2016).
20. Chauvin, J.-M. et al., "TIGIT and PD-1 impair tumor antigen-specific CD8$^+$ T cells in melanoma patients," *The Journal of Clinical Investigation* 125, 2046-2058 (2015).
21. Yu, H., Pardoll, D. & Jove, R., "STATs in cancer inflammation and immunity: a leading role for STAT3," *Nat Rev Cancer* 9, 798-809 (2009).
22. McAllister, F. et al., "Oncogenic Kras activates a hematopoietic-to-epithelial IL-17 signaling axis in preinvasive pancreatic neoplasia," *Cancer Cell* 25, 621-637 (2014).
23. Biankin, A. V. et al., "Pancreatic cancer genomes reveal aberrations in axon guidance pathway genes," *Nature* 491, 399-405 (2012).
24. Witkiewicz, A. K. et al., "Whole-exome sequencing of pancreatic cancer defines genetic diversity and therapeutic targets," *Nat Commun* 6, 6744 (2015).
25. Bailey, P. et al., "Genomic analyses identify molecular subtypes of pancreatic cancer," *Nature* 531, 47-52 (2016).
26. Hundal, J. et al., "pVAC-Seq: A genome-guided in silico approach to identifying tumor neoantigens," *Genome Med* 8, 11 (2016).
27. Sausen, M. et al., "Clinical implications of genomic alterations in the tumour and circulation of pancreatic cancer patients," *Nat Commun* 6, 7686 (2015).
28. Zitvogel, L., Ayyoub, M., Routy, B. & Kroemer, G., "Microbiome and Anticancer Immunosurveillance," Cell 165, 276-287 (2016).
29. Vétizou, M. et al., "Anticancer immunotherapy by CTLA-4 blockade relies on the gut microbiota," *Science* 350, 1079-1084 (2015).
30. Luksza, M. & Lassig, M, "A predictive fitness model for influenza," *Nature* 507, 57-61 (2014).
31. Deshwar, A. G. et al., "PhyloWGS: reconstructing subclonal composition and evolution from whole-genome sequencing of tumors," *Genome Biol.* 16, 35 (2015).
32. Chekmasova, A. A. et al., "Successful eradication of established peritoneal ovarian tumors in SCID-Beige mice following adoptive transfer of T cells genetically targeted to the MUC16 antigen," *Clin Cancer Res* 16, 3594-3606 (2010).
33. Morgado, M. et al., "Tumor necrosis factor-α and interferon-γ stimulate MUC16 (CA125) expression in breast, endometrial and ovarian cancers through NFκB.," *Oncotarget* 7, 14871-14884 (2016).
34. Das, S. et al., "Carboxyl-terminal domain of MUC16 imparts tumorigenic and metastatic functions through nuclear translocation of JAK2 to pancreatic cancer cells," *Oncotarget* 6, 5772-5787 (2015).
35. Shukla, S. K. et al., "MUC16-mediated activation of mTOR and c-Myc reprograms pancreatic cancer metabolism," *Oncotarget* 6, 19118-19131 (2015).
36. Muniyan, S. et al., "MUC16 contributes to the metastasis of pancreatic ductal adenocarcinoma through focal adhesion mediated signaling mechanism," *Genes Cancer* 7, 110-124 (2016).
37. Liu, Q. et al., "C-terminus of MUC16 activates Wnt signaling pathway through its interaction with β-catenin to promote tumorigenesis and metastasis," *Oncotarget* 7, 36800-36813 (2016).
38. Wang et al., "Expression of the Carboxy-Terminal Portion of MUC16/CA125 Induces Transformation and Tumor Invasion," *PLOS ONE* 75, 4669-4674 (2015).
39. Pearson, H. et al., "MHC class I-associated peptides derive from selective regions of the human genome," *The Journal of Clinical Investigation* (2016). doi:10. 1172/JCI88590
40. Gross, L., "Intradermal Immunization of C3H Mice against a Sarcoma That Originated in an Animal of the Same Line," *Cancer Res* 3, 326-333 (1943).
41. Haridas, D. et al., "Pathobiological implications of MUC16 expression in pancreatic cancer," *PLOS ONE* 6, e26839 (2011).
42. Tumeh, P. C. et al., "PD-1 blockade induces responses by inhibiting adaptive immune resistance," *Nature* 515, 568-571 (2014).
43. Nielsen, M. et al., "NetMHCpan, a method for quantitative predictions of peptide binding to any HLA-A and -B locus protein of known sequence,"*PLOS ONE* 2, e796 (2007).
44. McLaren, W. et al., "The Ensembl Variant Effect Predictor," *Genome Biol.* 17, 122 (2016).

All references cited herein are incorporated herein by reference in their entirety and for all purposes to the same extent as if each individual publication or patent or patent application was specifically and individually indicated to be incorporated by reference in its entirety for all purposes.

The present invention can be implemented as a computer program product that comprises a computer program mechanism embedded in a nontransitory computer readable storage medium. For instance, the computer program product could contain the program modules shown in any combination of FIG. 1 or 2 and/or described in FIG. 3, 37, 38, 39, 40 or 71. These program modules can be stored on a CD-ROM, DVD, magnetic disk storage product, USB key, or any other non-transitory computer readable data or program storage product.

Many modifications and variations of this invention can be made without departing from its spirit and scope, as will be apparent to those skilled in the art. The specific embodiments described herein are offered by way of example only. The embodiments were chosen and described in order to best explain the principles of the invention and its practical applications, to thereby enable others skilled in the art to best utilize the invention and various embodiments with various modifications as are suited to the particular use contemplated. The invention is to be limited only by the terms of the appended claims, along with the full scope of equivalents to which such claims are entitled.

What is claimed is:

1. A method for selecting a human subject afflicted with a cancer for treatment with a checkpoint blockade immunotherapy comprising:
 (A) obtaining a plurality of sequencing reads from one or more samples from the human cancer subject that is representative of the cancer;
 (B) determining a human leukocyte antigen (HLA) type of the human cancer subject;
 (C) determining a plurality of clones, and for each respective clone α in the plurality of clones, an initial frequency $X_\alpha$ of the respective clone α in the one or more samples;
 (D) for each respective clone α in the plurality of clones, computing a corresponding clone fitness score of the respective clone, thereby computing a plurality of clone fitness scores, each corresponding clone fitness score computed for a respective clone α by a first procedure comprising:
  (a) identifying a plurality of neoantigens in the respective clone α;
  (b) computing a recognition potential of each respective neoantigen in the plurality of neoantigens in the respective clone α by a second procedure comprising:
   (i) computing an amplitude A of the respective neoantigen as a function of the relative major histocompatibility complex (MHC) affinity of the respective neoantigen and the wildtype counterpart of the respective neoantigen given the HLA type of the subject,
   (ii) computing a probability of T-cell receptor recognition R of the respective neoantigen as a probability that the respective neoantigen is bound by T-cells that are specific to one or more known epitopes in a plurality of epitopes after class I MHC presentation, wherein the plurality of epitopes comprises $1\times10^6$ epitopes,
   wherein the probability of T-cell receptor recognition R is computed as:

$$R = Z(k)^{-1} \sum_{e \in D} \exp[-k(a - |s, e|)],$$

wherein
 a is a number that represents a horizontal displacement of a binding curve for the respective neoantigen,
 k is a number that sets the steepness of the binding curve at a,
 Z(k) is a partition function over the unbound state and all bound states of the respective neoantigen of the form $$1 + \sum_{e \in D} \exp[-k(a - |s, e|)]$$

wherein,
 D is the plurality of epitopes,
 each respective epitope e is an epitope from the plurality of epitopes that is positively recognized by T-cells after class I MHC presentation, and
 |s, e| is a measure of sequence similarity between the respective neoantigen s and the respective epitope e, and
   (iii) computing the recognition potential of the respective neoantigen as a function of the amplitude A of the respective neoantigen and the probability of T-cell receptor recognition R of the respective neoantigen; and
  (c) determining the corresponding clone fitness score of the respective clone α as an aggregate of the neoantigen recognition potentials across the plurality of neoantigens in the respective clone α;
 (E) computing a total fitness for the one or more samples as a sum of the clone fitness scores across the plurality of clones, wherein:
 each clone fitness score is weighted by the initial frequency $X_\alpha$ of the corresponding clone α, and
 the total fitness quantifies the likelihood that the human subject afflicted with the cancer will be responsive to the treatment regimen; and
 (F) administering ipilimumab or tremelimumab to the subject when the total fitness of the subject is lower than a predetermined threshold.

2. The method of claim 1, wherein the cancer is a carcinoma, a melanoma, a lymphoma/leukemia, a sarcoma, or a neuro-glial tumor.

3. The method of claim 1, wherein the cancer is lung cancer, pancreatic cancer, colon cancer, stomach or esophagus cancer, breast cancer, ovary cancer, prostate cancer, or liver cancer.

4. The method of claim 1, wherein
each clone α in the plurality of clones is uniquely defined by a unique set of somatic mutations, and
the plurality of clones is determined by a variant allele frequency of each respective somatic mutation in a plurality of somatic mutations determined from the plurality of sequencing reads.

5. The method of claim 4, wherein the somatic mutation is a single nucleotide variant or an indel.

6. The method of claim 1, wherein
each clone α in the plurality of clones is uniquely defined by a unique set of somatic mutations, and
the plurality of clones is determined by a combination of (i) a variant allele frequency of each respective somatic mutation in the plurality of somatic mutations determined from the plurality of sequencing reads and (ii) an identification of a plurality of inferred copy number variations using the whole-genome sequencing data.

7. The method of claim 1, wherein each neoantigen in the plurality of neoantigens of a clone in the plurality of clones is a peptide that is eight, nine, ten, or eleven residues in length.

8. The method of claim 1, the method further comprising identifying a population of neoantigens present in the one or more samples by a third procedure comprising:
determining a plurality of somatic single nucleotide polymorphisms (SNPs) in the plurality of sequencing reads by comparison of the plurality of sequencing reads to a reference human genome; and
evaluating each respective somatic SNP in the plurality of SNPs as a neoantigen candidate by evaluation of a peptide encoded by a portion of one or more sequencing reads in the plurality of sequencing reads that includes the respective somatic SNP against a classifier that has been trained to predict peptide binding to class 1 MHC of the HLA type of the cancer subject, wherein a neoantigen candidate having a binding score below a threshold value is deemed to be a neoantigen in the population of neoantigens, and
wherein the identifying the plurality of neoantigens in the respective clone α comprises matching the SNPs in the respective clone α to respective neoantigens in the population of neoantigens.

9. The method of claim 1, wherein the function of the relative class I MHC affinity of the respective neoantigen and the wildtype counterpart of the respective neoantigen given the HLA type of the subject is a ratio of:
(1) a dissociation constant between the respective neoantigen and the class I MHC presented by the cancer subject given the HLA type of the cancer subject, and
(2) a dissociation constant between the wildtype counterpart of the respective neoantigen and the class I MHC presented by the cancer subject given the HLA type of the cancer subject.

10. The method of claim 9, wherein:
the dissociation constant between the respective neoantigen and the class I MHC presented by the cancer subject is obtained as output from a first classifier upon inputting into the first classifier the amino acid sequence of the neoantigen,
the dissociation constant between the wildtype counterpart of the respective neoantigen and the class I MHC presented by the cancer subject of the HLA type of the subject is obtained as output from the first classifier upon inputting into the first classifier the amino acid sequence of the respective wildtype counterpart of the neoantigen, and
the first classifier is specific to the HLA type of the cancer subject and has been trained with the respective class I MHC binding coefficient and sequence data of each peptide epitope in a plurality of epitopes presented by class I MHC in a training population having the HLA type of the subject.

11. The method of claim 1, wherein the measure of sequence similarity |s, e| is computed as a sequence alignment between the sequence of the respective neoantigen s and the sequence of the respective epitope e using an amino-acid similarity matrix.

12. The method of claim 1, wherein the aggregate of the neoantigen recognition potentials across the plurality of neoantigens in the respective clone α is computed as:

$$F_\alpha = -\max_{i \in Clone\ \alpha} (A_i \times R_i)$$

wherein i is an index iterating over each neoantigen in the plurality of neoantigens in the respective clone α.

13. The method of claim 12, wherein the computing a total fitness for the one or more samples as a sum of the clone fitness scores across the plurality of clones is computed as:

$$n(\tau) = Z_\alpha X_\alpha \exp(F_\alpha \tau),$$

wherein τ is a characteristic evolutionary time scale.

14. The method of claim 1, wherein the aggregate of the neoantigen recognition potentials across the plurality of neoantigens in the respective clone α is computed as a summation of the recognition potential of all or a subset of the neoantigens in the plurality of neoantigens.

15. The method of claim 1, wherein the aggregate of the neoantigen recognition potentials across the plurality of neoantigens in the respective clone α is computed as a nonlinear combination of the recognition potential of all or a subset of the neoantigens in the plurality of neoantigens.

16. The method of claim 1, wherein the total fitness is inversely proportional to (a) a likelihood that the cancer subject will be responsive to immunotherapy and (b) an indication of survival of the cancer subject.

17. The method of claim 1, wherein the plurality of epitopes consists of epitopes that have been recognized by human T-cells from the human subject.

18. The method of claim 1, wherein the probability that the respective neoantigen is bound by T-cells that are specific to one or more known epitopes in the plurality of epitopes after class I MHC presentation is computed as:

$$R = Z(k)^{-1} \sum_{t \in F} \exp[-k(a - |s, t|)],$$

wherein
a is a number that represents a horizontal displacement of a binding curve for the respective neoantigen,
k is a number that sets the steepness of the binding curve at a,
Z(k) is a partition function over the unbound state and all bound states of the respective neoantigen of the form $$1 + \sum_{t \in F} \exp[-k(a - |s, t|)]$$

wherein,

F is a plurality of T-cell receptor sequences, each respective T-cell receptor t is a T-cell receptor from the plurality of T-cell receptor sequences F, and

|s, t| is a measure of affinity between the respective neoantigen s and the respective T-cell receptor t.

19. The method of claim 18, wherein the plurality of T-cell receptors is drawn exclusively from the subject.

20. The method of claim 1, wherein the plurality of clones is determined by identifying a plurality of inferred copy number variations using the plurality of sequencing reads.

21. A method for selecting an immunotherapy for treating a cancer in a subject in need thereof, the method comprising:

(A) obtaining a plurality of sequencing reads from one or more samples from a human cancer subject that is representative of the cancer;

(B) determining a human leukocyte antigen (HLA) type of the human cancer subject from the plurality of sequencing reads;

(C) determining a plurality of clones, and for each respective clone $\alpha$ in the plurality of clones, an initial frequency $X_\alpha$ of the respective clone $\alpha$ in the one or more samples from the plurality of sequencing reads;

(D) for each respective clone $\alpha$ in the plurality of clones, computing a corresponding clone fitness score of the respective clone, thereby computing a plurality of clone fitness scores, each corresponding clone fitness score computed for a respective clone $\alpha$ by a first procedure comprising:

(a) identifying a plurality of neoantigens in the respective clone $\alpha$;

(b) computing a recognition potential of each respective neoantigen in the plurality of neoantigens in the respective clone $\alpha$ by a second procedure comprising:

(i) computing an amplitude A of the respective neoantigen as a function of the relative major histocompatibility complex (MHC) affinity of the respective neoantigen and the wildtype counterpart of the respective neoantigen given the HLA type of the subject, (ii) computing a probability of T-cell receptor recognition R of the respective neoantigen as a probability that the respective neoantigen is bound by T-cells that are specific to one or more known epitopes in a plurality of epitopes after class I MHC presentation, wherein the plurality of epitopes comprises $1 \times 10^6$ epitopes, wherein the probability of T-cell receptor recognition R is computed as:

$$R = Z(k)^{-1} \sum_{e \in D} \exp[-k(a - |s, e|)],$$

wherein a is a number that represents a horizontal displacement of a binding curve for the respective neoantigen, k is a number that sets the steepness of the binding curve at a, Z(k) is a partition function over the unbound state and all bound states of the respective neoantigen of the form $$1 + \sum_{e \in D} \exp[-k(a - |s, e|)]$$

wherein,

D is the plurality of epitopes, each respective epitope e is an epitope from the plurality of epitopes that is positively recognized by T-cells after class I MHC presentation, and

|s, e| is a measure of sequence similarity between the respective neoantigen s and the respective epitope e, and (iii) computing the recognition potential of the respective neoantigen as a function of the amplitude A of the respective neoantigen and the probability of T-cell receptor recognition R of the respective neoantigen; and (c) determining the corresponding clone fitness score of the respective clone $\alpha$ as an aggregate of the neoantigen recognition potentials across the plurality of neoantigens in the respective clone $\alpha$; and (E) selecting at least a first neoantigen from a plurality of neoantigens for a respective clone $\alpha$ in the plurality of respective clones based upon the recognition potential of the at least first neoantigen as the immunotherapy for the cancer, (F) administering to the human cancer subject a vaccine comprising the at least first neoantigen, a vaccine comprising a polynucleotide encoding the at least first neoantigen, or a T cell population that targets the at least first neoantigen.

\* \* \* \* \*